(12) United States Patent
Verma et al.

(10) Patent No.: US 7,141,364 B1
(45) Date of Patent: Nov. 28, 2006

(54) UNIVERSAL PRIMERS FOR WILDLIFE IDENTIFICATION

(75) Inventors: Sunil Kumar Verma, Hyderabad (IN); Lalji Singh, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 236 days.

(21) Appl. No.: 09/821,782

(22) Filed: Mar. 29, 2001

(51) Int. Cl.
*C12Q 1/68* (2006.01)
*C12P 19/34* (2006.01)
*C07H 21/04* (2006.01)
(52) U.S. Cl. ..................... 435/6; 435/91.2; 536/24.33
(58) Field of Classification Search ............. 536/24.33, 536/23.44; 435/6, 91.2
See application file for complete search history.

(56) References Cited

OTHER PUBLICATIONS

Matthee et al. Cytochrome b phylogeny of the family Bovidae: resolution within the Alcelaphini, Antilopini, Neotragini, and Tragelaphini. Mol Phylogenet Evol., vol. 12, No. 1, pp. 31-46, 1999.*
Kocher et al. Dynamics of mitochondrial DNA evolution in animals: amplification and sequencing with conserved primers. Proc Natl. Acad. Sci. USA., vol. 86, pp. 6196-6200, 1989.*

* cited by examiner

*Primary Examiner*—Jeffrey Fredman
*Assistant Examiner*—Suryaprabha Chunduru
(74) *Attorney, Agent, or Firm*—Ladas & Parry LLP

(57) ABSTRACT

The invention provides novel universal primers that can amplify the fragment of cytochrome b gene of any animal species in polymerase chain reaction (PCR) and reveal the identity of the biological material of any unknown animal origin and a method for identification of the specific animal from a given biological sample.

16 Claims, 6 Drawing Sheets

Figure 1:
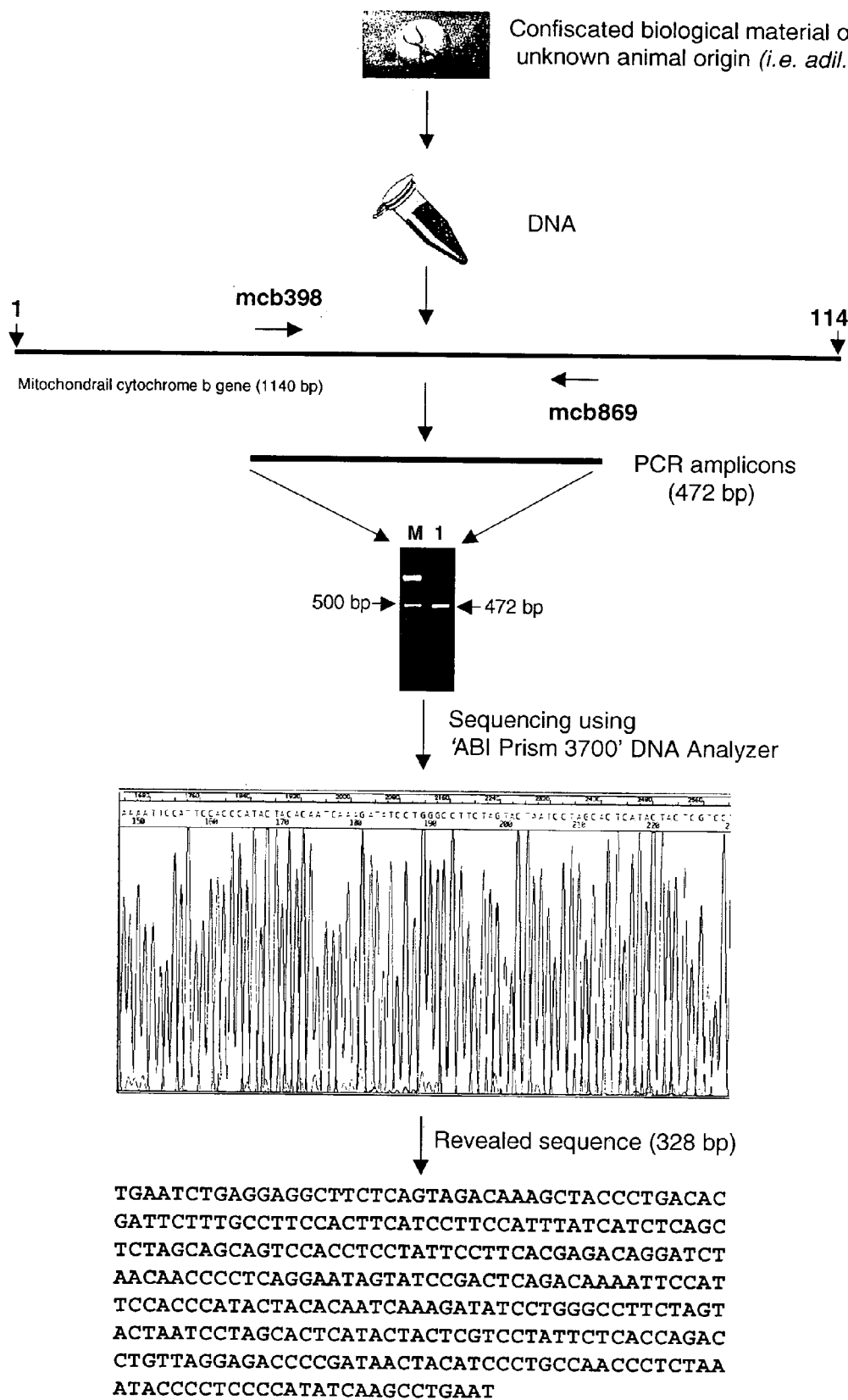

Sequence of cytochrome b gene (328 bp) revealed from biological material of unknown origin i.e. 'adil.flesh' using primers 'mcb398' and 'mcb869'

↓ Homology search in 'nr' database using 'BLAST'

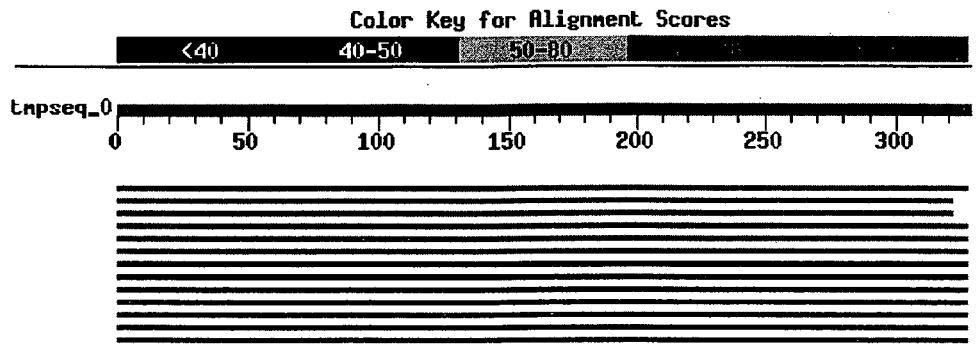

| Sequences producing significant alignments: | Score (bits) | E Value |
|---|---|---|
| gb\|AY005809.1\| *Panthera pardus* cytochrome b gene, partial c... | 603 | e-170 |
| gb\|AF053054.1\|AF053054 *Panthera tigris sumatrae* isolate Su1... | 527 | e-147 |
| gb\|AF053053.1\|AF053053 *Panthera tigris tigris* isolate B7 mi... | 527 | e-147 |
| gb\|AF053050.1\|AF053050 *Panthera tigris corbetti* isolate C2 ... | 476 | e-132 |
| gb\|AF053049.1\|AF053049 *Panthera tigris corbetti* isolate C1 ... | 476 | e-132 |

↓

Selection of reference animals based on above information and further analysis using primers 'mcb398' and 'mcb869'

↓ Multiple sequence alignments using 'Autoassembler'

Figure 1 b

SEQUENCE LISTING

<160> NUMBER OF SEQ ID NOS: 255

<210> SEQ ID NO 1
<211> LENGTH: 25
<212> TYPE: DNA
<213> ORGANISM: Artificial
<220> FEATURE:
<223> OTHER INFORMATION: Universal primer "mcb 398" for amplifying
      fragment of cytochrome b gene of animal species

<400> SEQUENCE: 1
taccatgagg acaaatatca ttctg                                          25

<210> SEQ ID NO 2
<211> LENGTH: 26
<212> TYPE: DNA
<213> ORGANISM: Artificial
<220> FEATURE:
<223> OTHER INFORMATION: Universal primer "mcb 869" for amplifying
      fragment of cytochrome b gene of animal species

<400> SEQUENCE: 2
cctcctagtt tgttagggat tgatcg                                         26

<210> SEQ ID NO 3
<211> LENGTH: 23
<212> TYPE: DNA
<213> ORGANISM: Artificial
<220> FEATURE:
<223> OTHER INFORMATION: primer "AFF" for amplifying fragment of
      cytochrome b gene of animal species

<400> SEQUENCE: 3
ctagtagaat gaatctgagg agg                                            23

<210> SEQ ID NO 4
<211> LENGTH: 23
<212> TYPE: DNA

```
<213> ORGANISM: Artificial
<220> FEATURE:
<223> OTHER INFORMATION: primer "AFR" for amplifying fragment of
      cytochrome b gene of animal species

<400> SEQUENCE: 4
tatgcaaata ggaagtatca ttc                                          23

<210> SEQ ID NO 5
<211> LENGTH: 328
<212> TYPE: DNA
<213> ORGANISM: adil.flesh
<220> FEATURE:
<221> NAME/KEY: misc_feature
<223> OTHER INFORMATION: DNA sequence generated from the confiscated
      skin of unknown animal origin using primers mcb398 and mcb869

<400> SEQUENCE: 5
tgaatctgag gaggcttctc agtagacaaa gctaccctga cacgattctt tgccttccac    60
ttcatccttc catttatcat ctcagctcta gcagcagtcc acctcctatt ccttcacgag   120
acaggatcta acaaccccuc aggaatagta tccgactcag acaaaattcc attccaccca   180
tactacacaa tcaaagatat cctgggcctt ctagtactaa tcctagcact catactactc   240
gtcctattct caccagacct gttaggagac ccgataact acatccctgc caaccctcta   300
aatacccctc cccatatcaa gcctgaat                                      328

<210> SEQ ID NO 6
<211> LENGTH: 328
<212> TYPE: DNA
<213> ORGANISM: bhz25t
<220> FEATURE:
<221> NAME/KEY: misc_feature
<222> LOCATION: (1)..(328)
<223> OTHER INFORMATION: DNA sequence generated from the known tiger
      (Panthera tigris tigris) animal number 1 using primers mcb398 and
      mcb869

<400> SEQUENCE: 6
tgaatctgag gaggcttctc agtagacaaa gccaccctga cacgattctt tgccttccac    60
ttcatccttc catttatcat ctcagcccta gcagcagtcc acctcctatt cctccatgag   120
acaggatcta acaaccccuc aggaatagta tctgactcag acaaaatccc gttccaccca   180
tactacacaa tcaaagacat cctgggcctt ctagtactaa tcctaacact catactactc   240
gtcctattct caccagacct attaggggac ccgataact acatccccgc caaccctcta   300
aacacccctc cccatatcaa gcgcgaat                                      328

<210> SEQ ID NO 7
<211> LENGTH: 328
<212> TYPE: DNA
<213> ORGANISM: bhz26t
<220> FEATURE:
<221> NAME/KEY: misc_feature
<222> LOCATION: (1)..(328)
<223> OTHER INFORMATION: DNA sequence generated from the known tiger
      (Panthera tigris tigris) animal number 3 using primers mcb398 and
      mcb869

<400> SEQUENCE: 7
tgaatctgag gaggcttctc agtagacaaa gccaccctga cacgattctt tgccttccac    60
ttcatccttc catttatcat ctcagcccta gcagcagtcc acctcctatt cctccatgag   120
acaggatcta acaaccccuc aggaatagta tctgactcag acaaaatccc gttccaccca   180
```

```
tactacacaa tcaaagacat cctgggcctt ctagtactaa tcctaacact catactactc      240
gtcctattct caccagacct attaggggac cccgataact acatcccgc caaccctcta       300 aacaccccctc cccatatcaa gcgcgaat                                         328
```

<210> SEQ ID NO 8
<211> LENGTH: 328
<212> TYPE: DNA
<213> ORGANISM: bhz30t
<220> FEATURE:
<221> NAME/KEY: misc_feature
<223> OTHER INFORMATION: DNA sequence generated from the known tiger
      (Panthera tigris tigris animal number 3 using primers mcb398 and
      mcb869)

<400> SEQUENCE: 8

```
tgaatctgag gaggcttctc agtagacaaa gccaccctga cacgattctt tgccttccac      60
ttcatccttc catttatcat ctcagcccta gcagcagtcc acctcctatt cctccatgag     120
acaggatcta acaacccctc aggaatagta tctgactcag acaaaatccc gttccaccca     180
tactacacaa tcaaagacat cctgggcctt ctagtactaa tcctaacact catactactc     240
gtcctattct caccagacct attaggggac cccgataact acatcccgc caaccctcta      300 aacaccccctc cccatatcaa gcgcgaat                                        328
```

<210> SEQ ID NO 9
<211> LENGTH: 328
<212> TYPE: DNA
<213> ORGANISM: bhz45t
<220> FEATURE:
<221> NAME/KEY: misc_feature
<223> OTHER INFORMATION: DNA sequence generated from the known tiger
      (Panthera tigris tigris) animal number 4 using primers mcb398 and
      mcb869

<400> SEQUENCE: 9

```
tgaatctgag gaggcttctc agtagacaaa gccaccctga cacgattctt tgccttccac      60
ttcatccttc catttatcat ctcagcccta gcagcagtcc acctcctatt cctccatgag     120
acaggatcta acaacccctc aggaatagta tctgactcag acaaaatccc gttccaccca     180
tactacacaa tcaaagacat cctgggcctt ctagtactaa tcctaacact catactactc     240
gtcctattct caccagacct attaggggac cccgataact acatcccgc caaccctcta      300 aacaccccctc cccatatcaa gcgcgaat                                        328
```

<210> SEQ ID NO 10
<211> LENGTH: 328
<212> TYPE: DNA
<213> ORGANISM: bhz56t
<220> FEATURE:
<221> NAME/KEY: misc_feature
<223> OTHER INFORMATION: DNA sequence generated from the known tiger
      (Panthera tigris tigris) animal number 5 using primers mcb398 and
      mcb869

<400> SEQUENCE: 10

```
tgaatctgag gaggcttctc agtagacaaa gccaccctga cacgattctt tgccttccac      60
ttcatccttc catttatcat ctcagcccta gcagcagtcc acctcctatt cctccatgag     120
acaggatcta acaacccctc aggaatagta tctgactcag acaaaatccc gttccaccca     180
tactacacaa tcaaagacat cctgggcctt ctagtactaa tcctaacact catactactc     240
gtcctattct caccagacct attaggggac cccgataact acatcccgc caaccctcta      300
```

```
aacacccctc cccatatcaa gcgcgaat                                        328
```

<210> SEQ ID NO 11
<211> LENGTH: 328
<212> TYPE: DNA
<213> ORGANISM: bhz63t
<220> FEATURE:
<221> NAME/KEY: misc_feature
<223> OTHER INFORMATION: DNA sequence generated from the known tiger
      (Panthera tigris tigris) animal number 6 using primers mcb398 and
      mcb869

<400> SEQUENCE: 11

```
tgaatctgag gaggcttctc agtagacaaa gccaccctga cacgattctt tgccttccac     60
ttcatccttc catttatcat ctcagcccta gcagcagtcc acctcctatt cctccatgag    120
acaggatcta acaaccctc aggaatagta tctgactcag acaaaatccc gttccaccca    180
tactacacaa tcaaagacat cctgggcctt ctagtactaa tcctaacact catactactc    240
gtcctattct caccagacct attaggggac cccgataact acatccccgc caaccctcta    300
aacacccctc cccatatcaa gcgcgaat                                        328
```

<210> SEQ ID NO 12
<211> LENGTH: 328
<212> TYPE: DNA
<213> ORGANISM: bhz20wt
<220> FEATURE:
<221> NAME/KEY: misc_feature
<223> OTHER INFORMATION: DNA sequence generated from the known tiger
      (Panthera tigris tigris) animal number 1 using primers mcb398 and
      mcb869
<220> FEATURE:
<221> NAME/KEY: misc_feature
<223> OTHER INFORMATION: DNA sequence generated from the known white
      tiger (Panthera tigris tigris) animal number 1 using primers
      mcb398 and mcb869

<400> SEQUENCE: 12

```
tgaatctgag gaggcttctc agtagacaaa gccaccctga cacgattctt tgccttccac     60
ttcatccttc catttatcat ctcagcccta gcagcagtcc acctcctatt cctccatgag    120
acaggatcta acaaccctc aggaatagta tctgactcag acaaaatccc gttccaccca    180
tactacacaa tcaaagacat cctgggcctt ctagtactaa tcctaacact catactactc    240
gtcctattct caccagacct attaggggac cccgataact acatccccgc caaccctcta    300
aacacccctc cccatatcaa gcgcgaat                                        328
```

<210> SEQ ID NO 13
<211> LENGTH: 328
<212> TYPE: DNA
<213> ORGANISM: bhz22wt
<220> FEATURE:
<221> NAME/KEY: misc_feature
<223> OTHER INFORMATION: DNA sequence generated from the known white
      tiger (Panthera tigris tigris) animal number 2 using primers
      mcb398 and mcb869

<400> SEQUENCE: 13

```
tgaatctgag gaggcttctc agtagacaaa gccaccctga cacgattctt tgccttccac     60
ttcatccttc catttatcat ctcagcccta gcagcagtcc acctcctatt cctccatgag    120
acaggatcta acaaccctc aggaatagta tctgactcag acaaaatccc gttccaccca    180
tactacacaa tcaaagacat cctgggcctt ctagtactaa tcctaacact catactactc    240
gtcctattct caccagacct attaggggac cccgataact acatccccgc caaccctcta    300
```

```
aacacccctc cccatatcaa gcgcgaat                                          328
```

<210> SEQ ID NO 14
<211> LENGTH: 328
<212> TYPE: DNA
<213> ORGANISM: bhz23wt
<220> FEATURE:
<221> NAME/KEY: misc_feature
<223> OTHER INFORMATION: DNA sequence generated from the known white
      tiger (Panthera tigris tigris) animal number 3 using primers
      mcb398 and mcb869

<400> SEQUENCE: 14

```
tgaatctgag gaggcttctc agtagacaaa gccaccctga cacgattctt tgccttccac      60
ttcatccttc catttatcat ctcagcccta gcagcagtcc acctcctatt cctccatgag    120
acaggatcta acaacccctc aggaatagta tctgactcag acaaaatccc gttccaccca    180
tactacacaa tcaaagacat cctgggcctt ctagtactaa tcctaacact catactactc    240
gtcctattct caccagacct attaggggac cccgataact catccccgc caaccctcta     300
aacacccctc cccatatcaa gcgcgaat                                        328
```

<210> SEQ ID NO 15
<211> LENGTH: 328
<212> TYPE: DNA
<213> ORGANISM: bhz28wt
<220> FEATURE:
<221> NAME/KEY: misc_feature
<223> OTHER INFORMATION: DNA sequence generated from the known white
      tiger (Panthera tigris tigris) animal number 4 using primers
      mcb398 and mcb869

<400> SEQUENCE: 15

```
tgaatctgag gaggcttctc agtagacaaa gccaccctga cacgattctt tgccttccac      60
ttcatccttc catttatcat ctcagcccta gcagcagtcc acctcctatt cctccatgag    120
acaggatcta acaacccctc aggaatagta tctgactcag acaaaatccc gttccaccca    180
tactacacaa tcaaagacat cctgggcctt ctagtactaa tcctaacact catactactc    240
gtcctattct caccagacct attaggggac cccgataact catccccgc caaccctcta     300
aacacccctc cccatatcaa gcgcgaat                                        328
```

<210> SEQ ID NO 16
<211> LENGTH: 328
<212> TYPE: DNA
<213> ORGANISM: gz1L
<220> FEATURE:
<221> NAME/KEY: misc_feature
<223> OTHER INFORMATION: DNA sequence generated from the known leopard
      (Panthera pardus) animal number 1 using primers mcb398 and mcb869
<220> FEATURE:
<221> NAME/KEY: misc_feature
<223> OTHER INFORMATION: DNA sequence generated from the known leopard
      (Panthera pardus) animal number 1 using primers mcb398 and mcb869
<220> FEATURE:
<221> NAME/KEY: misc_feature
<223> OTHER INFORMATION: DNA sequence generated from the known leopard
      (Panthera pardus) animal number 1 using primers mcb398 and mcb869

<400> SEQUENCE: 16

```
tgaatctgag gaggcttctc agtagacaaa gctaccttga cacgattctt tgccttccac      60
ttcatccttc catttatcat ctcagctcta gcagcagtcc acctcctatt ccttcacgag    120
acaggatcta acaacccctc aggaatagta tccgactcag acaaaattcc attccaccca    180
```

```
tactacacaa tcaaagatat cctgggcctt ctagtactaa tcctagcact catactactc    240
gtcctattct caccagacct gttaggagac cccgataact acatccctgc caaccctcta    300
aatacccctc cccatatcaa gcctgaat                                       328
```

<210> SEQ ID NO 17
<211> LENGTH: 328
<212> TYPE: DNA
<213> ORGANISM: gz2L
<220> FEATURE:
<221> NAME/KEY: misc_feature
<223> OTHER INFORMATION: DNA sequence generated from the known leopard
      (Panthera pardus) animal number 2 using primers mcb398 and mcb869
<220> FEATURE:
<221> NAME/KEY: misc_feature
<223> OTHER INFORMATION: DNA sequence generated from the known leopard
      (Panthera pardus) animal number 2 using primers mcb398 and mcb869

<400> SEQUENCE: 17

```
tgaatctgag gaggcttctc agtagacaaa gctaccttga cacgattctt tgccttccac    60
ttcatccttc catttatcat ctcagctcta gcagcagtcc acctcctatt ccttcacgag    120
acaggatcta acaaccctc aggaatagta tctgactcag acaaaattcc attccaccca    180
tactacacaa tcaaagacat cctgggcctt ctagtactaa tcttagcact catactactc    240
gtcctattct caccagacct gttgggagac cccgataact acatccccgc caaccctcta    300
aatacccctc cccatatcaa gcctgaat                                       328
```

<210> SEQ ID NO 18
<211> LENGTH: 328
<212> TYPE: DNA
<213> ORGANISM: gz3L
<220> FEATURE:
<221> NAME/KEY: misc_feature
<223> OTHER INFORMATION: DNA sequence generated from the known leopard
      (Panthera pardus) animal number 3 using primers mcb398 and mcb869
<220> FEATURE:
<221> NAME/KEY: misc_feature
<223> OTHER INFORMATION: DNA sequence generated from the known leopard
      (Panthera pardus) animal number 3 using primers mcb398 and mcb869

<400> SEQUENCE: 18

```
tgaatctgag gaggcttctc agtagacaaa gctaccttga cacgattctt tgccttccac    60
ttcatccttc catttatcat ctcagctcta gcagcagtcc acctcctatt ccttcacgag    120
acaggatcta acaaccctc aggaatagta tctgactcag acaaaattcc attccaccca    180
tactacacaa tcaaagacat cctgggcctt ctagtactaa tcttagcact catactactc    240
gtcctattct caccagacct gttgggagac cccgataact acatccccgc caaccctcta    300
aatacccctc cccatatcaa gcctgaat                                       328
```

<210> SEQ ID NO 19
<211> LENGTH: 327
<212> TYPE: DNA
<213> ORGANISM: gz21CL
<220> FEATURE:
<221> NAME/KEY: misc_feature
<223> OTHER INFORMATION: DNA sequence generated from the known clouded
      leopard (Neofelis nebulosa) animal number 1 using primers mcb398
      and mcb869

<400> SEQUENCE: 19

```
tgaatctgag gaggcttctc agtagacaaa gccaccctga cacgattttt cgccttccac    60
ttcatcctcc catttatcat ctcagcctta gcagcagttc accttctatt tctccatgaa    120
```

```
aaggatccaa taacccctca ggaatggtat ccgattcaga caaaatcccg ttccacccgt    180
actatacaat caaagatatc ctaggcctcc tagttctaat tctagcgctc acactacttg    240
ttctattctc cccagaccta ctaggagacc ctgacaatta cactcccgcc aaccctctaa    300
atacccctcc ccatatcaag cctgaat                                      327

<210> SEQ ID NO 20
<211> LENGTH: 327
<212> TYPE: DNA
<213> ORGANISM: gz22CL
<220> FEATURE:
<221> NAME/KEY: misc_feature
<223> OTHER INFORMATION: DNA sequence generated from the known clouded
      leopard (Neofelis nebulosa) animal number 2 using primers mcb398
      and mcb869

<400> SEQUENCE: 20
tgaatctgag gaggcttctc agtagacaaa gccaccctga cacgattttt cgccttccac    60
ttcatcctcc catttatcat ctcagcctta gcagcagttc accttctatt tctccatgaa   120
aaggatccaa taacccctca ggaatggtat ccgattcaga caaaatcccg ttccacccgt   180
actatacaat caaagatatc ctaggcctcc tagttctaat tctagcgctc acactacttg   240
ttctattctc cccagaccta ctaggagacc ctgacaatta cactcccgcc aaccctctaa   300
atacccctcc ccatatcaag cctgaat                                      327

<210> SEQ ID NO 21
<211> LENGTH: 328
<212> TYPE: DNA
<213> ORGANISM: darz14SL
<220> FEATURE:
<221> NAME/KEY: misc_feature
<222> LOCATION: (1)..(328)
<223> OTHER INFORMATION: DNA sequence generated from the known snow
      leopard (Panthera unica) animal number 1 using primers mcb398 and
      mcb869

<400> SEQUENCE: 21
tgaatctgag gaggcttctc agtacacaaa gccaccctga cacgattctt tgccttccac    60
ttcatccttc catttatcat ctcagcccta gcagcagtcc acctcctatt cctccatgag   120
acaggatcta acaaccctc aggaatagta tctgactcag acaaaatccc gttccaccca    180
tactacacaa tcaaagacat cctgggcctt ctagtactaa tcctaacact catactactc    240
gtcctattct caccagacct attaggggac gccgataact catcccgc caaccctcta    300 aacaccccctc cccatatcaa gcccgaat                                    328

<210> SEQ ID NO 22
<211> LENGTH: 328
<212> TYPE: DNA
<213> ORGANISM: darz15SL
<220> FEATURE:
<221> NAME/KEY: misc_feature
<223> OTHER INFORMATION: DNA sequence generated from the known snow
      leopard (Panthera unica) animal number 2 using primers mcb398 and
      mcb869

<400> SEQUENCE: 22
tgaatctgag gaggcttctc agtacacaaa gccaccctga cacgattctt tgccttccac    60
ttcatccttc catttatcat ctcagcccta gcagcagtcc acctcctatt cctccatgag   120
acaggatcta acaaccctc aggaatagta tctgactcag acaaaatccc gttccaccca    180
tactacacaa tcaaagacat cctgggcctt ctagtactaa tcctaacact catactactc    240
```

```
gtcctattct caccagacct attaggggac gccgataact acatccccgc caaccctcta    300
aacacccctc cccatatcaa gcccgaat                                       328
```

<210> SEQ ID NO 23
<211> LENGTH: 328
<212> TYPE: DNA
<213> ORGANISM: darz16SL
<220> FEATURE:
<221> NAME/KEY: misc_feature
<223> OTHER INFORMATION: DNA sequence generated from the known snow
      leopard (Panthera unica) animal number 3 using primers mcb398 and
      mcb869

<400> SEQUENCE: 23

```
tgaatctgag gaggcttctc agtacacaaa gccaccctga cacgattctt tgccttccac    60
ttcatccttc catttatcat ctcagcccta gcagcagtcc acctcctatt cctccatgag   120
acaggatcta acaaccctc aggaatagta tctgactcag acaaaatccc gttccaccca   180
tactacacaa tcaaagacat cctgggcctt ctagtactaa tcctaacact catactactc   240
gtcctattct caccagacct attaggggac gccgataact acatccccgc caaccctcta   300
aacacccctc cccatatcaa gcccgaat                                       328
```

<210> SEQ ID NO 24
<211> LENGTH: 328
<212> TYPE: DNA
<213> ORGANISM: sbz22AL
<220> FEATURE:
<221> NAME/KEY: misc_feature
<222> LOCATION: (1)..(328)
<223> OTHER INFORMATION: DNA sequence generated from the known asiatic
      lion (Panthera leopersica) animal number 1 using primers mcb398
      and mcb869

<400> SEQUENCE: 24

```
tgaatctgag gaggcttctc agtagacaaa gccaccctga cacgattctt tgccttccac    60
ttcatccttc catttatcat ctcagcccta gcagcagtcc acctcctgtt cctccatgaa   120
acaggatcta ataaccctc aggaatggta tctgactcag ataaaattcc attccatcca   180
tactatacaa tcaaagatat cctaggcctt ctagtactaa tcttaacact catactactc   240
gtcctattct caccagacct attaggagat cccgacaact ataccccgc caatcctcta   300 agcacccctc cccatatcaa acctgaat                                       328
```

<210> SEQ ID NO 25
<211> LENGTH: 328
<212> TYPE: DNA
<213> ORGANISM: sbz38AL
<220> FEATURE:
<221> NAME/KEY: misc_feature
<223> OTHER INFORMATION: DNA sequence generated from the known asiatic
      lion (Panthera leopersica) animal number 2 using primers mcb398
      and mcb869

<400> SEQUENCE: 25

```
tgaatctgag gaggcttctc agtagacaaa gccaccctga cacgattctt tgccttccac    60
ttcatccttc catttatcat ctcagcccta gcagcagtcc acctcctgtt cctccatgaa   120
acaggatcta ataaccctc aggaatggta tctgactcag ataaaattcc attccatcca   180
tactatacaa tcaaagatat cctaggcctt ctagtactaa tcttaacact catactactc   240
gtcctattct caccagacct attaggagat cccgacaact ataccccgc caatcctcta   300
```

```
agcacccctc cccatatcaa acctgaat                                    328
```

<210> SEQ ID NO 26
<211> LENGTH: 328
<212> TYPE: DNA
<213> ORGANISM: sbz39AL
<220> FEATURE:
<221> NAME/KEY: misc_feature
<223> OTHER INFORMATION: DNA sequence generated from the known asiatic
      lion (Panthera leopersica) animal number 3 using primers mcb398
      and mcb869

<400> SEQUENCE: 26

```
tgaatctgag gaggcttctc agtagacaaa gccaccctga cacgattctt tgccttccac    60
ttcatccttc catttatcat ctcagcccta gcagcagtcc acctcctgtt cctccatgaa   120
acaggatcta ataaccccct aggaatggta tctgactcag ataaaattcc attccatcca   180
tactatacaa tcaaagatat cctaggcctt ctagtactaa tcttaacact catactactc   240
gtcctattct caccagacct attaggagat cccgacaact ataccccgc caatcctcta    300 agcacccctc cccatatcaa acctgaat                                     328
```

<210> SEQ ID NO 27
<211> LENGTH: 328
<212> TYPE: DNA
<213> ORGANISM: humsk
<220> FEATURE:
<221> NAME/KEY: misc_feature
<223> OTHER INFORMATION: DNA sequence generated from the known human
      (Homo sapiens sapiens) using primers mcb398 and mcb869
<220> FEATURE:
<221> NAME/KEY: misc_feature
<223> OTHER INFORMATION: DNA sequence generated from the known human
      (Homo sapiens sapiens) using primers mcb398 and mcb869
<220> FEATURE:
<221> NAME/KEY: misc_feature
<223> OTHER INFORMATION: DNA sequence generated from the known human
      (Homo sapiens sapiens) using primers mcb398 and mcb869

<400> SEQUENCE: 27

```
tgaatctgag gaggctactc agtagacagt cccaccctca cacgattctt tacctttcac    60
ttcatcttgc ccttcattat tgcagcccta gcagcactcc acctcctatt cttgcacgaa   120
acgggatcaa acaaccccct aggaatcacc tcccattccg ataaaatcat cttccaccct   180
tactacacaa tcaaagacgc cctcggctta cttctcttcc ttctctcctt aatgacatta   240
acactattct caccagacct cctaggcgac ccagacaatt atacccctagc caaccccta    300 aacacccctc cccacatcaa gcccgaat                                     328
```

<210> SEQ ID NO 28
<211> LENGTH: 328
<212> TYPE: DNA
<213> ORGANISM: chimss
<220> FEATURE:
<221> NAME/KEY: misc_feature
<223> OTHER INFORMATION: DNA sequence generated from the known
      chimpanzee (pan troglodytes) animal using primers mcb398 and
      mcb869
<220> FEATURE:
<221> NAME/KEY: misc_feature
<223> OTHER INFORMATION: DNA sequence generated from the known
      chimpanzee (pan troglodytes) animal using primers mcb398 and
      mcb869
<220> FEATURE:
<221> NAME/KEY: misc_feature
<223> OTHER INFORMATION: DNA sequence generated from the known
      chimpanzee (pan troglodytes) animal using primers mcb398 and
      mcb869

```
<400> SEQUENCE: 28
tgaatctgag gaggctactc agtagacagc cctacccttat cacgattctt caccttccac    60
tttatcttac ccttcattat cacagcccta acaacacttc atctcctatt cttacacgaa   120
acaggatcaa ataaccccct gggaatcacc tcccactccg acaaaattac cttccacccc   180
tactacacaa tcaaagatat ccttggctta ttccttttcc tccttatcct aatgacatta   240
acactattct caccagacct cctgggcgat ccagacaact atacctagc taaccccta    300 aacaccccac cccacattaa acccgaat                                        328

<210> SEQ ID NO 29
<211> LENGTH: 472
<212> TYPE: DNA
<213> ORGANISM: Cervus nippon centralis

<400> SEQUENCE: 29
taccatgagg acaaatatca ttctgaggag caacagtcat taccaacctc ctctcagcaa    60
ttccatatat tggcacaaac ctagtcgaat ggatctgagg gggcttctca gtagataaag   120
caaccctaac ccgattttttc gctttccact ttattcttcc atttatcatc gcagcacttg   180
ctatagtaca cttactcttc cttcacgaga caggatccaa caacccaaca ggaatcccat   240
cggacgcaga caaaatcccc ttccatcctt actacaccat taaagatatc ttaggcatct   300
tacttctagt actcttccta atattactag tattattcgc accagacctg cttggagatc   360
cagacaacta tacccagca aatccactca acacacccc tcatcaaaa cctgaatgat    420 acttcctatt tgcatacgca atcctacgat caattcccaa caaactagga gg            472

<210> SEQ ID NO 30
<211> LENGTH: 472
<212> TYPE: DNA
<213> ORGANISM: Cervus nippon yesoensis

<400> SEQUENCE: 30
taccatgagg acaaatatca ttctgaggag caacagtcat taccaacctc ctctcagcaa    60
ttccatatat tggcacaaac ctagtcgaat ggatctgagg gggcttctca gtagataaag   120
caaccctaac ccgattttttc gctttccact ttattcttcc atttatcatc gcagcacttg   180
ctatagtaca cttactcttc cttcacgaga caggatccaa caacccaaca ggaatcccat   240
cggacgcaga caaaatcccc ttccatcctt actacaccat taaagatatc ttaggcatct   300
tacttctagt actcttccta atattactag tattattcgc accagacctg cttggagatc   360
cagacaacta tacccagca aatccactca acacacccc tcatcaaaa cctgaatgat    420 acttcctatt tgcatacgca atcctacgat caattcccaa caaactagga gg            472

<210> SEQ ID NO 31
<211> LENGTH: 472
<212> TYPE: DNA
<213> ORGANISM: Cervus nippon keramae

<400> SEQUENCE: 31
taccatgagg acaaatatca ttctgaggag caacagtcat taccaacctt ctctcagcaa    60
ttccatacat tggcacaaac ctagtcgaat ggatctgagg aggcttttca gtagataaag   120
caaccctaac ccgattttttc gccttccact ttattcttcc atttatcatc acagcactcg   180
ctatagtaca cttactcttc cttcacgaga caggatccaa caacccaaca ggaatcccat   240
```

```
cggacgcaga caaaatcccc ttccatcctt actataccat aaagatatc ctaggcatct    300 tacttctagt actcttcctg atattactag tattattcgc accagacctg cttggagatc    360
cagacaacta caccccagca aatccgctca acacaccccc tcacatcaaa cctgaatgat    420
atttcctatt tgcatacgca atcctacgat caattcccaa caaactagga gg            472
```

<210> SEQ ID NO 32
<211> LENGTH: 472
<212> TYPE: DNA
<213> ORGANISM: Cervus nippon pulchellus

<400> SEQUENCE: 32

```
taccatgagg acaaatatca ttctgaggag caacagtcat taccaacctt ctctcagcaa    60
ttccatacat tggcacaaac ctagtcgaat ggatctgagg aggcttttca gtagataaag    120
caaccctaac ccgattttc gccttccact ttattcttcc atttatcatc acagcactcg    180
ctatagtaca cttactcttc cttcacgaga caggatccaa caaccaaca ggaatcccat    240 cggacgcaga caaaatcccc ttccatcctt actataccat aaagatatc ctaggcatct    300 tacttctagt actcttcctg atattactag tattattcgc accagacctg cttggagatc    360
cagacaacta caccccagca aatccgctca acacaccccc tcacatcaaa cctgaatgat    420
atttcctatt tgcatacgca atcctacgat caattcccaa caaactagga gg            472
```

<210> SEQ ID NO 33
<211> LENGTH: 472
<212> TYPE: DNA
<213> ORGANISM: Cervus nippon nippon

<400> SEQUENCE: 33

```
taccatgagg acaaatatca ttctgaggag caacagtcat taccaacctc ctctcagcaa    60
ttccatacat tggcacaaac ctagtcgaat ggatctgagg aggcttttca gtagataaag    120
caaccctaac ccgattttc gccttccact ttattcttcc atttatcatc acagcactcg    180
ctatagtaca cttactcttc cttcacgaga caggatccaa caaccaaca ggaatcccat    240 cggacgcaga caaaatcccc ttccatcctt actataccat aaagatatc ctaggcatct    300 tacttctagt actcttcctg atattactag tattattcgc accagacctg cttggagatc    360
cagacaacta caccccagca aatccgctca acacaccccc tcacatcaaa cctgaatgat    420
atttcctatt tgcatacgca atcctacgat caattcccaa caaactagga gg            472
```

<210> SEQ ID NO 34
<211> LENGTH: 472
<212> TYPE: DNA
<213> ORGANISM: Cervus elaphus scoticus

<400> SEQUENCE: 34

```
taccatgagg acaaatatca ttctgaggag caacagtcat caccaacctt ctctcagcaa    60
ttccatatat tgggacaaac ctagtcgaat ggatctgagg aggcttttca gtagacaaag    120
caaccctaac ccgattttc gctttccact ttattctccc atttatcatc gcagcactcg    180
ctatagtaca cttactcttc cttcacgaaa caggatctaa taccccaaca ggaattccat    240
cagacgcaga caaaatcccc tttcatcctt attataccat aaagatatc ttaggcatct    300 tacttcttgt actcttctta atattactag tattattcgc accagaccta cttggagatc    360
cagataacta caccccagca aacccactca acacaccccc tcatattaaa cctgaatgat    420
atttcctatt tgcatacgca atcctacgat caattcccaa caaactagga gg            472
```

<210> SEQ ID NO 35
<211> LENGTH: 472
<212> TYPE: DNA
<213> ORGANISM: Cervus dama

<400> SEQUENCE: 35

```
taccatgagg acaaatatca ttctgaggag caacagttat taccaatctt ctctcagcaa      60
tcccatacat tggtacaaac ctagttgaat gaatctgagg aggcttttca gtagacaaag     120
caaccttaac tcgattcttc gctttccact ttattctacc attcatcatt gcggcacttg     180
ctatagtaca tttactcttt cttcacgaga caggatccaa taacccaaca ggaatcccat     240
cagatgtaga taaaattccc tttcatccct actacaccat taaagatatt ttaggcatcc     300
tattcctatt tctcttctta ataacactag tactatttgc accagacttg cttggagacc     360
cagacaaata cactccagca aatccactca acacacctcc tcatattaaa cccgaatgat     420
acttcctatt tgcatacgca atcctacgat caattcccaa taaattagga gg             472
```

<210> SEQ ID NO 36
<211> LENGTH: 472
<212> TYPE: DNA
<213> ORGANISM: Rangifer tarandus

<400> SEQUENCE: 36

```
taccatgagg acaaatatca ttctgaggag caacagttat cacaaacctc ctctcagcaa      60
ttccatatat tggtacaaat ctagtcgaat gaatttgagg aggattttct gtagataaag     120
caaccctaac ccgattttt gcttttcact ttattcttcc atttattatc gcagcactcg     180
ctatagtcca tttgcttttc cttcacgaaa cagggtctaa caatccaaca ggaattccat     240
cagactcaga taaaattcca ttccatccct attatactat caaagacatt ctaggcatcc     300
tactcctaat tctcttcctt atactactag tattatttgc accagactta ctaggagacc     360
cagacaacta taccccagca aacccactca acactccccc tcatattaaa cctgaatgat     420
actttctatt cgcatacgca atcctacgat caattccaaa taaactagga gg             472
```

<210> SEQ ID NO 37
<211> LENGTH: 472
<212> TYPE: DNA
<213> ORGANISM: Moschus fuscus

<400> SEQUENCE: 37

```
taccttgagg acaaatatct ttctgaggag cgacagttat taccaatctt ctctcagcaa      60
ttccatacat tggtactaat ctggttgaat gaatttgagg aggcttctca gtagacaaag     120
caacactcac tcgattcttt gcctttcact tcattctccc atttatcatc gcagcactcg     180
ctatggttca cctactcttt ctccacgaaa caggatccaa caacccaaca ggaatcacat     240
cagatataga caaaatccca ttccaccct actacaccat caaagacatt ctaggtgtcc     300
tattactaat cttagtctta ataacactag tactattcac acctgattta cttggagacc     360
cggacaatta taccccagca aacccattaa atacgccccc acatattaaa cccgaatgat     420
atttcctatt tgcatatgcc attctacgat caattcccaa caaactagga gg             472
```

<210> SEQ ID NO 38
<211> LENGTH: 472
<212> TYPE: DNA
<213> ORGANISM: Moschus leucogaster

```
<400> SEQUENCE: 38
taccttgagg acaaatatct ttctgaggag caacagttat taccaatctt ctctcagcaa      60
ttccatacat tggtactaat ctggttgaat gaatttgagg aggcttctca gtagacaaag     120
caacactcac ccgattcttt gccttccact tcattctccc atttatcatc gcagcactcg     180
ctatggttca cctactcttt ctccacgaaa caggatccaa caacccaaca ggaatcacat     240
cagatataga caaaatccca ttccaccct actacaccat caaagacatt ctaggtgtcc      300
tattactaat cttagtctta ataacactag tactattcac acctgattta cttggagacc     360
cggacaatta taccccagca aacccattaa atacaccccc acatattaaa cccgaatgat     420
atttcctatt tgcatatgcc attctacgat caattcccaa caaactagga gg             472

<210> SEQ ID NO 39
<211> LENGTH: 472
<212> TYPE: DNA
<213> ORGANISM: Moschus chrysogaster

<400> SEQUENCE: 39
taccttgagg acaaatatct ttctgaggag caacagttat taccaatctt ctctcagcaa      60
ttccatacat tggtactaac ctggttgaat gaatttgagg aggtttctca gtagacaaag     120
caacactcac tcgattcttt gccttccact tcattctccc atttatcatc gcagcactcg     180
ctatggttca cctactcttt ctccacgaaa caggatccaa caacccaaca ggaatcacat     240
cagacataga caaaatccca ttccaccct actacaccat caaagacatt ctaggtgtcc      300
tattactaat cctagtctta ataacactag tactattcac acctgattta cttggagacc     360
cggacaatta taccccggca aacccattaa atacgccccc acatattaaa cccgaatgat     420
acttcctatt tgcatatgcc atcctacgat caattcccaa caaactagga gg             472

<210> SEQ ID NO 40
<211> LENGTH: 472
<212> TYPE: DNA
<213> ORGANISM: Moschus berezovskii

<400> SEQUENCE: 40
taccttgagg acaaatatct ttctgaggag caacagttat taccaatctt ctctcagcaa      60
ttccttacat tggtactaat ctggttgaat gaatctgagg aggcttctca gtagacaaag     120
caacactcac ccgattcttt gccttccact tcatcctccc atttatcatc gcagcactcg     180
ctatggttca cctactcttt ctccacgaaa caggatccaa caacccaaca ggaatcatat     240
cagacataga caaaatccca ttccaccct actacactat caaagacatt ctaggtgtcc      300
taatactaat cttagtctta atagtactag tactattcac acccgattta cttggagacc     360
cggacaatta taccccagca aacccattaa acacaccacc acatattaaa cccgaatgat     420
acttcctatt tgcatatgcc attctacgat caattcccaa caaactagga gg             472

<210> SEQ ID NO 41
<211> LENGTH: 472
<212> TYPE: DNA
<213> ORGANISM: Moschus moschiferus

<400> SEQUENCE: 41
taccttgagg acaaatatct ttctgaggag caacagtcat cactaacctt ctctcagcaa      60
ttccctacat tggtactaac ctggttgagt gaatttgagg aggcttctca gtagacaaag     120
caacactcac ccgattcttt gcctttcact ttatcctccc atttatcatt gcagcactcg     180
```

```
ccatggttca tctactcttt ctccatgaaa caggatccaa taacccaaca ggaatcacat        240
cagacataga caaaatccca tttcacccct actacaccat caaagatatt ctaggtatcc        300
tattactaat cttaatctta atagcactag tgctatttac acccgaccta cttggagatc        360
cggacaacta tactccagca aacccattaa atacacctcc acatattaaa cccgaatggt        420
actttctatt tgcatatgcc attctacgat caattcctaa taaactagga gg                472

<210> SEQ ID NO 42
<211> LENGTH: 472
<212> TYPE: DNA
<213> ORGANISM: Kobus ellipsiprymnus

<400> SEQUENCE: 42
taccatgagg acaaatatcc ttctgaggag caacagtcat caccaatctc ctttcagcaa        60
ttccatacat tggcacaaac ctagtcgaat gaatctgagg aggattttca gtagataagg        120
caacccttac ccgcttcttc gccttccact ttattctccc atttatcatc gcggctatta        180
ccatagtcca tcttctgttt ctccatgaaa caggatccaa taatcccaca ggaatctcat        240
cagacataga taaaatccca ttccacccct actacaccat caaagacatt ctaggcgccc        300
tactactaat cctagtccta atactccagt tctattcgc ccccgaccta cttggagatc        360
ctgacaacta tgccccagca aacccactta acacgcccct cacaattaaa cctgaatgat        420
acttcttatt cgcatatgca attctacgat caatccccaa caaactagga gg                472

<210> SEQ ID NO 43
<211> LENGTH: 472
<212> TYPE: DNA
<213> ORGANISM: Kobus megaceros

<400> SEQUENCE: 43
taccatgagg acaaatatcc ttctgaggag cgacagtcat cactaatctc ctttcagcaa        60
tcccatatat cggcacaaac ctagtcgaat gaatctgagg aggattctca gtagacaaag        120
caacccttac ccgcttcttc gccttccact ttatcctccc atttatcatc gcagctatcg        180
ctatagttca cctactattc cttcatgaaa caggatctaa caaccctaca gggatttcat        240
cagacacaga caaaatccca ttccacccat attataccat caaagatatt ctaggtgccc        300
tcctattaat cctaatacta atactcctag tactatttgc ccccgaccta cttggagacc        360
ctgacaatta taccccagca aacccactta atacacctcc ccatattaaa cccgaatgat        420
atttcttatt cgcatacgca attttacggt caattcctaa taaactggga gg                472

<210> SEQ ID NO 44
<211> LENGTH: 472
<212> TYPE: DNA
<213> ORGANISM: Redunca arundinum

<400> SEQUENCE: 44
taccatgagg acaaatatcc ttctgaggag caacagttat cactaatctt ctctcagcaa        60
tcccatacat cggcacaaac ctagtcgaat gaatctgagg aggattctca gtcgataaag        120
caacccttac ccgattcttc gccttccact ttatcctccc attcattatc acagccctcg        180
ctatagtaca cctactattc ctccacgaaa caggatccaa caaccctaca ggaatctcat        240
cagatgtaga caaaatccca tttcatccat actatactat caaggacgtc ctaggcgccc        300
tactgctaat cctagtccta atgctcttag tattattcac ccctgaccta ctcggagatc        360
```

```
ccgacaatta tactccagca aatccactca acacaccccc tcatattaaa cccgaatgat    420
acttcttatt tgcatatgca atcctacgat caatccccaa taaactagga gg            472
```

<210> SEQ ID NO 45
<211> LENGTH: 472
<212> TYPE: DNA
<213> ORGANISM: Redunca fulvorufula
<220> FEATURE:
<221> NAME/KEY: misc_feature
<222> LOCATION: (269)..(269)
<223> OTHER INFORMATION: unknown
<220> FEATURE:
<221> NAME/KEY: misc_feature
<222> LOCATION: (431)..(431)
<223> OTHER INFORMATION: unknown

<400> SEQUENCE: 45

```
tgccatgggg acaaatatcc ttctgaggag caacagttat cactaacctt ctctcagcaa    60
tcccatacat cggcacaarc ctagttgaat gaatctgagg aggrttctca gtggataaag    120
caaccctcac tcgattcttc gccttccact ttatcctccc atttatcatc atagccctcg    180
ctatagtcca cctactattc ctccatgaaa caggatccaa caaccccaca ggggtttcat    240
cagayatgga caaaatccca ttccacccnt actacaccat caaagayatt ctaggtgccc    300
tactactaat cctggcccta acactattag tactattcac ccctgaccta ctcggagacc    360
cggacaatta caccccagca aacccactca acacaccccc tcacatcaaa ccagaatggt    420
acttcttatt ngcatacgca atcctacgat caatccccaa taaactagga gg            472
```

<210> SEQ ID NO 46
<211> LENGTH: 472
<212> TYPE: DNA
<213> ORGANISM: Neotragus moschatus

<400> SEQUENCE: 46

```
tgccatgggg acaaatatcc ttctgaggag caacagtcat caccaatcta ctatcagcaa    60
tcccatatat cggcacaaac ctagtcgaat gaatctgagg gggtttctca gtagacaaag    120
caaccctcac ccgattttttt gccttccact tcattctccc atttatcatc gcagcactcg    180
ccatagtcca cttactcttc ctacacgaaa caggatccaa caaccccaca ggaatctcat    240
cagacgcaga caaaatccca ttccacccct actacaccat taaagacatt ctaggcgcca    300
tcctactaat tctagtgcta acactcttag ttttatttgc acctgacctt ttaggagacc    360
cagacaacta caccccgca aaccctctta acacgcctcc ccatatcaaa cccgaatgat    420 acttttatt cgcatacgca atcctacgat caatccccaa taaactagga gg             472
```

<210> SEQ ID NO 47
<211> LENGTH: 472
<212> TYPE: DNA
<213> ORGANISM: Pelea capreolus

<400> SEQUENCE: 47

```
taccatgagg acaaatatcc ttctgaggag caacagtcat caccaacctt ctctcagcaa    60
tcccatacat tggtacaaac ctagtcgaat gaatctgagg gggattttca gtagacaaag    120
caaccctcac ccgattttttt gctttccact ttattctccc atttatcatt gcagccctca    180
ccatagtaca cttgcttttt ctcatgaaa caggatctaa taaccccacg ggaattccat     240
ccgacataga caaaattcca ttccacccat actacaccat taaagatatt ctaggcgcct    300
tattactaat cctaatccta acactcctag tattatttac ccctgaccta ttaggagacc    360
```

```
ctgacaatta cacccctgca aacccgctca acacaccccc tcatatcaaa cccgaatgat    420
atttcctatt tgcatatgcg attctacgat caattcccaa caaactagga gg            472
```

<210> SEQ ID NO 48
<211> LENGTH: 472
<212> TYPE: DNA
<213> ORGANISM: Antilope cervicapra

<400> SEQUENCE: 48

```
taccatgagg acaaatatct ttttgaggag caacagtcat caccaatctc ctttcagcaa    60
tcccatacat cggtacaaac ctagtagaat gaatctgagg agggttctca gtagataaag    120 caaccettac ccgatttttc gccttccact ttatcctccc atttatcatt gcagcccttg    180
ccatagtaca cctactgttt ctccacgaaa caggatccaa caaccccaca ggaatctcat    240
cagacgcaga caaaattcca ttccacccct actacactat caaagatatc ctaggagctc    300
tactattaat tttaaccctc atgcttctag tcctattctc accggacctg cttggagacc    360
cagacaacta taccagca aacccactta atacaccccc acatatcaag cccgaatgat    420
acttcctatt tgcatacgca atcctccgat caattcctaa caaactagga gg            472
```

<210> SEQ ID NO 49
<211> LENGTH: 472
<212> TYPE: DNA
<213> ORGANISM: Saiga tatarica

<400> SEQUENCE: 49

```
taccatgagg acaaatatct ttctgaggag caacagtcat caccaatctc ctttcagcaa    60
tcccatatat cggcacagac ctagtagaat gaatctgagg gggttttca gtagataaag     120 caaccctcac ccgattcttc gccttccact tcatcctccc atttattatc gcagctctcg    180
ctatagtcca cctacttttt cttcacgaaa caggatctaa caaccccaca ggaatcccat    240
cagattcaga caaaatccca ttccacccct actacaccat taaagacatt ctaggcgccc    300
tactacttat tctaatcctc atacttctag tcctattttc accagacctg cttggagacc    360
cagacaacta cacrccagca aacccactta acacaccccc acatattaaa cccgaatgat    420
acttcctatt cgcatacgca atcctccgat caattcctaa taaactagga gg            472
```

<210> SEQ ID NO 50
<211> LENGTH: 472
<212> TYPE: DNA
<213> ORGANISM: Gazella dama

<400> SEQUENCE: 50

```
taccatgagg acaaatatct ttctgagggg caacagttat cactaacctc ctctcagcaa    60
tcccatacat cggcacagac ctagtagaat gaatctgagg aggattctca gtagataagg    120
caacactcac ccgattcttt gccttccatt tcatcttccc attcatcatt gcagcccttg    180
ccatagttca tctattattt cttcacgaaa caggatccaa caaccccaca ggaatttcat    240
cagatgcaga caaaattccg ttccacccct actacaccat caaagacatt ctaggagcac    300
tactattaat tctagccctc atactccttag ttctattcac accagatctg cttggagacc    360
cagacaacta cacaccagca aatccactca atacaccccc acatattaag cctgagcgat    420
atttcctatt tgcatacgca attctccgat caattcctaa taaactagga gg            472
```

<210> SEQ ID NO 51

```
<211> LENGTH: 472
<212> TYPE: DNA
<213> ORGANISM: Ourebia ourebi

<400> SEQUENCE: 51
taccatgagg acaaatatcc ttttgaggag caacagtcat caccaacctc ctctcagcaa      60
ttccatacat tggtacaaac ctagtcgaat gaatctgagg agggttctca gtagacaagg     120
caactctaac ccgattcttt gccttccact tcatcctccc attcatcatt gcagcccttg     180
ccacagtcca cctactattc cttcacgaaa cgggatccaa caatcccaca ggaatttcat     240
cagatgcaga caaggtccca ttccacccct actacaccat taaagacatc ctaggcgcct     300
tcctactaat tctagccctc atgctcctag tcctattcac accagacctg cttggagacc     360
cagacaacta taccagca aacccactaa atacacccc acatattaaa cctgagtggt       420
atttcctatt cgcatacgca attctccgat cgattcccaa caaactagga gg            472

<210> SEQ ID NO 52
<211> LENGTH: 472
<212> TYPE: DNA
<213> ORGANISM: Gazela gazella

<400> SEQUENCE: 52
taccatgagg acaaatatct ttctgaggag caacagttat cacgaacctc ctctcagcaa      60
tcccatacat cggcacaaac ctagtagaat gaatctgagg gggattctcg gtagataaag     120
caacactcac ccgattcttt gcttttcact ttatcctccc attcatcatt gcagccctcg     180
ctatagtcca cttattattc cttcatgaaa caggatccaa taaccccaca ggaatttcat     240
cagacgcaga caaaatccca tttcacccct actacaccat caaggacatt ctaggagcac     300
tactactaat cctagttctt atactcctag ttctgttctc accggaccta ctcggagacc     360
cagacaacta taccagca aatccactca acacaccccc acacatcaaa cctgaatggt      420
acttcttatt cgcatatgca attctccgat caattcccaa taaactagga gg            472

<210> SEQ ID NO 53
<211> LENGTH: 472
<212> TYPE: DNA
<213> ORGANISM: Raphicerus melanotis

<400> SEQUENCE: 53
taccatgggg acaaatatcc ttttgaggag caacagtcat cactaatctc ctctcagcaa      60
ttccctacat tggcacaaac ctagtagaat ggatctgagg aggattttca gttgataaag     120
caaccctcac ccgattcttc gcttttcact tcagttctcc atttatcatc gcagccctag     180
ctatagttca cctactttc ctccacgaaa ctggatccaa caaccccaca ggaagtttat      240
cagatataga caaaatccca tttcacccct actacaccat taaagacatt ttaggagccc     300
tcctattaat cctaacccctt atgcttctag ttctattcgc accagaccta ctcggagacc    360
cagacaacta taccagca aacccactca acacaccccc acatatcaaa cccgaatggt      420
attttctatt cgcatatgca attctccggt caattcccaa taaattagga gg             472

<210> SEQ ID NO 54
<211> LENGTH: 472
<212> TYPE: DNA
<213> ORGANISM: Madoqua kirkii

<400> SEQUENCE: 54
tgccatgagg acaaatatcc ttctgaggag caacagttat cactaacctc ctctcagcaa      60
```

```
tcccatatat cggcacaaac ttagttgaat gaatctgagg gggcttctca gtagacaaag      120
caaccctcac ccgattcttc gccttccatt ttattctccc attcattatt gcagccctag      180
ccatggttca cctcctcttt ctccatgaaa cgggatccaa cagccccaca ggcatttcat      240
cagacgcaga cggaatccca ttccgcccct actacactat aaagacatc  ctaggcgccc      300 tactactaat tataggcctc atactcctag ttctattctc accagacctg ctcggagacc      360
cagacaacta cacaccagca aatcccctta acacgccccc acacattaaa cctgaatgat      420
atttcctatt cgcatatgca atcctccgat caatccctaa caaactaggg gg              472

<210> SEQ ID NO 55
<211> LENGTH: 472
<212> TYPE: DNA
<213> ORGANISM: Antilocapra americana

<400> SEQUENCE: 55
taccatgagg acaaatatca ttctgagggg caacagtcat tactaaccta ctctcagcaa       60
tcccatacat tggtactaac ctagtagaat gaatctgagg gggattctca gtagacaaag      120
caaccctcac ccgattcttc gcattccact ttatcctccc attcatcatt gcagcactag      180
ccatagtaca cttactattc ctccacgaaa caggatccaa caaccccaca ggaatcccat      240
cagacgcaga caaaatccca ttccacccat actacaccat caaagacatt ctaggagcac      300
tactaataat cttagcccta ataatactag tactattctc accagacctg ttaggagacc      360
ccgacaacta cacaccagct aacccactca acactccccc acacattaag ccagaatgat      420
atttcctatt cgcatacgca atcctacgat caatccctaa caaactagga gg              472

<210> SEQ ID NO 56
<211> LENGTH: 472
<212> TYPE: DNA
<213> ORGANISM: Tragulus javanicus

<400> SEQUENCE: 56
taccctgagg acagatatct ttctgaggag ccacagtcat caccaacctc ttatcagcta       60
tcccatacat tggcacagac ttggtcgaat gaatctgagg tggttttca  gtagacaaag      120 caaccttac  acgattcttt gccttccact ttatccttcc atttatcatt acagccctag      180
tcctagtcca cctttattt  ctccacgaaa caggatctaa taaccccaca ggaatcccct      240
cagacgcaga caaaatcccc ttccacccat actacactat aaagacatt  ctaggggttc      300 tagccctatt tctagcccta atactactag tcctattctc acccgaccta cttggagacc      360
cagataacta caccccgcc  aaccccctta acacaccacc ccatatcaaa cccgaatgat      420
atttcttatt tgcatacgca attcttcggt caatccccaa taaactagga gg              472

<210> SEQ ID NO 57
<211> LENGTH: 472
<212> TYPE: DNA
<213> ORGANISM: Tragulus napu

<400> SEQUENCE: 57
taccctgagg gcaaatatct ttttgaggag ctacagtcat cactaaccct ctttcagcaa       60 tccctatat  cggcaccgaa ctagttgaat gaatctgagg cgggttctca gtagacaaag      120 caaccttac  acgatttttt gccttccact tcatcctccc atttgtcatt acagccctag      180
ccctagtcca tcttttattt ctccacgaga caggatcaaa taaccccaca ggaatccct       240
```

```
cagacgcaga caagatcccc ttccacccat actacaccat caaagatgtc ctaggggctc     300
tagtcctaat actagtcctt ctattactag tcctattttc accggacttg ttgggagacc     360
ccgacaatta cactccggca aacccctca acacaccacc tcatattaag ccagagtggt      420
atttcctatt cgcatacgca atcctacgat caatccccaa taaattagga gg             472
```

<210> SEQ ID NO 58
<211> LENGTH: 472
<212> TYPE: DNA
<213> ORGANISM: Balaenoptera acutorostrata

<400> SEQUENCE: 58

```
taccctgagg acaaatatca ttttgaggtg caaccgtcat caccaacctc ctatcagcaa     60
tcccatatat tggtactacc ttagtcgaat gaatctgagg tggcttctct gtagacaaag     120
caacattaac acgcttttt gccttccact tcatcctccc ttttattatc ctagcattag      180
caattgtcca cctcattttc ctccacgaaa caggatccaa taaccccaca ggtatcccat     240
ctgacataga caaaatccca ttccacccct actacacaat caaagacatt ctaggcgccc     300
tactactaat tctaacccta ctagcactaa cctatcgc accggacctg cttggagacc       360
ccgacaacta taccccagca aacccactca gtaccccagc acacattaaa ccagaatgat     420
acttcctatt cgcatacgca atcctacgat caatccctaa taaactaggc gg            472
```

<210> SEQ ID NO 59
<211> LENGTH: 472
<212> TYPE: DNA
<213> ORGANISM: Balaenoptera bonaerensis

<400> SEQUENCE: 59

```
taccctgagg acaaatatca ttttgaggcg caaccgtcat caccaacctc ctatcagcaa     60
tcccatacat tggtaccacc ttagttgaat gaatctgagg tggcttctct gtagacaaag     120
caacattaac acgcttttc gccttccact tcatcctccc tttcattatc ctagcattag      180
caattgtcca cctcattttc ctccgcgaaa caggatccaa taaccccaca ggtattccat     240
ctgatataga caaaatccca ttccaccct attacacaat caaagacatt ctaggcgccc      300
tactactaat tctaacccta ctaacactaa cctatcgc accgacctg ctcggagacc        360 ccgacaacta caccccagca aacccactca gtaccccagc acacattaaa ccagaatgat     420
attttctatt cgcatacgca atcctacgat caatccccaa taaactaggc gg             472
```

<210> SEQ ID NO 60
<211> LENGTH: 472
<212> TYPE: DNA
<213> ORGANISM: Balaenoptera borealis

<400> SEQUENCE: 60

```
taccctgagg acaaatatca ttttgaggcg caaccgtcat caccaacctc ttatcagcaa     60
tcccatacat tggtactacc ctagtcgaat ggatctgagg cggtttctct gtagataaag     120
caacactaac acgcttttt gccttccact tcattctccc cttcattatt ctagcactag      180
caatggtcca cctcattttc ctccatgaaa caggatccaa caaccccaca ggtattccat     240
ccgacataga caaaatccca ttccacccct actacacagt aaagacatt ctaggcgccc      300 tactactaat cctaacccta ctaatactaa cctatcgc accgacctg cttggagacc        360 cagacaacta caccccagca aatccactca gtaccccagc acacattaaa ccagaatgat     420
atttcctatt tgcatacgca atcctacgat caatccccaa caaattaggc gg             472
```

<210> SEQ ID NO 61
<211> LENGTH: 472
<212> TYPE: DNA
<213> ORGANISM: Balaenoptera edeni

<400> SEQUENCE: 61

```
taccctgagg acaaatatca ttttgaggcg caaccgtcat caccaacctc ttatcagcaa      60
tcccatacat tggtactacc ctagtcgaat gaatctgggg cggtttctct gtagataaag     120
caacactaac acgcttttt gccttccact ttatcctccc cttcattatt ctagcactag     180
caatggtcca cctcattttc ctccacgaaa caggatccaa taaccccaca ggtattccat     240
ccaacataga caaatcccca ttccacccct attacacaac taaagacatt ctaggcgccc     300
tactactaat cctaacccta ctaatgctaa ccctattcgt acccgaccta cttggagacc     360
cagacaacta cactccagca aatccactca gtacccaac acacattaaa ccagaatgat      420
atttcctatt tgcatacgca atcctacgat caattcccaa caaattaggc gg             472
```

<210> SEQ ID NO 62
<211> LENGTH: 472
<212> TYPE: DNA
<213> ORGANISM: Eschrichtius robustus

<400> SEQUENCE: 62

```
taccctgagg acaaatatca ttctgaggcg caaccgttat caccaacctc ctatcagcaa     60
tcccatacat tggcactacc ctagtcgaat gggtctgagg cggttttttct gtagataaag    120
caacactaac acgcttcttt gccttccact tcatccttcc attcattatc ctagcactag     180
caattgtcca cctcattttc ctccacgaaa cgggatccaa caaccccaca ggcattccat     240
ccaacataga caatatccca ttccacccct attacacaat taaagacata ctaggcgccc     300
tgctactaat cctaacccta ctaatactaa ccctattcgc acccgacctg ctcggagacc     360
cagacaacta taccccagca aacccactca gcaccccaac acatattaaa ccagagtgat     420
atttcctatt tgcatacgca atcctacgat cgatccccaa caaattaggc gg             472
```

<210> SEQ ID NO 63
<211> LENGTH: 472
<212> TYPE: DNA
<213> ORGANISM: Balaenoptera musculus

<400> SEQUENCE: 63

```
tgccctgagg acaaatatca ttctgaggcg caaccgtcat caccaacctc ctatcagcaa     60
tcccatacat tggtactacc ctagtcgaat gaatctgagg cggttttttct gtggataaag    120
caacactaac acgcttcttt gccttccact tcattctccc cttcatcatt atagcattag     180
caatcgtcca cctcatcttc cttcacgaaa caggatccaa caaccccaca ggtatcccat     240
ctgacataga taaaattcca ttccacccct actacacaat taaagacatt ctaggcgccc     300
tactactaat cctaacccta ctaatattaa ctctatttgc acccgactta ctcggagacc     360
cagacaacta caccccagca aacccactca gtaccccagc acacattaaa ccagagtgat     420
atttcctatt tgcatatgca atcctacgat caatccccaa caaattaggc gg             472
```

<210> SEQ ID NO 64
<211> LENGTH: 472
<212> TYPE: DNA
<213> ORGANISM: Megaptera novaeangliae

```
<400> SEQUENCE: 64
taccctgagg acaaatatca ttctgaggcg caaccgtcat caccaacctt ctatcagcaa      60
tcccatacat tggtactacc ctagtcgaat gaatctgggg cggttttttcc gtagacaaag    120 caacactaac acgtttcttt gctttccact tcatcctccc cttcatcatt acagcattag    180
caatcgtcca cctcattttc ctccacgaaa caggatccaa caaccccaca ggcatcccat    240
ccaacataga caaaatccca ttccaccctt actacacaat caaagacact ctaggcgccc    300
tattactaat cctaacccta ctaatgttaa ccctattcgc acctgacctg cttggagacc    360
cagataacta caccccagca aacccactca gtacccagc acacattaaa ccagagtgat    420
atttcctatt tgcatacgca atcctacgat caatccccaa caaactaggc gg            472

<210> SEQ ID NO 65
<211> LENGTH: 472
<212> TYPE: DNA
<213> ORGANISM: Balaenoptera physalus

<400> SEQUENCE: 65
tgccctgagg acaaatatca ttctgaggcg caactgtaat cactaacctc ctatcagcaa     60
tcccatacat tggtaccacc ctagtcgaat gaatctgagg cggtttctct gtagataaag    120
caacactaac acgcttttttt gccttttcact ttatcctccc cttcatcatc ctagcattag   180
caattgtcca ccttattttc cttcacgaaa caggatccaa caaccccaca ggcatcccat    240
ccgacataga taaaatccca ttccacccct accacacaat taaagacatt ctaggtgccc    300
tattactaat cctaatccta ctaatactaa ccctattcgc acccgaccta cttggagacc    360
cagacaacta taccccagca aacccactca gtacccagc acacattaaa ccagaatggt    420
attttctatt cgcatacgca atcctacgat caatccccaa caaactaggc gg             472

<210> SEQ ID NO 66
<211> LENGTH: 472
<212> TYPE: DNA
<213> ORGANISM: Caperea marginata

<400> SEQUENCE: 66
tgccctgagg acagatatca ttctgaggcg caaccgtcat caccaacctc ctatcagcaa     60
tcccatatat tggtaccacc ctagttgaat gaatctgggg tggcttctcc gtagacaaag    120
cgacactaac tcgcttcttt gctttccact tcatcctccc tttcattatt ctagcgctag    180
cagctgttca tctcctttttc ctccacgaaa caggatctaa caaccccaca ggcatcccat    240
ccaacataga caaaattcca ttccacccct actacacaat taaagacatc ctgggcgtcc    300
tactactaat cctgaccta ctaatattaa ccttatttac acctgacctg cttggagacc    360
ctgacaacta caccccagca aatcccctca gcaccccagc acacatcaag ccagaatgat    420
acttcctatt tgcatatgca atcctacgat caattcctaa taaattaggt gg            472

<210> SEQ ID NO 67
<211> LENGTH: 472
<212> TYPE: DNA
<213> ORGANISM: Cephalorhynchus commersonii

<400> SEQUENCE: 67
taccctgggg acagatatca ttttgaggtg caacagtcat caccaacctc ctatcagcaa     60 tccccctacat cggtactacc ttagtagaat gaatctgagg cggattttcc gtagacaaag   120
caacactaac acgcttttttc gccttccact ttatcctccc attcatcatc acagcattag   180
```

```
cagccgtcca cctactattc ctacacgaaa caggatccaa caaccccaca ggaatcccat    240
ccaacataga cataatccca ttccaccctt attacacaat taaagacatc ctaggcgctt    300
tattcctaat cctaaccctc ctagcattaa ccctatttgc ccccgaccta ctaggagacc    360
ctgataacta taccccagca aatccattaa gcaccccgc acacatcaaa ccagagtgat     420
acttcctatt cgcatatgca atcctacgat caattcccaa taaacttgga gg            472
```

<210> SEQ ID NO 68
<211> LENGTH: 472
<212> TYPE: DNA
<213> ORGANISM: Cephalorhynchus eutropia

<400> SEQUENCE: 68

```
taccctgggg acagatatca ttttgaggtg caacagtcat caccaacctc ctatcagcaa    60 tccectacat cggtactacc ttagtagaat gaatctgagg cggattttcc gtagacaaag    120
caacactaac acgcttttc gccttccact ttatcctccc attcatcatc acagcattag    180
cagccgtcca cctactattc ctacacgaaa caggatccaa caaccccaca ggaatcccat    240
ccaacataga cataatccca ttccaccctt attacacaat taaagacatc ctaggcgctt    300
tattcctaat cctaaccctc ctagcactaa ccctattcgc ccctgaccta ctaggagacc    360
ctgataacta taccccagca aatccattaa gcaccccgc acacatcaaa ccagaatgat     420
acttcctatt cgcatatgca atcctacgat caattcctaa taaacttgga gg            472
```

<210> SEQ ID NO 69
<211> LENGTH: 472
<212> TYPE: DNA
<213> ORGANISM: Lagenorhynchus obliquidens

<400> SEQUENCE: 69

```
taccctgagg acagatatca ttctgaggtg caacagtcat caccaacctc ctatcagcaa    60 tccectacat cggtactacc ttagtagaat gaatctgagg cggattttcc gtagacaaag    120
caacactaac acgcttttc gctttccact ttatcctccc attcatcatc acagcattag    180
cagccgtcca cctactattc ctacacgaaa caggatccaa caaccccaca ggaatcccat    240
ccaacataga cataatccca ttccaccctt attacacaat taaagacatc ctaggcgctt    300
tattcctaat tctaacccta ctagcactaa ccctattcac ccctgaccta ctaggagacc    360
ctgataacta taccccagca aatccattaa gcaccccgc acacatcaaa ccagaatggt     420
acttcctatt cgcatatgca atcctacgat caattcctaa taaacttgga gg            472
```

<210> SEQ ID NO 70
<211> LENGTH: 472
<212> TYPE: DNA
<213> ORGANISM: Cephalorhynchus heavisidii

<400> SEQUENCE: 70

```
taccctgagg acaaatatca ttttgaggcg caacagtcat caccaacctc ctatcagcaa    60 tccectacat cggtactacc ttagtagaat gaatctgagg cggattttcc gtggacaaag    120
caacactaac acgcttttc gccttccact ttatcctccc attcatcatc acagcattag    180
cagccgtcca tctactattc ctacacgaaa caggatccaa caaccccaca ggaatcccat    240
ccaacataga cataatccca ttccaccctt attacacaat taaagacatc ctaggcgctt    300
tattcctaat tctagcccta ctagcactaa ccctattcgc ccctgaccta ctgggagacc    360
```

```
ctgataacta taccccagca aatccattaa gcaccccgc acacatcaaa ccagaatgat      420
acttcctatt cgcatatgca atcctacgat caatccctaa taaacttgga gg             472
```

<210> SEQ ID NO 71
<211> LENGTH: 472
<212> TYPE: DNA
<213> ORGANISM: cephalorhynchus hectori

<400> SEQUENCE: 71

```
taccctgagg acaaatatca ttttgaggtg caacagtcat caccaacctc ctatcagcaa      60
tcccctacat cggcactacc ttagtagaat gaatctgagg aggattttcc gtagacaaag     120
caacactaac acgcttttc gcctttcact ttatcctccc attcatcatc acagcattaa     180
cagccgtcca cctactattc ctacacgaaa caggatccaa caaccccaca ggaattccat    240
ccaacataga cataatccca ttccaccctt attacacaat taaagacatc ttaggcgctt    300
tattcctaat tctaatccta ctagcactaa ccctattcgc ccctgaccta ctaggagacc    360
ctgataacta taccccagca aatccattaa acaccccgc acacatcaaa ccagaatgat     420
acttcctatt cgcatatgca atcctacgat caattcctaa taaacttgga gg             472
```

<210> SEQ ID NO 72
<211> LENGTH: 472
<212> TYPE: DNA
<213> ORGANISM: Lagenorhynchus australis

<400> SEQUENCE: 72

```
taccctgagg acagatatca ttttgaggtg caacagtcat caccaacctc ctatcagcaa      60
tcccctacat cggtactacc ttagtagaat gaatctgagg cggattttcc gtagataaag    120
caacactaac acgcttttc gctttccact ttatcctccc attcatcatc acagcattag    180
cagccgtcca cttactattc ttacacgaaa caggatccaa caaccccaca ggaatcccat    240
ccaacataga cataatccca ttccaccctt actacacaac taaagacatc ctaggcgctt    300
tattcctaat tctagcccta ctagcactaa ccctattcac ccctgaccta ctaggagacc    360
ctgacaacta taccccagca aatccattaa gcaccccgc acacatcaaa ccagaatgat     420
atttcctatt cgcatatgca atcctacgat caattcctaa taaactcgga gg             472
```

<210> SEQ ID NO 73
<211> LENGTH: 472
<212> TYPE: DNA
<213> ORGANISM: Lagenorhynchus cruciger

<400> SEQUENCE: 73

```
taccctgagg acagatatca ttttgaggtg caacagtcat caccaacctc ctatcagcaa      60
tcccctacat cggtactacc ttagtagaat gaatctgagg cggattttcc gtagacaaag    120
caacactaac acgcttttc gctttccact tcatcctccc attcatcatc acagcattag    180
cagccgtcca cctgctattc ctacacgaaa caggatccaa caaccccaca ggaatcccat    240
ccaacataga cataatccca ttccaccctt actacacaat taaagacatc ctaggcgctt    300
tattcctaat cctaacccta ctagcactaa ccctgttcac ccctgaccta ctaggagacc    360
ctgacaacta taccccagca aatccattaa gcaccccgc acacatcaaa ccagaatgat     420
atttcctatt cgcatatgca atcctacgat caattcctaa taaactcgga gg             472
```

<210> SEQ ID NO 74
<211> LENGTH: 472

```
<212> TYPE: DNA
<213> ORGANISM: Lagenorhynchus obscurus

<400> SEQUENCE: 74
taccctgagg acagatatca ttttgaggtg caacagtcat caccaacctc ctatcagcaa      60
tcccctacat tggtactacc ttagtagaat gaatctgagg cggattttcc gtagacaaag     120
caacactaac acgcttttc gctttccact ttatcctccc attcatcatc acagcattag      180
cagccgtcca cctactattc ctacacgaaa cagaatccaa caccccaca ggaatcccat      240
ccaacataga cataatccca ttccacccctt attacacaat taaagacatc ctaggtgctt     300
tattcctaat tctagcccta ctaacactaa ccttattcac ccccgaccta ctaggagacc     360
ctgataacta cccccagca aatccattaa gcaccccagc acacatcaaa ccagaatgat      420
atttcctatt cgcatacgca atcctacgat caattcctaa taaacttgga gg             472

<210> SEQ ID NO 75
<211> LENGTH: 472
<212> TYPE: DNA
<213> ORGANISM: Lissodelphis borealis

<400> SEQUENCE: 75
taccctgagg gcagatatca ttttgaggtg caaccgtcat caccaacctc ctatcagcaa      60
tcccctacat cggtactacc ttagtagaat gaatctgagg cggattttcc gtagacaaag     120
caacactaac acgcttttc gctttccact ttatcctccc attcatcatc acagcattag      180
cagctgttca cctactattc ctacacgaaa caggatccaa caccccaca ggaattccat      240
ccaacataga cataatccca ttccacccctt attacacaat taaagacatc ctgggcgctt     300
tattcttaat tctggcccta ctagcactaa ccctattcac ccctgaccta ttaggagacc     360
ctgataacta caccccagca aatccattaa gcaccccctgc acacatcaaa ccagaatggt     420
acttcctatt tgcatacgca atcctacgat caattcctaa taaacttgga gg             472

<210> SEQ ID NO 76
<211> LENGTH: 472
<212> TYPE: DNA
<213> ORGANISM: Lissodelphis peronii

<400> SEQUENCE: 76
taccctgagg acagatatca ttttgaggtg caaccgtcat caccaacctc ctatcagcaa      60
tcccctacat cggtactacc ttagtagaat gaatctgagg cggattttcc gtagacaaag     120
caacactaac acgcttttc gctttccact ttatcctccc attcatcatc acagcattag      180
cagctgttca cctactgttc ctacacgaga caggatccaa taccccaca ggaattccat      240
ccaacataga cataatccca ttccacccctt attacacaat taaagacatc ctgggcgctt     300
tattcttaat tctgacccta ctagcactaa ccctatttac ccctgacctg ttaggagatc     360
ctgataacta caccccagca aatccattaa gcaccccctgc acacatcaaa ccagaatggt     420
actttctatt cgcatacgca atcctacgat caattcctaa taaacttgga gg             472

<210> SEQ ID NO 77
<211> LENGTH: 472
<212> TYPE: DNA
<213> ORGANISM: Globicephala macrorhynchus

<400> SEQUENCE: 77
taccctgagg acagatatca ttctgaggcg caaccgtcat caccaatctc ctatcagcaa      60
```

```
tcccttacat cggcaccacc ttagtagaat gaatctgagg tggattttcc gtagacaaag    120
caacactaac acgttttttc gctttccact ttatcctccc attcatcatc acagcattag    180
tagctgtcca cctgctattc ctacacgaaa caggatccaa taacccata ggaatcccat     240 ccaacataga cataattcca ttccacccct attatacaat taaagacatc ctaggcgccc    300
tactcttaat cctagcacta ctaacactaa ccctattcac ccctgaccta ctaggagacc    360
ctgataacta tactccagca aatccactaa gcacccctgc acacatcaaa ccagaatgat    420
atttcctatt cgcatatgca atcttacgat caattcccaa taaacttgga gg            472

<210> SEQ ID NO 78
<211> LENGTH: 472
<212> TYPE: DNA
<213> ORGANISM: Globicephala melas

<400> SEQUENCE: 78
taccctgagg acagatatca ttctgaggcg caaccgtcat caccaatctc ctatcagcaa    60
tcccttacat cggcactacc ttagtagaat gaatctgagg tggattttcc gtagacaaag    120
caacactaac acgttttttc gctttccact ttatcctccc attcatcatc acaacattag    180
tagctgtcca cctgctattc ctacacgaaa caggatccaa taacccata ggaatcccat     240 ccaacataga cataattcca ttccacccct attatacaat taaagatatc ctaggcgccc    300
tactcttaat cctagcacta ctaacactaa ccctattcac ccctgaccta ctaggagacc    360
ctgataacta tactccagca aacccactaa gcacccctgc acacatcaaa ccagaatgat    420
atttcctatt cgcatatgca atcttacgat caattcccaa taaacttgga gg            472

<210> SEQ ID NO 79
<211> LENGTH: 472
<212> TYPE: DNA
<213> ORGANISM: Feresa attenuata

<400> SEQUENCE: 79
taccctgagg acagatatca ttctgaggcg caaccgtcat caccaatctc ctatcagcaa    60
tcccttacat cggcaccact ttagtagaat gaatctgagg tggattttcc gtagacaaag    120
caacactaac acgttttttc gctttccact ttatcctccc attcatcatc acagcattag    180
tagctgttca cctgctattc ctacacgaaa caggatccaa taacccaca ggaatcccat     240 ccaacataga cataattcca ttccacccct attatacaac taaagatatc ctaggtgccc    300
tactcttaat tctaacatta ctaacactaa ccctgttcac ccctgaccta ctaggagacc    360
ctgataacta tactccagca aacccactaa gcacccctgc acacatcaaa ccagagtgat    420
atttcctatt cgcgtatgca atcttacgat caattcctaa taaacttgga gg            472

<210> SEQ ID NO 80
<211> LENGTH: 472
<212> TYPE: DNA
<213> ORGANISM: Peponocephala electra

<400> SEQUENCE: 80
taccctgagg acagatatca ttctgaggcg caaccgtcat caccaatctc ctatcagcaa    60
tcccttacat cggaaccacc ttagtagaat gaatctgagg tggattttcc gtagacaaag    120
caacactaac acgttttttc gctttccact tcatcctccc attcatcatc acagcattgg    180
tagctgtcca cctgctattc ctacacgaaa caggatccaa taaccctaca ggaatcccat     240
ccaacataga cataattcca ttccacccct attatacaat taaagacatc ctaggcgctc    300
```

```
tactcttaat cttagcacta ctaacactaa ccctattcac ccctgaccta ctaggagacc      360
ctaacaacta taccccagca aacccactaa gcacccctgc acacatcaaa ccagaatgat      420
atttcctatt cgcatatgca atcttacgat caattcccaa taaacttgga gg              472

<210> SEQ ID NO 81
<211> LENGTH: 472
<212> TYPE: DNA
<213> ORGANISM: Grampus griseus

<400> SEQUENCE: 81
taccctgagg acaaatatca ttctgaggcg caaccgtcat caccaatctc ctatcagcaa       60 tccctacat cggtactact ttagtagaat gaatctgagg tggattttcc gtagacaaag      120
caacactaac acgttttttc gctttccact ttatcctccc attcatcatc acagcattag      180
tagctgttca cctgctattc ctacacgaga caggatccaa taccccaca ggaatcccat      240 ccaacataga cataattcca ttccacccct attacacaat aaagacatc ctaggcgccc      300 tactcctaat cctaacacta ctaacactaa ccctattcac ccctgaccta ctaggagacc      360
ctgataacta cactccagca aacccgctaa gcacccctgc acacatcaaa ccagaatgat      420
atttcctatt cgcatatgca atcttgcgat caattcccaa caaacttgga gg              472

<210> SEQ ID NO 82
<211> LENGTH: 472
<212> TYPE: DNA
<213> ORGANISM: Pseudorca crassidens

<400> SEQUENCE: 82
taccctgagg acagatatca ttctgaggcg caaccgtcat caccaatctt ctatcagcaa       60 tccctacat cggtaccact ttagtagaat gaatctgagg aggattttcc gtagacaaag      120
caacactaac acgtttttc actctccact ttatcctccc attcatcatt acagcactaa      180
cagctaccca cctactattc ctacacgaga ctggatccaa taccccaca ggaatcccat      240 ccaacataga cataattcca ttccacccct tattacacaat aaagatatc ctaggcgccc      300 tactcttaat tctaacacta ctaacactaa ccctattcac ccccgaccta ctaggagacc      360
ctgataacta tattccagca aacccactaa acacccctgc acacatcaaa ccagaatgat      420
atttcctatt cgcatatgca atcttacgat caattcctaa taaacttgga gg              472

<210> SEQ ID NO 83
<211> LENGTH: 472
<212> TYPE: DNA
<213> ORGANISM: Lagenorhynchus acutus

<400> SEQUENCE: 83
taccatgagg acaaatatca ttctgaggcg caaccgttat caccaatctc ctatcagcaa       60
tcccttacat cggcactacc ctagtagaat gaatctgagg cggattttcc gtagacaaag      120
caacactgac acgttttttc gccttccatt tcatcctccc attcataatt acagcattag      180
cagctgttca cctgctgttc ctacacgaga caggatccaa taccctaca ggaatcccat      240 ctaacataga tataatcccg ttccacccct tattatacaat aaagatatc ctaggcgctt      300 tactcttaat tctaaccccta ctagcactaa ccctattcac ccctgaccta ctaggagacc      360
ctgataacta cactccagca aatccactaa gcacccctgc acacatcaaa ccagaatgat      420
atttcctatt cgcatatgca atcctacgat caattcccaa caaacttgga gg              472
```

<210> SEQ ID NO 84
<211> LENGTH: 472
<212> TYPE: DNA
<213> ORGANISM: Orcinus orca

<400> SEQUENCE: 84

```
taccctgagg acagatatct ttctgaggcg caaccgtcat tactaatctc ctatcagcaa      60
tcccttacat cggcaccacc ttagtagaat gaatctgagg tggattttcc gtagacaaag     120
caacactaac acgtttcttt gccttccact ttatcctccc attcatcatc acagcattaa     180
cagctgttca cctactgttc ctacacgaga caggatccaa taccccaca ggaatcccat      240
ccaacataga tataatccca ttccacccct atcacacaat taaagatacc ctaggcgccc     300
tactcttaat cctaaccctg ctagcactaa ccttattcgc ccctgaccta ctaggagacc     360
ctgacaacta taccccagca aatccactaa gcaccctgc acacatcaaa ccagaatgat      420
acttcctatt cgcatacgca atcctacgat cagttcccaa taaacttgga gg            472
```

<210> SEQ ID NO 85
<211> LENGTH: 472
<212> TYPE: DNA
<213> ORGANISM: Orcaella brevirostris

<400> SEQUENCE: 85

```
taccctgagg acagatatcc ttctgaggtg caaccgtcat caccaatctc ctatcagcaa      60
tcccttacat cggcactacc ctagtagaat gaatctgagg tggattttcc gtagacaaag     120
caacactaac acgttttttc gccttccact ttatccttcc attcatcatc acagcactag     180
taactgttca cctactattc ctacacgaaa caggatccaa caatcctaca ggaatcccat      240
ccaacataga cataatccca ttccaccctt atcatacatt taaagacatc ctaggcgccc     300
tactcttaat cttagtccta ctaacactaa ccctgttcac ccccgaccta ctaggagacc     360
ctgataacta tactccagca aatccactaa gcaccctgc acacatcaaa ccagaatgat      420
acttcctatt cgcatacgcg atcctacgat caattcctaa taaactcggg gg            472
```

<210> SEQ ID NO 86
<211> LENGTH: 472
<212> TYPE: DNA
<213> ORGANISM: Delphinus capensis

<400> SEQUENCE: 86

```
tgccctgggg acaaatatca ttctgaggcg caaccgtcat caccaacctc ttatcagcaa      60
tcccttatat tggcactacc ttagtcgaat gaatctgagg tggattctcc gtagacaaag     120
caacattaac acgttttttc gctttccact ttatccttcc attcatcatc acagcattag     180
cagccgttca cctgctattc ctacacgaaa caggatccaa taccccaca ggaatcccat      240
ccaatataga cataatccca ttccacccct tattatacaat caaagatatc ctaggtgcct     300
tactcctaat cttaacccta ctagcactga ccctattcac tccagaccta ctaggagacc     360
ctgataacta taccccagca aatccactaa gcaccctgc acatatcaaa ccagaatgat      420
actttctatt cgcatacgca atcttacgat caatccctaa taaacttgga gg            472
```

<210> SEQ ID NO 87
<211> LENGTH: 472
<212> TYPE: DNA
<213> ORGANISM: Delphinus tropicalis

<400> SEQUENCE: 87

```
tgccctgagg acaaatatca ttctgaggcg caaccgtcat caccaacctc ttatcagcaa    60
tcccttatat tggcactacc ttagtcgaat gaatctgagg tggattctcc gtagacaaag   120
caacattaac acgctttttc gctttccact ttatcctccc attcatcatc acagcattag   180
cagccgttca cctgctattc ctacacgaaa caggatccaa taaccccaca ggaatcccat   240
ccaacataga cataatccca ttccacccct tattatacaat caaagatatc ctaggtgccc   300
tactcctaat cttaacctta ctagcactga ccctattcac tcccgaccta ctaggagacc   360
ctgataacta taccccagca aatccactaa gcaccctgc acatatcaaa ccagaatgat   420
actttctatt cgcatacgca atcttacgat caatccctaa taaacttgga gg           472

<210> SEQ ID NO 88
<211> LENGTH: 472
<212> TYPE: DNA
<213> ORGANISM: Delphinus delphis

<400> SEQUENCE: 88
tgccctgagg acaaatatca ttctgaggcg caaccgtcat caccaacctc ttatcagcaa    60
tcccttatat tggcactacc ttagtcgaat gaatctgagg tggattctcc gtagacaaag   120
caacattaac acgctttttc gctttccact ttatcctccc attcatcatc acagcactag   180
cagccgttca cctgctattc ctacacgaaa caggatccaa taaccccaca ggaatcccat   240
ccaatataga cataatccca ttccacccct tattatacaat caaagatatc ctaggtgcct   300
tactcctaat cttaaccctta ctagcactaa ccctattcac tcccgaccta ctaggagacc   360
ctgataacta taccccagca aatccactaa gcaccctgc acacatcaaa ccagaatgat   420
actttctatt cgcatatgca atcttacgat caatccctaa taaacttgga gg           472

<210> SEQ ID NO 89
<211> LENGTH: 472
<212> TYPE: DNA
<213> ORGANISM: Stenella clymene

<400> SEQUENCE: 89
tgccctgagg acaaatatca ttctgaggcg caaccgtcat caccaacctc ctatcagcaa    60
tcccttatat tggcactacc ttagtcgaat gaatctgagg tggattctcc gtagacaaag   120
caacattaac acgctttttc gctttccact ttatcctccc gttcatcatc acagcattag   180
cagccgttca cctgctattc ctacacgaaa caggatccaa taaccccaca ggaattccat   240
ccaatataga cataatccca ttccacccct tattatacaat caaagatatc ctaggtgcct   300
tactcctaat cttaaccctta ctagcactaa ccctattcac ccccgaccta ctaggagacc   360
ctgacaacta taccccagca aatccactaa gcaccctgc acacatcaaa ccagaatgat   420
actttctatt cgcatatgca atcttacgat caatccctaa taaacttgga gg           472

<210> SEQ ID NO 90
<211> LENGTH: 472
<212> TYPE: DNA
<213> ORGANISM: Stenella coeruleoalba

<400> SEQUENCE: 90
tgccctgagg acaaatatca ttctgaggcg caaccgtcat caccaacctc ttatcagcaa    60
tcccttatat tggcactacc ttagtcgaat gaatctgagg tggattctcc gtagacaaag   120
caacattaac acgctttttc gctttccact ttatcctccc gttcattatc acagcattag   180
```

```
cagccgttca cctgctattc ctacacgaaa caggatccaa taacccaaca ggaattccat      240
ccaatataga cataattcca ttccacccct attatacaat aaagatatc  ctaggtgcct      300 tactcctaat cttaacccta ctagcactaa ccctattcac ccccgaccta ctaggagacc      360
ctgataacta taccccagca aatccactaa gcacccctgc acacatcaaa ccagaatgat      420
actttctatt cgcatacgca atcttacgat caatccctaa caaacttgga gg              472
```

<210> SEQ ID NO 91
<211> LENGTH: 472
<212> TYPE: DNA
<213> ORGANISM: Tursiops aduncus

<400> SEQUENCE: 91

```
tgccctgagg acaaatatca ttctgaggcg caaccgtcat caccaacctc ttatcagcaa      60
tcccttatat tggcactacc ttagtcgaat gaatctgagg tggattctcc gtagacaaag     120
caacactaac acgttttttc gctttccact ttatcctccc gttcgtcatc acagcattag     180
cagccgttca cctgctattc ctacacgaaa caggatccaa taacccccaca ggaatcccat     240 ccaatataga cataatccca tttcacccctt attatacaat caaagacatc ctaggtgcct     300
tactcctaat cttaaccccta ctagcactaa ccctattcac ccccgaccta ctaggaaacc     360
ctgataacta tacccagca  aatccactaa gtaccccgc  acacatcaaa ccagagtgat      420
actttctatt cgcatacgca atcttacgat caatccctaa taaacttgga gg              472
```

<210> SEQ ID NO 92
<211> LENGTH: 472
<212> TYPE: DNA
<213> ORGANISM: Stenella frontalis

<400> SEQUENCE: 92

```
tgccctgagg acaaatatca ttctgaggcg caaccgtcat caccaacctc ttatcagcaa      60
tcccttatat tggcactacc ttagtagaat gaatctgagg tggattctcc gtagacaaag     120
caacattaac acgttttttc gctttccact ttatcctccc gttcatcatc acagcattag     180
cagccgttca cctactattc ctacacgaaa caggatccaa taacccccaca ggaatcccat     240 ccaatataga cataatccca ttccacccctt attatacaat caaagacatc ctaggcgcct     300
tactcctaat cctaaccccta ctagcactaa ccctattcac ccccgaccta ctaggagacc     360
ctgacaatta taccccagca aatccactaa gcacccctgc acacatcaaa ccagaatgat     420
actttctatt cgcatacgca atcttacgat caatccctaa taaacttgga gg              472
```

<210> SEQ ID NO 93
<211> LENGTH: 472
<212> TYPE: DNA
<213> ORGANISM: Sousa chinensis

<400> SEQUENCE: 93

```
tgccctgagg acaaatatca ttctgaggcg caaccgttat caccaacctc ctatcagcaa      60
tcccttacat tggcactacc ttagtttgaat gaatctgagg cggatttttcc gtagacaaag    120 caacattaac acgttttttc gctttccact ttatctttcc cttcatcatc acagcattag     180
tagccgttca cctgctattc ctacacgaaa caggatccaa taaccctaca ggaattccat     240
ccaacataga cataatccca tttcacccctt attatacaat caaagacatc ctaggtgcct     300
tactcctaat cttaaccccta ctagcactaa ccctattcac ccccgaccta ctaggagacc     360
ccgataacta taccccagca aatccactaa gcacccctgc acacatcaaa ccagaatgat     420
```

-continued

```
atttcctatt cgcatacgca atcttacggt caatccctaa taaacttgga gg        472
```

<210> SEQ ID NO 94
<211> LENGTH: 472
<212> TYPE: DNA
<213> ORGANISM: Stenella longirostris

<400> SEQUENCE: 94

```
taccctgagg acaaatatca ttctgaggtg caaccgtcat caccaacctc ctatcagcaa    60
tcccttatat tggcactacc ctagttgaat gaatctgagg tggattttcc gtagacaaag   120
caacattaac acgcttttc gctttccatt ttatcctccc attcatcatc acagcattag    180
cagccgtcca cctactattc ctacacgaaa caggatccaa taaccccaca ggaatcccat   240
ccaacataga cataatccca ttccacccctt attatacaat caaagacatc ctaggtggct   300
tactcttaat cttaacccta ctagcactaa ccctattcac ccctgactta ctaggagacc   360
ctgataacta taccccagca aatccactaa acacccctgc acacatcaaa ccagaatgat   420
atttcctatt cgcatacgca atcttacgat caatccctaa taaacttgga gg           472
```

<210> SEQ ID NO 95
<211> LENGTH: 472
<212> TYPE: DNA
<213> ORGANISM: Tursiops truncatus

<400> SEQUENCE: 95

```
tgccctgagg acaaatatca ttctgaggcg caaccgtcat caccaacctc ttatcagcaa    60
tcccttatat cggcactacc ttagtcgaat gaatctgagg tggattttcc gtagacaaag   120
caacattaac acgcttttc gccttccact ttattcttcc attcatcatc acagcattgg    180
cagccgttca cctactattc ctacacgaaa caggatccaa caaccccaca ggaatcccat   240
ccaatataga cataatccca ttccacccctt attatacaat caaagacatc ctaggcgcct   300
tactcttaat cttaacctta ctagcattaa ccctattcgc ccccgaccta ctaggagacc   360
ctgataacta caccccagca aacccactaa gcacccctgc acacatcaaa ccagaatgat   420
actttctatt cgcatacgca atcttacgat caatccctaa taagctcgga gg           472
```

<210> SEQ ID NO 96
<211> LENGTH: 472
<212> TYPE: DNA
<213> ORGANISM: Lagenorhynchus alborostris

<400> SEQUENCE: 96

```
taccctgagg acaaatatca ttctgaggcg caaccgtcat cactaatctc ctatcagcaa    60
tcccttatat cggtactacc ctagtagaat gaatctgagg tggattctcc gtagacaaag   120
caacactaac acgcttcttc gctttccact ttatcctccc attcatcatc acagcactag   180
tagctgttca cctactattt ttacacgaga caggatccaa caaccccaca ggaatcccat   240
ccaacataga tataattcca ttccacccctt attacacaat caaagacatc ctaggcgctt   300
tacttttaat cctaacctta ctagcactaa ccctatttac ccccgaccta ctaggagatc   360
ccgataacta taccccagca aatccactaa gcactcctgc acacatcaaa ccagaatggt   420
atttcctatt cgcatatgca atcctacgat caatccctaa caaacttgga gg           472
```

<210> SEQ ID NO 97
<211> LENGTH: 472
<212> TYPE: DNA

<213> ORGANISM: Steno bredanensis

<400> SEQUENCE: 97

```
taccctgagg acaaatatca ttctgaggtg caaccgtcat taccaacctc ctgtcagcaa        60
tcccttacat cggcactacc ttggtagaat gaatctgagg cggattttcc gtagacaaag       120
caacactaac acgttttttc gctttccact ttatcctccc attcatcatc atagcattag       180
caactgtcca cctactattc ctacacgaga caggatccaa caatcccaca ggaatcccat       240
ccaacataga tataatccca ttccacccctt attacacaat caaagacatc ctaggcgcct      300
tacttttaat cctaacttta ctagcactaa ccctattcac ccccgaccta ctaggagacc       360
ccgacaacta tacccagca aatccactaa gcacccctgc acacatcaaa ccagaatggt        420
atttcctatt cgcatacgca atcttacgat caatccccca caaacttgga gg              472
```

<210> SEQ ID NO 98
<211> LENGTH: 472
<212> TYPE: DNA
<213> ORGANISM: Sotalia fluviatilis

<400> SEQUENCE: 98

```
taccctgagg acaaatatca ttctgaggcg caaccgtcat taccaatctc ctatcagcaa       60
tcccttacat cggcactacc ttagtagaat gaatctgagg cggattctcc gtagacaaag      120
caacactaac acgcttttc gccttccact ttatcctccc atttatcatc acagcattag       180
cagccgttca cctgctattc ctacacgaaa caggatccaa taatcccaca ggaatcccat      240
ccaacataga tataattcca ttccaccctt attacacaat caaagatatc ctaggcgcct      300
tactcctaat cctgaccctsa ctagcactaa ccctattcac ccccgaccta ctaggagatc      360
ccgacaacta tactccagca aatccactta acacccctgc acacatcaaa ccagaatgat       420
atttcctatt cgcatatgca atcttacgat caatccctaa taaacttgga gg              472
```

<210> SEQ ID NO 99
<211> LENGTH: 472
<212> TYPE: DNA
<213> ORGANISM: Delphinapterus leucas

<400> SEQUENCE: 99

```
taccctgagg acaaatatca ttctgaggcg caaccgtcat taccaatctc ctatcagcaa       60
tcccttacat cggtaacacc ttagtagaat gaatctgagg tgggttctcc gtagacaaag      120
caacactaac acgcttcttc accttccact ttatcctccc attcatcatt acagcgctag      180
tagccgtcca tttattattc ctacacgaaa caggatccaa caaccccaca ggaatcccat      240
ccaacatgga tacaatccca ttccaccccct actacacaat caaagacatc ctaggtgctt      300
tactactaat cctaaccta ttaacagtaa ccctattcac acctgacctc ctaggagacc      360
cagacaatta cacccccagca aacccactaa acacccccgc acacatcaaa ccagaatggt       420
acttcctatt tgcatacaca atcctacgat caatccccaa caaactagga gg              472
```

<210> SEQ ID NO 100
<211> LENGTH: 472
<212> TYPE: DNA
<213> ORGANISM: Monodon monoceros

<400> SEQUENCE: 100

```
taccctgagg acaaatatca ttctgaggtg caaccgtcat caccaacctc ctatcagcaa        60
tcccttacat cggcaacacc ttagtagaat gaatctgagg tgggttttct gtagataaag       120
```

```
caacactaac acgcttcttc accttccact ttatcctccc attcatcatc acagcactag    180
tggccgtcca cttattattc ctacacgaaa caggatccaa caccccaca ggaatcccat     240 ccaacataga cataatcccc ttccatccct actacacaat caaagacatg ctaggcgctt    300
tcctactaat cctaattcta ctagcaataa ccctactcac acctgacctc ctaggagacc    360
ctgacaatta tacccagca aacccactaa gcacccctgc acacatcaaa ccagaatgat     420
atttcctatt tgcatacgca atcctacgat caatccccaa caaactagga gg            472

<210> SEQ ID NO 101
<211> LENGTH: 472
<212> TYPE: DNA
<213> ORGANISM: Platanista gangetica

<400> SEQUENCE: 101
taccctgagg acaaatatca ttctgaggtg caaccgtcat caccaacctt ttatcagcaa    60
tcccttatat cggcagtacc ctagtcgagt gaatctgagg tggcttttcc gtagataaag    120
caacactaac acgattcttt gcctttcact tcatcctccc tttcatcatc ctaacactag    180
caattatcca cctactattc ctacacgaaa caggctcaaa caccccaca ggaattccat     240 ccgacactga caaaatccct ttccacccct actacacaat caaagacacc ctaggcgccc    300
tcatcctaat cctaacctca ctcacattaa ccttatttac acctgaccta ctaggagacc    360
ccgataacta caccccagca aacccgctta ataccccagc acatatcaaa ccagagtgat    420
atttcctatt tgcatacgca atcttacggt caatccccaa taaactagga gg            472

<210> SEQ ID NO 102
<211> LENGTH: 472
<212> TYPE: DNA
<213> ORGANISM: Platanista minor

<400> SEQUENCE: 102
taccctgagg acaaatatca ttctgaggtg caaccgtcat caccaacctt ttatcagcaa    60
tcccttatat cggcagtacc ctagtcgagt gaatctgagg tggcttttcc gtagataaag    120
caacactaac acgattcttt gcctttcact tcatcctccc tttcatcatc ctaacactag    180
cagttatcca cctactattc ctacacgaaa caggctcaaa caccccaca ggaattccat     240 ccaacactga caaaatccct ttccacccct actacacaat caaagacacc ctaggcgccc    300
tcatcctaat cctaacctca ctcacattaa ccttatttac acctgaccta ctaggagacc    360
ccgataacta caccccagca aacccgctta ataccccagc acatatcaaa ccagagtgat    420
atttcctatt tgcatacgca atcttacggt caatccccaa taaactagga gg            472

<210> SEQ ID NO 103
<211> LENGTH: 472
<212> TYPE: DNA
<213> ORGANISM: Kogia breviceps

<400> SEQUENCE: 103
taccctgagg ccaaatatca ttctgaggag caaccgtcat caccaacctt atatccgcaa    60
ttccttatat cggcaccacc ctagtagaat gagtctgagg tggcttctcc gtagacaaag    120
ccacattaac acgcttcttt gcctttcact tcatcctccc ctttatcatc ctagcactgg    180
caatggtcca cctcttattt ctccacgaaa caggatccaa caccccata ggaatcccat     240 ccgacataga caaaatccca ttccacccct actacacaat caaggacatc ttaggcgccc    300
```

```
tactgctaat ctcagcgcta cttacattaa ccctattcgc accagaccta ttaggagacc    360
ctgacaacta caccccagca aacccactaa gcaccccggc acacattaaa ccagaatgat    420
atttcctatt tgcatatgcc atcctacgat ccatccctaa caaactaggg gg            472
```

<210> SEQ ID NO 104
<211> LENGTH: 472
<212> TYPE: DNA
<213> ORGANISM: Kogia simus

<400> SEQUENCE: 104

```
tgccctgagg ccaaatatca ttctgaggag caaccgtcat cacaaacctt atatccgcaa    60
tcccttacat cggcaccacc ctagtggaat gagtctgagg tggcttctcc gtggacaaag   120
ctacgctaac acgcttcttt gctttccact ttattctccc cttcatcatc ctagcactag   180
caataatcca cctcctattt ctccacgaaa caggatccaa caacccccta ggaattcctt   240
ctgatataga caaaatccca ttccacccct actacacaat caaagatatc ctaggcgccc   300
tactactaat ctcagcacta ctcacactga ccctgttcgc acctgatcta ctaggagacc   360
ccgacaacta taccccagca aacccactaa gcaccccggc acacattaaa ccagaatgat   420
actttctatt cgcatacgcc attctacgat caattcctaa caaactggga gg            472
```

<210> SEQ ID NO 105
<211> LENGTH: 472
<212> TYPE: DNA
<213> ORGANISM: Physeter catodon

<400> SEQUENCE: 105

```
tgccctgagg acaaatatca ttctgagccg caaccgttat cacaaacctt ctatcagcaa    60
ttccctatat cggcaccacc ctagtagagt gagtttgagg cggtttctcc gtagataagg   120
caacactgac acgcttcttc actctccact tcatcctccc ctttatcacc ctaacactaa   180
caatagtaca tctcctattt ctccatgaaa caggatccaa caacccccaca ggaattccct   240 ccaacataga caaaatccca ttccacccct accacacaat caaagacacc ataggtgccc   300
tactactaat cctatcccta cttacactaa ccctgttcgc acccgacctg ctaggagatc   360
ctgacaacta caccccagca aatccactaa atacccccaac acacatcaaa ccagaatggt   420
atttcctatt cgcgtacgcc atcctacgat ctgtccccaa taaactagga gg            472
```

<210> SEQ ID NO 106
<211> LENGTH: 472
<212> TYPE: DNA
<213> ORGANISM: Lipotes vexillifer

<400> SEQUENCE: 106

```
taccctgagg acaaatatca ttttgaggcg caaccgtcat cactaatctt ctatcagcaa    60
tcccttacat cggaaccacc ctagtagagt gagtctgagg gggattctca gtagacaaag   120
caacattaac ccgcttcttc gctctccatt tcatccttcc atttattatt gtagcactaa   180
caaccgtcca cttactattt ctccatgaaa caggatccaa cacccaata ggaattccat    240 ctaacataga caaaatccca ttccacccct accacacaat taaagatatc ttaggcgccc   300
ttctattaat atttgttcta ctcacactaa ccttacttgc accagaccta ctcggagatc   360
ctgataatta taccccagca aacccactaa acactcccgc acacatcaaa ccagaatgat   420
atttcctctt cgcatacgca attctacgat caattcccaa taaattagga gg            472
```

<210> SEQ ID NO 107
<211> LENGTH: 472
<212> TYPE: DNA
<213> ORGANISM: Phocoena sinus

<400> SEQUENCE: 107

```
tgccctgggg acaaatatca ttttgaggtg ctaccgtcat cacaaacctc ttatcagcaa      60
tcccttacat cggcagcacg ctagtggagt gaatctgagg tggattctcc gtagacaaag     120
caacactaac acgcttcttc gccttccatt ttatccttcc atttatcatt acagcactaa     180
taatcgtcca tctactattc ctccatgaaa caggctccaa caatcccaca ggaatcccgt     240
ctaacataga cataatcccc ttccaccctt actatacaat caaagatatc ctaggcgccc     300
tactatttat tctaacttta ctaacactaa ccttattttt acctgacctt ctaggagacc     360
ccgataacta cattccagca aacccactaa gcaccccagc acacattaaa ccagaatgat     420
atttcctctt cgcatacgca atcctacgat caatccccaa taaactagga gg             472
```

<210> SEQ ID NO 108
<211> LENGTH: 472
<212> TYPE: DNA
<213> ORGANISM: Berardius bairdii

<400> SEQUENCE: 108

```
tgccttgagg gcaaatatca ttctgaggtg caaccgtcat caccaacctc ctatccgcta      60
ttccttatat cggcaccact cttgtcgaat gaatctgagg tggcttctcc gtagataaag     120
ccacactaac acgcttcttt gccttccact ttatcctccc ttttatcatt ctaaccctag     180
cagccgtcca cttactattc ctccacgaaa caggatccaa caaccccaca ggaatcccat     240
ccaatataga taaaattcca ttccacccct actatacaat caaagatatc ctaggagccc     300
tactactaat cctagcccta ctcacgctaa ccctatttgc acccgaccta ctaggagagc     360
ccgacaacta taccccggca aacccgctca gcaccccaac acatattaag ccagaatgat     420
acttcctgtt cgcatacgca atcttacgat cagtccctaa taaactaggg gg             472
```

<210> SEQ ID NO 109
<211> LENGTH: 472
<212> TYPE: DNA
<213> ORGANISM: Ziphius cavirostris

<400> SEQUENCE: 109

```
taccttgagg acaaatatca ttctgaggtg caaccgtcat cacaaacctc ttatccgcta      60 tccccctatat cggcactact ctagtcgaat gaatctgagg tggtttttca gtagataaag    120
ccacactaac acgcttcttt gccttccatt tcatccttcc atttattatt ttagccctag     180
cagccgtcca cttactattt ctccacgaaa caggatctaa taaccccaca ggaatcccat     240
ccgatataga caaaatccca ttccaccctt attacacaat caaagacatc ctaggagccc     300
tactattaat cgtaattcta ctcgcactaa ccctattcgc acccgacctg ctaggagacc     360
ccgataacta taccccagca aatccactca gcaccccagc acacattaag ccagaatgat     420
acttcctatt cgcatacgca atcctacgat caattcccaa taaactagga gg             472
```

<210> SEQ ID NO 110
<211> LENGTH: 472
<212> TYPE: DNA
<213> ORGANISM: Mesoplodon europaeus

<400> SEQUENCE: 110

```
ttccctgagg acaaatatca ttctgaggcg caaccgttat taccaacctc ctatccgcca    60
tccctatat tggcactact ctagtcgaat gaatctgagg tggcttttcc gtagataaag    120
ctacactaac acgcttcttt gctttccact ttatccttcc attcattatt ctagccctaa   180
caatcgtcca cttactattt ctccatgaaa caggatccaa taaccctaca ggaatcccat   240
ctgatataga caaaatccca ttccatcctt actacacaat caaagatatc ctaggggctc   300
tactactaat tctagcccta ctcacccctaa ccctattcgc acccgacctg ctaggagacc  360
ccgacaatta cacccagca aacccactta atactccagc acacatcaaa ccagaatgat   420
acttcctatt cgcatatgca attctacgat caattcccaa caaactagga gg           472

<210> SEQ ID NO 111
<211> LENGTH: 472
<212> TYPE: DNA
<213> ORGANISM: Mesoplodon bidens

<400> SEQUENCE: 111
taccctgagg acaaatatca ttctgaggcg caactgttat tactaacctc ctatccgcta    60
ttccctacat cggcactacc ctagttgaat gaatctgagg tggcttttcc gtagacaaag   120
ccacattaac acgcttcttc gccttccact ttatcctccc atttattatt ttagccctag   180
caatcgtcca cctactattt ctccatgaaa caggatctaa caaccctaca ggaattccat   240
ccgacataga taaaattcca ttccaccct actacacaat taaagatatc ctgggagccc    300
tactactaat tctaacccta ctcgcactaa ccctattcgc acctgacctg ctaggagacc   360
ccgacaacta taccccagca aacccactca gcaccccagc ccacatcaaa ccagagtggt  420
atttcctatt cgcatacgca atcttacgat caattcctaa taaactagga gg            472

<210> SEQ ID NO 112
<211> LENGTH: 472
<212> TYPE: DNA
<213> ORGANISM: Mesoplodon densirostris

<400> SEQUENCE: 112
taccatgagg acaaatatcc ttctgaggtg caactgtcat taccaatctt ctatccgcta    60
ttccctatat tggcaccacc ctagtcgagt gaatctgagg tggttttcc gtagacaaag    120
ccacattaac acgcttcttc gctttcact tcatcctccc ctttattatt ctagccctaa    180
caatggtcca cctactattc ctccatgaaa caggatctaa taaccctaca ggaatcccat   240
ctgacataga taaaattcca tttcacccctt attacacaat caaagatatt ttaggagccc  300
tactattaat tctggcccta cttatactaa ccctatttgc acctgaccta ctaggagacc   360
ccgataatta tactccagca aacccactca acactccagc acacatcaaa ccagagtggt  420
attttctatt tgcatacgca atcctacgat caatccccaa caaattagga gg            472

<210> SEQ ID NO 113
<211> LENGTH: 472
<212> TYPE: DNA
<213> ORGANISM: Hyperoodon ampullatus

<400> SEQUENCE: 113
taccctgagg acaaatatca ttctgaggcg caaccgtcat caccaatctc ctatccgcca    60
ttccctatat cggcactacc ctagttgaat gaatctgagg tggtttctcc gtagacaaag   120
ccacattaac ccgcttttc gccctccact ttatcctccc attcattatt ctagccctag    180
caatcgtcca cctactattc ctccatgaaa caggatccaa caatcccaca ggaattccat   240
```

-continued

```
ctgacataga caaaatcccg ttccacccat actacacaat caaagacact ctaggggccc      300
tattactaat cctagtccta ctcacattaa ccctattcgc acccgaccta ctaggagacc      360
ctgataacta taccccagca aacccactca gcactccagc acacatcaaa ccagaatggt      420
acttcttatt tgcatacgca atcctacgtt caatccctaa caaactagga gg              472
```

<210> SEQ ID NO 114
<211> LENGTH: 472
<212> TYPE: DNA
<213> ORGANISM: Hyperoodon ampullatus

<400> SEQUENCE: 114

```
taccctgagg acaaatatca ttctgaggcg caaccgtcat caccaatctc ctatccgcca      60
ttccctatat cggcactacc ctagttgaat gaatctgagg tggtttctcc gtagacaaag      120
ccacattaac ccgcttttc gccctccact ttatcctccc attcattatt ctagccctag       180
caatcgtcca cctactattc ctccatgaaa caggatccaa caatcccaca ggaattccat      240
ctgacataga caaaatcccg ttccacccat actacacaat caaagacact ctaggggccc      300
tattactaat cctagtccta ctcacattaa ccctattcgc acccgaccta ctaggagacc      360
ctgataacta taccccagca aacccactca gcactccagc acacatcaaa ccagaatggt      420
acttcttatt tgcatacgca atcctacgtt caatccctaa caaactagga gg              472
```

<210> SEQ ID NO 115
<211> LENGTH: 472
<212> TYPE: DNA
<213> ORGANISM: Mesoplodon peruvianus

<400> SEQUENCE: 115

```
taccttgagg acaaatatca ttctgaggcg caactgtcat tactaatctt ttatctgcta      60
tcccttatat tggcaccacc ctagttgaat gaatttgagg tggcttctcc gtagataaag      120
ctacattaac acgattttt gccttccact ttattctccc atttattatc ttagctctaa       180
caattgtcca tttactattt ctacacgaaa caggatctaa taatcccata ggaatctctt      240
ctgacataga caaaattcca tttcatcctt actatacaat taaagatatc ttaggagccc      300
tattattaat tatagtccta cttatactaa ccctattgc acctgaccta ttaggagatc       360
ctgacaatta cactccagca aacccactta gcaccccagc acatattaaa ccagaatgat      420
attttctatt tgcatatgca attttacgat cagttcctaa taaactagga gg              472
```

<210> SEQ ID NO 116
<211> LENGTH: 472
<212> TYPE: DNA
<213> ORGANISM: Pontoporia blainvillei

<400> SEQUENCE: 116

```
taccctgagg acaaatgtca ttctgaggtg ccactgtcat cactaacctc ctatcagcga      60 tccccctacat cggaactacc cttgtagaat ggatctgagg tggtttctct gtagacaaag     120
caacactaac gcgattcttc gctttccatt ttatccttcc attcattatt acagccctag      180
ttatagtcca cctgctattc ctacacgaaa ctggatccaa caaccaaca ggaatctcat       240 ctaacataga tgccatccca tttcaccct actacacaat taaagatatc ctaggggccc       300
tattaataat cctaacaata ctcacgctga ctctattcac ccctgaccta ttaggagacc      360
cagacaacta tatcccagca aacccatga atacccccaga gcacattaaa ccagaatggt      420
```

```
atttcctatt tgcctacgcc atcctacgat caattcccaa taaactggga gg          472
```

<210> SEQ ID NO 117
<211> LENGTH: 472
<212> TYPE: DNA
<213> ORGANISM: Hippopotamus amphibius

<400> SEQUENCE: 117

```
tgccatgagg acaaatgtca ttctgagggg caacagtcat taccaactta ctgtcagcta   60
tcccctatat tggaacagac ctagtagaat gaatctgagg aggcttttcc gtagacaaag  120
ccacccttac acgattcttt gccttccact ttattcttcc attcgttatc acagcactag  180
ccatcgtcca tctactattc ctccatgaaa caggatccaa caacccaaca ggaatcccct  240
caaacgcaga caaaatccca ttccacccct attacacaat caaggacatc ctaggtatcc  300
tactcctaat aacaacacta ctcacactaa ccttatttgc cccagacctc ctaggggacc  360
cagacaacta caccccgca aaccccctta gcacaccacc acacattaaa ccagaatgat  420
atttcctgtt cgcgtacgcg attctccgat caatcccaa caaactagga gg          472
```

<210> SEQ ID NO 118
<211> LENGTH: 472
<212> TYPE: DNA
<213> ORGANISM: Hexaprotodon liberiensis

<400> SEQUENCE: 118

```
taccatgagg acaaatatca ttctgagggg caacagtcat caccaactta ctatcagcta   60
tcccctacat tggaacagac ctagtagaat gaatctgagg aggcttttct gtagataaag  120
ccacccttac acgattcttt gccttccact ttattcttcc attcatcatc atagcactag  180
ccgccgtcca cctactgttt ctccacgaaa cagggtccaa caacccaaca ggaatcccct  240
caaacgcaga caaaatccca ttccacccct attacacaat caaagatatc ctgggcgtac  300
tacttctaat aacaatacta ctcacactaa ccttatttgc cccagacctc ctaggggacc  360
cagacaacta cacccccgca aaccccctta gcacaccacc acacatcaaa ccagaatgat  420
atttcctgtt cgcatacgca attctccgat caatccctaa caaactggga gg          472
```

<210> SEQ ID NO 119
<211> LENGTH: 472
<212> TYPE: DNA
<213> ORGANISM: Rhinoceros sondaicus

<400> SEQUENCE: 119

```
taccatgagg tcaaatatcc ttctgagggg ctacagtcat tacaaatctc ctctcagcca   60
tcccctatat cggtaccaac cttgtagagt gaatctgagg aggattctca gtcgacaaag  120
ctacccttac ccgattcttt gccttccact tcatccttcc ctttattatc ctagctctag  180
cgatcaccca cttactattc ctacacgaaa caggatccaa taaccatca ggaattccat  240
ctaacacaga caaaattcca tttcacccctt actacacaat caaagacatc ctaggagccc  300
tgcttctaat tatagtatta ctcacccctag tcctattctc ccctgacatc ctaggggacc  360
cagacaacta catcccagcc aaccctctca gcaccctcc acatatcaaa ccagaatggt  420
atttcctatt tgcttacgca atcctacgat ccatcccaaa caaactaggc gg          472
```

<210> SEQ ID NO 120
<211> LENGTH: 472
<212> TYPE: DNA
<213> ORGANISM: Ceratotherium simum

<400> SEQUENCE: 120

```
taccatgagg ccaaatatcc ttctgagggg ctacagtcat cacaaacctc ctctcagcta      60
tcccttacat cggcaccaac ctcgtagaat gaatctgagg aggattttcc gttgacaaag     120
ccacacttac acgattcttc gcctttcact ttatcctccc ctttattatc atagccctag     180
caatcaccca cctactattc cttcacgaaa caggatccaa taaccatcca ggaatcccat     240
ccaacataga caaaatccca ttccacccat actacacaat caaagacatc ctgggaattt     300
tactcctaat cctagcacta ctcgccctag ttctattctc accagacatc ctaggagacc     360
ctgacaacta caccctgcc aatcctctca gcactccccc acatatcaaa ccagaatgat     420
actttctatt tgcttacgca atcctacgat ccatccctaa caaactaggc gg             472
```

<210> SEQ ID NO 121
<211> LENGTH: 472
<212> TYPE: DNA
<213> ORGANISM: Dicerorhinus sumatrensis

<400> SEQUENCE: 121

```
taccatgagg tcaaatatcc ttctgaggag ccacagttat cacaaatctc ctctcagcca      60
tcccatacat cggcaccgac cttgtagaat gaatctgagg gggattctcc gtagacaaag     120
ccaccctcac ccggttcttt gctttccact tcatcctccc cttcatcatc ctagccctag     180
caattaccca cctgctattc ctacatgaaa caggatccaa caacccatca ggaatcccat     240
ctaacataga caaaatccca tttcacccat actatacaat caaagacatc ctaggagccc     300
tacttctaat cctagcccta ctcaccctag ttctattctc gcctgacctc ctaggagacc     360
cggacaacta cacaccccgcc aaccctctca gcaccccctcc acacattaaa ccagaatggt     420
acttcctatt cgcctacgca atcctacgat ccatccccaa taaactaggc gg             472
```

<210> SEQ ID NO 122
<211> LENGTH: 472
<212> TYPE: DNA
<213> ORGANISM: Equus asinus

<400> SEQUENCE: 122

```
taccatgagg acaaatatcc ttctgaggag caacggtcat acaaacctc ctatcagcaa       60
tccctacat cggtactacg ctcgtcgaat gaatctgagg tggattctca gtagacaaag      120
ccacccttac ccgattttt gcttccact ttattctacc ctttatcatc acagccctgg       180
taatcgtcca tctactattc ctccacgaaa caggatccaa caacccctca ggaatcccat     240
ctgacataga caaaatccca ttccacccgt actacacaat taaagacatc ctaggacttc     300
tcctcctagt cctactccta ctaaccctag tattattctc ccctgacctc ctaggagacc     360
cagacaacta caccccagct aaccccctca gcactccccc tcatattaag ccagaatggt     420
atttcctatt tgcttacgcc atcctacgct ccattcccaa caaactaggt gg             472
```

<210> SEQ ID NO 123
<211> LENGTH: 472
<212> TYPE: DNA
<213> ORGANISM: Babyrousa babyrussa

<400> SEQUENCE: 123

```
taccttgagg acaaatatca ttttgaggag ctaccgtcat tacaaaccta ctatcagcca      60
ttccctatat cggaacggac ctcgtagaat ggatctgagg aggcttctcc gtcgataaag     120
```

```
caaccctcac acgattcttt gctttccact ttattctacc cttcatcatc accgctctcg    180
caaccgtaca tctattattc cttcacgaaa ctggatccaa taaccctact ggaatttcat    240
cagatataga caaaatccca ttccacccct actataccat aaagacatt ctaggagccc     300 tactcataat tatagctctt ctaatcctag tactattctc accagatcta ctaggagacc    360
cggacaacta tactccagca aacccactaa atacaccacc ccacattaag ccagaatgat    420
acttcctatt tgcctacgcc atcctacgct caatccccaa caaattaggc gg            472
```

<210> SEQ ID NO 124
<211> LENGTH: 472
<212> TYPE: DNA
<213> ORGANISM: Phacochoerus africanus

<400> SEQUENCE: 124

```
taccctgagg acaaatatcg ttctgaggag ccacagtcat cacaaaccta ctatcagcca    60
tcccctacat tggaacaaat cttgtagaat gaatctgagg aggtttctcc gtcgacaaag    120
caactctcac acgattcttt gccttccact tcattttacc ttttatcatc gctgccctag    180
caaccgtaca tctcttgttc ctacacgaaa ctggatctaa caaccctact ggaatctcat    240
cagacataga caaaatccca ttccacccat actacaccat aaagatatc ctaggagccc      300 tattcataat actaatcctg ctaatcctag tattattctc cccagaccta ctaggagacc    360
cagacaacta taccccagca aacccattaa acacaccacc ccacatcaaa ccagaatgat    420
acttcctatt cgcctacgcc atcctacgtt caatccctaa taaattaggt gg            472
```

<210> SEQ ID NO 125
<211> LENGTH: 472
<212> TYPE: DNA
<213> ORGANISM: Sus scrofa haplotype EWB3

<400> SEQUENCE: 125

```
tgccctgagg acaaatatca ttctgaggag ctacggtcat cacaaatcta ctatcagcta    60
tcccttatat cggaacagac ctcgtagaat gaatctgagg gggcttttcc gtcgacaaag    120
caaccctcac acgattcttc gccttccact ttatcctgcc attcatcatt accgccctcg    180
cagccgtaca tctcctattc ctgcacgaaa ccggatccaa taaccctacc ggaatctcat    240
cagacataga caaaattcca tttcacccat actacacatat aaagacatt ctaggagcct    300 tatttataat actaatccta ctaatccttg tactattctc accagaccta ctaggagacc    360
cagacaacta caccccagca aacccactaa acaccccacc ccatattaaa ccagaatgat    420
atttcttatt cgcctacgct attctacgtt caattcctaa taaactaggt gg            472
```

<210> SEQ ID NO 126
<211> LENGTH: 472
<212> TYPE: DNA
<213> ORGANISM: Sus barbatus

<400> SEQUENCE: 126

```
tgccctgagg acaaatatca ttctgaggag ctacggtcat cacaaatcta ctatcagcta    60 tccctatat cggaacagac ctcgtagaat gaatctgagg gggcttttcc gtcgacaaag      120 caaccttac acgattcttc gcctttcact ttatcctgcc cttcgtcatt accgccctcg      180
cagccgtaca tctcctattc ctacacgaaa ccggatccaa taaccccacc ggaatttcat    240
cagacataga caaaattcca tttcacccat actacactat caaagacatt ctaggagcct    300
tatttataat actaatccta ctaatcttag tactattctc accagaccta ctaggagacc    360
```

```
cagacaacta cacccccagca aacccactaa acaccccacc ccatattaaa ccagaatgat    420
acttcttatt cgcctacgct attctacgtt caatccccaa taaactaggc gg             472
```

<210> SEQ ID NO 127
<211> LENGTH: 472
<212> TYPE: DNA
<213> ORGANISM: Lama glama

<400> SEQUENCE: 127

```
tcccatgagg acaaatatca ttttgagggg caacagtaat tacaaatcta ctctcggcaa    60
ttccatatgt tggcacaaca ctagtcgaat gaatttgagg aggattctcc gtagacaaag    120
ccacccttac acgattcttc gccttccact ttatcttacc ttttgtcatt gcagctctag    180
caggagtaca tctactattt ttacacgaaa caggctccaa caatccaaca ggaatttctt    240
cggatataga caaaatcccc ttccatccct actatacaat taaagacatt ctaggagcac    300
tactacttat tctaaccta cttctactcg tactattctc accagaccta ctaggagacc    360
ccgacaacta tactcccgct aaccccctca acacaccgcc ccatattaaa ccagaatgat    420
acttcctatt tgcatacgcc atcctacgat ccatccccaa taaattaggc gg             472
```

<210> SEQ ID NO 128
<211> LENGTH: 472
<212> TYPE: DNA
<213> ORGANISM: lama guanicoe

<400> SEQUENCE: 128

```
tcccatgagg ccaaatatca ttttgagggg caacagtaat tacaaaccta ctctcggcaa    60
ttccatatgt tggcacaaca ctagtcgaat gaatttgagg gggttctcc gtagataaag     120 ccacccttac rcgattcttc gccttccact ttatcttacc ttttgtcatt gcagctctag    180
caggagtgca tctactattt ttacacgaaa caggctccaa caatccaaca ggaatttctt    240
cggatataga caaaatcccc ttccatccct actatacaat taaagacatt ctaggagtac    300
tactacttat tctgaccta cttctactcg tactattctc accagaccta ctaggagacc     360
ccgacaacta tactcccgct aaccccctca acacaccgcc tcatattaaa ccagaatgat    420
acttcctatt tgcatatgcc atcctacgat ccatccccaa caaattaggc gg             472
```

<210> SEQ ID NO 129
<211> LENGTH: 472
<212> TYPE: DNA
<213> ORGANISM: Vicugna vicugna

<400> SEQUENCE: 129

```
tcccatgagg acaaatatca ttttgagggg caacagtaat tacaaaccta ctctcagcaa    60
ttccatacgt tggtacaaca ctagtcgagt ggatttgagg aggattctcc gtagataaag    120
ccacccttaa ccgattcttc gcctttcact ttatcttacc tttcatcatt gcagctctag    180
cgggagtaca tctactattt ttacacgaaa caggctccaa caacccaaca ggaatttctt    240
cagatataga caaaattccc ttccatccct actacacaat taaagacatt ttaggagcac    300
tactacttat tctgattcta ctcctactcg tactattctc accagactta ctaggagacc    360
ccgacaacta tacccccgct aaccccctta acacaccacc ccacattaaa ccagaatgat    420
atttcctatt tgcatatgct attctacgat cgatccccaa taaattaggc gg             472
```

<210> SEQ ID NO 130

```
<211> LENGTH: 472
<212> TYPE: DNA
<213> ORGANISM: Camelus bactrianus

<400> SEQUENCE: 130
tcccatgagg acagatatca ttctggggag caacagtaat taccaaccta ctctcagcaa      60
ttccctatat cggcacaaca ctagtagaat gaatttgagg tggcttctcc gtagacaaag     120
ccaccctcac acgattcttt gccttccact tcatcctgcc atttattatc acggccctag     180
tagccgtaca cctattattc ctacacgaaa caggctctaa taacccgaca ggaatctcct     240
cagacataga caaaatccca ttccacccct actacacaat aaagacatc  ctaggagcac     300
tgctactaat attaattctc cttattctcg tactgttctc accagactta ttaggagatc     360
ctgacaacta tactcccgct aaccccctca atacaccacc acacattaag ccggaatgat     420
atttcctatt cgcatacgct atcctacgat ccatccccaa caaattggga gg             472

<210> SEQ ID NO 131
<211> LENGTH: 472
<212> TYPE: DNA
<213> ORGANISM: Arctocephalus forsteri

<400> SEQUENCE: 131
ttccatgagg acaaatatca ttctgaggag cgaccgtcat taccaacctc ctatcagcag      60
tccctacat  tgggaccaac ctagtagaat gaatctgagg aggattttca gttgataaag     120
caaccctaac acgattcttc gcctttcact tcattctccc cttcgtagca tcagcactag     180
taatagtaca tctgctattc ctacatgaaa caggatccaa taacccatca ggagtctcct     240
ctgactcaga caaaatccca ttccacccat attatacaat aaagatatc  ctgggagccc     300
tcctactaat cttgattcta atattactag taatattttc accagatctg ctgggagacc     360
cagacaacta caccccagcc aaccccctca gcactccacc acatattaaa cctgaatgat     420
attttctatt cgcttacgcc attttacgat ctatccccaa caaactagga gg             472

<210> SEQ ID NO 132
<211> LENGTH: 472
<212> TYPE: DNA
<213> ORGANISM: Arctocephalus gazella

<400> SEQUENCE: 132
ttccatgagg acagatatca ttctgaggag caaccgtcat taccaacctc ctgtcagcaa      60
tccctacat  cggaactaac ctagtagaat gaatctgagg aggattttca gttgataagg     120
caaccctaac acgattcttc gcctttcact ttattcttcc cttcgtagta tcagcactag     180
taatagtgca cctactattc ctacacgaaa caggatccaa caacccatca ggagtctcct     240
ctgactcgga caaaattcca ttccacccat attatacaat aaagatatc  ctgggagccc     300
tcttactaat cttaattcta atattactag taatattttc accagatctg ctaggagacc     360
cagacaacta catcccagcc aaccccctca gtactccacc acatatcaaa cctgaatggt     420
attttctatt cgcctatgcc attttacgat ctatccccaa caaactagga gg             472

<210> SEQ ID NO 133
<211> LENGTH: 472
<212> TYPE: DNA
<213> ORGANISM: Eumetopias jubatus

<400> SEQUENCE: 133
ttccgtgagg acaaatatca ttctgaggag caaccgtcat taccaacctc ctatcagcta      60
```

```
tcccttacat cggaaccaac ttagtagaat gaatttgagg gggatttcca gtcgacaaag      120
caaccctaac acgattcttc gccttccact ttattctccc cttcgtagca tcagcactag      180
taatagtaca cctattattc ctacacgaaa ctggatccaa caatccatca ggaatctcct      240
ccaactcaga caaaattcca ttccatccat attacacaat taaagatatc ctgggaaccc      300
tcctactaat cttaatccta atactactag taatattttc accagacctg ctgggagacc      360
cagacaacta catcccagcc aaccccctca gcactccacc acatattaaa cccgaatgat      420
atttcctatt cgcctatgct attttacgat ccatccccaa caaattaggg gg              472
```

<210> SEQ ID NO 134
<211> LENGTH: 472
<212> TYPE: DNA
<213> ORGANISM: Zalophus californianus

<400> SEQUENCE: 134

```
ttccatgagg acaaatatca ttttgaggag caaccgtcat taccaacctc ctatcagcag      60
tcccttacat cggaaccaac ctagtagaat gaatttgagg gggattttca gtcgacaaag      120
caaccctaac acgattcttt gccttccact ttattctccc cttcatagca tcagcactag      180
taatagtaca cctattattc ctacacgaaa ctgggtccaa caacccatca ggaatctcct      240
ctgactcaga caaaattcca ttccacccat attacacaat taaagatatc ctaggaaccc      300
tcctactaat cttaaccccta atactactag taatattttc accggacctg ctgggagacc      360
cagacaacta tattccagcc aaccccctca gcactccacc acatattaaa cctgagtgat      420
atttcctatt cgcctatgct attttacgat ccatccccaa caaattaggg gg              472
```

<210> SEQ ID NO 135
<211> LENGTH: 472
<212> TYPE: DNA
<213> ORGANISM: Odobenus rosmarus

<400> SEQUENCE: 135

```
taccatgagg acaaatatcc ttctgaggag caaccgtcat caccaacctt ctgtcagcaa      60
ttccctatgt agggactgac ttggtcgaat gagtctgagg ggggttttca gttgataaag      120
caaccctaac acgattcctc gccctccact tcgttcttcc attcatggca ttagcactaa      180
cagcagtaca cctactattt ctccacgaaa caggatctaa caacccttcg ggaatcctat      240
ctgactcaga caaaatccca tttcacccgt actacacaat taaagatatc ctagggctca      300
tcattctaat cctaatccta atactactag tactattctc accagattta ctgggagacc      360
cggacaatta caccccagcc aaccctctca gcacccccacc ccatatcaaa cccgaatgat      420
atttcctatt cgcctacgct atcctccgat ctattcccaa caaactcggg gg              472
```

<210> SEQ ID NO 136
<211> LENGTH: 472
<212> TYPE: DNA
<213> ORGANISM: Phoca vitulina

<400> SEQUENCE: 136

```
taccatgagg acaaatatca ttttgaggag caacagtcat caccaatcta ctatcagcaa      60 tccccctatgt cggaaccgac cttgtacaat gaatctgagg agggttttca gtagataaag      120
caaccttaac acgattcttc gccttccact tcatcctgcc attcgtagta tcagccctag      180
cagcagtcca cctactattc ctacacgaaa caggatcaaa caacccctcc ggaatcatat      240
```

```
ccaactcaga caaaatccca ttccacccgt actatacaat taaagatatc ctaggggccc      300
tacttctcat tctagtcctg acactactag tgctattctc acccgacctg ttaggagacc      360
ccgacaacta tatccctgcc aatcccctaa gcaccccacc acatatcaaa cctgaatggt      420
acttcctatt tgcctacgca atcttacgat ccatccccaa caaactagga gg              472
```

<210> SEQ ID NO 137
<211> LENGTH: 472
<212> TYPE: DNA
<213> ORGANISM: Phoca fasciata

<400> SEQUENCE: 137

```
taccatgagg acaaatatca ttctgaggag caacagtcat cactaatcta ctatcagcaa      60
ttccctatat cggaaccgac ctagtacaat gaatctgagg aggattttca gttgataaag      120
caaccctaac acgattttte gctttccact ttatcctacc atttgtagta tcagcactag      180
cggcagttca cctactattc ctacacgaaa caggatccaa caaccccctcc ggaatcgtat      240 ccgactcaga caaaatccca ttccacccat actatacaat taaagatatc ctaggagccc      300
tactcctcat cctagtccta atactactag tactattctc acccgaccta ctaggagacc      360
ccgacaacta caccctgcc aaccccctaa gcaccccacc acatatcaag cccgaatgat       420
actttctatt tgcctacgca atcctacgat caatccccaa caaactagga gg              472
```

<210> SEQ ID NO 138
<211> LENGTH: 472
<212> TYPE: DNA
<213> ORGANISM: Phoca groenlandica

<400> SEQUENCE: 138

```
taccatgagg gcaaatgtca ttctgaggag caacagttat cactaatcta ctatcagcaa      60 tccctacat cggaaccgat ctagtacaat gaatctgagg agggttctca gttgataaag       120
caaccctaac acgattttc gccttccact tcatcttacc attcgtagta ttagcactag       180
cggcagttca tctactattc ttacacgaaa caggatccaa caaccccacc ggaatcgtat      240
ccgactcaga caaaatcccg ctccacccat attatacaat taaagatatc ctaggagccc      300
tactcctcat cctggtcctt atactactag tactgttctc acccgaccta ctgggagacc      360
ccgacaacta catccctgcc aatcccctaa gtaccccacc acatatcaag cccgaatgat      420 acttttatt tgcctacgca atcctacgat caattcccaa caaactagga gg               472
```

<210> SEQ ID NO 139
<211> LENGTH: 472
<212> TYPE: DNA
<213> ORGANISM: Cystophora cristata

<400> SEQUENCE: 139

```
taccgtgagg acaaatatca ttttgaggag cgacagtcat caccaaccta ctatcagcaa      60 tccctacat cggagccgat ctagtagaat gaatctgagg gggattttca gtcgataaag       120
caactctaac acggtttttc gccttccact tcatcctacc attcgtcgta tcagcactag      180
caacagtcca cctactattc ctacacgaaa caggatctaa taatccctcc ggaatcacat      240
ccgactcaga caaaatccca ttccacccat actatacaat taaagacatc ctaggagccc      300
tactcctcat cctagttcta acactactag tgctattctc acccgatctg ctaggagacc      360
ccgacaacta taccctgcc aaccccctaa gtaccccacc acatattaaa cctgaatgat       420
acttcctatt cgcctatgca atcctacgat ctatccccaa caaactagga gg              472
```

<210> SEQ ID NO 140
<211> LENGTH: 472
<212> TYPE: DNA
<213> ORGANISM: Hydrurga leptonyx

<400> SEQUENCE: 140

```
tgccatgagg acaaatatca ttttgaggag caaccgttat taccaactta ctatcagcaa      60
ttccctacat cggaaccgac ctagtacaat gaatttgagg cggattttca gtcgacaaag     120
caaccctaac acgattcttc gccttccact ttatccttcc cttcgtagta tcagcactag     180
cagcagtaca tctactattc ttacacgaaa caggatccaa taaccccctcc ggaattccat     240
ccaactcaga caaaatccca tttcacccct actacacaat caaagacatc ctaggagccc     300
tattcctcat tctaacccta atactactag tattattctc acccgaccta ctaggagacc     360
ccgacaacta tattcctgct aaccccctaa gcaccccacc acatatcaaa cccgaatgat     420
atttcctatt tgcctacgca atcctacgat ccattcccaa taaactagga gg             472
```

<210> SEQ ID NO 141
<211> LENGTH: 472
<212> TYPE: DNA
<213> ORGANISM: Leptonychotes weddelli

<400> SEQUENCE: 141

```
taccatgagg acaaatatca ttctgaggag caaccgtcat taccaactta ctatcagcaa      60
ttccctacat cggaactgac ttagtacaat gaatctgagg cggattttca gttgacaaag     120
caacccgtaac acgattcttc gccttccact ttatccttcc cttcgtagta tcagcactag     180
cagcagtaca tctactattc ttacacgaga caggatccaa caaccccctcc ggaattccat     240
ctgactcaga caaaatccca tttcacccct actacacaat caaagacatc ctaggagccc     300
tactcctcat tctaacccta atattactag tattattctc acccgacctg ctaggagatc     360
ccgacaacta tactcccgct aatcccctaa gtactccacc acatatcaaa cccgaatgat     420
atttcctatt tgcctacgca atcttacgat ccatccctaa caaactagga gg             472
```

<210> SEQ ID NO 142
<211> LENGTH: 472
<212> TYPE: DNA
<213> ORGANISM: Mirounga leonina

<400> SEQUENCE: 142

```
tgccatgagg acaaatatca ttttgaggag caaccgtcat taccaaccta ctatcagcag      60
tccccctatgt cggagacgac ctagtacaat gaatctgagg aggattttca atcgacaaag     120
caacccgtaac acgattcttc gccctccact ttatcctacc attcgtagca ctagcactag     180
cagcagtaca tctactattc ctacacgaaa caggatccaa caaccccctct ggaatcccat     240
ccgactcaga caaaatccca ttccacccat actacacaat caaagatatc ttaggagccc     300
tacttcttat tctaacccta atactattag tgttattctc acccgactta ttaggagacc     360
ccgacaacta caccctgcc aatcccctaa gcaccccacc acatattaaa cccgaatgat     420
atttcctatt tgcctacgca atcctacgat ctattcccaa caaactagga gg             472
```

<210> SEQ ID NO 143
<211> LENGTH: 472
<212> TYPE: DNA
<213> ORGANISM: Erignathus barbatus

```
<400> SEQUENCE: 143
taccatgagg gcaaatatca ttttgaggag caaccgttat caccaaccta ctatcagcaa    60
tcccctacat cgggactgat ctagtacaat gaatctgagg aggattctca gttgacaaag   120
caaccctaac acgattcttc gccttccact ttatcctacc atttgtagta ttagcattag   180
cagcagtcca cctattattc ctacacgaaa caggatccaa caaccctct ggaatctcgt    240 ccgactcaga taaaattcca ttccacccat actatacagt caaggacatc ttaggggcct   300
tacttctaat cctagttctt atacttctag tgctattctc acccgaccta ctgggagatc   360
ccgacaacta cactcccgct aaccccctaa gcacccacc acatattaag cccgaatgat    420
atttcctatt cgcctatgca atcctacgat ccatccccaa caaacttgga gg           472

<210> SEQ ID NO 144
<211> LENGTH: 472
<212> TYPE: DNA
<213> ORGANISM: Monachus schauinslandi

<400> SEQUENCE: 144
taccatgagg acaaatatcc ttctgagggg cgaccgtcat caccaaccta ctatcagcaa    60
tcccttacat cggaaccgat ctagtacaat gaatctgagg cgggttctca gtagataaag   120
caaccctaac acgattcttc gctttccatt ttattatacc cttcatagta ttagcactag   180
cagcagtcca tttattattt ctacacgaaa caggatccaa caatccctcc ggaattccat   240
ccaactcaga caaaatccca ttccacccat actatacaat taaagacatt ctaggagctt   300
tactccttat cctaattcta atactactag tactattctc acccgactta ctaggagacc   360
ctgacaacta catccctgcc aacccttaa acactccacc acacattaaa cccgaatgat    420
acttcctatt cgcctacgca atcctacgat ctatccccaa taaactagga gg            472

<210> SEQ ID NO 145
<211> LENGTH: 472
<212> TYPE: DNA
<213> ORGANISM: Helarctos malayanus

<400> SEQUENCE: 145
taccctgagg ccaaatgtcc ttctgaggag caactgtcat taccaatctc ttatcagcca    60
tcccctatat tggaacggac ctagtagaat gagtctgagg aggcttttcc gtagacaagg   120
cgactctaac acgattcttt gccttccact ttatccttcc gttcatcatc ttggcactaa   180
cagcggtcca cctattattc ctacacgaaa cagggtccaa caatccctct ggaatcccat   240
ctgactcaga caaaatccca tttcacccgt actatacaat taggacatc ctaggcgccc    300 tacttcttac cctagcccta acaaccctag ttctattctc gcccgactta ctaggagacc   360
ctgacaacta catccccgca aatccattga gcaccccacc ccacatcaaa cccgaatggt   420
actttctatt tgcctacgct atcctacgat ccatccctaa taaactagga gg            472

<210> SEQ ID NO 146
<211> LENGTH: 472
<212> TYPE: DNA
<213> ORGANISM: Selenarctos thibetanus

<400> SEQUENCE: 146
taccctgagg ccaaatatcc ttctgaggag cgactgtcat taccaacctc ctatcagcca    60
tcccctatat tggaacagac ctagtagaat gaatctgagg gggcttttct gtagataaag   120
caaccctaac acgattcttt gctttccact ttatccttcc gttcatcatc ctagcactag   180
```

```
cagcagttca tctattgttc ctacacgaaa caggatccaa caaccttct ggaatcccat      240 ccaactcgga caaaatccca tttcacccat actatacaat taaagacgcc ctaggcgccc      300
tacttctcat cctagcctta gcaactctag tcctattctc gcccgactta ctaggagacc      360
ctgataacta tacccccgca aacccactga gcaccccacc ccacatcaaa cccgaatgat      420 acttttatt tgcttacgct atcctacgat ccatccccaa caaactagga gg               472
```

<210> SEQ ID NO 147
<211> LENGTH: 472
<212> TYPE: DNA
<213> ORGANISM: Ailurus fulgens

<400> SEQUENCE: 147

```
tgccctgagg acagatatca ttctgaggag caaccgttat caccaaccta ctatcagcca      60
ttccctatat tggaactaac cttgtagagt gaatctgagg aggtttctca gtcgacaaag      120
caactctaac tcgattcttc gccttccact tcattcttcc atttatcatt gcaacactag      180
caactatcca tctcttattc ctacatgaaa caggatctaa taaccctca ggcatcccat       240 ccaactcaga caaaattcca ttccatccct attatacaat taaagatatc ttgggcgctc      300
tactccttat cctaattctc atgacattag tactattctt acctgacttg cttggtgatc      360
ctgataacta tattcccgct aacccattaa gcacaccacc catattaaa cctgagtggt       420 atttcctatt cgcatatgca attctacgat ccatcccaaa caaactagga gg              472
```

<210> SEQ ID NO 148
<211> LENGTH: 472
<212> TYPE: DNA
<213> ORGANISM: Felis catus

<400> SEQUENCE: 148

```
taccatgagg ccaaatgtcc ttctgaggag caaccgtaat cactaacctc ctgtcagcaa      60
ttccatacat cgggactgaa ctagtagaat gaatctgagg ggggttctca gtagacaaag      120
ccaccctaac acgattcttt ggcttccact tcattcttcc attcattatc tcagccttag      180
caggagtaca cctcttattc cttcatgaaa caggatctaa caacccctca ggaattacat      240
ccgattcaga caaaatccca ttccacccat actatacaat caaagacatc ctaggtcttc      300
tagtactagt tttaacactc atactactcg tcctatttc accagacctg ctaggagacc       360
cagacaacta catcccagcc aacccttaa atacccctcc ccatattaaa cctgaatgat      420
acttcctatt cgcatacgca attctccgat ccatccctaa caaactaggg gg              472
```

<210> SEQ ID NO 149
<211> LENGTH: 472
<212> TYPE: DNA
<213> ORGANISM: Canis familiaris

<400> SEQUENCE: 149

```
taccatgagg acaaatatca ttttgaggag caactgtaat cactaatctt ctctctgcca      60
tcccttatat cggaactgac ttagtagaat ggatctgagg cggcttctca gtggacaaag      120
caaccctaac acgattcttt gcattccatt tcatcctccc tttcatcatc gcagctctag      180
caatagtaca cctcctatt ctacacgaaa ccggatccaa caacccttca ggaatcacat       240
cagactcaga caaaattcca tttcacccct actacacaat caaggatatc ctaggagcct      300
tactcctact cctaatccta atatcactag ttttattttc acctgaccta ttaggagacc      360
```

```
cagataacta caccoctgca aaccoctaa acaccoctcc acatattaaa cctgagtgat      420
attttctatt cgcctatgct atcctacgat ccattcctaa taaattagga gg             472

<210> SEQ ID NO 150
<211> LENGTH: 472
<212> TYPE: DNA
<213> ORGANISM: Talpa europaea

<400> SEQUENCE: 150
taccatgggg tcaaatatcc ttttgaggtg caacggtaat tacaaattta ctgtcagcca      60
ttccttacat cggtacagac ttagtagaat gaatttgagg tgggttctca gtagacaaag     120
cgacactcac acgattcttc gccttccact tcattctgcc atttattatt gcggcactag     180
ctggagttca cctgttattt cttcacgaaa caggatcaaa caacccatca ggactctcat     240
cagatacgga taaaattcca tttcaccoct attacactat aaagacatc ctaggagcac     300 taatcctaat tatagctcta tcatcattag tattattttc acctgaccta ctaggagacc     360
cagacaatta catcccggca aaccgctaa acacaccacc ccatattaaa cccgaatggt     420
acttcctatt tgcatatgcc atcctacgat caattcctaa taaattagga gg             472

<210> SEQ ID NO 151
<211> LENGTH: 472
<212> TYPE: DNA
<213> ORGANISM: Glaucomys sabrinus

<400> SEQUENCE: 151
taccctgagg acaaatatct ttctgaggag ccaccgtcat caccaacctt ctctcagcta      60
ttccttatat tgggacaaca cttgtagaat gaatctgagg aggcttctct gtcgacaaag     120
ctaccctaac ccgatttttt gcatttcatt ttgtcctccc ttttattatt gctgccctag     180
ccataatcca tctactcttt ttacacgaaa caggatccaa taacccatca ggactaatct     240
ctgactcaga taaaatccca ttccacccott atttctcaat taaagacacc ctaggattct     300
taatcctcat cttaatcttc ataacccag ttctcttcac ccctgatctt ctaggagacc     360
cagacaacta taccccagcc aacccactca acaccoctcc ccacatcaaa ccagaatgat     420
actttctatt tgcatacgca attctacgat ctattccaaa taaactagga gg              472

<210> SEQ ID NO 152
<211> LENGTH: 472
<212> TYPE: DNA
<213> ORGANISM: Glaucomys volans

<400> SEQUENCE: 152
taccctgagg acaaatatcc ttctgaggag ctactgtcat caccaacctt ctctcagcta      60
ttccttatat tggtacaaca cttgtagaat gaatctgagg gggcttctct gttgataaag     120
ctaccttaac ccgattcttt gcatttcact tcattcttcc ttttatcatt gccgctctag     180
ccataatcca tctactcttt ctacacgaaa caggatccaa taacccatca ggactaatct     240
ctgactcaga caaaatccca ttccaccoct acttctcaat taaagatacc ctaggattct     300
taatccttat cttaatcttc ataacccag ttctcttcac cccggatctt ctaggagacc     360
cagacaacta tactccagcc aacccactca acggccctcc ccatatcaag ccagagtgat     420
actttctatt tgcgtatgca attctacgat ctatcccaaa taaactagga gg              472

<210> SEQ ID NO 153
<211> LENGTH: 472
```

<210> SEQ ID NO 153
<211> LENGTH: 472
<212> TYPE: DNA
<213> ORGANISM: Hylopetes phayrei

<400> SEQUENCE: 153

```
taccatgagg acaaatatcc ttctgagggg ctaccgttat tacaaaccta ctatctgcca    60
tcccctacat tggaacagtc cttgtcgaat gaatttgagg gggattttcc gtagataagg   120
ctaccctaac ccgattcttc gcattccact ttgtgctgcc ctttattatt gcagcactag   180
ctataattca ccttctcttt ctacacgaaa caggatcaaa taacccatca ggcctaattt   240
ccgattcaga caaaatccca tttcacccat actattcaat taaagatctc ctaggcgccc   300
ttattcttct cctaatcttt ataaacttag tactattttc ccccgatctt ttaggagacc   360
ctgacaacta cacccccgcc aacccactta cacccctcc tcatattaaa ccagaatgat    420
actttctatt cgcatacgca atcctacgat ctattcccaa taaattagga gg           472
```

<210> SEQ ID NO 154
<211> LENGTH: 472
<212> TYPE: DNA
<213> ORGANISM: Petinomys setosus

<400> SEQUENCE: 154

```
taccatgagg acaaatatcc ttctgagggg ctaccgttat tacaaaccta ctatctgcca    60
tcccctatat tggaacagtc cttgtcgaat gaatttgagg gggattttcc gtagataagg   120
ctaccctaac ccgattcttc gcattccact ttgtgctgcc ctttattatt gcggcactgg   180
ctataatcca ccttctcttt ctacacgaaa cagggtcaaa taatccatca ggtctaattt   240
ccgattcaga caaattccca tttcacccat actattcaat taaagatctc ctaggggccc   300
ttattcttct cctaatcttt ataaacttag tactattctc ccccgatctt ttaggagacc   360
ctgacaacta cacccccgcc aacccactta cacccctcc tcatattaaa ccagaatgat    420
actttctatt cgcatacgca atcctacgat ctattcccaa taaattagga gg           472
```

<210> SEQ ID NO 155
<211> LENGTH: 472
<212> TYPE: DNA
<213> ORGANISM: Belomys pearsonii

<400> SEQUENCE: 155

```
taccatgagg acaaatatct ttctgaggag ccactgtcat cacaaacctc ctttcagcta    60
tcccttatat tggaactgat ctagtagagt gaatctgagg ggggttttca gttgacaagg   120
caaccctaac acgattcttc gcattccact ttatcttacc atttatcgta gcagcccttg   180
caatagtcca ccttcttttc ctccacgaaa ttgggtcaaa taatcccccc ggattaattt   240
ctgaatctga taaagtacca ttccacccat acttcacaat caaagatatt cttggcgccc   300
taatcttcgg cctatatttt acaaccctta ttctattcgc ccctgatctc ctaggagacc   360
ctgacaacta tactccggcc aatccactta cacccctcc ccacattaaa ccagaatgat    420
actttctaat ttattacgca atccttcgat ccatccccaa caaactagga gg           472
```

<210> SEQ ID NO 156
<211> LENGTH: 472
<212> TYPE: DNA
<213> ORGANISM: Pteromys momonga

<400> SEQUENCE: 156

```
taccctgagg acaaatatca ttctgaggcg ccactgtcat caccaacctg ctatccgcca    60
```

```
tcccttatat cggcaccaac cttgttgaat ggatctgagg tggtttctca gttgataaag      120
ctaccctaac acgattcttt gcattccact ttgtcctccc cttcattatc gcagccctag      180
caatagttca cctactttc cttcatgaaa cagggtccaa caacccatct ggacttacct       240
ccgaatccga caaaatccca ttccacccct acttcacaat aaagacatt ttaggagcac       300 ttctccttgg cctcctattc ataatcttag tcctctttac tccagacctc cttggagacc      360
ccgacaacta taccccagcc aaccccctca cactcccccc tcatatcaaa ccagagtgat      420
atttcctatt cgcatatgct atcttacgat ctatccctaa caaactaggc gg              472
```

<210> SEQ ID NO 157
<211> LENGTH: 472
<212> TYPE: DNA
<213> ORGANISM: Galagoides demidoff

<400> SEQUENCE: 157

```
ttccatgagg ccaaatatca ttctgaggtg ctaccgtaat cactaacctg ctctcagcta       60
tcccatatat agggcctact ctagtagaat gaatctgagg ggggttttcg gtagacaaag      120
ctacccttac ccgattcttt gctttccact ttatcctccc atttatcatt acagcaatag      180
tcataatcca cctcctattc cttcacgaaa caggatcaaa caacccctca ggacttccat      240
cagactcaga caaaatcccc tttcacccct attacataat caaggatctc ctaggactga      300
ttattctctt actaactctg ttctccctag taatattctc cccggacctg ctaggagacc      360
ctgacaacta caccccgcc aaccccctaa acacccacc acatatcaaa ccagagtgat         420
atttcctatt tgcctacgcc atcctacgat ctatccccaa caaactagga gg              472
```

<210> SEQ ID NO 158
<211> LENGTH: 472
<212> TYPE: DNA
<213> ORGANISM: Perodicticus potto

<400> SEQUENCE: 158

```
tcccatgagg acaaatatca ttctgaggtg ccacagtaat cacaaacctc ctatcagcaa       60
tcccatatgt aggtacaacc ctggtagaat gaatttgagg gggattctca gtagacaaag      120
ctaccctaac acgattcttc gccttccact tcatcctccc ctttattatc acagcactag      180
ccacaactca cctcttattt cttcacgaaa caggatcaaa taacccagca ggaattccat      240
cagaatcaga caaaatcccc ttccacccct actacaccac caaagactta ctaggagcca      300
tctttcttct actaatccta ctcaccctag tcctattctc cccagaccta ttaggagacc      360
ctgacaacta caccccagcc aaccccctaa acaccccacc acatatcaaa ccagaatggt      420
actttctatt cgcctacgcc atcttacgat ccatcccaaa caaactggga gg              472
```

<210> SEQ ID NO 159
<211> LENGTH: 472
<212> TYPE: DNA
<213> ORGANISM: Galago matschiei

<400> SEQUENCE: 159

```
tcccatgagg acaaatatca ttctgaggcg ctaccgtaat cacaaatctc ctctccgcaa       60
ttccttacat gggtaccggc ctagtagaat gaatctgagg gggattttca gtagacaaag      120
ccacccttac tcgattcttc gcttttcact tcatcctacc tttcattatt gcagccctag      180
ccataattca cctctttttc ctacatgaaa caggatcaaa caacccttca ggaatctcat      240
cagactccga caaaatccca ttccacccct actacacaat aaagaccta ctaggagtaa       300
```

```
tcttcttact actatgccta ttctctctag tactattttc ccccgatctg ttaggagacc      360
cagacaattt taccccgct aatcccttaa acaccccacc acacatcaaa ccagaatgat      420
acttcttatt tgcttatgcc atccttcgat caattcccaa caaactagga gg             472

<210> SEQ ID NO 160
<211> LENGTH: 472
<212> TYPE: DNA
<213> ORGANISM: Galago moholi

<400> SEQUENCE: 160
ttccgtgagg acaaatatca ttctgaggcg ctaccgtaat cactaacctc ctctcagcaa      60
ttccctatat aggaactggc ctagtagaat gaatctgagg agggttctca gtagacaaag     120
ctactcttac ccgattttc gcttttcact tcatcctgcc tttcatcatc gcggccctag      180
ccataattca tcttcttttt ttacatgaaa cagggtcaaa taaccccttcg ggaatctcat     240 cagactccga caaaatcccc ttccacccct actacacaat taaagaccta ctaggagcaa     300
tcctcttact attatcccta ttctctctag tactattctc ccctgacctg ctgggagacc     360
cagacaatta tatccctgcc aaccccctaa acaccccacc acatattaaa ccagaatgat     420
acttcttatt tgcctacgcc atccttcgat caatccccaa caaactagga gg             472

<210> SEQ ID NO 161
<211> LENGTH: 472
<212> TYPE: DNA
<213> ORGANISM: Otolemur garnettii

<400> SEQUENCE: 161
tcccatgagg acaaatgtca ttctgaggcg caaccgtaat tacaaatctc ctctcagcaa      60
ttccctacat aggaactaac ctagtagagt gaatctgagg gggattttca gtagacaaag     120
caaccctcac ccggtttttt gctttccact ttatcctgcc tttcatcatc gcagccctag     180
tcataatcca cctccttttc ctccacgaat caggatcaaa caacccttca ggaatcccat     240
cagactctga caaaatcccc ttccacccct attacacaat taaagacctt ctaggggcta     300
tcctcctcct tctaacccta ttctccctag tcctattctc ccccgacctt ctaggagacc     360
cagacaacta caccctgcc aacccctaa acacaccgcc ccatatcaaa cccgaatgat      420
atttcctatt tgcttatgct atcttacgat ccatcccaaa taaactagga gg             472

<210> SEQ ID NO 162
<211> LENGTH: 472
<212> TYPE: DNA
<213> ORGANISM: Loris tardigradus

<400> SEQUENCE: 162
tcccatgagg acaaatatca ttctgaggag ccacagtaat taccaaccta ctatcagcaa      60
tcccttacat cggaactaac ctagttgaat gaatctgagg ggggttctca gtagataaag     120
caaccctcac acgattcttc gcctttcact tcatccttcc attcatcatc acagcattaa     180
ctgcaattca cctactttc ctacacgaat caggatcaaa taacccatcc ggaataacat     240
cagactctga caaaatccca tttcacccct actacacatt aaaagatatt ctaggagtaa     300
ttgctctctt aatcacctta tcaactctag ttctattctc ccctgacctt ttaggagacc     360
ccgataatta cacaccagct aaccctttaa acaccccacc ccacatcaaa ccagaatggt     420
atttcctatt cgcatacgca atcctacgat caatccccaa taaactaggt gg             472
```

<210> SEQ ID NO 163
<211> LENGTH: 472
<212> TYPE: DNA
<213> ORGANISM: Nycticebus coucang

<400> SEQUENCE: 163

| | | | | | |
|---|---|---|---|---|---|
| tcccatgagg | acaaatatca | ttctgaggtg | ccaccgtcat | cactaaccta | ctatcggcaa | 60 |
| tcccctatat | tggcacaaac | ctagttgaat | gggtctgagg | aggcttctca | gtagataaag | 120 |
| ccacactcac | acgattcttc | gccttccact | ttatcctccc | cttcatcgtc | gctgctctag | 180 |
| ttgtgattca | cctcatcttt | ctacatgaaa | caggctcaaa | taatccatca | ggaatctcat | 240 |
| cagactcaga | taagattcca | tttcacccct | actactcact | aaagacctc | ctaggagtgg | 300 |
| ttttcctatt | agcaacccta | tctattctag | tcttattctc | ccctgacctc | ctaggagacc | 360 |
| ccgacaacta | taccccgcc | aaccccttag | tcacccctcc | acatatcaaa | ccagaatgat | 420 |
| attttctatt | cgcctacgcc | atccttcgat | caatccccaa | caaactagga | gg | 472 |

<210> SEQ ID NO 164
<211> LENGTH: 472
<212> TYPE: DNA
<213> ORGANISM: Mus musculus

<400> SEQUENCE: 164

| | | | | | |
|---|---|---|---|---|---|
| ttccatgagg | acaaatatca | ttctgaggtg | ccacagttat | tacaaacctc | ctatcagcca | 60 |
| tcccatatat | tggaacaacc | ctagtcgaat | gaatttgagg | gggcttctca | gtagacaaag | 120 |
| ccaccttgac | ccgattcttc | gctttccact | tcatcttacc | atttattatc | gcggccctag | 180 |
| caatcgttca | cctcctcttc | ctccacgaaa | caggatcaaa | caacccaaca | ggattaaact | 240 |
| cagatgcaga | taaaattcca | tttcacccct | actatacaat | caaagatatc | ctaggtatcc | 300 |
| taatcatatt | cttaattctc | ataaccctag | tattatttt | cccagacata | ctaggagacc | 360 |
| cagacaacta | cataccagct | aatccactaa | acaccccacc | ccatattaaa | cccgaatgat | 420 |
| atttcctatt | tgcatacgcc | attctacgct | caatccccaa | taaactagga | gg | 472 |

<210> SEQ ID NO 165
<211> LENGTH: 472
<212> TYPE: DNA
<213> ORGANISM: Gorilla gorilla

<400> SEQUENCE: 165

| | | | | | |
|---|---|---|---|---|---|
| tcccatgagg | ccaaatatcc | ttctgaggag | ccacagtaat | cacaaacttg | ctatccgcca | 60 |
| tcccgtacat | cggaacagac | ctagtccaat | gagtttgagg | tggttactca | gtagatagcc | 120 |
| ctacccttac | acgattcttt | accttccact | ttatcctacc | cttcatcatc | acagccctaa | 180 |
| caaccctcca | tctcctattt | ctacacgaaa | caggatcaaa | caaccctcta | ggcatccct | 240 |
| cccactctga | caaaatcacc | ttccacccct | actacacaat | caaagacatc | ctaggcctat | 300 |
| tcctctttct | cctgaccttg | ataacattaa | cactattctc | accagacctc | ctaggagacc | 360 |
| cagacaacta | caccttagcc | aacccctaa | gcaccccacc | ccacatcaaa | cccgaatgat | 420 |
| atttcctatt | tgcctacgca | attctccgat | ctgtccccaa | taaactagga | gg | 472 |

<210> SEQ ID NO 166
<211> LENGTH: 472
<212> TYPE: DNA
<213> ORGANISM: Homo sapiens sapiens

<400> SEQUENCE: 166

-continued

```
tcccgtgagg ccaaatatca ttctgagggg ccacagtaat tacaaactta ctatccgcca      60
tcccatacat tgggacagac ctagttcaat gaatctgagg aggctactca gtagacagtc     120
ccaccctcac acgattcttt acctttcact tcatcttgcc cttcattatt gcagccctag     180
caacactcca cctcctattc ttgcacgaaa cgggatcaaa caaccccta ggaatcacct      240 cccattccga taaaatcacc ttccaccctt actacacaat caaagacgcc ctcggcttac     300
ttctcttcct tctctcctta atgacattaa cactattctc accagacctc ctaggcgacc     360
cagacaatta taccctagcc aacccttaa acacccctcc ccacatcaag cccgaatgat      420
atttcctatt cgcctacaca attctccgat ccgtccctaa caaactagga gg             472

<210> SEQ ID NO 167
<211> LENGTH: 472
<212> TYPE: DNA
<213> ORGANISM: Dugong dugong

<400> SEQUENCE: 167
tcccatgagg acaaatatca ttctgaggag caaccgttat tactaacctc ctgtcagcta      60 tccctacat cggcaccaac ctagtcgaat gagtttgagg gggattctca gtagacaaag     120
ccaccctcac ccgattcttc gccctacact tcatcctacc cttcatcgta accgccctag     180
taatagtcca cttactattc ctccacgaaa caggctccaa caccccacg ggactgatct      240 ccgactcaga caaaatccca ttccacccat attattcagt caaagacctc ctaggcctat     300
tcctcctcat tctagtctta ctcctactaa ccctgttctc cccggacata ctgggagacc     360
cagacaacta caccagcc aacccactaa cacccctcc ccacattaaa ccagaatgat        420
actttctatt ccgatacgct atcctccgat ctatccctaa taaactaggc gg             472

<210> SEQ ID NO 168
<211> LENGTH: 472
<212> TYPE: DNA
<213> ORGANISM: Elephas maximus

<400> SEQUENCE: 168
ttccatgagg acaaatatca ttctgagggg caaccgtaat tactaacctc ttctcagcaa      60
ttccctacat cggcacaaac ctagtagaat gaatttgagg aggcttttcg gtagataaag     120
caaccttaaa ccgattcttc gccttccatt tcatccttcc atttactata gttgcactag     180
caggagtgca cctaaccttt cttcacgaaa caggctcaaa cacccacta ggtctcactt      240 cagactcaga caaaattccc tttcacccgt actatactat caaagacttc ctagggctac     300
ttatcctaat tttactcctt ctactcttag ccctactatc tccagacata ctaggagacc     360
ctgacaacta cataccagct gatccactaa atactcccct acacatcaaa ccagagtgat     420
acttcctttt tgcttacgcc attctacgat ctgtaccaaa caaactagga gg             472

<210> SEQ ID NO 169
<211> LENGTH: 472
<212> TYPE: DNA
<213> ORGANISM: Afropavo congensis

<400> SEQUENCE: 169
tcccatgagg ccaaatatca ttctgagggg caactgtcat cacaaaccta tactcagcaa      60 tccctatat tggtcaaacc ctagtagaat gggcctgagg aggattctca gttgacaacc     120
caaccctcac ccgattcttc gccctacact tcttctcccc ctttctaatt gcgggaatta     180
```

```
caattatcca cctcacattc cttcatgaat caggctcaaa caacccactg ggcatctcat    240
ccaattcaga taaaatccca ttccacccgt actactccct caaagatatc ctaggcttag    300
cactcatgct cattccattc ctgacactag ccctactctc ccccaacctc ttaggtgatc    360
cagaaaactt caccccagca aaccctctag taactccccc acacattaaa ccagaatggt    420
atttcttatt tgcctatgcc atccttcgct caatcccaaa caaactagga gg            472
```

<210> SEQ ID NO 170
<211> LENGTH: 472
<212> TYPE: DNA
<213> ORGANISM: Pavo muticus

<400> SEQUENCE: 170

```
tcccatgagg tcaaatgtca ttctgagggg caactgttat cacaaatcta ttctcagcaa     60
tcccttatat tggacaaacc ctagtagaat gagcctgagg gggattctca gtcgacaacc    120
caaccctcac ccgattcttc gccctacact ttctcctccc ctttgtaatc gcaggaatta    180
caattatcca cctcacattc ctccatgaat caggctcaaa taatccacta ggcatctcat    240
ccaactcaga caaaattccg ttccacccat actactccct caaagatatc ctaggcttaa    300
ctcttatatt tatcccattc ctaacactag ccctattctc ccccaatctc ctaggtgacc    360
cagaaaactt taccccagca aaccccctag tacccccccc gcacattaaa ccagaatgat    420
acttcttatt tgcctacgcc atccttcgtt caatccccaa caaactagga gg            472
```

<210> SEQ ID NO 171
<211> LENGTH: 472
<212> TYPE: DNA
<213> ORGANISM: Tragopan blythii

<400> SEQUENCE: 171

```
tcccatgagg acaaatatca ttttgagggg ctaccgtcat cacaaactta ttctcagcaa     60
tcccatacat tggccaaacc ttagtagaat gagcctgagg aggcttttca gttgacaatc    120
caaccctcac tcgattcttc gccctacact tcctcctccc atttgtaatc gcaggaatta    180
ccatcatgca cctcatcttc ttacatgaat caggctctaa taacccactg ggcatctcat    240
ctaactctga caaaatccca ttccacccgt actactccct caaagatatc ctgggtctaa    300
cactcatgct cacccccctc ctcacactag cattattctc accgaaccta ttaggcgacc    360
cagaaaactt caccccagca aaccactag taaccccctcc ccatatcaaa ccagaatgat    420
acttcctatt cgcttatgcc atcctgcgct caatcccaaa caaacttggg gg            472
```

<210> SEQ ID NO 172
<211> LENGTH: 472
<212> TYPE: DNA
<213> ORGANISM: Tragopan satyra

<400> SEQUENCE: 172

```
tcccatgagg acaaatatca ttttgagggg ctaccgtcat tacaaattta ttctcagcaa     60
tcccatacat tggtcaaacc ctagtagaat gagcgtgagg cggcttttca gttgacaatc    120
caaccctcac ccgattcttc gccctacact tcctcctccc atttgtaatc gcaggaatta    180
ctatcataca cctcatcttc ttacatgaat caggctctaa taacccactg ggcatctcat    240
ccaactctga caaaatccca tttcatccat actactccct caaggatatc ctaggcctaa    300
cactcatgct cacccccctc ctcacactag cctattctc accaaaccta ctaggtgatc    360
cagaaaactt caccccagca aacccactag taaccccctcc ccatattaaa ccagaatgat    420
```

―continued

```
acttcctatt cgcctacgcc atcctacgct caatcccaaa caaacttgga gg        472
```

<210> SEQ ID NO 173
<211> LENGTH: 472
<212> TYPE: DNA
<213> ORGANISM: Tragopan caboti

<400> SEQUENCE: 173

```
tcccatgagg acaaatatca ttttgaggag ctaccgtcat cacaaattta ttttcagcaa    60
tcccatacat tggccaaact ctagtagaat gggcctgagg gggcttttca gttgacaatc   120
caacccttac ccgattcttt gcctacact tcctcctccc atttgtaatc gcaggaatca    180
ccatcatcca cctcatcttc ctacatgaat caggctctaa caaccctctg ggcatctcat   240
ctgactctga caaaatccca ttccacccgt actactccct caaagatatc ctgggcctaa   300
cactcatact cactcctctc ctcacactag ccttattttc accaaaccta ctaggtgacc   360
cagaaaactt caccccagca aacccattgg taactcctcc ccatatcaag ccagaatggt   420
atttcctgtt cgcttatgcc atcctacgct caatcccaaa caaactcgga gg           472
```

<210> SEQ ID NO 174
<211> LENGTH: 472
<212> TYPE: DNA
<213> ORGANISM: Tragopan temminckii

<400> SEQUENCE: 174

```
tcccatgagg acaaatatca ttttgagggg ctaccgtcat cacaaattta ttctcagcaa    60
tcccatacat tggccaaacc ctagtagaat gagcttgagg gggcttttca gttgacaatc   120
caacccttac ccgattcttt gcctacact tcctcctccc atttgtaatc gcaggaatta    180
ccatcatcca cctcatcttc ctacatgaat caggctcaaa caaccctcta ggcatctcat   240
ctaactctga caaaatccca ttccacccgt actactccct caaagatatc ctaggcctaa   300
cactcatact cactcccctc ctcacactag ccttattttc accaaaccta ctaggtgatc   360
cagaaaactt caccccagca aacccactag taactcctcc ccatatcaaa ccagaatgat   420
attttctgtt cgcttatgcc atcctgcgct caattccaaa caaactcgga gg            472
```

<210> SEQ ID NO 175
<211> LENGTH: 472
<212> TYPE: DNA
<213> ORGANISM: Argusianus argus

<400> SEQUENCE: 175

```
tcccatgagg acaaatatca ttttgaggag ctaccgtcat cacaaaccta ttctcagcaa    60
tcccttatat tggacaaacc ctagtagagt gagcctgagg aggattttca gtcgacaacc   120
ccacccttac ccgattcttt gctctacatt tcctcctacc cttcgtaatc gcaggaatca   180
ccatcatcca cctcacattc ctacacgaat caggctcaaa caacccacta ggcatctcat   240
ctaactctga caaaatccca ttccacccat actactccct caaagacatc ctaggcctaa   300
cactcatact cgctccattc cttacactaa ccctattcta cccaaaccta ctaggtgacc   360
cagaaaactt caccccagca aacccattag taactccacc ccacatcaag ccagaatgat   420
acttcctatt cgcctatgcc atcctacgct caatcccaaa caaactagga gg            472
```

<210> SEQ ID NO 176
<211> LENGTH: 472
<212> TYPE: DNA

```
<213> ORGANISM: Catreus wallichi

<400> SEQUENCE: 176
ttccatgggg acaaatatca ttttgagggg ctactgtcat cacaaatcta ttctcagcaa      60
tcccttacat cggacagacc ctagtagaat gagcctgagg aggattctca gttgacaatc     120
caactctcac ccgattcttc gccctgcact tcctccttcc cttcgtaatt gcaggaatca     180
ccatcaccca tctcatattc ctacatgaat caggctcaaa taaccccta ggcatctcat      240 ctaactccga caaaatccca ttccacccat actactccct caaagatatc ctaggcctag     300
cacttatatt caccccattc ctaacactag ccctattctc accaaatctt ctgggcgacc     360
cagaaaactt caccccagca aatccattag taaccccacc acacattaaa ccagaatggt     420
acttcttatt tgcctacgct atcctacgct caatcccaaa taaactcgga gg              472

<210> SEQ ID NO 177
<211> LENGTH: 472
<212> TYPE: DNA
<213> ORGANISM: Crossoptilon crossoptilon

<400> SEQUENCE: 177
tcccatgagg acaaatatca ttttgagggg gtaccgtcat cacaaatcta ttctcagcaa      60
tcccttacat tggacaaacc ctagtcgagt gagcctgagg gggattctca gttgacaacc     120
caaccctcac ccgattcttc gccctacact tcctcctccc cttcgtaatt gcaggaatta     180
ctgtcaccca cctcatattc ctacacgaat caggctcaaa caacccacta ggcatctcat     240
ctaattccga caaaatccca ttccaccct actactccct caaagacatc ctaggcctag     300
cacttatact caccccattc ctaacactag ccctattctc acctaaccttt ctgggcgacc    360 cagagaactt caccccagca aacccactag taacccccc tcacattaaa ccagaatgat     420
acttcctatt tgcctatgct atcctgcgct caatcccaaa taaactcgga gg              472

<210> SEQ ID NO 178
<211> LENGTH: 472
<212> TYPE: DNA
<213> ORGANISM: Syrmaticus reevesi

<400> SEQUENCE: 178
tcccatgagg acaaatatca ttttgagggg caaccgtcat cacaaattta ttctcagcaa      60 tccctacat cggacaaacc ctagtagagt gggcctgagg aggattctca gttgacaacc      120
caaccctcac ccgattcttc gcccttcact ttctcctacc cttcgtaatc acaggaatca     180
ccatcacaca tcttatgttc ctacacgaat caggctcaaa caacccacta ggcatttcat     240
ctaactctga caaaatcccc tttcacccat actactctct caaagatatc ctaggcctag     300
cacttatact caccccattc ctcacactag ccctattctc acctaacctg ctaggcgacc     360
cagaaaactt caccccagca aacccactag taaccctcc tcacattaaa ccagaatgat      420
acttcctatt tgcctacgcc atcctacgct caatcccaaa caaactgggg gg              472

<210> SEQ ID NO 179
<211> LENGTH: 472
<212> TYPE: DNA
<213> ORGANISM: Bambusicola thoracica

<400> SEQUENCE: 179
tcccatgggg ccaaatatcc ttttgagggg ctaccgtcat cacaaattta ttctcagcaa      60
ttccctacat cggacaaacc ctagtagaat gagcctgggg gggattctca gtagacaacc     120
```

```
caactctcac cgattcttc gccttacact tcctactccc cttcgtaatc gcaggaatta      180
ccattatcca cctcacattc ttacacgaat caggatcaaa caacccccta ggcatctcat      240
ctaactccga caaaatccca ttccaccat actactcctt aaagacatt ctcggcctag      300 cccttatatt catcccattc ctgacactag ccctattctc ccctaacctc ctaggagacc      360
cagaaaactt cacccagca aacccactag taacccctcc acacatcaaa ccagagtggt      420
acttcctatt cgcgtatgct atcgtacgat caatccccaa caaactcgga gg            472

<210> SEQ ID NO 180
<211> LENGTH: 472
<212> TYPE: DNA
<213> ORGANISM: Francolinus francolinus

<400> SEQUENCE: 180
tcccatgagg ccaaatatca ttctgagggg ctaccgtcat tacgaaccta ttctcagcaa       60
ttccctacat tggacaaacc ttagtagagt gagcctgagg gggattctca gtagataacc      120
caaccctcac cgattcttc gccctacact tccttctccc cttcgtaatt gcaggaatca      180
ctatcatcca cctcacattt ctgcacgaat caggctcaaa caacccccta ggcatctcat      240
ctgactctga caaaatccca ttccaccat actacaccct caaagacatc ctaggcctaa      300
cccttatatt catccctctc cttacactag ccctattctc cccaacctc ctaggcgacc      360 ccgaaaactt cacccagca aacccactag taactcctcc ccacatcaaa ccagaatgat      420
acttcctatt tgcctacgcc atcctacgct caatccccaa caaactcgga gg            472

<210> SEQ ID NO 181
<211> LENGTH: 472
<212> TYPE: DNA
<213> ORGANISM: Ithaginis cruentus

<400> SEQUENCE: 181
taccatgagg acaaatatca ttctgaggag ccactgtaat cacaaaccta ctctcagcaa       60
ttccctacat cggccaaact ctggtagaat gagcttgagg aggatttttca gtagacaacc      120 caaccctcac cgattcttc gccctacact ttctcctccc cttcgcaatc gcaggaatta      180
ctgtcatcca ccttacactc ctccacgaat caggttcaaa taacccacta ggcatctcat      240
ctaactctga caaaatccca tttcaccat actactccct caaagacatc ctaggcctag      300
cacttatact catcccctttt cttacactag tcctatttttc ccccaacctc ctaggagatc      360
cagaaaactt tagtccagca aaccccctag taaccccacc ccatattaaa ccagaatgat      420
acttcctatt tgcctacgct attctacgct caatccccaa taaacttgga gg            472

<210> SEQ ID NO 182
<211> LENGTH: 472
<212> TYPE: DNA
<213> ORGANISM: Anthropoides paradisea

<400> SEQUENCE: 182
taccatgagg acaaatgtca ttttgagggg ctacagtcat caccaatctc ttctcagccg       60
tcccatatat cggccaaacc cttgtagaat gagcttgagg gggtttctca gtagacaatc      120
ccacattaac tcgattcttc actttacact tcctccttcc attcataatt atgggcctca      180
ccctaatcca cctcaccttc cttcacgagt ccggctcaaa caacccccta ggcattgtat      240
caaactgcga taaaatccca ttccacccct attttttcctt aaaagatatc ctaggattca      300
```

```
tactcatact actcccactc ataaccctag ctctattctc accaaactta ctaggagacc      360
cagaaaactt caccccagca aaccccctag tcacacctcc ccatatcaaa ccagaatgat      420
atttcttatt tgcgtatgcc atcctacgtt caattccaaa caaactagga gg              472
```

<210> SEQ ID NO 183
<211> LENGTH: 472
<212> TYPE: DNA
<213> ORGANISM: Anthropoides virgo

<400> SEQUENCE: 183

```
taccatgggg acaaatgtca ttttgagggg ctacagttat caccaatctc ttctcagccg      60
tcccatacat cggccaaacc cttgtagaat gagcttgagg gggttttttca gtagataatc     120 ccacattaac tcgattcttc acgttacact tcctccttcc attcataatt atgggcctca     180
ccctaatcca cctcaccttc cttcacgaat ccggctcaaa caaccccta ggcatcgtat      240 caaactgcga taaaatccca ttccacccct attttccctt aaaagatatc ctaggattca    300
tactcatact actcccactc ataaccctag ctctattctc accaaactta ctaggagacc    360
cagaaaactt ccccccagca aatccctag tcacacctcc ctatattaaa ccagaatgat     420
atttcttatt tgcatacgcc atcctacgtt caattccaaa caaactagga gg             472
```

<210> SEQ ID NO 184
<211> LENGTH: 472
<212> TYPE: DNA
<213> ORGANISM: Grus antigone antigone

<400> SEQUENCE: 184

```
taccatgagg acaaatatca ttttgagggg ctacagtcat caccaatctc ttctcagccg      60 tccctacat cggccaaacc cttgtagaat gagcttgagg gggcttctca gtagacaatc     120
ccacattaac tcgattcttc actttacact tcctccttcc attcataatc ataggcctca   180
ccctaatcca cctcaccttc cttcacgaat ccggctcaaa caaccccta ggcatcgtat     240 caaactgcga taaaatccca ttccacccct acttttcctt aaaagatatc ctaggattca   300
cactcatact acttccactc ataaccctag ccctattctc accaaaccta ctaggagacc    360
cagaaaactt caccccagca aaccccctag tcacacctcc tcatatcaag ccagaatgat    420
actttttatt tgcatacgcc atcctacgtt caatcccaaa caaactagga gg             472
```

<210> SEQ ID NO 185
<211> LENGTH: 472
<212> TYPE: DNA
<213> ORGANISM: Grus antigone gillae

<400> SEQUENCE: 185

```
taccatgagg acaaatatca ttttgagggg ctacagtcat caccaatctc ttctcagccg     60 tccctacat cggccaaacc cttgtagaat gagcttgagg gggcttctca gtagacaatc    120
ccacattaac tcgattcttc actttacact tcctccttcc attcataatc ataggcctca   180
ccctaatcca cctcaccttc cttcacgaat ccggctcaaa caaccccta ggcatcgtat    240 caaactgcga taaaatccca ttccacccct acttttcctt aaaagatatc ctaggattca   300
cactcatact acttccactc ataaccctag ccctattctc accaaaccta ctaggagacc   360
cagaaaactt caccccagca aaccccctag tcacacctcc tcatatcaag ccagaatgat   420
actttttatt tgcatacgcc atcctacgtt caatcccaaa caaactagga gg            472
```

<210> SEQ ID NO 186
<211> LENGTH: 472
<212> TYPE: DNA
<213> ORGANISM: Grus antigone sharpei

<400> SEQUENCE: 186

| | | | | | |
|---|---|---|---|---|---|
| taccatgagg | acaaatatca | ttttgagggg | ctacagtcat | caccaatctc | ttctcagccg | 60 |
| tcccctacgg | cggccaaacc | cttgtagaat | gagcttgagg | gggcttctca | gtagacaatc | 120 |
| ccacattaac | tcgattcttc | actttacact | tcctccttcc | cttcataatc | ataggcctca | 180 |
| ccctaatcca | cctcaccttc | cttcacgaat | ccggttcaaa | caaccccta | ggcatcgtat | 240 |
| caaactgcga | taaaatccca | ttccacccct | acttttcctt | aaaagatatc | ctaggattca | 300 |
| cactcatact | acttccactc | ataaccctag | ccctattctc | accaaaccta | ctaggagacc | 360 |
| cagaaaactt | caccccagca | aaccccctag | tcacacctcc | ccatatcaag | ccagaatgat | 420 |
| acttttatt | tgcatacgcc | atcctacgtt | caatcccaaa | caaactagga | gg | 472 |

<210> SEQ ID NO 187
<211> LENGTH: 472
<212> TYPE: DNA
<213> ORGANISM: Grus leucogeranus

<400> SEQUENCE: 187

| | | | | | |
|---|---|---|---|---|---|
| taccatgagg | acaaatatca | ttttgagggg | ctacagtcat | caccaatctc | ttctcagccg | 60 |
| tcccctacat | cggccaaacc | cttgtagaat | gagcttgagg | gggcttctca | gtagacaacc | 120 |
| ccacattaac | tcgattcttc | actttacact | tcctccttcc | attcataatc | ataggcctca | 180 |
| ccctaatcca | cctcaccttc | cttcacgaat | ccggctcaaa | caaccccta | ggcatcgtat | 240 |
| caaactgcga | taaaatccca | ttccacccct | acttttcctt | aaaagatatc | ctagggttca | 300 |
| tactcatact | acttccactc | ataaccttag | ccctattctc | accaaactta | ctaggagacc | 360 |
| cagaaaactt | cactccagca | aaccccctag | taacacccc | acatattaaa | ccagaatgat | 420 |
| acttcctatt | tgcatacgcc | atccgacgtt | caatcccaaa | caaactagga | gg | 472 |

<210> SEQ ID NO 188
<211> LENGTH: 472
<212> TYPE: DNA
<213> ORGANISM: Grus canadensis pratensis

<400> SEQUENCE: 188

| | | | | | |
|---|---|---|---|---|---|
| tgccatgagg | acaaatatca | ttctgagggg | ctacagtcat | taccaacctc | ttctcagccg | 60 |
| tcccatacat | cggccaaacc | ctcgtagaat | gggcttgagg | gggcttctca | gtagacaatc | 120 |
| ccacattaac | ccgattcttc | actttacact | tcctcctccc | attcataatt | ataggcctca | 180 |
| ccctaatcca | cctcaccttc | cttcacgaat | ccggctcaaa | caaccccta | ggcattgtat | 240 |
| caaactgcga | taaaatccca | ttccacccct | attttcctt | aaaagatatc | ctagggttca | 300 |
| tactcatact | acttccactc | ataaccctag | ctctattttc | accaaactta | ctaggagacc | 360 |
| cagaaaactt | caccccagca | gaccccctag | tcacacctcc | ccatatcaaa | ccagaatgat | 420 |
| acttttatt | tgcctacgcc | atcttacgct | caatcccaaa | caaactagga | gg | 472 |

<210> SEQ ID NO 189
<211> LENGTH: 472
<212> TYPE: DNA
<213> ORGANISM: Grus canadensis rowani

<400> SEQUENCE: 189

```
tgccatgagg acaaatatca ttctgagggg ctacagtcat taccaacctc ttctcagccg        60
tcccatacat cggccaaacc ctcgtagaat gggcttgagg gggcttctca gtagacaatc       120
ccacattaac ccgattcttc actttacact tcctcctccc attcataatt ataggcctca       180
ccctaatcca cctcaccttc cttcacgaat ccggctcaaa caatccccta ggcattgtat       240
caaactgcga taaaatccca ttccacccct attttcctt aaaagatatc ctagggttca        300
tactcatact acttccactc ataaccctag ctctattttc accaaactta ctaggagacc       360
cagaaaactt cacccccagca aacccccctag tcacacctcc ccatatcaaa ccagaatgat    420 acttttttatt tgcctacgcc atcttacgct caatcccaaa caaactagga gg              472
```

<210> SEQ ID NO 190
<211> LENGTH: 472
<212> TYPE: DNA
<213> ORGANISM: Grus canadensis tabida

<400> SEQUENCE: 190

```
taccatgagg acaaatatca ttctgagggg ctacagtcat taccaacctc ttctcagccg        60
tcccatacat cggccaaacc ctcgtagaat gggcttgagg gggcttctca gtagacaatc       120
ccacattaac ccgattcttc actttacact tcctcctccc attcataatt ataggcctca       180
ccctaatcca cctcaccttc cttcacgaat ccggctcaaa caacccccta ggcattgtat       240
caaactgcga taaaatccca ttccacccct attttcctt aaaagatatc ctagggttca        300
tactcatact acttccactc ataaccctag ctctattttc accaaactta ctaggagacc       360
cagaaaactt cacccccagca aacccccctag tcacacctcc ccatatcaaa ccagaatgat    420 acttttttatt tgcctactcc atcttacgct caatcccaaa caaactagga gg              472
```

<210> SEQ ID NO 191
<211> LENGTH: 472
<212> TYPE: DNA
<213> ORGANISM: Grus canadensis canadensis

<400> SEQUENCE: 191

```
taccatgggg acaaatatca ttctgagggg ctacagtcat taccaacctc ttctcagccg        60
tcccatacat cggccaaacc ctcgtagaat gggcttgagg gggcttctca gtagacaatc       120
ccacattaac ccgattcttc actttacact tcctcctccc attcataatt ataggcctca       180
ccctaatcca cctcaccttc cttcacgaat ccggctcaaa caacccccta ggcattgtat       240
caaactgcga taaaatccca ttccacccct attttcctt aaaagatatc ctagggttca        300
tactcatact acttccactt ataaccctag ctctattctc accaaactta ctaggagacc       360
cagaaaactt cacccccagca aacccccctag tcacacctcc ccatatcaaa ccagaatgat    420 acttttttatt tgcctacgcc atcttacgct caatcccaaa caaactagga gg              472
```

<210> SEQ ID NO 192
<211> LENGTH: 472
<212> TYPE: DNA
<213> ORGANISM: Grus americana

<400> SEQUENCE: 192

```
taccatgagg acaaatatca ttttgagggg ctacagttat caccaatctc ttctcagccg        60
tcccatacat cggccaaacc atcgtagaat gagcttgagg gggcttctct gtagacaacc       120
ccacattaac ccgattcttc actttacact tcctcctccc attcataatc ataggcctca       180
ccctaatcca cctcaccttc ctccacgaat ccggctcaaa caacccccta ggcatcgtat       240
```

```
caaactgcga taaaatccca ttccaccect attttteett aaaagacatc ctaggattca      300
cactcatatt acttccactc ataaccctag ctctattttc accaaactta ctaggagacc      360
cagaaaactt caccccagca aaccccctag tgacacctcc ccatattaag ccggaatgat      420 acttttatt  tgcatacgcc atcctacgtt caatcccaaa caaactagga gg              472
```

<210> SEQ ID NO 193
<211> LENGTH: 472
<212> TYPE: DNA
<213> ORGANISM: Grus grus

<400> SEQUENCE: 193

```
taccatgggg acaaatgtca ttttgagggg ctacagttat caccaatctc ttctcagccg       60
tcccatacat cggccaaacc ctcgtagaat gagcttgagg gggcttctca gtagacaacc      120
ccacattaac ccgattcttc accttacact tcctcctccc attcataatc ataggcctca      180
ccctaatcca cctcaccttc cttcacgaat ccggctcaaa caaccccta  ggcatcgtat      240 caaactgcga taaatccca  ttccacccct attttteett aaaagatatc ctagggttca      300
tactcatatt acttccactc ataaccctag ctctattttc accaaactta ctaggagacc      360
cagaaaactt caccccagca aaccctctag tcacacctcc ccatattaag ccggaatgat      420 acttttatt  tgcatacgcc atcctccgtt caatcccaaa caaactagga gg              472
```

<210> SEQ ID NO 194
<211> LENGTH: 472
<212> TYPE: DNA
<213> ORGANISM: Grus monacha

<400> SEQUENCE: 194

```
taccatgagg acaaatatca ttttgagggg ctacagttat caccaacctc ttctcagccg       60
tcccatacat cggccaaacc ctcgtagaat gagcttgagg aggcttctca gtagacaacc      120
ccacattaac tcgattcttc accttacact tcctcctccc attcataatc ataggcctca      180
ccctaatcca cctcaccttc ctccacgaat ccggctcaaa caaccccta  ggcatcgtat      240 caaactgcga taaattcca  ttccaccect attttteett aaaagatatc ctaggattca      300
tattcatatt acttccactc ataaccctag ctctattttc accaaactta ctaggagacc      360
cagaaaactt caccccagca aaccccctag tcacacctcc tcatattaaa ccggaatgat      420
actttctatt tgcatacgcc gtcctacgtt caatcccaaa caaactagga gg              472
```

<210> SEQ ID NO 195
<211> LENGTH: 472
<212> TYPE: DNA
<213> ORGANISM: Grus nigricollis

<400> SEQUENCE: 195

```
taccatgagg acaaatatca ttttgagggg ctacagttat caccaacctc ttctcagccg       60
tcccatacat cggccaaacc ctcgtagaat gagcttgagg aggcttctca gtagacaacc      120
ccacattaac tcgattcttc accttacact tcctcctccc attcataatc ataggcctca      180
ccctaatcca cctcaccttc ctccacgaat ccggctcaaa caaccccta  ggcatcgtat      240 caaactgcga taaattcca  ttccaccect attttteett aaaagatacc ctaggattca      300
tattcatatt acttccactc ataaccctag ctctattttc accaaactta ctaggagacc      360
cagaaaactt caccccagca aaccccctag tcacacctcc ccatattaag ccggaatgat      420
```

```
actttctatt tgcatacgct atcctacgtt caatcccaaa caaactagga gg    472
```

<210> SEQ ID NO 196
<211> LENGTH: 472
<212> TYPE: DNA
<213> ORGANISM: Grus japonensis

<400> SEQUENCE: 196

```
taccatgggg acaaatatcc ttttgagggg ctacagttat caccaatctc ttctcagccg    60
tcccatacat cggccaaacc ctcgtagaat gagcttgagg gggcttctca gtagacaacc   120
ccacattaac tcgattcttt accttacact tcctcctccc attcataatc ataggcctca   180
ccctaatcca tctcactttc ctccacgaat ccggctcaaa cacccccta ggcatcgtat    240
caaactgtga taaaatccca ttccacccct attttccttt aaaagatatc ttaggattta   300
cactcatatt acttccactc ataaccctag ccctattctc accaaactta ctaggagacc   360
cagaaaactt caccccagca aaccccctag ttacacctcc ccatattaag ccggaatgat   420
acttcttatt tgcatacgct attctgcgtt caatcccaaa caaactagga gg            472
```

<210> SEQ ID NO 197
<211> LENGTH: 472
<212> TYPE: DNA
<213> ORGANISM: Ciconia boyciana

<400> SEQUENCE: 197

```
tgccatgagg acagatatca ttctgagggg ctacagtcat caccaaccta ttttcagcta    60
tccctacat cggccaaacc ctcgtagaat gggcctgagg gggcttctcc gtcgataacc    120
caacactaac ccgattcttc gccctacact tccttctccc cttcgcaatc gcaggcctca   180
ccctaatcca cctcaccttc cttcacgagt ccggctcaaa cacccccta ggcatcatct    240
caaactgcga caaaattcca ttccacccct acttctccct caaagatatc ctaggcctta   300
cactcctact tctgccacta accaccctgg ccctattctc acccaaccta ctaggtgacc   360
cagagaactt caccccagcc aaccccctag tcacacccccc tcacatcaag ccagagtggt   420
acttcctctt tgcatacgcc atcctacgct ccatccccaa caaactagga gg            472
```

<210> SEQ ID NO 198
<211> LENGTH: 472
<212> TYPE: DNA
<213> ORGANISM: Rhea americana

<400> SEQUENCE: 198

```
taccatgagg acaaatatca ttctgaggag ctacagttat taccaaccta ttctcagcca    60
tcccgtacat cggacaaacc ttggtagaat gagcttgagg ggggttttca gtagacaacc   120
ctaccctaac ccgattcttc gccctgcact tccttctccc cttcctaatc gcaggcatta   180
ctcttatcca cctcaccttc ctacacgaaa ccgggtccaa cacccccta ggaatcgtat    240
ctcactctga caaaatccca ttccacccct acttctccct aaaagatgcc ctaggactag   300
ctctcatatt tatcccgctc ctaacccctag ccttcttctc acccaacctc ctaggggacc   360
cagaaaactt caccccagcc aaccccctag ttacaccccc tcacatcaag ccagaatgat   420
atttcctatt cgcttacgcc atcttacgct ccatccccaa caaactagga gg            472
```

<210> SEQ ID NO 199
<211> LENGTH: 472
<212> TYPE: DNA
<213> ORGANISM: Anthracoceros albirostris -continued

<400> SEQUENCE: 199

```
taccatgagg gcaaatatca ttctgaggcg ccaccgtcat caccaaccta ttctcagcca        60
tcccatacat cggccaaacc ttagtagaat gggcctgagg gggattctcc gttgacaacc       120
caaccctgac acgattcttc gccctacact ttctcctccc gttcataatc gcaggcctag       180
tcctaattca cctggcattc ctccacgaat caggctcaaa caacccacta ggcatcacat       240
ccaactgcga caaaatccca ttccacccat actttgccct aaaggacatc ctaggattca       300
cagtaatact cctcctccta acctcccctag ccctcttctc ccccaaccta ctaggagacc      360
cagaaaactt cacaccagca aaccccctgg taactccccc ccatattaag ccagaatggt       420
atttcctatt cgcatatgcc atcctacgct caatccccaa taaactagga gg               472
```

<210> SEQ ID NO 200
<211> LENGTH: 472
<212> TYPE: DNA
<213> ORGANISM: Falco femoralis

<400> SEQUENCE: 200

```
taccctgagg acaaatatca ttctgagggg ctacagttat caccaaccta ttttcagcaa        60
tcccatacat cggtcaaacc ctagtcgagt gggcctgagg aggattttca gtagacaatc       120
caacactgac ccgattcttc gccctacact tcctcctacc attcctaatc gcagggctca       180
ccttaatcca cctcaccttc ctacatgaat caggttcaaa caaccccccta ggaatcacat      240 caaactgcga taaaatccca ttccatccct attactctct caaagacctc ctaggattca       300
tactcatata cctcccccta ataaccttag ccctattcac tcccaaccta ctaggagacc       360
cagaaaactt tacaccagca aatccccctag tcacccccccc acacatcaaa ccagaatgat     420
acttcctatt cgcctacgcc atcctacgct caatccccaa caaactaggt gg               472
```

<210> SEQ ID NO 201
<211> LENGTH: 472
<212> TYPE: DNA
<213> ORGANISM: Falco verpertinus

<400> SEQUENCE: 201

```
taccctgagg acaaatatca ttctggggag ccacagtcat cactaaccta ttttcagcaa        60
tcccatacat cggccaaacc ctagtcgaat gggcctgagg aggattttca gtagataacc       120
caacactaac ccgattcttc gccctacact ttctcctacc attcctaatc gcagggctca       180
ccctaattca cctcaccttc ctacacgaat caggttcaaa caaccccccta ggaatcacat      240 caaactgcga caaaatccca ttccatccct actactctct aaaagacctt ttaggagtca       300
tactcatata cctcccccta ataaccctag ccctatttac cccaaactta ctaggagacc       360
cagaaaactt cacaccagca aaccccctag tcacacccccc acacatcaaa ccagaatgat      420
acttcctatt tgcctacgcc atcctacgct caatccccaa caaactgggt gg               472
```

<210> SEQ ID NO 202
<211> LENGTH: 472
<212> TYPE: DNA
<213> ORGANISM: Falco peregrinus

<400> SEQUENCE: 202

```
taccctgagg acaaatatca ttctgaggag ccacagtcat taccaaccta ttctcagcaa        60
tcccatacat cggccaaacc ctagtcgaat gagcttgagg gggattttca gtagacaacc       120
```

```
caacactgac cgattcttc gccctacact tcctacttcc attcctaatc gcaggactca    180
ccctaatcca cctcaccttc ctacatgaat caggctcaaa taaccccta  ggaatcacat    240 caaattgcga caaaatccca ttccacccat actactctct caaagatatc ctaggattta    300
tactcatata cctgcccta  ataaccctag ccctatttac cccaaacctg ctaggagacc    360
cagaaaactt tacaccagca atcccttag  tcacccccc  acacatcaaa ccagaatgat    420
acttcctatt tgcttacgcc atcctacgct caatccccaa taaactgggc gg            472
```

<210> SEQ ID NO 203
<211> LENGTH: 472
<212> TYPE: DNA
<213> ORGANISM: Falco sparverius

<400> SEQUENCE: 203

```
taccctgagg acaaatgtca ttctgaggag ccacagtcat taccaaccta ttctcagcaa    60
tcccatatat cggccaaacc ctagtcgaat gggcctgagg aggattctca gtagacaacc    120
caacactaac ccgcttcttc gccttacact tcctcctacc attcctaatc gcagggctta    180
ccttaatcca cctcaccttc ctacatgaat caggttccaa caacccccta ggagtcacat    240
caaactgtga caaaatccca ttccacccct actactctct caaagacctc ctaggtttta    300
tgctcatact cctgcccta  atagccctag ccctattcac cccaaacctg ctaggagacc    360
cagaaaactt cacaccagcg aaccccctag tcacccccacc acacatcaaa ccagaatgat    420
acttcctatt tgcctacgct attctacgct caattcccaa caaattaggc gg            472
```

<210> SEQ ID NO 204
<211> LENGTH: 472
<212> TYPE: DNA
<213> ORGANISM: Aythya americana

<400> SEQUENCE: 204

```
taccatgagg acaaatatca ttctgagggg ccaccgtgat cactaacctg ttctcagccc    60
tcccatacat cgggcaaacc cttgtagaat gggcctgagg aggattctcg gtagacaacc    120
caaccctaac tcgattcttc gccatccact tcctactacc cttcctaatc gcaggaatca    180
ccctagtcca cctaactttc ctgcacgagt caggctcaaa caacccccta ggcattgtat    240
cagactgcga caaaatccca tttcacccct acttctcctt caaagacatc ctaggattta    300
tcctcatgct cacccccta  atagcactag ccctattctc accaaacctc ctaggagacc    360
cagaaaactt taccccagca aacccactag taacccccacc ccacatcaaa ccagaatgat    420
acttcctatt cgcctacgcc atcctgcgat caatcccgaa taaactagga gg            472
```

<210> SEQ ID NO 205
<211> LENGTH: 472
<212> TYPE: DNA
<213> ORGANISM: Smithornis sharpei

<400> SEQUENCE: 205

```
tcccatgagg ccaaatatca ttctgaggtg ctacagtaat caccaacctc ttctcagcta    60
ttccatacat cggacaaacc ctagtagaat gagcttgggg aggattttca gtagacaacc    120 ccaccttac  ccgattcttc tcccttcact tcctcctccc atttatcatc gcaagcctga    180
cactcatcca tctcaccttc ctcatgaaa  caggttcaaa caaccctcta ggtatctcat    240
ctaactccga taaaatccca ttccacccat acttctccat aaaagacatt ctaggctttg    300
caatcatact aacaccacta ataaccctag ccatattctc tcctaacctc ctaggagacc    360
```

```
cagaaaattt cacacccgcc aactccctcg tcactccccc tcatatcaaa cccgaatgat    420
attttttatt tgcatacgct attctgcgat caattccaaa caaactagga gg           472

<210> SEQ ID NO 206
<211> LENGTH: 472
<212> TYPE: DNA
<213> ORGANISM: Vidua chalybeata

<400> SEQUENCE: 206
tgccatgagg acaaatatca ttctgaggag ccacagtaat cacaaaccta ttctcagcaa     60
ttccatacat tggccaaacc ctagtagaat gagcctgagg aggattctca gtagacaacc    120
caacactcac ccgattcttc gccctacact tccttctacc cttcgtcatt gcaggactca    180
ctctagtcca cctcacattc ctacacgaaa caggatcaaa caatccaata ggaattccat    240
cagactgtga caaaattcca ttccacccat actacaccac aaaggacatc ctaggcttcg    300
tactaatatt cgcactccta gcttccatag ccctattctc cccaaacata ctaggagatc    360
cagaaaactt cactccggcc aaccccctaa tcacaccacc acatatcaaa cccgaatgat    420
acttcctatt cgcctacgcc atcctacgat ccatcccaaa caaactagga gg            472

<210> SEQ ID NO 207
<211> LENGTH: 472
<212> TYPE: DNA
<213> ORGANISM: Chrysemys picta

<400> SEQUENCE: 207
taccatgggg ccaaatatcc ttctgaggtg ccaccgttat tactaacctc ctctcagcca     60
tcccattcat tggtaacaca ttagtacaat gaatctgagg tggattctca gtagacaacg    120
caaccttaac ccgatttttt accttcact tccttctacc atttacaatc ataggtctaa    180
caatagtaca cctactttt ctacatgaaa ctggatcaaa caacccaaca ggattaaact    240
caaacactga caaaatccca ttccacccct atttctcata taaagacctt ttaggcgtca    300
ttctaatact aaccctccta ctaaccctaa cactattctc tccaaacctt ttaggggacc    360
cagataactt cacaccggcc aaccccctat ctaccccacc acatattaaa ccagaatgat    420
actttctttt cgcttacgca attctacgat ccatcccaaa caaattaggt gg            472

<210> SEQ ID NO 208
<211> LENGTH: 472
<212> TYPE: DNA
<213> ORGANISM: Emys orbicularis

<400> SEQUENCE: 208
taccatgagg ccaaatatcc ttctgaggtg ccaccgttat tactaacctc ctctcagccg     60
tcccatacat tggcaataca ctagtgcaat gaatctgagg gggattctca gtagataacg    120
caaccctaac ccgattcttc actttccatt tcttactgcc atttaccatt ataggcctaa    180
caatagtaca cctactcttc ctacacgaaa ccggatcaaa caatccaaca ggattaaact    240
caaacaccga taaaatccct ttccatccct acttctcata caaagaccta ttaggactca    300
tcctaatact agccttcctg ctaaccctaa cactattctc tcctaacctt ctaggagacc    360
cagataactt tacaccagct aacccgctat ccaccccacc acatattaag ccagagtgat    420
actttctttt tgcctacgca atcctacgat caatcccaaa caaattagga gg            472

<210> SEQ ID NO 209
```

<211> LENGTH: 472
<212> TYPE: DNA
<213> ORGANISM: Chelonia mydas

<400> SEQUENCE: 209

```
taccatgagg acaaatatca ttttgagggg ccaccgtcat cacaaaccta ctctcagcca    60
tcccatacat cggcaacaca ctagtacaat gaatctgagg agggttttca gtagacaatg   120
caaccctaac ccgattcttc accttccact tcctatacc atttgccatt accggcctta   180
cagcagtaca tctattattc ctgcacgaaa caggatcaaa caacccaaca ggattaaatt   240
caaataccga caaaatcccc ttccacccct acttctccta caaagactta ctaggactca   300
ttttaatact aactttcctc ctaaccttaa cacttttctc cccctactta ctaggagacc   360
cagacaactt cacaccagcc aaccctctat ccactcctcc ccacatcaaa ccagaatgat   420
acttcctatt tgcctacgca atcctacgat caatcccaaa caaactaggc gg           472
```

<210> SEQ ID NO 210
<211> LENGTH: 472
<212> TYPE: DNA
<213> ORGANISM: Eumeces egregius

<400> SEQUENCE: 210

```
tcccatgggg acagatatcc ttctgaggcg caaccgtaat tacaaaccta ttatcagcaa    60
ttccatacat tggcaccaac ctagtagaat gaatttgagg gggcttttcc gtagacaacg   120
caaccctcac ccgattttc acattccact tccttctgcc attcgctatt ataggggcct   180
caataattca cctactattt cttcacgaaa caggatcaaa taacccaacc ggactaaatt   240
ctagcacaga taaggtgcca ttccacccat attacacata caaagacctt cttggtttca   300
tcattatact gtctgttcta ctagccctcg cccttttctc accaaacctt ctaggcgacc   360
cagaaaattt taccccagca aaccccctgg taacacccc acatattaag ccagagtgat   420
acttcttatt tgcctacgcc atcctacgct ctattccaaa caaactaggc gg           472
```

<210> SEQ ID NO 211
<211> LENGTH: 472
<212> TYPE: DNA
<213> ORGANISM: Antelope cervicapra

<400> SEQUENCE: 211

```
taccatgagg acaaatatct ttttgaggag caacagtcat caccaatctc ctttcagcaa    60
tcccatacat cggtacaaac ctagtagaat gaatctgagg agggttctca gtagataaag   120
caacccttac ccgatttttc gccttccact ttatcctccc atttatcatt gcagccctta   180
ccatagtaca cctactgttt ctccacgaaa caggatccaa caaccccaca ggaatctcat   240
cagacgcaga caaaattcca ttccacccct actacactat caaagatatc ctaggagctc   300
tactattaat tttaaccctc atgcttctag tcctattctc accggacctg cttggagacc   360
cagacaacta tacaccagca aacccactta atacacccc acatatcaag cccgaatgat   420
acttcctatt tgcatacgca atcctccgat caattcctaa caaactagga gg           472
```

<210> SEQ ID NO 212
<211> LENGTH: 25
<212> TYPE: DNA
<213> ORGANISM: Artificial Sequence
<220> FEATURE:
<223> OTHER INFORMATION: Universal primer for amplifying a fragment of
      cytochrome b gene of animal species in polymerase chain reaction -continued

```
<400> SEQUENCE: 212
taccatgagg acaaatatca ttctg                                          25

<210> SEQ ID NO 213
<211> LENGTH: 26
<212> TYPE: DNA
<213> ORGANISM: Artificial Sequence
<220> FEATURE:
<223> OTHER INFORMATION: Universal primer for amplifying a fragment of
      cytochrome b gene of animal species in polymerase chain reaction

<400> SEQUENCE: 213
cctcctagtt tgttagggat tgatcg                                         26

<210> SEQ ID NO 214
<211> LENGTH: 22
<212> TYPE: DNA
<213> ORGANISM: Artificial Sequence
<220> FEATURE:
<223> OTHER INFORMATION: Universal primer for amplifying a fragment of
      cytochrome b gene of animal species in polymerase chain reaction

<400> SEQUENCE: 214
tagtagaatg aatctgagga gg                                             22

<210> SEQ ID NO 215
<211> LENGTH: 22
<212> TYPE: DNA
<213> ORGANISM: Artificial Sequence
<220> FEATURE:
<223> OTHER INFORMATION: Universal primer for amplifying a fragment of
      cytochrome b gene of animal species in polymerase chain reaction

<400> SEQUENCE: 215
atgcaaatag gaagtatcat tc                                             22

<210> SEQ ID NO 216
<211> LENGTH: 472
<212> TYPE: DNA
<213> ORGANISM: Aepyceros melampus
<220> FEATURE:
<221> NAME/KEY: misc_feature
<222> LOCATION: (104)..(104)
<223> OTHER INFORMATION: uknown
<220> FEATURE:
<221> NAME/KEY: misc_feature
<222> LOCATION: (107)..(107)
<223> OTHER INFORMATION: uknown
<220> FEATURE:
<221> NAME/KEY: misc_feature
<222> LOCATION: (128)..(128)
<223> OTHER INFORMATION: uknown
<220> FEATURE:
<221> NAME/KEY: misc_feature
<222> LOCATION: (368)..(368)
<223> OTHER INFORMATION: uknown
<220> FEATURE:
<221> NAME/KEY: misc_feature
<222> LOCATION: (369)..(369)
<223> OTHER INFORMATION: uknown
<220> FEATURE:
<221> NAME/KEY: misc_feature
<222> LOCATION: (431)..(431)
<223> OTHER INFORMATION: uknown

<400> SEQUENCE: 216
tgccatgagg acaaatatca ttctgaggag caacagtcat tacaaatctc ctctcagcaa    60
tcccatacat tggtacaaac ctagtagaat gaatctgagg aggnttntca gtagacaaag   120
```

```
caaccctnac ccgattttc gcyttccact tcatcyttcc attcatcatt gcggcactag    180
ccatagtcca cctactcttt cttcacgaaa caggatctaa caaccctaca ggaatcttat    240
cagattcaga taaaattcca ttccacccett actatactat traagacatc ctaggaatcc    300
tattaataat tctagtccta atactcctag tactattcat acccgaccta ctaggagacc    360
cagacaanna catccccgca aaccactca acacccctcc ccacatcaag cccgaatggt    420
acttcctgtt ngcatacgca atcctacgat caatccccaa taaactagga gg           472
```

<210> SEQ ID NO 217
<211> LENGTH: 472
<212> TYPE: DNA
<213> ORGANISM: Oreotragus oreotragus
<220> FEATURE:
<221> NAME/KEY: misc_feature
<222> LOCATION: (425)..(425)
<223> OTHER INFORMATION: unknown
<220> FEATURE:
<221> NAME/KEY: misc_feature
<222> LOCATION: (431)..(431)
<223> OTHER INFORMATION: unknown

<400> SEQUENCE: 217

```
ttccgtgagg acaaatatca ttttgagggg ctacagtcat tactaatctc ctctcagcaa    60
ttccatatat tggcacaaac ctggtagaat gaatctgagg aggattctcg gtggacaaag   120
caacccttac ccgattcttt gcctttcact tcatctttcc atttatcatc gcagccctag   180
ccatagtaca cctactcttt ctccacgaaa cagggtccaa taaccccaca ggaatctcat   240
cagacacaga caaaatccca tttcatcctt attacacaat caaagatatc ctaggcgccc   300
tattactaat tctagcttta ttactcttag tattattcac acctgaccta cttggagacc   360
cagataacta caccccagca aacccactca acactccccc tcacattaaa ccagaatggt   420
atttnctatt ngcatatgca atcctacgat caatccccaa taaactagga gg           472
```

<210> SEQ ID NO 218
<211> LENGTH: 472
<212> TYPE: DNA
<213> ORGANISM: Addax nasomaculatus

<400> SEQUENCE: 218

```
tgccatgagg acaaatatca ttctgaggag caacagtcat caccaacctt ctctcagcaa    60
tcccatatat cggcacagac ctggtcgaat gaatctgagg aggattctcc gtagacaaag   120
caacccttac ccgattttc gccttccact ttattctccc ctttattatc gctgcccttg   180
ccatagtcca tctactcttt ctccacgaaa caggctccaa caaccctaca ggaatctcct   240
cagacacaga caaaatccca ttccacccett actataccat taaagacatc ttaggcgccc   300
tactactaat tctagtcctc atactactag tattattcac acccgaccta cttggagacc   360
cagacaatta taccccagca aatccactta gcacgccccc tcacatcaaa cctgaatgat   420
atttcctatt tgcatacgca attctacgat caatccccaa caaactagga gg           472
```

<210> SEQ ID NO 219
<211> LENGTH: 472
<212> TYPE: DNA
<213> ORGANISM: Oryx damah

<400> SEQUENCE: 219

```
taccatgagg acaaatatca ttttgagggg caacagttat cactaacctt ctctcagcaa    60
tcccatacat cggcacaaat ctagtcgaat gaatttgagg gggattctcc gtagacaaag   120
```

-continued

```
caaccctcac ccgattttc gccttccact ttattctccc ttttattatc gctgcccttg    180
ccatagtcca cctactcttt ctccacgaaa caggctccaa caaccctaca ggaatcacct    240
cagacacaga caaaattccg ttccacccct attataccat taaagatatc ttaggcgccc    300
tactactaat cctagcccct atgttgctag tattattcgc acccgaccta cttggagacc    360
cagataatta taccagca aatccactta acacaccccc tcacatcaaa cccgaatgat    420
atttcctatt tgcatatgcg atcttacgat caatccccaa caaactagga gg           472

<210> SEQ ID NO 220
<211> LENGTH: 472
<212> TYPE: DNA
<213> ORGANISM: Hippotragus equinus

<400> SEQUENCE: 220
taccatgagg acaaatatca ttctgaggag caacagtcat caccaacctc ctctcagcaa     60
tcccatatat tggcacaaac ctagtcgaat gaatctgagg gggattctcc gtagacaaag    120
caaccctcac ccgattcttc gccttccact ttattcttcc ctttatcatc actgcccttg    180
ccatagtaca cctactcttt ctccatgaga caggctccaa caaccccaca ggaatttgat    240
cagactccga taaaaccccca ttccacccct actacaccat taaagacatt ctaggcgccc    300
tactactaat tctagccctc atactactag tactattcgc acccgaccta cttggagacc    360
cagacaacta tgccccagca aacccactca acacggcccc tcacattaaa cccgaatgat    420
attttttatt cgcgtacgca attctacgat cgatccccaa taagctggga gg            472

<210> SEQ ID NO 221
<211> LENGTH: 472
<212> TYPE: DNA
<213> ORGANISM: Alcelaphus buselaphus

<400> SEQUENCE: 221
tgccatgagg acaaatatca ttctgagggg caacagtcat caccaatctc ctctcagcaa     60
tcccatatat tggcacagac ctagtagaat gaatctgagg gggattctca gtagacaaag    120
caacccttac ccgattttt gccttccact tcattcttcc attcatcatt gcagcccttg    180
ccatagttca cctcttattc ctccacgaaa caggatctaa caaccccaca ggaatctcat    240
cagacgcaga taaaatccca ttccaccccct actatacaat caaggacatt ctaggcgccc    300
tattactaat cctagccctc atactactag tactattcgc acccgacctg ctcggagacc    360
cagacaacta caccccgcg aacccactta acacaccccc tcacatcaag cccgaatgat    420
atttcctatt tgcatatgca atcctacgat caatccctaa caaactagga gg            472

<210> SEQ ID NO 222
<211> LENGTH: 472
<212> TYPE: DNA
<213> ORGANISM: Sigmoceros lichtensteinii

<400> SEQUENCE: 222
tgccatgagg acaaatatca ttctgagggg caacagtcat caccaatctc ctctcagcaa     60
tcccatatat tggcacagac ctagtagaat gaatctgagg aggattatca gtagacaaag    120
caacccttac ccgattttt gccttccact tcattctccc attcatcatt gcagcccttg    180
ccatagttca cctcttattc ctccacgaaa caggatctaa caaccccaca ggaatctcgt    240
cagacgcaga taaaatccca ttccacccct actatacaat caaggacatt ctaggcgccc    300
```

-continued

| | | |
|---|---|---|
| tattactaat tctagccctc atactactag tactattcgc acccgacctg ctcggagacc | 360 | |
| cagacaacta caccccgcg aacccactta acacacccc tcacatcaag cccgaatgat | 420 | |
| atttcctatt tgcatacgca atcctacgat caatccctaa caaactagga gg | 472 | |

<210> SEQ ID NO 223
<211> LENGTH: 472
<212> TYPE: DNA
<213> ORGANISM: Beatragus hunteri

<400> SEQUENCE: 223

| | |
|---|---|
| tgccatgagg acaaatatca ttctgaggag caacagtcat caccaacctc ctctcagcaa | 60 |
| ttccatatat tggtacaaac ctagtcgaat gaatctgagg aggcttctca gtagacaaag | 120 |
| caaccctcac ccgattttc gctttccact ttattctccc atttatcatt acagcccttg | 180 |
| ccatagtcca cctcttattt ctccacgaaa caggatctaa caaccccaca ggaatctcgt | 240 |
| cagatgcaga taaaattcca ttccacccct actacaccat caaagacatc ctaggcgccc | 300 |
| tactactaat tctagccctc atattactag tactatttgc acccgacctg ctcggagacc | 360 |
| cagacaacta cacccccgca aacccactta atacaccccc tcacatcaaa cccgaatgat | 420 |
| atttcctatt tgcatacgca atcctacgat caatccccaa taaactagga gg | 472 |

<210> SEQ ID NO 224
<211> LENGTH: 472
<212> TYPE: DNA
<213> ORGANISM: Damaliscus lunatus

<400> SEQUENCE: 224

| | |
|---|---|
| tgccatgagg acaaatatca ttctgaggag caacagtcat cactaacctc ctctcagcaa | 60 |
| ttccatacat cggcacaaat ctagtcgaat ggatctgagg gggcttctca gtagacaaag | 120 |
| ccaccctcac ccgattcttt gccttccact tcatcttccc atttatcatc gtagctcttg | 180 |
| ccatagtgca cctcttattc ctccatgaaa caggatctaa caaccccaca ggaatctcat | 240 |
| cagatgcgga caaatcccg tttcacccct actacactat caaagacgcc ctagggccc | 300 |
| tactactaat tctagccctc atactactag tactatttgc acccgacctg ctcggagacc | 360 |
| cagacaacta caccctgca aacccactca acacgccccc tcacatcaag cccgagtgat | 420 |
| atttcctatt cgcatacgca atcctacgtt cgatccccca cgagctagga gg | 472 |

<210> SEQ ID NO 225
<211> LENGTH: 472
<212> TYPE: DNA
<213> ORGANISM: Connochaetes taurinus

<400> SEQUENCE: 225

| | |
|---|---|
| taccatgagg acaaatatcc ttttgaggag caacagtcat caccaacctc ctctcagcaa | 60 |
| tcccatacat tggcactaac ctagtcgaat gaatctgagg gggattctca gtagacaaag | 120 |
| caacccttac ccgatttttc gccttccact tcattcctcc atttatcatc acagcccttg | 180 |
| ctatagtcca tctcctattc ctccacgaaa caggatctaa caatcccaca ggaatttcat | 240 |
| ccgacaccga taaaatccca ttccccccct attacaccat caaagacatc ctaggcgctc | 300 |
| tattactaat tctagcccta atactactag tactattcgc gcccgattta cttggagacc | 360 |
| cagacaacta caccccgca aatccactca acacaccccc tcacatcaag cccgaatgat | 420 |
| acttcctatt tgcatatgca atcctacgat caatccccaa cggactagga gg | 472 |

<210> SEQ ID NO 226
<211> LENGTH: 472
<212> TYPE: DNA
<213> ORGANISM: Bison bonasus
<220> FEATURE:
<221> NAME/KEY: misc_feature
<222> LOCATION: (437)..(437)
<223> OTHER INFORMATION: unknown

<400> SEQUENCE: 226

```
taccatgagg acaaatatca ttttgaggag caacagtcat taccaacctc ctatcagcaa      60
tcccatacat cggcacaaat ctagtcgaat gaatctgagg cggattctca gtagacaaag     120
caacccttac ccgattttc gctttccact ttatcctccc atttattatc atagcaattg     180
ccatagttca cctactattc ctccacgaaa caggttctaa caatccaaca ggaatttcct     240
cagacacaga caaaattcca ttccacccct actataccat taaagacatc ctaggagcct     300
tattactaat tctaactcta atactactag tactattcgc accggacctc ctcggagacc     360
cagataacta caccccagca aatccactta acacacctcc ccacatcaaa cccgaatgat     420
acttcttatt tgcatangca attttacggt caatccccaa caaactagga gg            472
```

<210> SEQ ID NO 227
<211> LENGTH: 472
<212> TYPE: DNA
<213> ORGANISM: Bos grunniens

<400> SEQUENCE: 227

```
taccatgagg acaaatatca ttttgagggg caacagtcat taccaacctc ctatcagcaa      60
ttccatacat cggcacaaat ttagtcgaat ggatttgagg tgggttctca gtagacaaag     120
caaccctcac ccgattcttc gctttccact ttatcctccc atttattatt acagcaattg     180
ccatagtcca cctactattc ctccacgaaa caggctccaa caatccaaca ggaatctcct     240
cagacgcaga caaaattcca tttcaccccct actataccat taaagacatc ttaggagcct     300
tattactaat tctagcccta atacttctgg tactattcac acccgacctc ctcggagacc     360
cagacaacta caccccagca aatccactca acacacctcc ccacatcaaa cccgaatgat     420
acttcttatt tgcatacgca attttacgat caatccccaa taaactagga gg            472
```

<210> SEQ ID NO 228
<211> LENGTH: 472
<212> TYPE: DNA
<213> ORGANISM: Bos tragocamelus

<400> SEQUENCE: 228

```
taccatgagg acaaatatca ttttgaggag caacagttat taccaatcta ttatcagcaa      60
tcccatacat cggcacaaac ctagttgaat gaatctgagg cgggttctca gtagacaaag     120
caaccctaac ccgattcttc gctttccact ttatcctccc attcatcatt gcagccctcg     180
caataatcca tctactcttc ctccatgaaa cagggtctaa caatccaaca ggaatttcat     240
cagacgcaga taaaatccca tttcaccccct actacactat taaagacatt ctaggagccc     300
tactacttat tctagcccta ataatactag tactattcgc acccgacctc ctcggagacc     360
cagacaacta caccccagca aacccactta gcacacctcc ccatattaag cccgaatggt     420
atttcctgtt cgcatacgca attctacgat caatccccaa caaactagga gg            472
```

<210> SEQ ID NO 229
<211> LENGTH: 472
<212> TYPE: DNA

```
<213> ORGANISM: Bubalus bubalis

<400> SEQUENCE: 229
tgccatgagg acaaatatca ttctgagggg caacagtcat caccaacctt ctctcagcaa    60
tcccatacat tggtacaagt ctggttgaat gaatttgagg gggattctca gtagacaaag   120
caaccctcac ccgattcttc gcatttcact tcatcctccc attcattatc gcaggacttg   180
caatagtcca cctattattt ctccacgaaa caggatccaa caacccaaca ggaatctcat   240
cagacacaga caaaatccca ttccacccct attaccacat taaagacatc ctaggcgccc   300
tactattaat cctagcccta atactattag tactattcgc acccgacctc ctcggggacc   360
cagacaacta caccccagca aacccactca acacacctcc ccacatcaag cctgaatggt   420
acttcctatt cgcatacgca atcttacgat caattcctaa caaactagga gg           472

<210> SEQ ID NO 230
<211> LENGTH: 472
<212> TYPE: DNA
<213> ORGANISM: Bubalus mindorensis

<400> SEQUENCE: 230
tgccatgagg acaaatatca ttctgaggag caacagtcat caccaacctt ctctcagcaa    60
tcccatacat tggcacaaac ctagttgagt gaatttgagg gggattctca gtagacaaag   120
caaccctcac ccgattcttc gcatttcact tcatcctccc attcattatc gcagcacttg   180
caatagtcca cctattattt ctccacgaaa caggatccaa caacccaaca ggaatctcat   240
cagacacaga caaaatccca ttccacccct actacaccat taaagacatt ctaggcgccc   300
tgctattaat cctagcccta atactattag tactattcac acccgacctc ctcggggacc   360
cagacaacta caccccagca aacccactca acacacctcc ccatatcaaa cctgaatggt   420
acttcctatt cgcatacgca atcttacgat cagttcctaa caaactagga gg           472

<210> SEQ ID NO 231
<211> LENGTH: 472
<212> TYPE: DNA
<213> ORGANISM: Tragelaphus angasii

<400> SEQUENCE: 231
tgccatgagg acaaatatca ttctgaggag caacggtcat cacaaacctc ctatcagcaa    60
tcccatatat tggcaccaac ctagttgaat gaatctgagg aggcttctcg gtagacaagg   120
caaccctaac ccgatttttc gccttccact tcatcctccc gtttattatt acagcgctgg   180
ttatggtcca cctattattc ctccatgaaa caggatccaa caacccaaca ggaatctcat   240
cagacataga caaaattcca ttccaccccc attacactat caaggacatc ctaggcgccc   300
tactattaat cctagcccta atagtactag tactattcac acctgacctc ctcggagacc   360
ccgacaacta caccccagcg aacccccctca atacacctcc ccatatcaaa cctgaatgat   420
atttcctgtt cgcatatgca atcctacgat ctatccccaa caagctagga gg           472

<210> SEQ ID NO 232
<211> LENGTH: 472
<212> TYPE: DNA
<213> ORGANISM: Tragelaphus eurycerus

<400> SEQUENCE: 232
taccatgagg acaaatatca ttttgaggag caacagtcat cacaaacctt ctatcagcaa    60
tcccttatat tggcaccagc ctagtcgaat gaatctgagg gggcttttca gtagacaaag   120
```

```
caaccttaac cgattcttc gccttccact ttatccttcc atttattatt acagcactag        180
ccatggtaca cctactattc ctccacgaaa caggatccaa caacccaaca ggratctcat        240
craacataga caaaattcca tttcacccct actacactat taaggacatc ctaggtgccc        300
tactgctaat cctaactcta atactcctag tactattcgc acccgacctt ctcggagacc        360
ccgacaacta caccccagca aacccactca acacaccacc tcatatcaaa cctgaatgat        420
acttcctatt cgcatatgca atcctacgat caatccctaa taaactagga gg               472

<210> SEQ ID NO 233
<211> LENGTH: 472
<212> TYPE: DNA
<213> ORGANISM: Nemorhaedus caudatus

<400> SEQUENCE: 233
taccatgagg acagatatca ttctgagggg caacagttat taccaatctt ctctcagcaa         60
tcccatatat tggcacaaac ctagtcgaat gaatctgagg gggattctca gtagacaaag        120
ctactctcac ccgattcttc gccttccact tcatcctccc atttatcatt acagctactg        180
ctatagtcca cctactttc ctccatgaga taggatccaa caaccccaca ggtatcccat         240
cagacataga caaaatccca tttcacccct attatacaat caaagatatt ctaggcgcta        300
tactactaat cctcacccct attttactgg tattattcac acctgactta cttggagatc        360
cagacaacta tacccccagca aacccactca gcacacccccc tcacattaaa cctgaatgat        420
atttcctatt tgcatatgca atcttacgat caatcccccaa taaactaggc gg                472

<210> SEQ ID NO 234
<211> LENGTH: 472
<212> TYPE: DNA
<213> ORGANISM: Pseudois nayaur

<400> SEQUENCE: 234
tgccatgagg acaaatatca ttttgagggg caacagtcat caccaacctt ctctcagcaa         60 tccccctatat tggcacaaat ctagtcgaat ggatctgagg gggattctca gtagacaagg        120
ccactctcac ccgattcttc gccttccact tcatcctccc atttattatt atagccctcg        180
ccatagtcca cctactttc ctccacgaaa caggatctaa caaccccaca ggaatcccat         240
cagacacaga caaaatccca ttccacccct actacaccat taaagatatt ctaggcgctg        300
cactgctaat cctcgccctg atattactag tattatttac acccgaccta ctcggagacc        360
cagacaacta caccccagca aacccactca acacacccccc tcacattaaa cccgagtgat        420
acttcctatt tgcatacgca atcctacgat caattcccaa caagctagga gg                472

<210> SEQ ID NO 235
<211> LENGTH: 472
<212> TYPE: DNA
<213> ORGANISM: Ammotragus lervia

<400> SEQUENCE: 235
tgccatgagg acagatatca ttctgagggg caacagtcat caccaacctt ctctcagcaa         60
tcccatacat tggcacagac ctggtcgaat gaatctgagg gggattctca gtagacaaag        120
ctactctcac ccgattcttc gccttccact tcatcctccc atttgtaatc gcagccctag        180
ccatagtcca cttactttc ctccatgaaa cgggatccaa caaccccaca ggaatttcat         240
cagacgcaga caaaatccca ttccacccct actacaccat caaagatatt ctaggcgcca        300
```

```
tgctactaat cctcaccctc acactactag tactatttac acccgatcta ctcggggacc      360
cagacaacta taccccagca aatccactca acacaccccc tcatattaaa cctgaatgat      420
acttcctatt tgcatacgca atcctacgat caatccctaa taaactggga gg              472
```

<210> SEQ ID NO 236
<211> LENGTH: 472
<212> TYPE: DNA
<213> ORGANISM: Capra falconeri

<400> SEQUENCE: 236

```
taccatgagg acaaatatca ttctgagggg caacagtcat caccaatctc ctctcagcaa       60
tcccatatat tggcacaaac ctagtcgaat gaatctgagg aggattctca gtagataaag      120
ccaccctcac ccgattcttc gccttccact ttatcctccc attcatcatt gcaggcctcg      180
ccatagtcca cctactcttc ctccacgaaa caggatccaa caatcccaca ggaattccat      240
cagacacaga caaaatccca tttcacccct actacaccat aaagatatc ctaggcgcca      300 tactactaat tctcgccctg atgctactag tactattcac acctgaccta ctcggagacc      360
cagataacta tatcccagca aatccactca atacaccccc tcatatcaaa cctgagtggt      420
acttcctatt tgcatacgca atcctacgat caatccccaa caaactagga gg              472
```

<210> SEQ ID NO 237
<211> LENGTH: 472
<212> TYPE: DNA
<213> ORGANISM: Capra ibex

<400> SEQUENCE: 237

```
taccatgagg acaaatatca ttctgagggg caacagtcat cactaacctt ctctcagcaa       60
tcccatatat tggcacaaac ctagtcgaat gaatctgagg gggattctca gtagacaaag      120
ccactctcac ccgattcttc gccttccact tcatcctccc attcatcatt acagccctcg      180
ccatagtcca cctgctcttc ctccacgaaa cgggatccaa caaccccaca ggaattccat      240
cagacacaga caaaatccca ttccacccct actacaccat aaagatatc ttaggcgcca      300 tgctactaat tcttgtccta atattactag tactattcac acccgaccta ctcggggacc      360
cagacaacta taccccagca aacccactca atacaccccc tcacattaaa cctgaatgat      420
atttcctatt tgcatacgca atcctacgat caattcccaa caaactaggg gg              472
```

<210> SEQ ID NO 238
<211> LENGTH: 472
<212> TYPE: DNA
<213> ORGANISM: Hemitragus jemlahicus

<400> SEQUENCE: 238

```
taccatgagg acagatatca ttctgagggg caacagtcat caccaacctt ctctcagcaa       60
ttccatatat cggcacaaac ctagtcgaat gaatctgagg aggattctca gtagacaaag      120
ctaccctaac ccgattcttc gctttccact tcattctccc attcatcatt gcagccctcg      180
ccatagtcca cctgctcttc ctccacgaaa cagggtccaa caaccccaca gggattccat      240
cagatacaga caaaatccca tttcacccct actacaccat aaagatatt ttaggcgcca      300 tactactaat tcttgtccta atattactag tactatttat acccgaccta cttggagacc      360
cagacaacta taccccagca aatccactca acacaccccc tcacattaaa cctgaatgat      420
attttctatt tgcatacgcg atcctacgat caattcccaa caaactagga gg              472
```

```
<210> SEQ ID NO 239
<211> LENGTH: 472
<212> TYPE: DNA
<213> ORGANISM: Rupicapra pyrenaica

<400> SEQUENCE: 239
taccatgagg acagatatca ttctgaggag caacagttat taccaatctc ctctcagcaa      60
tcccatacat tggcatagac ttagtcgagt gaatctgagg gggcttctcg gtagacaaag     120
ctaccctcac ccgattcttt gcctttcact tcatcctccc attcatcatt gcagccttag     180
ccatagtcca cctactcttc ctccatgaaa caggatcaaa caaccccaca ggaatcccat     240
cagatgcgga traaatccca tttcacccct actataccat taaagacatt ctaggcgcca     300
tactactaat cctcaccctt atactactgg tactatttac acctgaccta ctcggagacc     360
cagataacta taccccagcg aacccactca acacaccccc tcacatcaaa cccgaatgat     420
atttcttgtt tgcatatgcg atcctacgat caattcccaa caaacttgga gg            472

<210> SEQ ID NO 240
<211> LENGTH: 472
<212> TYPE: DNA
<213> ORGANISM: Rupicapra rupicapra
<220> FEATURE:
<221> NAME/KEY: misc_feature
<222> LOCATION: (246)..(264)
<223> OTHER INFORMATION: unknown
<220> FEATURE:
<221> NAME/KEY: misc_feature
<222> LOCATION: (338)..(338)
<223> OTHER INFORMATION: unknown

<400> SEQUENCE: 240
taccatgagg acagatatca ttctggggag caacagttat taccaacctc ctctcagcga      60
tcccgtatat tggcacagac ttagtcgaat gaatctgagg aggcttctcg gtagacaagg     120
ctaccctcac ccgattcttt gcttccact tcatcctccc atttatcatt gcagccttag     180
ccctagtcca cctactcttc ctccacgaaa caggatctaa caaccccaca ggaatcccat     240
cagatgcgga caaaatccca tttnacccct attataccat caaagacatt ctgggcgcca     300
tactactaat cctcaccctc atactactag tactattnac acctgaccta ctcggagacc     360
cagataatta cacccagcg aacccactca acacaccccc tcacattaaa cccgagtgat     420
atttcttatt tgcatatgca attctacgat caatccccaa caaacttgga gg            472

<210> SEQ ID NO 241
<211> LENGTH: 472
<212> TYPE: DNA
<213> ORGANISM: Pantholops hodgsoni

<400> SEQUENCE: 241
taccatgagg acaaatatca ttctgaggag caacagtaat taccaacctc ctttcagcaa      60
tcccatacat tggcacagac ctagtcgaat gaatctgagg gggattctca gtagacaaag     120
ctacccttac ccgattcttt gcttccatt tcattctccc attcatcatc gcagccctcg     180
ccatagtcca cctactcttc ctccacgaaa caggatccaa caaccccaca ggaattccat     240
cagatgcaga caaaatccca tttcacccct actataccat taaagacatc ctaggcgcta     300
tactactaat cctaatcctc atattactag tactattttc acccgaccta ctcggagacc     360
cagacaatta taccccagca aaccccctca acacaccacc ccacattaaa cctgaatggt     420
actttctatt tgcatacgca atcctacgat caatccccaa caaactagga gg            472
```

<210> SEQ ID NO 242
<211> LENGTH: 472
<212> TYPE: DNA
<213> ORGANISM: Budorcas taxicolor taxicolor

<400> SEQUENCE: 242

```
taccatgagg acaaatatca ttttgaggag caacagtcat taccaacctc ctctcagcaa      60
tcccatacat tggcacaaac ctagttgagt gaatctgagg aggattctca gtagacaaag     120
catccctcac ccgattcttt gcctttcact tcatcctccc atttatcatc gcagacctcg     180
ccatagtcca tttactttc ctccacgaaa caggatccaa caaccccaca ggaattccgt      240
cagatgcaga taaaattcca tttcacccctt attacaccat taaagatatc ctaggagtca    300
tactactaat cctcgtcctc atgttgctag tactatttat acttgacgta cttggagacc     360
cagataatta taccccagca aatccactca acacaccccc tcacatcaaa cctgaatgat     420
atttcctatt tgcatacgca atcttacgat caatccccaa caaactagga gg             472
```

<210> SEQ ID NO 243
<211> LENGTH: 472
<212> TYPE: DNA
<213> ORGANISM: Ovis ammon

<400> SEQUENCE: 243

```
taccatgagg acaaatatca ttctgaggag caacagttat taccaacctc ctttcagcaa      60
ttccatatat tggcacaaac ctagtcgaat gaatctgagg gggattctca gtagacaaag     120
ccaccctgac ccgattcttc gcctttcact ttatttcc attcatcatc gcagccctcg       180
ccatagtcca cctactcttc ctccacgaaa caggatccaa caaccccaca ggaatcccat     240
cggacacaga taaaattccc ttccacccctt actacaccat taaagacatc ctaggtgcca    300
tcctactaat cctcaccctc atactactag tactattcac gcctgaccta ctcggagacc     360
cagacaacta caccccagca aacccactta acactccccc tcacatcaaa cctgaatgat     420
acttcctatt tgcatacgca atcttacgat caatccctaa taaactagga gg             472
```

<210> SEQ ID NO 244
<211> LENGTH: 472
<212> TYPE: DNA
<213> ORGANISM: Ovis vignei
<220> FEATURE:
<221> NAME/KEY: misc_feature
<222> LOCATION: (264)..(264)
<223> OTHER INFORMATION: unknown
<220> FEATURE:
<221> NAME/KEY: misc_feature
<222> LOCATION: (265)..(265)
<223> OTHER INFORMATION: unknown
<220> FEATURE:
<221> NAME/KEY: misc_feature
<222> LOCATION: (266)..(266)
<223> OTHER INFORMATION: unknown
<220> FEATURE:
<221> NAME/KEY: misc_feature
<222> LOCATION: (267)..(267)
<223> OTHER INFORMATION: unknown
<220> FEATURE:
<221> NAME/KEY: misc_feature
<222> LOCATION: (268)..(268)
<223> OTHER INFORMATION: unknown
<220> FEATURE:
<221> NAME/KEY: misc_feature
<222> LOCATION: (269)..(269)
<223> OTHER INFORMATION: unknown
<220> FEATURE:
<221> NAME/KEY: misc_feature

```
<222> LOCATION: (270)..(270)
<223> OTHER INFORMATION: unknown
<220> FEATURE:
<221> NAME/KEY: misc_feature
<222> LOCATION: (271)..(271)
<223> OTHER INFORMATION: unknown
<220> FEATURE:
<221> NAME/KEY: misc_feature
<222> LOCATION: (272)..(272)
<223> OTHER INFORMATION: unknown
<220> FEATURE:
<221> NAME/KEY: misc_feature
<222> LOCATION: (273)..(273)
<223> OTHER INFORMATION: unknown
<220> FEATURE:
<221> NAME/KEY: misc_feature
<222> LOCATION: (274)..(274)
<223> OTHER INFORMATION: unknown
<220> FEATURE:
<221> NAME/KEY: misc_feature
<222> LOCATION: (275)..(275)
<223> OTHER INFORMATION: unknown
<220> FEATURE:
<221> NAME/KEY: misc_feature
<222> LOCATION: (276)..(276)
<223> OTHER INFORMATION: unknown
<220> FEATURE:
<221> NAME/KEY: misc_feature
<222> LOCATION: (277)..(277)
<223> OTHER INFORMATION: unknown
<220> FEATURE:
<221> NAME/KEY: misc_feature
<222> LOCATION: (278)..(278)
<223> OTHER INFORMATION: unknown

<400> SEQUENCE: 244
taccatgagg acaaatatca ttctgaggag caacagttat taccaacctc ctttcagcaa      60
ttccatatat tggcacaaac ctagtcgaat gaatctgagg aggattctca gtagacaaag     120
ctaccctcac ccgattttc gcctttcact ttattttccc attcatcatc gcagccctcg      180
ctatagttca cctactcttc ctccacgaaa caggatccaa taaccccaca ggaattccat     240
cggacacaga caaaatcccc ttcnnnnnnn nnnnnnnnat taaagacatt ctgggtgcca     300
tcctactaat cctcatcctc atgctgctag tactattcac gcctgactta cttggagacc     360
cagacaacta cacccccagca aacccactta acactccccc tcacatcaaa cctgaatgat     420
atttcctatt tgcatatgca atcttacgat caatccctaa taaactagga gg             472

<210> SEQ ID NO 245
<211> LENGTH: 472
<212> TYPE: DNA
<213> ORGANISM: Capcornis crispus

<400> SEQUENCE: 245
taccatgagg acaaatatca ttctgagggg ctacagtcat tactaacctc ctctcagcaa      60
tcccatatat tggcacaaac ttagtagaat gaatctgagg aggattctcc gtagacaaag     120
ccaccctcac ccgattcttt gccttccatt tcattctccc attcatcatc acagccctcg      180
ccatagtgca cctactttc ctccacgaaa caggatccaa caaccccaca ggaatctcat     240
cagacacaga caaaatccca ttccaccct actacacaat caaagatatc ctaggcatcg     300
tgctactaat cctcaccctc atactactag tactgttcac acccgaccta ctcggagacc     360
cagacaacta cactccagca aacccactca acacacccccc tcacatcaag cccgagtgat     420
acttcctatt tgcatacgca atcctacgat caatccccaa caaactaggc gg             472

<210> SEQ ID NO 246
```

```
<211> LENGTH: 472
<212> TYPE: DNA
<213> ORGANISM: Ovibos moschatus

<400> SEQUENCE: 246
taccatgagg acaaatatca ttctgaggag ctacagtcat cactaacctc ctctcagcaa      60
tcccatacat cggcacaaac ctagtcgaat gaatctgagg aggattctcc gtagacaaag     120
ccaccctcac ccgattttt gcttttcact ttatcctccc atttatcatc gtagccctcg     180
ctatagtaca tttgctcttc ctccacgaaa caggatccaa caaccccaca ggaattccat     240
cagacacgga caaaatccca ttccacccct actataacaat caaagacatt ctaggcgcca     300
tactactaat ccttacccttt atactactag tattattcac acccgaccta cttggagacc     360
cagacaacta taccccagca aacccactca acacaccccc tcacattaaa ccagagtgat     420
acttcctatt tgcatacgca atcctacgat caattcctaa caaactaggc gg             472

<210> SEQ ID NO 247
<211> LENGTH: 472
<212> TYPE: DNA
<213> ORGANISM: Oreamnos americanus

<400> SEQUENCE: 247
taccatgagg acaaatatca ttctgaggag caacagttat taccaacctc ctttcagcaa      60
ttccatatat tggcacaaac ctagtcgaat gaatctgagg gggattctca gtagacaaag     120
ccaccctgac ccgattcttc gcctttcact ttatttttccc attcatcatc gcagccctcg     180
ccatagtcca cctactcttc ctccacgaaa caggatccaa caaccccaca ggaatcccat     240
cggacacaga taaaattccc ttccaccctt actacaccat aaagacatc ctaggtgcca     300
tcctactaat cctcaccctc atactactag tactattcac gcctgaccta ctcggagacc     360
cagacaacta caccccagca aacccactta acactccccc tcacatcaaa cctgaatgat     420
acttcctatt tgcatacgca atcttacgat caatcctaa taaactagga gg              472

<210> SEQ ID NO 248
<211> LENGTH: 472
<212> TYPE: DNA
<213> ORGANISM: Cephalophus dorsalis

<400> SEQUENCE: 248
tcccatgagg gcaaatatca ttctgaggag ccacagtcat taccaacctc ctctcagcaa      60
tcccatacat tggtacaaac ttagtcgaat gaatctgagg aggcttttca gtagacaaag     120
caactctcac ccgattcttt gctttccact ttatcttccc ttttattatt gcagccctcg     180
ccatagttca cctactcttc ctccatgaaa caggatccaa caaccccaca ggagtctcat     240
cggacgcaga caaaatccca ttccacccct actacaccat aaagacatc ctaggcgccc     300
tactactcat tctagcccta ataatccag tattattctc acccgactta cttggagacc     360
cagataacta caccccagca aacccactca acacacctcc ccatattaaa cccgaatgat     420
acttcctatt tgcatacgca atcctacgat caattccaaa caaactagga gg              472

<210> SEQ ID NO 249
<211> LENGTH: 472
<212> TYPE: DNA
<213> ORGANISM: Cephalophus maxwellii

<400> SEQUENCE: 249
tcccatgagg acaaatatca ttctgaggag ccacagtcat taccaacctc ctctcagcaa      60
```

-continued

```
tcccatatat cggcacaaac ttagttgagt gaatctgagg gggcttttca gtagacaaag      120
caaccctcac tcgattttc gccttccact ttatcttccc atttatcatc gcagcccttg       180
ccatagtcca cctactattc ctccacgaaa caggatctaa taaccccaca ggaatctcat      240
cagacgcaga caaatcccg ttccacccct actacactat caaagacatc ctaggcgccc       300
tattacttat tctagcccta ataatcctag tactattctc acccgactta ctcggagatc     360
cagataatta tactccagca aacccactta acacacctcc ccacatcaag cccgaatgat    420
atttcctatt cgcgtacgca attctacgat caattccaaa taaattagga gg            472
```

<210> SEQ ID NO 250
<211> LENGTH: 472
<212> TYPE: DNA
<213> ORGANISM: Alces alces

<400> SEQUENCE: 250

```
taccatgagg acagatatca ttctgagggg caacagtcat tactaacctc ctttcagcaa     60
ttccatacat tggtactaat ctagttgaat gaatttgagg cggttttca gtagacaaag     120 caactctaac ccgattttc gccttccact ttattctccc atttatcatc gcagcacttg      180
ccatagtcca cttactttc ctccacgaaa caggatccaa caaccaaca ggaattccat        240 cagacgcaga caaatccca tttcacccctt actacactat caaagatatc ttaggtgccc     300
tactcttaac tcttttccta atactactag tactctttc accagacctg cttggagacc     360
cagacaacta caccccagct aatccactca acacacccc tcatattaag cctgaatggt   420
atttcttatt tgcatacgca attctacgat caatccccaa taaactaggg gg             472
```

<210> SEQ ID NO 251
<211> LENGTH: 472
<212> TYPE: DNA
<213> ORGANISM: Hydropotes inermis

<400> SEQUENCE: 251

```
ttccatgagg acaaatatca ttctgaggag caacggtcat tactaatctc ctgtcagcaa     60
ttccatacgt cggtacaaat ctagtcgaat gaatctgagg tggcttttca gtagataaag     120
ctaccctgac ccgattcttc gccttccact tcattcttcc atttatcatt gcagctcttg     180
ccatagtgca cttacttttt ctccacgaaa caggatccaa taacccaaca ggaattccat      240
cagatgcaga taaaattcca tttcatccct actacaccat taaagatatt ctaggtgtac     300
tccttctaat tctttttccta atgttattag tcctattttc acctgacctg cttggagacc    360
cagacaatta tactccagca aacccactca atacacccc tcacattaaa ccagaatgat    420
atttcttatt tgcatacgca attctacgat ctatccctaa caaattagga gg              472
```

<210> SEQ ID NO 252
<211> LENGTH: 472
<212> TYPE: DNA
<213> ORGANISM: Muntiacus muntjak

<400> SEQUENCE: 252

```
taccatgagg acaaatatca ttttgaggag caacagtcat cactaacctc ctttcagcaa     60
ttccatatat tggcacaaac ttagtcgaat gaatctgagg aggcttttca gttgataaag     120
caaccctcac ccgattcttt gccttccact ttatcctccc atttattatt gcagcacttg     180
ctatagtcca cctactttc ctccacgaaa caggatccaa caatccaaca ggaattccat       240
```

-continued

```
cagatgtaga caaaattcct ttccatccct actataccat taaagatatt ttaggtgccc    300
tacttctaat tctcttccta atattattag tattattcgt accagacctg ctcggagacc    360
ccgacaatta tacccagca aacccactca atacaccccc tcacatcaag cctgaatgat     420
atttcctatt tgcatacgct attctacgat caattcctaa caaactagga gg            472
```

<210> SEQ ID NO 253
<211> LENGTH: 472
<212> TYPE: DNA
<213> ORGANISM: Cervus elaphus kansuensis

<400> SEQUENCE: 253

```
taccatgagg acaaatatca ttctgaggag caacagtcat taccaacctt ctctcagcaa    60
ttccatacat tggcacaaac ctagtcgaat ggatctgagg aggcttttca gtagataaag    120
caaccctaac ccgattttc gctttccact ttattctccc atttatcatc gcagcactcg     180
ctatagtaca cttactcttc cttcacgaaa caggatccaa taccaaca ggaatcccat      240 cagacgcaga caaaatcccc ttccatcctt actataccat taaagatatc ttaggcatct    300
tacttctagt actcttccta atattactag tattattcgc accagacctg cttggagacc    360
cagacaacta taccccagca aatccactca atacaccccc tcacattaaa cctgaatgat    420
atttcctatt tgcatacgca atcctacgat cgattcccaa caaactagga gg            472
```

<210> SEQ ID NO 254
<211> LENGTH: 472
<212> TYPE: DNA
<213> ORGANISM: Cervus elaphus xanthopygus

<400> SEQUENCE: 254

```
taccatgagg acaaatatca ttctgaggag caacggtcat taccaacctt ctctcagcaa    60
ttccatacat tggcacaaac ctagtcgaat ggatctgagg aggcttttca gtagataaag    120
caaccctaac ccgattttc gctttccact ttattctccc atttatcatc gcagcactcg     180
ctatagtaca cttactcttc cttcacgaga caggatccaa taccaaca ggaattccat      240 cagacgcaga caaaatcccc ttccatcctt actataccat taaagatatc ttaggcatct    300
tacttctagt actcttccta atattactag tattattcgc accagacctg cttggagacc    360
cagacaacta taccccagca aatccactca acacaccccc tcacattaaa cctgaatgat    420
atttcctatt tgcatacgca atcctacgat cgattcccaa caaactagga gg            472
```

<210> SEQ ID NO 255
<211> LENGTH: 472
<212> TYPE: DNA
<213> ORGANISM: Cervus elaphus canadensis
<400> SEQUENCE: 255

```
taccatgagg acaaatatca ttctgaggag caacagtcat taccaacctt ctctcagcaa    60
ttccatacat tggcacaaac ctagtcgaat gggtctgagg aggcttttca gtagataaag    120
caaccctaac ccgattcttc gctttccact ttattctccc atttatcatc gcagcactcg    180
ctatagtaca cttactcttc cttcacgaga caggatctaa taccaaca ggaatcccat      240 cagacgcaga caaaatcccc ttccacccctt actatacgat taaagatatc ttaggtatct   300
tacttctaat actcttccta atattactag tattattcgc accagatctg cttggagacc    360
cagacaacta taccccagca aatccactca acacaccccc tcacattaaa cctgaatgat    420
atttcctatt tgcatacgca atcctacgat caattcccaa caaactagga gg            472
```

UNIVERSAL PRIMERS FOR WILDLIFE IDENTIFICATION

FIELD OF THE INVENTION

The invention relates to the identification of novel universal primers that can amplify the fragment of cytochrome b gene of any animal species in polymerase chain reaction (PCR) and reveal the identity of the biological material of any unknown animal origin at species and sub-species sources. The invention also provides a method for the identification of fragments on mitochondrial cytochrome b gene in biological material of unknown origin.

BACKGROUND & PRIOR ART REFERENCES

A large number of studies in evolutionary biology utilize phylogenetic information obtained from mitochondrial cytochrome b gene. It has been identified a potent molecule to distinguish the phylogenetic depth of different lineages to family, genus and species in molecular taxonomy[1-66]. A vast database of the sequences of cytochrome b gene of different animal species has accumulated in public databases such as GenBank, NCBI (http://www.ncbi.nlm.nih.gov) etc. We have utilized this capacity of cytochrome b gene in establishing the identity of the origin of animal parts and product to its family, genus and species sources. The technique developed is based on a pair of universal primer that can amplify a small fragment of cytochrome b gene from a vast range of animal species.

Establishing identity of confiscated animal parts and products is a great challenge to law enforcement agencies because none of the methods available till date is too efficient to reveal the identity of animal remains beyond a reasonable doubt. Morphological markers, described for certain species allow the identification of complete specimen of animals[67]. However, a complete specimen is confiscated very rarely by the investigation agencies; therefore, these marker are not practical in wildlife forensics. The biochemical traits such as the bile characteristics[68] blood heam analysis[69,70] etc. have also been employed in wildlife forensic for identification of individual species. The difficulty of these markers are that these markers are limited in number and are rarely found in their natural forms in which these were originally described as the characteristic of a particular species.

The molecular approaches such as micro-satellite based identification[71], Restriction fragment length polymorphism analysis of mitochondrial genes or PCR based species specific STS markers require the prior information of the species to establish the identity[72,73]. These methods also need a significant amount of DNA material to be analysed. We may not have the prior information about the species origin of confiscated animal parts and product in forensics, therefore, these methods are not really useful and practical in wildlife identification. The technique invented by us is universal, therefore does not require any background information to establish the identity of any unknown confiscated remains at family, genus and species sources. Being a PCR based procedure it can be applied with trace amount of any biological material. Because the amplicon length is small (472 bp); therefore, it can work perfectly with the mutilated remains, which are commonly seized by the crime investigation agencies. It does not require the large amount of genetic material i.e. DNA to be analyzed to establish the identity, hence, can detect a minute amount of adulteration in food products. The procedure described is simple and very fast. Due to the said advantages, the procedure invented by us is most suited for forensic wildlife identification.

OBJECTS OF THE INVENTION

The main object of the invention is to identify a fragment on mitochondrial cytochrome b gene capable of significantly discriminating among various evolutionary lineages of different animal species.

Another object is to identify a fragment on mitochondrial cytochrome b gene which is flanked by the highly conserved sequences at a vast range of animal species.

Yet another object is to detect a fragment on mitochondrial cytochrome b gene which is polymorphic inter-specifically, but monomorphic at intra species sources.

Still another object is to develop the universal primers to amplify the fragment on mitochondrial cytochrome b gene using polymerase chain reaction.

Another object is to develop a PCR protocol that works universally with DNA template of any unknown origin (i.e. all the animal species).

Yet another object is to provide a universal method for identification of species of analyzed material (i.e. the DNA isolated from confiscated animal remain of unknown origin) using the public databases such as GenBank, NCBI etc.

Still another object is to provide a universal method of animal identification to establish the crime with the criminal beyond a reasonably doubt.

Another object is provide a universal method to establish the identity of biological materials such as skin, horns etc confiscated from animal poachers, if it is that of an endangered species.

Yet another object is to provide a universal method for establishment of the identity of confiscated animal parts and products of endangered animal species for the purpose of production of molecular evidence of animal hunting and related crime in the court of law, so that the human violation to the wildlife resources could be controlled.

Still another object is to provide a universal technique to have an idea of the geographical location of the commitment of wildlife crime based on the haplotype of poached animal identified by the universal primer invented.

Another object is to provide a universal technique of animal identification to detect the adulteration of animal meat/products in vegetarian food product for the purpose of food fortification, by the food fortification agencies.

Yet another object is to provide a universal technique for detection of the origin of blood or blood stains etc collected from the scene of crime related to offences such as murder, rape etc, in order to establish the origin of blood found at scene of crime when it sounds as if criminals have wontedly spread the blood of an animal at the scene of crime, to confuse the crime investigation agencies and forensic scientists with human blood.

Another object is to invent and authenticate a universal technique that can be converted to a (a) 'MOLECUALR KIT' and (b) 'DNA CHIPS' based application to meet the requirements of above objectives.

SUMMARY OF THE INVENTION

Accordingly, the invention provides novel universal primers that can amplify the fragment of cytochrome b gene of any animal species in polymerase chain reaction (PCR) and reveal the identity of the biological material of any unknown animal origin

DETAILED DESCRIPTION OF THE INVENTION

Keeping in view the above objectives, the cytochrome b gene sequences (1140 bp) of 221 distantly related animal species (listed in Table 1) representing various families were obtained from public database NCBI (http://www.ncbi.nlm-.nih.gov). These sequences were aligned using the software Clustal X(1.8)(NCBI, USA) and a fragment (of 472 bp, alignment shown in Table 2) of gene was identified which had all the features mentioned above under column 1, 2 and 3 of sub-heading 'Objectives of invention'. As for the identity of this fragment we would like to mention that it includes the nucleotides between 398 to 869 in *Antilope cervicapra* and *Felis catus*; however, 399 to 870 in *Homo sapiens sapiens* species. Except at few positions (marked as star (*) in Table 2, the nucleotide sequences of this fragment are highly variable amongst the animal species, giving rise to their unique molecular signature. These molecular signatures are characteristic of its species and form the basis of revealing the identity of the biological material of an unknown animal origin by the procedure invented by us. Considering *Antilope cervicapra* as a representative species, the sequence of this fragment is mentioned herewith:

Mitochondrial cytochrome b gene sequence (398–869 bp) of *Antilope cervicapra*:

its 3' end are highly conserved amongst a vast range of animal species (shown in Table 2). As mentioned above, the DNA fragment (sequence of which is shown above) targeted by these primers is highly polymorphic inter-specifically; however, it is monomorphic among the individual of same species (Tables 6, 7a, 7b, 7c, 7d and 8, respectively). These unique features of the targeted region enable these primers to generate the molecular signatures of an individual species; thereby, enabling them to differentiate amongst the animals of different species (see in FIG. 1c). The variation within the fragment amplified by these primers increase with increasing distances of evolutionary lineages of two animals (Table 8). These unique features of the fragment amplified by the universal primers 'mcb398' and 'mcb869' invented by the applicants fulfill the objectives of invention.

Figure 1C:
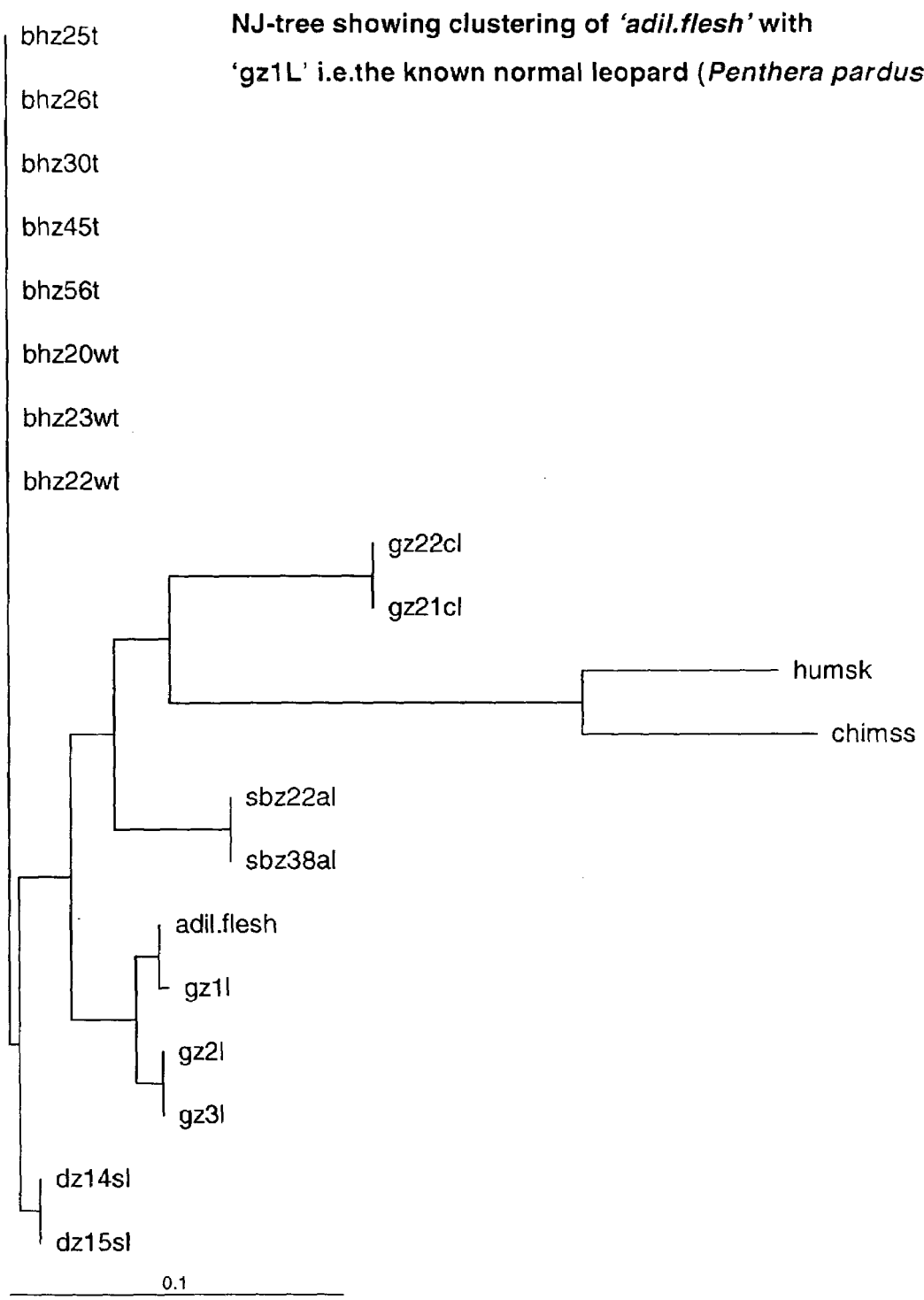

Thus, the primers invented by us can generate the molecular signature from any biological material of unknown animal origin, which actually is the characteristic of its family, genus and more precisely, the species. When these signatures are compared in-silico with the signatures already available in public databases (viz., GenBank, NCBI database etc) using 'BLAST software[73], it indicates identity of the family, genus or species of the analyzed material, which in turn is confirmed practically by comparing with the reference animals of the revealed family, genus or species, by including them in the further analysis by the primers 'mcb398' and 'mcb869'. The complete procedure involved in the analyses (the word, 'analyses' should be understood with the stepwise procedure to establish the identity of the biological remain of any unknown animal origin for the aims mentioned in columns 1–13 under sub-heading 'Objectives of invention') is briefed under 'Examples 5 and 6, respectively, as well as illustrated in FIGS. 1a, 1b and 1c, respectively.

```
"taccatgaggacaaatatcttttgaggagcaacagtcatcaccaatctcctttcagcaatcccatacatcggtacaaacctagtaga atgaatctgaggagggttctcagtagataaagcaaccttacccgattttcgccttccactttatcctcccatttatcattgcagccctta ccatagtacacctactgtttctccacgaaacaggatccaacaacccacaggaatctcatcagacgcagacaaaattccattccaccc ctactacactatcaaagatatcctaggagctctactattaattttaaccctcatgcttctagtcctattctcaccggacctgcttggagacc cagacaactatacaccagcaaacccacttaatacaccccacatatcaagcccgaatgatacttcctatttgcatacgcaatcctccga tcaattcctaacaaactaggagg"
```

A pair of universal primer was designed to amplify this fragment in polymerase chain reaction (PCR). These primers were named as 'mcb398' and 'mcb869' because of its property to amplify a region of mitochondrial cytochrome b gene between nucleotides 398 to 869 of *Antilope cervicapra*, a representative animal species for this invention. We took this animal species as representative species because the idea of developing such a novel primers came in the mind of inventors while they were working on the genome of this animal in Centre for Cellular and Molecular Biology, Hyderabad, India. These primers work universally because

BRIEF DESCRIPTION OF DRAWING AND TABLES

FIGS. 1a–1c illustrate the step-wise procedure involved in analyses. The unknown biological material i.e. 'Adil-.flesh' refers to the confiscated skin mentioned in 'Example 6'. The arrow marks indicate the stepwise procedure involved. The brief description of FIG. 1a is as follows:

The biological material i.e. the confiscated skin 'adil-.flesh' was subjected to DNA isolation using the standard procedures[74]. The DNA obtained was amplified using the primers 'mcb398' and 'mcb869' in PCR, fractionated in 2% (w/v) agarose gel, visualized and photographed under UV light using Gel Documentation System (Syngene, USA). The lane 'M' shown in the photograph represents the molecular weight marker (Marker XIII, Boehringer mannheim). Lane 1 shows the PCR amplicon (472 bp) obtained from 'adil.flesh' using primers 'mcb398' and 'mcb869'. The PCR amplicon obtained were sequenced at both the strand using "ABI Prism 3700 DNA Analyzes, PE-Applied Biosystems). The chromatogram shows the sequences (about 80 bp long, i.e. between 150–230 bp of sequence (328 bp), revealed from the PCR product of 472 bp length) obtained from 'adil.flesh' (SEQ ID NO: 5).

FIG. 1b illustrates the further steps involved in analyses. The sequence (328 bp) revealed from 'adil.flesh' was subjected to homology search in nr (i.e. non-redundant) database of Netional Centre for Biological Information (NCBI), USA. The sequences producing significant alignments are shown along with its bits score and E values. It indicates the extent of homology amongst the sequence enquired (i.e. the 328 bp sequence from adil.flesh) and the sequences registered in nr database of NCBI. BLAST analysis revealed the highest homology of the sequence revealed from 'adil.flesh' with the sequence of *Panthera pardus* (gene bank registration number 'AY005809'), indicating the identity of adil.flesh as that of a leopard (*Panthera pardus*) origin. FIG. 1b further illustrates the multiple alignments of the sequences obtained from reference animals (listed in Table 5) along with the sequence obtained from 'adil.flesh'. The sequences of 'adil.flesh' is similar to the sequences of 'gz1L' further confirming the identity of the source of confiscated remain 'adil.flesh' as that of a *Panthera pardus* origin.

FIG. 1C illustrates the NJ-tree (Neighbor Joining tree) constructed using CLUSTAL X (1.8) from the sequences revealed from 'adil.flesh' and reference animals listed in Table 5. The animals belonging to similar species cluster together; however, the animals of different species group in different clusters. The confiscated material under investigation (i.e. 'adil.flesh') clusters with 'gz1L' (i.e. the known normal leopard '*Panthera pardus*') indicating the identity of the species of 'adil.flesh' as that of a *Panthera pardus* source.

Figure 2:
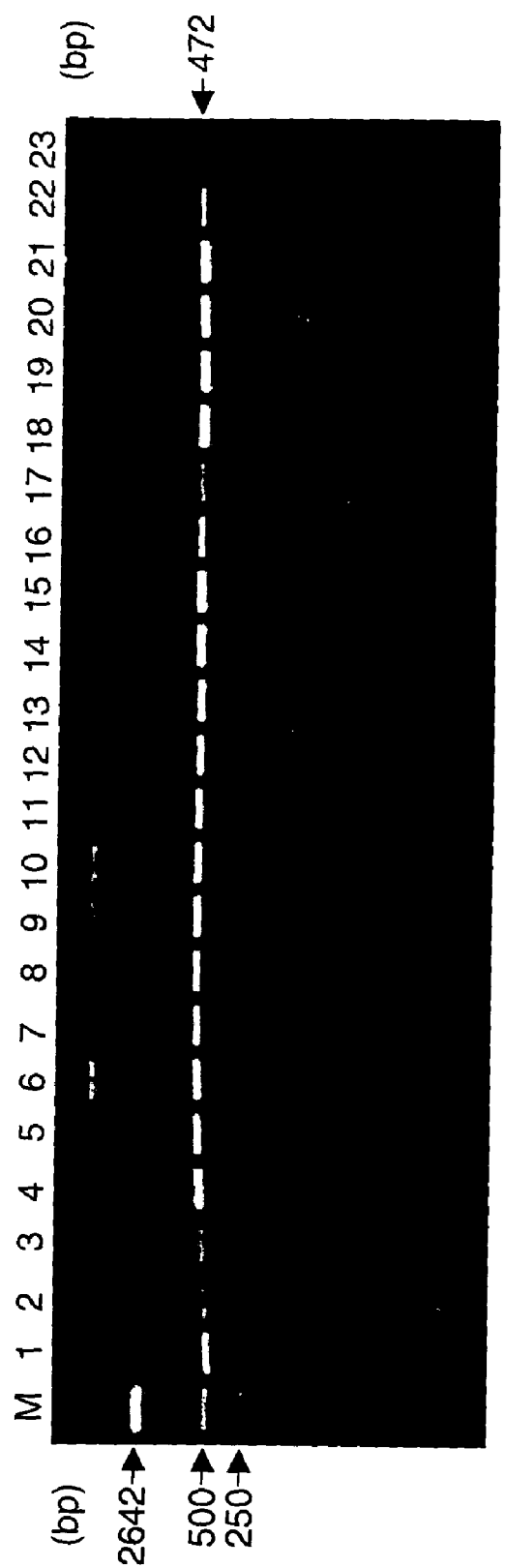

FIG. 2 shows the Agarose gel electrophorogram showing the PCR amplicons (472 bp) obtained from the reference animals of family felidae listed in Table 5, using universal primers 'mcb398 and 'mcb869'. Description of different lanes is as follows:

Lanes 1–21: The PCR profiles of the animals 1–21, respectively, listed in Table 5.

Lane 22: The PCR profiles of DNA isolated from confiscated skin of unknown animal origin 'i.e. adil.flesh'

Lane 23: Negative control (no DNA)

Lane M: Molecular weight marker (marker XIII, Boehringer mannheim)

Figure 3:
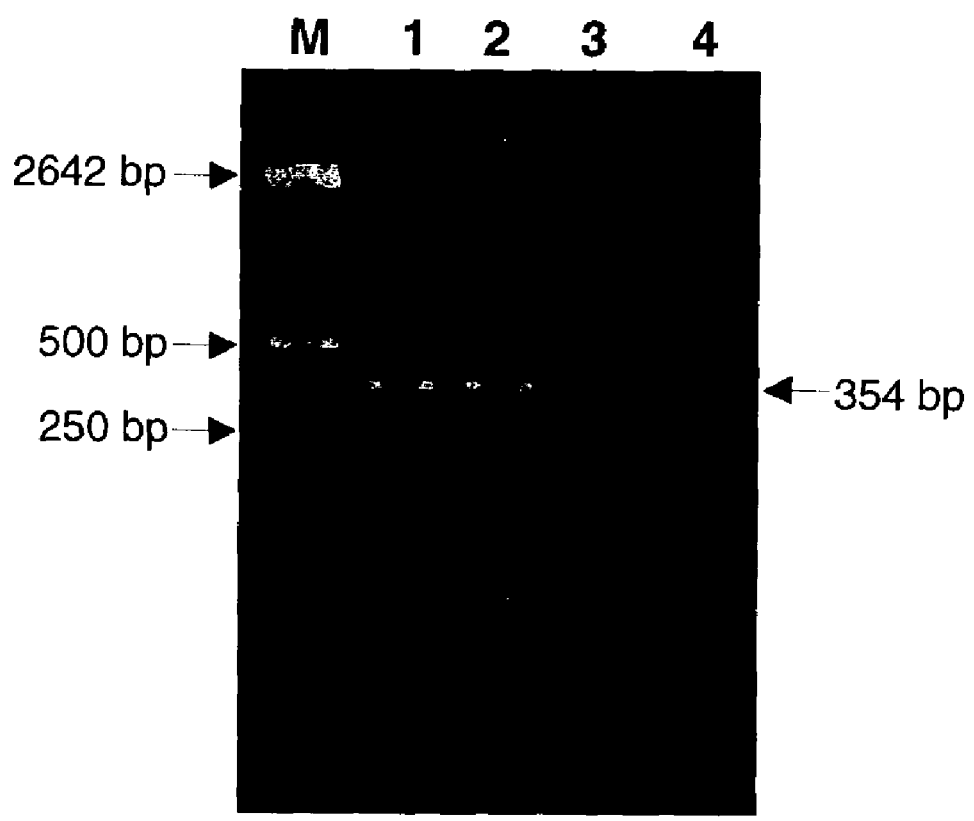

FIG. 3. Shows PCR amplicons obtained from animals listed in Table 9. The primers used in PCR are 'AFF' and 'AFR'. The description of different lanes shown is as follows:

Lane 1–4: The PCR profiles of animals 1–4, respectively, listed in Table 9, showing amplicons of 354 bp.

Lane M: Molecular weight marker (marker XIII, Boehringer mannheim)

Figure 4:
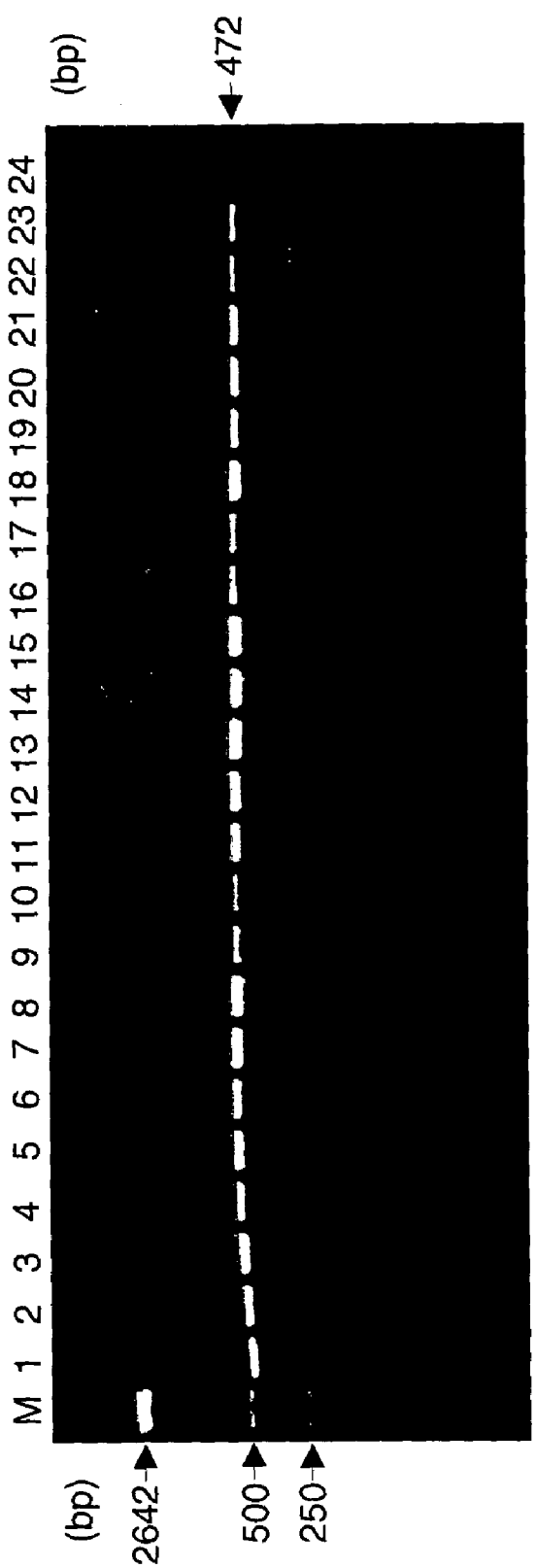

FIG. 4. Shows PCR amplicons obtained from animals listed in Table 12. This experiment demonstrates the universal nature of our primers among a vast range of animal species. Description of different lanes shown is as follows:

Lanes 1–23: The PCR profiles of the animals 1–23, respectively, listed in Table 12. The PCR product of 472 bp is amplified universally from all the animal species analyzed.

Lane 24: Negative control (no DNA)

Lane M: Molecular weight marker (marker XIII, Boehringer mannheim)

Table 1. List of 221 animal species used for In-silico analysis to design the universal primers 'mcb398' and 'mcb869'. Table also demonstrate the 'P,S scores' of 'mcb398' and 'mcb869' for different templates. The descriptions of various symbols used in this table are as follows:

Symbol (#) refers to Number

Symbol (*) refers to the animal species which is either protected species (listed in Wildlife (Protection) Act, 1972 (Central Act NO 53 of 1972), or an endangered/rare animal species Symbol ($P,S/F) refers to Probability of match and Stability of match of primer 'mcb398' with different templates (i.e. the cytochrome b gene from different species origin). A higher P,S score refers to the higher probabilities of significant amplification of specific template by the primer. It is calculated by Amplify (1.2) software.

Symbol ($^\Psi$P,S/R) refers to Probability of match and Stability of match of primer 'mcb869' with different templates. A higher P,S score refers to the higher probabilities of significant amplification of specific template by the primer. It is calculated by Amplify (1.2) software.

Table 2. Multiple sequence alignment of 472 bp fragment of mitochondrial cytochrome b gene (identified by inventors to fulfill the requirements of column 1, 2 and 3 mention under sub-heading 'Objectives of invention') of 221 animal species listed in Table 1. Alignments also show the binding sites for universal primers 'mcb398' and 'mcb869'. The symbol (*) refers to the nucleotide bases which are conserved amongst 221 animal species listed in Table 1). The alignments have been done using software CLUSTAL X (1.8). The nucleitide positions that are unmarked are variable amongst 221 animal species analyzed. These variable sites together constitute the molecular signature of an individual species, giving rise to molecular basis of species identification by our primers.

Table 3. Results of the blast analysis of the sequence revealed from 'adil.flesh' in 'mito' database of NCBI. It shows the most significant alignment of cytochrome b sequence (328 bp) revealed from confiscated skin piece 'adil.flesh' with *felis catus* cytochrome b gene sequence (genbank registration number NC_001700.1, bits score 365, E value, e-101) registered in NCBI database (bits score 365 and E value e-101). It gives an indication that the species of analyzed material belongs to family felidae. It also fulfills the requirements of column 6 mention above under sub-heading 'Objectives of invention'.

Table 4. Results of the blast analysis of the sequence revealed from 'adil.flesh' in 'nr' database of NCBI. It shows the most significant alignment of cytochrome b sequence (328 bp) revealed from confiscated skin piece 'adil.flesh' with *Panthera pardus* cytochrome b gene sequence (genbank registration number AY005809, bits score 603, E value, e-170) registered in NCBI database. It gives an indication that the species of analyzed material belongs to *Panthera paurdus* origin. It also fulfills the requirements of column 6 mention above under sub-heading 'Objectives of invention'.

Table 5. Reference animal belonging to family felidae selected for comparison with 'adil.flesh' to confirm the findings of BLAST analysis results of which are mentioned in Table 3 and 4, respectively. The animals listed in SN. 1–21 represent different species of family felidae. SN. 22 and 23 are primate species taken for out-group comparisons.

Table 6 Multiple sequence alignments of cytochrome b sequences (328 bp) revealed from 'adil.flesh' and reference animals listed in Table 5. The positions that have a common nucleotide in all the animal species under investigation are shown with a star (*) mark; however, the positions that are variable in any of the animals under investigation are unmarked. The nucleotides at these positions constitute the molecular signature of an individual species, which are unique and highly specific for its species. These signatures are the molecular basis of identification of individual animal species using our primers 'mcb398' and 'mcb869'.

Table 7 (Tables 7a, 7b, 7c and 7d). The comparison of the molecular signatures of different animal species investigated along with 'adil.flesh', the confiscated skin of unknown animal origin. This table demonstrates the variable positions (i.e. the positions which are not marked with star (*) symbol in Table 6), amongst the 328 bp fragment revealed from the animals listed in Table 5. The dot (.) mark represents the presence of the similar nucleotide as listed in lane 1 i.e. the sequence from "adil.flesh" at that position. It demonstrates that the signatures of each species are unique and specific to its species. The molecular signatures of 'adil.flesh' are comparable (except for position 37 which has a transition from 'T' to 'C') to the molecular signature of 'gz1L' i.e. the known leopard '*Panthera pardus*' source, indicating the identity of the source of confiscated skin 'adil.flesh' as that of a leopard '*Panthera pardus*' source. The nucleotide variations (at the positions 153, 198, 223, 264, among the known leopards, (i.e. gz1L, gz2L, and gz3L, respectively)), give an idea about the geographical habitat of each animals. Various studies referring to molecular evolution of different animal species support this hypothesis[75]; however, it could further be confirmed by taking the reference animals from different geographical areas and analyzing by our primers 'mcb 398' and 'mcb869'. If we could generate the database of different haplotypes (i.e. habitat specific molecular signatures) of the animal species, it would also enable our primers to reveal the geographical location of the committment of wildlife crime.

Table 8. Percent similarity matrix calculated by pair-vise comparisons of nucleotide sequences aligned (illustrated in Table 6). The cytochrome b gene sequence of DNA isolated from confiscated material had maximum similarity (99.7% and 98.2%, with the lineages of animals 'gz2L' and 'gz3L', respectively) with the sequences obtained from known normal leopard source, indicating its identity as that of a leopard origin. The similarity matrix has been calculated using the software PHYLIP (3.5).

Table 9. Animals selected for validation of minimum P,S score for efficient amplification of cytochrome b gene of different origin by the primers 'mcb398' and 'mcb869'. P,S score of primers 'AFF' and 'AFR' for these animals are shown.

Table 10. BLAST analysis of primers 'mcb398' in nr database of NCBI. It demonstrates that the 3' end of this primer is highly conserved among a vast range of animal species. It also shows the significant homology among the primer and templates (i.e. the cytochrome b gene fragment of different animal species), confirming the universal nature of our primer Table 11. BLAST analysis of primers 'mcb869' in nr database of NCBI. It demonstrates that the 3' end of this primer is highly conserved among a vast range of animal species. It also shows the significant homology among the primer and templates (i.e. the cytochrome b gene fragment of different animal species), confirming the universal nature of our primer.

Table 12. Other animal belonging to distantly related animal species, investigated to confirm the universal nature of primers 'mcb398' and 'mcb869'. Gel photograph showing the PCR amplicons from these animals are shown in FIG. 4.

The mitochondrial cytochrome b gene has very widely been used in molecular taxonomic studies. It has immense capabilities to reveal different evolutionary lineages of animals in family, genus and species specific manner. It has also been used to classify the population of a particular species according to its demographic distributions[75]. The vast database of cytochrome b sequences of different animal species has accumulated in public databases such as Genbank and NCBI[1–65]. We have explored these unique characteristics of cytochrome b gene to establish the identity of confiscated remains of any unknown animal by inventing a pair of novel primers, 'mcb398' and 'mcb869', that can amplify a small fragment (472 bp) of cytochrome b gene of wide range of animal species in universal manner. These primers work universally because its 3' ends target within a highly conserved region.

The fragment of cytochrome b gene identified had all the features mentioned in columns 1, 2 and 3 listed under sub-heading 'Objective of invention'. We identified this fragment by aligning the cytochrome b gene sequences (1140 bp) of 221 different animal species listed in Table 1. These sequences are publicly available in NCBI DNA databases. These sequences were aligned using the software CLUSTAL X (1.8). As mentioned before, the 472 bp fragment of cytochrome b gene identified by us to have the features mentioned in columns 1, 2 and 3 listed under sub-heading 'Objective of invention' includes the nucleotides between 398 to 869 in *Antilope cervicapra* and *Felis catus*; however, 399 to 870 in *Homo sapiens sapiens* species. Except at few positions (marked as star (*) in Table 2, the nucleotide sequences of this fragment are highly variable amongst the animal species, revealing the identity of the biological material belonging to that of an unknown animal origin by the procedure invented by us. As for identity of this fragment we are considering *Antilope cervicapra* as a representative species, and the sequence the above fragment of cytochrome b gene of *Antilope cervicapra* is mentioned herewith:

Mitochondrial cytochrome b gene sequence (398–869 bp) of *Antilope cervicapra*

"taccatgaggacaaatatcttttgaggagcaacagtcatcaccaatctcctttcagcaatcccatacatcggtacaaacctagtaga atgaatctgaggagggttctcagtagataaagcaaccctTacccgattTttcgccttccactttatcctcccatttatcattgcagccctta ccatagtacacctactgtttctccacgaaacaggatccaacaacccacaggaatctcatcagacgcagacaaaattccattccaccc ctactacactatcaaagatatcctaggagctctactattaattttaaccctcatgcttctagtcctattctcaccggacctgcttggagacc cagacaactatacaccagcaaacccacttaatacacccccacatatcaagcccgaatgatacttcctatttgcatacgcaatcctccga tcaattcctaacaaactaggagg Table 2 presents the alignment of the above fragment of cytochrome b gene of 221 animal species. Each species in table 2 has been represented by a unique code, which is decoded in Table 1. We selected these species to represent the vast range of animal families of distant orders. Of 221 species, about 65 were the protected/endangered or rare species listed in Wildlife (Protection) Act, 1972 (Central Act NO 53 of 1972). These species are marked with symbol (*) in Table 1. The NCBI accession number refers to its registration number in NCBI database and the number in superscript represent the reference cited. Based on the aligned cytochrome b sequences of different 221 animal species the primers designed were as follow:

| Primers name | Sequence (5'-3') |
|---|---|
| 'mcb398' | "TACCATGAGGACAAATATCATTCTG" |
| 'mcb869' | "CCTCCTAGTTTGTTAGGGATTGATCG" |

Tables 2, 10 and 11, respectively, demonstrates that the 3, ends of the primers are highly conserved amongst all the animal species analyzed in-silico (In total 221 animal species listed in Table 1 and about 500 species listed in Tables 10 and 11, respectively) Also, the 5' end of the primers were selected within the conserved region of cytochrome b gene to improve the probability and stability of match of the primers to their target sequences (i.e. the above mentioned 472 bp fragment of cytochrome b gene). The primers were thoroughly checked for internal stabilities, loop or dimmer formation using different software viz., 'Amplify (1.2)', 'Primer3' (http://www.genome.wi.mit.edu/cgi-bin/primer/primer3.cgi) as well as manually. We assigned the P,S score (P=Probability of match, S=Stability of match) to the primers for each template using the software Amplify (1.2). The higher scores of P and S ensure a good amplification if all other conditions standard (which are mentioned under 'Example 3') are optimum. The Highest score for 'mcb398' was 98,63 (i.e. the situation where the primer has perfect match with template); however, the highest P, S for 'mcb869' was recorded as 98, 68 for a complete match between the primer and template.

The lowest P,S score observed for 'mcb398' was 81,50 for species Talpa europaea whereas 'mcb869' had a high P, S score for this species (92, 57). The another species which have lowest P, S score for one of the two primers were Eumeces egregious and Equus ainus. Eumeces egregious had P, S score 86, 55 and 73,51 for 'mcb398' and 'mcb869', respectively; however, the P, S score of Equus ainus was calculated as 91,61 and 73, 51 for 'mcb398' and 'mcb869', respectively. All other animals had higher P, S scores then the above mentioned species. To ensure that these primers would work efficiently with the DNA template from the animals having the lowest P, S score for one of the primers, we designed an another experiment to validate the lower limits of one of the two primers sufficient for efficient amplification in PCR. We designed an another primer pair (AFF=5'tagtagaatgaatctgaggagg3' and AFR=5'atgcaaataggaagtatcattc3'.) having more mis-pairing at their annealing sites (but not at ends), therefore have less internal stability and lower P, S scores for its templates (listed in Table 9). The P,S scores of 'AFF' and 'AFR' were as calculated as low as 41 and 49 for Platanista gangetica and Sus scrofa These species were amplified efficiently using the primers 'AFF' and 'AFR' (results shown in FIG. 3) (keeping all other conditions standard i.e. the conditions mentioned in 'Example 3'). The lowest P,S scores (86, 55 and 73,51 for species Eumeces egregious) for our primers 'mcb398' and 'mcb869', respectively, were higher then the above range of combined P, S scores of 'AFF' and 'AFR' for species Sus scrofa (87, 52 and 87, 41), which was efficiently amplified by the primers 'AFF' and 'AFR'. It gives an indication that the primers 'mcb 398' and 'mcb 869' would work with all the species including Eumeces egregious efficiently to give rise to the expected product in PCR. This experiment confirmed that the primers 'mcb398' and 'mcb 869' are capable of amplifying the cytochrome b fragment of most of the animal species in a universal manner.

For further confirmation of universal nature of our primers, we blasted the sequence of our primers against the mito and nr databases of NCBI using BLAST software. The results of these analyses are shown in Tables 10, and 11, respectively.

Finally, the universal nature of the primers was tested in our laboratory with some more animal species listed in Table 12. These primers amplified all the animal species efficiently, giving rise to the band of expected size (472 bp). The results are shown in FIG. 4. This experiments substantiated the results of P,S analysis and other in-silico analyses to show that the primers 'mcb398' and 'mcb 869' are universal primers.

The flow chart of establishing identity of the species of biological material of unknown animal origin using primers 'mcb398' and 'mcb869'

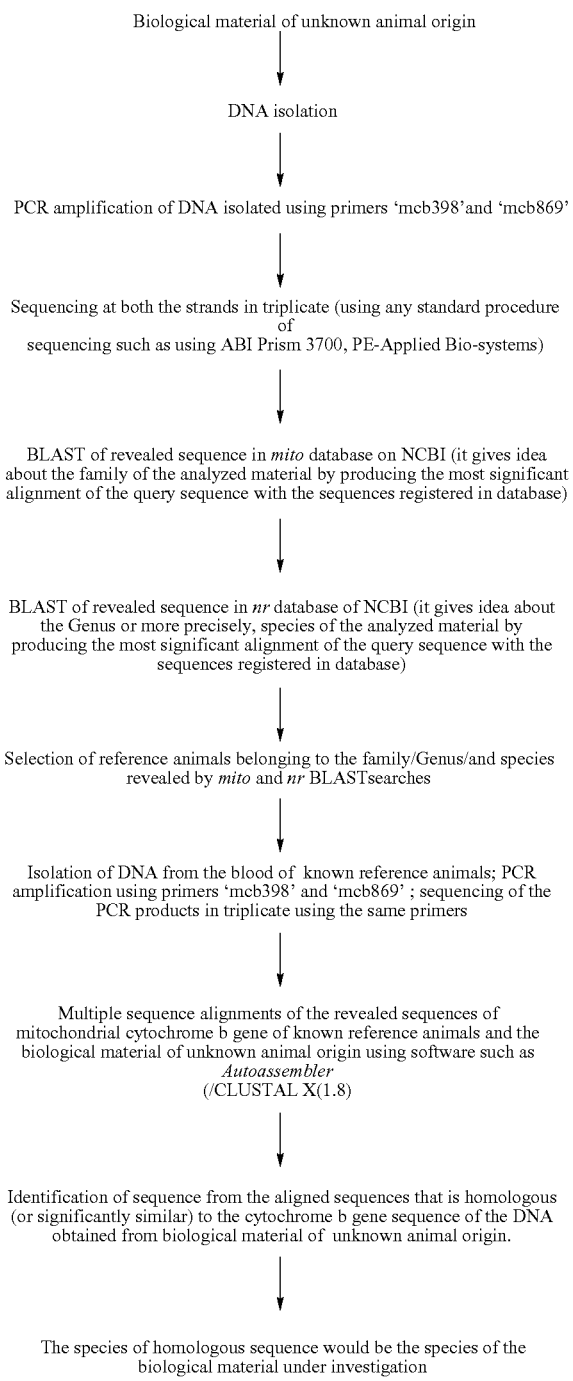

EXAMPLES

Example 1

Example for Identification of a Fragment of Cytochrome B Gene Fulfilling the Requirements of Columns 1, 2 and 3 Mentioned Under Sub-Heading 'Objectives of Invention' of Heading 'Brief Summary of Invention'

The cytochrome b molecule has very vastly been used in molecular taxonomic studies. Being a slow evolving gene, It has a tremendous information in its nucleotide sequences to distinguish the animals to their family, genus and species sources[1–65]. A vast database of the sequences of cytochrome b gene of different animal species has accumulated in the nr and mito databases of NCBI. We have explored these qualities of cytochrome b gene to establish the identity of confiscated remains of unknown animal origin to its family, genus and species sources. For this purpose, we have identified a fragment of cytochrome b gene which is highly polymorphic inter-specifically, however, it is monomorphic among the individual of same species, therefore it can group the individual of an unknown species with the known individuals of reference species to which it belongs. In order to amplify this fragment from DNA isolated form any unknown origin, it was necessary that it remain flanked with the highly conserved sequences amongst a vast range of animal families. To identify such a unique fragment within the cytochrome b gene, we aligned the sequences of 221 distantly related animal species (listed in Table 1) representing various families using software CLUSTAL X (1.8). These sequences were obtained from public database NCBI (http://www.ncbi.nlm.nih.gov). The aligned data was examined carefully for the conserved sites amongst all the species included in in-silico analysis. We identified a fragment (472 bp) of cytochrome b gene that was fulfilling all the requirements mentioned above and also under column 1, 2 and 3 of sub-heading 'Objectives of invention'.

As for the identity of this fragment we would like to mention that it includes the nucleotides between 398 to 869 in *Antilope cervicapra* and *Felis catus*; however, 399 to 870 in *Homo sapiens sapiens* species. Except at few positions marked as star (*) in Table 2, the nucleotide sequences of this fragment are highly variable amongst the animal species, giving rise to their unique molecular signature. These molecular signatures are characteristic of its species and form the basis of revealing the identity of the biological material of an unknown animal origin by the procedure invented by us. Considering *Antilope cervicapra* as a representative species, the sequence of this fragment is mentioned herewith:

Mitochondrial cytochrome b gene sequence (398–869 bp) of *Antilope cervicapra*

"taccatgaggacaaatatcttttgaggagcaacagtcatcaccaatctcctttcagcaatcccatacatcggtacaaacctagtaga atgaatctgaggaggttctcagtagataaagcaaccttacccgattttcgccttccactttatcctcccatttatcattgcagccctta ccatagtacacctactgttctccacgaaacaggatccaacaacccacaggaatctcatcagacgcagacaaaattccattccaccc -continued

```
ctactacactatcaaagatatcctaggagctctactattaattttaaccctcatgcttctagtcctattctcaccggacctgcttggagacc cagacaactatacaccagcaaacccacttaatacaccccccacatatcaagcccgaatgatacttcctatttgcatacgcaatcctccga tcaattcctaacaaactaggagg"
```

Example 2

Example for Development of Universal Primers to Amplify the Fragment Identified Mentioned under 'Example 1'

A pair of universal primer was designed which has the following features:

1. It targets the fragment identified (mentioned under 'Example 1') to amplify it in polymerase chain reaction (PCR).
2. Its 3' and 5' ends that are highly conserved (marked as star (*) in Table 2), amongst a vast range of animal species ensuring the amplification of the fragment mentioned above in a universal manner. The sequencing of the fragment amplified by these primes reveals the molecular signature of the species of analyzed material, which on comparison with the sequences of the known reference animals reveals the identity of the species of unknown biological material under investigation.
3. The tm (melting temperature) of both primers was almost similar (about 58 degree centigrade) ensuring the significant annealing of both the primers to its template, therefore significant amplification of targeted region in PCR.
4. The internal stability and P, S, score of the primers were ensured higher while designing it. The possibilities of internal loop formation, dimmer formation etc were also excluded by selecting its sequence uniquely. This ensured that the primer would be a good primer to be used in PCR for amplification of DNA from unknown animal origin.
5. The 3' end of the primers were ensured to have either 'G' or 'C' to increase the probability of strong bonding at its 3'ends, which is necessary for efficient amplification of DNA template in PCR. It also strengthens the universal nature of the primer.
6. The sequences of the primers were ensured to be unique so that it does not give rise to non-specific and spurious products in PCR leading to confusion. It improved the efficiency and quality of the technique invented by us.
7. These primers were named as 'mcb398' and 'mcb869' because of its property to amplify a region of mitochondrial cytochrome b gene between nucleotides 398 to 869 of *Antilope cervicapra*, a representative animal species for this invention. We took this animal species as representative species because the idea of developing such a novel primers came in the mind of inventors while they were working on the genome of this animal in Centre for Cellular and Molecular Biology, Hyderabad, India.
8. The sequences of the universal primers invented are as follows:

| Primers name | Sequence (5'-3') |
|---|---|
| 'mcb398' | "TACCATGAGGACAAATATCATTCTG" |
| 'mcb869' | "CCTCCTAGTTTGTTAGGGATTGATCG" |

Example 3

Example for Development of Universal PCR Conditions to Ensure the Amplification of a Template of any Unknown Origin in PCR, Hence Strengthening the Universal Nature of the Technique Invented by Us The PCR conditions developed had the following unique features:

1. These were capable of amplifying the DNA template of any animal origin in an universal manner using the universal primers mentioned under 'Example 2'.
2. The conditions were selected to ensure the comparable annealing temperature for both the primers i.e. 'mcb398' and 'mcb869'.
3. The PCR conditions standardized herewith are universal; therefore, the possibility of PCR failure with a template of unknown origin due to non-standard conditions is excluded. It ensures the universal nature of our technique to be used in wildlife forensics.
4. The universal conditions mentioned above are:

Amplification reactions should be carried out in 20 µl reaction volume containing approximately 20ηg of template DNA, 100 µm each of dNTPs, 1.25 pmole of each primer, 1.5 mM $MgCl_2$, 0.5 unit of AmpliTaq Gold (Perkin-Elmer-Cetus, USA) DNA polymerase and 1×PCR buffer (10 mM Tris-HCl, pH 8.3, and 50 mM KCl). The amplification profiles followed should be: an initial denaturation at 95° C. for 10 min, followed by 35 cycles each of denaturation at 95° C. for 45 s, annealing at 51° C. for 1 min, and extension at 72° C. for 2 min. The extension step at $35^{th}$ cycles should be held for 10 min.

Example 4

Establishing the Universal Nature of our Primer and Experimental Evidences to Demonstrate the Universal Nature of Primers:

The universal nature of the primers 'mcb398'and 'mcb 869' was ensured by the following measures:

(a) Selecting the primers from the aligned cytochrome b gene sequences of 221 animal of distantly related species:

The cytochrome b gene sequences (1140 bp) were aligned using software CLUSTAL X (1.8). The region of cytochrome b gene that was most conserved amongst 221 animal species was selected to design the primers.

(b) Selecting the 3' and 5' ends of the primers at the highly conserved positions of cytochrome b gene:

The 3' and 5' ends of the primers were ensured to anneal to a highly conserved position amongst 221 animal species representing a vast range of animal families. It was done to ensure an efficient amplification of all the species in PCR. These positions are shown with star (*) mark in Table 2.

(c) Ensuring either 'G' or 'C' at the 3' end of the primers:

It was ensured the primers to have either 'G' or 'C' at its 3' ends as these are the nucleotides that ensure the strong bonding at the 3' ends of the primers due to three hydrogen bonds while pairing with each other. The strong bonding at 3' ends helps the primers to anneal properly with its template resulting in significant amplification in PCR.

(d) Selecting the sequences of the primers to ensure a higher internal stability, higher P, S score, and no primer dimmer and loop formation:

The sequences of the primers were selected to have a high P, S score for a vast range of animal species (Shown in Table 1). The care was taken to exclude the possibilities of loop or primer dimmer formation that could reduce the efficiency of the primers in PCR.

(e) Selecting the sequence of the primers with a comparable melting temperature:

The sequences of the primers were selected to have a comparable melting temperature so that these could work together to amplify a DNA template in PCR at a similar annealing temperature. The melting temperature of both the primers was about 58 degree centigrade and the annealing temperature used in PCR is 51 degree centigrade.

Experimental Evidences to Demonstrate the Universal Nature of Primers:

(1) Evidence from In-silico analysis:

(a) Selecting the primers within the most conserved region of mitochondrial cytochrome b gene As mentioned above, the primers were designed to anneal within a highly conserved region of mitochondrial cytochrome b gene fragment of 472 bp. Table 2 presents the alignment of the above fragment of cytochrome b gene of 221 animal species representing a vast range of animal families. The conserved positions of nucleotide sequences are shown with star (*) mark in Table 2

Table 2 also demonstrates that the 3' ends of the primers are highly conserved amongst all the animal species analyzed in-silico. In the aligned sequences, the conserved nucleotides are marked with symbol (*). Also, the 5' end of the primers were selected within the conserved region of cytochrome b gene to improve the probability and stability of match of the primers to their target sequences (i.e. the above mentioned 472 bp fragment of cytochrome b gene). The primers were thoroughly checked for internal stabilities, loop or dimmer formation using different software viz., 'Amplify (1.2)', 'Primer3' (http://www.genome.wi.mit.edu/cgi-bin/primer/primer3.cgi) as well as manually.

(b) P, S, score analysis:

We assigned the P,S score (P=Probability of match, S=Stability of match) to the primers for each template using the software Amplify (1.2). The higher scores of P and S ensure a good amplification if all other conditions standard (which are mentioned under 'Example 3') are optimum. The Highest score for 'mcb398' was 98,63 (i.e. the situation where the primer has perfect match with template); however, the highest P, S for 'mcb869' was recorded as 98, 68 for a complete match between the primer and template. The lowest P,S score observed for 'mcb398' was 81,50 for species *Talpa europaea* whereas 'mcb869' had a high P, S score for this species (92, 57). The another species which have lowest P, S score for one of the two primers were *Eumeces egregious* and *Equus ainus*. Eumeces egregious had P, S score 86, 55 and 73,51 for 'mcb398' and 'mcb869', respectively; however, the P, S score of *Equus ainus* was calculated as 91,61 and 73, 51 for 'mcb398' and 'mcb869', respectively. All other animals had higher P, S scores then the above mentioned species. To ensure that these primers would work efficiently with the DNA template from the animals having the lowest P, S score for one of the primers, we designed an another experiment to validate the lower limits of one of the two primers sufficient for efficient amplification in PCR. We designed an another primer pair (AFF=$5'$ctagtagaatgaatctgaggagg$3'$ and AFR=$5'$tatgcaaataggaagtatcattc$3'$.) that have more mis-pairing at their annealing sites (but not at ends), therefore have less internal stability and lower P, S scores for its templates (listed in Table 9). The P,S scores of 'AFF' and 'AFR' were as calculated as low as 41 and 49 for *Platanista gangetica* and *Sus scrofa* These species were amplified efficiently using the primers 'AFF' and 'AFR' (results shown in FIG. 3) (keeping all other conditions standard i.e. the conditions mentioned in 'Example 3'). The lowest P,S scores (86, 55 and 73,51 for species *Eumeces egregious*) for our primers 'mcb398' and 'mcb869', respectively, were higher then the above range of combined P, S scores of 'AFF' and 'AFR' for species *Sus scrofa* (87, 52 and 87, 41), which was efficiently amplified by the primers 'AFF' and 'AFR'. It gives an indication that the primers 'mcb 398' and 'mcb 869' would work with all the species including Eumeces egregious efficiently to give rise to the expected product in PCR. This experiment confirmed that the primers 'mcb398' and 'mcb 869' are capable of amplifying the cytochrome b fragment of most of the animal species in a universal manner.

© BLAST analysis:

The sequences of primers 'mcb398' and 'mcb869' were blasted against mito and nr databases of NCBI to see its significant alignments with the sequences registered in GenBank. As expected, the most significant alignments of the sequences were found with the cytochrome b gene regions (within the 472 bp fragment mentioned in 'Example 1') of different animal species. This analysis also showed that the 3' as well as 5' ends of the primers were highly conserved amongst a vast range of animal species, confirming the universal nature of the primers (Tables 10 and 11, respectively)

(2) Evidence from Bench Work/Experiments Done in Laboratory Conditions:

The DNA from different animals belonging to distantly related species (mentioned in Table 12) was isolated and subjected to PCR amplification using the primers invented by us i.e. the primers 'mcb398' and 'mcb869' The PCR products amplified were resolved in agarose gel by electrophoresis and visualized under UV light. The PCR products of expected size (472 bp) were obtained from all the animals confirming the universal nature of our primers. These results are shown in FIG. 4.

Example 5

Example to Establish the Identity of Confiscated Remains from Unknown Animal Origin Using the Universal Primers 'mcb398' and 'mcb869'.

The step-vise procedure to establish the identity of the biological material from an unknown animal source is mentioned below:

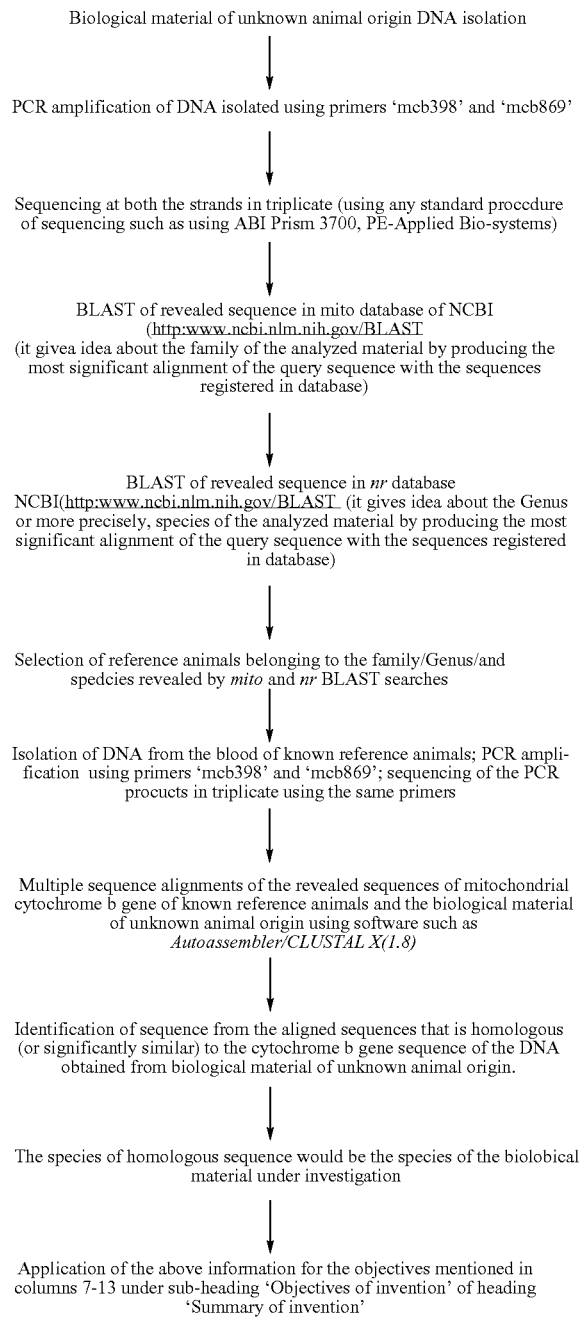

Example 6

The Actual Execution of the Technique Invented

As a first application and to demonstrate the ease and utility of this method, we investigated a case of forensic identification submitted at our laboratory to seek scientific opinion on animal hunting evidence. In this case, we received the half burned remains of an unknown animal, confiscated by the crime investigation agencies. The DNA was isolated from the above material following standard methods[74] and subjected to PCR amplification using the primers mentioned above (viz., 'mcb398' and 'mcb869'). Amplification reactions were carried out in 20 μl reaction volume containing 20 ηg of template DNA, 100 μm each of dNTPs, 1.25 pmole of each primer, 1.5 mM MgCl$_2$, 0.5 unit of AmpliTaq Gold (Perkin-Elmer-Cetus, USA) DNA polymerase and 1× PCR buffer (10MM Tris-HCl, pH 8.3, and 50 mM KCl). The amplification profiles followed were: an initial denaturation at 95° C. for 10 min, followed by 35 cycles each of denaturation at 95° C. for 45 s, annealing at 51° C. for 1 min, and extension at 72° C. for 2 min. The extension step at 35$^{th}$ cycles was held for 10 min.

The PCR products obtained were sequenced in automated work station (ABI Prism 3700, PE-Biosystems) on both strands in triplicate and the sequence resolved (328 bp, shown in FIG. 1a) was blasted against mito databases of NCBI using BLAST program[73]. The most significant alignment (bits Value 365, E value e$^{-101}$) of this sequence was produced with the cytochrome b gene sequence of *Felis catus*, (Table 3) indicating that species of analyzed material belongs to family felidae. Further, the above sequence revealed from the confiscated remain was blasted against nr databases of NCBI using BLAST program. The most significant alignment (bits Value 603, E value e-170) of this sequence was produced with the cytochrome b gene sequence of *Panthera pardus* (Table 4), indicating the identity of the analyzed material as that of a *Panthera pardus* source. Based on this information, we selected the reference animals listed in Table 5 representing different species and subspecies of felidae. The DNA isolated from reference animals was amplified and sequenced on both strands in triplicate using the primer pair mentioned above. Consensus sequences obtained were aligned using program CLUSTAL X (1.8) (Table 6). Sequence comparisons identified 113 variable sites in total amongst all animals analyzed (Table 7). Pair-vise comparisons of sequences were performed to find out the variation among different animals investigated. All the species investigated were differentiated by a their unique nucleotides sequences. The molecular signatures of different reference animals were compared with the molecular signature of the confiscated skin 'adil.flesh'. Table 7 demonstrate that the maximum similarity of the adil.flesh with 'gz1l' i.e. known Leopard (*Panthera pardus*) species, indicating the identity of the adil.flesh, the confiscated skin, as that of a *Panthera pardus* origin. We also calculated the similarity matrix showing the pair-vise similarity amongst the animal species under investigation using PHYLIP software This matrix is shown in Table 8. It demonstrates that the animals belonging to different species had more variation; however, the animals of same species had maximum similarity among their cytochrome b sequences. The cytochrome b gene sequence of DNA isolated from confiscated material had maximum similarity with the sequences obtained from known Leopard source(99.7%, and 98.2 with 'gz1l' and 'gz2l', respectively); establishing the identity of the source of confiscated material as that of a Normal leopard (*Penthera pardus*) species. The step-vise procedure involved in above analysis is illustrated in FIGS. 1a, 1b and 1c, respectively.

Thus, the primers invented by us can generate the molecular signature from any biological material of unknown animal origin, which actually is the characteristic of its family, genus and more precisely, the species. When these signatures are compared in-silico with the signatures already available in public databases (viz., GenBank, NCBI database etc) using BLAST software[73], it indicates identity of the family, genus or species of the analyzed material, which in turn is confirmed practically by comparing with the reference animals of the revealed family, genus or species, by including them in the further analysis by the primers 'mcb398' and 'mcb869'. Application of the information revealed could be in fulfilling the requirements of objectives mentioned in columns 7–13 under sub-heading 'Objective of invention' of heading 'Summary of invention' The method of the invention can be used to establish the identity of confiscated animal parts and products is one of the key requirements of wildlife identification in forensics. It is needed to establish the crime with the criminal beyond a reasonable doubt to avoid the human violation of wildlife resources. Various morphological biochemical and molecular approaches have been given for this purpose; however, none of the current methods is universally applicable to detect the mutilated animal remains of unknown origin. We have identified a fragment on the mitochondrial cytochrome b gene, which has enormous information to differentiate among various animal species back to the family, genus and species sources. We have also found that this fragment is flanked by the highly conserved sequences amongst a vast range of animal species. We invented a pair of universal primer that can amplify this fragment of DNA isolated from the biological material of an unknown animal origin in polymerase chain reaction (PCR) to reveal its identity at species and sub-species sources. This novel invention has great potential to revolutionize the whole scenario of wildlife forensic identification and crime investigation.

Table 1. List of 221 animal species used for In-silico analysis to design the universal primers 'mcb398'and ' mcb869'. Table also demonstrate the 'P,S scores' of 'mcb398' and 'mcb869' for different templates. The descriptions of various symbols used in this table are as follows:

Symbol (#) refers to Number

Symbol (*) refers to the animal species which is either protected species (listed in Wildlife (Protection) Act, 1972 (Central Act NO 53 of 1972), or an endangered/rare animal species Symbol ($P,S/F) refers to Probability of match and Stability of match of primer 'mcb398' with different templates (i.e. the cytochrome b gene from different species origin). A higher P,S score refers to the higher probabilities of significant amplification of specific template by the primer. It is calculated by Amplify (1.2) software.

Symbol ($\Psi$P,S/R) refers to Probability of match and Stability of match of primer 'mcb869' with different templates. A higher P,S score refers to the higher probabilities of significant amplification of specific template by the primer. It is calculated by Amplify (1.2) software.

TABLE 1

The animal species included in the study for *in-silico* analysis

| SN. | Code | Name | NCBI accession # | $^S$P,S/F | $^\Psi$P,S/R |
|---|---|---|---|---|---|
| 1 | aep.mel | *Aepyceros melampus* | AF036289[1] | 97, 60 | 94, 62 |
| 2 | ore.ore | *Oreotragus oreotragus* | AF036288[1] | 88, 52 | 94, 62 |
| 3 | add.nas | *Addax nasomaculatus* | AF034722[2] | 97, 60 | 95, 66 |
| 4 | ory.dam | *Oryx damah* | AJ222685[1] | 90, 58 | 95, 66 |
| 5 | hip.equ | *Hippotragus equinus* | AF022060[3] | 98, 63 | 85, 55 |
| 6 | alc.bus | *Alcelaphus buselaphus* | AJ222681[1] | 97, 60 | 98, 68 |
| 7 | sig.lic | *Sigmoceros lichtensteinii* | AF034967[4] | 97, 60 | 98, 68 |
| 8 | bea.hun | *Beatragus hunteri* | AF034968[4] | 97, 60 | 94, 62 |
| 9 | dam.lun | *Damaliscus lunatus* | AF016635[3] | 97, 60 | 77, 55 |
| 10 | con.tau | *Connochaetes taurinus* | AF016638[3] | 82, 56 | 93, 62 |
| 11 | bis.bon | *Bison bonasus* | Y15005[5] | 90, 58 | 87, 63 |
| 12 | bos.gru | *Bos grunniens*\* | AF091631[6] | 90, 58 | 94, 62 |
| 13 | bos.tra | *Bos tragocamelus*\* | AJ222679[1] | 90, 58 | 95, 66 |
| 14 | buba.bub | *Bubalus bubalis*\* | D34637[7] | 97, 60 | 93, 64 |
| 15 | bub.min | *Bubalus mindorensis* | D82895[8] | 97, 60 | 87, 62 |
| 16 | tra.ang | *Tragelaphus angasii* | AF091633[6] | 97, 60 | 87, 63 |
| 17 | tra.eur | *Tragelaphus eurycerus* | AF036276[1] | 90, 58 | 97, 64 |
| 18 | nem.cau | *Nemorhaedus caudatus*\* | U17861[9] | 95, 61 | 93, 59 |
| 19 | pse.nay | *Pseudois nayaur* | AF034732[2] | 89, 55 | 89, 59 |
| 20 | amm.ler | *Ammotragus lervia* | AF034731[2] | 94, 58 | 97, 63 |
| 21 | cap.fal | *Capra falconeri*\* | D84202[10] | 98, 63 | 95, 66 |
| 22 | cap.ibe | *Capra ibex*\* | AF034735[2] | 98, 63 | 89, 58 |
| 23 | hem.jem | *Hemitragus jemlahicus*\* | AF034733[2] | 95, 61 | 90, 61 |
| 24 | rup.pyr | *Rupicapra pyrenaica* | AF034726[2] | 95, 61 | 89, 59 |
| 25 | rup.rup | *Rupicapra rupicapra* | AF034725[2] | 95, 61 | 94, 64 |
| 26 | pan.hod | *Pantholops hodgsoni* | AF034724[2] | 98, 63 | 95, 66 |
| 27 | bud.tax.tax | *Budorcas taxicolor taxicolor*\* | U17868[9] | 90, 58 | 95, 66 |
| 28 | ovi.anim | *Ovis ammon*\* | AF034727[2] | 98, 63 | 97, 64 |
| 29 | ovi.vig | *Ovis vignei*\* | AF034729[2] | 98, 63 | 97, 64 |
| 30 | cap.cri | *Capcornis crispus*\* | AJ304502[11] | 98, 63 | 94, 63 |
| 31 | ovi.mos | *Ovibos moschatus* | U17862[9] | 98, 63 | 92, 61 |
| 32 | ore.ame | *Oreamnos americanus* | AF190632[12] | 98, 63 | 94, 62 |
| 33 | cep.dor | *Cephalophus dorsalis* | AF091634[6] | 97, 58 | 90, 61 |
| 34 | cep.max | *Cephalophus maxwellii* | AF096629[13] | 97, 60 | 88, 53 |
| 35 | alc.alc | *Alces alces* | AJ000026[14] | 95, 61 | 93, 59 |
| 36 | hyd.ine | *Hydropotes inermis* | AJ000028[14] | 97, 60 | 90, 63 |
| 37 | mun.mun | *Muntiacus muntjak*\* | AF042718[15] | 90, 58 | 93, 64 |
| 38 | cer.ele.kan | *Cervus elaphus kansuensis*\* | AB021098[16] | 98, 63 | 82, 59 |
| 39 | cer.ele.xan | *Cervus elaphus xanthopygus*\* | AB021097[16] | 98, 63 | 82, 59 |
| 40 | cer.ele.can | *Cervus elaphus canadensis*\* | AB021096[16] | 98, 63 | 90, 61 |
| 41 | cer.nip.ce | *Cervus nippon centralis* | AB021094[16] | 98, 63 | 90, 61 |
| 42 | cer.nip.ye | *Cervus nipponyesoensis* | AB021095[16] | 98, 63 | 90, 61 |

TABLE 1-continued

The animal species included in the study for *in-silico* analysis

| SN. | Code | Name | NCBI accession # | $^S$P,S/F | $^\Psi$P,S/R |
|---|---|---|---|---|---|
| 43 | cer.nip.ke | *Cervus nippon keramae* | AB021091[16] | 98, 63 | 90, 61 |
| 44 | cer.nip.pu | *Cervus nipponpuichellus* | AB021090[16] | 98, 63 | 90, 61 |
| 45 | cer.nip.ni | *Cervus nippon nippon* | AB021093[16] | 98, 63 | 90, 61 |
| 46 | cer.ela.sc | *Cervus elaphus scoticus* | AB021099[16] | 98, 63 | 90, 61 |
| 47 | cer.dam | *Cervus dama* | AJ000022[14] | 98, 63 | 88, 53 |
| 48 | ran.tar | *Rangifer tarandus* | AJ000029[14] | 98, 63 | 89, 57 |
| 49 | mos.fus | *Moschus fuscus** | AF026888[17] | 90, 59 | 90, 61 |
| 50 | mos.leu | *Moschus leucogaster** | AF026889[17] | 90, 59 | 90, 61 |
| 51 | mos.chr | *Moschus chrysogaster** | AF026887[17] | 90, 59 | 90, 61 |
| 52 | mos.ber | *Moschus berezovskii** | AF026886[17] | 90, 59 | 90, 61 |
| 53 | mos.mos | *Moschus moschiferus** | AF026883[17] | 90, 59 | 92, 61 |
| 54 | kob.ell | *Kobus ellipsiprymnus* | AF022059[3] | 91, 61 | 95, 66 |
| 55 | kob.meg | *Kobus megaceros* | AJ222686[1] | 91, 61 | 83, 56 |
| 56 | red.aru | *Redunca arundinum* | AF096628[13] | 91, 61 | 94, 62 |
| 57 | red.ful | *Redunca fulvorufula* | AF036284[1] | 89, 57 | 94, 62 |
| 58 | neo.mos | *Neotragus moschatus* | AJ222683[1] | 89, 57 | 94, 62 |
| 59 | pel.cap | *Pelea capreolus* | AF022055[3] | 91, 61 | 90, 61 |
| 60 | ant.cer | *Antilope cervicapra** | AF022058[3] | 82, 56 | 93, 64 |
| 61 | sai.tat | *Saiga tatarica* | AF064487[18] | 91, 61 | 92, 61 |
| 62 | gaz.dam | *Gazella dama* | AF025954[3] | 91, 61 | 92, 61 |
| 63 | our.our | *Ourebia ourebi* | AF036288[1] | 82, 56 | 82, 59 |
| 64 | gaz.gaz | *Gazela gazella** | AJ222682[1] | 91, 61 | 89, 57 |
| 65 | rap.mel | *Raphicerus melanotis* | AF022053[3] | 81, 54 | 80, 50 |
| 66 | mad.kir | *Madoqua kirkii* | AF022070[3] | 90, 58 | 97, 65 |
| 67 | ant.ame | *Antilocapra americana* | AF091629[6] | 98, 63 | 98, 68 |
| 68 | tra.jav | *Tragulus javanicus** | D32189[19] | 86, 57 | 86, 59 |
| 69 | tra.nap | *Tragulus napu** | X56288[20] | 81, 52 | 93, 58 |
| 70 | bal.acu | *Balaenoptera acutorostrata* | X75753[21] | 89, 56 | 97, 61 |
| 71 | bal.bon | *Balaenoptera bonaerensis* | X75581[21] | 89, 56 | 93, 59 |
| 72 | bal.bor | *Balaenoptera borealis** | X75582[21] | 89, 56 | 93, 59 |
| 73 | bal.edi | *Balaenoptera edeni* | X75583[21] | 89, 56 | 88, 54 |
| 74 | esc.rob | *Eschrichtius robustus** | X75585[21] | 97, 61 | 86, 57 |
| 75 | bal.mus | *Balaenoptera musculus** | NC_001601[22] | 97, 57 | 93, 59 |
| 76 | meg.nov | *Megaptera novaeangliae** | X75584[21] | 97, 61 | 94, 63 |
| 77 | bal.phy | *Balaenoptera physalus** | NC_001321[23] | 97, 57 | 94, 63 |
| 78 | cap.mar | *Caperea marginata* | X75586[21] | 93, 55 | 91, 53 |
| 79 | cep.com | *Cephalorhynchus commersonii* | AF084073[24] | 85, 51 | 88, 55 |
| 80 | cep.eut | *Cephalorhynchus eutropia** | AF084072[24] | 85, 51 | 92, 59 |
| 81 | lag.obl | *Lagenorhynchus obliquidens* | AF084067[24] | 94, 59 | 92, 59 |
| 82 | cep.hea | *Cephalorhynchus heavisidii* | AF084070[24] | 89, 56 | 97, 63 |
| 83 | cep.hec | *cephalorhynchus hectori** | AF084071[24] | 89, 56 | 92, 59 |
| 84 | lag.aus | *Lagenorhynchus australis* | AF084069[24] | 86, 54 | 92, 59 |
| 85 | lag.cru | *Lagenorhynchus cruciger* | AF084068[24] | 86, 54 | 92, 59 |
| 86 | lag.obs | *Lagenorhynchus obscurus* | AF084066[24] | 86, 54 | 92, 59 |
| 87 | lis.bor | *Lissodelphis borealis* | AF084064[24] | 85, 51 | 92, 59 |
| 88 | lis.per | *Lissodelphis peronii* | AF084065[24] | 86, 54 | 92, 59 |
| 89 | glo.mac | *Globicephala macrorhynchus* | AF084055[24] | 94, 59 | 88, 55 |
| 90 | glo.mel | *Globicephala melas* | AF084056[24] | 94, 59 | 88, 55 |
| 91 | fer.att | *Feresa attenuata** | AF084052[24] | 94, 59 | 92, 59 |
| 92 | pep.ele | *Peponocephala electra** | AF084053[24] | 94, 59 | 88, 55 |
| 93 | gra.gri | *Grampus griseus* | AF084059[24] | 97, 61 | 89, 59 |
| 94 | pse.cra | *Pseudorca crassidens** | AF084057[24] | 94, 59 | 92, 59 |
| 95 | lag.acu | *Lagenorhynchus acutus* | AF084075[24] | 98, 63 | 89, 59 |
| 96 | orci.bre | *Orcinus orca* | AF084061[24] | 86, 57 | 82, 52 |
| 97 | orca.bre | *Orcaella brevirostris* | AF084063[24] | 86, 57 | 91, 54 |
| 98 | del.cap | *Delphinus capensis* | AF084087[24] | 86, 54 | 97, 63 |
| 99 | del.tro | *Delphinus tropicalis* | AF084088[24] | 97, 57 | 97, 63 |
| 100 | del.del | *Delphinus delphis* | AF084085[24] | 97, 57 | 97, 63 |
| 101 | sten.cly | *Stenella clymene* | AF084083[24] | 97, 57 | 97, 63 |
| 102 | sten.coe | *Stenella coeruleoalba* | AF084082[24] | 97, 57 | 97, 66 |
| 103 | tur.adu | *Tursiops aduncus* | AF084092[24] | 97, 57 | 97, 63 |
| 104 | sten.fro | *Stenella frontalis* | AF084090[24] | 97, 57 | 97, 63 |
| 105 | saus.chi | *Sousa chinensis* | AF084080[24] | 97, 57 | 88, 59 |
| 106 | sten.lon | *Stenella longirostris* | AF084103[24] | 97, 61 | 97, 63 |
| 107 | turs.tru | *Tursiops truncatus* | AF084095[24] | 97, 57 | 96, 59 |
| 108 | lage.alb | *Lagenorhynchus alborostris* | AF084074[24] | 97, 61 | 97, 66 |
| 109 | sten.bre | *Steno bredanensis* | AF084077[24] | 97, 61 | 94, 64 |
| 110 | sota.flu | *Sotalia fluviatilis* | AF304067[25] | 97, 61 | 97, 63 |
| 111 | del.leu | *Delphinapterus leucas* | U72037[26] | 97, 61 | 95, 66 |
| 112 | mono.mon | *Monodon monoceros* | U72038[26] | 97, 61 | 95, 66 |
| 113 | plat.gan | *Platanista gangetica** | AF304070[25] | 97, 61 | 86, 59 |
| 114 | plat.min | *Platanista minor** | X92543[27] | 97, 61 | 86, 59 |
| 115 | kogi.bre | *Kogia breviceps* | U72040[26] | 97, 59 | 90, 63 |

TABLE 1-continued

The animal species included in the study for *in-silico* analysis

| SN. | Code | Name | NCBI accession # | $^S$P,S/F | $^\Psi$P,S/R |
|---|---|---|---|---|---|
| 116 | kogi.sim | *Kogia simus* | AF304072[28] | 96, 55 | 92, 63 |
| 117 | phys.cat | *Physeter catodon* | AF304073[25] | 97, 57 | 80, 58 |
| 118 | lipo.vex | *Lipotes vexillifer**  | AF304071[25] | 89, 56 | 88, 53 |
| 119 | phoc.sin | *phocoena sinus* | AF084051[24] | 87, 49 | 92, 62 |
| 120 | bera.bai | *Berardius bairdii* | X92541[27] | 96, 55 | 90, 59 |
| 121 | ziph.car | *Ziphius cavirostris* | X92540[27] | 97, 61 | 89, 57 |
| 122 | meso.eur | *Mesoplodon europaeus* | X92537[27] | 97, 57 | 90, 61 |
| 123 | meso.bid | *Mesoplodon bidens* | X92538[27] | 97, 61 | 92, 61 |
| 124 | meso.den | *Mesoplodon densirostris* | X92536[27] | 91, 61 | 94, 63 |
| 125 | hype.amp | *Hyperoodon ampullatus**  | X92539[27] | 97, 61 | 90, 65 |
| 126 | meso.per | *Mesoplodon peruvianus* | AF304074[28] | 97, 61 | 86, 58 |
| 127 | pont.bla | *Pontoporia blainvillei* | AF304069[25] | 92, 59 | 88, 55 |
| 128 | hipp.amp | *Hippopotamus amphibius* | Y08813[29] | 92, 58 | 95, 66 |
| 129 | hex.lib | *Hexaprotodon liberiensis* | Y08814[29] | 98, 63 | 97, 66 |
| 130 | rhin.son | *Rhinoceros sondaicus**  | AJ245725[30] | 90, 59 | 87, 61 |
| 131 | cera | *Ceratotherium simum* | NC_001808[32] | 90, 59 | 90, 63 |
| 132 | dic.sum | *Dicerorhinus sumatrensis* | AJ245723[30] | 90, 59 | 86, 57 |
| 133 | equu | *Equus asinus* | NC_001788[31] | 91, 61 | 73, 51 |
| 134 | baby.bab | *Babyrousa babyrussa* | Z50106[33] | 89, 56 | 85, 56 |
| 135 | phac.afr | *Phacochoerus africanus* | Z50090[33] | 90, 59 | 87, 54 |
| 136 | sus.scr.ew | *Sus scrofa haplotype EWB3**  | AF136549[34] | 97, 57 | 83, 54 |
| 137 | sus.bar | *Sus barbatus* | Z50107[33] | 97, 57 | 85, 55 |
| 138 | lama.gla | *Lama glama* | U06429[35] | 89, 55 | 85, 53 |
| 139 | lama.gua | *lama guanicoe* | Y08812[29] | 88, 54 | 86, 57 |
| 140 | vic.vic | *Vicugna vicugna* | U06430[35] | 89, 55 | 85, 53 |
| 141 | cam.bac | *Camelus bactrianus* | U06427[35] | 94, 58 | 86, 58 |
| 142 | arc.for | *Arctocephalus forsteri* | X82293[36] | 97, 60 | 87, 64 |
| 143 | arc.gaz | *Arctocephalus gazella* | X82292[36] | 94, 58 | 87, 64 |
| 144 | eum.jub | *Eumetopias jubatus* | X82311[36] | 97, 57 | 86, 57 |
| 145 | zal.cal | *Zalophus californianus* | X82310[36] | 89, 55 | 86, 57 |
| 146 | odo.ros | *Odobenus rosmarus* | X82299[36] | 91, 61 | 81, 52 |
| 147 | pho.vit | *Phoca vitulina* | X82306[36] | 90, 58 | 87, 64 |
| 148 | pho.fascia | *Phoca fasciata* | X82302[36] | 98, 63 | 95, 66 |
| 149 | pho.gro | *Phoca groenlandica* | X82303[36] | 92, 59 | 90, 61 |
| 150 | cys.cri | *Cystophora cristata* | X82294[36] | 89, 56 | 87, 64 |
| 151 | hyd.lep | *Hydrurga leptonyx* | X82297[36] | 89, 55 | 82, 54 |
| 152 | lep.wed | *Leptonychotes weddelli* | X72005[37] | 98, 63 | 91, 66 |
| 153 | mir.leo | *Mirounga leonina* | X82298[36] | 89, 55 | 82, 59 |
| 154 | eri.bar | *Erignathus barbatus* | X82295[36] | 89, 56 | 87, 63 |
| 155 | mon.sch | *Monachus schauinslandi* | X72209[37] | 91, 61 | 87, 60 |
| 156 | hela.mal | *Helarctos malayanus**  | U18899[38] | 84, 54 | 90, 63 |
| 157 | sel.thi | *Selenarctos thibetanus**  | AB020910[39] | 89, 57 | 87, 64 |
| 158 | ail.ful | *Ailurus fulgen*s*  | X94919[40] | 93, 55 | 87, 64 |
| 159 | fel | *Felis catus* | NC_001700[41] | 85, 56 | 90, 63 |
| 160 | can | *Canis familiaris* | NC_002008[42] | 98, 58 | 84, 54 |
| 161 | tal | *Talpa europaea* | NC_002391[43] | 81, 50 | 92, 57 |
| 162 | gla.sab | *Glaucomys sabrinus* | AF011738[44] | 90, 59 | 82, 54 |
| 163 | gla.vol | *Glaucomys volans* | AB030261[45] | 90, 59 | 87, 60 |
| 164 | hyl.pha | *Hylopetes phayrei**  | AB030259[45] | 91, 61 | 81, 50 |
| 165 | pet.set | *Petinomys setosus**  | AB030260[45] | 91, 61 | 81, 50 |
| 166 | bel.pea | *Belomys pearsonii**  | AB030262[45] | 91, 61 | 87, 64 |
| 167 | pte.mom | *Pteromys momonga**  | AB030263[45] | 97, 61 | 90, 63 |
| 168 | gala.demi | *Galagoides demidoff* | AF271411[46] | 97, 58 | 87, 64 |
| 169 | pero.pot | *Perodicticus potto* | AF271413[46] | 97, 60 | 87, 63 |
| 170 | gala.mat | *Galago matschiei* | AF271409[46] | 97, 60 | 90, 61 |
| 171 | gala.moh | *Galago moholi* | AF271410[46] | 97, 57 | 95, 66 |
| 172 | oto.gar | *Otolemur garnettii* | AF271412[46] | 92, 58 | 87, 60 |
| 173 | lor.tar | *Loris tardigradus**  | U53581[47] | 97, 60 | 93, 59 |
| 174 | nyc.cou | *Nycticebus coucang**  | U53580[47] | 97, 60 | 95, 66 |
| 175 | mus | Mus musculus | NC_001569[48] | 97, 60 | 86, 59 |
| 176 | gorr | Gorilla gorilla | NC_001645[49] | 89, 57 | 80, 58 |
| 177 | homo | Homo sapiens sapiens | NC_001807[50] | 96, 55 | 84, 64 |
| 178 | dug.dug | *Dugong dugong**  | U07564[51] | 97, 60 | 89, 59 |
| 179 | ele.max | *Elephas maximus**  | AB002412[52] | 97, 60 | 76, 57 |
| 180 | afr.con | *Afropavo congensis* | AF013760[53] | 97, 58 | 87, 63 |
| 181 | pavo.mut | *Pavo muticus**  | AF013763[53] | 97, 57 | 87, 63 |
| 182 | tra.bly | *Tragopan blythii* | *AF200722[54] | 89, 55 | 85, 57 |
| 183 | tra.sat | *Tragopan satyra**  | AF229837[54] | 89, 55 | 86, 61 |
| 184 | tra.cob | *Tragopan caboti* | AF200723[54] | 89, 55 | 86, 61 |
| 185 | tra.tem | *Tragopan temminckii**  | AF028802[55] | 89, 55 | 81, 56 |
| 186 | arg.arg | *Argusianus argus* | AF013761[53] | 89, 55 | 87, 63 |
| 187 | cat.wal | *Catreus wallichi**  | AF028792[53] | 88, 54 | 85, 57 |
| 188 | cro.cro | *Crossoptilon crossoptilon**  | AF028794[53] | 89, 55 | 85, 57 |
| 189 | sym.ree | *Syrmaticus reevesi**  | AF028801[53] | 89, 55 | 85, 57 |

TABLE 1-continued

The animal species included in the study for in-silico analysis

| SN. | Code | Name | NCBI accession # | $^S$P,S/F | $^\Psi$P,S/R |
|---|---|---|---|---|---|
| 190 | bam.tho | Bambusicola thoracica* | AF028790[53] | 80, 48 | 94, 64 |
| 191 | fra.fra | Francolinus francolinus | AF013762[53] | 97, 58 | 86, 61 |
| 192 | ith.cru | Ithaginis cruentus* | AF068193[53] | 98, 63 | 85, 57 |
| 193 | ant.par | Anthropoides paradisea | U27557[56] | 85, 56 | 82, 58 |
| 194 | ant.vir | Anthropoides virgo | U27545[56] | 84, 54 | 82, 52 |
| 195 | gru.ant.an | Grus antigone antigone | U11060[57] | 90, 58 | 87, 63 |
| 196 | gru.ant.gi | Grus antigone gillae | U11064[57] | 90, 58 | 87, 63 |
| 197 | gru.any.sh | Grus antigone sharpei | U11061[57] | 90, 58 | 87, 63 |
| 198 | grn.leu | Grus leucogeranus* | U27549[56] | 90, 58 | 87, 63 |
| 199 | gru.can.pr | Grus canadensis pratensis | U27553[56] | 97, 60 | 87, 63 |
| 200 | gni.can.ro | Grus canadensis rowani | U27552[56] | 97, 60 | 87, 63 |
| 201 | gru.can.ta | Grus canadensis tabida | U27551[56] | 98, 63 | 87, 63 |
| 202 | gru.can.ca | Grus canadensis canadensis | U27554[56] | 97, 61 | 87, 63 |
| 203 | gru.ame | Grus americana | U27555[56] | 90, 58 | 87, 63 |
| 204 | gru.gru | Grus grus | U27546[56] | 89, 54 | 87, 63 |
| 205 | gru.mon | Grus monacha* | U27548[56] | 90, 58 | 87, 63 |
| 206 | gru.nig | Grus nigricollis | *U27547[56] | 90, 58 | 87, 63 |
| 207 | gru.jap | Grus japonensis | U27550[56] | 81, 54 | 87, 63 |
| 208 | cic.boy | Ciconia boyciana* | NC_002196[58] | 94, 58 | 79, 60 |
| 209 | rhe.ame | Rhea americana | AF090339[59] | 93, 63 | 79, 60 |
| 210 | ant.alb | Anthracoceros albirostris* | U89190[60] | 97, 61 | 86, 59 |
| 211 | fal.fam | Falcofemoralis | U83310[61] | 97, 61 | 86, 60 |
| 212 | fal.ver | Falco verpertinus | U83311[61] | 97, 61 | 85, 57 |
| 213 | fal.par | Falco peregrinus* | U83307[61] | 97, 61 | 84, 52 |
| 214 | fal.spa | Falco sparverius | U83306[61] | 92, 59 | 80, 51 |
| 215 | ayt.ame | Aythya americana | NC_000877[62] | 98, 63 | 94, 62 |
| 216 | smi.sha | Smithornis sharpei | NC_000879[59] | 97, 58 | 90, 61 |
| 217 | vid.cha | Vidua chalybeata | NC_0O0880[59] | 97, 60 | 87, 64 |
| 218 | chry.pic | Chrysemys picta | NC_002073[63] | 89, 56 | 86, 57 |
| 219 | emy.orb.ku | Emys orbicularis | AJ131425[64] | 90, 59 | 94, 63 |
| 220 | che.mud | Chelonia mydas* | AB012104[65] | 90, 58 | 94, 63 |
| 221 | eum.egr | Eumeces egregius | AB016606[65] | 86, 55 | 73, 51 |

Table 2. Multiple sequence alignment of 472 bp fragment of mitochondrial cytochrome b gene (identified by inventors to fulfill the requirements of column 1, 2 and 3 mention under sub-heading 'Objectives of invention') of 221 animal species listed in Table 1. Alignments also show the binding sites for universal primers 'mcb398' and 'mcb869'. The symbol (*) refers to the nucleotide bases which are conserved amongst 221 animal species listed in Table 1). The alignments have been done using software CLUSTAL X (1.8). The nucleitide positions that are unmarked are variable amongst 221 animal species analyzed. These variable sites together constitute the molecular signature of an individual species, giving rise to molecular basis of species identification by our primers.

TABLE 2

Multiple sequence alignment of 472 bp fregment of mitochondrial cytochrome b gene of 221 animal species

```
PRIMER 'mcb398'    TACCATGAGGACAAATATCATTCTG
                   *          *  *      **   *
 
aep.mel
TGCCATGAGGACAAATATCATTCTGAGGAGCAACAGTCATTACAAATCTCCTCTCAGCAA 60 ore.ore
TTCCGTGAGGACAAATATCATTTTGAGGGGCTACAGTCATTACTAATCTCCTCTCAGCAA 60 add.nas
TGCCATGAGGACAAATATCATTCTGAGGAGCAACAGTCATCACCAACCTTCTCTCAGCAA 60 ory.dam
TACCATGAGGACAAATATCATTTTGAGGGGCAACAGTTATCACTAACCTTCTCTCAGCAA 60 hip.equ
TACCATGAGGACAAATATCATTCTGAGGAGCAACAGTCATCACCAACCTCCTCTCAGCAA 60 alc.bus
TGCCATGAGGACAAATATCATTCTGAGGGGCAACAGTCATCACCAATCTCCTCTCAGCAA 60 sig.lic
```

TABLE 2-continued

Multiple sequence alignment of 472 bp fregment of mitochondrial cytochrome b gene of 221 animal species

TGCCATGAGGACAAATATCATTCTGAGGGGCAACAGTCATCACCAATCTCCTCTCAGCAA 60 bea.hun
TGCCATGAGGACAAATATCATTCTGAGGAGCAACAGTCATCACCAACCTCCTCTCAGCAA 60 dam.lun
TGCCATGAGGACAAATATCATTCTGAGGAGCAACAGTCATCACTAACCTCCTCTCAGCAA 60 con.tau
TACCATGAGGACAAATATCCTTTTGAGGAGCAACAGTCATCACCAACCTCCTCTCAGCAA 60 amm.ler
TGCCATGAGGACAGATATCATTCTGAGGGGCAACAGTCATCACCAACCTTCTCTCAGCAA 60 pse.nay
TGCCATGAGGACAAATATCATTTTGAGGGGCAACAGTCATCACCAACCTTCTCTCAGCAA 60 cap.ibe
TACCATGAGGACAAATATCATTCTGAGGGGCAACAGTCATCACTAACCTTCTCTCAGCAA 60 hem.jem
TACCATGAGGACAGATATCATTCTGAGGGGCAACAGTCATCACCAACCTTCTCTCAGCAA 60 cap.fal
TACCATGAGGACAAATATCATTCTGAGGGGCAACAGTCATCACCAATCTCCTCTCAGCAA 60 rup.pyr
TACCATGAGGACAGATATCATTCTGAGGAGCAACAGTTATTACCAATCTCCTCTCAGCAA 60 rup.rup
TACCATGAGGACAGATATCATTCTGGGGAGCAACAGTTATTACCAACCTCCTCTCAGCGA 60 nem.cau
TACCATGAGGACAGATATCATTCTGAGGGGCAACAGTTATTACCAATCTTCTCTCAGCAA 60 bud.tax.tax
TACCATGAGGACAAATATCATTTTGAGGAGCAACAGTCATTACCAACCTCCTCTCAGCAA 60 pan.hod
TACCATGAGGACAAATATCATTCTGAGGAGCAACAGTAATTACCAACCTCCTTTCAGCAA 60 ovi.amm
TACCATGAGGACAAATATCATTCTGAGGAGCAACAGTTATTACCAACCTCCTTTCAGCAA 60 ovi.vig
TACCATGAGGACAAATATCATTCTGAGGAGCAACAGTTATTACCAACCTCCTTTCAGCAA 60 cap.cri
TACCATGAGGACAAATATCATTCTGAGGGGCTACAGTCATTACTAACCTCCTCTCAGCAA 60 ovi.mos
TACCATGAGGACAAATATCATTCTGAGGAGCTACAGTCATCACTAACCTCCTCTCAGCAA 60 ore.ame
TACCATGAGGACAAATATCATTCTGAGGAGCAACAGTCATNACCAATCTCCTTTCAGCAA 60 cep.dor
TCCCATGAGGGCAAATATCATTCTGAGGAGCCACAGTCATTACCAACCTCCTCTCAGCAA 60 cep.max
TCCCATGAGGACAAATATCATTCTGAGGAGCCACAGTCATTACCAACCTCCTCTCAGCAA 60 bis.bon
TACCATGAGGACAAATATCATTTTGAGGAGCAACAGTCATTACCAACCTCCTATCAGCAA 60 bos.gru
TACCATGAGGACAAATATCATTTTGAGGGGCAACAGTGATTACCAACCTCCTATCAGCAA 60 bos.tra
TACCATGAGGACAAATATCATTTTGAGGAGCAACAGTTATTACCAATCTATTATCAGCAA 60 bub.min
TGCCATGAGGACAAATATCATTCTGAGGAGCAACAGTCATCACCAACCTTCTCTCAGCAA 60 buba.bub
TGCCATGAGGACAAATATCATTCTGAGGGGCAACAGTCATCACCAACCTTCTCTCAGCAA 60

TABLE 2-continued

Multiple sequence alignment of 472 bp fregment of mitochondrial
cytochrome b gene of 221 animal species tra.ang
TGCCATGAGGACAAATATCATTCTGAGGAGCAACGGTCATCACAAACCTCCTATCAGCAA 60 tra.eur
TACCATGAGGACAAATATCATTTTGAGGAGCAACAGTCATCACAAACCTTCTATCAGCAA 60 kob.ell
TACCATGAGGACAAATATCCTTCTGAGGAGCAACAGTCATCACCAATCTCCTTTCAGCAA 60 kob.meg
TACCATGAGGACAAATATCCTTCTGAGGAGCGACAGTCATCACTAATCTCCTTTCAGCAA 60 red.aru
TACCATGAGGACAAATATCCTTCTGAGGAGCAACAGTTATCACTAATCTTCTCTCAGCAA 60 red.ful
TGCCATGGGACAAATATCCTTCTGAGGAGCAACAGTTATCACTAACCTTCTCTCAGCAA 60 neo.mos
TGCCATGGGGACAAATATCCTTCTGAGGAGCAACAGTCATCACCAATCTACTATCAGCAA 60 pel.cap
TACCATGAGGACAAATATCCTTCTGAGGAGCAACAGTCATCACCAACCTTCTCTCAGCAA 60 gaz.dam
TACCATGAGGACAAATATCTTTCTGAGGGGCAACAGTTATCACTAACCTCCTCTCAGCAA 60 our.our
TACCATGAGGACAAATATCCTTTTGAGGAGCAACAGTCATCACCAACCTCCTCTCAGCAA 60 ant.cer
TACCATGAGGACAAATATCTTTTTGAGGAGCAACAGTCATCACCAATCTCCTTTCAGCAA 60 sai.tat
TACCATGAGGACAAATATCTTTCTGAGGAGCAACAGTCATCACCAATCTCCTTTCAGCAA 60 mad.kir
TGCCATGAGGACAAATATCCTTCTGAGGAGCAACAGTTATCACTAACCTCCTCTCAGCAA 60 rap.mel
TACCATGGGGACAAATATCCTTTTGAGGAGCAACAGTCATCACTAATCTCCTCTCAGCAA 60 gaz.gaz
TACCATGAGGACAAATATCTTTCTGAGGAGCAACAGTTATCACGAACCTCCTCTCAGCAA 60 ant.ame
TACCATGAGGACAAATATCATTCTGAGGGGCAACAGTCATTACTAACCTACTCTCAGCAA 60 hyd.ine
TTCCATGAGGACAAATATCATTCTGAGGAGCAACGGTCATTACTAATCTCCTGTCAGCAA 60 mun.mun
TACCATGAGGACAAATATCATTTTGAGGAGCAACAGTCATCACTAACCTCCTTTCAGCAA 60 alc.alc
TACCATGAGGACAGATATCATTCTGAGGGGCAACAGTCATTACTAACCTCCTTTCAGCAA 60 cer.ela.kan
TACCATGAGGACAAATATCATTCTGAGGAGCAACAGTCATTACCAACCTTCTCTCAGCAA 60 cer.ela.xan
TACCATGAGGACAAATATCATTCTGAGGAGCAACGGTCATTACCAACCTTCTCTCAGCAA 60 cer.ela.can
TACCATGAGGACAAATATCATTCTGAGGAGCAACAGTCATTACCAACCTTCTCTCAGCAA 60 cer.nip.cent
TACCATGAGGACAAATATCATTCTGAGGAGCAACAGTCATTACCAACCTCCTCTCAGCAA 60 cer.nip.yes
TACCATGAGGACAAATATCATTCTGAGGAGCAACAGTCATTACCAACCTCCTCTCAGCAA 60 cer.nip.ker
TACCATGAGGACAAATATCATTCTGAGGAGCAACAGTCATTACCAACCTTCTCTCAGCAA 60

TABLE 2-continued

Multiple sequence alignment of 472 bp fregment of mitochondrial cytochrome b gene of 221 animal species cer.nip.pul
TACCATGAGGACAAATATCATTCTGAGGAGCAACAGTCATTACCAACCTTCTCTCAGCAA 60 cer.nip.nip
TACCATGAGGACAAATATCATTCTGAGGAGCAACAGTCATTACCAACCTCCTCTCAGCAA 60 cer.ela.sco
TACCATGAGGACAAATATCATTCTGAGGAGCAACAGTCATCACCAACCTTCTCTCAGCAA 60 cer.dam
TACCATGAGGACAAATATCATTCTGAGGAGCAACAGTTATTACCAATCTTCTCTCAGCAA 60 ran.tar
TACCATGAGGACAAATATCATTCTGAGGAGCAACAGTTATCACAAACCTCCTCTCAGCAA 60 mos.fus
TACCTTGAGGACAAATATCTTTCTGAGGAGCGACAGTTATTACCAATCTTCTCTCAGCAA 60 mos.leu
TACCTTGAGGACAAATATCTTTCTGAGGAGCAACAGTTATTACCAATCTTCTCTCAGCAA 60 mos.chr
TACCTTGAGGACAAATATCTTTCTGAGGAGCAACAGTTATTACCAATCTTCTCTCAGCAA 60 mos.ber
TACCTTGAGGACAAATATCTTTCTGAGGAGCAACAGTTATTACCAATCTTCTCTCAGCAA 60 mos.mos
TACCTTGAGGACAAATATCTTTCTGAGGAGCAACAGTCATCACTAACCTTCTCTCAGCAA 60 tra.jav
TACCCTGAGGACAGATATCTTTCTGAGGAGCCACAGTCATCACCAACCTCTTATCAGCTA 60 trag.nap
TACCCTGAGGGCAAATATCTTTTTGAGGAGCTACAGTCATCACTAACCTTCTTTCAGCAA 60 bala.acu
TACCCTGAGGACAAATATCATTTTGAGGTGCAACCGTCATCACCAACCTCCTATCAGCAA 60 bala.bon
TACCCTGAGGACAAATATCATTTTGAGGCGCAACCGTCATCACCAACCTCCTATCAGCAA 60 bala.bor
TACCCTGAGGACAAATATCATTTTGAGGCGCAACCGTCATCACCAACCTCTTATCAGCAA 60 bala.edi
TACCCTGAGGACAAATATCATTTTGAGGCGCAACCGTCATCACCAACCTCTTATCAGCAA 60 esch.rob
TACCCTGAGGACAAATATCATTCTGAGGCGCAACCGTTATCACCAACCTCCTATCAGCAA 60 bala.mus
TGCCCTGAGGACAAATATCATTCTGAGGCGCAACCGTCATCACCAACCTCCTATCAGCAA 60 mega.nov
TACCCTGAGGACAAATATCATTCTGAGGCGCAACCGTCATCACCAACCTTCTATCAGCAA 60 bala.phy
TGCCCTGAGGACAAATATCATTCTGAGGCGCAACTGTAATCACTAACCTCCTATCAGCAA 60 cap.mar
TGCCCTGAGGACAGATATCATTCTGAGGCGCAACCGTCATCACCAACCTCCTATCAGCAA 60 ceph.com
TACCCTGGGGACAGATATCATTTTGAGGTGCAACAGTCATCACCAACCTCCTATCAGCAA 60 ceph.eut
TACCCTGGGGACAGATATCATTTTGAGGTGCAACAGTCATCACCAACCTCCTATCAGCAA 60 lage.obl
TACCCTGAGGACAGATATCATTCTGAGGTGCAACAGTCATCACCAACCTCCTATCAGCAA 60 ceph.hea
TACCCTGAGGACAAATATCATTTTGAGGCGCAACAGTCATCACCAACCTCCTATCAGCAA 60 ceph.hec

TABLE 2-continued

Multiple sequence alignment of 472 bp fregment of mitochondrial
cytochrome b gene of 221 animal species

```
TACCCTGAGGACAAATATCATTTTGAGGTGCAACAGTCATCACCAACCTCCTATCAGCAA 60 lage.aus
TACCCTGAGGACAGATATCATTTTGAGGTGCAACAGTCATCACCAACCTCCTATCAGCAA 60 lage.cru
TACCCTGAGGACAGATATCATTTTGAGGTGCAACAGTCATCACCAACCTCCTATCAGCAA 60 lage.obs
TACCCTGAGGACAGATATCATTTTGAGGTGCAACAGTCATCACCAACCTCCTATCAGCAA 60 lisso.bor
TACCCTGAGGGCAGATATCATTTTGAGGTGCAACCGTCATCACCAACCTCCTATCAGCAA 60 lisso.per
TACCCTGAGGACAGATATCATTTTGAGGTGCAACCGTCATCACCAACCTCCTATCAGCAA 60 glo.mac
TACCCTGAGGACAGATATCATTCTGAGGCGCAACCGTCATCACCAATCTCCTATCAGCAA 60 glo.mel
TACCCTGAGGACAGATATCATTCTGAGGCGCAACCGTCATCACCAATCTCCTATCAGCAA 60 fere.att
TACCCTGAGGACAGATATCATTCTGAGGCGCAACCGTCATCACCAATCTCCTATCAGCAA 60 pepo.ele
TACCCTGAGGACAGATATCATTCTGAGGCGCAACCGTCATCACCAATCTCCTATCAGCAA 60 gram.gri
TACCCTGAGGACAAATATCATTCTGAGGCGCAACCGTCATCACCAATCTCCTATCAGCAA 60 pse.cra
TACCCTGAGGACAGATATCATTCTGAGGCGCAACCGTCATCACCAATCTTCTATCAGCAA 60 lage.acu
TACCATGAGGACAAATATCATTCTGAGGCGCAACCGTTATCACCAATCTCCTATCAGCAA 60 orci.bre
TACCCTGAGGACAGATATCTTTCTGAGGCGCAACCGTCATTACTAATCTCCTATCAGCAA 60 orca.bre
TACCCTGAGGACAGATATCCTTCTGAGGTGCAACCGTCATCACCAATCTCCTATCAGCAA 60 del.cap
TGCCCTGGGGACAAATATCATTCTGAGGCGCAACCGTCATCACCAACCTCTTATCAGCAA 60 del.tro
TGCCCTGAGGACAAATATCATTCTGAGGCGCAACCGTCATCACCAACCTCTTATCAGCAA 60 del.del
TGCCCTGAGGACAAATATCATTCTGAGGCGCAACCGTCATCACCAACCTCTTATCAGCAA 60 sten.cly
TGCCCTGAGGACAAATATCATTCTGAGGCGCAACCGTCATCACCAACCTCCTATCAGCAA 60 sten.coe
TGCCCTGAGGACAAATATCATTCTGAGGCGCAACCGTCATCACCAACCTCTTATCAGCAA 60 tur.adu
TGCCCTGAGGACAAATATCATTCTGAGGCGCAACCGTCATCACCAACCTCTTATCAGCAA 60 sten.fro
TGCCCTGAGGACAAATATCATTCTGAGGCGCAACCGTCATCACCAACCTCTTATCAGCAA 60 saus.chi
TGCCCTGAGGACAAATATCATTCTGAGGCGCAACCGTTATCACCAACCTCCTATCAGCAA 60 sten.lon
TACCCTGAGGACAAATATCATTCTGAGGTGCAACCGTCATCACCAACCTCCTATCAGCAA 60 turs.tru
TGCCCTGAGGACAAATATCATTCTGAGGCGCAACCGTCATCACCAACCTCTTATCAGCAA 60
```

TABLE 2-continued

Multiple sequence alignment of 472 bp fregment of mitochondrial
cytochrome b gene of 221 animal species lage.alb
TACCCTGAGGACAAATATCATTCTGAGGCGCAACCGTCATCACTAATCTCCTATCAGCAA 60 sten.bre
TACCCTGAGGACAAATATCATTCTGAGGTGCAACCGTCATTACCAACCTCCTGTCAGCAA 60 sota.flu
TACCCTGAGGACAAATATCATTCTGAGGCGCAACCGTCATTACCAATCTCCTATCAGCAA 60 del.leu
TACCCTGAGGACAAATATCATTCTGAGGCGCAACCGTCATTACCAATCTCCTATCAGCAA 60 mono.mon
TACCCTGAGGACAAATATCATTCTGAGGTGCAACCGTCATCACCAACCTCCTATCAGCAA 60 plat.gan
TACCCTGAGGACAAATATCATTCTGAGGTGCAACCGTCATCACCAACCTTTTATCAGCAA 60 plat.min
TACCCTGAGGACAAATATCATTCTGAGGTGCAACCGTCATCACCAACCTTTTATCAGCAA 60 kogi.bre
TACCCTGAGGCCAAATATCATTCTGAGGAGCAACCGTCATCACCAACCTTATATCCGCAA 60 kogi.sim
TGCCCTGAGGCCAAATATCATTCTGAGGAGCAACCGTCATCACAAACCTTATATCCGCAA 60 phys.cat
TGCCCTGAGGACAAATATCATTCTGAGCCGCAACCGTTATCACAAACCTTCTATCAGCAA 60 lipo.vex
TACCCTGAGGACAAATATCATTTTGAGGCGCAACCGTCATCACTAATCTTCTATCAGCAA 60 phoc.sin
TGCCCTGGGGACAAATATCATTTTGAGGTGCTACCGTCATCACAAACCTCTTATCAGCAA 60 bera.bai
TGCCTTGAGGGCAAATATCATTCTGAGGTGCAACCGTCATCACCAACCTCCTATCCGCTA 60 ziph.car
TACCTTGAGGACAAATATCATTCTGAGGTGCAACCGTCATCACAAACCTCTTATCCGCTA 60 meso.eur
TTCCCTGAGGACAAATATCATTCTGAGGCGCAACCGTTATTACCAACCTCCTATCCGCCA 60 meso.bid
TACCCTGAGGACAAATATCATTCTGAGGCGCAACTGTTATTACTAACCTCCTATCCGCTA 60 meso.den
TACCATGAGGACAAATATCCTTCTGAGGTGCAACTGTCATTACCAATCTTCTATCCGCTA 60 hype.amp
TACCCTGAGGACAAATATCATTCTGAGGCGCAACCGTCATCACCAATCTCCTATCCGCCA 60 meso.per
TACCTTGAGGACAAATATCATTCTGAGGCGCAACTGTCATTACTAATCTTTTATCTGCTA 60 pont.bla
TACCCTGAGGACAAATGTCATTCTGAGGTGCCACTGTCATCACTAACCTCCTATCAGCGA 60 hex.lib
TACCATGAGGACAAATATCATTCTGAGGGGCAACAGTCATCACCAACTTACTATCAGCTA 60 hipp.amp
TGCCATGAGGACAAATGTCATTCTGAGGGGCAACAGTCATTACCAACTTACTGTCAGCTA 60 dic.sum
TACCATGAGGTCAAATATCCTTCTGAGGAGCCACAGTTATCACAAATCTCCTCTCAGCCA 60 rhin.son
TACCATGAGGTCAAATATCCTTCTGAGGGGCTACAGTCATTACAAATCTCCTCTCAGCCA 60 cera
TACCATGAGGCCAAATATCCTTCTGAGGGGCTACAGTCATCACAAACCTCCTCTCAGCTA 60 equu

TABLE 2-continued

Multiple sequence alignment of 472 bp fregment of mitochondrial cytochrome b gene of 221 animal species

TACCATGAGGACAAATATCCTTCTGAGGAGCAACGGTCATTACAAACCTCCTATCAGCAA 60 baby.bab
TACCTTGAGGACAAATATCATTTTGAGGAGCTACCGTCATTACAAACCTACTATCAGCCA 60 phac.afr
TACCCTGAGGACAAATATCGTTCTGAGGAGCCACAGTCATCACAAACCTACTATCAGCCA 60 sus.bar
TGCCCTGAGGACAAATATCATTCTGAGGAGCTACGGTCATCACAAATCTACTATCAGCTA 60 sus.scr.ewb3
TGCCCTGAGGACAAATATCATTCTGAGGAGCTACGGTCATCACAAATCTACTATCAGCTA 60 lama.gla
TCCCATGAGGACAAATATCATTTTGAGGGGCAACAGTAATTACAAATCTACTCTCGGCAA 60 lama.gua
TCCCATGAGGCCAAATATCATTTTGAGGGGCAACAGTAATTACAAACCTACTCTCGGCAA 60 vic.vic
TCCCATGAGGACAAATATCATTTTGAGGGGCAACAGTAATTACAAACCTACTCTCAGCAA 60 cam.bac
TCCCATGAGGACAGATATCATTCTGGGGAGCAACAGTAATTACCAACCTACTCTCAGCAA 60 arc.for
TTCCATGAGGACAAATATCATTCTGAGGAGCGACCGTCATTACCAACCTCCTATCAGCAG 60 arc.gaz
TTCCATGAGGACAGATATCATTCTGAGGAGCAACCGTCATTACCAACCTCCTGTCAGCAA 60 eum.jub
TTCCGTGAGGACAAATATCATTCTGAGGAGCAACCGTCATTACCAACCTCCTATCAGCTA 60 zal.cal
TTCCATGAGGACAAATATCATTTTGAGGAGCAACCGTCATTACCAACCTCCTATCAGCAG 60 odo.ros
TACCATGAGGACAAATATCCTTCTGAGGAGCAACCGTCATCACCAACCTTCTGTCAGCAA 60 pho.fasciata
TACCATGAGGACAAATATCATTCTGAGGAGCAACAGTCATCACTAATCTACTATCAGCAA 60 pho.gro
TACCATGAGGGCAAATGTCATTCTGAGGAGCAACAGTTATCACTAATCTACTATCAGCAA 60 pho.vit
TACCATGAGGACAAATATCATTTTGAGGAGCAACAGTCATCACCAATCTACTATCAGCAA 60 cys.cri
TACCGTGAGGACAAATATCATTTTGAGGAGCGACAGTCATCACCAACCTACTATCAGCAA 60 hyd.lep
TGCCATGAGGACAAATATCATTTTGAGGAGCAACCGTTATTACCAACTTACTATCAGCAA 60 lep.wed
TACCATGAGGACAAATATCATTCTGAGGAGCAACCGTCATTACCAACTTACTATCAGCAA 60 mir.leo
TGCCATGAGGACAAATATCATTTTGAGGAGCAACCGTCATTACCAACCTACTATCAGCAG 60 eri.bar
TACCATGAGGGCAAATATCATTTTGAGGAGCAACCGTTATCACCAACCTACTATCAGCAA 60 mon.sch
TACCATGAGGACAAATATCCTTCTGAGGGGCGACCGTCATCACCAACCTACTATCAGCAA 60 hela.mal
TACCCTGAGGCCAAATGTCCTTCTGAGGAGCAACTGTCATTACCAATCTCTTATCAGCCA 60 sel.thi
TACCCTGAGGCCAAATATCCTTCTGAGGAGCGACTGTCATTACCAACCTCCTATCAGCCA 60 ail.ful
TGCCCTGAGGACAGATATCATTCTGAGGAGCAACCGTTATCACCAACCTACTATCAGCCA 60

TABLE 2-continued

Multiple sequence alignment of 472 bp fregment of mitochondrial cytochrome b gene of 221 animal species

```
fel
TACCATGAGGCCAAATGTCCTTCTGAGGAGCAACCGTAATCACTAACCTCCTGTCAGCAA 60 can
TACCATGAGGACAAATATCATTTTGAGGAGCAACTGTAATCACTAATCTTCTCTCTGCCA 60 tal
TACCATGGGGTCAAATATCCTTTTGAGGTGCAACGGTAATTACAAATTTACTGTCAGCCA 60 gla.sab
TACCCTGAGGACAAATATCTTTCTGAGGAGCCACCGTCATCACCAACCTTCTCTCAGCTA 60 gla.vol
TACCCTGAGGACAAATATCCTTCTGAGGAGCTACTGTCATCACCAACCTTCTCTCAGCTA 60 hyl.pha
TACCATGAGGACAAATATCCTTCTGAGGGGCTACCGTTATTACAAACCTACTATCTGCCA 60 pet.set
TACCATGAGGACAAATATCCTTCTGAGGGGCTACCGTTATTACAAACCTACTATCTGCCA 60 bel.pea
TACCATGAGGACAAATATCTTTCTGAGGAGCCACTGTCATCACAAACCTCCTTTCAGCTA 60 pte.mom
TACCCTGAGGACAAATATCATTCTGAGGCGCCACTGTCATCACCAACCTGCTATCCGCCA 60 gala.demi
TTCCATGAGGCCAAATATCATTCTGAGGTGCTACCGTAATCACTAACCTGCTCTCAGCTA 60 pero.pot
TCCCATGAGGACAAATATCATTCTGAGGTGCCACAGTAATCACAAACCTCCTATCAGCAA 60 gala.mat
TCCCATGAGGACAAATATCATTCTGAGGCGCTACCGTAATCACAAATCTCCTCTCCGCAA 60 gala.moh
TTCCGTGAGGACAAATATCATTCTGAGGCGCTACCGTAATCACTAACCTCCTCTCAGCAA 60 oto.gar
TCCCATGAGGACAAATGTCATTCTGAGGCGCAACCGTAATTACAAATCTCCTCTCAGCAA 60 lor.tar
TCCCATGAGGACAAATATCATTCTGAGGAGCCACAGTAATTACCAACCTACTATCAGCAA 60 nyc.cou
TCCCATGAGGACAAATATCATTCTGAGGTGCCACCGTCATCACTAACCTACTATCGGCAA 60 mus
TTCCATGAGGACAAATATCATTCTGAGGTGCCACAGTTATTACAAACCTCCTATCAGCCA 60 gorr
TCCCATGAGGCCAAATATCCTTCTGAGGAGCCACAGTAATCACAAACTTGCTATCCGCCA 60 homo
TCCCGTGAGGCCAAATATCATTCTGAGGGGCCACAGTAATTACAAACTTACTATCCGCCA 60 dug.dug
TCCCATGAGGACAAATATCATTCTGAGGAGCAACCGTTATTACTAACCTCCTGTCAGCTA 60 ele.max
TTCCATGAGGACAAATATCATTCTGAGGGGCAACCGTAATTACTAACCTCTTCTCAGCAA 60 afr.con
TCCCATGAGGCCAAATATCATTCTGAGGGGCAACTGTCATCACAAACCTATACTCAGCAA 60 pavo.mut
TCCCATGAGGTCAAATGTCATTCTGAGGGGCAACTGTTATCACAAATCTATTCTCAGCAA 60 tra.bly
TCCCATGAGGACAAATATCATTTTGAGGGGCTACCGTCATCACAAACTTATTCTCAGCAA 60 tra.sat
TCCCATGAGGACAAATATCATTTTGAGGGGCTACCGTCATTACAAATTTATTCTCAGCAA 60
```

TABLE 2-continued

Multiple sequence alignment of 472 bp fregment of mitochondrial cytochrome b gene of 221 animal species tra.cob
TCCCATGAGGACAAATATCATTTTGAGGAGCTACCGTCATCACAAATTTATTTTCAGCAA 60 tra.tem
TCCCATGAGGACAAATATCATTTTGAGGGGCTACCGTCATCACAAATTTATTCTCAGCAA 60 arg.arg
TCCCATGAGGACAAATATCATTTTGAGGAGCTACCGTCATCACAAACCTATTCTCAGCAA 60 cat.wal
TTCCATGGGACAAATATCATTTTGAGGGGCTACTGTCATCACAAATCTATTCTCAGCAA 60 cro.cro
TCCCATGAGGACAAATATCATTTTGAGGGGGTACCGTCATCACAAATCTATTCTCAGCAA 60 sym.ree
TCCCATGAGGACAAATATCATTTTGAGGGGCAACCGTCATCACAAATTTATTCTCAGCAA 60 bam.tho
TCCCATGGGGCCAAATATCCTTTTGAGGGGCTACCGTCATCACAAATTTATTCTCAGCAA 60 fra.fra
TCCCATGAGGCCAAATATCATTCTGAGGGGCTACCGTCATTACGAACCTATTCTCAGCAA 60 ith.cru
TACCATGAGGACAAATATCATTCTGAGGAGCCACTGTAATCACAAACCTACTCTCAGCAA 60 ant.par
TACCATGAGGACAAATGTCATTTTGAGGGGCTACAGTCATCACCAATCTCTTCTCAGCCG 60 ant.vir
TACCATGGGACAAATGTCATTTTGAGGGGCTACAGTTATCACCAATCTCTTCTCAGCCG 60 gru.ant.ant
TACCATGAGGACAAATATCATTTTGAGGGGCTACAGTCATCACCAATCTCTTCTCAGCCG 60 gru.ant.gil
TACCATGAGGACAAATATCATTTTGAGGGGCTACAGTCATCACCAATCTCTTCTCAGCCG 60 gru.ant.sha
TACCATGAGGACAAATATCATTTTGAGGGGCTACAGTCATCACCAATCTCTTCTCAGCCG 60 gru.leu
TACCATGAGGACAAATATCATTTTGAGGGGCTACAGTCATCACCAATCTCTTCTCAGCCG 60 gru.can.pra
TGCCATGAGGACAAATATCATTCTGAGGGGCTACAGTCATTACCAACCTCTTCTCAGCCG 60 gru.can.row
TGCCATGAGGACAAATATCATTCTGAGGGGCTACAGTCATTACCAACCTCTTCTCAGCCG 60 gru.can.tab
TACCATGAGGACAAATATCATTCTGAGGGGCTACAGTCATTACCAACCTCTTCTCAGCCG 60 gru.can.can
TACCATGGGGACAAATATCATTCTGAGGGGCTACAGTCATTACCAACCTCTTCTCAGCCG 60 gru.ame
TACCATGAGGACAAATATCATTTTGAGGGGCTACAGTTATCACCAATCTCTTCTCAGCCG 60 gru.gru
TACCATGGGGACAAATGTCATTTTGAGGGGCTACAGTTATCACCAATCTCTTCTCAGCCG 60 gru.mon
TACCATGAGGACAAATATCATTTTGAGGGGCTACAGTTATCACCAACCTCTTCTCAGCCG 60 gru.nig
TACCATGAGGACAAATATCATTTTGAGGGGCTACAGTTATCACCAACCTCTTCTCAGCCG 60 gru.jap
TACCATGGGGACAAATATCCTTTTGAGGGGCTACAGTTATCACCAATCTCTTCTCAGCCG 60 cic.boy
TGCCATGAGGACAGATATCATTCTGAGGGGCTACAGTCATCACCAACCTATTTTCAGCTA 60 rhe.ame

TABLE 2-continued

Multiple sequence alignment of 472 bp fregment of mitochondrial
cytochrome b gene of 221 animal species

TACCATGAGGACAAATATCATTCTGAGGAGCTACAGTTATTACCAACCTATTCTCAGCCA 60 ant.alb
TACCATGAGGGCAAATATCATTCTGAGGCGCCACCGTCATCACCAACCTATTCTCAGCCA 60 fal.fam
TACCCTGAGGACAAATATCATTCTGAGGGGCTACAGTTATCACCAACCTATTTTCAGCAA 60 fal.ver
TACCCTGAGGACAAATATCATTCTGGGGAGCCACAGTCATCACTAACCTATTTTCAGCAA 60 fal.per
TACCCTGAGGACAAATATCATTCTGAGGAGCCACAGTCATTACCAACCTATTCTCAGCAA 60 fal.spa
TACCCTGAGGACAAATGTCATTCTGAGGAGCCACAGTCATTACCAACCTATTCTCAGCAA 60 ayt.ame
TACCATGAGGACAAATATCATTCTGAGGGGCCACCGTGATCACTAACCTGTTCTCAGCCC 60 smi.sha
TCCCATGAGGCCAAATATCATTCTGAGGTGCTACAGTAATCACCAACCTCTTCTCAGCTA 60 vid.cha
TGCCATGAGGACAAATATCATTCTGAGGAGCCACAGTAATCACAAACCTATTCTCAGCAA 60 chry.pic
TACCATGGGGCCAAATATCCTTCTGAGGTGCCACCGTTATTACTAACCTCCTCTCAGCCA 60 emy.orb.kur
TACCATGAGGCCAAATATCCTTCTGAGGTGCCACCGTTATTACTAACCTCCTCTCAGCCG 60 che.mud
TACCATGAGGACAAATATCATTTTGAGGGGCCACCGTCATCACAAACCTACTCTCAGCCA 60 eum.egr
TCCCATGGGGACAGATATCCTTCTGAGGCGCAACCGTAATTACAAACCTATTATCAGCAA 60
                 *           *   *       **     * aep.mel
TCCCATACATTGGTACAAACCTAGTAGAATGAATCTGAGGAGGNTTNTCAGTAGACAAAG 120 ore.ore
TTCCATATATTGGCACAAACCTGGTAGAATGAATCTGAGGAGGATTCTCGGTGGACAAAG 120 add.nas
TCCCATATATCGGCACAGACCTGGTCGAATGAATCTGAGGAGGATTCTCCGTAGACAAAG 120 ory.dam
TCCCATACATCGGCACAAATCTAGTCGAATGAATTTGAGGGGGATTCTCCGTAGACAAAG 120 hip.equ
TCCCATATATTGGCACAAACCTAGTCGAATGAATCTGAGGGGGATTCTCCGTAGACAAAG 120 alc.bus
TCCCATATATTGGCACAGACCTAGTAGAATGAATCTGAGGGGGATTCTCAGTAGACAAAG 120 sig.lic
TCCCATATATTGGCACAGACCTAGTAGAATGAATCTGAGGAGGATTATCAGTAGACAAAG 120 bea.hun
TTCCATATATTGGTACAAACCTAGTCGAATGAATCTGAGGAGGCTTCTCAGTAGACAAAG 120 dam.lun
TTCCATACATCGGCACAAATCTAGTCGAATGGATCTGAGGGGGCTTCTCAGTAGACAAAG 120 con.tau
TCCCATACATTGGCACTAACCTAGTCGAATGAATCTGAGGGGGATTCTCAGTAGACAAAG 120 amm.ler
TCCCATACATTGGCACAGACCTGGTCGAATGAATCTGAGGGGGATTCTCAGTAGACAAAG 120 pse.nay
TCCCCTATATTGGCACAAATCTAGTCGAATGGATCTGAGGGGGATTCTCAGTAGACAAGG 120

TABLE 2-continued

Multiple sequence alignment of 472 bp fregment of mitochondrial cytochrome b gene of 221 animal species

```
cap.ibe
TCCCATATATTGGCACAAACCTAGTCGAATGAATCTGAGGGGGATTCTCAGTAGACAAAG 120 hem.jem
TTCCATATATCGGCACAAACCTAGTCGAATGAATCTGAGGAGGATTCTCAGTAGACAAAG 120 cap.fal
TCCCATATATTGGCACAAACCTAGTCGAATGAATCTGAGGAGGATTCTCAGTAGATAAAG 120 rup.pyr
TCCCATACATTGGCATAGACTTAGTCGAGTGAATCTGAGGGGGCTTCTCGGTAGACAAAG 120 rup.rup
TCCCGTATATTGGCACAGACTTAGTCGAATGAATCTGAGGAGGCTTCTCGGTAGACAAGG 120 nem.cau
TCCCATATATTGGCACAAACCTAGTCGAATGAATCTGAGGGGGATTCTCAGTAGACAAAG 120 bud.tax.tax
TCCCATACATTGGCACAAACCTAGTTGAGTGAATCTGAGGAGGATTCTCAGTAGACAAAG 120 pan.hod
TCCCATACATTGGCACAGACCTAGTCGAATGAATCTGAGGGGGATTCTCAGTAGACAAAG 120 ovi.amm
TTCCATATATTGGCACAAACCTAGTCGAATGAATCTGAGGGGGATTCTCAGTAGACAAAG 120 ovi.vig
TTCCATATATTGGCACAAACCTAGTCGAATGAATCTGAGGAGGATTCTCAGTAGACAAAG 120 cap.cri
TCCCATATATTGGCACAAACTTAGTAGAATGAATCTGAGGAGGATTCTCCGTAGACAAAG 120 ovi.mos
TCCCATACATCGGCACAAACCTAGTCGAATGAATCTGAGGAGGATTCTCCGTAGACAAAG 120 ore.ame
TTCCATACATCGGTACAGACCTAGTCGAATGAATCTGAGGGGGGTTCTCAGTAGACAAAG 120 cep.dor
TCCCATACATTGGTACAAACTTAGTCGAATGAATCTGAGGAGGCTTTTCAGTAGACAAAG 120 cep.max
TCCCATATATCGGCACAAACTTAGTTGAGTGAATCTGAGGGGGCTTTTCAGTAGACAAAG 120 bis.bon
TCCCATACATCGGCACAAATCTAGTCGAATGAATCTGAGGCGGATTCTCAGTAGACAAAG 120 bos.gru
TTCCATACATCGGCACAAATTTAGTCGAATGGATTTGAGGTGGGTTCTCAGTAGACAAAG 120 bos.tra
TCCCATACATCGGCACAAACCTAGTTGAATGAATCTGAGGCGGGTTCTCAGTAGACAAAG 120 bub.min
TCCCATACATTGGCACAAACCTAGTTGAGTGAATTTGAGGGGGATTCTCAGTAGACAAAG 120 buba.bub
TCCCATACATTGGTACAAGTCTGGTTGAATGAATTTGAGGGGGATTCTCAGTAGACAAAG 120 tra.ang
TCCCATATATTGGCACCAACCTAGTTGAATGAATCTGAGGAGGCTTCTCGGTAGACAAGG 120 tra.eur
TCCCTTATATTGGCACCAGCCTAGTCGAATGAATCTGAGGGGGCTTTTCAGTAGACAAAG 120 kob.ell
TTCCATACATTGGCACAAACCTAGTCGAATGAATCTGAGGAGGATTTTCAGTAGATAAGG 120 kob.meg
TCCCATATATCGGCACAAACCTAGTCGAATGAATCTGAGGAGGATTCTCAGTAGACAAAG 120 red.aru
TCCCATACATCGGCACAAACCTAGTCGAATGAATCTGAGGAGGATTCTCAGTCGATAAAG 120 red.ful
```

TABLE 2-continued

Multiple sequence alignment of 472 bp fregment of mitochondrial
cytochrome b gene of 221 animal species

TCCCATACATCGGCACAARCCTAGTTGAATGAATCTGAGGAGGRTTCTCAGTGGATAAAG 120 neo.mos
TCCCATATATCGGCACAAACCTAGTCGAATGAATCTGAGGGGGTTTCTCAGTAGACAAAG 120 pel.cap
TCCCATACATTGGTACAAACCTAGTCGAATGAATCTGAGGGGGATTTTCAGTAGACAAAG 120 gaz.dam
TCCCATACATCGGCACAGACCTAGTAGAATGAATCTGAGGAGGATTCTCAGTAGATAAGG 120 our.our
TTCCATACATTGGTACAAACCTAGTCGAATGAATCTGAGGAGGGTTCTCAGTAGACAAGG 120 ant.cer
TCCCATACATCGGTACAAACCTAGTAGAATGAATCTGAGGAGGGTTCTCAGTAGATAAAG 120 sai.tat
TCCCATATATCGGCACAGACCTAGTAGAATGAATCTGAGGGGGTTTTCAGTAGATAAAG 120 mad.kir
TCCCATATATCGGCACAAACTTAGTTGAATGAATCTGAGGGGGCTTCTCAGTAGACAAAG 120 rap.mel
TTCCCTACATTGGCACAAACCTAGTAGAATGGATCTGAGGAGGATTTTCAGTTGATAAAG 120 gaz.gaz
TCCCATACATCGGCACAAACCTAGTAGAATGAATCTGAGGGGGATTCTCGGTAGATAAAG 120 ant.ame
TCCCATACATTGGTACTAACCTAGTAGAATGAATCTGAGGGGGATTCTCAGTAGACAAAG 120 hyd.ine
TCCCATACGTCGGTACAAATCTAGTCGAATGAATCTGAGGTGGCTTTTCAGTAGATAAAG 120 mun.mun
TTCCATATATTGGCACAAACTTAGTCGAATGAATCTGAGGAGGCTTTTCAGTTGATAAAG 120 alc.alc
TTCCATACATTGGTACTAATCTAGTTGAATGAATTTGAGGCGGTTTTTCAGTAGACAAAG 120 cer.ela.kan
TTCCATACATTGGCACAAACCTAGTCGAATGGATCTGAGGAGGCTTTTCAGTAGATAAAG 120 cer.ela.xan
TTCCATACATTGGCACAAACCTAGTCGAATGGATCTGAGGAGGCTTTTCAGTAGATAAAG 120 cer.ela.can
TTCCATACATTGGCACAAACCTAGTCGAATGGGTCTGAGGAGGCTTTTCAGTAGATAAAG 120 cer.nip.cent
TTCCATATATTGGCACAAACCTAGTCGAATGGATCTGAGGGGGCTTCTCAGTAGATAAAG 120 cer.nip.yes
TTCCATATATTGGCACAAACCTAGTCGAATGGATCTGAGGGGGCTTCTCAGTAGATAAAG 120 cer.nip.ker
TTCCATACATTGGCACAAACCTAGTCGAATGGATCTGAGGAGGCTTTTCAGTAGATAAAG 120 cer.nip.pul
TTCCATACATTGGCACAAACCTAGTCGAATGGATCTGAGGAGGCTTTTCAGTAGATAAAG 120 cer.nip.nip
TTCCATACATTGGCACAAACCTAGTCGAATGGATCTGAGGAGGCTTTTCAGTAGATAAAG 120 cer.ela.sco
TTCCATATATTGGGACAAACCTAGTCGAATGGATCTGAGGAGGCTTTTCAGTAGACAAAG 120 cer.dam
TCCCATACATTGGTACAAACCTAGTTGAATGAATCTGAGGAGGCTTTTCAGTAGACAAAG 120 ran.tar
TTCCATATATTGGTACAAATCTAGTCGAATGAATTTGAGGAGGATTTTCTGTAGATAAAG 120 mos.fus
TTCCATACATTGGTACTAATCTGGTTGAATGAATTTGAGGAGGCTTCTCAGTAGACAAAG 120

TABLE 2-continued

Multiple sequence alignment of 472 bp fregment of mitochondrial
cytochrome b gene of 221 animal species mos.leu
TTCCATACATTGGTACTAATCTGGTTGAATGAATTTGAGGAGGCTTCTCAGTAGACAAAG 120 mos.chr
TTCCATACATTGGTACTAACCTGGTTGAATGAATTTGAGGAGGTTTGTCAGTAGACAAAG 120 mos.ber
TTCCTTACATTGGTACTAATCTGGTTGAATGAATCTGAGGAGGCTTCTCAGTAGACAAAG 120 mos.mos
TTCCCTACATTGGTACTAACCTGGTTGAGTGAATTTGAGGAGGCTTCTCAGTAGACAAAG 120 tra.jav
TCCCATACATTGGCACAGACTTGGTCGAATGAATCTGAGGTGGTTTTTCAGTAGACAAAG 120 trag.nap
TCCCCTATATCGGCACCGAACTAGTTGAATGAATCTGAGGCGGGTTCTCAGTAGACAAAG 120 bala.acu
TCCCATATATTGGTACTACCTTAGTCGAATGAATCTGAGGTGGCTTCTCTGTAGACAAAG 120 bala.bon
TCCCATACATTGGTACCACCTTAGTTGAATGAATCTGAGGTGGCTTCTCTGTAGACAAAG 120 bala.bor
TCCCATACATTGGTACTACCCTAGTCGAATGGATCTGAGGCGGTTTCTCTGTAGATAAAG 120 bala.edi
TCCCATACATTGGTACTACCCTAGTCGAATGAATCTGGGCGGTTTCTCTGTAGATAAAG 120 esch.rob
TCCCATACATTGGCACTACCCTAGTCGAATGGGTCTGAGGCGGTTTTTCTGTAGATAAAG 120 bala.mus
TCCCATACATTGGTACTACCCTAGTCGAATGAATCTGAGGCGGTTTTTCTGTGGATAAAG 120 mega.nov
TCCCATACATTGGTACTACCCTAGTCGAATGAATCTGGGCGGTTTTTCCGTAGACAAAG 120 bala.phy
TCCCATACATTGGTACCACCCTAGTCGAATGAATCTGAGGCGGTTTCTCTGTAGATAAAG 120 cap.mar
TCCCATATATTGGTACCACCCTAGTTGAATGAATCTGGGGTGGCTTCTCCGTAGACAAAG 120 ceph.com
TCCCCTACATCGGTACTACCTTAGTAGAATGAATCTGAGGCGGATTTTCCGTAGACAAAG 120 ceph.eut
TCCCCTACATCGGTACTACCTTAGTAGAATGAATCTGAGGCGGATTTTCCGTAGACAAAG 120 lage.obl
TCCCCTACATCGGTACTACCTTAGTAGAATGAATCTGAGGCGGATTTTCCGTAGACAAAG 120 ceph.hea
TCCCCTACATCGGTACTACCTTAGTAGAATGAATCTGAGGCGGATTTTCCGTGGACAAAG 120 ceph.hec
TCCCCTACATCGGCACTACCTTAGTAGAATGAATCTGAGGAGGATTTTCCGTAGACAAAG 120 lage.aus
TCCCCTACATCGGTACTACCTTAGTAGAATGAATCTGAGGCGGATTTTCCGTAGATAAAG 120 lage.cru
TCCCCTACATCGGTACTACCTTAGTAGAATGAATCTGAGGCGGATTTTCCGTAGACAAAG 120 lage.obs
TCCCCTACATTGGTACTACCTTAGTAGAATGAATCTGAGGCGGATTTTCCGTAGACAAAG 120 lisso.bor
TCCCCTACATCGGTACTACCTTAGTAGAATGAATCTGAGGCGGATTTTCCGTAGACAAAG 120 lisso.per
TCCCCTACATCGGTACTACCTTAGTAGAATGAATCTGAGGCGGATTTTCCGTAGACAAAG 120

TABLE 2-continued

Multiple sequence alignment of 472 bp fregment of mitochondrial cytochrome b gene of 221 animal species glo.mac
TCCCTTACATCGGCACCACCTTAGTAGAATGAATCTGAGGTGGATTTTCCGTAGACAAAG 120 glo.mel
TCCCTTACATCGGCACTACCTTAGTAGAATGAATCTGAGGTGGATTTTCCGTAGACAAAG 120 fere.att
TCCCTTACATCGGCACCACTTTAGTAGAATGAATCTGAGGTGGATTTTCCGTAGACAAAG 120 pepo.ele
TCCCTTACATCGGAACCACCTTAGTAGAATGAATCTGAGGTGGATTTTCCGTAGACAAAG 120 gram.gri
TCCCCTACATCGGTACTACTTTAGTAGAATGAATCTGAGGTGGATTTTCCGTAGACAAAG 120 pse.cra
TCCCCTACATCGGTACCACTTTAGTAGAATGAATCTGAGGAGGATTTTCCGTAGACAAAG 120 lage.acu
TCCCTTACATCGGCACTACCCTAGTAGAATGAATCTGAGGCGGATTTTCCGTAGACAAAG 120 orci.bre
TCCCTTACATCGGCACCACCTTAGTAGAATGAATCTGAGGTGGATTTTCCGTAGACAAAG 120 orca.bre
TCCCTTACATCGGCACTACCCTAGTAGAATGAATCTGAGGTGGATTTTCCGTAGACAAAG 120 del.cap
TCCCTTATATTGGCACTACCTTAGTCGAATGAATCTGAGGTGGATTCTCCGTAGACAAAG 120 del.tro
TCCCTTATATTGGCACTACCTTAGTCGAATGAATCTGAGGTGGATTCTCCGTAGACAAAG 120 del.del
TCCCTTATATTGGCACTACCTTAGTCGAATGAATCTGAGGTGGATTCTCCGTAGACAAAG 120 sten.cly
TCCCTTATATTGGCACTACCTTAGTCGAATGAATCTGAGGTGGATTCTCCGTAGACAAAG 120 sten.coe
TCCCTTATATTGGCACTACCTTAGTCGAATGAATCTGAGGTGGATTCTCCGTAGACAAAG 120 tur.adu
TCCCTTATATTGGCACTACCTTAGTCGAATGAATCTGAGGTGGATTCTCCGTAGACAAAG 120 sten.fro
TCCCTTATATTGGCACTACCTTAGTAGAATGAATCTGAGGTGGATTCTCCGTAGACAAAG 120 saus.chi
TCCCTTACATTGGCACTACCTTAGTTGAATGAATCTGAGGCGGATTTTCCGTAGACAAAG 120 sten.lon
TCCCTTATATTGGCACTACCCTAGTTGAATGAATCTGAGGTGGATTTTCCGTAGACAAAG 120 turs.tru
TCCCTTATATCGGCACTACCTTAGTCGAATGAATCTGAGGTGGATTTTCCGTAGACAAAG 120 lage.alb
TCCCTTATATCGGTACTACCCTAGTAGAATGAATCTGAGGTGGATTCTCCGTAGACAAAG 120 sten.bre
TCCCTTACATCGGCACTACCTTGGTAGAATGAATCTGAGGCGGATTTTCCGTAGACAAAG 120 sota.flu
TCCCTTACATCGGCACTACCTTAGTAGAATGAATCTGAGGCGGATTCTCCGTAGACAAAG 120 del.leu
TCCCTTACATCGGTAACACCTTAGTAGAATGAATCTGAGGTGGGTTCTCCGTAGACAAAG 120 mono.mon
TCCCTTACATCGGCAACACCTTAGTAGAATGAATCTGAGGTGGGTTTTCTGTAGATAAAG 120 plat.gan
TCCCTTATATCGGCAGTACCCTAGTCGAGTGAATCTGAGGTGGCTTTTCCGTAGATAAAG 120 plat.min

TABLE 2-continued

Multiple sequence alignment of 472 bp fregment of mitochondrial cytochrome b gene of 221 animal species

TCCCTTATATCGGCAGTACCCTAGTCGAGTGAATCTGAGGTGGCTTTTCCGTAGATAAAG 120 kogi.bre
TTCCTTATATCGGCACCACCCTAGTAGAATGAGTCTGAGGTGGCTTCTCCGTAGACAAAG 120 kogi.sim
TCCCTTACATCGGCACCACCCTAGTGGAATGAGTCTGAGGTGGCTTCTCCGTGGACAAAG 120 phys.cat
TTCCCTATATCGGCACCACCCTAGTAGAGTGAGTTTGAGGCGGTTTCTCCGTAGATAAGG 120 lipo.vex
TCCCTTACATCGGAACCACCCTAGTAGAGTGAGTCTGAGGGGGATTCTCAGTAGACAAAG 120 phoc.sin
TCCCTTACATCGGCAGCACGCTAGTGGAGTGAATCTGAGGTGGATTCTCCGTAGACAAAG 120 bera.bai
TTCCTTATATCGGCACCACTCTTGTCGAATGAATCTGAGGTGGCTTCTCCGTAGATAAAG 120 ziph.car
TCCCCTATATCGGCACTACTCTAGTCGAATGAATCTGAGGTGGTTTTTCAGTAGATAAAG 120 meso.eur
TCCCCTATATTGGCACTACTCTAGTCGAATGAATCTGAGGTGGCTTTTCCGTAGATAAAG 120 meso.bid
TTCCCTACATCGGCACTACCCTAGTTGAATGAATCTGAGGTGGCTTTTCCGTAGACAAAG 120 meso.den
TTCCCTATATTGGCACCACCCTAGTCGAGTGAATCTGAGGTGGTTTTTCCGTAGACAAAG 120 hype.amp
TTCCCTATATCGGCACTACCCTAGTTGAATGAATCTGAGGTGGTTTCTCCGTAGACAAAG 120 meso.per
TCCCTTATATTGGCACCACCCTAGTTGAATGAATTTGAGGTGGCTTCTCCGTAGATAAAG 120 pont.bla
TCCCCTACATCGGAACTACCCTTGTAGAATGGATCTGAGGTGGTTTCTCTGTAGACAAAG 120 hex.lib
TCCCCTACATTGGAACAGACCTAGTAGAATGAATCTGAGGAGGCTTTTCTGTAGATAAAG 120 hipp.amp
TCCCCTATATTGGAACAGACCTAGTAGAATGAATCTGAGGAGGCTTTTCCGTAGACAAAG 120 dic.sum
TCCCATACATCGGCACCGACCTTGTAGAATGAATCTGAGGGGGATTCTCCGTAGACAAAG 120 rhin.son
TCCCCTATATCGGTACCAACCTTGTAGAGTGAATCTGAGGAGGATTCTCAGTCGACAAAG 120 cera
TCCCTTACATCGGCACCAACCTCGTAGAATGAATCTGAGGAGGATTTTCCGTTGACAAAG 120 equu
TCCCCTACATCGGTACTACGCTCGTCGAATGAATCTGAGGTGGATTCTCAGTAGACAAAG 120 baby.bab
TTCCCTATATCGGAACGGACCTCGTAGAATGGATCTGAGGAGGCTTCTCCGTCGATAAAG 120 phac.afr
TTCCCTACATTGGAACAAATCTTGTAGAATGAATCTGAGGAGGTTTCTCCGTCGACAAAG 120 sus.bar
TCCCCTATATCGGAACAGACCTCGTAGAATGAATCTGAGGGGGCTTTTCCGTCGACAAAG 120 sus.scr.ewb3
TCCCTTATATCGGAACAGACCTCGTAGAATGAATCTGAGGGGGCTTTTCCGTCGACAAAG 120 lama.gla
TTCCATATGTTGGCACAACACTAGTCGAATGAATTTGAGGAGGATTCTCCGTAGACAAAG 120 lama.gua
TTCCATATGTTGGCACAACACTAGTCGAATGAATTTGAGGGGGGTTCTCCGTAGATAAAG 120

TABLE 2-continued

Multiple sequence alignment of 472 bp fregment of mitochondrial cytochrome b gene of 221 animal species

```
vic.vic
TTCCATACGTTGGTACAACACTAGTCGAGTGGATTTGAGGAGGATTCTCCGTAGATAAAG 120 cam.bac
TTCCCTATATCGGCACAACACTAGTAGAATGAATTTGAGGTGGCTTCTCCGTAGACAAAG 120 arc.for
TCCCCTACATTGGGACCAACCTAGTAGAATGAATCTGAGGAGGATTTTCAGTTGATAAAG 120 arc.gaz
TCCCCTACATCGGAACTAACCTAGTAGAATGAATCTGAGGAGGATTTTCAGTTGATAAGG 120 eum.jub
TCCCTTACATCGGAACCAACTTAGTAGAATGAATTTGAGGGGGATTTTCAGTCGACAAAG 120 zal.cal
TCCCTTACATCGGAACCAACCTAGTAGAATGAATTTGAGGGGGATTTTCAGTCGACAAAG 120 odo.ros
TTCCCTATGTAGGGACTGACTTGGTCGAATGAGTCTGAGGGGGGTTTTCAGTTGATAAAG 120 pho.fasciata
TTCCCTATATCGGAACCGACCTAGTACAATGAATCTGAGGAGGATTTTCAGTTGATAAAG 120 pho.gro
TCCCCTACATCGGAACCGATCTAGTACAATGAATCTGAGGAGGGTTCTCAGTTGATAAAG 120 pho.vit
TTCCCTATGTCGGAACCGACCTTGTACAATGAATCTGAGGAGGGTTTTCAGTAGATAAAG 120 cys.cri
TCCCCTACATCGGAGCCGATCTAGTAGAATGAATCTGAGGGGGATTTTCAGTCGATAAAG 120 hyd.lep
TTCCCTACATCGGAACCGACCTAGTACAATGAATTTGAGGCGGATTTTCAGTCGACAAAG 120 lep.wed
TTCCCTACATCGGAACTGACTTAGTACAATGAATCTGAGGCGGATTTTCAGTTGACAAAG 120 mir.leo
TCCCCTATGTCGGAGACGACCTAGTACAATGAATCTGAGGAGGATTTTCAATCGACAAAG 120 eri.bar
TCCCCTACATCGGGACTGATCTAGTACAATGAATCTGAGGAGGATTCTCAGTTGACAAAG 120 mon.sch
TCCCTTACATCGGAACCGATCTAGTACAATGAATCTGAGGCGGGTTCTCAGTAGATAAAG 120 hela.mal
TCCCCTATATTGGAACGGACCTAGTAGAATGAGTCTGAGGAGGCTTTTCCGTAGACAAGG 120 sel.thi
TCCCCTATATTGGAACAGACCTAGTAGAATGAATCTGAGGGGGCTTTTCTGTAGATAAAG 120 ail.ful
TTCCCTATATTGGAACTAACCTTGTAGAGTGAATCTGAGGAGGTTTCTCAGTCGACAAAG 120 fel
TTCCATACATCGGGACTGAACTAGTAGAATGAATCTGAGGGGGGTTCTCAGTAGACAAAG 120 can
TCCCTTATATCGGAACTGACTTAGTAGAATGGATCTGAGGCGGCTTCTCAGTGGACAAAG 120 tal
TTCCTTACATCGGTACAGACTTAGTAGAATGAATTTGAGGTGGGTTCTCAGTAGACAAAG 120 gla.sab
TTCCTTATATTGGGACAACACTTGTAGAATGAATCTGAGGAGGCTTCTCTGTCGACAAAG 120 gla.vol
TTCCTTATATTGGTACAACACTTGTAGAATGAATCTGAGGGGGCTTCTCTGTTGATAAAG 120 hyl.pha
TCCCCTACATTGGAACAGTCCTTGTCGAATGAATTTGAGGGGGATTTTCCGTAGATAAGG 120
```

TABLE 2-continued

Multiple sequence alignment of 472 bp fregment of mitochondrial
cytochrome b gene of 221 animal species pet.set
TCCCCTATATTGGAACAGTCCTTGTCGAATGAATTTGAGGGGGATTTTCCGTAGATAAGG 120 bel.pea
TCCCTTATATTGGAACTGATCTAGTAGAGTGAATCTGAGGGGGGTTTTCAGTTGACAAGG 120 pte.mom
TCCCTTATATCGGCACCAACCTTGTTGAATGGATCTGAGGTGGTTTCTCAGTTGATAAAG 120 gala.demi
TCCCATATATAGGGCCTACTCTAGTAGAATGAATCTGAGGGGGTTTTCGTAGACAAAG 120 pero.pot
TCCCATATGTAGGTACAACCCTGGTAGAATGAATTTGAGGGGGATTCTCAGTAGACAAAG 120 gala.mat
TTCCTTACATGGGTACCGGCCTAGTAGAATGAATCTGAGGGGGATTTTCAGTAGACAAAG 120 gala.moh
TTCCCTATATAGGAACTGGCCTAGTAGAATGAATCTGAGGAGGGTTCTCAGTAGACAAAG 120 oto.gar
TTCCCTACATAGGAACTAACCTAGTAGAGTGAATCTGAGGGGGATTTTCAGTAGACAAAG 120 lor.tar
TCCCTTACATCGGAACTAACCTAGTTGAATGAATCTGAGGGGGGTTCTCAGTAGATAAAG 120 nyc.cou
TCCCCTATATTGGCACAAACCTAGTTGAATGGGTCTGAGGAGGCTTCTCAGTAGATAAAG 120 mus
TCCCATATATTGGAACAACCCTAGTCGAATGAATTTGAGGGGGCTTCTCAGTAGACAAAG 120 gorr
TCCCGTACATCGGAACAGACCTAGTCCAATGAGTTTGAGGTGGTTACTCAGTAGATAGCC 120 homo
TCCCATACATTGGGACAGACCTAGTTCAATGAATCTGAGGAGGCTACTCAGTAGACAGTC 120 dug.dug
TCCCCTACATCGGCACCAACCTAGTCGAATGAGTTTGAGGGGGATTCTCAGTAGACAAAG 120 ele.max
TTCCCTACATCGGCACAAACCTAGTAGAATGAATTTGAGGAGGCTTTTCGGTAGATAAAG 120 afr.con
TCCCCTATATTGGTCAAACCCTAGTAGAATGGGCCTGAGGAGGATTCTCAGTTGACAACC 120 pavo.mut
TCCCTTATATTGGACAAACCCTAGTAGAATGAGCCTGAGGGGGATTCTCAGTCGACAACC 120 tra.bly
TCCCATACATTGGCCAAACCTTAGTAGAATGAGCCTGAGGAGGCTTTTCAGTTGACAATC 120 tra.sat
TCCCATACATTGGTCAAACCCTAGTAGAATGAGCGTGAGGCGGCTTTTCAGTTGACAATC 120 tra.cob
TCCCATACATTGGCCAAACTCTAGTAGAATGGGCCTGAGGGGGCTTTTCAGTTGACAATC 120 tra.tem
TCCCATACATTGGCCAAACCCTAGTAGAATGAGCTTGAGGGGGCTTTTCAGTTGACAATC 120 arg.arg
TCCCTTATATTGGACAAACCCTAGTAGAGTGAGCCTGAGGAGGATTTTCAGTCGACAACC 120 cat.wal
TCCCTTACATCGGACAGACCCTAGTAGAATGAGCCTGAGGAGGATTCTCAGTTGACAATC 120 cro.cro
TCCCTTACATTGGACAAACCCTAGTCGAGTGAGCCTGAGGGGGATTCTCAGTTGACAACC 120 sym.ree
TCCCCTACATCGGACAAACCCTAGTAGAGTGGGCCTGAGGAGGATTCTCAGTTGACAACC 120 bam.tho

TABLE 2-continued

Multiple sequence alignment of 472 bp fregment of mitochondrial cytochrome b gene of 221 animal species

```
TTCCCTACATCGGACAAACCCTAGTAGAATGAGCCTGGGGGGATTCTCAGTAGACAACC  120 fra.fra
TTCCCTACATTGGACAAACCTTAGTAGAGTGAGCCTGAGGGGGATTCTCAGTAGATAACC  120 ith.cru
TTCCCTACATCGGCCAAACTCTGGTAGAATGAGCTTGAGGAGGATTTTCAGTAGACAACC  120 ant.par
TCCCATATATCGGCCAAACCCTTGTAGAATGAGCTTGAGGGGGTTTCTCAGTAGACAATC  120 ant.vir
TCCCATACATCGGCCAAACCCTTGTAGAATGAGCTTGAGGGGGTTTTTCAGTAGATAATC  120 gru.ant.ant
TCCCCTACATCGGCCAAACCCTTGTAGAATGAGCTTGAGGGGGCTTCTCAGTAGACAATC  120 gru.ant.gil
TCCCCTACATCGGCCAAACCCTTGTAGAATGAGCTTGAGGGGGCTTCTCAGTAGACAATC  120 gru.ant.sha
TCCCCTACGGCGGCCAAACCCTTGTAGAATGAGCTTGAGGGGGCTTCTCAGTAGACAATC  120 gru.leu
TCCCCTACATCGGCCAAACCCTTGTAGAATGAGCTTGAGGGGGCTTCTCAGTAGACAACC  120 gru.can.pra
TCCCATACATCGGCCAAACCCTCGTAGAATGGGCTTGAGGGGGCTTCTCAGTAGACAATC  120 gru.can.row
TCCCATACATCGGCCAAACCCTCGTAGAATGGGCTTGAGGGGGCTTCTCAGTAGACAATC  120 gru.can.tab
TCCCATACATCGGCCAAACCCTCGTAGAATGGGCTTGAGGGGGCTTCTCAGTAGACAATC  120 gru.can.can
TCCCATACATCGGCCAAACCCTCGTAGAATGGGCTTGAGGGGGCTTCTCAGTAGACAATC  120 gru.ame
TCCCATACATCGGCCAAACCATCGTAGAATGAGCTTGAGGGGGCTTCTCTGTAGACAACC  120 gru.gru
TCCCATACATCGGCCAAACCCTGGTAGAATGAGCTTGAGGGGGCTTCTCAGTAGACAACC  120 gru.mon
TCCCATACATCGGCCAAACCCTCGTAGAATGAGCTTGAGGAGGCTTCTCAGTAGACAACC  120 gru.nig
TCCCATACATCGGCCAAACCCTCGTAGAATGAGCTTGAGGAGGCTTCTCAGTAGACAACC  120 gru.jap
TCGCATACATCGGCCAAACGCTCGTAGAATGAGCTTGAGGGGGCTTCTCAGTAGACAACC  120 cic.boy
TCCCCTACATCGGGCAAACCCTCGTAGAATGGGCCTGAGGGGGCTTCTCCGTCGATAACC  120 rhe.ame
TCCCGTACATCGGACAAACCTTGGTAGAATGAGCTTGAGGGGGGTTTTCAGTAGACAACC  120 ant.alb
TCCCATACATCGGCCAAACCTTAGTAGAATGGGCCTGAGGGGGATTCTCCGTTGACAACC  120 fal.fam
TCCCATACATCGGTCAAACCCTAGTCGAGTGGGCCTGAGGAGGATTTTCAGTAGACAATC  120 fal.ver
TCCCATACATCGGCCAAACCCTAGTCGAATGGGCCTGAGGAGGATTTTCAGTAGATAACC  120 fal. er
TCCCATACATCGGCCAAACCCTAGTCGAATGAGCTTGAGGGGGATTTTCAGTAGACAACC  120 fal.spa
TCCCATATATCGGCAAACCCTAGTCGAATGGGCCTGAGGAGGATTCTCAGTAGACAACC  120 ayt.ame
TCCCATACATCGGGCAAACCCTTGTAGAATGGGCCTGAGGAGGATTCTCGGTAGACAACC  120
```

TABLE 2-continued

Multiple sequence alignment of 472 bp fregment of mitochondrial
cytochrome b gene of 221 animal species smi.sha
TTCCATACATCGGACAAACCCTAGTAGAATGAGCTTGGGGAGGATTTTCAGTAGACAACC 120 vid.cha
TTCCATACATTGGCCAAACCCTAGTAGAATGAGCCTGAGGAGGATTCTCAGTAGACAACC 120 chry.pic
TCCCATTCATTGGTAACACATTAGTACAATGAATCTGAGGTGGATTCTCAGTAGACAACG 120 emy.orb.kur
TCCCATACATTGGCAATACACTAGTGCAATGAATCTGAGGGGGATTCTCAGTAGATAACG 120 che.mud
TCCCATACATCGGCAACACACTAGTACAATGAATCTGAGGAGGGTTTTCAGTAGACAATG 120 eum.egr
TTCCATACATTGGCACCAACCTAGTAGAATGAATTTGAGGGGGCTTTTCCGTAGACAACG 120
             *  ** *        **           *  **   *             *   **   *
** * aep.mel
CAACCCTNACCCGATTTTTCGCYTTCCACTTCATCYTTCCATTCATCATTGCGGCACTAG 180 ore.ore
CAACCCTTACCCGATTCTTTGCCTTTCACTTCATCTTTCCATTTATCATCGCAGCCCTAG 180 add.nas
CAACCCTTACCCGATTTTTCGCCTTCCACTTTATTCTCCCCTTTATTATCGCTGCCCTTG 180 ory.dam
CAACCCTCACCCGATTTTTCGCCTTCCACTTTATTCTCCCTTTTATTATCGCTGCCCTTG 180 hip.equ
CAACCCTCACCCGATTCTTCGCCTTCCACTTTATTCTTGCCTTTATCATCACTGCCCTTG 180 alc.bus
CAACCCTTACCCGATTTTTTGCCTTCCACTTCATTCTTCCATTCATCATTGCAGCCCTTG 180 sig.lic
CAACCCTTACCCGATTTTTTGCCTTCCACTTCATTCTCCCATTCATCATTGCAGCCCTTG 180 bea.hun
CAACCCTCACCCGATTTTTCGCTTTCCACTTTATTCTCCCATTTATCATTACAGCCCTTG 180 dam.lun
CCACCCTCACCCGATTCTTTGCCTTCCACTTCATCTTCCCATTTATCATCGTAGCTCTTG 180 con.tau
CAACCCTTACCCGATTTTTCGCCTTCCACTTCATTCGTCCATTTATCATCACAGCCCTTG 180 amm.ler
CTACTCTCACCCGATTCTTCGCCTTCCACTTCATCCTCCCATTTGTAATCGCAGCCCTAG 180 pse.nay
CCACTCTGACCCGATTCTTCGCCTTCCACTTCATCCTCCCATTTATTATTATAGCCCTCG 180 cap.ibe
CCACTCTCACCCGATTCTTCGCCTTCCACTTCATCCTCCCATTCATCATTACAGCCCTCG 180 hem.jem
CTACCCTAACCCGATTCTTCGCTTTCCACTTCATTCTCCCATTCATCATTGCAGCCCTCG 180 cap.fal
CCACCCTCACCCGATTCTTCGCCTTCCACTTTATCCTCCCATTCATCATTGCAGGCCTCG 180 rup.pyr
CTACCCTCACCCGATTCTTTGCCTTTCACTTCATCCTCCCATTCATCATTGCAGCCTTAG 180 rup.rup
CTACCCTCACCCGATTCTTTGCCTTCCACTTCATCCTCCCATTTATCATTGCAGCCTTAG 180 nem.cau
CTACTCTCACCCGATTCTTCGCCTTCCACTTCATCCTCCCATTTATCATTACAGCTACTG 180 bud.tax.tax

TABLE 2-continued

Multiple sequence alignment of 472 bp fregment of mitochondrial cytochrome b gene of 221 animal species

```
CATCCCTCACCCGATTCTTTGCCTTTCACTTCATCCTCCCATTTATCATCGCAGACCTCG 180 pan.hod
CTACCCTTACCCGATTCTTTGCCTTCCATTTCATTCTCCCATTCATCATCGCAGCCCTCG 180 ovi.amm
CCACCCTGACCCGATTCTTCGCCTTTCACTTTATTTTCCCATTCATCATCGCAGCCCTCG 180 ovi.vig
CTACCCTCAGCCGATTTTTCGCCTTTCACTTTATTTTCCCATTCATCATCGCAGCCCTCG 180 cap.cri
CCACCCTCACCCGATTCTTTGCCTTCCATTTCATTCTCCCATTCATCATCACAGCCCTCG 180 ovi.mos
CCACCCTCACCCGATTTTTTGCTTTTCACTTTATCCTCCCATTTATCATCGTAGCCCTCG 180 ore.ame
CTACCCTCACCCGATTTTTTCGCCTTCCACTTCATTCTCCCATTTATCATCGCAGCCCTCG 180 cep.dor
CAACTCTCACCCGATTCTTTGCTTTCCACTTTATCTTCGGTTTTATTATTGCAGCCCTCG 180 cep.max
CAACCCTCACTCGATTTTTCGCCTTGCACTTTATCTTCCCATTTATCATCGCAGCCCTTG 180 bis.bon
CAACCCTTACCCGATTTTTCGCTTTCCACTTTATCCTCCCATTTATTATCATAGCAATTG 180 bos.gru
CAACCCTCACCCGATTCTTCGCTTTCCACTTTATCCTCCCATTTATTATTACAGCAATTG 180 bos.tra
CAACCCTAACCCGATTCTTCGCTTTCCACTTTATCCTCCCATTCATCATTGCAGCCCTCG 180 bub.min
CAACCCTCACCCGATTCTTCGCATTTCACTTCATCCTCCCATTCATTATCGCAGCACTTG 180 buba.bub
CAACCCTCACCCGATTCTTCGCATTTCACTTCATCCTCCCATTCATTATCGCAGGACTTG 180 tra.ang
CAACCCTAACCCGATTTTTCGCCTTCCACTTCATCCTCGCGTTTATTATTACAGCGCTGG 180 tra.eur
CAACCTTAACCCGATTCTTCGCCTTCCACTTTATCCTTCCATTTATTATTACAGCACTAG 180 kob.ell
CAACCCTTACCCGCTTGTTCGCCTTCCACTTTATTCTCCCATTTATGATCGCGGCTATTA 180 kob.meg
CAACCCTTACCCGCTTCTTCGCCTTCCACTTTATCCTCCCATTTATCATCGCAGCTATCG 180 red.aru
CAACCCTTACCCGATTCTTCGCCTTCCACTTTATCCTCCCATTCATTATCACAGCCCTCG 180 red.ful
CAACCCTCACTCGATTCTTCGCCTTCCACTTTATCCTCCCATTTATGATCATAGCCCTCG 180 neo.mos
CAACCCTCACCCGATTTTTTGCCTTCCACTTCATTCTCCCATTTATCATCGCAGCACTCG 180 pel.cap
CAACCCTCACCCGATTTTTTGCTTTCCACTTTATTCTCCCATTTATCATTGCAGCCCTCA 180 gaz.dam
CAACACTCACCCGATTCTTTGCCTTCCATTTCATCTTCCCATTCATCATTGCAGCCCTTG 180 our.our
CAACTCTAACCCGATTCTTTGCCTTCCACTTCATCCTCCCATTCATCATTGCAGCCCTTG 180 ant.cer
CAACCCTTACCCGATTTTTCGCCTTCCACTTTATCCTCCCATTTATCATTGCAGCCCTTA 180 sai.tat
CAACCGTCACCGGATTCTTCGCCTTCCACTTCATCCTCCCATTTATTATCGCAGCTGTCG 180
```

TABLE 2-continued

Multiple sequence alignment of 472 bp fregment of mitochondrial cytochrome b gene of 221 animal species

```
mad.kir
CAACCCTCACCCGATTCTTCGCCTTCCATTTTATTCTCCCATTCATTATTGCAGCCCTAG 180 rap.mel
CAACCCTCACGCGATTCTTCGCTTTTCACTTCAGTTCTCCATTTATCATCGCAGCCCTAG 180 gaz.gaz
CAACACTCACCCGATTCTTTGCTTTTCAGTTTATCCTCCCATTCATCATTGCAGCCCTCG 180 ant.ame
CAACCCTCACCCGATTGTTCGCATTCCACTTTATCCTCCCATTCATCATTGCAGCACTAG 180 hyd.ine
CTACCCTGACCCGATTCTTCGCCTTCCACTTCATTCTTCCATTTATCATTGCAGCTCTTG 180 mun.mun
CAACCCTCACCCGATTCTTTGCCTTCCACTTTATCCTCCCATTTATTATTGCAGCACTTG 180 alc.alc
CAACTCTAACCCGATTTTTCGCCTTCCACTTTATTCTCCCATTTATCATCGCAGCACTTG 180 cer.ela.kan
CAACCCTAACCCGATTTTTCGCTTTCCACTTTATTCTCCCATTTATCATCGCAGCACTCG 180 cer.ela.xan
CAACCCTAACCCGATTTTTCGCTTTCCACTTTATTCTCGCATTTATCATCGCAGCAGTCG 180 cer.ela.can
CAACCCTAACCCGATTCTTCGCTTTCCACTTTATTCTCCCATTTATCATCGCAGCACTCG 180 cer.nip.cent
CAACCCTAACCCGATTTTTCGCTTTCCACTTTATTCTTCCATTTATCATCGCAGCACTTG 180 cer.nip.yes
CAACCCTAACCCGATTTTTCGCTTTCCACTTTATTCTTCCATTTATCATCGCAGCACTTG 180 cer.nip.ker
CAACCCTAACCGGATTTTTCGCCTTCCAGTTTATTCTTCCATTTATCATCACAGCACTCG 180 cer.nip.pul
CAACCCTAACCCGATTTTTCGCCTTCCACTTTATTCTTCCATTTATCATCACAGCACTCG 180 cer.nip.nip
CAACCCTAACCCGATTTTTCGCCTTCCACTTTATTCTTCCATTTATCATCACAGCACTCG 180 cer.ela.sco
CAACCCTAACCCGATTTTTCGCTTTCCACTTTATTCTCCCATTTATCATCGCAGCAGTCG 180 cer.dam
CAACCTTAACTCGATTCTTCGCTTTCCACTTTATTCTACCATTCATCATTGCGGCACTTG 180 ran.tar
CAACCCTAACCCGATTTTTTGCTTTTCACTTTATTCTTCCATTTATTATCGCAGCACTCG 180 mos.fus
CAACACTCACTCGATTCTTTGCCTTTCACTTCATTCTCCCATTTATCATCGCAGCACTCG 180 mos.leu
CAACACTCACCCGATTCTTTGCCTTCCACTTCATTCTCCCATTTATCATCCCAGCACTCG 180 mos.chr
CAACACTCACTCGATTCTTTGCCTTCCACTTCATTCTCCCATTTATCATGGCAGCACTCG 180 mos.ber
CAACACTCACCCGATTCTTTGCCTTCCACTTCATCCTCCCATTTATCATCGGAGCACTCG 180 mos.mos
CAACACTCACCCGATTCTTTGCCTTTCACTTTATCCTCCCATTTATCATTGCAGCACTCG 180 tra.jav
CAACCCTTACACGATTCTTTGCCTTCCACTTTATCCTTCCATTTATCATTACAGCCCTAG 180 trag.nap
CAACCCTTACACGATTTTTTGCCTTCCACTTCATCCTCCCATTTGTCATTACAGCCCTAG 180
```

TABLE 2-continued

Multiple sequence alignment of 472 bp fregment of mitochondrial
cytochrome b gene of 221 animal species

```
bala.acu
CAACATTAACACGCTTTTTTGCCTTCCACTTCATCCTCCCTTTTATTATCCTAGCATTAG 180 bala.bon
CAACATTAACACCCTTTTTCGCCTTCCACTTCATCCTCCCTTTCATTATCCTAGCATTAG 180 bala.bor
CAACACTAACACGCTTTTTTGCCTTCCACTTCATTCTCCCCTTCATTATTCTAGCACTAG 180 bala.edi
CAACACTAACACGCTTTTTTGCCTTCCACTTTATCCTCCCCTTCATTATTGTAGCACTAG 180 esch.rob
CAACACTAACACGCTTCTTTGCGTTCCACTTCATCCTTCCATTCATTATCCTAGCACTAG 180 bala.mus
CAACACTAACAGGCTTCTTTGCCTTCCACTTCATTCTCCCCTTCATCATTATAGCATTAG 180 mega.nov
CAACACTAACACGTTTCTTTGCTTTCCACTTCATCCTCCCCTTCATCATTACAGCATTAG 180 bala.phy
CAACACTAACACGCTTTTTTGCCTTTCACTTTATCCTCCCCTTCATCATCCTAGCATTAG 180 cap.mar
GGACACTAACTCGCTTCTTTGCTTTCCACTTCATCCTCCCTTTCATTATTCTAGCGCTAG 180 ceph.com
CAACACTAACACGCTTTTTTCGCCTTCCACTTTATCCTCCCATTCATCATCACAGCATTAG 180 ceph.eut
CAACACTAACACGCTTTTTTCGCCTTCCACTTTATCCTCCCATTCATCATCACAGCATTAG 180 lage.obl
CAACACTAACACGCTTTTTTCGCTTTCCACTTTATCCTCCCATTCATCATCACAGCATTAG 180 ceph.hea
CAACACTAACACGCTTTTTTCGCCTTCCACTTTATCCTCCCATTCATCATCACAGCATTAG 180 ceph.hec
CAACACTAACACGCTTTTTTCGCCTTTCACTTTATCCTCCCATTCATCATCACAGCATTAA 180 lage.aus
CAACACTAACACGCTTTTTTCGCTTTCCACTTTATCCTCCCATTCATCATCACAGCATTAG 180 lage.cru
CAACACTAACACGCTTTTTTCGCTTTCCACTTCATCCTCCCATTCATCATCACAGCATTAG 180 lage.obs
CAACACTAACACGCTTTTTTCGCTTTCCACTTTATCCTCCCATTCATCATCACAGCATTAG 180 lisso.bor
CAACACTAACACGCTTTTTTCGCTTTCCACTTTATCCTCCCATTCATCATCACAGCATTAG 180 lisso.per
CAACACTAACACGCTTTTTTCGCTTTCCACTTTATCCTCCCATTCATCATCACAGCATTAG 180 glo.mac
CAACACTAACACGTTTTTTCGCTTTCCACTTTATCCTCCCATTCATCATCACAGCATTAG 180 glo.mel
CAACACTAACACGTTTTTTCGCTTTCCACTTTATCCTCCCATTCATCATCACAACATTAG 180 fere.att
CAACACTAACACGTTTTTTCGCTTTCCACTTTATCCTCCCATTCATCATCACAGCATTAG 180 pepo.ele
CAACACTAACACGTTTTTTCGCTTTCCACTTCATCCTCCCATTCATCATCACAGCATTGG 180 gram.gri
CAACACTAACACGCTTTTTCGCTTTCCACTTTATCCTCCCATTCATCATCACAGCATTAG 180 pse.cra
CAACACTAACACGTTTTTTCACTCTCCACTTTATCCTCCCATTCATCATTACAGCACTAA 180 lage.acu
```

TABLE 2-continued

Multiple sequence alignment of 472 bp fregment of mitochondrial
cytochrome b gene of 221 animal species

```
CAACACTGACACGCTTTTTCGCCTTCCATTTCATCCTCCGATTCATAATTACAGCATTAG 180 orci.bre
CAACACTAACACGTTTCTTTGCCTTGCACTTTATCCTCCCATTCATCATCACAGCATTAA 180 orca.bre
CAACACTAACACGTTTTTTCGCCTTCCACTTTATCCTTCCATTCATCATCACAGCACTAG 180 del.cap
CAACATTAACACGCTTTTTCGCTTTCCACTTTATCCTTCCATTCATCATCACAGCATTAG 180 del.tro
CAACATTAACACGCTTTTTCGCTTTCCACTTTATCCTCCCATTCATCATCACAGCATTAG 180 del.del
CAACATTAACACGCTTTTTCGCTTTCCACTTTATCCTCCCATTCATCATCACAGCACTAG 180 sten.cly
CAACATTAACACGCTTTTTCGCTTTCCACTTTATCCTCCCGTTCATCATCACAGCATTAG 180 sten.coe
CAACATTAACACGCTTTTTCGCTTTCCACTTTATCCTCCCGTTCATTATCACAGCATTAG 180 tur.adu
CAACACTAACACGCTTTTTCGCTTTCCACTTTATCCTCCCGTTCGTCATCACAGCATTAG 180 sten.fro
CAACATTAACACGCTTTTTGGCTTTCCACTTTATCCTCCCGTTCATCATCACAGCATTAG 180 saus.chi
CAACATTAACACGCTTTTTCGCTTTCCACTTTATCTTTCCCTTCATCATCACAGCATTAG 180 sten.lon
CAACATTAACACGCTTTTTCGCTTTCCATTTTATCCTCCCATTCATCATCACAGCATTAG 180 turs.tru
CAACATTAACACGCTTTTTCGCCTTCCACTTTATTCTTCCATTCATCATCACAGCATTGG 180 lage.alb
CAACACTAACACGCTTCTTCGCTTTCCACTTTATCCTCCCATTCATCATCACAGCACTAG 180 sten.bre
GAACACTAACACGTTTTTTCGCTTTCGACTTTATCCTCCCATTCATCATCATAGCATTAG 180 sota.flu
CAACACTAACACGCTTTTTCGCCTTCCACTTTATCCTGCCATTTATCATCACAGGATTAG 180 del.leu
CAACACTAACACGCTTCTTCACCTTCCACTTTATCCTCCCATTCATCATTACAGCGCTAG 180 mono.mon
CAACACTAACACGCTTCTTGACCTTCCACTTTATCCTCCCATTCATCATGACAGCACTAG 180 plat.gan
CAACACTAACACGATTCTTTGCCTTTCACTTCATCCTCCCTTTCATCATCCTAACACTAG 180 plat.min
CAACACTAACACGATTCTTTGCCTTTCACTTCATCCTCCCTTTCATCATCCTAACACTAG 180 kogi.bre
CCACATTAACACGCTTCTTTGCCTTTCACTTCATCCTCCCCTTTATCATCCTAGCACTGG 180 kogi.sim
CTACGCTAACACGCTTCTTTGCTTTCCACTTTATTCTCCCCTTCATCATCCTAGGACTAG 180 phys.cat
CAACACTGACACGCTTCTTCACTCTCCACTTCATCCTCCCCTTTATCACCCTAACACTAA 180 lipo.vex
CAACATTAACCCGCTTCTTCGCTCTCCATTTCATCCTTCCATTTATTATTGTAGCACTAA 180 phoc.sin
CAACACTAACACGCTTCTTCGCCTTGCATTTATCCTTCCATTTATCATTACAGCACTAA 180 bera.bai
CCACACTAACACGCTTCTTTGCCTTCCACTTTATCCTGCCTTTTATCATTCTAACCCTAG 180
```

TABLE 2-continued

Multiple sequence alignment of 472 bp fregment of mitochondrial
cytochrome b gene of 221 animal species ziph.car
CCACACTAACACGCTTCTTTGCCTTCCATTTCATCCTTCCATTTATTATTTTAGCCCTAG 180 meso.eur
CTACACTAACACGCTTCTTTGCTTTCCACTTTATCCTTGCATTCATTATTGTAGCGCTAA 180 meso.bid
CCACATTAACACGCTTCTTCGCCTTCCACTTTATCCTCCCATTTATTATTTTAGCCCTAG 180 meso.den
CCACATTAACACGCTTCTTCGCTTTTCACTTCATCCTCCCCTTTATTATTCTAGCCCTAA 180 hype.amp
CCACATTAACCCGCTTTTTCGCCCTCCACTTTATCCTCCCATTCATTATTCTAGCCCTAG 180 meso.per
CTACATTAACACGATTTTTTGCCTTCCACTTTATTCTCCCATTTATTATCTTAGCTCTAA 180 pont.bla
CAACACTAACGCGATTCTTCGCTTTCCATTTATCCTTCCATTCATTATTACAGCCCTAG 180 hex.lib
CCACCCTTACACGATTCTTTGCCTTCCACTTTATTCTTCCATTCATCATCATAGCACTAG 180 hipp.amp
CCACCCTTACACGATTCTTTGCCTTCCACTTTATTCTTCCATTCGTTATCACAGCACTAG 180 dic.sum
CCACCCTCACCCGGTTCTTTGCTTTCCACTTCATCCTCCCCTTCATCATCCTAGCCCTAG 180 rhin.son
CTACCCTTACCCGATTCTTTGCCTTCCACTTCATCCTTCCCTTTATTATCCTAGCTCTAG 180 cera
CCACACTTACACGATTCTTCGCCTTTCACTTTATCCTCCCGTTTATTATCATAGCCCTAG 180 equu
CCACCCTTACCCGATTTTTTGCCTTCCACTTTATTCTACCCTTTATCATCACAGCCCTGG 180 baby.bab
CAACCCTCACACGATTCTTTGCTTTCCACTTTATTCTACGCTTCATCATCACGGCTCTCG 180 phac.afr
CAACTCTCACACGATTCTTTGCCTTCCACTTCATTTTACCTTTTATCATCGCTGGCCTAG 180 sus.bar
CAACCCTTACACGATTCTTCGCCTTTCACTTTATCCTGCCCTTCGTCATTACCGCCCTCG 180 sus.scr.ewb3
CAACCCTCACACGATTCTTCGCCTTCCACTTTATCCTGCCATTCATCATTACCGCCCTCG 180 lama.gla
CCACCCTTACACGATTCTTCGCCTTCCACTTTATCTTACCTTTTGTCATTGCAGCTCTAG 180 lama.gua
CCACCCTTACRCGATTCTTCGCCTTCCACTTTATCTTACCTTTTGTCATTGCAGCTCTAG 180 vic.vic
CCACCCTTAACCGATTCTTCGCCTTTCACTTTATCTTACCTTTCATCATTGCAGCTCTAG 180 cam.bac
CCACCCTGACACGATTCTTTGCCTTCCACTTCATCCTGCCATTTATTATCACGGCCGTAG 180 arc.for
CAACCCTAACACGATTCTTCGCCTTTCACTTCATTCTCCCCTTCGTAGCATCAGCACTAG 180 arc.gaz
CAACCCTAACACGATTCTTCGCCTTTCACTTTATTCTTCGCTTCGTAGTATCAGCACTAG 180 eum.jub
CAACCCTAACACGATTCTTCGCCTTCCACTTTATTCTCCCCTTCGTAGCATCAGCACTAG 180 zal.cal
CAACCCTAACACGATTCTTTGCCTTCCACTTTATTCTCCCCTTCATAGCATCAGCACTAG 180

TABLE 2-continued

Multiple sequence alignment of 472 bp fregment of mitochondrial cytochrome b gene of 221 animal species odo.ros
CAACCCTAACACGATTCCTCGCCCTCCACTTCGTTCTTCCATTCATGGCATTAGCACTAA 180 pho.fasciata
CAACCCTAACACGATTTTTCGCTTTCCACTTTATCCTACCATTTGTAGTATCAGCACTAG 180 pho.gro
CAACCCTAACACGATTTTTCGCCTTCCACTTCATCTTACCATTCGTAGTATTAGCACTAG 180 pho.vit
CAACCTTAACACGATTCTTCGCCTTGCACTTCATCCTGCCATTCGTAGTATCAGCCCTAG 180 cys.cri
CAACTCTAACACGGTTTTTCGCCTTCCACTTCATCCTACCATTCGTCGTATCAGCACTAG 180 hyd.lep
CAACCCTAACACGATTCTTCGCCTTCCACTTTATCCTTCCCTTCGTAGTATCAGCACTAG 180 lep.wed
GAACCCTAACACGATTCTTCGCCTTCCACTTTATCCTTCCCTTCGTAGTATCAGCACTAG 180 mir.leo
CAACCCTAACACGATTCTTCGCCCTCCACTTTATCCTACCATTCGTAGCACTAGCACTAG 180 eri.bar
CAACCCTAACAGGATTCTTCGCCTTCCACTTTATCCTACCATTTGTAGTATTAGCATTAG 180 mon.sch
CAACCCTAACACGATTCTTCGCTTTCCATTTTATTATACCCTTCATAGTATTAGCACTAG 180 hela.mal
CGACTCTAACACGATTCTTTGCCTTCCACTTTATCCTTCCGTTCATCATCTTGGCACTAA 180 sel.thi
CAACCCTAACACGATTCTTTGCTTTCCACTTTATCCTTCCGTTCATCATCCTAGCACTAG 180 ail.ful
CAACTCTAACTCGATTCTTCGCCTTCCACTTCATTCTTCCATTTATGATTGCAACACTAG 180 fel
CCACCCTAACACGATTCTTTGGCTTCCACTTCATTCTTCCATTCATTATCTCAGCCTTAG 180 can
CAACCCTAACACGATTCTTTGCATTCCATTTCATCCTCCCTTTCATCATCGCAGCTCTAG 180 tal
CGACACTCACACGATTCTTCGCCTTCCACTTCATTCTGCCATTTATTATTGCGGCACTAG 180 gla.sab
CTACCCTAACCCGATTTTTTGCATTTCATTTTGTCCTCCCTTTTATTATTGCTGCCCTAG 180 gla.vol
CTACCTTAACCCGATTCTTTGCATTTCACTTCATTCTTCCTTTTATCATTGCCGCTCTAG 180 hyl.pha
CTACCCTAACCCGATTCTTCGCATTCCACTTTGTGCTGCCGTTTATTATTGCAGCACTAG 180 pet.set
CTACCCTAACCCGATTCTTCGCATTCCACTTTGTGCTGCCCTTTATTATTGCGGCACTGG 180 bel.pea
CAACCCTAACACGATTCTTCGCATTCCACTTTATCTTACCATTTATCGTAGCAGCCCTTG 180 pte.mom
CTACCCTAACACGATTCTTTGCATTCCACTTTGTCCTCCCCTTCATTATCGCAGCCCTAG 180 gala.demi
CTACCCTTACCCGATTCTTTGCTTTCCACTTTATCCTCCCATTTATCATTACAGCAATAG 180 pero.pot
CTACCGTAACACGATTCTTCGCCTTCCACTTCATCCTCCCCTTTATTATCACAGCACTAG 180 gala.mat
CCACCCTTACTCGATTCTTCGCTTTTCACTTCATCCTAGGTTTCATTATTGCAGCCCTAG 180 gala.moh

TABLE 2-continued

Multiple sequence alignment of 472 bp fregment of mitochondrial cytochrome b gene of 221 animal species

```
CTACTCTTACCCGATTTTTCGCTTTTCACTTCATCCTGCCTTTCATCATCGCGGCCCTAG 180 oto.gar
CAACCCTCACCCGGTTTTTTGCTTTCCACTTTATCCTGCCTTTCATCATCGCAGCCCTAG 180 lor.tar
CAACCCTCACACGATTCTTCGCCTTTCACTTCATCCTTGCATTCATCATCACAGCATTAA 180 nyc.cou
CCACACTCACACGATTCTTCGCCTTCCACTTTATCCTCCCCTTCATCGTCGCTGCTCTAG 180 mus
GCACCTTGACCCGATTCTTCGCTTTCCACTTCATCTTACCATTTATTATCGCGGCCCTAG 180 gorr
CTACGCTTACACGATTCTTTACCTTCCACTTTATCCTACCCTTCATCATCACAGCCCTAA 180 homo
CCACCCTCACACGATTCTTTACCTTTCACTTCATCTTGCCCTTCATTATTGCAGCCCTAG 180 dug.dug
CCACCCTCACCCGATTCTTCGCCCTACACTTCATCCTACCCTTCATCGTAACCGCCCTAG 180 ele.max
CAACCTTAAACCGATTCTTCGCCTTCCATTTCATCCTTCCATTTACTATAGTTGCACTAG 180 afr.con
CAACCCTCACCCGATTCTTCGCCCTACACTTTCTTCTCCCCTTTCTAATTGCGGGAATTA 180 pavo.mut
CAACCCTCACCCGATTCTTCGCCCTACACTTTCTCCTCCCCTTTGTAATCGCAGGAATTA 180 tra.bly
CAACCCTCACTCGATTCTTCGCCCTACACTTCCTCCTCCCATTTGTAATCGCAGGAATTA 180 tra.sat
CAACCCTCACCCGATTCTTCGCCCTACACTTCCTCGTCCCATTTGTAATCGCAGGAATTA 180 tra.cob
CAACCCTTACCCGATTCTTTGCCCTACACTTCCTCCTCCCATTTGTAATCGCAGGAATCA 180 tra.tem
CAACCCTTACCCGATTCTTTGCCCTACACTTCCTCCTCCCATTTGTAATCGCAGGAATTA 180 arg.arg
CCACCCTTACCCGATTCTTTGCTCTACATTTCCTCCTACCCTTCGTAATCGCAGGAATCA 180 cat.wal
CAACTCTCACCCGATTCTTCGCGCTGCACTTCCTCCTTCCCTTCGTAATTGCACGAATCA 180 cro.cro
CAACCCTCACCCGATTCTTCGCCCTACACTTCCTCCTCCCCTTCGTAATTGCAGGAATTA 180 sym.ree
CAACCCTCACCCGATTCTTCGCCCTTCACTTTCTCCTACCCTTGGTAATCACAGGAATCA 180 bam.tho
CAACTCTCACCCGATTCTTCGCCTTACACTTCCTACTCCCCTTGGTAATCGCAGGAATTA 180 fra.fra
CAACCGTCACCCGATTCTTCGCCCTACACTTCCTTCTCCCCTTCGTAATTGCAGGAATCA 180 ith.cru
CAACCCTCACCCGATTCTTCGCCCTACACTTTCTCCTCCCCTTCGCAATCGCAGGAATTA 180 ant.par
CCACATTAACTCGATTCTTCACTTTACACTTCCTCCTTCCATTCATAATTATGGGCCTCA 180 ant.vir
CCACATTAACTCGATTCTTCACGTTACACTTCCTCCTTCCATTCATAATTATGGGCCTCA 180 gru.ant.ant
CCACATTAACTGGATTCTTCACTTTACACTTCCTCCTTCCATTCATAATCATAGGCCTCA 180 gru.ant.gil
CCACATTAACTCGATTCTTCACTTTACACTTCCTCCTTGCATTCATAATCATAGGCCTCA 180
```

TABLE 2-continued

Multiple sequence alignment of 472 bp fregment of mitochondrial
cytochrome b gene of 221 animal species gru.ant.sha
CCACATTAACTCGATTCTTCACTTTACACTTCCTCCTTCCCTTCATAATCATAGGCCTCA 180 gru.leu
CCACATTAACTCGATTCTTCACTTTACACTTCCTCCTTCCATTCATAATCATAGGCCTCA 180 gru.can.pra
CCACATTAACCCGATTCTTCACTTTACACTTCCTCCTCCCATTCATAATTATAGGCCTCA 180 gru.can.row
CCACATTAACCCGATTCTTCACTTTACACTTCCTCCTCCCATTCATAATTATAGGCCTCA 180 gru.can.tab
CCACATTAACCCGATTCTTCACTTTACACTTCCTCCTCCCATTCATAATTATAGGCCTCA 180 gru.can.can
CCACATTAACCCGATTCTTCACTTTACACTTCCTCCTCCCATTCATAATTATAGGCCTCA 180 gru.ame
CCACATTAACCCGATTCTTCACTTTACACTTCCTCCTCCCATTCATAATCATAGGCCTCA 180 gru.gru
CCACATTAACCCGATTCTTCACCTTACACTTCCTCCTCCCATTCATAATCATAGGCCTCA 180 gru.mon
CCACATTAACTCGATTCTTCACCTTACACTTCCTCCTCCCATTCATAATCATAGGCCTCA 180 gru.nig
CCACATTAACTCGATTCTTCACCTTACAGTTCCTCCTCCCATTCATAATCATAGGCCTCA 180 gru.jap
CCACATTAACTCGATTCTTTACCTTACACTTCCTCCTCCCATTCATAATCATAGGCCTCA 180 cic.boy
CAACACTAACCCGATTCTTCGCCCTACACTTTCTTCTCCCCTTCGCAATCGCAGGCCTCA 180 rhe.ame
CTACCCTAACCCGATTCTTCGCCCTGCAGTTCCTTCTCCCCTTCCTAATCGCAGGCATTA 180 ant.alb
CAACCCTGACACGATTCTTCGCCCTACACTTTCTCCTCCCGTTCATAATCGCAGGCGTAG 180 fal.fam
CAACACTGACCCGATTCTTCGCCCTACACTTCCTCCTACCATTCCTAATCGCAGGGCTCA 180 fal.ver
CAACACTAACCCGATTCTTGGCCCTACACTTTCTCCTACCATTCCTAATCGCAGGGCTCA 180 fal.per
CAACACTGACCCGATTCTTCGCCCTACACTTCCTACTTCCATTCCTAATCGCAGGACTCA 180 fal.spa
CAACACTAACCCGCTTCTTCGCCTTACACTTCCTCCTACCATTCCTAATCGCAGGGGTTA 180 ayt.ame
CAACCCTAACTCGATTCTTCGCCATCCACTTCCTACTACCCTTCCTAATCGCAGGAATCA 180 smi.sha
CCACCCTTACCCGATTCTTCTCCCTTCACTTCCTCCTCCCATTTATGATCGCAAGCCTGA 180 vid.cha
CAACACTCACCCGATTCTTCGCCCTACACTTCCTTCTACCCTTCGTCATTGCAGGACTCA 180 chry.pic
CAACCTTAACCCGATTTTTTACCCTTCACTTCCTTCTACCATTTACAATCATAGGTCTAA 180 emy.orb.kur
CAACCCTAACCCGATTCTTCACTTTCCATTTCTTACTGCCATTTACCATTATAGGCCTAA 180 che.mud
CAACCCTAACCCGATTCTTCACCTTCCACTTCCTATTACCATTTGCCATTACCGGCCTTA 180 eum.egr
CAACCCTCACCCGATTTTTCACATTCCACTTCCTTGTGCCATTCGCTATTATAGGGGCCT 180
         *  *   *  *      *      *

TABLE 2-continued

Multiple sequence alignment of 472 bp fregment of mitochondrial cytochrome b gene of 221 animal species

```
aep.mel
CCATAGTCGACCTACTCTTTCTTCACGAAACAGGATCTAACAACCCTACAGGAATCTTAT 240 ore.ore
CCATAGTACACCTACTCTTTCTCCACGAAACAGGGTCCAATAACCCCACAGGAATCTCAT 240 add.nas
CCATAGTCCATCTACTCTTTCTCCACGAAACAGGCTCCAACAACCCTACAGGAATCTCGT 240 ory.dam
CCATAGTCCACCTACTCTTTCTCCACGAAACAGGCTCCAACAACCCTACAGGAATCACCT 240 hip.equ
CCATAGTACACCTACTCTTTCTCCATGAGACAGGCTCCAACAACCCCACAGGAATTTGAT 240 alc.bus
CCATAGTTCACCTCTTATTCCTCCACGAAACAGGATCTAACAACCCCACAGGAATCTCAT 240 sig.lic
CCATAGTTCACCTCTTATTCCTCCACGAAACAGGATCTAACAACCCCACAGGAATCTCGT 240 bea.hun
CCATAGTCCACCTCTTATTTCTCCACGAAACAGGATCTAACAACCCCACAGGAATCTCGT 240 dam.lun
CCATAGTGCACCTCTTATTCCTCCATGAAACAGGATCTAACAACCGCACAGGAATCTCAT 240 con.tau
CTATAGTCCATCTCCTATTCCTCCACGAACAGGATCTAACAAATCCCACAGGAATTTAAT 240 amm.ler
CCATAGTCCACTTACTTTTCCTCCATGAAACGGGATCCAACAACCCCACAGGAATTTCAT 240 pse.nay
CCATAGTCCACCTACTTTTCCTCCACGAAACAGGATCTAAGAACCCCACAGGAATCCCAT 240 cap.ibe
CCATAGTCCACCTGCTCTTCCTCCACGAAACGGGATCCAACAACCCCACAGGAATTCCAT 240 hem.jem
CCATAGTCCACCTGCTCTTCCTCCACGAAACAGGGTCCAACAACCCCACAGGGATTCCAT 240 cap.fal
CCATAGTCCACCTACTCTTCCTCCACGAAACAGGATCCAACAATCCCACAGGAATTCCAT 240 rup.pyr
CCATAGTCCACCTACTCTTCCTCCATGAAACAGGATCAAACAACCCCACAGGAATCCCAT 240 rup.rup
CCCTAGTCCACCTACTCTTCCTCCACGAAACAGGATCTAACAACCCCACAGGAATCCCAT 240 nem.cau
CTATAGTCCACCTACTTTTCCTCCATGAGATAGGATCCAACAACCCCACAGGTATCCCAT 240 bud.tax.tax
CCATAGTCCATTTACTTTTCCTCCACGAAACAGGATCCAACAACCCCACAGGAATTCCGT 240 pan.hod
CCATAGTCCACCTACTCTTCCTCCACGAAACAGGATCCAACAACCCCACAGGAATTCCAT 240 ovi.amm
CCATAGTCCACCTACTCTTCGTCCACGAAACAGGATCCAACAACCCCACAGGAATCCCAT 240 ovi.vig
CTATAGTTCACCTACTCTTCCTCCACGAAACAGGATCCAATAACCCCACAGGAATTCCAT 240 cap.cri
CCATAGTGCACCTACTTTTCCTCCACGAAACAGGATCCAACAACCCCACAGGAATCTCAT 240 ovi.mos
CTATAGTACATTTGCTCTTCCTCCACGAAACAGGATCCAACAACCCCACAGGAATTCCAT 240 ore.ame
CCATAGTCCACTTACTTTTGCTCCACGAAACAGGATCTAATAACCCAACAGGAATTTTAT 240
```

TABLE 2-continued

Multiple sequence alignment of 472 bp fregment of mitochondrial cytochrome b gene of 221 animal species cep.dor
CCATAGTTCACCTACTCTTCCTCCATGAAACAGGATCCAACAACCCGACAGGAGTCTCAT 240 cep.max
CCATAGTCCACCTACTATTCCTCCACGAAACAGGATCTAATAACCCCACAGGAATCTCAT 240 bis.bon
CCATAGTTCACCTACTATTCCTCCACGAAACAGGTTCTAACAATCCAACAGGAATTTCCT 240 bos.gru
CCATAGTCCACCTACTATTCCTCCACGAAACAGGCTCCAACAATCCAACAGGAATCTCCT 240 bos.tra
CAATAATCCATCTACTCTTCCTCCATGAAACAGGGTCTAACAATCCAACAGGAATTTCAT 240 bub.min
CAATAGTCCACCTATTATTTCTCCACGAAACAGGATCCAACAACCCAACAGGAATCTCAT 240 buba.bub
CAATAGTCCACCTATTATTTCTCCACGAAACAGGATCCAACAACCCAACAGGAATCTCAT 240 tra.ang
TTATGGTCCACCTATTATTCCTCCATGAAACAGGATCCAACAACCCAAGAGGAATCTCAT 240 tra.eur
CCATGGTACACCTACTATTCGTCCACGAAACAGGATCCAACAACCGAACAGGRATCTCAT 240 kob.ell
CCATAGTCCATCTTCTGTTTCTCCATGAAACAGGATCCAATAATCCCACAGGAATCTCAT 240 kob.meg
CTATAGTTCACCTACTATTCCTTCATGAAACAGGATCTAACAACCCTACAGGGATTTGAT 240 red.aru
CTATAGTACACCTACTATTCGTCCACGAAACAGGATCCAACAACCCTACAGGAATCTCAT 240 red.ful
CTATAGTCCACCTACTATTCCTCCATGAAACAGGATCCAACAACGCCACAGGGGTTTCAT 240 neo.mos
CCATAGTCCACTTACTCTTCCTACACGAAACAGGATCCAACAACCCCACAGGAATCTCAT 240 pel.cap
CCATAGTACACTTGCTTTTTCTTCATGAAACAGGATCTAATAACCCCACGGGAATTCCAT 240 gaz.dam
CCATAGTTCATCTATTATTTCTTCACGAAACAGGATGCAACAACCCCACAGGAATTTCAT 240 our.our
CCACAGTCCACCTACTATTCCTTCACGAAACGGGATCCAACAATCCCACAGGAATTTCAT 240 ant.cer
CCATAGTACACCTACTGTTTCTCCACGAAACAGGATCCAACAACGCCACAGGAATCTCAT 240 sai.tat
CTATAGTCCACCTACTTTTTCTTCACGAAACAGGATGTAACAACCCCACAGGAATCCCAT 240 mad.kir
CCATGGTTCACCTCCTCTTTCTCCATGAAACGGGATCCAACAGCCCCACAGGGATTTCAT 240 rap.mel
CTATAGTTCACCTACTTTTCCTCCACGAAACTGGATCCAACAACCCCACAGGAAGTTTAT 240 gaz.gaz
CTATAGTCCACTTATTATTCCTTCATGAAACAGGATCCAATAACCCCACAGGAATTTCAT 240 ant.ame
CCATAGTACACTTACTATTCCTCCACGAAACAGGATCCAACAACCCCACAGGAATCCCAT 240 hyd.ine
CCATAGTGCACTTACTTTTTCTCCACGAAACAGGATCCAATAACCCAACAGGAATTCCAT 240 mun.mun
CTATAGTCCACCTACTTTTCCTCCACGAAACAGGATCCAACAATCCAACAGGAATTCCAT 240 alc.alc

TABLE 2-continued

Multiple sequence alignment of 472 bp fregment of mitochondrial
cytochrome b gene of 221 animal species

```
CCATAGTCCACTTACTTTTCCTCCACGAAACAGGATCCAACAACCCAACAGGAATTCCAT 240 cer.ela.kan
CTATAGTACACTTACTCTTCCTTCACGAAAGAGGATCCAATAACCCAACAGGAATCCCAT 240 cer.ela.xan
CTATAGTACACTTACTCTTCCTTCACGAGACAGCATCCAATAACCCAACAGGAATTCCAT 240 cer.ela.can
CTATAGTACACTTACTCTTCCTTCACGAGACAGGATCTAATAACCCAACAGGAATCCCAT 240 cer.nip.cent
CTATAGTACACTTACTCTTCCTTCACGAGACAGGATCCAACAACCCAACAGGAATCCCAT 240 cer.nip.yes
CTATAGTACACTTACTCTTCCTTCACGAGAGAGGATCCAACAACCCAACAGGAATCCCAT 240 cer.nip.ker
CTATAGTACACTTACTCTTCCTTCACGAGACAGGATCCAACAACCCAACAGGAATCCCAT 240 cer.nip.pul
CTATAGTACACTTACTCTTCCTTCACGAGACAGGATCCAACAACCCAACAGGAATCCCAT 240 cer.nip.nip
CTATAGTACACTTACTCTTCCTTCACGAGACAGGATCCAACAACCCAACAGGAATCCCAT 240 cer.ela.sco
CTATAGTACACTTACTGTTCCTTCACGAAACAGGATCTAATAACCCAACAGGAATTCCAT 240 cer.dam
CTATAGTACATTTACTCTTTCTTCACGAGACAGGATCCAATAACCGAACAGGAATCCCAT 240 ran.tar
CTATAGTCCATTTGCTTTTCCTTCACGAAACAGGGTCTAACAATCCAACAGGAATTCCAT 240 mos.fus
CTATGGTTCACCTACTCTTTCTCCACGAAACAGGATCCAACAACCCAACAGGAATCACAT 240 mos.leu
CTATGGTTCACCTACTCTTTCTCCACGAAACAGGATCCAACAACCCAACAGGAATCACAT 240 mos.chr
CTATGGTTCACCTACTCTTTCTCCACGAAACAGGATCCAACAACCCAACAGGAATCACAT 240 mos.ber
CTATGGTTCACCTACTCTTTCTCCACGAAACAGGATCCAACAACCCAACAGGAATCATAT 240 mos.mos
CCATGGTTCATCTACTCTTTCTCCATGAAACAGGATCCAATAACCCAACAGGAATCACAT 240 tra.jav
TCCTAGTCCACCTTTTATTTCTCCACGAAACAGGATCTAATAACCCCACAGGAATCCCCT 240 trag.nap
CCCTAGTCCATCTTTTATTTCTCCACGAGACAGGATCAAATAACCCCACAGGAATCCGCT 240 bala.acu
CAATTGTCCACCTCATTTTCCTCCACGAAACAGGATCCAATAACCCCACAGGTATCCCAT 240 bala.bon
CAATTGTCCACCTCATTTTCCTCCGCGAAACAGGATCCAATAACCCCACAGGTATTCCAT 240 bala.bor
CAATGGTCCACCTCATTTTCCTCCATGAAACAGGATCCAACAACCCCACAGGTATTCCAT 240 bala.edi
CAATGGTCCACCTCATTTTCCTGCACGAAACAGGATCCAATAACCCCACAGGTATTCCAT 240 esch.rob
CAATTGTCCACCTCATTTTCCTCCACGAAACGGGATCCAACAACCCCACAGGCATTCCAT 240 bala.mus
CAATCGTCCACCTCATCTTCCTTCACGAAACAGGATCCAACAACCCCACAGGTATCCCAT 240 mega.nov
CAATCGTCGACCTCATTTTCGTCCACGAAACAGGATCCAACAACCCCACAGGCATCCCAT 240
```

TABLE 2-continued

Multiple sequence alignment of 472 bp fregment of mitochondrial cytochrome b gene of 221 animal species

```
bala.phy
CAATTGTCCACCTTATTTTCCTTCACGAAACAGGATCCAACAACCCCACAGGCATCCCAT 240 cap.mar
CAGCTGTTCATCTCCTTTTCCTCCACGAAACAGGATCTAACAACCCCACAGGGATCCCAT 240 ceph.com
CAGCCGTCCACCTACTATTCCTACACGAAACAGGATCCAACAACCCCACAGGAATCCCAT 240 ceph.eut
CAGCCGTCCACCTACTATTCCTACACGAAACAGGATCCAACAACCCCACAGGAATCCCAT 240 lage.obl
CAGCCGTCCACCTACTATTCCTACACGAAACAGGATCCAACAACCCCACAGGAATCCCAT 240 ceph.hea
CAGCCGTCCATCTACTATTCCTACACGAAACAGGATCCAACAACGCCACAGGAATCCCAT 240 ceph.hec
CAGCCGTCCACCTACTATTCCTACACGAAACAGGATCCAACAACCCCACAGGAATTCCAT 240 lage.aus
CAGCCGTCCACTTACTATTCTTACACGAAACAGGATCCAACAACCCCACAGGAATCCCAT 240 lage.cru
CAGCCGTCCACCTGCTATTCCTACACGAAACAGGATCCAACAACCCCACAGGAATGCCAT 240 lage.obs
CAGCCGTCCACCTACTATTCCTACACGAAACAGAATCCAACAACCCCACAGGAATCCCAT 240 lisso.bor
CAGCTGTTCACCTACTATTCCTACACGAAACAGGATCCAACAACCCCACAGGAATTCCAT 240 lisso.per
CAGCTGTTCACCTACTGTTCCTACACGAGACAGGATGCAATAACCCCAGAGGAATTCCAT 240 glo.mac
TAGCTGTCCACCTGCTATTCCTACACGAAACAGGATCCAATAACCCCATAGGAATCCCAT 240 glo.mel
TAGCTGTCCACCTGCTATTCCTACACGAAACAGGATCCAATAACCCCATAGGAATCCCAT 240 fere.att
TAGCTGTTCACCTGCTATTCCTACACGAAAGAGGATCCAATAACCCCACAGGAATCCCAT 240 pepo.ele
TAGCTGTCCACCTGCTATTCCTACACGAAACAGGATCCAATAACCCTACAGGAATCCCAT 240 gram.gri
TAGCTGTTCACCTGCTATTCCTACACGAGACAGGATGCAATAACCCCACAGGAATCCCAT 240 pse.cra
CAGCTACCCACCTACTATTCCTACACGAGACTGGATCCAATAACCCCACAGGAATCCCAT 240 lage.acu
CAGCTGTTCACCTGCTGTTCGTACACGAGACAGGATCCAATAACCCTACAGGAATCCCAT 240 orci.bre
CAGCTGTTGACCTACTGTTCCTACACGAGACAGGATCCAATAACCCCACAGGAATCCCAT 240 orca.bre
TAACTGTTCACCTACTATTCCTACACGAAACAGGATCCAACAATCCTACAGGAATCCCAT 240 del.cap
CAGCCGTTCACCTGCTATTCCTACACGAAACAGGATCCAATAACCCCACAGGAATCCCAT 240 del.tro
CAGCCGTTCACCTGCTATTCCTACACGAAACAGGATCCAATAACCCCACAGGAATCCCAT 240 del.del
CAGCCGTTCACCTGCTATTCCTACACGAAACAGGATCCAATAACCCCACAGGAATCCCAT 240 sten.cly
CAGCCGTTCACCTGCTATTCCTACACGAAACAGGATCCAATAACCCCACAGGAATTCCAT 240
```

TABLE 2-continued

Multiple sequence alignment of 472 bp fregment of mitochondrial cytochrome b gene of 221 animal species

```
sten.coe
CAGCCGTTCACCTGCTATTCCTACACGAAACAGGATCCAATAACCCAACAGGAATTCCAT 240 tur.adu
CAGCCGTTCACCTGCTATTCCTACACGAAACAGGATCCAATAACCCCACAGGAATCCCAT 240 sten.fro
CAGCCGTTCACCTACTATTCCTACACGAAACAGGATCCAATAACCCCACAGGAATCCCAT 240 saus.chi
TAGCCGTTCACCTGGTATTGCTACACGAAACAGGATCCAATAACCCTACAGGAATTCCAT 240 sten.lon
CAGCCGTCCACCTACTATTCCTACACGAAACAGGATCCAATAACCCCACAGGAATCCCAT 240 turs.tru
CAGCCGTTCACCTACTATTCCTACACGAAACAGGATCCAACAACCCCACAGGAATCCCAT 240 lage.alb
TAGCTGTTCACCTACTATTTTTACACGAGACAGGATCCAACAACCCCACAGGAATCCCAT 240 sten.bre
CAACTGTCCACCTACTATTCCTACACGAGACAGGATCCAACAATCCCACAGGAATCCCAT 240 sota.flu
CAGCCGTTCACCTGCTATTCCTACACGAAACAGGATCCAATAATCCCACAGGAATCCCAT 240 del.leu
TAGCCGTCCATTTATTATTCCTACACGAAACAGGATCCAACAACCCCACAGGAATCCCAT 240 mono.mon
TGGCCGTCCACTTATTATTCCTACACGAAACAGGATCCAACAACCCCACAGGAATCCCAT 240 plat.gan
CAATTATCCACCTACTATTCCTACACGAAACAGGCTCAAACAAGCCCACAGGAATTCCAT 240 plat.min
CAGTTATCGACCTACTATTCCTACACGAAACAGGCTCAAACAACCCCACAGGAATTCCAT 240 kogi.bre
CAATGGTCCACCTCTTATTTCTCCACGAAACAGGATCCAACAACCCCATAGGAATCCCAT 240 kogi.sim
CAATAATCCACCTCCTATTTCTCCACGAAACAGGATCCAACAACCCCCTAGGAATTCCTT 240 phys.cat
CAATAGTACATCTCCTATTTCTCCATGAAACAGGATCCAACAACCCCACAGGAATTCCCT 240 lipo.vex
CAACCGTCCACTTACTATTTCTCCATGAAACAGGATCCAACAACCCAATAGGAATTCCAT 240 phoc.sin
TAATCGTCCATCTACTATTCCTCCATGAAACAGGCTCCAACAATCCCACAGGAATCCCGT 240 bera.bai
CAGCCGTCCACTTACTATTCCTCCACGAAACAGGATCCAACAACCCCACAGGAATGCCAT 240 ziph.car
CAGCCGTCCACTTACTATTTCTCCACGAAACAGGATCTAATAACCCCACAGGAATCCCAT 240 meso.eur
CAATCGTCCACTTACTATTTCTCCATGAAACAGGATCCAATAACCCTACAGGAATCCCAT 240 meso.bid
CAATCGTCCACCTACTATTTCTCCATGAAACAGGATCTAACAACCCTACAGGAATTCCAT 240 meso.den
CAATGGTCCACCTACTATTCCTCCATGAAACAGGATCTAATAACGCTACAGGAATCCCAT 240 hype.amp
CAATCGTCCACCTACTATTCCTCCATGAAACAGGATCCAACAATCCCACAGGAATTCCAT 240 meso.per
CAATTGTCCATTTACTATTTCTACACGAAACAGGATCTAATAATCCCATAGGAATCTCTT 240 pont.bla
```

TABLE 2-continued

Multiple sequence alignment of 472 bp fregment of mitochondrial cytochrome b gene of 221 animal species

```
TTATAGTCCACCTGCTATTCCTACACGAAACTGGATCCAACAACCCAACAGGAATCTCAT 240 hex.lib
CCGCCGTCCACCTACTGTTTCTCCACGAAACAGGGTCCAACAACCCAACAGGAATCCCCT 240 hipp.amp
CCATCGTCCATCTACTATTCCTCCATGAAACAGGATCCAACAACCCAACAGGAATCCCCT 240 dic.sum
CAATTACCCACCTGCTATTCCTACATGAAACAGGATCCAACAACCCATCAGGAATCCCAT 240 rhin.son
CGATCACCCACTTACTATTCCTACACGAAACAGGATCCAATAACCCATCAGGAATTCCAT 240 cera
CAATCACCCACCTACTATTCCTTCACGAAACAGGATCCAATAACCCATCAGGAATCCCAT 240 equu
TAATCGTCCATCTACTATTCCTCCACGAAACAGGATCCAACAACCCCTCAGGAATCCCAT 240 baby.bab
CAACCGTACATCTATTATTCCTTCACGAAACTGGATCCAATAACCCTACTGGAATTTCAT 240 phac.afr
CAACCGTACATCTCTTGTTCCTACACGAAACTGGATCTAACAACCCTACTGGAATCTCAT 240 sus.bar
CAGCCGTACATCTGCTATTCCTACACGAAACCGGATCCAATAACCCCACCGGAATTTCAT 240 sus.scr.ewb3
CAGCCGTACATCTCCTATTCCTGCACGAAACCGGATCCAATAACCCTACCGGAATCTCAT 240 lama.gla
CAGGAGTACATCTACTATTTTTACACGAAACAGGCTCCAACAATCCAACAGGAATTTCTT 240 lama.gua
CAGGAGTGCATCTACTATTTTTACACGAAACAGGCTCCAACAATCCAACAGGAATTTCTT 240 vic.vic
CGGGAGTACATCTACTATTTTTACACGAAACAGGCTCCAACAACCCAACAGGAATTTCTT 240 cam.bac
TAGCCGTACACCTATTATTCCTACACGAAACAGGCTCTAATAACCCGACAGGAATGTCCT 240 arc.for
TAATAGTACATCTGCTATTCCTACATGAAACAGGATCCAATAACGCATCAGGAGTCTCCT 240 arc.gaz
TAATAGTGCACCTACTATTCCTACACGAAACAGGATCCAACAACCCATCAGGAGTCTCCT 240 eum.jub
TAATAGTACACCTATTATTCCTACACGAAACTGGATCCAACAATCCATCAGGAATCTCCT 240 zal.cal
TAATAGTACACCTATTATTCCTACACGAAACTGGGTCCAACAACCCATCAGGAATCTCCT 240 odo.ros
CAGCAGTACACCTACTATTTCTCCACGAAACAGGATCTAACAACCCTTCGGGAATCCTAT 240 pho.fasciata
CGGCAGTTCACCTACTATTCCTACACGAAACAGGATCCAACAACCCCTCCGGAATGGTAT 240 pho.gro
CGGCAGTTCATCTACTATTCTTACACGAAACAGGATCCAACAACCCGACCGGAATCGTAT 240 pho.vit
CAGCAGTCCACCTACTATTCCTACACGAAACAGGATCAAACAACCCCTCCGGAATCATAT 240 cys.cri
CAACAGTCCACCTACTATTCCTACACGAAACAGGATCTAATAATCCCTCCGGAATCACAT 240 hyd.lep
CAGCAGTACATCTACTATTCTTACAGGAAACAGGATCCAATAACCCCTCCGGAATTCCAT 240 lep.wed
CAGCAGTACATCTACTATTCTTACACGAGACAGGATCCAACAACCCCTCCGGAATTCCAT 240
```

TABLE 2-continued

Multiple sequence alignment of 472 bp fregment of mitochondrial cytochrome b gene of 221 animal species

```
mir.leo
CAGCAGTACATCTACTATTCCTACACGAAACAGGATCCAACAACCCCTCTGGAATCCCAT 240 eri.bar
CAGCAGTCCACCTATTATTCCTACACGAAACAGGATCCAACAACCCCTCTGGAATCTCGT 240 mon.sch
CAGCAGTCCATTTATTATTTCTACACGAAAGAGGATCCAACAATCCCTCCGGAATTCCAT 240 hela.mal
CAGCGGTCCACCTATTATTCCTACACGAAACAGGGTCCAACAATCCCTCTGGAATCCCAT 240 sel.thi
CAGCAGTTCATCTATTGTTCCTACACGAAACAGGATCCAACAACCCTTCTGGAATCCCAT 240 ail.ful
CAACTATCCATCTCTTATTCCTACATGAAACAGGATCTAATAACCCCTCAGGCATCCCAT 240 fel
CAGGAGTACACCTCTTATTCCTTCATGAAACAGGATCTAACAACCCCTCAGGAATTACAT 240 can
CAATAGTACACCTCCTATTTCTACACGAAACCGGATCCAACAAGCCTTCAGGAATCACAT 240 tal
CTGGAGTTCACCTGTTATTTCTTCACGAAACAGGATCAAACAACCCATCAGGACTCTCAT 240 gla.sab
CCATAATCCATCTACTCTTTTTACACGAAACAGGATCCAATAACCCATCAGGACTAATCT 240 gla.vol
CCATAATCCATCTACTCTTTCTACACGAAACAGGATCCAATAACCCATCAGGACTAATCT 240 hyl.pha
CTATAATTCACCTTCTCTTTCTACACGAAACAGGATCAAATAACCCATCAGGCCTAATTT 240 pet.set
CTATAATCCACCTTCTCTTTCTACACGAAACAGGGTCAAATAATCCATCAGGTCTAATTT 240 bel.pea
CAATAGTCCACCTTCTTTTCCTCCACGAAATTGGGTCAAATAATCCCCCGGATTAATTT 240 pte.mom
CAATAGTTCACCTACTTTTCCTTCATGAAACAGGGTCCAACAACCCATCTGGACTTACCT 240 gala.demi
TCATAATCCACCTCCTATTCCTTCACGAAACAGGATCAAACAACCCCTCAGGACTTCCAT 240 pero.pot
CCACAACTCACCTCTTATTTCTTCACGAAACAGGATCAAATAACCCAGCAGGAATTCCAT 240 gala.mat
CCATAATTCACCTTCTTTTCCTACATGAAACAGGATCAAACAACCCTTCAGGAATCTCAT 240 gala.moh
CCATAATTCATCTTCTTTTTTTACATGAAACAGGGTCAAATAACCCTTCGGGAATCTCAT 240 oto.gar
TCATAATCCACCTCCTTTTCCTCCACGAATCAGGATCAAACAACCCTTCAGGAATCCCAT 240 lor.tar
CTGCAATTCACCTACTTTTCCTACACGAATCAGGATCAAATAACCCATCCGGAATAACAT 240 nyc.cou
TTGTGATTCACCTCATCTTTCTACATGAAACAGGCTCAAATAATCCATCAGGAATCTGAT 240 mus
CAATCGTTCACCTCCTGTTCCTCCACGAAAGAGGATCAAACAACCCAACAGGATTAAACT 240 gorr
CAACCCTCCATCTCCTATTTCTACACGAAACAGGATCAAACAACCCTCTAGGCATCCCCT 240 homo
CAACACTCCACCTCCTATTCTTGCACGAAACGGGATCAAACAACCCCCTAGGAATCACCT 240
```

TABLE 2-continued

Multiple sequence alignment of 472 bp fregment of mitochondrial
cytochrome b gene of 221 animal species dug.dug
TAATAGTCCACTTACTATTCCTCCACGAAACAGGCTCCAACAACCCCACGGGACTGATCT 240 ele.max
CAGGAGTGCACCTAACCTTTCTTCACGAAACAGGCTCAAACAACCCACTAGGTCTCACTT 240 afr.con
CAATTATCCACCTCACATTCCTTCATGAATCAGGCTCAAACAACCCACTGGGCATCTCAT 240 pavo.mut
CAATTATCCACCTCACATTCCTCCATGAATCAGGCTCAAATAATCCACTAGGCATCTCAT 240 tra.bly
CCATCATGCACCTCATCTTCTTACATGAATCAGGCTCTAATAACCCACTGGGCATCTCAT 240 tra.sat
CTATCATACACCTCATCTTCTTACATGAATCAGGCTCTAATAACCCACTGGGCATCTCAT 240 tra.cob
CCATCATCCACCTCATCTTCCTACATGAATCAGGCTCTAACAACCCTCTGGGCATCTCAT 240 tra.tem
CCATCATCCACCTCATCTTCCTACATGAATCAGGCTCAAACAACCCTCTAGGCATCTCAT 240 arg.arg
CCATCATCCACCTCACATTCCTACACGATCAGGCTCAAACAAACCCACTAGGCATCTCAT 240 cat.wal
CCATCACCCATCTCATATTCCTACATGAATCAGGCTCAAATAACCCCCTAGGCATCTCAT 240 cro.cro
CTGTCACCCACCTCATATTCCTACACGAATCAGGCTCAAACAACCCACTAGGCATCTCAT 240 sym.ree
CCATCACACATCTTATGTTCCTACACGAATCAGGCTCAAACAACCCACTAGGCATTTCAT 240 bam.tho
CCATTATCCACCTCACATTCTTACACGAATCAGGATCAAACAACCCCCTAGGCATGTCAT 240 fra.fra
CTATCATCCACCTCACATTTCTGCACGAATCAGGCTCAAACAACCCCCTAGGCATCTCAT 240 ith.cru
CTGTCATCCACCTTACACTCCTCCACGAATCAGGTTCAAATAACCCACTAGGCATCTCAT 240 ant.par
CCCTAATCCACCTCACCTTCCTTCACGAGTCCGGCTCAAACAACCCCCTAGGCATTGTAT 240 ant.vir
GCCTAATCCACCTCACCTTCCTTCACGAATCCGGCTCAAACAACCCCCTAGGCATCGTAT 240 gru.ant.ant
CCCTAATCCACCTCACCTTCCTTCACGAATCCGGCTCAAACAACCCCCTAGGCATCGTAT 240 gru.ant.gil
GCCTAATCCACCTCACCTTCCTTCACGAATCCGGCTCAAACAACCCCCTAGGCATCGTAT 240 gru.ant.sha
CCCTAATCCACCTCACCTTCCTTCACGAATCCGGTTCAAACAACCCCCTAGGCATGGTAT 240 gru.leu
CCCTAATCCACCTCACCTTCCTTCACGAATCCGGCTCAAACAACCCCCTAGGCATCGTAT 240 gru.can.pra
CCCTAATCCACCTCACCTTCCTTCACGAATCCGGCTCAAACAACCCCCTAGGCATTGTAT 240 gru.can.row
CCCTAATCGACCTCACCTTCCTTCACGAATCCGGCTCAAACAATCCCCTAGGCATTGTAT 240 gru.can.tab
CCCTAATCCACGTCACCTTCCTTCACGAATCCGGCTCAAACAAGCCCCTAGGCATTGTAT 240 gru.can.can
CCCTAATCCACCTCACCTTCGTTCACGAATCCGGCTCAAACAACCCCCTAGGCATTGTAT 240 gru.ame

TABLE 2-continued

Multiple sequence alignment of 472 bp fregment of mitochondrial
cytochrome b gene of 221 animal species

```
CCCTAATCCACCTCACCTTCCTCCACGAATCCGGCTCAAACAACCCCCTAGGCATCGTAT 240 gru.gru
CCCTAATCCACCTCACCTTCCTTCACGAATCCGGCTCAAACAACCCCCTAGGCATCGTAT 240 gru.mon
CCCTAATCCACCTCACCTTCGTCCACGAATCCGGCTCAAACAACCCCCTAGGCATCGTAT 240 gru.nig
CCCTAATCCACCTCACCTTCCTCCACGAATCCGGCTCAAACAACCCCCTAGGCATCGTAT 240 gru.jap
CCCTAATCCATCTCACTTTCCTCCACGAATCCGGCTCAAACAACCCCCTAGGCATCGTAT 240 cic.boy
CCCTAATCCACCTCACGTTCCTTCACGAGTCCGGCTCAAACAACCCCGTAGGCATCATCT 240 rhe.ame
CTCTTATCCACCTCACCTTCCTACACGAAACCGGGTCCAACAACCCCTTAGGAATCGTAT 240 ant.alb
TCCTAATTCACGTGGCATTCCTCCACGAATCAGGCTCAAACAACCCACTAGGCATCACAT 240 fal.fam
CCTTAATCCACCTCACCTTCCTACATGAATCAGGTTCAAACAACCCCCTAGGAATCACAT 240 fal.ver
CCCTAATTCACCTCACCTTCCTACACGAATCAGGTTCAAACAACCCCCTAGGAATCACAT 240 fal.per
GCCTAATCCACCTCACCTTCCTACATGAATCAGGCTCAAATAACCCCCTAGGAATCACAT 240 fal.spa
CCTTAATCCACCTCACCTTCCTACATGAATCAGGTTCCAACAACCCCCTAGGAGTCAGAT 240 ayt.ame
CCCTAGTCCACCTAACTTTCCTGCACGAGTCAGGCTCAAACAACCCCCTAGGCATTGTAT 240 smi.sha
CACTCATCCATCTCACCTTCCTCCATGAAACAGGTTCAAACAACCCTCTAGGTATCTCAT 240 vid.cha
CTCTAGTCCACCTCACATTCCTACACGAAACAGGATCAAACAATGCAATAGGAATTCCAT 240 chry.pic
CAATAGTACACCTACTTTTTCTACATGAAACTGGATCAAACAACCCAACAGGATTAAACT 240 emy.orb.kur
CAATAGTACACCTACTCTTCCTACACGAAACCGGATCAAACAATCCAACAGGATTAAACT 240 che.mud
CAGCAGTACATCTATTATTCCTGCACGAAACAGGATCAAACAACCCAACAGGATTAAATT 240 eum.egr
CAATAATTCACCTACTATTTCTTCACGAAACAGGATCAAATAACCCAACCGGACTAAATT 240
               **  *      *  * *  **      *  ** ** *   **       **
* aep.mel
CAGATTCAGATAAAATTCCATTCCACCCTTACTATACTATTRAAGACATCCTAGGAATCC 300 ore.ore
CAGACACAGACAAAATCCCATTTCATCCTTATTACACAATCAAAGATATCCTAGGCGCCC 300 add.nas
CAGACACAGACAAAATCCCATTGCACCCTTACTATACCATTAAAGACATCTTAGGCGCCC 300 ory.dam
CAGACACAGACAAAATTCCGTTCCACCCTTATTATACCATTAAAGATATCTTAGGCGCCC 300 hip.equ
CAGACTCCGATAAAACCCCATTCCACCCCTACTACACCATTAAAGACATTCTAGGCGCCC 300 alc.bus
CAGACGCAGATAAAATCCCATTCCACCCCTACTATACAATCAAGGACATTCTAGGCGCCC 300
```

TABLE 2-continued

Multiple sequence alignment of 472 bp fregment of mitochondrial
cytochrome b gene of 221 animal species sig.lic
CAGACGCAGATAAAATCCCATTCCACCCCTACTATACAATCAAGGACATTCTAGGCGCCC 300 bea.hun
CAGATGGAGATAAAATTCCATTCCACCCCTACTACACGATCAAAGACATCCTAGGCGCCC 300 dam.lun
CAGATGCGGACAAAATCCCGTTTCACCCCTACTACACTATCAAAGACGCCCTAGGGGCCC 300 con.tau
CCGACACCGATAAAATCCCATTCCCCCCCTATTACACGATGAAAGACATCCTAGGCGCTC 300 amm.ler
CAGACGCAGACAAAATCCCATTCCACCCTTACTACACCATCAAAGATATTCTAGGCGCCA 300 pse.nay
CAGACACAGACAAAATCCCATTCCACCCTTACTACACCATTAAAGATATTCTAGGCGCTG 300 cap.ibe
CAGACACAGACAAAATCCCATTCCACCCCTACTACACCATTAAAGATATCTTAGGCGCCA 300 hem.jem
CAGATACAGACAAAATCCCATTTCACCCTTACTACACCATTAAAGATATTTTAGGCGCCA 300 cap.fal
CAGACACAGACAAAATCCCATTTCACCCTTACTACACCATTAAAGATATCCTAGGCGCCA 300 rup.pyr
CAGATGCGGATRAAATCCCATTTCACCCCTACTATACCATTAAAGACATTCTAGGCGCCA 300 rup.rup
CAGATGCGGACAAAATCCCATTTNACCCCTATTATAGCATCAAAGACATTCTGGGCGCCA 300 nem.cau
CAGACATAGACAAAATCCCATTTCACCCTTATTATACAATCAAAGATATTCTAGGCGCTA 300 bud.tax.tax
CAGATGCAGATAAAATTCCATTTCACCCTTATTACACCATTAAAGATATCCTAGGAGTCA 300 pan.hod
CAGATGCAGACAAAATCCCATTTCACCCCTACTATACCATTAAAGACATCCTAGGCGCTA 300 ovi.amm
CGGACACAGATAAAATTCCCTTCCACCCTTACTACACGATTAAAGACATCCTAGGTGCCA 300 ovi.vig
CGGACACAGACAAAATCCCCTTCNNNNNNNNNNNNNNNNATTAAAGACATTCTGGGTGCCA 300 cap.cri
CAGACACAGACAAAATCCCATTCCACCCCTACTACACAATCAAAGATATCCTAGGCATCG 300 ovi.mos
CAGACACGGACAAAATCGCATTCCACCCCTACTATACAATCAAAGACATTCTAGGCGCCA 300 ore.ame
CAGACGCAGACAAAATTCCATTTCACCCCTACTAATACTATTAAGATATCCTAGGCGCCA 300 cep.dor
CGGACGCAGACAAAATCCCATTCCACCCCTACTACACCATTAAAGACATCCTAGGCGCCC 300 cep.max
CAGACGCAGACAAAATCCCGTTCCACCCCTACTACACTATCAAAGACATCCTAGGCGCCG 300 bis.bon
CAGACACAGACAAAATTCCATTCCACCCTTAGTATACCATTAAAGACATCCTAGGAGCCT 300 bos.gru
CAGACGCAGACAAAATTCCATTTCACCCCTACTATACCATTAAAGACATCTTAGGAGCCT 300 bos.tra
CAGACGCAGATAAAATCCCATTTCACCCCTACTACACTATTAAAGACATTCTAGGAGCCC 300 bub.min
CAGACACAGACAAAATCCCATTCCACCCCTACTACACCATTAAAGACATTCTAGGCGCCC 300 buba.bub

TABLE 2-continued

Multiple sequence alignment of 472 bp fregment of mitochondrial
cytochrome b gene of 221 animal species

```
CAGACACAGACAAAATCCCATTCCACCCCTATTACACCATTAAAGACATCCTAGGCGCCC 300 tra.ang
CAGACATAGACAAAATTCCATTCCACCCCTATTACACTATCAAGGACATCCTAGGCGCCC 300 tra.eur
CRAACATAGACAAAATTCCATTTCACCCTTACTACACTATTAAGGACATCCTAGGTGCCC 300 kob.ell
CAGACATAGATAAAATCCCATTCCACCCCTACTACACCATCAAAGACATTCTAGGCGCCC 300 kob.meg
CAGACACAGACAAAATCCCATTCCACCCATATTATACCATCAAAGATATTCTAGGTGCCC 300 red.aru
CAGATGTAGACAAAATCCCATTTCATCCATACTATACTATCAAGGACGTCCTAGGCGCCC 300 red.ful
CAGAYATGGACAAAATCCCATTCCACCCNTACTACACCATCAAAGAYATTCTAGGTGCCC 300 neo.mos
CAGACGCAGACAAAATCCCATTCCACCCCTACTACACCATTAAAGACATTCTAGGCGCCA 300 pel.cap
CCGACATAGACAAAATTCCATTCGACCCATACTACACCATTAAAGATATTCTAGGCGCCT 300 gaz.dam
CAGATGCAGACAAAATTCCGTTCGACCCCTACTACACCATCAAAGACATTCTAGGAGCAC 300 our.our
CAGATGCAGACAAGGTCCCATTCCACCCCTACTACACCATTAAAGACATCCTAGGCGCCT 300 ant.cer
GAGACGCAGACAAAATTCCATTCCACCCGTACTACACTATCAAAGATATCCTAGGAGGTC 300 sai.tat
CAGATTCAGACAAAATCCCATTGCACCCCTACTACACCATTAAAGACATTCTAGGGGCCG 300 mad.kir
CAGACGCAGACGGAATGCCATTCCGCCCCTACTACACTATTAAAGACATCCTAGGCGCCC 300 rap.mel
CAGATATAGACAAAATCCCATTTCACCCCTACTACACCATTAAAGACATTTTAGGAGCCC 300 gaz.gaz
CAGACGCAGACAAAATCCCATTTCACCCCTACTACACCATCAAGGACATTCTAGGAGGAC 300 ant.ame
CAGACGCAGACAAAATCCCATTCCACCCATACTACACCATCAAAGAGATTCTAGGAGCAC 300 hyd.ine
CAGATGCAGATAAAATTCCATTTCATCCCTACTACACCATTAAAGATATTCTAGGTGTAC 300 mun.mun
CAGATGTAGACAAAATTCCTTTCCATCGCTACTATACCATTAAAGATATTTTAGGTGCCC 300 alc.alc
CAGACGCAGACAAAATCCCATTTCACCCTTACTACACTATCAAAGATATCTTAGGTGCCC 300 cer.ela.kan
CAGACGCAGACAAAATCCCCTTCCATCCTTACTATACCATTAAAGATATCTTAGGCATCT 300 cer.ela.xan
CAGACGCAGACAAAATCCCCTTCCATCCTTACTATACCATTAAAGATATCTTAGGCATCT 300 cer.ela.can
CAGACGCAGACAAAATCGGCTTCCACCCTTACTATACGATTAAAGATATCTTAGGTATCT 300 cer.nip.cent
CGGACGCAGACAAAATCCCCTTCCATCCTTACTACACCATTAAAGATATCTTAGGCATCT 300 cer.nip.yes
CGGACGCAGACAAAATGCCCTTCCATCCTTACTACACCATTAAAGATATCTTAGGCATCT 300 cer.nip.ker
CGGACCCAGACAAAATCCCCTTCCATCCTTACTATACCATTAAAGATATCCTAGGCATCT 300
```

TABLE 2-continued

Multiple sequence alignment of 472 bp fregment of mitochondrial
cytochrome b gene of 221 animal species

```
cer.nip.pul
CGGACGCAGACAAAATGCCCTTCCATCCTTACTATACCATTAAAGATATCCTAGGCATCT 300 cer.nip.nip
CGGACGCACACAAAATCCCCTTCCATCCTTACTATACCATTAAAGATATCCTAGGCATCT 300 cer.ela.sco
CAGACGCAGACAAAATCCCCTTTCATCCTTATTATACCATTAAAGATATCTTAGGCATCT 300 cer.dam
CAGATGTAGATAAAATTCCCTTTCATCCCTACTACACCATTAAAGATATTTTAGGCATCC 300 ran.tar
CAGACTCAGATAAAATTCCATTCCATCCCTATTATACTATCAAAGAGATTCTAGGCATCC 300 mos.fus
CAGATATAGACAAAATCCCATTCCACCCCTACTACACCATCAAAGACATTCTAGGTGTCC 300 mos.leu
CAGATATAGACAAAATCCCATTCCACCCCTACTACACCATCAAAGACATTCTAGGTGTCC 300 mos.chr
CAGACATAGACAAAATCCCATTCCACCCCTACTACACCATCAAAGACATTCTAGGTGTCC 300 mos.ber
CAGACATAGACAAAATGCCATTCCACCCCTACTACACTATCAAAGACATTCTAGGTGTCC 300 mos.mos
CAGACATAGACAAAATCCCATTTCACCCCTACTACACCATCAAAGATATTCTAGGTATCC 300 tra.jav
CAGACGCAGACAAAATCCCCTTCCACCCATACTACACTATTAAAGACATTCTAGGGGTTC 300 trag.nap
CAGACGCAGACAAGATCCCCTTCCACCCATACTACACCATCAAAGATGTCCTAGGGGCTC 300 bala.acu
CTGACATAGACAAAATCCCATTCCACCCCTACTACACAATCAAAGACATTCTAGGCGCCC 300 bala.bon
CTGATATAGACAAAATCCCATTCCACCCCTATTACACAATCAAAGACATTCTAGGCGCCC 300 bala.bor
CCGACATAGACAAAATGCCATTCCACCCTTACTACACAGTTAAAGACATTCTAGGCGCCC 300 bala.edi
CCAACATAGACAAAATCCCATTCCACCCCTATTACACAACTAAAGACATTCTAGGCGCCG 300 esch.rob
CCAAGATAGACAATATCCCATTCCACCCCTATTACACAATTAAAGACATACTAGGCGCCC 300 bala.mus
CTGACATAGATAAAATTCCATTCCACCCCTACTACACAATTAAAGACATTCTAGGCGCCC 300 mega.nov
CCAACATAGACAAAATCCCATTCCACGCTTACTACACAATCAAAGACACTCTAGGCGCCC 300 bala.phy
CCGACATAGATAAAATCCCATTCCACCCCTACCACACAATTAAAGACATTCTAGGTGCCC 300 cap.mar
CCAACATAGACAAAATTCCATTCCACCCCTACTACACAATTAAAGACATCCTGGGCGTCC 300 ceph.com
CCAACATAGACATAATCCCATTCCACCCTTATTACACAATTAAAGACATCCTAGGCGCTT 300 ceph.eut
CCAACATAGACATAATCCCATTCCACCCTTATTACACAATTAAAGACATCCTAGGCGCTT 300 lage.obl
CGAACATAGACATAATCCCATTCCACCCTTATTACACAATTAAAGACATCCTAGGCGCTT 300 ceph.hea
CCAAGATAGACATAATCCCATTCCACCCTTATTACACAATTAAAGACATGCTAGGCGCTT 300
```

TABLE 2-continued

Multiple sequence alignment of 472 bp fregment of mitochondrial cytochrome b gene of 221 animal species ceph.hec
CCAACATAGAGATAATCCCATTCCACCCTTATTACACAATTAAAGACATCTTAGGCGCTT 300 lage.aus
CCAACATAGACATAATCCCATTCCACCCTTACTACACAACTAAAGACATCCTAGGCGCTT 300 lage.cru
CCAACATAGACATAATCCCATTCCACCCTTACTACACAATTAAAGACATCCTAGGCGCTT 300 lage.obs
CCAACATAGACATAATCCCATTCCACCCTTATTAGACAATTAAAGACATCCTAGGTGCTT 300 lisso.bor
CCAACATAGACATAATCCCATTCCACCCTTATTACACAATTAAAGACATCCTGGGCGCTT 300 lisso.per
CCAACATAGACATAATCCCATTCCACCCTTATTACACAATTAAAGACATCGTGGGCGCTT 300 glo.mac
CCAACATAGACATAATTCCATTCCACCCCTATTATACAATTAAAGACATCCTAGGCGCCC 300 glo.mel
CCAAGATAGACATAATTCCATTCCACCCCTATTATACAATTAAAGATATCCTAGGCGCCC 300 fere.att
CCAACATAGACATAATTCCATTCCACCCCTATTATACAACTAAAGATATCCTAGGTGCCC 300 pepo.ele
CCAACATAGACATAATTCCATTCCACCCCTATTATACAATTAAAGACATCCTAGGCGCTC 300 gram.gri
CCAACATAGACATAATTGCATTCCACCCCTATTACACAATTAAAGACATCCTAGGCGCCC 300 pse.cra
CCAACATAGACATAATTCCATTCCACCCTTATTACACAATTAAAGATATCCTAGGCGCCC 300 lage.acu
CTAACATAGATATAATCCCGTTCCACCCTTATTATACAATTAAAGATATCGTAGGCGCTT 300 orci.bre
CCAACATAGATATAATCGCATTCCACCCTTATCACAGAATTAAAGATACCCTAGGCGCCC 300 orca.bre
CCAACATAGACATAATCCCATTCCACCCTTATCATACATTTAAAGACATCCTAGGGGCCC 300 del.cap
CCAATATAGACATAATCCCATTCCACCCTTATTATACAATCAAAGATATCCTAGGTGCCT 300 del.tro
CCAACATAGACATAATCCCATTCCACCCTTATTATACAATCAAAGATATCCTAGGTGCCC 300 del.del
CCAATATAGACATAATCCCATTCCACCCTTATTATACAATCAAAGATATCCTAGGTGCCT 300 sten.cly
CCAATATAGACATAATCCCATTCCACCCTTATTATACAATCAAAGATATCCTAGGTGCCT 300 sten.coe
CCAATATAGACATAATTCCATTCCACCGTTATTATACAATAAAAGATATCCTAGGTGCCT 300 tur.adu
CCAATATAGACATAATGCCATTTCAGCCTTATTATACAATCAAAGACATCCTAGGTGCCT 300 sten.fro
CCAATATAGACATAATCCCATTCCACCCTTATTATACAATCAAAGACATCCTAGGCGCCT 300 saus.chi
CCAACATAGACATAATCCCATTTCACCCTTATTATACAATCAAAGACATCCTAGGTGGCT 300 sten.lon
CCAACATAGAGATAATCCCATTCCACCCTTATTATACAATCAAAGACATCCTAGGTGGCT 300 turs.tru
CCAATATAGACATAATCCCATTCCACCCTTATTATACAATCAAAGACATCCTAGGCGCCT 300 lage.alb

TABLE 2-continued

Multiple sequence alignment of 472 bp fregment of mitochondrial
cytochrome b gene of 221 animal species

```
CCAACATAGATATAATTCCATTCCACCCTTATTACACAAATCAAGACATCCTAGGCGCTT 300 sten.bre
CCAACATAGATATAATCCCATTCCACCCTTATTACACAATCAAAGACATCGTAGGCGGCT 300 sota.flu
CCAACATAGATATAATTCCATTCCACCCTTATTACACAATCAAAGATATCCTAGGCGCCT 300 del.leu
CCAACATGGATACAATCCCATTCCACCCCTACTACACAATCAAAGACATCCTAGGTGCTT 300 mono.mon
CCAACATAGACATAATCCCCTTCCATCCCTACTACACAATCAAAGACATGCTAGGCGCTT 300 plat.gan
GCGACACTGAGAAAATCCCTTTCCACCCCTACTACACAATCAAAGACACCCTAGGCGCCG 300 plat.min
CGAACACTGACAAAATCCCTTTCCAGCCCTACTACACAATCAAAGACACCCTAGGCGCCC 300 kogi.bre
CCGACATAGACAAATCCCATTCCACCCCTACTACACAATCAAAGGACATCTTAGGCGCCC 300 kogi.sim
CTGATATAGACAAAATCCCATTCCACCCCTAGTAGACAAATCAAGATATCCTAGGCGCCC 300 phys.cat
CCAACATAGACAAAATCCCATTCCACCCCTACCACACAATCAAAGACACCATAGGTGCCC 300 lipo.vex
CTAACATAGACAAAATCCCATTCCACCCCTACCAGACAATTAAAGATATCTTAGGCGCCC 300 phoc.sin
CTAACATAGACATAATCCCCTTCCACCCTTACTATACAATCAAAGATATCCTAGGCGCCC 300 bera.bai
CCAATATAGATAAAATTCCATTCCACCCCTACTATACAATCAAAGATATCCTAGGAGCCC 300 ziph.car
CCGATATAGACAAAATCCCATTCCACCCTTATTACACAAATCAAGACATCCTAGGAGCCC 300 mesa.eur
CTGATATAGACAAAATCCCATTCCATCCTTACTACACAATCAAAGATATCCTAGGGGCTC 300 meso.bid
CCGACATAGATAAAATTCCATTCCACCCCTACTACACAATTAAAGATATCCTGGGAGCCC 300 mesa.den
CTGACATAGATAAAATTCCATTTCACCCTTATTACACAATCAAAGATATTTTAGGAGCCC 300 hype.amp
CTGACATAGACAAAATCCCGTTCCACCCATACTACACAATCAAAGACACTCTAGGGGCCC 300 mesa.per
CTGACATAGACAAAATTCCATTTCATCCTTACTATACAATTAAAGATATCTTAGGAGCCC 300 pont.bla
CTAACATAGATGCCATCCCATTTCACCCCTACTACACAATTAAAGATATCCTAGGGGCCC 300 hex.lib
CAAACGCAGACAAAATCCCATTCCACCCCTATTACACAATCAAAGATATCCTGGGCGTAC 300 hipp.amp
CAAACGCAGACAAAATCCCATTCCACCCCTATTACACAATCAAGGACATCCTAGGTATCC 300 dic.sum
CTAACATAGACAAAATCCCATTTCACCCATACTATACAAATCAAGACATCCTAGGAGCCC 300 rhin.son
CTAACACAGACAAAATTCCATTTCACCCTTACTACACAATCAAAGAGATCCTAGGAGCCC 300 cera
CCAACATAGACAAAATCCCATTCCACCCATACTACACAATCAAAGACATCCTGGGAATTT 300 equu
CTGACATAGACAAAATCCCATTCCACCCGTACTACACAATTAAAGACATCGTAGGACTTC 300
```

TABLE 2-continued

Multiple sequence alignment of 472 bp fregment of mitochondrial cytochrome b gene of 221 animal species

```
baby.bab
CAGATATAGACAAAATCCCATTCCACCCCTACTATACCATTAAAGACATTCTAGGAGCCC 300 phac.afr
CAGACATAGACAAAATCCCATTGCACCCATACTACAGCATTAAAGATATCCTAGGAGCGC 300 sus.bar
CAGATATAGACAAAATTCCATTTCACCCATACTACACTATCAAAGACATTCTAGGAGCCT 300 sus.scr.ewb3
CAGACATAGACAAAATTCCATTTCACCCATACTACACTATTAAAGACATTCTAGGAGCCT 300 lama.gla
CGGATATAGACAAAATCCCCTTCCATCCCTACTATACAATTAAAGACATTCTAGGAGCAC 300 lama.gua
CGGATATAGACAAAATCCCCTTCCATCCCTACTATACAATTAAAGACATTCTAGGAGTAC 300 vic.vic
CAGATATAGACAAAATTCCGTTCCATCCCTACTAGACAATTAAAGACATTTTAGGAGCAC 300 cam.bac
CAGACATAGACAAAATCCCATTCCACCCCTACTACACAATTAAAGACATCCTAGGAGCAC 300 arc.far
CTGACTCAGACAAAATCCCATTCCACCCATATTATACAATTAAAGATATCCTGGGAGCCC 300 arc.gaz
CTGACTCGGACAAAATTCCATTCCACCCATATTATACAATTAAAGATATCCTGGGAGCCC 300 eum.jub
CCAACTCAGACAAAATTGCATTCCATCCATATTACACAATTAAAGATATCCTGGGAACGC 300 zal.cal
CTGACTCAGACAAAATTCCATTCCACCCATATTACACAATTAAAGATATCCTAGGAACCC 300 odo.ros
CTGACTCAGACAAAATCCCATTTCACCCGTACTACACAATTAAAGATATCCTAGGGCTCA 300 pho.fasciata
CCGACTCAGACAAAATCCCATTCCACCCATAGTATACAATTAAAGATATGCTAGGAGCCC 300 pho.gro
CCGACTCAGACAAAATGCCGCTCCACCCATATTATACAATTAAAGATATCCTAGGAGCCC 300 pho.vit
CCAACTCAGACAAAATCCCATTCCACCCGTACTATACAATTAAAGATATCCTAGGGGCCC 300 cys.cri
CCGACTCAGACAAAATCCCATTCCACCCATACTATACAATTAAAGACATCCTAGGAGCCC 300 hyd.lep
CCAACTCAGACAAAATCCCATTTCACCCCTACTACACAATCAAAGACATCCTAGGAGCCG 300 lep.wed
CTGACTCAGACAAAATCCCATTTCACCCCTACTACACAATCAAAGACATCCTAGGAGCCC 300 mir.leo
CCGACTCAGACAAAATCCCATTCCACCCATACTACACAATCAAAGATATCTTAGGAGCCC 300 eri.bar
CCGACTCAGATAAAATTCCATTCCACCCATACTATACAGTCAAGGACATCTTAGGGGCCT 300 mon.sch
CCAACTCAGACAAAATCCCATTCCACCCATACTATACAATTAAAGACATTCTAGGAGCTT 300 hela.mal
CTGACTCAGACAAAATCCCATTTCACCCGTACTATACAATTAAGGACATCCTAGGCGCCC 300 sel.thi
CCAACTCGGACAAAATCCCATTTCACCCATACTATACAATTAAAGACGCCCTAGGCGCCC 300 ail.ful
CCAACTCAGACAAAATTCCATTCCATCCCTATTATACAATTAAAGATATCTTGGGCGCTC 300
```

TABLE 2-continued

Multiple sequence alignment of 472 bp fregment of mitochondrial cytochrome b gene of 221 animal species fel
CCGATTCAGACAAAATCCCATTGCACCCATACTATACAATGAAAGACATCCTAGGTCTTC 300 can
CAGACTCAGACAAAATTCCATTTCACCCTTACTACACAATCAAGGATATCCTAGGAGCCT 300 tal
CAGATACGGATAAAATTCCATTTCACCCCTATTACACTATTAAAGACATCCTAGGAGCAC 300 gla.sab
CTGACTCAGATAAAATCCCATTCCACCCTTATTTGTCAATTAAAGACACCCTAGGATTCT 300 gla.vol
CTGACTCAGACAAAATCCCATTCCACCCCTACTTCTCAATTAAAGATACCCTAGGATTCT 300 hyl.pha
CCGATTCAGACAAAATCCCATTTCACCCATACTATTCAATTAAAGATCTCCTAGGCGCCC 300 pet.set
CCGATTCAGACAAAATTCCCATTTCACCCATACTATTCAATTAAAGATCTCCTAGGGGCCC 300 bel.pea
CTGAATCTGATAAAGTACCATTCCACCCATACTTCACAATCAAAGATATTCTTGGCGCCC 300 pte.mom
CCGAATCCGACAAAATCCCATTCCACCCCTACTTCACAATTAAAGACATTTTAGGAGCAC 300 gala.demi
CAGACTCAGACAAAATCCCCTTTCACCCCTATTACATAATCAAGGATCTCCTAGGACTGA 300 pero.pot
CAGAATCAGACAAAATCCCCTTCCACCCCTACTAGACCACCAAAGACTTACTAGGAGCCA 300 gala.mat
CAGACTCCGACAAAATCCCATTCCACCCCTACTACACAATTAAAGACCTACTAGGAGTAA 300 gala.moh
CAGACTGCGACAAAATCCCCTTCCAGCCCTACTACACAATTAAAGACCTACTAGGAGCAA 300 oto.gar
CAGACTCTGACAAAATCCCCTTCCACCCCTATTACACAATTAAAGACCTTCTACGGGCTA 300 lor.tar
GAGACTCTGACAAAATCCCATTTCACCGCTACTACACATTAAAAGATATTCTAGGAGTAA 300 nyc.cou
CAGACTCAGATAAGATTCCATTTCACCCGTACTACTCACTTAAAGACCTCCTAGGAGTGG 300 mus
CAGATGCAGATAAAATTCCATTTCACCCCTACTATACAATCAAAGATATCCTAGGTATCC 300 gorr
CCCACTCTGACAAAATCACCTTCCACCCCTACTACACAATCAAAGACATCCTAGGCCTAT 300 homo
CCCATTCCGATAAAATCACCTTCCACCCTTACTACACAATCAAAGACGCCCTCGGCTTAC 300 dug.dug
CCGACTCAGACAAAATCCCATTCCACCCATATTATTCAGTCAAAGACCTCCTAGGCCTAT 300 ele.max
CAGACTCAGACAAAATTCCCTTTCACCCGTACTATACTATCAAAGACTTCCTAGGGCTAC 300 afr.con
CCAATTCAGATAAAATCCCATTCCACGCGTACTACTCCCTCAAAGATATCCTAGGCTTAG 300 pavo.mut
CCAACTCAGACAAAATTCCGTTCCACCCATACTACTCCCTCAAAGATATCCTAGGCTTAA 300 tra.bly
CTAAGTCTGACAAAATCCCATTCCACCCGTACTACTCCCTCAAAGATATCCTGGGTCTAA 300 tra.sat
CCAACTCTGACAAAATCCCATTTCATCCATACTACTCCCTCAAGGATATCCTAGGCCTAA 300 tra.cob

TABLE 2-continued

Multiple sequence alignment of 472 bp fregment of mitochondrial
cytochrome b gene of 221 animal species

```
CTGACTCTGACAAAATCCCATTCCACCCGTACTACTCCCTCAAAGATATCCTGGCCTAA 300 tra.tem
CTAACTCTGACAAAATCCCATTCCACCCGTACTACTCCCTCAAAGATATCCTAGGCCTAA 300 arg.arg
CTAACTCTGACAAAATCCCATTCCACCCATACTACTCCCTCAAAAGACATCCTAGGCCTAA 300 cat.wal
CTAACTCCGACAAAATCCCATTCCACCCATACTACTCCCTCAAAGATATCCTAGGCCTAG 300 cro.cro
CTAATTCCGACAAAATCCCATTCGACCCCTACTACTCCCTCAAAGACATCCTAGGCCTAG 300 sym.ree
CTAACTCTGACAAAATCCCCTTTCACCCATACTACTCTCTCAAAGATATCCTAGGCCTAG 300 bam.tho
CTAACTCCGACAAAATCGCATTCCACCCATACTACTCCTTTAAAGACATTCTCGGCCTAG 300 fra.fra
CTGACTCTGACAAAATCCCATTCCACCCATACTACACCCTGAAAGACATCCTAGGCCTAA 300 ith.cru
CTAACTCTGACAAAATCCCATTTCACCCATACTACTCCCTCAAAGACATCCTAGGCCTAG 300 ant.par
CAAACTGCGATAAAATCCCATTCCACCCCTATTTTTCGTTAAAAGATATCCTAGGATTCA 300 ant.vir
CAAACTGCGATAAAATCCCATTCCACCCCTATTTTTCCTTAAAAGATATCCTAGGATTCA 300 gru.ant.ant
CAAACTGCGATAAAATCCCATTCCACCCCTACTTTTCCTTAAAAGATATCCTAGGATTCA 300 gru.ant.gil
CAAACTGCGATAAAATCCCATTCCACCCCTACTTTTCCTTAAAAGATATCCTAGGATTCA 300 gru.ant.sha
CAAAGTGCGATAAAATCCCATTCCACCCCTACTTTTCCTTAAAAGATATCCTAGGATTCA 300 gru.leu
CAAACTGCGATAAAATCGCATTCCACCCCTACTTTTCCTTAAAAGATATCCTAGGGTTCA 300 gru.can.pra
CAAACTGCGATAAAATCCCATTCCACCCCTATTTTTCCTTAAAAGATATCCTAGGGTTCA 300 gru.can.row
CAAACTGCGATAAAATCCCATTCCACCCCTATTTTTCCTTAAAAGATATCCTAGGGTTGA 300 gru.can.tab
CAAACTGCGATAAAATCCCATTCCACCCCTATTTTTCCTTAAAAGATATCCTAGGGTTCA 300 gru.can.can
CAAACTGCGATAAAATCCCATTCCACCCCTATTTTTCCTTAAAAGATATCCTAGGGTTCA 300 gru.ame
CAAACTGCGATAAAATCCCATTCCACCCCTATTTTTCCTTAAAAGACATCCTAGGATTCA 300 gru.gru
CAAACTGCGATAAAATCCCATTCCACCCCTATTTTTCCTTAAAAGATATCCTAGGGTTCA 300 gru.mon
CAAACTGCGATAAAATTCCATTCCACCCCTATTTTTCCTTAAAAGATATCCTAGGATTCA 300 gru.nig
CAAACTGCGATAAAATTCCATTCCACCCCTATTTTTCCTTAAAAGATACCCTAGGATTCA 300 gru.jap
CAAACTGTGATAAAATCCCATTCCACCCCTATTTTTCCTTAAAAGATATCTTAGGATTTA 300 cic.boy
CAAACTGCGACAAAATTCCATTCCACCCCTACTTCTCCCTCAAAGATATCCTAGGCCTTA 300 rhe.ame
CTCACTCTGACAAATCCCATTCCACCCCTACTTCTCCCTAAAAAGATGCCCTAGGACTAG 300
```

TABLE 2-continued

Multiple sequence alignment of 472 bp fregment of mitochondrial cytochrome b gene of 221 animal species

```
ant.alb
CCAACTGCGACAAAATCCCATTCCACCCATACTTTGCCCTAAAGGACATCCTAGGATTCA 300 fal.fam
CAAACTGCGATAAAATCCCATTCCATCCCTATTACTCTCTCAAAGACCTCCTAGGATTCA 300 fal.ver
CAAACTGCGACAAAATCGCATTCCATCCCTACTACTCTCTAAAAGACCTTTTAGGAGTGA 300 fal.per
CAAATTGCGACAAAATCCCATTCCACCCATACTACTCTCTGAAAGATATCGTAGGATTTA 300 fal.spa
CAAACTGTGACAAAATCCCATTCCACCCCTACTACTCTCTCAAAGACCTCCTAGGTTTTA 300 ayt.ame
CAGACTGCGACAAAATCCCATTTCACCCCTACTTCTCCTTCAAAGACATCCTAGGATTTA 300 smi.sha
CTAACTCCGATAAAATCCCATTCCACCCATACTTCTCCATAAAAGACATTCTAGGCTTTG 300 vid.cha
CAGACTGTGACAAAATTCCATTCCACCCATACTACACCACAAAGGACATCCTAGGCTTCG 300 chry.pic
CAAACACTGACAAAATCCCATTCCACCCTTATTTCTCATATAAAGACCTTTTAGGCGTCA 300 emy.orb.kur
CAAACACCGATAAAATCCCTTTCCATCCCTACTTCTCATACAAAGACCTATTAGGACTCA 300 che.mud
CAAATACCGACAAAATGCCCTTCCACCCCTACTTCTCCTACAAAGACTTACTAGGACTCA 300 eum.egr
CTAGGACAGATAAGGTGCCATTCCACGCATATTACACATACAAAGACCTTCTTGGTTTCA 300
         *    **    *  *                         * **    *
** aep.mel
TATTAATAATTCTAGTCCTAATACTCCTAGTACTATTCATACCCGACCTACTAGGAGACC 360 ore.ore
TATTACTAATTCTAGCTTTATTACTCTTAGTATTATTCACACGTGACCTACTTGGAGACC 360 add.nas
TACTACTAATTCTAGTCCTGATACTACTAGTATTATTCACACCCGACCTACTTGGAGACC 360 ory.dam
TACTACTAATCCTAGCCCTTATGTTGCTAGTATTATTCGCACCCGACCTACTTGGAGACC 360 hip.equ
TACTACTAATTCTAGCCCTCATACTACTAGTACTATTCGCACCCGACCTACTTGGAGACC 360 aic.bus
TATTACTAATCCTAGGCCTCATACTACTAGTACTATTCGCACCCGACCTGCTCGGAGACG 360 sig.lic
TATTACTAATTCTAGCCCTCATACTACTAGTACTATTCGCACCCGACCTGCTCGGAGACC 360 bea.hun
TACTACTAATTCTAGGCCTCATATTACTAGTACTATTTGCACCCGACCTGCTCGGAGACC 360 dam.lun
TAGTACTAATTCTAGCCCTCATACTACTAGTACTATTTGCACCCGACCTGCTCGGAGACC 360 con.tau
TATTACTAATTCTAGCCCTAATACTACTAGTACTATTCGCGCCCGATTTACTTGGAGACC 360 amm.ler
TGCTACTAATCCTCACCCTCACACTACTAGTACTATTTACACCGGATCTACTCGGGGACC 360 pse.nay
CACTGCTAATCCTCGCCCTGATATTACTAGTATTATTTACACCCGACCTACTCGGAGACC 360 cap.ibe
```

TABLE 2-continued

Multiple sequence alignment of 472 bp fregment of mitochondrial cytochrome b gene of 221 animal species

```
TGCTACTAATTCTTGTCCTAATATTACTAGTACTATTCAGACCCGACCTACTCGGGGACC 360 hem.jem
TACTACTAATTCTTGTCCTAATATTACTAGTACTATTTATACCCGACCTACTTGGAGACC 360 cap.fal
TACTACTAATTCTCGCCCTGATGCTACTAGTACTATTCACACCTGACCTACTCGGAGACC 360 rup.pyr
TACTACTAATCCTCAGCCTTATACTACTGGTACTATTTACACCTGACCTACTCGGAGACC 360 rup.rup
TACTACTAATCCTCACCCTCATACTACTAGTACTATTNACACCTGACCTACTCGGAGACC 360 nem.cau
TACTACTAATCCTCACCCTTATTTTACTGGTATTATTCACACCTGACTTACTTGGAGATC 360 bud.tax.tax
TACTACTAATCCTCGTGCTCATGTTGCTAGTACTATTTATACTTGACGTACTTGGAGACC 360 pan.hod
TACTACTAATCCTAATCCTCATATTACTAGTACTATTTTCACCCGACGTACTCGGAGACC 360 ovi.amm
TCCTACTAATCCTCACCCTCATACTACTAGTACTATTCACGCCTGACCTACTCGGAGACC 360 ovi.vig
TCCTACTAATCCTCATCCTCATGCTGCTAGTACTATTCACGCCTGACTTACTTGGAGACC 360 cap.cri
TGCTACTAATCCTCACCCTCATACTACTAGTACTGTTCACACCCGACCTACTCGGAGACC 360 ovi.mos
TACTACTAATCCTTACCCTTATACTACTAGTATTATTCACACCCGACCTACTTGGAGACC 360 ore.ame
TACTACTGATCCTCACCCTTATACTACTAGTATTATTCTCACCCGACTTACTCGGAGACC 360 cep.dor
TACTACTCATTCTAGCCCTAATAATCCTAGTATTATTCTCACCCGACTTACTTGGAGACC 360 cep.max
TATTACTTATTCTAGCCCTAATAATCCTAGTACTATTCTCACCCGAGTTACTCGGAGATC 360 bis.bon
TATTACTAATTCTAACTCTAATACTACTAGTACTATTCGCACCGGACCTCCTCGGAGACC 360 bos.gru
TATTACTAATTCTAGCCCTAATACTTCTGGTACTATTCACACCCGACCTCCTCGGAGACC 360 bos.tra
TACTACTTATTCTAGCCCTAATAATACTAGTACTATTCGCACCCGACCTCCTCGGAGACC 360 bub.min
TGCTATTAATCCTAGCCGTAATACTATTAGTACTATTCACACCCGACCTCCTCGGGGACC 360 buba.bub
TACTATTAATCGTAGCCCTAATACTATTAGTACTATTCGCACCCGAGCTCCTCGGGGACC 360 tra.ang
TACTATTAATCCTAGCCCTAATAGTACTAGTACTATTCACACCTGACCTCCTCGGAGACC 360 tra.eur
TACTGCTAATCCTAACTCTAATACTCCTAGTACTATTCGCACCCGACCTTCTCGGAGACC 360 kob.ell
TACTACTAATCCTAGTCCTAATACTCCTAGTTCTATTCGCCCCCGACCTACTTGGAGATC 360 kob.meg
TCCTATTAATCCTAATACTAATACTCCTAGTACTATTTGCCCCCGACCTACTTGGAGACC 360 red.aru
TACTGGTAATCCTAGTCCTAATGCTCTTAGTATTATTCACCCCTGACCTACTCGGAGATC 360 red.ful
TACTACTAATCCTGGCCCTAACACTATTAGTACTATTCACCCCTGACCTACTCGGAGACC 360
```

TABLE 2-continued

Multiple sequence alignment of 472 bp fregment of mitochondrial cytochrome b gene of 221 animal species

```
neo.mos
TCCTACTAATTCTAGTGCTAACACTCTTAGTTTTATTTGCACCTGACCTTTTAGGAGACC 360 pel.cap
TATTACTAATCCTAATCCTAACACTCCTAGTATTATTTACCCCTGACCTATTAGGAGACC 360 gaz.dam
TACTATTAATTCTAGCCCTCATACTCCTAGTTCTATTCACACCAGATCTGCTTGGAGACC 360 our.our
TCCTACTAATTCTAGCCCTGATGCTCCTAGTCCTATTCACACCAGAGCTGCTTGGAGACC 360 ant.cer
TACTATTAATTTTAACCCTCATGCTTCTAGTCCTATTCTCACCGGACCTGCTTGGAGACC 360 sai.tat
TACTACTTATTCTAATCCTCATACTTCTAGTCCTATTTTCACCAGACCTGCTTGGAGACC 360 mad.kir
TACTACTAATTATAGGCCTCATACTCCTAGTTCTATTCTCACCAGACCTGGTCGGAGACC 360 rap.mel
TCCTATTAATCCTAACCCTTATGCTTCTAGTTCTATTCGCACCAGACCTACTCGGAGACC 360 gaz.gaz
TACTACTAATCCTAGTTCTTATACTCCTAGTTCTGTTCTCACCGGACCTACTCGGAGACC 360 ant.ame
TACTAATAATCTTAGCCCTAATAATACTAGTACTATTCTCACCAGACCTGTTAGGAGACC 360 hyd.ine
TCGTTCTAATTCTTTTCCTAATGTTATTAGTCCTATTTTCACCTGACCTGCTTGGAGACC 360 mun.mun
TACTTCTAATTCTCTTCCTAATATTATTAGTATTATTCGTACCAGACCTGCTCGGAGACC 360 alc.alc
TACTCTTAACTCTTTTCCTAATACTACTAGTACTCTTTTCACCAGACCTGCTTGGAGACC 360 cer.ela.kan
TACTTCTAGTACTCTTCCTAATATTACTAGTATTATTCGCACCAGACCTGCTTGGAGACC 360 cer.ela.xan
TACTTCTAGTACTCTTCCTAATATTACTAGTATTATTCGCACCAGACCTGCTTGGAGACC 360 cer.ela.can
TACTTCTAATACTCTTCCTAATATTACTAGTATTATTCGCACCAGATCTGCTTGGAGACC 360 cer.nip.cent
TACTTCTAGTACTCTTCCTAATATTACTAGTATTATTCGCACCAGACCTGCTTGGAGATC 360 cer.nip.yes
TACTTCTAGTACTCTTCCTAATATTACTAGTATTATTCGCACCAGACCTGCTTGGAGATC 360 cer.nip.ker
TACTTCTAGTACTCTTCCTGATATTACTAGTATTATTCGCACCAGACCTGCTTGGAGATC 360 cer.nip.pul
TACTTCTAGTACTCTTCCTGATATTACTAGTATTATTCGCACCAGACCTGCTTGGAGATC 360 cer.nip.nip
TACTTCTAGTACTCTTCCTGATATTACTAGTATTATTCGCACCAGACCTGCTTGGAGATC 360 cer.ela.sco
TACTTCTTGTACTCTTCTTAATATTACTAGTATTATTCGCACCAGACCTACTTGGAGATC 360 cer.dam
TATTCCTATTTCTCTTCTTAATAACACTAGTACTATTTGGACCAGACTTGCTTGGAGACC 360 ran.tar
TACTCCTAATTCTCTTCCTTATACTACTAGTATTATTTGCACCAGACTTACTAGGAGACC 360 mos.fus
TATTACTAATCTTAGTCTTAATAACACTAGTACTATTCACACCTGATTTACTTGGAGACC 360
```

TABLE 2-continued

Multiple sequence alignment of 472 bp fregment of mitochondrial cytochrome b gene of 221 animal species mos.leu
TATTACTAATCTTAGTCTTAATAACACTAGTACTATTCACACCTGATTTACTTGGAGACC 360 mos.chr
TATTACTAATCCTAGTCTTAATAACACTAGTACTATTCACACCTGATTTACTTGGAGACC 360 mos.ber
TAATACTAATCTTAGTCTTAATAGTACTAGTACTATTCACACCCGATTTACTTGGAGACC 360 mos.mos
TATTACTAATCTTAATCTTAATAGCACTAGTGCTATTTACACCCGACCTACTTGGAGATC 360 tra.jav
TAGCCCTATTTCTAGCCCTAATACTACTAGTCCTATTCTCACCCGACCTACTTGGAGACC 360 trag.nap
TAGTCCTAATACTAGTCCTTCTATTACTACTCCTATTTTCACCGGACTTGTTGGCAGACC 360 bala.acu
TACTACTAATTCTAACCCTACTAGCACTAACCCTATTCGCACCGGACCTGCTTGGAGACC 360 bala.bon
TACTACTAATTCTAACCCTACTAACACTAACCCTATTCGCACCCCACCTCCTCCGAGACC 360 bala.bor
TACTACTAATCCTAACCCTACTAATACTAACCCTATTCGCACCCGACCTGCTTGGAGACC 360 bala.edi
TACTACTAATCCTAACCCTACTAATGCTAACCCTATTCGTACCCGACCTACTTGCAGACC 360 esch.rob
TGCTACTAATCCTAACCCTACTAATACTAACCCTATTCGCACCCGACCTGCTCGGAGACC 360 bala.mus
TACTACTAATCCTAACCCTACTAATATTAACTCTATTTGCACCCGACTTACTCGGAGACC 360 mega.nov
TATTACTAATCCTAACCCTACTAATGTTAAGCCTATTCGCACCTGACCTGCTTGGAGACC 360 bala.phy
TATTACTAATCCTAATCCTAGTAATACTAACCCTATTCGCACCCGACCTACTTGGAGACC 360 cap.mar
TACTACTAATCCTGACCCTACTAATATTAACCTTATTTACACCTGACCTGCTTGGAGACC 360 ceph.com
TATTCCTAATCCTAACCCTACTAGCATTAACCCTATTTGCCCCCGACCTACTAGGAGACC 360 ceph.eut
TATTCCTAATCCTAACCCTACTAGCACTAACCCTATTCGCCCCTGACCTACTAGGAGACC 360 lage.obl
TATTCCTAATTCTAACCCTACTAGCACTAACCCTATTCACCCCTGACCTACTAGGAGACC 360
ceph.hea
TATTCCTAATTCTAGCCCTACTAGCACTAAGCCTATTCGCCCCTGACCTACTGGGAGACC 360 ceph.hec
TATTCCTAATTCTAATCCTACTAGCACTAACCCTATTCGCCCCTGACCTACTAGGAGACC 360 lage.aus
TATTCCTAATTCTAGCCCTACTAGCACTAACCCTATTCACCCCTGACCTACTAGGAGACC 360 lage.cru
TATTCCTAATCCTAAGCCTACTAGCACTAACCCTGTTCACCCCTGACCTACTAGGAGACC 360 lage.obs
TATTCCTAATTCTAGCCCTACTAACACTAACCTTATTCACCCCCGACCTACTAGGAGACC 360 lisso.bor
TATTCTTAATTCTGGCCCTACTAGCACTAACCCTATTCACCCCTGACCTATTAGGAGACC 360 lisso.per
TATTCTTAATTCTGACCCTACTAGCACTAACCCTATTTACCCCTGACCTGTTAGGAGATC 360 glo.mac
TACTCTTAATCCTAGCACTACTAACACTAACCCTATTCACCCCTGACCTACTAGGAGACC 360

TABLE 2-continued

Multiple sequence alignment of 472 bp fregment of mitochondrial cytochrome b gene of 221 animal species

```
glo.mel
TACTCTTAATCCTAGCACTACTAACACTAACCCTATTCACCCCTGACCTACTAGGAGACC 360 fere.att
TACTCTTAATTCTAACATTACTAACACTAACCCTGTTCACCCCTGACCTACTAGGAGACC 360 pepo.ele
TACTCTTAATCTTAGCACTACTAACACTAACCCTATTCACCCCTGACCTACTAGGAGACC 360 gram.gri
TACTCCTAATCCTAACACTACTAACACTAACCCTATTCACCCCTGACCTACTAGGAGACC 360 pse.cra
TACTCTTAATTCTAACACTACTAAGACTAACCCTATTCACCCCCGACCTACTAGGAGACC 360 lage.acu
TACTCTTAATTCTAACCCTACTAGCACTAACCCTATTCACCCCTGACCTACTAGGAGACC 360 orci.bre
TACTCTTAATCCTAACCCTGCTAGGACTAACCTTATTCGCCCCTGACCTACTAGGAGACC 360 orca.bre
TACTCTTAATCTTAGTCCTACTAACACTAACCCTGTTCACCCCCGACCTACTAGGAGACC 360 del.cap
TACTCCTAATCTTAACCCTACTAGCACTGACCCTATTCACTCCAGACCTACTAGGAGACC 360 del.tro
TACTCCTAATCTTAACCTTACTAGCACTGACCCTATTCACTCCCGACCTACTAGGAGACC 360 del.del
TACTCCTAATCTTAACCCTACTAGCACTAACCCTATTCACTCCCGACCTACTAGGAGACC 360 sten.cly
TAGTCCTAATCTTAACCCTACTAGCACTAACCCTATTCACCCCCGACCTACTAGGAGACC 360 sten.coe
TACTCCTAATCTTAACCCTACTAGCACTAACCCTATTCACCCCCGACCTACTAGGAGACC 360 tur.adu
TACTCCTAATCTTAACCCTACTAGCACTAACCCTATTCACCCCCGACCTACTAGGAAAGC 360 sten.fro
TACTCCTAATCCTAACCCTACTAGCACTAACCCTATTCACCCCCGACCTACTAGGAGACC 360 saus.chi
TACTCCTAATCTTAAGCCTACTAGCACTAACCCTATTCACCCCCGACCTACTAGGAGACC 360 sten.lon
TACTCTTAATCTTAACCCTACTAGCAGTAACCCTATTCACCCCTGACTTACTAGGAGACC 360 turs.tru
TACTCTTAATCTTAACCTTACTAGCATTAACCCTATTGGCCCCCGACCTACTAGGAGACC 360 lage.alb
TACTTTTAATCCTAACCTTACTAGCAGTAACCCTATTTACCCCCGACCTACTAGGAGATC 360 sten.bre
TACTTTTAATCCTAACTTTACTAGCACTAACCCTATTCACCCCCGACCTACTAGGAGACC 360 sota.flu
TACTCCTAATCCTGACCCTACTAGCACTAACCCTATTCACCCCCGACCTACTAGGAGATC 360 del.leu
TACTACTAATCCTAAGCCTATTAACAGTAACCCTATTCACACCTGACCTCCTAGGAGACC 360 mono.mon
TCCTACTAATCGTAATTCTACTAGCAATAACCCTACTCACACCTGACCTCCTAGGAGACC 360 plat.gan
TCATCCTAATCCTAACCTCACTCACATTAACCTTATTTACACCTGACCTACTAGGAGACC 360 plat.min
TCATCCTAATCCTAACCTCACTCACATTAACCTTATTTACACCTGACCTACTAGGAGACC 360
```

TABLE 2-continued

Multiple sequence alignment of 472 bp fregment of mitochondrial
cytochrome b gene of 221 animal species kogi.bre
TACTGCTAATCTCAGCGCTACTTACATTAACGCTATTCGCACCAGACGTATTAGGAGACC 360 kogi.sim
TACTACTAATCTCAGCACTACTCACACTGACCCTGTTCGCACCTGATCTACTAGGAGACC 360 phys.cat
TACTACTAATCCTATCCCTACTTACACTAACCCTGTTCGCACCCGACCTGCTAGGAGATC 360 lipo.vex
TTCTATTAATATTTGTTCTACTCACACTAACCTTACTTGCACCAGACCTACTCGGAGATC 360 phoc.sin
TACTATTTATTCTAACTTTACTAACACTAACCTTATTTTTACCTGACCTTCTAGGAGACC 360 bera.bai
TACTACTAATCCTAGCCCTACTCACGCTAACCCTATTTGCACCCGACCTACTAGGAGAGC 360 ziph.car
TACTATTAATCGTAATTCTACTCGCACTAACCCTATTCGCACCCGACCTGCTAGGAGACC 360 meso.eur
TACTACTAATTCTAGCCCTACTCACCCTAACCCTATTCGCACCCGACCTGCTAGGAGACC 360 meso.bid
TACTACTAATTCTAACCGTACTCGCACTAACCCTATTCGGACCTGACCTGCTAGGAGACC 360 meso.den
TACTATTAATTCTGGCCCTACTTATAGTAACCCTATTTGCACCTGACCTACTAGGAGACC 360 hype.amp
TATTACTAATCCTAGTCCTACTCACATTAACCCTATTCGCACCCGACCTACTAGGAGACC 360 meso.per
TATTATTAATTATAGTCCTACTTATACTAACCCTATTTGCACCTGACCTATTAGGAGATC 360 pont.bla
TATTAATAATCCTAACAATACTCACGCTGACTCTATTCACCCCTGACCTATTAGGAGACC 360 hex.lib
TACTTCTAATAACAATACTACTCACACTAACCTTATTTGCCCCAGACCTCCTAGGGGACC 360 hipp.amp
TACTCCTAATAACAACACTACTCACACTAACCTTATTTGCCCCAGACCTCCTAGGGGACC 360 dic.sum
TACTTCTAATCCTAGCCCTACTCACCCTAGTTCTATTCTCGCCTGAGCTCCTAGGAGACC 360 rhin.son
TGCTTCTAATTATAGTATTACTCACCGTAGTCCTATTCTCCCCTGACATCCTAGGGGACC 360 cera
TACTCCTAATCCTAGCACTACTCGCCCTAGTTCTATTCTCACCAGACATCCTAGGAGACC 360 equu
TCCTCCTAGTCCTACTCCTACTAACCGTAGTATTATTCTCCCCTGACCTCCTAGGAGACC 360 baby.bab
TACTCATAATTATAGCTCTTCTAATCCTAGTACTATTCTCACCAGATCTACTAGGAGACC 360 phac.afr
TATTCATAATACTAATCCTGCTAATCCTAGTATTATTCTCCGCAGAGCTACTAGGAGACC 360 sus.bar
TATTTATAATACTAATCCTACTAATCTTAGTACTATTCTCACCAGACCTACTAGGAGACC 360 sus.sor.ewb3
TATTTATAATACTAATCCTACTAATCCTTGTACTATTCTCACCAGAGCTACTAGGAGACC 360 lama.gla
TACTACTTATTCTAACCCTACTTCTACTCGTACTATTCTCACCAGACCTACTAGGAGACC 360 lama.gua
TACTACTTATTCTGACCCTACTTCTACTCGTACTATTCTCACCAGACCTACTAGGAGACC 360 vic.vic

TABLE 2-continued

Multiple sequence alignment of 472 bp fregment of mitochondrial cytochrome b gene of 221 animal species

```
TACTACTTATTCTGATTCTACTCCTACTCGTACTATTCTCACCAGACTTACTAGGAGACC 360 cam.bac
TGCTACTAATATTAATTCTCCTTATTCTCGTACTGTTCTCACCAGACTTATTAGGAGATC 360 arc.for
TCCTACTAATCTTGATTCTAATATTACTAGTAATATTTTCACCAGATCTGCTGGGAGACC 360 arc.gaz
TCTTACTAATCTTAATTCTAATATTACTAGTAATATTTTCACCAGATCTGCTAGGAGACC 360 eum.jub
TCCTACTAATCTTAATCCTAATACTACTAGTAATATTTTCACCAGACCTGCTGGGAGACC 360 zal.cal
TCCTACTAATCTTAACCCTAATACTACTAGTAATATTTTCACCGGACCTGCTGGGAGACC 360 odo.ros
TCATTCTAATCCTAATCCTAATACTACTAGTACTATTCTCACCAGATTTACTGGGAGACC 360 pho.fasciata
TACTCCTCATCCTAGTCCTAATACTACTAGTACTATTCTCACCCGACCTACTAGGAGACC 360 pho.gro
TACTCCTCATCCTGGTCCTTATACTACTAGTACTGTTCTCACCCGACCTACTGGGAGACC 360 pho.vit
TACTTCTCATTCTAGTCCTGACACTACTAGTGCTATTCTCACCCGACCTGTTAGGAGACC 360 cys.cri
TACTCCTCATCCTAGTTCTAACACTACTAGTGCTATTCTCACCCGATCTGCTAGGAGACC 360 hyd.lep
TATTCCTCATTCTAACCCTAATACTACTAGTATTATTCTCACCCGACCTACTAGGAGACC 360 lep.wed
TACTCCTCATTCTAACCGTAATATTACTAGTATTATTCTCACCCGACCTGCTAGGAGATC 360 mir.leo
TACTTCTTATTCTAACGCTAATACTATTAGTGTTATTCTCACCCGACTTATTAGGAGACC 360 eri.bar
TACTTCTAATCCTAGTTCTTATACTTCTAGTGCTATTCTCACCCGACCTACTGGGAGATC 360 mon.sch
TACTCCTTATCCTAATTCTAATACTACTAGTACTATTCTCACCCGACTTACTAGGAGAGC 360 hela.mal
TACTTCTTACCCTAGCCCTAACAACCCTAGTTCTATTCTCGCCCGACTTACTAGGAGACC 360 sel.thi
TACTTCTCATCCTAGCCTTAGCAACTCTAGTCCTATTCTCGCCCGACTTACTAGGAGACC 360 ail.ful
TACTCCTTATCCTAATTCTCATGACATTAGTACTATTCTTACCTGACTTGCTTGGTGATC 360 fel
TAGTACTAGTTTTAACACTCATACTACTCGTCCTATTTTCACCAGACCTGCTAGGAGACC 360 can
TACTCCTACTCCTAATCCTAATATCACTAGTTTTATTTTCACCTGACCTATTAGGAGACC 360 tal
TAATCCTAATTATAGCTCTATCATCATTAGTATTATTTTCACCTGACCTACTAGGAGACC 360 gla.sab
TAATCCTCATCTTAATCTTCATAACCCTAGTTCTCTTCACCCCTGATCTTGTAGGAGACC 360 gla.vol
TAATCCTTATGTTAATCTTCATAACCCTAGTTCTCTTCACCCGGGATCTTCTAGGAGACC 360 hyl.pha
TTATTCTTCTCCTAATCTTTATAAACTTAGTACTATTTTCGGGCGATCTTTTAGGAGACC 360 pet.set
TTATTCTTCTCCTAATCTTTATAAACTTAGTACTATTCTCCCCCGATCTTTTAGGAGACC 360
```

TABLE 2-continued

Multiple sequence alignment of 472 bp fregment of mitochondrial cytochrome b gene of 221 animal species

```
bel.pea
TAATCTTCGGCCTTATATTTACAACCCTTATTCTATTCGCCCCTGATCTCCTAGGAGACC   360 pte.mom
TTCTCCTTGGCCTCCTATTCATAATCTTAGTCCTCTTTACTCCAGACCTCCTTGGAGACC   360 gala. demi
TTATTCTCTTACTAACTCTGTTCTCCCTAGTAATATTCTCCCCGGACCTGCTAGGAGACC   360 pero.pot
TCTTTCTTCTACTAATCCTACTCACCCTAGTCCTATTCTCCCCAGACCTATTAGGAGACC   360 gala.mat
TCTTCTTACTACTATGCCTATTCTCTCTAGTACTATTTTCCCCGATCTGTTAGGAGACC   360 gala.moh
TCCTCTTACTATTATCCCTATTCTCTCTAGTACTATTCTCCCCTGACCTGCTGGGAGACC   360 oto.gar
TCCTCCTCCTTCTAACCCTATTCTCCCTAGTCCTATTCTCCCCGACCTTCTAGGAGACC   360 lor.tar
TTGCTCTCTTAATCACCTTATCAACTCTAGTTCTATTCTCCCCTGACCTTTTAGGAGACC   360 nyc.cou
TTTTCCTATTAGCAACCCTATCTATTCTAGTGTTATTCTCCCCTGACCTCCTAGGAGACC   360 mus
TAATCATATTCTTAATTCTCATAACCCTAGTATTATTTTTCCCAGACATACTAGGAGACC   360 gorr
TCCTCTTTCTCCTGACCTTGATAACATTAACACTATTCTCACCAGACCTCCTAGGAGACC   360 homo
TTCTCTTCCTTCTCTCCTTAATGACATTAACACTATTCTCACCAGACCTCCTAGGCGACC   360 dug.dug
TCCTCCTCATTCTAGTCTTACTCCTACTAACCCTGTTCTCCCCGGACATACTGGGAGACC   360 ele.max
TTATCCTAATTTTACTCCTTCTACTCTTAGCCCTACTATCTCCAGACATACTAGGAGACC   360 afr.con
CACTCATGCTCATTCCATTCCTGACACTAGCCCTACTCTCCCCCAACCTCTTAGGTGATC   360 pavo.mut
CTCTTATATTTATCCCATTCCTAACACTAGCCCTATTCTCCCCCAATCTCCTAGGTGACC   360 tra.bly
CACTCATGCTCACCCCCCTCCTCACACTAGCATTATTCTCACCGAACCTATTAGGCGACC   360 tra.sat
CACTCATGCTCACCCCCCTCCTCACACTAGCCTTATTCTCACCAAACCTACTAGGTGATC   360 tra.cob
CACTCATACTCACTCCTCTCCTCACACTAGCCTTATTTTCAGCAAACCTACTAGGTGACC   360 tra.tem
CACTCATACTCACTCCCCTCCTCACACTAGGCTTATTTTCACCAAACCTACTAGGTGATC   360 arg.arg
CACTCATACTCGGTCCATTCCTTACACTAACCCTATTCTACCCAAACCTACTAGGTGACC   360 cat.wal
CACTTATATTCACCCCATTCCTAACACTAGCCCTATTCTCACCAAATCTTCTGGGCGACC   360 cro.cro
CACTTATACTCACCCCATTCCTAACACTAGCCCTATTCTCACCTAACCTTCTGGGCGACC   360 sym.ree
CACTTATACTCACCCCATTCCTCACACTAGCCCTATTCTCACCTAACCTGCTAGGCGACC   360 bam.tho
CCCTTATATTCATCCCATTCCTGACACTAGCCCTATTCTCCCCTAACCTCCTAGGAGACC   360
```

TABLE 2-continued

Multiple sequence alignment of 472 bp fregment of mitochondrial cytochrome b gene of 221 animal species

```
fra.fra
CCCTTATATTCATCCCTCTCCTTACACTAGCCCTATTCTCCCCCAACCTCCTAGGCGACC  360 ith.cru
CACTTATACTGATCCCCTTTCTTACACTAGTCCTATTTTCCCCCAAGCTCCTAGGAGATC  360 ant.par
TACTCATACTACTCCCACTCATAACCCTAGCTCTATTCTCACCAAACTTACTAGGAGACC  360 ant.vir
TACTCATACTACTCCCACTCATAACCCTAGCTCTATTCTCACCAAACTTACTAGGAGACC  360 gru.ant.ant
CACTCATACTACTTCCACTCATAACCCTAGCCCTATTCTCACCAAACCTACTAGGAGACC  360 gru.ant.gil
CACTCATACTACTTCCACTCATAACCCTAGCCCTATTCTCACCAAACCTACTAGGAGACC  360 gru.ant.sha
CACTCATACTACTTCCACTCATAACCCTAGCGCTATTCTCACCAAACCTACTAGGAGACC  360 gru.leu
TACTCATACTACTTCCACTCATAACCTTAGCCCTATTCTCACCAAACTTACTAGGAGACC  360 gru.can.pra
TACTCATACTACTTCCACTCATAACCCTAGCTCTATTTTCACCAAACTTACTAGGAGACC  360 gru.can.row
TACTCATACTACTTCGACTCATAACCCTAGCTCTATTTTCACCAAACTTACTAGGAGACC  360 gru.can.tab
TACTCATACTACTTCCACTCATAACCCTAGCTCTATTTTCACCAAACTTACTAGGAGACC  360 gru.can.can
TACTCATACTACTTCCACTTATAACCCTAGCTCTATTCTCACCAAACTTACTAGGAGACC  360 gru.ame
CACTCATATTACTTCCACTCATAACCCTAGCTCTATTTTCACCAAACTTACTAGGAGACC  360 gru.gru
TACTCATATTACTTCCACTCATAACCCTAGCTCTATTTTCACCAAACTTACTAGGAGACC  360 gru.mon
TATTCATATTACTTCCACTCATAACCCTAGCTCTATTTTCACCAAACTTACTAGGAGACC  360 gru.nig
TATTCATATTACTTCCACTCATAACCCTAGCTCTATTTTCACCAAACTTACTAGGAGACC  360 gru.jap
CACTCATATTACTTCCACTCATAACCCTAGCCCTATTCTCACCAAACTTACTAGGAGACC  360 cic.boy
CAGTCCTACTTCTGCCACTAACCACCCTGGCCCTATTCTCACCCAACCTACTAGGTGACC  360 rhe.ame
CTCTCATATTTATCCCGGTCCTAACCCTAGCCTTCTTCTCACCCAACCTCCTAGGGGACC  360 ant.alb
CAGTAATACTCCTCCTCCTAACCTCCCTAGCCCTCTTCTCCCCCAACCTACTAGGAGACC  360 fal.fam
TACTCATATACCTCCCCCTAATAACCTTAGCCCTATTGACTCCCAACCTACTAGGAGACC  360 fal.ver
TACTCATATACCTCCCCCTAATAACCCTAGCCCTATTTACGCCAAACTTACTAGGAGACC  360 fal.per
TACTCATATACCTGCCCCTAATAACCGTAGCCCTATTTACCCCAAACCTGCTAGGAGACC  360 fal.spa
TGCTCATACTCCTGCCCCTAATAGCCCTAGCCCTATTCACCCCAAACCTGCTAGGAGACC  360 ayt.ame
TCCTCATGCTCACCCCCCTAATAGCACTAGCCCTATTCTCACCAAACCTCCTAGGAGACC  360 smi.sha
```

TABLE 2-continued

Multiple sequence alignment of 472 bp fregment of mitochondrial
cytochrome b gene of 221 animal species

CAATCATACTAACACCACTAATAACCCTAGCCATATTCTCTGCTAACCTCCTAGGAGACC 360 vid.cha
TACTAATATTCGCACTCCTAGCTTCCATAGCCCTATTCTCCCCAAACATACTAGGAGATC 360 chry.pic
TTCTAATACTAACCCTCCTACTAACCCTAACACTATTCTCTCCAAACCTTTTAGGGGACC 360 emy.orb.kur
TCCTAATACTAGCCTTCCTGCTAACCCTAACACTATTCTCTCCTAACCTTCTAGGAGACC 360 che.mud
TTTTAATACTAACTTTCCTCCTAACCTTAACACTTTTCTCCCCTACTTACTAGGAGACC 360 eum.egr
TCATTATACTGTCTGTTCTACTAGCCCTCGCCCTTTTCTCACCAAACCTTCTAGGCGACC 360
                *                   *   *   *   *   *   *
**   *   * aep.mel
CAGACAANNACATCCCCGCAAACCCACTCAACACCCCTCCCCACATCAAGCCCGAATGGT 420 ore.ore
CAGATAACTACACCCCAGCAAACCCACTCAACACTCCCCCTCACATTAAACCAGAATGGT 420 add.nas
CAGACAATTATACCCGAGCAAATCCACTTAGCACGCCCCCTCACATCAAACCTGAATGAT 420 ory.dam
CAGATAATTATACACCAGCAAATCCACTTAACACACCGCCTCACATCAAACCCGAATGAT 420 hip.equ
CAGACAACTATGCCCCAGCAAACCCACTCAACACGGCCCCTCACATTAAACCCGAATGAT 420 alc.bus
CAGACAACTACACCCCGCGAACCCACTTAACACACCCCCTCACATCAAGCCCGAATGAT 420 sig.lic
CAGACAACTACACCCCGCGAACCCACTTAACACACCCCCTCACATCAAGCCCGAATGAT 420 bea.hun
CAGACAACTACACCCCGCAAACCCACTTAATACACCCCCTCACATCAAACCCGAATGAT 420 dam.lun
CAGAGAACTACACCCCTGGAAACCCACTCAACACGCCCCCTCACATGAAGCCCGAGTGAT 420 con.tau
CAGACAACTACAGCCCCGCAAATCCACTCAACACACCCCCTCACATCAAGCCCGAATGAT 420 amm.ler
CAGACAACTATACCCCAGCAAATCCACTCAACACACCCCCTCATATTAAACCTGAATGAT 420 pse.nay
CAGACAACTACACCCCAGCAAACCCACTCAACACACCCCCTCACATTAAACCCGAGTGAT 420 cap.ibe
CAGACAACTATACCCCAGCAAACCCACTCAATACACCCCCTGACATTAAACCTGAATGAT 420 hem.jem
CAGACAACTATACCCCAGCAAATCCACTCAACACACCCCCTCACATTAAACCTGAATGAT 420 cap.fal
CAGATAACTATATCCGAGCAAATCCACTCAATACACCCGCTCATATCAAACCTGAGTGGT 420 rup.pyr
CAGATAACTATACCCCAGCGAACCCACTCAACACACCCCCTCACATCAAACCCGAATGAT 420 rup.rup
CAGATAATTACACCCCAGCGAACCCACTCAACACACCGCCTCACATTAAACCCGAGTGAT 420 nem.cau
CAGACAACTATACCCCAGCAAACCCACTCAGCACACCCCCTCACATTAAACCTGAATGAT 420 bud.tax.tax
CAGATAATTATACCCCAGCAAATCCACTCAACACACCCCCTCACATCAAACCTGAATGAT 420

TABLE 2-continued

Multiple sequence alignment of 472 bp fregment of mitochondrial
cytochrome b gene of 221 animal species pan.hod
CAGACAATTATACCCCAGCAAACCCCTCAACACACCACCCCACATTAAACCTGAATGGT 420 ovi.amm
CAGACAACTACACCCCAGCAAACCCACTTAACACTCCCCCTCACATCAAACCTGAATGAT 420 ovi.vig
CAGACAACTACACCCCAGCAAACCGACTTAACACTCCCCCTCACATCAAACCTGAATGAT 420 cap.cri
CAGACAACTACACTCCAGCAAACGCACTCAACACACCCCCTGACATCAAGCCCGAGTGAT 420 ovi.mos
CAGACAACTATACCCCAGCAAACCCACTCAACACACCCCCTCACATTAAACCAGAGTGAT 420 ore.ame
CAGACAACTACACTCCAGCAAACCCGCTAATACACCTCCCCATATCAAAGCCGGAATGAT 420 cep.dor
CAGATAACTACACCCCAGCAAACCCACTCAACACACCTCCGCATATTAAACCCGAATGAT 420 cep.max
CAGATAATTATACTCCAGCAAACCCACTTAACACACCTCCCCACATCAAGCCCGAATGAT 420 bis.bon
CAGATAACTACACCCCAGCAAATCCACTTAACACACCTCCCCACATCAAACCCGAATGAT 420 bos.gru
CAGACAACTACACCCCAGCAAATCCACTCAACACACCTCCCCAGATCAAACCCGAATGAT 420 bos.tra
CAGACAACTACACCCCAGCAAACCCACTTAGCACACCTCCCCATATTAAGCCCGAATGGT 420 bub.min
CAGACAACTACACCCCAGCAAACCCACTCAACACACCTCCCCATATCAAACCTGAATGGT 420 buba.bub
CAGACAACTACACCCCAGCAAACCCACTCAACAGACCTCCCCACATCAAGCCTGAATGGT 420 tra.ang
CCGACAACTACACCCCAGCGAACCCCCTCAATACACCTCCCCATATCAAACCTGAATGAT 420 tra.eur
CCGACAACTACACGCCAGCAAACCCACTCAACACACCACCTCATATCAAACCTGAATGAT 420 kob.eli
CTGACAACTATGCCCCAGCAACCCACTTAACACGCCCCTCACAAATTAAACCTGAATGAT 420 kob.meg
CTGACAATTATACCGCAGCAAACCCACTTAATACACCTCCCCATATTAAACCCGAATGAT 420 red.aru
CCGACAATTATACTCCAGCAAATCCACTCAACACACCCCCTCATATTAAACCCGAATGAT 420 red.ful
CGGACAATTACACCCCAGCAAAGCCACTCAACACACCCCCTCACATCAAACCAGAATGGT 420 neo.mos
CAGACAACTACACCCCCGCAAACCCTCTTAACACGCCTCCCCATATCAAACCCGAATGAT 420 pel.cap
CTGACAATTACACCCCTGCAAACCCGCTCAACACACCCCCTCATATCAAACCCGAATGAT 420 gaz.dam
CAGACAACTACACACCAGCAAATCCACTCAATACACCCCCACATATTAAGCCTGAGCGAT 420 our.our
CAGACAACTATACACCAGCAAACCCACTAAATACACCCCGACATATTAAACCTGAGTGGT 420 ant.cer
CAGACAACTATACACCAGCAAACCCACTTAATACACCCCCACATATCAAGCCCGAATGAT 420 sai.tat
CAGACAACTACACRCCAGCAAACCCACTTAAGACACGCCCACATATTAAACCCGAATGAT 420 mad.kir

TABLE 2-continued

Multiple sequence alignment of 472 bp fregment of mitochondrial cytochrome b gene of 221 animal species

```
GAGAGAACTACACACCAGCAAATCCCCTTAACACGCCCCCACACATTAAACCTGAATGAT 420 rap.mel
CAGACAACTATACACCAGCAAACCCACTCAACACACCCCCACATATCAAACCCGAATGGT 420 gaz.gaz
CACACAACTATACACCAGCAAATCCACTCAACACACCCCCACACATCAAACCTGAATGGT 420 ant.ame
CCGACAACTACACACCAGCTAACCCACTCAACACTCCCCCACACATTAAGCCAGAATGAT 420 hyd.ine
CAGACAATTATACTCCAGCAAACCCACTCAATACACCCCCTCACATTAAACCAGAATGAT 420 mun.mun
CCGACAATTATACCCCAGCAAACCCACTCAATACACCCCCTCACATCAAGCCTGAATGAT 420 alc.alc
CAGACAACTACACCCCAGCTAATCCACTCAACACACCCCCTCATATTAAGCCTGAATGGT 420 cer.ela.kan
CAGACAACTATACCCCAGCAAATCCACTCAATACACCCCCTCACATTAAACGTGAATGAT 420 cer.ela.xan
CAGACAACTATACCCCAGCAAATCCACTCAACACACGCCCTCACATTAAACCTGAATGAT 420 cer.ela.can
CAGACAACTATACGCCAGCAAATCCACTCAACACACCCCCTGACATTAAACCTGAATGAT 420 cer.nip.cent
CAGACAACTATACCCCAGCAAATCCACTCAACACACCCCCTCACATCAAACCTGAATGAT 420 cer.nip.yes
CAGACAACTATACCCCAGCAAATGCACTCAACACACCCCCTCACATCAAACCTGAATGAT 420 cer.nip.ker
CAGACAACTACACCCCAGCAAATCCGCTCAACACACCCCCTCACATCAAACCTGAATGAT 420 cer.nip.pul
CAGACAACTACACCCCAGCAAATCCGCTCAACACACCCCGTCACATCAAACCTGAATGAT 420 cer.nip.nip
CAGACAACTACACCCCAGCAAATCCGCTCAACACACCCCCTCACATCAAACCTGAATGAT 420 cer.ela.sco
CAGATAACTACACCCCAGCAAACCCACTCAACACACCCCCTGATATTAAACCTGAATGAT 420 cer.dam
CAGACAAATACACTCCAGCAAATCCACTCAACACACCTCCTCATATTAAACCCGAATGAT 420 ran.tar
CAGACAACTATACCCCAGCAAACCCACTCAACACTCCCCCTCATATTAAACCTGAATGAT 420 mos.fus
CGGACAATTATACCCCAGCAAACCCATTAAATACGCCCCCACATATTAAACCCGAATGAT 420 mos.leu
CGGACAATTATACCCCAGCAAACGCATTAAATACACCCCCACATATTAAACCCGAATGAT 420 mos.chr
CGGACAATTATACCCCGGCAAACCCATTAAATACGCCCCCACATATTAAACCCGAATGAT 420 mos.ber
CGGACAATTATACCCCAGCAAACCCATTAAACACACCACCACATATTAAACCCGAATGAT 420 mos.mos
CGGACAACTATACTCCAGCAAACCCATTAAATACACCTCCACATATTAAACCCGAATGGT 420 tra.jav
CAGATAACTACACCCCCGCCAACCCCCTTAACACACCACCCCATATCAAACCCGAATGAT 420 trag.nap
GCGACAATTACACTCCGGCAAACCGCCTCAACACACCACCTCATATTAAGCCAGAGTGGT 420 bala.acu
CCGACAACTATACCCCAGCAAACCCACTCAGTACCCGAGCACACATTAAACCAGAATGAT 420
```

TABLE 2-continued

Multiple sequence alignment of 472 bp fregment of mitochondrial
cytochrome b gene of 221 animal species

```
bala.bon
CCGACAACTACACCCCAGCAAACCCACTCAGTACCCCAGCACACATTAAACCAGAATGAT 420 bala.bor
CAGACAACTACACCCCAGCAAATCCACTCAGTACCCCAGCACACATTAAACCAGAATGAT 420 bala.edi
CAGACAACTACACTCCAGCAAATCCACTCAGTACCCCAACACACATTAAACCAGAATGAT 420 esch.rob
CAGACAACTATACCCCAGCAAACCCACTCAGCACCCCAACACATATTAAACCAGAGTGAT 420 bala.mus
CAGACAACTACACCCCAGCAACCCACTCAGTACCCCAGCACACATTAAACCAGAGTAAAT 420 mega.nov
CAGATAACTACACCCCAGCAAACCCACTCAGTACCCCAGCACACATTAAACCAGAGTGAT 420 bala.phy
CAGACAACTATACCCCAGCAAACCCACTCAGTACCCCAGCACACATTAAACCAGAATGGT 420 cap.mar
CTGACAACTAGACCCCAGCAAATCCCCTCAGCACCCCAGCACACATCAAGCCAGAATGAT 420 ceph.com
CTGATAACTATACCCCAGCAAATCCATTAAGCACCCCGCACACATCAAACCAGAGTGAT 420 ceph.eut
CTGATAACTATACCCCAGCAAATCCATTAAGCACCCCGCACACATCAAACCAGAATGAT 420 lage.obl
CTGATAACTATACCCCAGCAAATCCATTAAGCACCCCGCACACATGAAACCAGAATGGT 420 ceph.hea
CTGATAACTATACCCCAGCAAATCCATTAAGCACCCCGCACACATCAAACCAGAATGAT 420 ceph.hec
CTGATAACTATACCCCAGCAAATCCATTAAACACCCCGCACACATCAAACCAGAATGAT 420 lage.aus
CTGACAACTATACCCCAGCAAATCCATTAAGCACCCCGCACACATCAAACCAGAATGAT 420 lage.cru
CTGACAACTATACCCCAGCAAATCCATTAAGCACCCCGCACACATCAAACCAGAATGAT 420 lage.obs
CTGATAACTATACCCCAGCAAATCCATTAAGCACCCCAGCACACATCAAACCAGAATGAT 420 lisso.bor
CTGATAACTACACCCCAGCAAATCCATTAAGCACCCCTGCACACATCAAACCAGAATGGT 420 lisso.per
CTGATAACTACACCCCAGCAAATCCATTAAGCACCCCTGCACACATCAAACCAGAATGGT 420 glo.mac
CTGATAACTATACTCCAGCAAATCCACTAAGCACCCCTGCACACATCAAACCAGAATGAT 420 glo.mel
CTGATAACTATACTCCAGCAAACCCACTAAGCACCCCTGCACACATCAAACCAGAATGAT 420 fere.att
CTGATAACTATACTCCAGCAAACCCACTAAGCACCCCTGCACACATCAAACCAGAGTGAT 420 pepo.ele
CTAACAACTATACCCCAGCAAACCCACTAAGCACCCCTGCACACATCAAACCAGAATGAT 420 gram.gri
CTGATAACTACACTCCAGCAAACCCGCTAAGCACCCCTGCACACATCAAACCAGAATGAT 420 pse.cra
CTGATAACTATATTCCAGCAAACCCACTAAACAGCCCTGCACACATCAAACCAGAATGAT 420 lage.acu
CTGATAACTACACTCCAGCAAATCCACTAAGCACCCCTGCACACATCAAACCAGAATGAT 420
```

TABLE 2-continued

Multiple sequence alignment of 472 bp fregment of mitochondrial cytochrome b gene of 221 animal species

```
orci.bre
CTGACAACTATACCCCAGCAAATCCACTAAGCACCCCTGCACACATCAAACCAGAATGAT 420 orca.bre
CTGATAACTATACTCCAGCAAATCCACTAAGCACCCCTGCACAGATCAAACCAGAATGAT 420 del.cap
CTGATAACTATACCCCAGCAAATCCACTAAGCACCCCTGCACATATCAAACCAGAATGAT 420 del.tro
CTGATAACTATACCCCAGCAAATCCACTAAGCACCCCTGCACATATCAAACCAGAATGAT 420 del.del
CTGATAACTATACCCCAGGAAATCCACTAAGCACCCCTGCACACATCAAACCAGAATGAT 420 sten.cly
CTGACAACTATACCCCAGCAAATCCACTAAGCACCCCTGCACACATCAAACCAGAATGAT 420 sten.coe
CTGACAACTATACCCCAGCAAATCCACTAAGCACCCGTGCACACATCAAACCAGAATGAT 420 tur.adu
CTGATAACTATATCCCAGCAAATCCACTAAGTACCCCCGCACACATCAAACCAGAGTGAT 420 sten.fro
CTGACAATTATACCCCAGCAAATCCACTAAGCACCCCTGCACACATCAAACCAGAATGAT 420 saus.chi
CCGATAACTATACCCCAGCAAATCCACTAAGCACCCCTGCACACATCAAACCAGAATGAT 420 sten.lon
CTGATAACTATACCCCAGCAAATCCACTAAACACCCCTGCACACATCAAACCAGAATGAT 420 turs.tru
CTGATAACTACACCCCAGCAAACCCACTAAGCACCCGTGCACACATCAAACCAGAATGAT 420 lage.alb
CCGATAACTATACCCCAGCAAATCCACTAAGCACTCCTGCACACATCAAACCAGAATGGT 420 sten.bre
CCGACAACTATACCCCAGCAAATCCACTAAGCACCCCTGCACACATCAAACCAGAATGGT 420 sota.flu
CCGACAACTATACTCCAGCAAATCCACTTAACACCCCTGCACACATCAAACCAGAATGAT 420 del.leu
CAGACAATTACACCCCAGCAAACCCACTAAACACCCCCGCACACATCAAACCAGAATGGT 420 mono.mon
CTGACAATTATACCCCAGCAAACCCACTAAGCACCCCTGCACACATCAAACCAGAATGAT 420 plat.gan
CCGATAACTACACCCCAGCAAACCCGCTTAATACCCCAGCACATATCAAACCAGAGTGAT 420 plat.min
CCGATAACTACACCCCAGCAAACCCGCTTAATACCCCAGCACATATCAAACCAGAGTGAT 420 kogi.bre
CTGACAACTACACCGCAGCAAACCCACTAAGCACCCCGGCACACATTAAACCAGAATGAT 420 kogi.sim
CCGACAACTATACCCCAGCAAACCCACTAAGCACCCCCGCACACATTAAACCAGAATGAT 420 phys.cat
CTGACAACTACACCCCAGCAAATCCACTAAATACCCCAACACACATCAAACCAGAATGGT 420 lipo.vex
CTGATAATTATACCCCAGCAAACCCACTAAACACTCCCGCACACATCAAACCAGAATGAT 420 phoc.sin
CCGATAACTACATTCCAGCAACCCAACTAAGCACCCCAGCACACATTAAACCAGAATGAT 420 bera.bai
CCGACAACTATACCCCGGCAAACCCGCTCAGCACCCCAACACATATTAAGCCAGAATGAT 420 ziph.car
```

TABLE 2-continued

Multiple sequence alignment of 472 bp fragment of mitochondrial cytochrome b gene of 221 animal species

```
CCGATAACTATACCCCAGCAAATCCACTCAGCACCCGAGCACACATTAAGCCAGAATGAT  420 meso.eur
CCGACAATTAGACCCCAGCAAAGCCACTTAATACTCCAGCACACATCAAACCAGAATGAT  420 meso.bid
CCGACAACTATACCCCAGCAAACCCACTCAGCACCCCAGCCCACATCAAACCAGAGTGGT  420 meso.den
CCGATAATTATACTCCAGCAAACGCACTCAACACTCCAGCACACATCAAACCAGAGTGGT  420 hype.amp
CTGATAACTATACCCCAGCAAACCCACTGAGCACTCCAGCACACATCAAACCAGAATGGT  420 meso.per
CTGACAATTACACTCCAGCAAACCCACTTAGCACCCCAGCACATATTAAACCAGAATGAT  420 pont.bla
CAGACAACTATATCCCAGCAAACCCCATGAATACCCCAGAGCACATTAAACCAGAATGGT  420 hex.lib
CAGACAACTACACCCCGCAAACCCCCTTAGCACACCACCACACATCAAACCAGAATGAT  420 hipp.amp
CAGACAACTACACCCCGCAAACCCCCTTAGCACACCACCACAGATTAAACCAGAATGAT  420 dic.sum
CGGACAACTACACACCCGCCAAACCCTCTCAGCACCCCTCCACACATTAACCAGAATGGT  420 rhin.son
CAGACAACTACATCCCAGCCAAAGCCTCTCAGCACCCCTCCACATATCAACCAGAATGGT  420 cera
CTGACAACTACACCCCTGCCAATCCTCTCAGCACTCCCCCACATATCAAACCAGAATGAT  420 equu
CAGACAACTACACCCCAGCTAACCCCCTCAGCACTCCCCCTCATATTAAGCCAGAATGGT  420 baby.bab
CGGACAACTATACTCCAGCAAACCCACTAAATACACCACCCCACATTAAGCCAGAATCAT  420 phac.afr
CAGACAACTATACCCCAGCAAACCCATTAAACACACCACCCCACATCAAACCAGAATGAT  420 sus.bar
CAGACAACTACACCCCAGCAAACCCACTAAACACCCCAGCCCATATTAAACCAGAATGAT  420 sus.sor.ewb3
CAGACAACTACACCCCAGCAAACCCACTAAACACCCCACCCCATATTAAACCAGAATGAT  420 lama.gla
CCGACAACTATACTCCCGCTAACCCCCTCAACACACCGCCCCATATTAAACCAGAATGAT  420 lama.gua
CCGACAACTATACTCCCGCTAACCCCCTCAACACACCGCCTCATATTAAACCAGAATGAT  420 vic.vic
CCGACAACTATACCCCGCTAACCCCCTTAACACACCACCCCACATTAAACCAGAATGAT  420 cam.bac
CTGACAACTATACTCCGGCTAACCCGCTCAATACACCACCACACATTAACCCGGAATGAT  420 arc.for
CAGACAACTACACCCCAGCCAAGCCCCTCAGCACTCCACCACATATTAAACCTGAATGAT  420 arc.gaz
CAGACAACTACATCCCAGCCAACCCCCTCAGTACTCCACCACATATCAAACCTGAATGGT  420 eum.jub
CAGACAACTACATCCCAGCCAACCCCCTCAGCACTCCACCACATATTAAACCCGAATGAT  420 zal.cal
CAGACAACTATATTCCAGCCAACCCCCTCAGCACTCCACCACATATTAAACCTGAGTGAT  420 odo.ros
CGGACAATTACACCCCAGCCAACCCTCTCAGCACCCCACCCCATATCAAACCCGAATGAT  420
```

TABLE 2-continued

Multiple sequence alignment of 472 bp fregment of mitochondrial
cytochrome b gene of 221 animal species pho.fasciata
CCGACAACTACACCCCTGCCAACCCGCTAAGCACCCCACCAGATATCAAGCCCGAATGAT 420 pho.gro
CCGACAACTACATCCGTGCCAATCCCCTAAGTACCCCACCACATATCAAGCCCGAATGAT 420 pho.vit
CCGACAACTATATGCCTGCCAATCCCCTAAGCACCCCACCACATATCAAACCTGAATGGT 420 cys.cri
CCGACAACTATACCCCTGCCAACCCCCTAAGTACCCGACCACATATTAAACCTGAATGAT 420 hyd.lep
CCGACAACTATATTCCTGCTAACCCCCTAAGCACCCCACCACATATCAAACCCGAATGAT 420 lep.wed
CCGACAACTATACTCCCGCTAATCCCCTAAGTACTCCACCACATATCAAACCCGAATGAT 420 mir.leo
CCGACAACTACACCCCTGCCAATCCCCTAAGCACCCGACCACATATTAAACCCGAATGAT 420 eri.bar
CCGACAACTACACTGCCGCTAACCCCCTAAGCACCCCACCACATATTAAGCCCGAATGAT 420 mon.sch
CTGACAACTACATCCCTGCCAACCCCTTAAACACTCCACCACACATTAAACCCGAATGAT 420 hela.mal
CTGACAACTACATCCCCGCAAATCCATTGAGCAGCCCACCCCACATCAAACCCGAATGGT 420 sel.thi
CTGATAACTATACCCCCGCAAACCCACTGAGCACCCCACCCCACATCAAACCCGAATGAT 420 ail.ful
CTGATAACTATATTCCCGCTAACCCATTAAGCACACCACCCCATATTAAACCTGAGTGGT 420 fel
CAGACAACTACATCCCAGCCAACCCTTTAAATACCCCTCCCCATATTAAACCTGAATGAT 420 can
CAGATAACTACACCCCTGCAAACCCCCTAAACACCCCTCCACATATTAACCCTGAGTGAT 420 tal
CAGACAATTACATCCCGGCAAACCCGCTAAACACACCACCCCATATTAAACCCGAATGGT 420 gla.sab
CAGACAACTATACCCCAGCCAACCCACTCAACACCCCTCCCCACATCAAACCAGAATGAT 420 gla.vol
CAGACAACTATACTCCAGCCAACCCACTCAACGGCGCTCCCCATATCAAGCCAGAGTGAT 420 hyl.pha
CTGACAACTACACCCCCGCCAACCCACTTAACACCCCTCCTCATATTAAACCAGAATGAT 420 pet.set
CTGACAACTACACCCCCGCCAACCCACTTAACACCCCTCCTCATATTAAACCAGAATGAT 420 bel.pea
CTGACAACTATACTCCGGCCAATCCACTTAACACCCCTCCCCACATTAAACCAGAATGAT 420 pte.mom
CCGACAACTATACCCCAGCCAACCCCCTCAACACTCCCCCTCATATCAAACCAGAGTGAT 420 gala.demi
CTGACAACTACACCCCCGCCAACCCCCTAAACACCCCACCACATATCAAACCAGAGTGAT 420 pero.pot
CTGACAACTACACCCCAGCCAACCCCCTAAACACCCCACCACATATCAAACCAGAATGGT 420 gala.mat
CAGACAATTTTACCCCCGCTAATCCCTTAAACACCCCACCACACATCAAACCAGAATGAT 420 gala.moh
CAGACAATTATATCCCTGCCAACCCCCTAAACACCCCACCACATATTAAACCAGAATGAT 420

TABLE 2-continued

Multiple sequence alignment of 472 bp fregment of mitochondrial cytochrome b gene of 221 animal species oto.gar
CAGACAACTACACCCCTGCCAACCCCCTAAACACACCGCCCCATATCAAACCCGAATGAT 420 lor.tar
CCGATAATTACACACCAGCTAACCCTTTAAACACCCCACCCCACATCAACCAGAAATGGT 420 nyc.cou
GCGACAACTATACCCCCGCCAACCCCCTTAGTCACCCCTCCACATATCAAACCAGAATGAT 420 mus
CAGACAACTACATACCAGCTAATCCACTAAACACCCCACCCCATATTAAACCCGAATGAT 420 gorr
CAGACAACTACACCTTAGCCAACGCCCTAAGCACCCCACCCCACATCAAACCCGAATGAT 420 homo
CAGACAATTATACCCTAGCCAACCCCTTAAACACCCCTCCCCACATCAAGCCCGAATGAT 420 dug.dug
CAGACAACTACACACCAGCCAACCCACTAAACACCCCTCCCCACATTAAACCAGAATGAT 420 ele.max
CTGACAACTACATACCAGCTGATCCACTAAATACTCCCCTACACATCAAACCAGAGTGAT 420 afr.con
CAGAAAACTTCACCCCAGCAAACCCTCTAGTAACTCCCCCACACATTAAACCAGAATGGT 420 pavo.mut
CAGAAAACTTTACCCCAGCAAACCCCCTAGTAACCCCCCCGCACATTAAACCAGAATGAT 420 tra.bly
CAGAAAACTTCACGCCAGCAAACCCACTAGTAACCCCTCCCCATATCAAACCAGAATGAT 420 tra.sat
GAGAAAACTTCACCCCAGCAAACCCACTAGTAACCCCTCCCCATATTAAACCAGAATGAT 420 tra.cob
CAGAAAACTTCACCCCAGCAAACCCATTGGTAACTCCTCCCCATATCAAGCCAGAATGGT 420 tra.tem
CAGAAAACTTCACCCCAGCAAACCCACTAGTAACTCCTCCCCATATCAAACCAGAATGAT 420 arg.arg
CAGAAAACTTCACCCCAGCAAACCCATTAGTAACTCCACCCCACATCAAGGGAGAATGAT 420 cat.wal
CAGAAAACTTCACCCCAGCAAATCCATTAGTAACCCCACCACACATTAAACCAGAATGGT 420 cro.cro
CAGAGAACTTCACCCCAGCAAACCCACTAGTAACCCCCCCTCACATTAAACCAGAATGAT 420 sym.ree
CAGAAAACTTCACCCCAGCAAACCCACTAGTAACCCCTCCTCACATTAAACCAGAATGAT 420 bam.tho
CAGAAAACTTCACCCCAGCAAACCCACTAGTAACCGCTCCACACATCAAACCAGAGTGGT 420 fra.fra
CCGAAAACTTCACCCCAGCAAACCCACTAGTAACTCCTCCCCACATCAAACCAGAATGAT 420 ith.cru
CAGAAAACTTTAGTCCAGCAAACCCCCTAGTAACCCCACCCCATATTAAACCAGAATGAT 420 ant.par
CAGAAAACTTCACGCCAGCAAACCCCCTAGTCACACCTCCCCATATCAAACCAGAATGAT 420 ant.vir
CAGAAAACTTCCCCCCAGCAAATCCCCTAGTCACACCTCCCTATATTAAACCAGAATGAT 420 gru.ant.ant
CAGAAAACTTCACCCCAGCAAACCCCCTAGTCACACCTCCTCATATCAAGCCAGAATGAT 420 gru.ant.gil
CAGAAAACTTCACCCCAGCAAACCCCCTAGTCAGACCTCCTCATATCAAGCCAGAATGAT 420 gru.ant.sha

TABLE 2-continued

Multiple sequence alignment of 472 bp fregment of mitochondrial cytochrome b gene of 221 animal species

```
CAGAAAACTTCACCCGAGCAAACCCCTAGTCACACCTCCCCATATCAAGCCAGAATGAT 420 gru.leu
CAGAAAACTTCACTCCAGCAAACCCCTAGTAACACCCCACATATTAAACCAGAATGAT 420 gru.can.pra
CAGAAAACTTCACCCCAGCAGACCCCTAGTCACACCTCCCCATATCAAACCAGAATGAT 420 gru.can.row
CAGAAAACTTCACCCCAGCAAACCCCTAGTCACACCTCCCCATATCAAACCAGAATGAT 420 gru.can.tab
CAGAAAACTTCACCCCAGCAAACCCCTAGTCACACCTCCCCATATCAAACCAGAATGAT 420 gru.can.can
CAGAAAACTTCACCCCAGCAAACCCCTAGTCACACCTCCCCATATCAAACCAGAATGAT 420 gru.ame
CAGAAAACTTCACCCCAGCAAACCCCTAGTGACACCTCCCCATATTAAGCCGGAATGAT 420 gru.gru
CAGAAAAGTTCACCCCAGCAAACCCTCTAGTCACACCTCCCCATATTAAGCCGGAATGAT 420 gru.mon
CAGAAAACTTCACCCCAGCAAACCCCTAGTCACACCTCCTCATATTAAACCGGAATGAT 420 gru.nig
CAGAAAACTTCACCCCAGCAAACCCCTAGTCACACCTCCCCATATTAAGCCGGAATGAT 420 gru.jap
CAGAAAACTTCACCCCAGCAAACCCCTAGTTACACCTCCCCATATTAAGCCGGAATGAT 420 cic.boy
CAGAGAACTTCACCCCAGCCAACCCCTAGTCACACCCCCTCACATGAAGCCAGAGTGGT 420 rhe.ame
CAGAAAACTTCACGCCAGCCAACCCCCTAGTTACACCCCCTCACATCAAGCCAGAATGAT 420 ant.alb
CAGAAAAGTTGACACCAGCAAACCCCCTGGTAACTCCCCCCATATTAAGCCAGAATGGT 420 fal.fam
CAGAAAACTTTACACCAGCAAATCCCCTAGTCACCCCCCCACACATCAAACCAGAATGAT 420 fal.ver
CAGAAAACTTCACACCAGCAAACCCCCTAGTCACACCCCCACACATGAAACCAGAATGAT 420 fal.per
GAGAAAACTTTACACCAGCAAATCCCTTAGTCACCCCCCCACAGATCAAACCAGAATGAT 420 fal.spa
CAGAAAACTTCACACCAGCGAACCCCCTAGTCACCCCACCACACATCAAACCAGAATGAT 420 ayt.ame
CAGAAAACTTTACCCCAGCAAACCCACTAGTAACCCCACCCCACATCAAACCAGAATGAT 420 smi.sha
CAGAAAATTTCACACCCGCCAACTCCCTCGTCACTGCCCCTCATATCAAACCCGAATGAT 420 vid.cha
CAGAAAACTTCACTCCGGCCAACCCCCTAATCACACCACCACATATCAAACCCGAATGAT 420 chry.pic
CAGATAACTTCACACCGGCCAACCCCCTATCTACCCCACCACATATTAAACCAGAATGAT 420 emy.orb.kur
CAGATAACTTTACACCAGCTAACCCGCTATCCACCCCACCACATATTAAGCCAGAGTGAT 420 che.mud
CAGACAACTTCACACCAGCCAACCCTCTATCCACTCCTCCCCACATCAAACCAGAATGAT 420 eum.egr
CAGAAAATTTTACCCCAGCAAACCCCCTGGTAACACCCCCACATATTAAGCCAGAGTGAT 420
                *  * **        ** * *       *     ** ** **
**  *  *
```

TABLE 2-continued

Multiple sequence alignment of 472 bp fregment of mitochondrial cytochrome b gene of 221 animal species

```
aep.mel
ACTTCCTGTTNGCATACGCAATCCTACGATCAATCCCCAATAAACTAGGAGG 472 ore.ore
ATTTNCTATTNGCATATGCAATCCTACGATCAATCCCCAATAAACTAGGAGG 472 add.nas
ATTTCCTATTTGCATACGCAATTCTACGATCAATCCCCAACAAACTAGGAGG 472 ory.dam
ATTTCCTATTTGCATATGCGATCTTACGATCAATCCCCAACAAACTAGGAGG 472 hip.equ
ATTTTTTATTCGCGTACGCAATTCTACGATCGATCCCCAATAAGCTGGGAGG 472 alc.bus
ATTTCCTATTTGCATATGCAATCCTACGATCAATCCCTAACAAACTAGGAGG 472 sig.lic
ATTTCCTATTTGCATACGCAATCCTACGATCAATCCCTAACAAACTACGAGG 472 bea.hun
ATTTCCTATTTGCATACGCAATCCTACGATCAATCCCCAATAAACTAGGAGG 472 dam.lun
ATTTCCTATTCGCATACGCAATCCTACGTTCCATCCCCAACGAGCTAGGAGG 472 con.tau
ACTTCCTATTTGCATATGCAATCCTACGATCAATCCCCAACGGACTAGGAGG 472 amm.ler
ACTTCCTATTTGCATACGCAATCCTACGATCAATCCCTAATAAACTGGGAGG 472 pse.nay
ACTTCCTATTTGCATACGCAATCCTACGATCAATTCCCAACAAGCTAGGAGG 472 cap.ibe
ATTTCCTATTTGCATACGCAATCCTACGATCAATTCCCAACAAACTAGGGGG 472 hem.jem
ATTTTCTATTTGCATACGCGATCCTACGATCAATTCCCAACAAACTAGGAGG 472 cap.fal
ACTTCCTATTTGCATACGCAATCCTACGATCAATCCCCAACAAACTAGGAGG 472 rup.pyr
ATTTCTTGTTTGCATATGCGATCCTACGATCAATTCCCAACAAACTTGGAGG 472 rup.rup
ATTTCTTATTTGCATATGCAATTCTACGATCAATCCCCAACAAACTTGGAGG 472 nem.cau
ATTTCCTATTTGCATATGCAATCTTACGATCAATCCCCAATAAACTAGGCGG 472 bud.tax.tax
ATTTCCTATTTGCATACGCAATCTTACGATCAATCCCCAACAAACTAGGAGG 472 pan.hod
ACTTTCTATTTGCATACGCAATCCTACGATCAATCCCCAACAAACTAGGAGG 472 ovi.amm
ACTTCCTATTTGCATACGCAATCTTACGATCAATCCCTAATAAACTAGGAGG 472 ovi.vig
ATTTCCTATTTGCATATGCAATCTTACGATCAATCCCTAATAAACTAGGAGG 472 cap.cri
ACTTCCTATTTGCATACGCAATCCTACGATCAATCCCCAACAAACTAGGCGG 472 ovi.mos
ACTTCCTATTTGCATACGCAATCCTACGATCAATTCCTAACAAACTAGGCGG 472 ore.ame
ACTTCCTATTTGCATACGCAATCTTACGATCAATCCCCAATAAACTAGGAGG 472 cep.dor
```

TABLE 2-continued

Multiple sequence alignment of 472 bp fregment of mitochondrial cytochrome b gene of 221 animal species

```
ACTTCCTATTTGCATACGCAATCCTACGATCAATTCCAAACAAACTAGGAGG 472 cep.max
ATTTCCTATTCGCGTACGCAATTCTACGATCAATTCCAAATAAATTAGGAGG 472 bis.bon
ACTTCTTATTTGCATANGCAATTTTACGGTCAATCCCCAACAAACTAGGAGG 472 bos.gru
ACTTCTTATTTGCATACGCAATTTTACGATCAATCCGCAATAAACTAGGAGG 472 bos.tra
ATTTCCTGTTCGCATACGCAATTCTACGATCAATCCCCAAACAACTAGGAGG 472 bub.min
ACTTCCTATTCGCATACGCAATCTTACGATCAGTTCCTAAAAAACTAGGAGG 472 buba.bub
ACTTCCTATTCGCATACGCAATCTTACGATCAATTCCTAACAAACTAGGAGG 472 tra.ang
ATTTCCTGTTCGCATATGCAATCCTACGATCTATCCCCAACAAGCTAGGAGG 472 tra.eur
ACTTCCTATTCGCATATGCAATCCTACGATCAATCCCTAATAAACTAGGAGG 472 kob.eli
ACTTCTTATTGGCATATGCAATTCTACGATCAATCCCCAACAAACTAGGAGG 472 kob.meg
ATTTCTTATTCGCATACGCAATTTTACGGTCAATTCCTAATAAACTGGGAGG 472 red.aru
ACTTCTTATTTGCATATGCAATCCTACGATCAATCCCCAATAAACTAGGAGG 472 red.ful
ACTTCTTATTNGCATACGCAATCCTACGATCAATCCCCAATAAACTAGGAGG 472 neo.mos
ACTTTTTATTCGCATACGCAATCCTACGATCAATCCCCAATAAACTAGGAGG 472 pel.cap
ATTTCCTATTTGCATATGCGATTCTACGATCAATTCCCAACAAACTAGGAGG 472 gaz.dam
ATTTCCTATTTGCATACGCAATTCTCCGATCAATTCCTAATAAACTAGGAGG 472 our.our
ATTTCCTATTCGCATACGCAATTCTCCGATCGATTCCCAACAAACTAGGAGG 472 ant.cer
ACTTCCTATTTGCATACGCAATCCTCCGATCAATTCCTAACAAACTAGGAGG 472 sai.tat
ACTTCCTATTCGCATACGCAATCCTCCGATCAATTCCTAATAAACTAGGAGG 472 mad.kir
ATTTCCTATTCGCATATGCAATCCTCCGATCAATCCCTAACAAACTAGGGGG 472 rap.mel
ATTTTCTATTCGCATATGCAATTCTCGGGTCAATTCCCAATAAATTAGGAGG 472 gaz.gaz
ACTTCTTATTCGCATATGCAATTCTCCGATCAATTCCCAATAAACTAGGAGG 472 ant.ame
ATTTCCTATTCGCATACGCAATCCTACGATCAATCCCTAACAAACTAGGAGG 472 hyd.ine
ATTTGTTATTTGCATACGCAATTCTACGATCTATCCCTAACAAATTAGGAGG 472 mun.mun
ATTTCCTATTTGCATACGCTATTCTACGATCAATTCCTAACAAACTAGGAGG 472 alc.alc
ATTTCTTATTTGCATACGCAATTCTACGATCAATCCCCAATAAACTAGGGGG 472
```

TABLE 2-continued

Multiple sequence alignment of 472 bp fregment of mitochondrial cytochrome b gene of 221 animal species

```
cer.ela.kan
ATTTCCTATTTGCATACGCAATCCTACGATCGATTCCGAACAAACTAGGAGG 472 cer.ela.xan
ATTTCCTATTTGCATACGCAATCGTACGATCGATTCCCAACAAACTAGGAGG 472 cer.ela.can
ATTTCCTATTTGCATACGCAATCCTACGATCAATTCCCAACAAACTAGGAGG 472 cer.nip.cent
ACTTGCTATTTGCATACGCAATCCTACGATCAATTCGCAACAAACTAGGAGG 472 cer.nip.yes
ACTTCCTATTTGCATACGCAATCCTACGATGAATTCCCAACAAACTAGGAGG 472 cer.nip.ker
ATTTCCTATTTGCATACGCAATCCTACGATCAATTCCCAACAAACTAGCACG 472 cer.nip.pul
ATTTCCTATTTGCATACGCAATCCTACGATCAATTCCCAACAAACTAGGAGG 472 cer.nip.nip
ATTTCCTATTTGCATACGCAATCCTACGATCAATTCCCAACAAACTAGGAGG 472 cer.ela.sco
ATTTCCTATTTGCATACGCAATCCTACGATCAATTCCCAACAAACTAGGAGG 472 cer.dam
ACTTCCTATTTGCATACGCAATCCTACGATCAATTCCCAATAAATTAGGAGG 472 ran.tar
ACTTTCTATTCGCATACGCAATCCTACGATCAATTCCAAATAAACTAGGAGG 472 mos.fus
ATTTCCTATTTGCATATGCCATTCTACGATCAATTCCCAACAAACTAGGAGG 472 mos.leu
ATTTCCTATTTGCATATGCCATTCTACGATCAATTCCCAACAAACTAGGAGG 472 mos.chr
ACTTCCTATTTGCATATGCCATCCTACGATCAATTCCCAACAAACTAGGAGG 472 mos.ber
ACTTCCTATTTGCATATGCCATTCTACGATCAATTCCCAACAAACTAGGAGG 472 mos.mos
ACTTTCTATTTGCATATGCCATTCTACGATCAATTGCTAATAAACTAGGAGG 472 tra.jav
ATTTCTTATTTGCATACGCAATTCTTCGGTCAATCCCCAATAAACTAGGAGG 472 trag.nap
ATTTCCTATTCGCATACGCAATCCTACGATCAATCCCCAATAAATTAGGAGG 472 bala.acu
ACTTCCTATTCGCATACGCAATCCTACGATCAATCCCTAATAAACTAGGCGG 472 bala.bon
ATTTTCTATTCGCATACGCAATCCTACGATGAATCCCCAATAAACTAGGCGG 472 bala.bor
ATTTGCTATTTGCATACGCAATGCTACGATCAATCCCCAACAAATTAGGCGG 472 bala.edi
ATTTCCTATTTGCATACGCAATCCTACGATCAATTCCCAACAAATTAGGCGG 472 esch.rob
ATTTCCTATTTGCATACGCAATCCTACGATCGATCCGCAACAAATTAGGCGG 472 bala.mus
ATTTCCTATTTGCATATGCAATCCTACGATCAATCCCCAACAAATTAGGCGG 472 mega.nov
ATTTCCTATTTGCATACGCAATCCTACGATCAATCCCCAACAAACTAGGCGG 472
```

TABLE 2-continued

Multiple sequence alignment of 472 bp fregment of mitochondrial cytochrome b gene of 221 animal species bala.phy
ATTTTCTATTCGCATACGGATCCTACGATCAAATCCCCAACAAACTAGGCGG 472 cap.mar
ACTTCCTATTTGCATATGCAATCCTACGATCAATTCCTAATAAATTAGGTGG 472 ceph.com
ACTTCCTATTCGCATATGCAATCCTACGATCAATTCCCAATAAACTTGGAGG 472 ceph.eut
ACTTCCTATTCGCATATGGAATCCTACGATCAATTCCTAATAAACTTGGAGG 472 lage.obi
ACTTCCTATTCGCATATGCAATCCTACGATGAATTCCTAATAAACTTGGAGG 472 ceph.hea
ACTTCCTATTCGCATATGCAATCCTACGATCAATGCCTAATAAACTTGGAGG 472 ceph.hec
ACTTCCTATTCGCATATGCAATCCTACGATCAATTCCTAATAAACTTGGAGG 472 lage.aus
ATTTCCTATTCGCATATGCAATCCTACGATCAATTCCTAATAAACTCGGAGG 472 lage.cru
ATTTCCTATTCGCATATGCAATCCTACGATCAATTCCTAATAAACTCGGAGG 472 lage.obs
ATTTCCTATTCGCATACGCAATCCTACGATCAATTCCTAATAAACTTGGAGG 472 lisso.bar
ACTTCCTATTTGCATACGCAATCCTACGATCAATTCCTAATAAACTTGGAGG 472 lisso.per
ACTTTCTATTCGCATACGCAATCCTACGATCAATTCCTAATAAACTTGGAGG 472 glo.mac
ATTTCCTATTCGCATATGCAATCTTACGATCAATTCCCAATAAACTTGGAGG 472 glo.mel
ATTTCCTATTCGCATATGCAATCTTACGATCAATTCCCAATAAACTTGGAGG 472 fere.att
ATTTCCTATTCGCGTATGCAATCTTACGATCAATTCCTAATAAACTTGGAGG 472 pepo.ele
ATTTCCTATTCGCATATGCAATCTTACGATCAATTCCCAATAAACTTGGAGG 472 gram.gri
ATTTCCTATTCGCATATGCAATCTTGCGATCAATTCCCAACAAACTTGGAGG 472 pse.cra
ATTTCCTATTCGCATATGCAATCTTACGATCAATTCCTAATAAACTTGGAGG 472 lage.acu
ATTTCCTATTCGCATATGCAATCCTACGATCAATTCCCAACAAACTTGGAGG 472 orci.bre
ACTTCCTATTCGCATACGCAATCCTACGATCAGTTCCCAATAAACTTGGAGG 472 orca.bre
ACTTCCTATTCGCATACGCGATCCTACGATCAATTCCTAATAAACTCGGGGG 472 del.cap
ACTTTCTATTCGCATACGCAATCTTACGATCAATCCCTAATAAACTTGGAGG 472 del.tro
ACTTTCTATTCGCATACGGAATCTTACGATCAATCCCTAATAAACTTGGAGG 472 del.del
ACTTTCTATTCGCATATGCAATCTTACGATCAATCCCTAATAAACTTGGAGG 472 sten.cly
ACTTTCTATTCGCATATGCAATCTTACGATCAATCCCTAATAAACTTGGAGG 472 sten.coe

TABLE 2-continued

Multiple sequence alignment of 472 bp fregment of mitochondrial cytochrome b gene of 221 animal species

ACTTTCTATTCGCATACCCAATCTTACCATCAATCCCTAACAAACTTGGAGG 472 tur.adu
ACTTTCTATTCGCATACGCAATCTTACGATCAATCCCTAATAAACTTGGAGG 472 sten.fro
ACTTTCTATTCGCATACGCAATCTTACGATCAATCCCTAATAAACTTGGAGG 472 saus.chi
ATTTCCTATTCGCATACGCAATCTTACGGTCAATCCCTAATAAACTTGGAGG 472 sten.lon
ATTTCCTATTCGCATACGCAATCTTACGATCAATCCCTAATAAACTTGGAGG 472 turs.tru
ACTTTGTATTCGCATACGCAATCTTACGATCAATCCCTAATAAGCTCGGAGG 472 lage.alb
ATTTCCTATTCGCATATGCAATCCTACGATCAATCCCTAACAAACTTGGAGG 472 sten.bre
ATTTCCTATTCGCATACGCAATCTTACGATCAATCCCCAACAAACTTGGAGG 472 sota.flu
ATTTCCTATTCGCATATGCAATCTTACGATCAATCCCTAATAAACTTGGAGG 472 del.leu
ACTTCCTATTTGCATACACAATCCTACGATCAATCCCCAACAAACTAGGAGG 472 mono.mon
ATTTCCTATTTGCATACGGAATCCTACGATCAATCGGCAACAAACTAGGAGG 472 plat.gan
ATTTCCTATTTGCATACGCAATGTTACGGTCAATCCCCAATAAACTAGGAGG 472 plat.min
ATTTCCTATTTGCATACGCAATCTTACGGTCAATCCCCAATAAACTAGGAGG 472 kogi.bre
ATTTCCTATTTGCATATGCCATCCTACGATCCATCCCTAACAAACTAGGGGG 472 kogi.sim
ACTTTCTATTCGCATACGCCATTCTACGATCAATTCCTAACAAACTGGGAGG 472 phys.oat
ATTTCCTATTCGCGTACGCCATCCTACGATCTGTCCCCAATAAACTAGGAGG 472 lipo.vex
ATTTCCTCTTCGCATACGGAATTCTACGATCAATTCCCAATAAATTAGGAGG 472 phoc.sin
ATTTCCTCTTCGCATACGCAATCCTACGATCAATCCCCAATAAACTAGGAGG 472 bera.bai
ACTTCCTGTTCGCATACGCAATCTTACGATCAGTCCCTAATAAACTAGGGGC 472 ziph.car
ACTTCCTATTCGCATACGGAATCCTACGATCAATTCCCAATAAACTAGGAGG 472 meso.eur
ACTTCCTATTCGCATATGCAATTCTACGATCAATTCCGAACAAACTAGGAGG 472 meso.bid
ATTTCCTATTCGCATACGCAATCTTACGATCAATTCCTAATAAACTAGGAGG 472 mesa.den
ATTTTCTATTTGCATACGCAATCCTACGATCAATCCCCAACAAATTAGGAGG 472 hype.amp
ACTTCTTATTTGCATACGCAATCCTACGTTCAATCGCTAACAAACTAGGAGG 472 meso.per
ATTTTCTATTTGCATATGCAATTTTACGATCAGTTCCTAATAAACTAGGAGG 472 pont.bla
ATTTCCTATTTGCCTACGCCATCCTACGATCAATTCCCAATAAACTGGGAGG 472

TABLE 2-continued

Multiple sequence alignment of 472 bp fregment of mitochondrial cytochrome b gene of 221 animal species

```
hex.lib
ATTTCCTGTTCGCATACGCAATTCTCCGATCAATCCCTAACAAACTGGGAGG 472 hipp.amp
ATTTCCTGTTCGCGTACGCGATTCTCCGATCAATCCCCAACAAACTAGGAGG 472 dic.sum
ACTTGCTATTCGCCTACCCAATCCTACGATCCATCCCCAATAAACTAGGCGG 472 rhin.son
ATTTCCTATTTGCTTACGCAATCCTACGATCCATCCCAAACAAACTAGGCGG 472 cera
ACTTTCTATTTGCTTACGCAATCCTACGATCCATCCCTAACAAACTAGGCGG 472 equu
ATTTCCTATTTGCTTACGGCATCCTACGCTCCATTCCCAACAAACTAGGTGG 472 baby.bab
ACTTCCTATTTGCCTACGCCATCCTACGCTCAATCCCCAACAAATTAGGCGG 472 phac.afr
ACTTCCTATTCGCCTACGCCATCCTACGTTCAATCCCTAATAAATTAGGTGG 472 sus.bar
ACTTCTTATTCGCCTACGCTATTCTACGTTCAATCCCCAATAAACTAGGCGG 472 sus.scr.ewb3
ATTTCTTATTCGCCTACGCTATTCTACGTTCAATTCCTAATAAACTAGGTGG 472 lama.gia
ACTTCCTATTTGCATACGCCATCCTACGATCCATCCCCAATAAATTAGGCGG 472 lama.gua
ACTTCCTATTTGCATATGCCATCCTACGATCCATCCCCAAACAATTAGGCGG 472 vic.vic
ATTTCCTATTTGCATATGCTATTCTACGATCGATCCCCAATAAATTAGGCGG 472 cam.bac
ATTTCCTATTCGCATACGCTATCCTACGATCCATCCCCAACAAATTGGGAGG 472 arc.for
ATTTTCTATTCGCTTACGCCATTTTACGATCTATCCCCAACAAACTAGGAGG 472 arc.gaz
ATTTTCTATTCGCCTATGCCATTTTACGATCTATCCCGAACAAACTAGGAGG 472 eum.jub
ATTTCCTATTCGCCTATGCTATTTTACGATCCATCCCCAACAAATTAGGGGG 472 zal.cal
ATTTCCTATTCGCCTATGCTATTTTACGATCCATCCCCAACAAATTAGGGGG 472 ado.ros
ATTTCCTATTCGCCTACGCTATCCTCCGATCTATTCCCAACAAACTCGGGGG 472 pha.fasciata
ACTTTCTATTTGCCTACGCAATCCTACGATCAATCCCCAACAAACTAGGAGG 472 pho.gro
ACTTTTTATTTGCCTACGCAATCCTACGATCAATTCCCAACAAACTAGGAGG 472 pho.vit
ACTTCCTATTTGCCTACGCATCTTACGATCGATCCCCAAACAAACTAGGAGG 472 cys.cri
ACTTCCTATTCGCCTATGCAATCCTACGATCTATCCCCAACAAACTAGGAGG 472 hyd.lep
ATTTCCTATTTGCCTACGCAATCCTACGATCCATTCCCAATAAACTAGGAGG 472 lep.wed
ATTTCCTATTTGCCTACGCAATCTTACGATCCATCCCTAACAAACTAGGAGG 472
```

TABLE 2-continued

Multiple sequence alignment of 472 bp fregment of mitochondrial cytochrome b gene of 221 animal species mir.leo
ATTTCCTATTTGCCTACGCAATCCTACGATCTATTCCCAACAAACTAGGAGG 472 eri.bar
ATTTCCTATTCGCCTATGCAATCCTACGATCCATCCCCAACAAACTTGGAGG 472 mon.sch
ACTTCCTATTCGCCTACGCAATCCTACGATCTATCCCCAATAAACTAGGAGG 472 hela.mal
ACTTTCTATTTGCCTACGCTATCCTACGATCCATCCCTAATAAACTAGGAGG 472 sel.thi
ACTTTTTATTTGCTTACGCTATCCTACGATCCATCCCCAACAAACTAGGAGG 472 ail.ful
ATTTCCTATTCGCATATGCAATTCTACGATCCATCCCAAACAAACTAGGAGG 472 fel
ACTTCCTATTCGCATACGCAATTCTCCGATCCATCCCTAACAAACTAGGGGG 472 can
ATTTTCTATTCGCCTATGCTATCCTACGATCCATTCCTAATAAATTAGGAGG 472 tal
ACTTCCTATTTGCATATGCCATCCTACGATCAATTCCTAATAAATTAGGAGG 472 gla.sab
ACTTTCTATTTGCATACGCAATTCTACGATCTATTCCAAATAAACTAGGAGG 472 gla.vol
ACTTTCTATTTGCGTATGCAATTCTACGATCTATCCCAAATAAACTAGGAGG 472 hyl.pha
ACTTTCTATTCGCATACGCAATCCTACGATCTATTCCCAATAAATTAGGAGG 472 pet.set
ACTTTCTATTCGCATACGCAATGCTACGATCTATTCCCAATAAATTAGGAGG 472 bel.pea
ACTTTCTAATTTATTACGCAATCGTTCGATCCATCCCCAACAAACTAGGAGG 472 pte.mom
ATTTCCTATTCGCATATGCTATCTTACGATCTATCCCTAACAAACTAGGCGG 472 gala.demi
ATTTCCTATTTGCCTACGCCATCCTACGATCTATCCCCAACAAACTAGGAGG 472 pero.pot
ACTTTCTATTCGCCTACGCCATCTTACGATCCATCCCAAACAAACTGGGAGG 472 gala.mat
ACTTCTTATTTGCTTATGCCATGCTTCGATCAATTCCCAACAAACTAGGAGG 472 gala.moh
ACTTCTTATTTGCCTACGCCATCCTTCGATCAATCCCCAACAAACTAGGAGG 472 oto.gar
ATTTCCTATTTGCTTATGCTATCTTACGATCCATCCCAAATAAACTAGGAGG 472 lor.tar
ATTTCCTATTCGCATACGCAATCCTACGATCAATCCCCAATAAACTAGGTGG 472 nyc.cou
ATTTTCTATTCGCCTACGCCATCCTTCGATCAATCCCCAACAAACTAGGAGG 472 mus
ATTTCCTATTTGCATACGCCATTCTACGCTCAATCCCCAATAAACTAGGAGG 472 gorr
ATTTCCTATTTGCCTACGCAATTCTCCGATCTGTCCCCAATAAACTAGGAGG 472 homo
ATTTCCTATTCGCCTACACAATTCTCCGATCCGTCGCTAACAAACTAGGAGG 472 dug.dug

TABLE 2-continued

Multiple sequence alignment of 472 bp fregment of mitochondrial cytochrome b gene of 221 animal species

```
ACTTTCTATTCCGATACGCTATCCTCCGATCTATCCCTAATAAACTAGGGGG 472 ele.max
ACTTCCTTTTTGCTTACGCCATTCTACGATCTGTACCAAACAAACTAGGAGG 472 afr.con
ATTTCTTATTTGCCTATGCCATCCTTCGGTCAATCCCAAACAAACTAGGAGG 472 pavo.mut
ACTTCTTATTTGCCTACGCCATCCTTCGTTCAATCCCCAACAAACTAGGAGG 472 tra.bly
ACTTCCTATTCGCTTATGCCATCCTGCGCTCAATCCCAAACAAACTTGGGGG 472 tra.sat
ACTTCCTATTCGCCTACGCCATCCTACGCTCAATCGCAAACAAACTTGGAGG 472 tra.cob
ATTTCCTGTTCGCTTATGCCATCCTACGCTCAATCCCAAACAAACTCGGAGG 472 tra.tem
ATTTTGTGTTCGCTTATGCCATCCTGCGCTCAATTCCAAACAAACTCGGAGG 472 arg.arg
ACTTCCTATTCGCCTATGCCATCCTACGCTCAATCCCAAACAAACTAGGAGG 472 cat.wal
ACTTCTTATTTGCCTACGCTATCCTACGGTCAATCCCAAATAAACTCGGAGG 472 cro.cro
ACTTCCTATTTGCCTATGCTATCCTGCGCTCAATCCCAAATAAACTCGGAGG 472 sym.ree
ACTTCCTATTTGCCTACGCCATCCTACGCTCAATCCCAAACAAACTGGGGGG 472 bam.tho
ACTTCCTATTCGCGTATGCTATCGTACGATCAATCCCCAACAAACTCGGAGG 472 fra.fra
ACTTCCTATTTGCCTACGCCATCCTACGCTCAATCCCCAACAAACTCGGAGG 472 ith.cru
ACTTCCTATTTGCCTACGCTATTCTACGCTCAATCCCCAATAAACTTGGAGG 472 ant.par
ATTTCTTATTTGCGTATGCCATCCTACGTTCAATTCCAAACAAACTAGGAGG 472 ant.vir
ATTTCTTATTTGCATACGCCATCCTACGTTCAATTCCAAACAAACTAGGAGG 472 gru.ant.ant
ACTTTTTATTTGCATACGCCATCCTACGTTCAATCCCAAACAAACTAGGAGG 472 gru.ant.gil
ACTTTTTATTTGCATACGCCATCCTACGTTCAATCCCAAACAAACTAGGAGG 472 gru.ant.sha
ACTTTTTATTTGCATACGCCATCCTACGTTCAATCCCAAACAAACTAGGAGG 472 gru.leu
ACTTGCTATTTGCATACGCCATCCGAGGTTCAATCCCAAACAAACTAGGAGG 472 gru.can.pra
ACTTTTTATTTGCCTACGCCATCTTACGCTCAATCCCAAAGAAACTAGGAGG 472 gru.can.row
ACTTTTTATTTGCCTACGCCATCTTACGCTCAATCCCAAACAAACTAGGAGG 472 gru.can.tab
ACTTTTTATTTGCCTACTCCATCTTACGCTCAATCCCAAACAAACTAGGAGG 472 gru.can.can
ACTTTTTATTTGCCTACGCCATCTTACGCTCAATCCCAAACAAACTAGGAGG 472 gru.ame
ACTTTTTATTTGCATACGCCATCCTACGTTCAATCCCAAACAAACTAGGAGG 472
```

TABLE 2-continued

Multiple sequence alignment of 472 bp fregment of mitochondrial
cytochrome b gene of 221 animal species

```
gru.gru
ACTTTTTATTTGCATACGCCATCCTCCGTTCAATCCCAAACAAACTAGGAGG 472 gru.mon
ACTTTCTATTTGCATACGCCGTCCTACGTTCAATCCCAAACAAACTAGGAGG 472 gru.nig
ACTTTCTATTTGCATACGCTATCCTACGTTCAATCCCAAACAAACTAGGAGG 472 gru.jap
ACTTCTTATTTGCATACGCTATTCTGCGTTCAATCCCAAACAAACTAGGAGG 472 cic.boy
ACTTCCTCTTTGCATACGCCATCCTACGCTCCATCCCCAACAAACTAGGAGG 472 rhe.ame
ATTTCCTATTCGCTTACGCCATCTTACGCTCCATCCCCAACAAACTAGGAGG 472 ant.alb
ATTTCCTATTCGCATATGCCATCCTACGCTCAATCCCCAATAAACTAGGAGG 472 fal.fam
ACTTCCTATTCGCCTACGCCATCCTACGCTCAATCCCCAACAAACTAGGTGG 472 fal.ver
ACTTCCTATTTGCCTACGCCATCCTACGCTCAATCCCCAACAAACTGGGTGG 472 fal.per
ACTTCCTATTTGCTTACGCCATCCTACGCTCAATCCCCAATAAACTGGGCGG 472 fal.spa
ACTTCCTATTTGCCTACGCTATTCTACGCTCAATTCCCAACAAATTAGGCGG 472 ayt.ame
ACTTCCTATTCGCCTACGCCATCCTGCGATCAATCCCGAATAAACTAGGAGG 472 smi.sha
ATTTTTTATTTGCATACGCTATTCTGCGATCAATTCCAAACAAACTAGGAGG 472 vid.cha
ACTTCCTATTCGCCTACGCCATCCTACGATCCATCCCAAACAAACTAGGAGG 472 chry.pic
ACTTTCTTTTCGCTTACGCAATTCTACGATCCATCCGAAACAAATTAGGTGG 472 emy.orb.kur
ACTTTCTTTTTGCCTACGCAATCCTACGATCAATCCCAAAGAAATTAGGAGG 472 che.mud
ACTTCCTATTTGCCTACGCAATCCTACGATCAATCCCAAACAAACTAGGCGG 472 eum.egr
ACTTCTTATTTGCCTACGCCATCCTACGCTCTATTCCAAACAAACTAGGCGG 472

PRIMER 'mcb869'        CGATCAATCCCTAACAAACTAGGAGG
* **   *  *    **  *  *    ** **  * ** **      * ** **
```

Table 3. Results of the blast analysis of the sequence revealed from 'adil.flesh' in 'mito' database of NCBI. It shows the most significant alignment of cytochrome b sequence (328 bp) revealed from confiscated skin piece 'adil.flesh' with felis catus cytochrome b gene sequence (genbank registration number NC_001700.1, bits score 365, E value, $e^{-101}$) registered in NCBI database (bits score 365 and E value $e^{-101}$). It gives an indication that the species of analyzed material belongs to family felidae. It also fulfills the requirements of column 6 mention above under sub-heading 'Objectives of invention'.

```
<p><!--
QBlastInfoBegin
        Status=READY
QBlastInfoEnd
--><p>
<TITLE>Results for RID 984593689-1224-27770 </TITLE>
<HTML>
<HEAD>
<TITLE>BLAST Search Results </TITLE>
</HEAD>
<BODY BGCOLOR="#FFFFFF" LINK="#0000FF" VLINK="#660099" ALINK="#660099">
<A HREF="http://www.ncbi.nlm.nih.gov/BLAST/blast_form.map"> <IMG
SRC="http://www.ncbi.nlm.nih.gov/BLAST/blast_results.gif" BORDER=0 ISMAP></A>
<BR><BR><PRE>
<b>BLASTN 2.1.2 [Nov-13-2000]</b>

<b><a href="http://www.ncbi.nlm.nih.gov/htbin-
post/Entrez/query?uid=9254694&form=6&db=m&Dopt=r">Reference</a>:</b>
Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs", Nucleic Acids Res. 25:3389-3402.
<p>
RID: 984593689-1224-27770
<p>
<b>Query=</b>
         (328 letters)

<p>
<b>Database:</b> Sequences from complete mitochondrial genomes
          129 sequences; 3,164,247 total letters <p> <p>If you have any problems or questions with the results of this search
<br>please refer to the <b><a
href=http://www.ncbi.nlm.nih.gov/blast/blast_FAQs.html>BLAST FAQs</a></b><br><p>
<FORM NAME="BLASTFORM" METHOD="POST">
<a href="blast.cgi?RID=984593689-1224-27770&ALIGNMENT_VIEW=17" TARGET="Taxonomy
BLAST Results for 984593689-1224-27770">Taxonomy reports</a>
<BR>
</PRE>
<CENTER>
<H3><a href="/BLAST/newoptions.html#graphical-overview"> Distribution of 80
Blast Hits on the Query Sequence</a></H3>
<input name=defline size=80 value="Mouse-over to show defline and scores. Click
to show alignments">
</CENTER>
<map name=img_map>
<area shape=rect coords=62,101,526,106 href="#5835205"
ONMOUSEOVER='document.BLASTFORM.defline.value="NC_001700   Felis catus
mitochondrion, complete genome..S= 365 E=1e-101"'
ONMOUSEOUT='document.BLASTFORM.defline.value="Mouse-over to show defline and
scores. Click to show alignments"' >
<area shape=rect coords=62,108,469,113 href="#5834857"
ONMOUSEOVER='document.BLASTFORM.defline.value="NC_001325   Phoca vitulina
mitochondrion, complete genome..S= 198 E=1e-51"'
```

```
ONMOUSEOUT='document.BLASTFORM.defline.value="Mouse-over to show defline and
scores. Click to show alignments"' >
<area shape=rect coords=66,115,523,120 href="#5835652"
ONMOUSEOVER='document.BLASTFORM.defline.value="NC_002008  Canis familiaris
mitochondrion, complete genome..S= 190 E=4e-49"'
ONMOUSEOUT='document.BLASTFORM.defline.value="Mouse-over to show defline and
scores. Click to show alignments"' >
<area shape=rect coords=62,122,515,127 href="#5835009"
ONMOUSEOVER='document.BLASTFORM.defline.value="NC_001602  Halichoerus grypus
mitochondrion, complete genome..S= 180 E=3e-46"'
ONMOUSEOUT='document.BLASTFORM.defline.value="Mouse-over to show defline and
scores. Click to show alignments"' >
<area shape=rect coords=62,129,493,134 href="#5835988"
ONMOUSEOVER='document.BLASTFORM.defline.value="NC_000884  Cavia porcellus
complete mitochondrial genome..S= 176 E=5e-45"'
ONMOUSEOUT='document.BLASTFORM.defline.value="Mouse-over to show defline and
scores. Click to show alignments"' >
<area shape=rect coords=62,136,485,141 href="#5835401"
ONMOUSEOVER='document.BLASTFORM.defline.value="NC_001808  Ceratotherium simum
mitochondrion, complete genome..S= 165 E=2e-41"'
ONMOUSEOUT='document.BLASTFORM.defline.value="Mouse-over to show defline and
scores. Click to show alignments"' >
<area shape=rect coords=62,143,510,148 href="#5835484"
ONMOUSEOVER='document.BLASTFORM.defline.value="NC_001892  Myoxus glis
mitochondrion, complete genome..S= 153 E=8e-38"'
ONMOUSEOUT='document.BLASTFORM.defline.value="Mouse-over to show defline and
scores. Click to show alignments"' >
<area shape=rect coords=62,150,391,155 href="#5835345"
ONMOUSEOVER='document.BLASTFORM.defline.value="NC_001788  Equus asinus
mitochondrion, complete genome..S= 151 E=3e-37"'
ONMOUSEOUT='document.BLASTFORM.defline.value="Mouse-over to show defline and
scores. Click to show alignments"' >
<area shape=rect coords=70,157,447,162 href="#5835764"
ONMOUSEOVER='document.BLASTFORM.defline.value="NC_002078  Orycteropus afer
complete mitochondrial genome..S= 149 E=1e-36"'
ONMOUSEOUT='document.BLASTFORM.defline.value="Mouse-over to show defline and
scores. Click to show alignments"' >
<area shape=rect coords=62,164,348,169 href="#5835429"
ONMOUSEOVER='document.BLASTFORM.defline.value="NC_001821  Dasypus novemcinctus
mitochondrion, complete genome..S= 141 E=3e-34"'
ONMOUSEOUT='document.BLASTFORM.defline.value="Mouse-over to show defline and
scores. Click to show alignments"' >
<area shape=rect coords=62,171,522,176 href="#5835331"
ONMOUSEOVER='document.BLASTFORM.defline.value="NC_001779  R.unicornis complete
mitochondrial genome..S= 135 E=2e-32"'
ONMOUSEOUT='document.BLASTFORM.defline.value="Mouse-over to show defline and
scores. Click to show alignments"' >
<area shape=rect coords=62,178,348,183 href="#5834953"
ONMOUSEOVER='document.BLASTFORM.defline.value="NC_001569  Mus musculus
mitochondrion, complete genome..S= 133 E=7e-32"'
ONMOUSEOUT='document.BLASTFORM.defline.value="Mouse-over to show defline and
scores. Click to show alignments"' >
<area shape=rect coords=62,185,391,190 href="#5835107"
ONMOUSEOVER='document.BLASTFORM.defline.value="NC_001640  Equus caballus
mitochondrion, complete genome..S= 125 E=2e-29"'
ONMOUSEOUT='document.BLASTFORM.defline.value="Mouse-over to show defline and
scores. Click to show alignments"' >
```

```
<area shape=rect coords=62,192,348,197 href="#5836030"
ONMOUSEOVER='document.BLASTFORM.defline.value="NC_000889  Hippopotamus amphibius
mitochondrion, complete genome..S= 125 E=2e-29"'
ONMOUSEOUT='document.BLASTFORM.defline.value="Mouse-over to show defline and
scores. Click to show alignments"' >
<area shape=rect coords=62,199,341,204 href="#5835359"
ONMOUSEOVER='document.BLASTFORM.defline.value="NC_001794  Macropus robustus
mitochondrion, complete genome..S= 123 E=7e-29"'
ONMOUSEOUT='document.BLASTFORM.defline.value="Mouse-over to show defline and
scores. Click to show alignments"' >
<area shape=rect coords=62,206,510,211 href="#5835862"
ONMOUSEOVER='document.BLASTFORM.defline.value="NC_000845  Sus scrofa
mitochondrion, complete genome..S= 121 E=3e-28"'
ONMOUSEOUT='document.BLASTFORM.defline.value="Mouse-over to show defline and
scores. Click to show alignments"' >
<area shape=rect coords=62,213,476,218 href="#5834939"
ONMOUSEOVER='document.BLASTFORM.defline.value="NC_001567  Bos taurus
mitochondrion, complete genome..S= 121 E=3e-28"'
ONMOUSEOUT='document.BLASTFORM.defline.value="Mouse-over to show defline and
scores. Click to show alignments"' >
<area shape=rect coords=62,220,340,225 href="#5835177"
ONMOUSEOVER='document.BLASTFORM.defline.value="NC_001665  Rattus norvegicus
mitochondrial genome..S= 121 E=3e-28"'
ONMOUSEOUT='document.BLASTFORM.defline.value="Mouse-over to show defline and
scores. Click to show alignments"' >
<area shape=rect coords=67,227,348,232 href="#5835121"
ONMOUSEOVER='document.BLASTFORM.defline.value="NC_001643  Pan troglodytes
mitochondrion, complete genome..S= 117 E=4e-27"'
ONMOUSEOUT='document.BLASTFORM.defline.value="Mouse-over to show defline and
scores. Click to show alignments"' >
<area shape=rect coords=62,234,348,239 href="#5835554"
ONMOUSEOVER='document.BLASTFORM.defline.value="NC_001941  Ovis aries
mitochondrion, complete genome..S= 109 E=1e-24"'
ONMOUSEOUT='document.BLASTFORM.defline.value="Mouse-over to show defline and
scores. Click to show alignments"' >
<area shape=rect coords=62,241,515,246 href="#5835526"
ONMOUSEOVER='document.BLASTFORM.defline.value="NC_001913  Oryctolagus cuniculus
mitochondrion, complete genome..S= 103 E=7e-23"'
ONMOUSEOUT='document.BLASTFORM.defline.value="Mouse-over to show defline and
scores. Click to show alignments"' >
<area shape=rect coords=62,248,265,253 href="#7212513"
ONMOUSEOVER='document.BLASTFORM.defline.value="NC_002391  Talpa europaea
mitochondrion, complete genome..S= 103 E=7e-23"'
ONMOUSEOUT='document.BLASTFORM.defline.value="Mouse-over to show defline and
scores. Click to show alignments"' >
<area shape=rect coords=67,255,499,260 href="#5835135"
ONMOUSEOVER='document.BLASTFORM.defline.value="NC_001644  Pan paniscus
mitochondrion, complete genome..S= 101 E=3e-22"'
ONMOUSEOUT='document.BLASTFORM.defline.value="Mouse-over to show defline and
scores. Click to show alignments"' >
<area shape=rect coords=62,262,526,267 href="#6137796"
ONMOUSEOVER='document.BLASTFORM.defline.value="NC_001807  Human mitochondrion,
complete genome..S=97.6 E=4e-21"'
ONMOUSEOUT='document.BLASTFORM.defline.value="Mouse-over to show defline and
scores. Click to show alignments"' >
<area shape=rect coords=62,269,340,274 href="#5834995"
ONMOUSEOVER='document.BLASTFORM.defline.value="NC_001601  Balaenoptera musculus
```

```
mitochondrion, complete genome..S=97.6 E=4e-21"'
ONMOUSEOUT='document.BLASTFORM.defline.value="Mouse-over to show defline and
scores. Click to show alignments"' >
<area shape=rect coords=62,276,526,281 href="#5835666"
ONMOUSEOVER='document.BLASTFORM.defline.value="NC_002009   Artibeus jamaicensis
mitochondrion, complete genome..S=95.6 E=2e-20"'
ONMOUSEOUT='document.BLASTFORM.defline.value="Mouse-over to show defline and
scores. Click to show alignments"' >
<area shape=rect coords=106,283,515,288 href="#5835149"
ONMOUSEOVER='document.BLASTFORM.defline.value="NC_001645   Gorilla gorilla
mitochondrion, complete genome..S=91.7 E=2e-19"'
ONMOUSEOUT='document.BLASTFORM.defline.value="Mouse-over to show defline and
scores. Click to show alignments"' >
<area shape=rect coords=62,290,340,295 href="#5819095"
ONMOUSEOVER='document.BLASTFORM.defline.value="NC_001321   Balaenoptera physalus
mitochondrion, complete genome..S=89.7 E=1e-18"'
ONMOUSEOUT='document.BLASTFORM.defline.value="Mouse-over to show defline and
scores. Click to show alignments"' >
<area shape=rect coords=62,297,526,302 href="#5835037"
ONMOUSEOVER='document.BLASTFORM.defline.value="NC_001610   Didelphis virginiana
mitochondrion, complete genome..S=79.8 E=9e-16"'
ONMOUSEOUT='document.BLASTFORM.defline.value="Mouse-over to show defline and
scores. Click to show alignments"' >
<area shape=rect coords=62,304,321,309 href="#5835275"
ONMOUSEOVER='document.BLASTFORM.defline.value="NC_001727   Crossostoma lacustre
mitochondrion, complete genome..S=69.9 E=9e-13"'
ONMOUSEOUT='document.BLASTFORM.defline.value="Mouse-over to show defline and
scores. Click to show alignments"' >
<area shape=rect coords=67,311,515,316 href="#5835820"
ONMOUSEOVER='document.BLASTFORM.defline.value="NC_002082   Hylobates lar
mitochondrion, complete genome..S=69.9 E=9e-13"'
ONMOUSEOUT='document.BLASTFORM.defline.value="Mouse-over to show defline and
scores. Click to show alignments"' >
<area shape=rect coords=62,318,458,323 href="#5835373"
ONMOUSEOVER='document.BLASTFORM.defline.value="NC_001804   Latimeria chalumnae
mitochondrion, complete genome..S=67.9 E=4e-12"'
ONMOUSEOUT='document.BLASTFORM.defline.value="Mouse-over to show defline and
scores. Click to show alignments"' >
<area shape=rect coords=69,325,327,330 href="#5835974"
ONMOUSEOVER='document.BLASTFORM.defline.value="NC_000880   Vidua chalybeata
mitochondrion, complete genome..S=65.9 E=1e-11"'
ONMOUSEOUT='document.BLASTFORM.defline.value="Mouse-over to show defline and
scores. Click to show alignments"' >
<area shape=rect coords=70,332,341,337 href="#5835722"
ONMOUSEOVER='document.BLASTFORM.defline.value="NC_002069   Corvus frugilegus
mitochondrion, complete genome..S=63.9 E=6e-11"'
ONMOUSEOUT='document.BLASTFORM.defline.value="Mouse-over to show defline and
scores. Click to show alignments"' >
<area shape=rect coords=62,339,486,344 href="#5836002"
ONMOUSEOVER='document.BLASTFORM.defline.value="NC_000886   Chelonia mydas
mitochondrial DNA, complete sequence..S=61.9 E=2e-10"'
ONMOUSEOUT='document.BLASTFORM.defline.value="Mouse-over to show defline and
scores. Click to show alignments"' >
<area shape=rect coords=62,346,150,351 href="#5835023"
ONMOUSEOVER='document.BLASTFORM.defline.value="NC_001606   Cyprinus carpio
mitochondrion, complete genome..S=61.9 E=2e-10"'
```

ONMOUSEOUT='document.BLASTFORM.defline.value="Mouse-over to show defline and scores. Click to show alignments"' >
<area shape=rect coords=117,353,256,358 href="#5835163"
ONMOUSEOVER='document.BLASTFORM.defline.value="NC_001646  Pongo pygmaeus mitochondrion, complete genome..S=61.9 E=2e-10"'
ONMOUSEOUT='document.BLASTFORM.defline.value="Mouse-over to show defline and scores. Click to show alignments"' >
<area shape=rect coords=62,360,148,365 href="#5836044"
ONMOUSEOVER='document.BLASTFORM.defline.value="NC_000890  Mustelus manazo mitochondrion, complete genome..S=60.0 E=9e-10"'
ONMOUSEOUT='document.BLASTFORM.defline.value="Mouse-over to show defline and scores. Click to show alignments"' >
<area shape=rect coords=273,248,354,253 href="#5834843"
ONMOUSEOVER='document.BLASTFORM.defline.value="NC_001323  Gallus gallus mitochondrion, complete genome..S=60.0 E=9e-10"'
ONMOUSEOUT='document.BLASTFORM.defline.value="Mouse-over to show defline and scores. Click to show alignments"' >
<area shape=rect coords=62,367,321,372 href="#5835778"
ONMOUSEOVER='document.BLASTFORM.defline.value="NC_002079  Carassius auratus mitochondrion, complete genome..S=58.0 E=3e-09"'
ONMOUSEOUT='document.BLASTFORM.defline.value="Mouse-over to show defline and scores. Click to show alignments"' >
<area shape=rect coords=62,374,323,379 href="#6137801"
ONMOUSEOVER='document.BLASTFORM.defline.value="NC_000934  Loxodonta africana mitochondrion, complete genome..S=56.0 E=1e-08"'
ONMOUSEOUT='document.BLASTFORM.defline.value="Mouse-over to show defline and scores. Click to show alignments"' >
<area shape=rect coords=87,381,348,386 href="#5835946"
ONMOUSEOVER='document.BLASTFORM.defline.value="NC_000878  Falco peregrinus mitochondrion, complete genome..S=56.0 E=1e-08"'
ONMOUSEOUT='document.BLASTFORM.defline.value="Mouse-over to show defline and scores. Click to show alignments"' >
<area shape=rect coords=87,388,321,393 href="#5835498"
ONMOUSEOVER='document.BLASTFORM.defline.value="NC_000846  Rhea americana mitochondrion, complete genome..S=56.0 E=1e-08"'
ONMOUSEOUT='document.BLASTFORM.defline.value="Mouse-over to show defline and scores. Click to show alignments"' >
<area shape=rect coords=62,395,526,400 href="#5835624"
ONMOUSEOVER='document.BLASTFORM.defline.value="NC_001960  Salmo salar mitochondrion, complete genome..S=54.0 E=5e-08"'
ONMOUSEOUT='document.BLASTFORM.defline.value="Mouse-over to show defline and scores. Click to show alignments"' >
<area shape=rect coords=62,402,161,407 href="#5835317"
ONMOUSEOVER='document.BLASTFORM.defline.value="NC_001778  Polypterus ornatipinnis mitochondrion, complete genom..S=54.0 E=5e-08"'
ONMOUSEOUT='document.BLASTFORM.defline.value="Mouse-over to show defline and scores. Click to show alignments"' >
<area shape=rect coords=287,346,481,351 href="#7555761"
ONMOUSEOVER='document.BLASTFORM.defline.value="NC_002196  Ciconia boyciana mitochondrion, complete genome..S=54.0 E=5e-08"'
ONMOUSEOUT='document.BLASTFORM.defline.value="Mouse-over to show defline and scores. Click to show alignments"' >
<area shape=rect coords=62,409,131,414 href="#5835582"
ONMOUSEOVER='document.BLASTFORM.defline.value="NC_001947  Pelomedusa subrufa mitochondrion, complete genome..S=52.0 E=2e-07"'
ONMOUSEOUT='document.BLASTFORM.defline.value="Mouse-over to show defline and scores. Click to show alignments"' >

```
<area shape=rect coords=69,416,526,421 href="#5835610"
ONMOUSEOVER='document.BLASTFORM.defline.value="NC_001953  Struthio camelus
complete mitochondrial genome..S=52.0 E=2e-07"'
ONMOUSEOUT='document.BLASTFORM.defline.value="Mouse-over to show defline and
scores. Click to show alignments"' >
<area shape=rect coords=74,423,150,428 href="#5835303"
ONMOUSEOVER='document.BLASTFORM.defline.value="NC_001770  Arbacia lixula
mitochondrion, complete genome..S=52.0 E=2e-07"'
ONMOUSEOUT='document.BLASTFORM.defline.value="Mouse-over to show defline and
scores. Click to show alignments"' >
<area shape=rect coords=304,353,357,358 href="#5835834"
ONMOUSEOVER='document.BLASTFORM.defline.value="NC_002083  Pongo pygmaeus abelii
mitochondrion, complete genome..S=52.0 E=2e-07"'
ONMOUSEOUT='document.BLASTFORM.defline.value="Mouse-over to show defline and
scores. Click to show alignments"' >
</map>
<CENTER>
<IMG WIDTH=532 HEIGHT=430 USEMAP=#img_map BORDER=1 SRC="nph-
getgif.cgi?iblast11&207891705316209.gif" ISMAP></CENTER>
<HR>
<PRE>
<PRE>

Score      E
Sequences producing significant alignments:                 (bits)   Value <a
href="http://www.ncbi.nlm.nih.gov:80/entrez/query.fcgi?cmd=Retrieve&db=Nucleotid
e&list_uids=05835205&dopt=GenBank">ref|NC_001700.1|</a>  Felis catus
mitochondrion, complete genome      <a href = #5835205>365</a>   e-101
<a
href="http://www.ncbi.nlm.nih.gov:80/entrez/query.fcgi?cmd=Retrieve&db=Nucleotid
e&list_uids=05834857&dopt=GenBank">ref|NC_001325.1|</a>  Phoca vitulina
mitochondrion, complete genome      <a href = #5834857>198</a>   1e-51
<a
href="http://www.ncbi.nlm.nih.gov:80/entrez/query.fcgi?cmd=Retrieve&db=Nucleotid
e&list_uids=05835652&dopt=GenBank">ref|NC_002008.1|</a>  Canis familiaris
mitochondrion, complete g...        <a href = #5835652>190</a>   4e-49
<a
href="http://www.ncbi.nlm.nih.gov:80/entrez/query.fcgi?cmd=Retrieve&db=Nucleotid
e&list_uids=05835009&dopt=GenBank">ref|NC_001602.1|</a>  Halichoerus grypus
mitochondrion, complete...    <a href = #5835009>180</a>   3e-46
<a
href="http://www.ncbi.nlm.nih.gov:80/entrez/query.fcgi?cmd=Retrieve&db=Nucleotid
e&list_uids=05835988&dopt=GenBank">ref|NC_000884.1|</a>  Cavia porcellus
complete mitochondrial genome    <a href = #5835988>176</a>   5e-45
<a
href="http://www.ncbi.nlm.nih.gov:80/entrez/query.fcgi?cmd=Retrieve&db=Nucleotid
e&list_uids=05835401&dopt=GenBank">ref|NC_001808.1|</a>  Ceratotherium simum
mitochondrion, complet...    <a href = #5835401>165</a>   2e-41
<a
href="http://www.ncbi.nlm.nih.gov:80/entrez/query.fcgi?cmd=Retrieve&db=Nucleotid
e&list_uids=05835484&dopt=GenBank">ref|NC_001892.1|</a>  Myoxus glis
mitochondrion, complete genome      <a href = #5835484>153</a>   8e-38
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotide&list_uids=05835345&dopt=GenBank">ref|NC_001788.1|</a>   Equus asinus
mitochondrion, complete genome      <a href = #5835345>151</a>   3e-37
<a
href="http://www.ncbi.nlm.nih.gov:80/entrez/query.fcgi?cmd=Retrieve&db=Nucleotid
e&list_uids=05835764&dopt=GenBank">ref|NC_002078.1|</a>   Orycteropus afer
complete mitochondrial ge...    <a href = #5835764>149</a>   1e-36
<a
href="http://www.ncbi.nlm.nih.gov:80/entrez/query.fcgi?cmd=Retrieve&db=Nucleotid
e&list_uids=05835429&dopt=GenBank">ref|NC_001821.1|</a>   Dasypus novemcinctus
mitochondrion, comple...     <a href = #5835429>141</a>   3e-34
<a
href="http://www.ncbi.nlm.nih.gov:80/entrez/query.fcgi?cmd=Retrieve&db=Nucleotid
e&list_uids=05835331&dopt=GenBank">ref|NC_001779.1|</a>   R.unicornis complete
mitochondrial genome        <a href = #5835331>135</a>   2e-32
<a
href="http://www.ncbi.nlm.nih.gov:80/entrez/query.fcgi?cmd=Retrieve&db=Nucleotid
e&list_uids=05834953&dopt=GenBank">ref|NC_001569.1|</a>   Mus musculus
mitochondrion, complete genome     <a href = #5834953>133</a>   7e-32
<a
href="http://www.ncbi.nlm.nih.gov:80/entrez/query.fcgi?cmd=Retrieve&db=Nucleotid
e&list_uids=05836030&dopt=GenBank">ref|NC_000889.1|</a>   Hippopotamus amphibius
mitochondrion, comp...    <a href = #5836030>125</a>   2e-29
<a
href="http://www.ncbi.nlm.nih.gov:80/entrez/query.fcgi?cmd=Retrieve&db=Nucleotid
e&list_uids=05835107&dopt=GenBank">ref|NC_001640.1|</a>   Equus caballus
mitochondrion, complete genome     <a href = #5835107>125</a>   2e-29
<a
href="http://www.ncbi.nlm.nih.gov:80/entrez/query.fcgi?cmd=Retrieve&db=Nucleotid
e&list_uids=05835359&dopt=GenBank">ref|NC_001794.1|</a>   Macropus robustus
mitochondrion, complete ...    <a href = #5835359>123</a>   7e-29
<a
href="http://www.ncbi.nlm.nih.gov:80/entrez/query.fcgi?cmd=Retrieve&db=Nucleotid
e&list_uids=05835862&dopt=GenBank">ref|NC_000845.1|</a>   Sus scrofa
mitochondrion, complete genome        <a href = #5835862>121</a>   3e-28
<a
href="http://www.ncbi.nlm.nih.gov:80/entrez/query.fcgi?cmd=Retrieve&db=Nucleotid
e&list_uids=05835177&dopt=GenBank">ref|NC_001665.1|</a>   Rattus norvegicus
mitochondrial genome        <a href = #5835177>121</a>   3e-28
<a
href="http://www.ncbi.nlm.nih.gov:80/entrez/query.fcgi?cmd=Retrieve&db=Nucleotid
e&list_uids=05834939&dopt=GenBank">ref|NC_001567.1|</a>   Bos taurus
mitochondrion, complete genome      <a href = #5834939>121</a>   3e-28
<a
href="http://www.ncbi.nlm.nih.gov:80/entrez/query.fcgi?cmd=Retrieve&db=Nucleotid
e&list_uids=05835121&dopt=GenBank">ref|NC_001643.1|</a>   Pan troglodytes
mitochondrion, complete ge...    <a href = #5835121>117</a>   4e-27
<a
href="http://www.ncbi.nlm.nih.gov:80/entrez/query.fcgi?cmd=Retrieve&db=Nucleotid
e&list_uids=05835554&dopt=GenBank">ref|NC_001941.1|</a>   Ovis aries
mitochondrion, complete genome     <a href = #5835554>109</a>   1e-24
<a
href="http://www.ncbi.nlm.nih.gov:80/entrez/query.fcgi?cmd=Retrieve&db=Nucleotid
e&list_uids=07212513&dopt=GenBank">ref|NC_002391.1|</a>   Talpa europaea
mitochondrion, complete genome     <a href = #7212513>103</a>   7e-23
<a
href="http://www.ncbi.nlm.nih.gov:80/entrez/query.fcgi?cmd=Retrieve&db=Nucleotid
```

```
e&list_uids=05835526&dopt=GenBank">ref|NC_001913.1|</a>  Oryctolagus cuniculus
mitochondrion, compl...    <a href = #5835526>103</a>   7e-23
<a
href="http://www.ncbi.nlm.nih.gov:80/entrez/query.fcgi?cmd=Retrieve&db=Nucleotid
e&list_uids=05835135&dopt=GenBank">ref|NC_001644.1|</a>  Pan paniscus
mitochondrion, complete genome    <a href = #5835135>101</a>   3e-22
<a
href="http://www.ncbi.nlm.nih.gov:80/entrez/query.fcgi?cmd=Retrieve&db=Nucleotid
e&list_uids=06137796&dopt=GenBank">ref|NC_001807.2|</a>  Human mitochondrion,
complete genome         <a href = #6137796>  98</a>   4e-21
<a
href="http://www.ncbi.nlm.nih.gov:80/entrez/query.fcgi?cmd=Retrieve&db=Nucleotid
e&list_uids=05834995&dopt=GenBank">ref|NC_001601.1|</a>  Balaenoptera musculus
mitochondrion, compl...    <a href = #5834995>  98</a>   4e-21
<a
href="http://www.ncbi.nlm.nih.gov:80/entrez/query.fcgi?cmd=Retrieve&db=Nucleotid
e&list_uids=05835666&dopt=GenBank">ref|NC_002009.1|</a>  Artibeus jamaicensis
mitochondrion, comple...    <a href = #5835666>  96</a>   2e-20
<a
href="http://www.ncbi.nlm.nih.gov:80/entrez/query.fcgi?cmd=Retrieve&db=Nucleotid
e&list_uids=05835149&dopt=GenBank">ref|NC_001645.1|</a>  Gorilla gorilla
mitochondrion, complete ge...    <a href = #5835149>  92</a>   2e-19
<a
href="http://www.ncbi.nlm.nih.gov:80/entrez/query.fcgi?cmd=Retrieve&db=Nucleotid
e&list_uids=05819095&dopt=GenBank">ref|NC_001321.1|</a>  Balaenoptera physalus
mitochondrion, compl...    <a href = #5819095>  90</a>   1e-18
<a
href="http://www.ncbi.nlm.nih.gov:80/entrez/query.fcgi?cmd=Retrieve&db=Nucleotid
e&list_uids=05835037&dopt=GenBank">ref|NC_001610.1|</a>  Didelphis virginiana
mitochondrion, comple...    <a href = #5835037>  80</a>   9e-16
<a
href="http://www.ncbi.nlm.nih.gov:80/entrez/query.fcgi?cmd=Retrieve&db=Nucleotid
e&list_uids=05835820&dopt=GenBank">ref|NC_002082.1|</a>  Hylobates lar
mitochondrion, complete genome    <a href = #5835820>  70</a>   9e-13
<a
href="http://www.ncbi.nlm.nih.gov:80/entrez/query.fcgi?cmd=Retrieve&db=Nucleotid
e&list_uids=05835275&dopt=GenBank">ref|NC_001727.1|</a>  Crossostoma lacustre
mitochondrion, comple...    <a href = #5835275>  70</a>   9e-13
<a
href="http://www.ncbi.nlm.nih.gov:80/entrez/query.fcgi?cmd=Retrieve&db=Nucleotid
e&list_uids=05835373&dopt=GenBank">ref|NC_001804.1|</a>  Latimeria chalumnae
mitochondrion, complet...    <a href = #5835373>  68</a>   4e-12
<a
href="http://www.ncbi.nlm.nih.gov:80/entrez/query.fcgi?cmd=Retrieve&db=Nucleotid
e&list_uids=05835974&dopt=GenBank">ref|NC_000880.1|</a>  Vidua chalybeata
mitochondrion, complete g...    <a href = #5835974>  66</a>   1e-11
<a
href="http://www.ncbi.nlm.nih.gov:80/entrez/query.fcgi?cmd=Retrieve&db=Nucleotid
e&list_uids=05835722&dopt=GenBank">ref|NC_002069.1|</a>  Corvus frugilegus
mitochondrion, complete ...    <a href = #5835722>  64</a>   6e-11
<a
href="http://www.ncbi.nlm.nih.gov:80/entrez/query.fcgi?cmd=Retrieve&db=Nucleotid
e&list_uids=05836002&dopt=GenBank">ref|NC_000886.1|</a>  Chelonia mydas
mitochondrial DNA, complete...    <a href = #5836002>  62</a>   2e-10
<a
href="http://www.ncbi.nlm.nih.gov:80/entrez/query.fcgi?cmd=Retrieve&db=Nucleotid
``` e&list_uids=05835163&dopt=GenBank">ref|NC_001646.1|</a>   Pongo pygmaeus
mitochondrion, complete genome      <a href = #5835163> 62</a>   2e-10
<a
href="http://www.ncbi.nlm.nih.gov:80/entrez/query.fcgi?cmd=Retrieve&db=Nucleotid
e&list_uids=05835023&dopt=GenBank">ref|NC_001606.1|</a>   Cyprinus carpio
mitochondrion, complete ge...    <a href = #5835023> 62</a>   2e-10
<a
href="http://www.ncbi.nlm.nih.gov:80/entrez/query.fcgi?cmd=Retrieve&db=Nucleotid
e&list_uids=05836044&dopt=GenBank">ref|NC_000890.1|</a>   Mustelus manazo
mitochondrion, complete ge...    <a href = #5836044> 60</a>   9e-10
<a
href="http://www.ncbi.nlm.nih.gov:80/entrez/query.fcgi?cmd=Retrieve&db=Nucleotid
e&list_uids=05834843&dopt=GenBank">ref|NC_001323.1|</a>   Gallus gallus
mitochondrion, complete genome      <a href = #5834843> 60</a>   9e-10
<a
href="http://www.ncbi.nlm.nih.gov:80/entrez/query.fcgi?cmd=Retrieve&db=Nucleotid
e&list_uids=05835778&dopt=GenBank">ref|NC_002079.1|</a>   Carassius auratus
mitochondrion, complete ...    <a href = #5835778> 58</a>   3e-09
<a
href="http://www.ncbi.nlm.nih.gov:80/entrez/query.fcgi?cmd=Retrieve&db=Nucleotid
e&list_uids=06137801&dopt=GenBank">ref|NC_000934.1|</a>   Loxodonta africana
mitochondrion, complete...    <a href = #6137801> 56</a>   1e-08
<a
href="http://www.ncbi.nlm.nih.gov:80/entrez/query.fcgi?cmd=Retrieve&db=Nucleotid
e&list_uids=05835946&dopt=GenBank">ref|NC_000878.1|</a>   Falco peregrinus
mitochondrion, complete g...    <a href = #5835946> 56</a>   1e-08
<a
href="http://www.ncbi.nlm.nih.gov:80/entrez/query.fcgi?cmd=Retrieve&db=Nucleotid
e&list_uids=05835498&dopt=GenBank">ref|NC_000846.1|</a>   Rhea americana
mitochondrion, complete genome      <a href = #5835498> 56</a>   1e-08
<a
href="http://www.ncbi.nlm.nih.gov:80/entrez/query.fcgi?cmd=Retrieve&db=Nucleotid
e&list_uids=07555761&dopt=GenBank">ref|NC_002196.1|</a>   Ciconia boyciana
mitochondrion, complete g...    <a href = #7555761> 54</a>   5e-08
<a
href="http://www.ncbi.nlm.nih.gov:80/entrez/query.fcgi?cmd=Retrieve&db=Nucleotid
e&list_uids=05835624&dopt=GenBank">ref|NC_001960.1|</a>   Salmo salar
mitochondrion, complete genome      <a href = #5835624> 54</a>   5e-08
<a
href="http://www.ncbi.nlm.nih.gov:80/entrez/query.fcgi?cmd=Retrieve&db=Nucleotid
e&list_uids=05835317&dopt=GenBank">ref|NC_001778.1|</a>   Polypterus ornatipinnis
mitochondrion, com...    <a href = #5835317> 54</a>   5e-08
<a
href="http://www.ncbi.nlm.nih.gov:80/entrez/query.fcgi?cmd=Retrieve&db=Nucleotid
e&list_uids=05835834&dopt=GenBank">ref|NC_002083.1|</a>   Pongo pygmaeus abelii
mitochondrion, compl...    <a href = #5835834> 52</a>   2e-07
<a
href="http://www.ncbi.nlm.nih.gov:80/entrez/query.fcgi?cmd=Retrieve&db=Nucleotid
e&list_uids=05835610&dopt=GenBank">ref|NC_001953.1|</a>   Struthio camelus
complete mitochondrial ge...    <a href = #5835610> 52</a>   2e-07
<a
href="http://www.ncbi.nlm.nih.gov:80/entrez/query.fcgi?cmd=Retrieve&db=Nucleotid
e&list_uids=05835582&dopt=GenBank">ref|NC_001947.1|</a>   Pelomedusa subrufa
mitochondrion, complete...    <a href = #5835582> 52</a>   2e-07
<a
href="http://www.ncbi.nlm.nih.gov:80/entrez/query.fcgi?cmd=Retrieve&db=Nucleotid

```
e&list_uids=05835303&dopt=GenBank">ref|NC_001770.1|</a>   Arbacia lixula
mitochondrion, complete genome     <a href = #5835303> 52</a>   2e-07
</PRE>
<CENTER><b><FONT color="green">Alignments</FONT></b></CENTER>
<PRE>
tmpseq_0  1     tgaatctgaggaggcttctcagtagacaaagctaccctgacacgattctttgccttccac 60
<a name = 5835205></a><a
href=http://www.ncbi.nlm.nih.gov:80/entrez/query.fcgi?cmd=Retrieve&db=Nucleotide
&list_uids=05835205&dopt=GenBank>NC_001700</a> 15524
          ..........g..g.................c.....a.............g....... 15583
<a name = 5834857></a><a
href=http://www.ncbi.nlm.nih.gov:80/entrez/query.fcgi?cmd=Retrieve&db=Nucleotide
&list_uids=05834857&dopt=GenBank>NC_001325</a> 15580
          ..............a..t........t.....a...t.a...........c......... 15639
<a name = 5835652></a><a
href=http://www.ncbi.nlm.nih.gov:80/entrez/query.fcgi?cmd=Retrieve&db=Nucleotide
&list_uids=05835652&dopt=GenBank>NC_002008</a> 14673
        ........c.............g........a.....a...............a.....t 14729
<a name = 5835009></a><a
href=http://www.ncbi.nlm.nih.gov:80/entrez/query.fcgi?cmd=Retrieve&db=Nucleotide
&list_uids=05835009&dopt=GenBank>NC_001602</a> 15553
          ..............a..t.............a...t.a...g.......c......... 15612
<a name = 5835988></a><a
href=http://www.ncbi.nlm.nih.gov:80/entrez/query.fcgi?cmd=Retrieve&db=Nucleotide
&list_uids=05835988&dopt=GenBank>NC_000884</a> 14650
          ..........g..g.................c.....a.................... 14709
<a name = 5835401></a><a
href=http://www.ncbi.nlm.nih.gov:80/entrez/query.fcgi?cmd=Retrieve&db=Nucleotide
&list_uids=05835401&dopt=GenBank>NC_001808</a> 14662
          ..............a..t..c..t.........c..a..t............c.....t... 14721
<a name = 5835484></a><a
href=http://www.ncbi.nlm.nih.gov:80/entrez/query.fcgi?cmd=Retrieve&db=Nucleotide
&list_uids=05835484&dopt=GenBank>NC_001892</a> 14654
          .....t.....c..........c...............t..a..c.....t.....a..t... 14713
<a name = 5835345></a><a
href=http://www.ncbi.nlm.nih.gov:80/entrez/query.fcgi?cmd=Retrieve&db=Nucleotide
&list_uids=05835345&dopt=GenBank>NC_001788</a> 14671
          ...........t..a...................c.....t..c.....t............ 14730
<a name = 5835764></a><a
href=http://www.ncbi.nlm.nih.gov:80/entrez/query.fcgi?cmd=Retrieve&db=Nucleotide
&list_uids=05835764&dopt=GenBank>NC_002078</a> 14663
          .....c.....t.....t.........a..a..a...........c......... 14716
<a name = 5835429></a><a
href=http://www.ncbi.nlm.nih.gov:80/entrez/query.fcgi?cmd=Retrieve&db=Nucleotide
&list_uids=05835429&dopt=GenBank>NC_001821</a> 14657
          ...................a..t..a.....c......c......... 14716
<a name = 5835331></a><a
href=http://www.ncbi.nlm.nih.gov:80/entrez/query.fcgi?cmd=Retrieve&db=Nucleotide
&list_uids=05835331&dopt=GenBank>NC_001779</a> 14664
          ..........a........c......c.....c..c.....t............ 14723
<a name = 5834953></a><a
href=http://www.ncbi.nlm.nih.gov:80/entrez/query.fcgi?cmd=Retrieve&db=Nucleotide
&list_uids=05834953&dopt=GenBank>NC_001569</a> 14625
          .....t.....g.....................c...t.....c.........c..t...... 14684
<a name = 5836030></a><a
href=http://www.ncbi.nlm.nih.gov:80/entrez/query.fcgi?cmd=Retrieve&db=Nucleotide
```

```
&list_uids=05836030&dopt=GenBank>NC_000889</a> 14658
.............t..c..............c.....t.............. 14717
<a name = 5835107></a><a
href=http://www.ncbi.nlm.nih.gov:80/entrez/query.fcgi?cmd=Retrieve&db=Nucleotide
&list_uids=05835107&dopt=GenBank>NC_001640</a> 14674
.........t..a................c.....t..c.....t.....t...... 14733
<a name = 5835359></a><a
href=http://www.ncbi.nlm.nih.gov:80/entrez/query.fcgi?cmd=Retrieve&db=Nucleotide
&list_uids=05835359&dopt=GenBank>NC_001794</a> 14670
..........g..a.....c.......c.....c..c...c..t..c.....t..t 14729
<a name = 5835862></a><a
href=http://www.ncbi.nlm.nih.gov:80/entrez/query.fcgi?cmd=Retrieve&db=Nucleotide
&list_uids=05835862&dopt=GenBank>NC_000845</a> 15828
...........g.....t..c..c........a.....c...........c......... 15887
<a name = 5835177></a><a
href=http://www.ncbi.nlm.nih.gov:80/entrez/query.fcgi?cmd=Retrieve&db=Nucleotide
&list_uids=05835177&dopt=GenBank>NC_001665</a> 14610
.............................a......a......c.....c...a...... 14669
<a name = 5834939></a><a
href=http://www.ncbi.nlm.nih.gov:80/entrez/query.fcgi?cmd=Retrieve&db=Nucleotide
&list_uids=05834939&dopt=GenBank>NC_001567</a> 15000
...........c..a..................a.....t..c.........c..t.....t 15059
<a name = 5835121></a><a
href=http://www.ncbi.nlm.nih.gov:80/entrez/query.fcgi?cmd=Retrieve&db=Nucleotide
&list_uids=05835121&dopt=GenBank>NC_001643</a> 14655
............a...........gcc.......t............ca........ 14710
<a name = 5835554></a><a
href=http://www.ncbi.nlm.nih.gov:80/entrez/query.fcgi?cmd=Retrieve&db=Nucleotide
&list_uids=05835554&dopt=GenBank>NC_001941</a> 14645
.........g.....a......................c..c.....t..c......t... 14704
<a name = 7212513></a><a
href=http://www.ncbi.nlm.nih.gov:80/entrez/query.fcgi?cmd=Retrieve&db=Nucleotide
&list_uids=07212513&dopt=GenBank>NC_002391</a> 14671
.....t.....t..g.........g..a..c............c......... 14730
<a name = 5835526></a><a
href=http://www.ncbi.nlm.nih.gov:80/entrez/query.fcgi?cmd=Retrieve&db=Nucleotide
&list_uids=05835526&dopt=GenBank>NC_001913</a> 14661
.............a..t......t.t......c..t..t..c........c..t..t... 14720
<a name = 5835135></a><a
href=http://www.ncbi.nlm.nih.gov:80/entrez/query.fcgi?cmd=Retrieve&db=Nucleotide
&list_uids=05835135&dopt=GenBank>NC_001644</a> 14656
............a...........gcc......,...t............ca..c..... 14711
<a name = 6137796></a><a
href=http://www.ncbi.nlm.nih.gov:80/entrez/query.fcgi?cmd=Retrieve&db=Nucleotide
&list_uids=06137796&dopt=GenBank>NC_001807</a> 15233
..................a...........gtc.c.....c.............a....t... 15292
<a name = 5834995></a><a
href=http://www.ncbi.nlm.nih.gov:80/entrez/query.fcgi?cmd=Retrieve&db=Nucleotide
&list_uids=05834995&dopt=GenBank>NC_001601</a> 15096
...........c..t..t..t..g..t......a...a..a.....c............... 15155
<a name = 5835666></a><a
href=http://www.ncbi.nlm.nih.gov:80/entrez/query.fcgi?cmd=Retrieve&db=Nucleotide
&list_uids=05835666&dopt=GenBank>NC_002009</a> 14636
...........t......t..c...........a..t..c...c.........c........t 14695
<a name = 5835149></a><a
href=http://www.ncbi.nlm.nih.gov:80/entrez/query.fcgi?cmd=Retrieve&db=Nucleotide
```

&list_uids=05835149&dopt=GenBank>NC_001645</a> 14686
.......t.............a.......... 14714
<a name = 5819095></a><a
href=http://www.ncbi.nlm.nih.gov:80/entrez/query.fcgi?cmd=Retrieve&db=Nucleotide
&list_uids=05819095&dopt=GenBank>NC_001321</a> 15099
...........c..t......t......t.....a..a.....a......c..t.........t... 15158
<a name = 5835037></a><a
href=http://www.ncbi.nlm.nih.gov:80/entrez/query.fcgi?cmd=Retrieve&db=Nucleotide
&list_uids=05835037&dopt=GenBank>NC_001610</a> 14663
.....t.........a......c..t..t...........a...a..c.....t.....t..t... 14722
<a name = 5835820></a><a
href=http://www.ncbi.nlm.nih.gov:80/entrez/query.fcgi?cmd=Retrieve&db=Nucleotide
&list_uids=05835820&dopt=GenBank>NC_002082</a> 14657
.......c.....a...........t..c..c..a..c.....c..t..ca....t... 14712
<a name = 5835275></a><a
href=http://www.ncbi.nlm.nih.gov:80/entrez/query.fcgi?cmd=Retrieve&db=Nucleotide
&list_uids=05835275&dopt=GenBank>NC_001727</a> 15764
...........g..g.............t...a...t........g......c.......... 15823
<a name = 5835373></a><a
href=http://www.ncbi.nlm.nih.gov:80/entrez/query.fcgi?cmd=Retrieve&db=Nucleotide
&list_uids=05835373&dopt=GenBank>NC_001804</a> 14829
..............t..t..c.........c..c..a..c..g................. 14888
<a name = 5835974></a><a
href=http://www.ncbi.nlm.nih.gov:80/entrez/query.fcgi?cmd=Retrieve&db=Nucleotide
&list_uids=05835974&dopt=GenBank>NC_000880</a> 15477
.........a............... 15500
<a name = 5835722></a><a
href=http://www.ncbi.nlm.nih.gov:80/entrez/query.fcgi?cmd=Retrieve&db=Nucleotide
&list_uids=05835722&dopt=GenBank>NC_002069</a> 14190
.....t..a...............cc.c...a...a..c................... 14243
<a name = 5836002></a><a
href=http://www.ncbi.nlm.nih.gov:80/entrez/query.fcgi?cmd=Retrieve&db=Nucleotide
&list_uids=05836002&dopt=GenBank>NC_000886</a> 14718
..............g..t............t...a......a..c.........ca......... 14777
<a name = 5835163></a><a
href=http://www.ncbi.nlm.nih.gov:80/entrez/query.fcgi?cmd=Retrieve&db=Nucleotide
&list_uids=05835163&dopt=GenBank>NC_001646</a> 14716
..............a..c.t... 14736
<a name = 5835023></a><a
href=http://www.ncbi.nlm.nih.gov:80/entrez/query.fcgi?cmd=Retrieve&db=Nucleotide
&list_uids=05835023&dopt=GenBank>NC_001606</a> 15779
...........t..g.............t...a...a..a...........c..a....... 15838
<a name = 5836044></a><a
href=http://www.ncbi.nlm.nih.gov:80/entrez/query.fcgi?cmd=Retrieve&db=Nucleotide
&list_uids=05836044&dopt=GenBank>NC_000890</a> 14841
...............g..t......c..c.....t......c..t.........t... 14900
<a name = 5835778></a><a
href=http://www.ncbi.nlm.nih.gov:80/entrez/query.fcgi?cmd=Retrieve&db=Nucleotide
&list_uids=05835778&dopt=GenBank>NC_002079</a> 15782
.....t.............c......t..t..a...at.a...........c..a...t... 15841
<a name = 6137801></a><a
href=http://www.ncbi.nlm.nih.gov:80/entrez/query.fcgi?cmd=Retrieve&db=Nucleotide
&list_uids=06137801&dopt=GenBank>NC_000934</a> 14633
................t......a...t.a.at.....t..c...c....t 14692
<a name = 5835946></a><a
href=http://www.ncbi.nlm.nih.gov:80/entrez/query.fcgi?cmd=Retrieve&db=Nucleotide

```
&list_uids=05835946&dopt=GenBank>NC_000878</a> 14222
...........cc.a..a......c.........c...c.a... 14263
<a name = 5835498></a><a
href=http://www.ncbi.nlm.nih.gov:80/entrez/query.fcgi?cmd=Retrieve&db=Nucleotide
&list_uids=05835498&dopt=GenBank>NC_000846</a> 14145
...........cc........a..c.........c...c.g... 14186
<a name = 5835624></a><a
href=http://www.ncbi.nlm.nih.gov:80/entrez/query.fcgi?cmd=Retrieve&db=Nucleotide
&list_uids=05835624&dopt=GenBank>NC_001960</a> 15870
.....t.........a..t..t.........c..c.....a........t..c.......... 15929
<a name = 5835317></a><a
href=http://www.ncbi.nlm.nih.gov:80/entrez/query.fcgi?cmd=Retrieve&db=Nucleotide
&list_uids=05835317&dopt=GenBank>NC_001778</a> 14763
..............g..t.....t..t...c.a...a..t..c..........a...... 14822
<a name = 5835610></a><a
href=http://www.ncbi.nlm.nih.gov:80/entrez/query.fcgi?cmd=Retrieve&db=Nucleotide
&list_uids=05835610&dopt=GenBank>NC_001953</a> 14115
......c..a........t.....cc.c.....a...............c.t... 14169
<a name = 5835582></a><a
href=http://www.ncbi.nlm.nih.gov:80/entrez/query.fcgi?cmd=Retrieve&db=Nucleotide
&list_uids=05835582&dopt=GenBank>NC_001947</a> 14805
...............a..t............t..a......a..c........      14854
<a name = 5835303></a><a
href=http://www.ncbi.nlm.nih.gov:80/entrez/query.fcgi?cmd=Retrieve&db=Nucleotide
&list_uids=05835303&dopt=GenBank>NC_001770</a> 15069
.....t.........t.........a.....a..c............t..t... 15119 tmpseq_0    61    ttcatccttccatttatcatctcagctctagcagcagtccacctcctattccttcacgag 120
<a
href=http://www.ncbi.nlm.nih.gov:80/entrez/query.fcgi?cmd=Retrieve&db=Nucleotide
&list_uids=05835205&dopt=GenBank>NC_001700</a> 15584
.....t.........c..t.........ct......g...a......t...........t..a 15643
<a
href=http://www.ncbi.nlm.nih.gov:80/entrez/query.fcgi?cmd=Retrieve&db=Nucleotide
&list_uids=05834857&dopt=GenBank>NC_001325</a> 15640
........a.....cg.ag.a.t...a....ac...........a.........a......a 15699
<a
href=http://www.ncbi.nlm.nih.gov:80/entrez/query.fcgi?cmd=Retrieve&db=Nucleotide
&list_uids=05835652&dopt=GenBank>NC_002008</a> 14730
.........c...t...c......g...........at...a............t..a......a 14789
<a
href=http://www.ncbi.nlm.nih.gov:80/entrez/query.fcgi?cmd=Retrieve&db=Nucleotide
&list_uids=05835009&dopt=GenBank>NC_001602</a> 15613
........a.....cg.ag.a.t...a...................a.........a.....a 15672
<a
href=http://www.ncbi.nlm.nih.gov:80/entrez/query.fcgi?cmd=Retrieve&db=Nucleotide
&list_uids=05835988&dopt=GenBank>NC_000884</a> 14710
..t..t.........c.......a.c..c....tgat..........t........c...... 14769
<a
href=http://www.ncbi.nlm.nih.gov:80/entrez/query.fcgi?cmd=Retrieve&db=Nucleotide
&list_uids=05835401&dopt=GenBank>NC_001808</a> 14722
..t......c..c......t...at...c......atcac......a...............a 14781
<a
href=http://www.ncbi.nlm.nih.gov:80/entrez/query.fcgi?cmd=Retrieve&db=Nucleotide
&list_uids=05835484&dopt=GenBank>NC_001892</a> 14714
..t..t..a..c..c..t..tg....c....t.at.........t..............a 14773
```

```
<a
href=http://www.ncbi.nlm.nih.gov:80/entrez/query.fcgi?cmd=Retrieve&db=Nucleotide
&list_uids=05835345&dopt=GenBank>NC_001788</a> 14731
..t..t..a..c..........a....c...g.t.atc.....t..a........c.....a 14790
<a
href=http://www.ncbi.nlm.nih.gov:80/entrez/query.fcgi?cmd=Retrieve&db=Nucleotide
&list_uids=05835764&dopt=GenBank>NC_002078</a> 14717
..t.....g........t..tg..........tat......t..a.....t..a......a 14776
<a
href=http://www.ncbi.nlm.nih.gov:80/entrez/query.fcgi?cmd=Retrieve&db=Nucleotide
&list_uids=05835429&dopt=GenBank>NC_001821</a> 14717
......t.a........t...a....a..c.t..t.........gt.......a.....a 14776
<a
href=http://www.ncbi.nlm.nih.gov:80/entrez/query.fcgi?cmd=Retrieve&db=Nucleotide
&list_uids=05835331&dopt=GenBank>NC_001779</a> 14724
..t.........c..c..t...ct...c......a..c..-....a.........a.....a 14783
                                          \
                                           |
                                           t
<a
href=http://www.ncbi.nlm.nih.gov:80/entrez/query.fcgi?cmd=Retrieve&db=Nucleotide
&list_uids=05834953&dopt=GenBank>NC_001569</a> 14685
......t.a........t...g.g..c......atc..t.........c.....c.....a 14744
<a
href=http://www.ncbi.nlm.nih.gov:80/entrez/query.fcgi?cmd=Retrieve&db=Nucleotide
&list_uids=05836030&dopt=GenBank>NC_000889</a> 14718
..t..t........cg.t...a....a.....catc.....t..a.........c..t..a 14777
<a
href=http://www.ncbi.nlm.nih.gov:80/entrez/query.fcgi?cmd=Retrieve&db=Nucleotide
&list_uids=05835107&dopt=GenBank>NC_001640</a> 14734
........a...c..c......a....c...g.t..tc..a...tt.a.....t........a 14793
<a
href=http://www.ncbi.nlm.nih.gov:80/entrez/query.fcgi?cmd=Retrieve&db=Nucleotide
&list_uids=05835359&dopt=GenBank>NC_001794</a> 14730
..t......a...........a......c.....t.ct...t..............a...... 14789
<a
href=http://www.ncbi.nlm.nih.gov:80/entrez/query.fcgi?cmd=Retrieve&db=Nucleotide
&list_uids=05835359&dopt=GenBank>NC_001794</a> 14462
...............   14475
<a
href=http://www.ncbi.nlm.nih.gov:80/entrez/query.fcgi?cmd=Retrieve&db=Nucleotide
&list_uids=05835862&dopt=GenBank>NC_000845</a> 15888
..t.....g.....c.....ta.c...c..c.....c...a..t...........g.....a 15947
<a
href=http://www.ncbi.nlm.nih.gov:80/entrez/query.fcgi?cmd=Retrieve&db=Nucleotide
&list_uids=05835177&dopt=GenBank>NC_001665</a> 14670
........c.....c...t...g.c..c..t...att..a...t..t..t.....c.....a 14729
<a
href=http://www.ncbi.nlm.nih.gov:80/entrez/query.fcgi?cmd=Retrieve&db=Nucleotide
&list_uids=05834939&dopt=GenBank>NC_001567</a> 15060
..t............at...aa.t..cat........a........c.....a 15119
<a
href=http://www.ncbi.nlm.nih.gov:80/entrez/query.fcgi?cmd=Retrieve&db=Nucleotide
&list_uids=05835121&dopt=GenBank>NC_001643</a> 14711
..t...t.a..c..c......a....c...a..a..c.t..t.........t.a.....a 14770
<a
href=http://www.ncbi.nlm.nih.gov:80/entrez/query.fcgi?cmd=Retrieve&db=Nucleotide
```

```
<a href=http://www.ncbi.nlm.nih.gov/80/entrez/query.fcgi?cmd=Retrieve&db=Nucleotide
&list_uids=05835554&dopt=GenBank>NC_001941</a> 14705
..t..tt.c......c......g....c..c..cat...t.....a..c......c.....a 14764
<a
href=http://www.ncbi.nlm.nih.gov:80/entrez/query.fcgi?cmd=Retrieve&db=Nucleotide
&list_uids=07212513&dopt=GenBank>NC_002391</a> 14731
.....t..g.........t..tg.g..a.....t.g...t.....gt....t.........a 14790
<a
href=http://www.ncbi.nlm.nih.gov:80/entrez/query.fcgi?cmd=Retrieve&db=Nucleotide
&list_uids=05835526&dopt=GenBank>NC_001913</a> 14721 ......t.g............
14740
<a
href=http://www.ncbi.nlm.nih.gov:80/entrez/query.fcgi?cmd=Retrieve&db=Nucleotide
&list_uids=05835135&dopt=GenBank>NC_001644</a> 14712
..t.....a..c..c..t...a....c...a..a..c.t..t..........t.a.....a 14771
<a
href=http://www.ncbi.nlm.nih.gov:80/entrez/query.fcgi?cmd=Retrieve&db=Nucleotide
&list_uids=06137796&dopt=GenBank>NC_001807</a> 15293
......t.g..c..c..t..tg....c......a..c...............t.g.....a 15352
<a
href=http://www.ncbi.nlm.nih.gov:80/entrez/query.fcgi?cmd=Retrieve&db=Nucleotide
&list_uids=05834995&dopt=GenBank>NC_001601</a> 15156
.....t..c..c..c.....tat...at.....atc.........a.c............a 15215
<a
href=http://www.ncbi.nlm.nih.gov:80/entrez/query.fcgi?cmd=Retrieve&db=Nucleotide
&list_uids=05835666&dopt=GenBank>NC_002009</a> 14696
..tc.a......c..c..tg.aa.........t.at.........tt....t..a.....a 14755
<a
href=http://www.ncbi.nlm.nih.gov:80/entrez/query.fcgi?cmd=Retrieve&db=Nucleotide
&list_uids=05835149&dopt=GenBank>NC_001645</a> 14715
..t.....a..c..c......a....c...a..a.cc....t.........t...a.....a 14774
<a
href=http://www.ncbi.nlm.nih.gov:80/entrez/query.fcgi?cmd=Retrieve&db=Nucleotide
&list_uids=05819095&dopt=GenBank>NC_001321</a> 15159
..t......c..c..c......ct...at.....att........ta.t............a 15218
<a
href=http://www.ncbi.nlm.nih.gov:80/entrez/query.fcgi?cmd=Retrieve&db=Nucleotide
&list_uids=05835037&dopt=GenBank>NC_001610</a> 14723
..t..t.........c......t.t....a...t..t...a..t..t.....t.........a 14782
<a
href=http://www.ncbi.nlm.nih.gov:80/entrez/query.fcgi?cmd=Retrieve&db=Nucleotide
&list_uids=05835820&dopt=GenBank>NC_002082</a> 14713
........a..t..c..t...a.g..c........cc.g.....t.........a....... 14772
<a
href=http://www.ncbi.nlm.nih.gov:80/entrez/query.fcgi?cmd=Retrieve&db=Nucleotide
&list_uids=05835275&dopt=GenBank>NC_001727</a> 15824 ...
15826
<a
href=http://www.ncbi.nlm.nih.gov:80/entrez/query.fcgi?cmd=Retrieve&db=Nucleotide
&list_uids=05835275&dopt=GenBank>NC_001727</a> 15872
............ 15883
<a
href=http://www.ncbi.nlm.nih.gov:80/entrez/query.fcgi?cmd=Retrieve&db=Nucleotide
&list_uids=05835373&dopt=GenBank>NC_001804</a> 14889 ...c....g.....
14902
<a
href=http://www.ncbi.nlm.nih.gov:80/entrez/query.fcgi?cmd=Retrieve&db=Nucleotide
```

```
&list_uids=05835373&dopt=GenBank>NC_001804</a> 14928
.....g..c.........t... 14948
<a
href=http://www.ncbi.nlm.nih.gov:80/entrez/query.fcgi?cmd=Retrieve&db=Nucleotide
&list_uids=05835974&dopt=GenBank>NC_000880</a> 15567
..........ac......a.....a 15591
<a
href=http://www.ncbi.nlm.nih.gov:80/entrez/query.fcgi?cmd=Retrieve&db=Nucleotide
&list_uids=05835722&dopt=GenBank>NC_002069</a> 14244
...c....a..c...g.a...g...gc...a..ct...t.....aacc...........a 14303
<a
href=http://www.ncbi.nlm.nih.gov:80/entrez/query.fcgi?cmd=Retrieve&db=Nucleotide
&list_uids=05836002&dopt=GenBank>NC_000886</a> 14778 ...
14780
<a
href=http://www.ncbi.nlm.nih.gov:80/entrez/query.fcgi?cmd=Retrieve&db=Nucleotide
&list_uids=05835163&dopt=GenBank>NC_001646</a> 14737
.....a..a..t..c.....ta........a..a.cc.t....................a 14796
<a
href=http://www.ncbi.nlm.nih.gov:80/entrez/query.fcgi?cmd=Retrieve&db=Nucleotide
&list_uids=05835023&dopt=GenBank>NC_001606</a> 15839 ...
15841
<a
href=http://www.ncbi.nlm.nih.gov:80/entrez/query.fcgi?cmd=Retrieve&db=Nucleotide
&list_uids=05836044&dopt=GenBank>NC_000890</a> 14901 ..
14902
<a
href=http://www.ncbi.nlm.nih.gov:80/entrez/query.fcgi?cmd=Retrieve&db=Nucleotide
&list_uids=05835778&dopt=GenBank>NC_002079</a> 15842 ...c....a............
15862
<a
href=http://www.ncbi.nlm.nih.gov:80/entrez/query.fcgi?cmd=Retrieve&db=Nucleotide
&list_uids=06137801&dopt=GenBank>NC_000934</a> 14693 .....t..........
14708
<a
href=http://www.ncbi.nlm.nih.gov:80/entrez/query.fcgi?cmd=Retrieve&db=Nucleotide
&list_uids=05835946&dopt=GenBank>NC_000878</a> 14264 ...c.a........
14277
<a
href=http://www.ncbi.nlm.nih.gov:80/entrez/query.fcgi?cmd=Retrieve&db=Nucleotide
&list_uids=05835498&dopt=GenBank>NC_000846</a> 14235
.....a.....a 14246
<a
href=http://www.ncbi.nlm.nih.gov:80/entrez/query.fcgi?cmd=Retrieve&db=Nucleotide
&list_uids=05835498&dopt=GenBank>NC_000846</a> 14187 ...
14189
<a
href=http://www.ncbi.nlm.nih.gov:80/entrez/query.fcgi?cmd=Retrieve&db=Nucleotide
&list_uids=05835624&dopt=GenBank>NC_001960</a> 15930 ...
15932
<a
href=http://www.ncbi.nlm.nih.gov:80/entrez/query.fcgi?cmd=Retrieve&db=Nucleotide
&list_uids=05835317&dopt=GenBank>NC_001778</a> 14823 .....t.....
14833
<a
href=http://www.ncbi.nlm.nih.gov:80/entrez/query.fcgi?cmd=Retrieve&db=Nucleotide
```

```
&list_uids=05835610&dopt=GenBank>NC_001953</a>  14170 ...c....c......
14184
<a
href=http://www.ncbi.nlm.nih.gov:80/entrez/query.fcgi?cmd=Retrieve&db=Nucleotide
&list_uids=05835303&dopt=GenBank>NC_001770</a>  15120 ...
15122 tmpseq_0   121    acaggatctaacaacccctcaggaatagtatccgactcagacaaaattccattccaccca 180
<a
href=http://www.ncbi.nlm.nih.gov:80/entrez/query.fcgi?cmd=Retrieve&db=Nucleotide
&list_uids=05835205&dopt=GenBank>NC_001700</a>  15644
.........................tac......t...........c............. 15703
<a
href=http://www.ncbi.nlm.nih.gov:80/entrez/query.fcgi?cmd=Retrieve&db=Nucleotide
&list_uids=05834857&dopt=GenBank>NC_001325</a>  15700
........a...........c.....ca....................c..........g 15759
<a
href=http://www.ncbi.nlm.nih.gov:80/entrez/query.fcgi?cmd=Retrieve&db=Nucleotide
&list_uids=05835652&dopt=GenBank>NC_002008</a>  14790
..c.....c........t........cac...a....................t.....t 14849
<a
href=http://www.ncbi.nlm.nih.gov:80/entrez/query.fcgi?cmd=Retrieve&db=Nucleotide
&list_uids=05835009&dopt=GenBank>NC_001602</a>  15673
........a...........c.....ca..c.................c..........g 15732
<a
href=http://www.ncbi.nlm.nih.gov:80/entrez/query.fcgi?cmd=Retrieve&db=Nucleotide
&list_uids=05835988&dopt=GenBank>NC_000884</a>  14770
........a........a......c...aac..a......c.........c.........t 14829
<a
href=http://www.ncbi.nlm.nih.gov:80/entrez/query.fcgi?cmd=Retrieve&db=Nucleotide
&list_uids=05835401&dopt=GenBank>NC_001808</a>  14782
........c..t.....a.........ccc....a...at..........c............ 14841
<a
href=http://www.ncbi.nlm.nih.gov:80/entrez/query.fcgi?cmd=Retrieve&db=Nucleotide
&list_uids=05835484&dopt=GenBank>NC_001892</a>  14774
........g..t.....a......t...aac..a...a...........c............t 14833
<a
href=http://www.ncbi.nlm.nih.gov:80/entrez/query.fcgi?cmd=Retrieve&db=Nucleotide
&list_uids=05835345&dopt=GenBank>NC_001788</a>  14791
........c....................ccc...t...at..........c...........g 14850
<a
href=http://www.ncbi.nlm.nih.gov:80/entrez/query.fcgi?cmd=Retrieve&db=Nucleotide
&list_uids=05835764&dopt=GenBank>NC_002078</a>  14777
................t.t....t..a.t..t...............c..t.........t 14836
<a
href=http://www.ncbi.nlm.nih.gov:80/entrez/query.fcgi?cmd=Retrieve&db=Nucleotide
&list_uids=05835429&dopt=GenBank>NC_001821</a>  14777
........a.........a....t..ctcg...aa..at.....c...c...........g 14836
<a
href=http://www.ncbi.nlm.nih.gov:80/entrez/query.fcgi?cmd=Retrieve&db=Nucleotide
&list_uids=05835331&dopt=GenBank>NC_001779</a>  14784
.....g..c........a........tcc....a..at..........c............t 14843
<a
href=http://www.ncbi.nlm.nih.gov:80/entrez/query.fcgi?cmd=Retrieve&db=Nucleotide
&list_uids=05834953&dopt=GenBank>NC_001569</a>  14745
........a........aa.....t..aac..a..tg....t............t.....c 14804
```

```
<a
href=http://www.ncbi.nlm.nih.gov:80/entrez/query.fcgi?cmd=Retrieve&db=Nucleotide
&list_uids=05836030&dopt=GenBank>NC_000889</a> 14778
........c.........aa.......cccc...aa..g..........c............c 14837
<a
href=http://www.ncbi.nlm.nih.gov:80/entrez/query.fcgi?cmd=Retrieve&db=Nucleotide
&list_uids=05835107&dopt=GenBank>NC_001640</a> 14794
...............t................ccc......tatg........c............. 14853
<a
href=http://www.ncbi.nlm.nih.gov:80/entrez/query.fcgi?cmd=Retrieve&db=Nucleotide
&list_uids=05835359&dopt=GenBank>NC_001794</a> 14790
..c..t..........a..t.....caacc.................c...........t 14849
<a
href=http://www.ncbi.nlm.nih.gov:80/entrez/query.fcgi?cmd=Retrieve&db=Nucleotide
&list_uids=05835862&dopt=GenBank>NC_000845</a> 15948
..c.....c........ta.c.....ctc...a...at................t...... 16007
<a
href=http://www.ncbi.nlm.nih.gov:80/entrez/query.fcgi?cmd=Retrieve&db=Nucleotide
&list_uids=05835177&dopt=GenBank>NC_001665</a> 14730
........a..t......a.....t..aac......g..........c........t... 14789
<a
href=http://www.ncbi.nlm.nih.gov:80/entrez/query.fcgi?cmd=Retrieve&db=Nucleotide
&list_uids=05834939&dopt=GenBank>NC_001567</a> 15120
.....c..c.........aa.......ttcc..a...gt..........c............c 15179
<a
href=http://www.ncbi.nlm.nih.gov:80/entrez/query.fcgi?cmd=Retrieve&db=Nucleotide
&list_uids=05835121&dopt=GenBank>NC_001643</a> 14771
........a..t......ct......cacc...c.....c..........a.c.........c 14830
<a
href=http://www.ncbi.nlm.nih.gov:80/entrez/query.fcgi?cmd=Retrieve&db=Nucleotide
&list_uids=05835554&dopt=GenBank>NC_001941</a> 14765
.......c.........a.......tcc...g...a....t.........c........t 14824
<a
href=http://www.ncbi.nlm.nih.gov:80/entrez/query.fcgi?cmd=Retrieve&db=Nucleotide
&list_uids=07212513&dopt=GenBank>NC_002391</a> 14791 ........a.........a.......
14814
<a
href=http://www.ncbi.nlm.nih.gov:80/entrez/query.fcgi?cmd=Retrieve&db=Nucleotide
&list_uids=05835526&dopt=GenBank>NC_001913</a> 14815
.......t......c..t.........c 14840
<a
href=http://www.ncbi.nlm.nih.gov:80/entrez/query.fcgi?cmd=Retrieve&db=Nucleotide
&list_uids=05835135&dopt=GenBank>NC_001644</a> 14772
........a..t......ct......cacc...c.....c..........a.c.........c 14831
<a
href=http://www.ncbi.nlm.nih.gov:80/entrez/query.fcgi?cmd=Retrieve&db=Nucleotide
&list_uids=06137796&dopt=GenBank>NC_001807</a> 15353
..g.....a..........ct......cacc...c.t..c..t......ca.c........t 15412
<a
href=http://www.ncbi.nlm.nih.gov:80/entrez/query.fcgi?cmd=Retrieve&db=Nucleotide
&list_uids=05834995&dopt=GenBank>NC_001601</a> 15216
........c..........a....t..ccc...t...at...t.................c 15275
<a
href=http://www.ncbi.nlm.nih.gov:80/entrez/query.fcgi?cmd=Retrieve&db=Nucleotide
&list_uids=05835666&dopt=GenBank>NC_002009</a> 14756
................a....c..tcc...a...c......t................c 14815
```

```
<a
href=http://www.ncbi.nlm.nih.gov:80/entrez/query.fcgi?cmd=Retrieve&db=Nucleotide
&list_uids=05835149&dopt=GenBank>NC_001645</a> 14775
........a........tct...c..cccc...c....t.........ca.c........c 14834
<a
href=http://www.ncbi.nlm.nih.gov:80/entrez/query.fcgi?cmd=Retrieve&db=Nucleotide
&list_uids=05819095&dopt=GenBank>NC_001321</a> 15219
........c.........a....c..ccc.......at...t.....c............c 15278
<a
href=http://www.ncbi.nlm.nih.gov:80/entrez/query.fcgi?cmd=Retrieve&db=Nucleotide
&list_uids=05835037&dopt=GenBank>NC_001610</a> 14783
........a.g...t..aa....cc...-....a.......t.................c 14842
                                          \
                                           |
                                           a
<a
href=http://www.ncbi.nlm.nih.gov:80/entrez/query.fcgi?cmd=Retrieve&db=Nucleotide
&list_uids=05835820&dopt=GenBank>NC_002082</a> 14773
........a.....t....t...c..ctcc...c.ac..........cg.c........c 14832
<a
href=http://www.ncbi.nlm.nih.gov:80/entrez/query.fcgi?cmd=Retrieve&db=Nucleotide
&list_uids=05835275&dopt=GenBank>NC_001727</a> 15884
.....c..c.........g....cc..aac......g....t.....ct.c......... 15943
<a
href=http://www.ncbi.nlm.nih.gov:80/entrez/query.fcgi?cmd=Retrieve&db=Nucleotide
&list_uids=05835373&dopt=GenBank>NC_001804</a> 14949 ........c........
14965
<a
href=http://www.ncbi.nlm.nih.gov:80/entrez/query.fcgi?cmd=Retrieve&db=Nucleotide
&list_uids=05835974&dopt=GenBank>NC_000880</a> 15592
........a.....t..aat......tcc...a.....gt.................... 15651
<a
href=http://www.ncbi.nlm.nih.gov:80/entrez/query.fcgi?cmd=Retrieve&db=Nucleotide
&list_uids=05835722&dopt=GenBank>NC_002069</a> 14304
.....c..a.......gct...t..tccc..a.....gc........c............ 14363
<a
href=http://www.ncbi.nlm.nih.gov:80/entrez/query.fcgi?cmd=Retrieve&db=Nucleotide
&list_uids=05835163&dopt=GenBank>NC_001646</a> 14797 ........a...t......
14814
<a name = 5834843></a><a
href=http://www.ncbi.nlm.nih.gov:80/entrez/query.fcgi?cmd=Retrieve&db=Nucleotide
&list_uids=05834843&dopt=GenBank>NC_001323</a> 15531
.........t.............t...... 15561
<a
href=http://www.ncbi.nlm.nih.gov:80/entrez/query.fcgi?cmd=Retrieve&db=Nucleotide
&list_uids=05835778&dopt=GenBank>NC_002079</a> 15939
...........t.t.......... 15961
<a
href=http://www.ncbi.nlm.nih.gov:80/entrez/query.fcgi?cmd=Retrieve&db=Nucleotide
&list_uids=06137801&dopt=GenBank>NC_000934</a> 14786
...............c..c..t...... 14812
<a
href=http://www.ncbi.nlm.nih.gov:80/entrez/query.fcgi?cmd=Retrieve&db=Nucleotide
&list_uids=05835946&dopt=GenBank>NC_000878</a> 14363
........c............ 14383
<a
href=http://www.ncbi.nlm.nih.gov:80/entrez/query.fcgi?cmd=Retrieve&db=Nucleotide
```

```
&list_uids=05835498&dopt=GenBank>NC_000846</a> 14247
..c..g..c...........t......c.....tc....t.........c............c 14306
<a name = 7555761></a><a
href=http://www.ncbi.nlm.nih.gov:80/entrez/query.fcgi?cmd=Retrieve&db=Nucleotide
&list_uids=07555761&dopt=GenBank>NC_002196</a> 16371
....................c 16391
<a name = 5835834></a><a
href=http://www.ncbi.nlm.nih.gov:80/entrez/query.fcgi?cmd=Retrieve&db=Nucleotide
&list_uids=05835834&dopt=GenBank>NC_002083</a> 14858
........c 14866
<a
href=http://www.ncbi.nlm.nih.gov:80/entrez/query.fcgi?cmd=Retrieve&db=Nucleotide
&list_uids=05835610&dopt=GenBank>NC_001953</a> 14269
........c..c......... 14289 tmpseq_0   181   tactacacaatcaaagatatcctgggccttctagtactaatcctagcactcatactactc 240
<a
href=http://www.ncbi.nlm.nih.gov:80/entrez/query.fcgi?cmd=Retrieve&db=Nucleotide
&list_uids=05835205&dopt=GenBank>NC_001700</a> 15704
.....t..........c.....a..t.............g.tt..a............... 15763
<a
href=http://www.ncbi.nlm.nih.gov:80/entrez/query.fcgi?cmd=Retrieve&db=Nucleotide
&list_uids=05834857&dopt=GenBank>NC_001325</a> 15760
.....t.....t...........a..ggcc...c.t..c...t....tc..a.c......a 15819
<a
href=http://www.ncbi.nlm.nih.gov:80/entrez/query.fcgi?cmd=Retrieve&db=Nucleotide
&list_uids=05835652&dopt=GenBank>NC_002008</a> 14850 ..............g........
14872
<a
href=http://www.ncbi.nlm.nih.gov:80/entrez/query.fcgi?cmd=Retrieve&db=Nucleotide
&list_uids=05835009&dopt=GenBank>NC_001602</a> 15733 .....t......t......c.....
15755
<a
href=http://www.ncbi.nlm.nih.gov:80/entrez/query.fcgi?cmd=Retrieve&db=Nucleotide
&list_uids=05835009&dopt=GenBank>NC_001602</a> 15786
......a 15792
<a
href=http://www.ncbi.nlm.nih.gov:80/entrez/query.fcgi?cmd=Retrieve&db=Nucleotide
&list_uids=05835988&dopt=GenBank>NC_000884</a> 14830 ..t..............
14846
<a
href=http://www.ncbi.nlm.nih.gov:80/entrez/query.fcgi?cmd=Retrieve&db=Nucleotide
&list_uids=05835401&dopt=GenBank>NC_001808</a> 14842
...................c.........aa..t..c.c..............ac.cgcc..a 14901
<a
href=http://www.ncbi.nlm.nih.gov:80/entrez/query.fcgi?cmd=Retrieve&db=Nucleotide
&list_uids=05835484&dopt=GenBank>NC_001892</a> 14834
..t.......t.........t..a......a..cc....c...tt.tctc......acc..a 14893
<a
href=http://www.ncbi.nlm.nih.gov:80/entrez/query.fcgi?cmd=Retrieve&db=Nucleotide
&list_uids=05835345&dopt=GenBank>NC_001788</a> 14851                       14882
...........t......c......a..a.....
<a
href=http://www.ncbi.nlm.nih.gov:80/entrez/query.fcgi?cmd=Retrieve&db=Nucleotide
&list_uids=05835345&dopt=GenBank>NC_001788</a> 15080
................       15095
```

```
<a
href=http://www.ncbi.nlm.nih.gov:80/entrez/query.fcgi?cmd=Retrieve&db=Nucleotide
&list_uids=05835764&dopt=GenBank>NC_002078</a> 14837 ..................
14853
<a
href=http://www.ncbi.nlm.nih.gov:80/entrez/query.fcgi?cmd=Retrieve&db=Nucleotide
&list_uids=05835429&dopt=GenBank>NC_001821</a> 14837 .....t.....t............
14859
<a
href=http://www.ncbi.nlm.nih.gov:80/entrez/query.fcgi?cmd=Retrieve&db=Nucleotide
&list_uids=05835331&dopt=GenBank>NC_001779</a> 14844 ................c.....
14866
<a
href=http://www.ncbi.nlm.nih.gov:80/entrez/query.fcgi?cmd=Retrieve&db=Nucleotide
&list_uids=05834953&dopt=GenBank>NC_001569</a> 14805 .....t.................
14827
<a
href=http://www.ncbi.nlm.nih.gov:80/entrez/query.fcgi?cmd=Retrieve&db=Nucleotide
&list_uids=05836030&dopt=GenBank>NC_000889</a> 14838 ..t...........g..c.....
14860
<a
href=http://www.ncbi.nlm.nih.gov:80/entrez/query.fcgi?cmd=Retrieve&db=Nucleotide
&list_uids=05835107&dopt=GenBank>NC_001640</a> 14854 ..t...t.....t......c.....
14876
<a
href=http://www.ncbi.nlm.nih.gov:80/entrez/query.fcgi?cmd=Retrieve&db=Nucleotide
&list_uids=05835107&dopt=GenBank>NC_001640</a> 15085
..............       15098
<a
href=http://www.ncbi.nlm.nih.gov:80/entrez/query.fcgi?cmd=Retrieve&db=Nucleotide
&list_uids=05835359&dopt=GenBank>NC_001794</a> 14850 ..t..t...t..........
14867
<a
href=http://www.ncbi.nlm.nih.gov:80/entrez/query.fcgi?cmd=Retrieve&db=Nucleotide
&list_uids=05835862&dopt=GenBank>NC_000845</a> 16008 ........t..t......
16024
<a
href=http://www.ncbi.nlm.nih.gov:80/entrez/query.fcgi?cmd=Retrieve&db=Nucleotide
&list_uids=05835177&dopt=GenBank>NC_001665</a> 14790 ..t..t.....t.....
14806
<a
href=http://www.ncbi.nlm.nih.gov:80/entrez/query.fcgi?cmd=Retrieve&db=Nucleotide
&list_uids=05834939&dopt=GenBank>NC_001567</a> 15180
.....t..c..t..g..c....t.......c...--........t......t..a.........a 15239
                                                          \
                                                           |
                                                          ag
<a
href=http://www.ncbi.nlm.nih.gov:80/entrez/query.fcgi?cmd=Retrieve&db=Nucleotide
&list_uids=05835121&dopt=GenBank>NC_001643</a> 14831 .......................
14853
<a
href=http://www.ncbi.nlm.nih.gov:80/entrez/query.fcgi?cmd=Retrieve&db=Nucleotide
&list_uids=05835554&dopt=GenBank>NC_001941</a> 14825 ..t.....c..t.....c.....
14847
<a
href=http://www.ncbi.nlm.nih.gov:80/entrez/query.fcgi?cmd=Retrieve&db=Nucleotide
```

```
&list_uids=05835526&dopt=GenBank>NC_001913</a> 14841 ................
14857
<a
href=http://www.ncbi.nlm.nih.gov:80/entrez/query.fcgi?cmd=Retrieve&db=Nucleotide
&list_uids=05835135&dopt=GenBank>NC_001644</a> 14832 ..........c.............
14854
<a
href=http://www.ncbi.nlm.nih.gov:80/entrez/query.fcgi?cmd=Retrieve&db=Nucleotide
&list_uids=06137796&dopt=GenBank>NC_001807</a> 15413 ................
15429
<a
href=http://www.ncbi.nlm.nih.gov:80/entrez/query.fcgi?cmd=Retrieve&db=Nucleotide
&list_uids=05834995&dopt=GenBank>NC_001601</a> 15276 ...........t.....
15292
<a
href=http://www.ncbi.nlm.nih.gov:80/entrez/query.fcgi?cmd=Retrieve&db=Nucleotide
&list_uids=05835666&dopt=GenBank>NC_002009</a> 14816 .....t..t..t........
14835
<a
href=http://www.ncbi.nlm.nih.gov:80/entrez/query.fcgi?cmd=Retrieve&db=Nucleotide
&list_uids=05835149&dopt=GenBank>NC_001645</a> 14835
.................c.....a.....                          14863
<a
href=http://www.ncbi.nlm.nih.gov:80/entrez/query.fcgi?cmd=Retrieve&db=Nucleotide
&list_uids=05819095&dopt=GenBank>NC_001321</a> 15279 ...c.......t.....
15295
<a
href=http://www.ncbi.nlm.nih.gov:80/entrez/query.fcgi?cmd=Retrieve&db=Nucleotide
&list_uids=05835037&dopt=GenBank>NC_001610</a> 14843 .....t..c..a...........
14865
<a
href=http://www.ncbi.nlm.nih.gov:80/entrez/query.fcgi?cmd=Retrieve&db=Nucleotide
&list_uids=05835820&dopt=GenBank>NC_002082</a> 14833 .....t...........c.....
14855
<a
href=http://www.ncbi.nlm.nih.gov:80/entrez/query.fcgi?cmd=Retrieve&db=Nucleotide
&list_uids=05835275&dopt=GenBank>NC_001727</a> 15944 ....
15947
<a
href=http://www.ncbi.nlm.nih.gov:80/entrez/query.fcgi?cmd=Retrieve&db=Nucleotide
&list_uids=05835974&dopt=GenBank>NC_000880</a> 15652 ........
15659
<a
href=http://www.ncbi.nlm.nih.gov:80/entrez/query.fcgi?cmd=Retrieve&db=Nucleotide
&list_uids=05835722&dopt=GenBank>NC_002069</a> 14364 ......t...........
14381
<a
href=http://www.ncbi.nlm.nih.gov:80/entrez/query.fcgi?cmd=Retrieve&db=Nucleotide
&list_uids=05834843&dopt=GenBank>NC_001323</a> 15562 ......t.ct.......c..t......
15588
<a
href=http://www.ncbi.nlm.nih.gov:80/entrez/query.fcgi?cmd=Retrieve&db=Nucleotide
&list_uids=05835778&dopt=GenBank>NC_002079</a> 15962 ....
15965
<a
href=http://www.ncbi.nlm.nih.gov:80/entrez/query.fcgi?cmd=Retrieve&db=Nucleotide
```

```
&list_uids=06137801&dopt=GenBank>NC_000934</a> 14813 .....
14817
<a
href=http://www.ncbi.nlm.nih.gov:80/entrez/query.fcgi?cmd=Retrieve&db=Nucleotide
&list_uids=05835946&dopt=GenBank>NC_000878</a> 14384 ......t.tc.............
14406
<a
href=http://www.ncbi.nlm.nih.gov:80/entrez/query.fcgi?cmd=Retrieve&db=Nucleotide
&list_uids=05835498&dopt=GenBank>NC_000846</a> 14307 ....
14310
<a
href=http://www.ncbi.nlm.nih.gov:80/entrez/query.fcgi?cmd=Retrieve&db=Nucleotide
&list_uids=07555761&dopt=GenBank>NC_002196</a> 16392
....t.t.cc..............a......                                  16421
<a
href=http://www.ncbi.nlm.nih.gov:80/entrez/query.fcgi?cmd=Retrieve&db=Nucleotide
&list_uids=05835834&dopt=GenBank>NC_002083</a> 14867
................c.....a.....                                     14895
<a
href=http://www.ncbi.nlm.nih.gov:80/entrez/query.fcgi?cmd=Retrieve&db=Nucleotide
&list_uids=05835610&dopt=GenBank>NC_001953</a> 14290 ....
14293 tmpseq_0   241   gtcctattctcaccagacctgttaggagaccccgataactacatccctgccaaccctcta   300
<a
href=http://www.ncbi.nlm.nih.gov:80/entrez/query.fcgi?cmd=Retrieve&db=Nucleotide
&list_uids=05835205&dopt=GenBank>NC_001700</a> 15764
........t............c..........a..c...........a.........t..    15823
<a
href=http://www.ncbi.nlm.nih.gov:80/entrez/query.fcgi?cmd=Retrieve&db=Nucleotide
&list_uids=05834857&dopt=GenBank>NC_001325</a> 15820
..g..........c..................a..c.....t......                 15867
<a
href=http://www.ncbi.nlm.nih.gov:80/entrez/query.fcgi?cmd=Retrieve&db=Nucleotide
&list_uids=05835652&dopt=GenBank>NC_002008</a> 14914
....t.....t......a...........a..........c......a.....c...        14969
<a
href=http://www.ncbi.nlm.nih.gov:80/entrez/query.fcgi?cmd=Retrieve&db=Nucleotide
&list_uids=05835009&dopt=GenBank>NC_001602</a> 15793
..a............c.....a..g..........c.................t..c...     15852
<a
href=http://www.ncbi.nlm.nih.gov:80/entrez/query.fcgi?cmd=Retrieve&db=Nucleotide
&list_uids=05835988&dopt=GenBank>NC_000884</a> 14900
....c.....a...........a..........ca..c.........g..g              14949
<a
href=http://www.ncbi.nlm.nih.gov:80/entrez/query.fcgi?cmd=Retrieve&db=Nucleotide
&list_uids=05835401&dopt=GenBank>NC_001808</a> 14902
..t.............a.cc........t..c........c...........t......      14960
<a
href=http://www.ncbi.nlm.nih.gov:80/entrez/query.fcgi?cmd=Retrieve&db=Nucleotide
&list_uids=05835484&dopt=GenBank>NC_001892</a> 14894
...t.......c......t.a.....................c...c........a...      14953
<a
href=http://www.ncbi.nlm.nih.gov:80/entrez/query.fcgi?cmd=Retrieve&db=Nucleotide
&list_uids=05835764&dopt=GenBank>NC_002078</a> 14909
........a...........                                              14928
```

```
<a
href=http://www.ncbi.nlm.nih.gov:80/entrez/query.fcgi?cmd=Retrieve&db=Nucleotide
&list_uids=05835862&dopt=GenBank>NC_000845</a> 16071
...............ac..........a..c.......c...a..a.....a... 16127
<a
href=http://www.ncbi.nlm.nih.gov:80/entrez/query.fcgi?cmd=Retrieve&db=Nucleotide
&list_uids=05834939&dopt=GenBank>NC_001567</a> 15240
..a......g....c.....cc.c........a...........c...a.....       15292
<a
href=http://www.ncbi.nlm.nih.gov:80/entrez/query.fcgi?cmd=Retrieve&db=Nucleotide
&list_uids=05835526&dopt=GenBank>NC_001913</a> 14901
........t............a...........a..c.......c...........c..t 14960
<a
href=http://www.ncbi.nlm.nih.gov:80/entrez/query.fcgi?cmd=Retrieve&db=Nucleotide
&list_uids=05835135&dopt=GenBank>NC_001644</a> 1484
......... 1492
<a
href=http://www.ncbi.nlm.nih.gov:80/entrez/query.fcgi?cmd=Retrieve&db=Nucleotide
&list_uids=06137796&dopt=GenBank>NC_001807</a> 15476
............cc....c.....a...c..t..t.c..ta........ct.. 15532
<a
href=http://www.ncbi.nlm.nih.gov:80/entrez/query.fcgi?cmd=Retrieve&db=Nucleotide
&list_uids=05835666&dopt=GenBank>NC_002009</a> 14880
....t..........cc..........a...c..t..t..t..a..a..t..a..t 14935
<a
href=http://www.ncbi.nlm.nih.gov:80/entrez/query.fcgi?cmd=Retrieve&db=Nucleotide
&list_uids=05835149&dopt=GenBank>NC_001645</a> 14898
................cc.........a...c.......c.tta........c... 14954
<a
href=http://www.ncbi.nlm.nih.gov:80/entrez/query.fcgi?cmd=Retrieve&db=Nucleotide
&list_uids=05835037&dopt=GenBank>NC_001610</a> 14907
.............t..t...........t..c....t..c...a..t..t..c..t 14962
<a
href=http://www.ncbi.nlm.nih.gov:80/entrez/query.fcgi?cmd=Retrieve&db=Nucleotide
&list_uids=05835820&dopt=GenBank>NC_002082</a> 14950
... 14952
<a
href=http://www.ncbi.nlm.nih.gov:80/entrez/query.fcgi?cmd=Retrieve&db=Nucleotide
&list_uids=05835373&dopt=GenBank>NC_001804</a> 15071
.......a.t...a....................a....       15108
<a
href=http://www.ncbi.nlm.nih.gov:80/entrez/query.fcgi?cmd=Retrieve&db=Nucleotide
&list_uids=05836002&dopt=GenBank>NC_000886</a> 14980
..........a..c....t...ca..a............. 15017
<a
href=http://www.ncbi.nlm.nih.gov:80/entrez/query.fcgi?cmd=Retrieve&db=Nucleotide
&list_uids=07555761&dopt=GenBank>NC_002196</a> 16454
.............ca....ac....t.....a..g....t..c...a.........       16507
<a
href=http://www.ncbi.nlm.nih.gov:80/entrez/query.fcgi?cmd=Retrieve&db=Nucleotide
&list_uids=05835624&dopt=GenBank>NC_001960</a> 16155
...........c... 16169 tmpseq_0   301   aataccoctccccatatcaagcctgaat 328
<a
href=http://www.ncbi.nlm.nih.gov:80/entrez/query.fcgi?cmd=Retrieve&db=Nucleotide
```

<a href=http://www.ncbi.nlm.nih.gov:80/entrez/query.fcgi?cmd=Retrieve&db=Nucleotide&list_uids=05835205&dopt=GenBank>NC_001700</a> 15824 ...................t..a....... 15851

<a href=http://www.ncbi.nlm.nih.gov:80/entrez/query.fcgi?cmd=Retrieve&db=Nucleotide&list_uids=05835652&dopt=GenBank>NC_002008</a> 14970 ..c........a.....t..a..... 14995

<a href=http://www.ncbi.nlm.nih.gov:80/entrez/query.fcgi?cmd=Retrieve&db=Nucleotide&list_uids=05835009&dopt=GenBank>NC_001602</a> 15853 .gc.....a..a........ 15872

<a href=http://www.ncbi.nlm.nih.gov:80/entrez/query.fcgi?cmd=Retrieve&db=Nucleotide&list_uids=05835988&dopt=GenBank>NC_000884</a> 14950 ..... 14954

<a href=http://www.ncbi.nlm.nih.gov:80/entrez/query.fcgi?cmd=Retrieve&db=Nucleotide&list_uids=05835484&dopt=GenBank>NC_001892</a> 14954 .g.............. 14970

<a href=http://www.ncbi.nlm.nih.gov:80/entrez/query.fcgi?cmd=Retrieve&db=Nucleotide&list_uids=05835331&dopt=GenBank>NC_001779</a> 3081           .............. 3094

<a href=http://www.ncbi.nlm.nih.gov:80/entrez/query.fcgi?cmd=Retrieve&db=Nucleotide&list_uids=05835862&dopt=GenBank>NC_000845</a> 16128 ..c.....a........ 16144

<a href=http://www.ncbi.nlm.nih.gov:80/entrez/query.fcgi?cmd=Retrieve&db=Nucleotide&list_uids=05835526&dopt=GenBank>NC_001913</a> 14961 .................... 14980

<a href=http://www.ncbi.nlm.nih.gov:80/entrez/query.fcgi?cmd=Retrieve&db=Nucleotide&list_uids=05835135&dopt=GenBank>NC_001644</a> 1493   ...c..... 1501

<a href=http://www.ncbi.nlm.nih.gov:80/entrez/query.fcgi?cmd=Retrieve&db=Nucleotide&list_uids=06137796&dopt=GenBank>NC_001807</a> 15533 ..c...........c........c.... 15560

<a href=http://www.ncbi.nlm.nih.gov:80/entrez/query.fcgi?cmd=Retrieve&db=Nucleotide&list_uids=05835666&dopt=GenBank>NC_002009</a> 14936 ..................t......a.... 14963

<a href=http://www.ncbi.nlm.nih.gov:80/entrez/query.fcgi?cmd=Retrieve&db=Nucleotide&list_uids=05835149&dopt=GenBank>NC_001645</a> 14955 .gc.....a......c..... 14974

<a href=http://www.ncbi.nlm.nih.gov:80/entrez/query.fcgi?cmd=Retrieve&db=Nucleotide&list_uids=05835037&dopt=GenBank>NC_001610</a> 14963 ..c.....g..t...........a.... 14990

<a href=http://www.ncbi.nlm.nih.gov:80/entrez/query.fcgi?cmd=Retrieve&db=Nucleotide&list_uids=05835820&dopt=GenBank>NC_002082</a> 14953 ..c...........c..... 14972

<a href=http://www.ncbi.nlm.nih.gov:80/entrez/query.fcgi?cmd=Retrieve&db=Nucleotide

```
&list_uids=05835624&dopt=GenBank>NC_001960</a> 16170
gt...t..a..t................. 16197
<a
href=http://www.ncbi.nlm.nih.gov:80/entrez/query.fcgi?cmd=Retrieve&db=Nucleotide
&list_uids=05835610&dopt=GenBank>NC_001953</a> 14416
..................c.... 14437
</PRE>

<PRE>
  Database: Sequences from complete mitochondrial genomes
    Posted date:  Jun 28, 2000 10:56 AM
  Number of letters in database: 3,164,247
  Number of sequences in database:  129

Lambda     K      H
   1.37    0.711    1.31

Gapped
Lambda     K      H
   1.37    0.711    1.31

Matrix: blastn matrix:1 -3
Gap Penalties: Existence: 5, Extension: 2
Number of Hits to DB: 788
Number of Sequences: 129
Number of extensions: 788
Number of successful extensions: 168
Number of sequences better than 10.0: 77
length of query: 328
length of database: 3,164,247
effective HSP length: 15
effective length of query: 313
effective length of database: 3,162,312
effective search space: 989803656
effective search space used: 989803656
T: 0
A: 30
X1: 6 (11.9 bits)
X2: 15 (29.7 bits)
S1: 12 (24.3 bits)
S2: 14 (28.2 bits)

</PRE>

</BODY>
</HTML>
</FORM>
</BODY>
</HTML>
```

Table 4. Results of the blast analysis of the sequence revealed from 'adil.flesh' in 'nr' database of NCBI. It shows the most significant alignment of cytochrome b sequence (328 bp) revealed from confiscated skin piece 'adil.flesh' with *Panthera pardus* cytochrome b gene sequence (genbank registration number AY005809, bits score 603, E value, e-170) registered in NCBI database. It gives an indication that the species of analyzed material belongs to Panthera paurdus origin. It also fulfills the requirements of column 6 mention above under sub-heading 'Objectives of invention'.

```
<p><!--
QBlastInfoBegin
       Status=READY
QBlastInfoEnd
--><p>
<TITLE>Results for RID 984593400-28182-3122 </TITLE>
<HTML>
<HEAD>
<TITLE>BLAST Search Results </TITLE>
</HEAD>
<BODY BGCOLOR="#FFFFFF" LINK="#0000FF" VLINK="#660099" ALINK="#660099">
<A HREF="http://www.ncbi.nlm.nih.gov/BLAST/blast_form.map"> <IMG
SRC="http://www.ncbi.nlm.nih.gov/BLAST/blast_results.gif" BORDER=0 ISMAP></A>
<BR><BR><PRE>
<b>BLASTN 2.1.2 [Nov-13-2000]</b>

<b><a href="http://www.ncbi.nlm.nih.gov/htbin-
post/Entrez/query?uid=9254694&form=6&db=m&Dopt=r">Reference</a>:</b>
Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs",  Nucleic Acids Res. 25:3389-3402.
<p>
RID: 984593400-28182-3122
<p>
<b>Query=</b>
         (328 letters)

<p>
<b>Database:</b> nt
           807,597 sequences; 2,863,827,885 total letters <p> <p>If you have any problems or questions with the results of this search
<br>please refer to the <b><a
href=http://www.ncbi.nlm.nih.gov/blast/blast_FAQs.html>BLAST FAQs</a></b><br><p>
<FORM NAME="BLASTFORM" METHOD="POST">
<a href="blast.cgi?RID=984593400-28182-3122&ALIGNMENT_VIEW=17" TARGET="Taxonomy
BLAST Results for 984593400-28182-3122">Taxonomy reports</a>
<BR>
</PRE>
<CENTER>
<H3><a href="/BLAST/newoptions.html#graphical-overview"> Distribution of 50
Blast Hits on the Query Sequence</a></H3>
<input name=defline size=80 value="Mouse-over to show defline and scores. Click
to show alignments">
</CENTER>
<map name=img_map>
<area shape=rect coords=62,101,526,106 href="#9795379"
ONMOUSEOVER='document.BLASTFORM.defline.value="AY005809   Panthera pardus
cytochrome b gene, partial cds; mitoc..S= 603 E=2e-170"'
ONMOUSEOUT='document.BLASTFORM.defline.value="Mouse-over to show defline and
scores. Click to show alignments"' >
<area shape=rect coords=62,108,518,113 href="#2995797"
ONMOUSEOVER='document.BLASTFORM.defline.value="AF053054   Panthera tigris
sumatrae isolate Su1 mitochondrial cy..S= 527 E=1e-147"'
```

```
ONMOUSEOUT='document.BLASTFORM.defline.value="Mouse-over to show defline and
scores. Click to show alignments"' >
<area shape=rect coords=62,115,518,120 href="#2995796"
ONMOUSEOVER='document.BLASTFORM.defline.value="AF053053  Panthera tigris tigris
isolate B7 mitochondrial cytoc..S= 527 E=1e-147"'
ONMOUSEOUT='document.BLASTFORM.defline.value="Mouse-over to show defline and
scores. Click to show alignments"' >
<area shape=rect coords=62,122,526,127 href="#2995790"
ONMOUSEOVER='document.BLASTFORM.defline.value="AF053050  Panthera tigris
corbetti isolate C2 cytochrome b (cyt..S= 476 E=4e-132"'
ONMOUSEOUT='document.BLASTFORM.defline.value="Mouse-over to show defline and
scores. Click to show alignments"' >
<area shape=rect coords=62,129,526,134 href="#2995788"
ONMOUSEOVER='document.BLASTFORM.defline.value="AF053049  Panthera tigris
corbetti isolate C1 cytochrome b (cyt..S= 476 E=4e-132"'
ONMOUSEOUT='document.BLASTFORM.defline.value="Mouse-over to show defline and
scores. Click to show alignments"' >
<area shape=rect coords=62,136,526,141 href="#2995732"
ONMOUSEOVER='document.BLASTFORM.defline.value="AF053021  Panthera tigris tigris
isolate B5 cytochrome b (cytb)..S= 460 E=2e-127"'
ONMOUSEOUT='document.BLASTFORM.defline.value="Mouse-over to show defline and
scores. Click to show alignments"' >
<area shape=rect coords=62,143,526,148 href="#2995738"
ONMOUSEOVER='document.BLASTFORM.defline.value="AF053024  Panthera tigris tigris
isolate B8 cytochrome b (cytb)..S= 460 E=2e-127"'
ONMOUSEOUT='document.BLASTFORM.defline.value="Mouse-over to show defline and
scores. Click to show alignments"' >
<area shape=rect coords=62,150,526,155 href="#2995736"
ONMOUSEOVER='document.BLASTFORM.defline.value="AF053023  Panthera tigris tigris
isolate B7 cytochrome b (cytb)..S= 460 E=2e-127"'
ONMOUSEOUT='document.BLASTFORM.defline.value="Mouse-over to show defline and
scores. Click to show alignments"' >
<area shape=rect coords=62,157,526,162 href="#2995740"
ONMOUSEOVER='document.BLASTFORM.defline.value="AF053025  Panthera tigris tigris
isolate B9 cytochrome b (cytb)..S= 460 E=2e-127"'
ONMOUSEOUT='document.BLASTFORM.defline.value="Mouse-over to show defline and
scores. Click to show alignments"' >
<area shape=rect coords=62,164,526,169 href="#2995734"
ONMOUSEOVER='document.BLASTFORM.defline.value="AF053022  Panthera tigris tigris
isolate B6 cytochrome b (cytb)..S= 460 E=2e-127"'
ONMOUSEOUT='document.BLASTFORM.defline.value="Mouse-over to show defline and
scores. Click to show alignments"' >
<area shape=rect coords=62,171,526,176 href="#2995726"
ONMOUSEOVER='document.BLASTFORM.defline.value="AF053018  Panthera tigris tigris
isolate B2 cytochrome b (cytb)..S= 460 E=2e-127"'
ONMOUSECUT='document.BLASTFORM.defline.value="Mouse-over to show defline and
scores. Click to show alignments"' >
<area shape=rect coords=62,178,526,183 href="#2995754"
ONMOUSEOVER='document.BLASTFORM.defline.value="AF053032  Panthera tigris altaica
isolate S7 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,185,526,190 href="#2995784"
ONMOUSEOVER='document.BLASTFORM.defline.value="AF053047  Panthera tigris
sumatrae isolate Su9 cytochrome b (cy..S= 452 E=5e-125"'
ONMOUSEOUT='document.BLASTFORM.defline.value="Mouse-over to show defline and
scores. Click to show alignments"' >
```

```
<area shape=rect coords=62,192,526,197 href="#2995782"
ONMOUSEOVER='document.BLASTFORM.defline.value="AF053046  Panthera tigris
sumatrae isolate Su7 cytochrome b (cy..S= 452 E=5e-125"'
ONMOUSEOUT='document.BLASTFORM.defline.value="Mouse-over to show defline and
scores. Click to show alignments"' >
<area shape=rect coords=62,199,526,204 href="#2995786"
ONMOUSEOVER='document.BLASTFORM.defline.value="AF053048  Panthera tigris
sumatrae isolate Su10 cytochrome b (c..S= 452 E=5e-125"'
ONMOUSEOUT='document.BLASTFORM.defline.value="Mouse-over to show defline and
scores. Click to show alignments"' >
<area shape=rect coords=62,206,526,211 href="#2995792"
ONMOUSEOVER='document.BLASTFORM.defline.value="AF053051  Panthera tigris
corbetti isolate C3 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,213,526,218 href="#2995762"
ONMOUSEOVER='document.BLASTFORM.defline.value="AF053036  Panthera tigris altaica
isolate S12 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,220,526,225 href="#2995760"
ONMOUSEOVER='document.BLASTFORM.defline.value="AF053035  Panthera tigris altaica
isolate S11 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,227,526,232 href="#2995766"
ONMOUSEOVER='document.BLASTFORM.defline.value="AF053038  Panthera tigris altaica
isolate S14 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,234,526,239 href="#2995768"
ONMOUSEOVER='document.BLASTFORM.defline.value="AF053039  Panthera tigris altaica
isolate S15 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,241,526,246 href="#2995770"
ONMOUSEOVER='document.BLASTFORM.defline.value="AF053040  Panthera tigris
sumatrae isolate Su1 cytochrome b (cy..S= 452 E=5e-125"'
ONMOUSEOUT='document.BLASTFORM.defline.value="Mouse-over to show defline and
scores. Click to show alignments"' >
<area shape=rect coords=62,248,526,253 href="#2995764"
ONMOUSEOVER='document.BLASTFORM.defline.value="AF053037  Panthera tigris altaica
isolate S13 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,255,526,260 href="#2995772"
ONMOUSEOVER='document.BLASTFORM.defline.value="AF053041  Panthera tigris
sumatrae isolate Su2 cytochrome b (cy..S= 452 E=5e-125"'
ONMOUSEOUT='document.BLASTFORM.defline.value="Mouse-over to show defline and
scores. Click to show alignments"' >
<area shape=rect coords=62,262,526,267 href="#2995774"
ONMOUSEOVER='document.BLASTFORM.defline.value="AF053042  Panthera tigris
sumatrae isolate Su3 cytochrome b (cy..S= 452 E=5e-125"'
ONMOUSEOUT='document.BLASTFORM.defline.value="Mouse-over to show defline and
scores. Click to show alignments"' >
<area shape=rect coords=62,269,526,274 href="#2995758"
ONMOUSEOVER='document.BLASTFORM.defline.value="AF053034  Panthera tigris altaica
```

```
isolate S10 cytochrome b (cyt..S= 452 E=5e-125"'
ONMOUSEOUT='document.BLASTFORM.defline.value="Mouse-over to show defline and
scores. Click to show alignments"' >
<area shape=rect coords=62,276,526,281 href="#2995756"
ONMOUSEOVER='document.BLASTFORM.defline.value="AF053033   Panthera tigris altaica
isolate S8 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,283,526,288 href="#2995728"
ONMOUSEOVER='document.BLASTFORM.defline.value="AF053019   Panthera tigris tigris
isolate B3 cytochrome b (cytb)..S= 452 E=5e-125"'
ONMOUSEOUT='document.BLASTFORM.defline.value="Mouse-over to show defline and
scores. Click to show alignments"' >
<area shape=rect coords=62,290,526,295 href="#2995752"
ONMOUSEOVER='document.BLASTFORM.defline.value="AF053031   Panthera tigris altaica
isolate S6 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,297,526,302 href="#2995750"
ONMOUSEOVER='document.BLASTFORM.defline.value="AF053030   Panthera tigris altaica
isolate S5 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,304,526,309 href="#2995748"
ONMOUSEOVER='document.BLASTFORM.defline.value="AF053029   Panthera tigris altaica
isolate S4 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,311,526,316 href="#2995730"
ONMOUSEOVER='document.BLASTFORM.defline.value="AF053020   Panthera tigris tigris
isolate B4 cytochrome b (cytb)..S= 452 E=5e-125"'
ONMOUSEOUT='document.BLASTFORM.defline.value="Mouse-over to show defline and
scores. Click to show alignments"' >
<area shape=rect coords=62,318,526,323 href="#2995742"
ONMOUSEOVER='document.BLASTFORM.defline.value="AF053026   Panthera tigris altaica
isolate S1 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,325,526,330 href="#2995778"
ONMOUSEOVER='document.BLASTFORM.defline.value="AF053044   Panthera tigris
sumatrae isolate Su5 cytochrome b (cy..S= 452 E=5e-125"'
ONMOUSEOUT='document.BLASTFORM.defline.value="Mouse-over to show defline and
scores. Click to show alignments"' >
<area shape=rect coords=62,332,526,337 href="#2995744"
ONMOUSEOVER='document.BLASTFORM.defline.value="AF053027   Panthera tigris altaica
isolate S2 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,339,526,344 href="#2995746"
ONMOUSEOVER='document.BLASTFORM.defline.value="AF053028   Panthera tigris altaica
isolate S3 cytochrome b (cytb..S= 452 E=5e-125"'
ONMOUSEOUT='document.BLASTFORM.defline.value="Mouse-over to show defline and
scores. Click to show alignments"' >
<area shape=rect coords=62,346,526,351 href="#2995780"
ONMOUSEOVER='document.BLASTFORM.defline.value="AF053045   Panthera tigris
sumatrae isolate Su6 cytochrome b (cy..S= 452 E=5e-125"'
```

```
ONMOUSEOUT='document.BLASTFORM.defline.value="Mouse-over to show defline and
scores. Click to show alignments"' >
<area shape=rect coords=62,353,526,358 href="#693979"
ONMOUSEOVER='document.BLASTFORM.defline.value="X82301  P.tigris mitochondrial
cytochrome b gene..S= 444 E=1e-122"'
ONMOUSEOUT='document.BLASTFORM.defline.value="Mouse-over to show defline and
scores. Click to show alignments"' >
<area shape=rect coords=62,360,526,365 href="#2995776"
ONMOUSEOVER='document.BLASTFORM.defline.value="AF053043  Panthera tigris
sumatrae isolate Su4 cytochrome b (cy..S= 444 E=1e-122"'
ONMOUSEOUT='document.BLASTFORM.defline.value="Mouse-over to show defline and
scores. Click to show alignments"' >
<area shape=rect coords=62,367,523,372 href="#2995794"
ONMOUSEOVER='document.BLASTFORM.defline.value="AF053052  Panthera leo cytochrome
b (cytb) gene, mitochondrial ..S= 440 E=2e-121"'
ONMOUSEOUT='document.BLASTFORM.defline.value="Mouse-over to show defline and
scores. Click to show alignments"' >
<area shape=rect coords=66,374,526,379 href="#693977"
ONMOUSEOVER='document.BLASTFORM.defline.value="X82300  P.leo mitochondrial
cytochrome b gene..S= 438 E=8e-121"'
ONMOUSEOUT='document.BLASTFORM.defline.value="Mouse-over to show defline and
scores. Click to show alignments"' >
<area shape=rect coords=62,381,526,386 href="#2575784"
ONMOUSEOVER='document.BLASTFORM.defline.value="AB004238  Felis catus
mitochondrial DNA for cytochrome b, compl..S= 389 E=7e-106"'
ONMOUSEOUT='document.BLASTFORM.defline.value="Mouse-over to show defline and
scores. Click to show alignments"' >
<area shape=rect coords=62,388,526,393 href="#2575782"
ONMOUSEOVER='document.BLASTFORM.defline.value="AB004237  Felis catus
mitochondrial DNA for cytochrome b, compl..S= 381 E=2e-103"'
ONMOUSEOUT='document.BLASTFORM.defline.value="Mouse-over to show defline and
scores. Click to show alignments"' >
<area shape=rect coords=62,395,526,400 href="#693961"
ONMOUSEOVER='document.BLASTFORM.defline.value="X82296  F.domesticus
mitochondrial cytochrome b gene..S= 377 E=3e-102"'
ONMOUSEOUT='document.BLASTFORM.defline.value="Mouse-over to show defline and
scores. Click to show alignments"' >
<area shape=rect coords=62,402,526,407 href="#1098523"
ONMOUSEOVER='document.BLASTFORM.defline.value="U20753  Felis catus
mitochondrion, complete genome..S= 365 E=1e-98"'
ONMOUSEOUT='document.BLASTFORM.defline.value="Mouse-over to show defline and
scores. Click to show alignments"' >
<area shape=rect coords=62,409,526,414 href="#5835205"
ONMOUSEOVER='document.BLASTFORM.defline.value="NC_001700  Felis catus
mitochondrion, complete genome..S= 365 E=1e-98"'
ONMOUSEOUT='document.BLASTFORM.defline.value="Mouse-over to show defline and
scores. Click to show alignments"' >
<area shape=rect coords=62,416,478,421 href="#12619334"
ONMOUSEOVER='document.BLASTFORM.defline.value="AF125145  Viverricula indica
cytochrome b gene, partial cds; mit..S= 276 E=7e-72"'
ONMOUSEOUT='document.BLASTFORM.defline.value="Mouse-over to show defline and
scores. Click to show alignments"' >
<area shape=rect coords=62,423,498,428 href="#12619332"
ONMOUSEOVER='document.BLASTFORM.defline.value="AF125144  Chrotogale owstoni
cytochrome b gene, partial cds; mit..S= 270 E=4e-70"'
ONMOUSEOUT='document.BLASTFORM.defline.value="Mouse-over to show defline and
scores. Click to show alignments"' >
```

```
<area shape=rect coords=62,430,510,435 href="#11275401"
ONMOUSEOVER='document.BLASTFORM.defline.value="AB051237  Martes martes
mitochondrial cytb gene for cytochrome b..S= 256 E=7e-66"'
ONMOUSEOUT='document.BLASTFORM.defline.value="Mouse-over to show defline and
scores. Click to show alignments"' >
<area shape=rect coords=62,437,510,442 href="#6760027"
ONMOUSEOVER='document.BLASTFORM.defline.value="AF154975  Martes martes
specimen_voucher AF17559 cytochrome b (c..S= 256 E=7e-66"'
ONMOUSEOUT='document.BLASTFORM.defline.value="Mouse-over to show defline and
scores. Click to show alignments"' >
<area shape=rect coords=62,444,498,449 href="#12619342"
ONMOUSEOVER='document.BLASTFORM.defline.value="AF125149  Viverra tangalunga
cytochrome b gene, partial cds; mit..S= 246 E=6e-63"'
ONMOUSEOUT='document.BLASTFORM.defline.value="Mouse-over to show defline and
scores. Click to show alignments"' >
</map>
<CENTER>
<IMG WIDTH=532 HEIGHT=451 USEMAP=#img_map BORDER=1 SRC="nph-
getgif.cgi?iblast11&207891705329345.gif" ISMAP></CENTER>
<HR>
<PRE>
<PRE>

Score     E
Sequences producing significant alignments:                      (bits) Value <a
href="http://www.ncbi.nlm.nih.gov:80/entrez/query.fcgi?cmd=Retrieve&db=Nucleotid
e&list_uids=09795379&dopt=GenBank">gb|AY005809.1|</a>  Panthera pardus
cytochrome b gene, partial c...    <a href = #9795379>603</a>  e-170
<a
href="http://www.ncbi.nlm.nih.gov:80/entrez/query.fcgi?cmd=Retrieve&db=Nucleotid
e&list_uids=02995797&dopt=GenBank">gb|AF053054.1|AF053054</a>  Panthera tigris
sumatrae isolate Su1...    <a href = #2995797>527</a>  e-147
<a
href="http://www.ncbi.nlm.nih.gov:80/entrez/query.fcgi?cmd=Retrieve&db=Nucleotid
e&list_uids=02995796&dopt=GenBank">gb|AF053053.1|AF053053</a>  Panthera tigris
tigris isolate B7 mi...    <a href = #2995796>527</a>  e-147
<a
href="http://www.ncbi.nlm.nih.gov:80/entrez/query.fcgi?cmd=Retrieve&db=Nucleotid
e&list_uids=02995790&dopt=GenBank">gb|AF053050.1|AF053050</a>  Panthera tigris
corbetti isolate C2 ...    <a href = #2995790>476</a>  e-132
<a
href="http://www.ncbi.nlm.nih.gov:80/entrez/query.fcgi?cmd=Retrieve&db=Nucleotid
e&list_uids=02995788&dopt=GenBank">gb|AF053049.1|AF053049</a>  Panthera tigris
corbetti isolate C1 ...    <a href = #2995788>476</a>  e-132
<a
href="http://www.ncbi.nlm.nih.gov:80/entrez/query.fcgi?cmd=Retrieve&db=Nucleotid
e&list_uids=02995740&dopt=GenBank">gb|AF053025.1|AF053025</a>  Panthera tigris
tigris isolate B9 cy...    <a href = #2995740>460</a>  e-127
<a
href="http://www.ncbi.nlm.nih.gov:80/entrez/query.fcgi?cmd=Retrieve&db=Nucleotid
e&list_uids=02995738&dopt=GenBank">gb|AF053024.1|AF053024</a>  Panthera tigris
tigris isolate B8 cy...    <a href = #2995738>460</a>  e-127
<a
href="http://www.ncbi.nlm.nih.gov:80/entrez/query.fcgi?cmd=Retrieve&db=Nucleotid
```

```
e&list_uids=02995736&dopt=GenBank">gb|AF053023.1|AF053023</a>  Panthera tigris
tigris isolate B7 cy...    <a href = #2995736>460</a>   e-127
<a
href="http://www.ncbi.nlm.nih.gov:80/entrez/query.fcgi?cmd=Retrieve&db=Nucleotid
e&list_uids=02995734&dopt=GenBank">gb|AF053022.1|AF053022</a>  Panthera tigris
tigris isolate B6 cy...    <a href = #2995734>460</a>   e-127
<a
href="http://www.ncbi.nlm.nih.gov:80/entrez/query.fcgi?cmd=Retrieve&db=Nucleotid
e&list_uids=02995732&dopt=GenBank">gb|AF053021.1|AF053021</a>  Panthera tigris
tigris isolate B5 cy...    <a href = #2995732>460</a>   e-127
<a
href="http://www.ncbi.nlm.nih.gov:80/entrez/query.fcgi?cmd=Retrieve&db=Nucleotid
e&list_uids=02995726&dopt=GenBank">gb|AF053018.1|AF053018</a>  Panthera tigris
tigris isolate B2 cy...    <a href = #2995726>460</a>   e-127
<a
href="http://www.ncbi.nlm.nih.gov:80/entrez/query.fcgi?cmd=Retrieve&db=Nucleotid
e&list_uids=02995792&dopt=GenBank">gb|AF053051.1|AF053051</a>  Panthera tigris
corbetti isolate C3 ...    <a href = #2995792>452</a>   e-125
<a
href="http://www.ncbi.nlm.nih.gov:80/entrez/query.fcgi?cmd=Retrieve&db=Nucleotid
e&list_uids=02995786&dopt=GenBank">gb|AF053048.1|AF053048</a>  Panthera tigris
sumatrae isolate Su1...    <a href = #2995786>452</a>   e-125
<a
href="http://www.ncbi.nlm.nih.gov:80/entrez/query.fcgi?cmd=Retrieve&db=Nucleotid
e&list_uids=02995784&dopt=GenBank">gb|AF053047.1|AF053047</a>  Panthera tigris
sumatrae isolate Su9...    <a href = #2995784>452</a>   e-125
<a
href="http://www.ncbi.nlm.nih.gov:80/entrez/query.fcgi?cmd=Retrieve&db=Nucleotid
e&list_uids=02995782&dopt=GenBank">gb|AF053046.1|AF053046</a>  Panthera tigris
sumatrae isolate Su7...    <a href = #2995782>452</a>   e-125
<a
href="http://www.ncbi.nlm.nih.gov:80/entrez/query.fcgi?cmd=Retrieve&db=Nucleotid
e&list_uids=02995780&dopt=GenBank">gb|AF053045.1|AF053045</a>  Panthera tigris
sumatrae isolate Su6...    <a href = #2995780>452</a>   e-125
<a
href="http://www.ncbi.nlm.nih.gov:80/entrez/query.fcgi?cmd=Retrieve&db=Nucleotid
e&list_uids=02995778&dopt=GenBank">gb|AF053044.1|AF053044</a>  Panthera tigris
sumatrae isolate Su5...    <a href = #2995778>452</a>   e-125
<a
href="http://www.ncbi.nlm.nih.gov:80/entrez/query.fcgi?cmd=Retrieve&db=Nucleotid
e&list_uids=02995774&dopt=GenBank">gb|AF053042.1|AF053042</a>  Panthera tigris
sumatrae isolate Su3...    <a href = #2995774>452</a>   e-125
<a
href="http://www.ncbi.nlm.nih.gov:80/entrez/query.fcgi?cmd=Retrieve&db=Nucleotid
e&list_uids=02995772&dopt=GenBank">gb|AF053041.1|AF053041</a>  Panthera tigris
sumatrae isolate Su2...    <a href = #2995772>452</a>   e-125
<a
href="http://www.ncbi.nlm.nih.gov:80/entrez/query.fcgi?cmd=Retrieve&db=Nucleotid
e&list_uids=02995770&dopt=GenBank">gb|AF053040.1|AF053040</a>  Panthera tigris
sumatrae isolate Su1...    <a href = #2995770>452</a>   e-125
<a
href="http://www.ncbi.nlm.nih.gov:80/entrez/query.fcgi?cmd=Retrieve&db=Nucleotid
e&list_uids=02995768&dopt=GenBank">gb|AF053039.1|AF053039</a>  Panthera tigris
altaica isolate S15 ...    <a href = #2995768>452</a>   e-125
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=02995766&dopt=GenBank">gb|AF053038.1|AF053038</a>  Panthera tigris
altaica isolate S14 ...   <a href = #2995766>452</a>  e-125
<a
href="http://www.ncbi.nlm.nih.gov:80/entrez/query.fcgi?cmd=Retrieve&db=Nucleotid
e&list_uids=02995764&dopt=GenBank">gb|AF053037.1|AF053037</a>  Panthera tigris
altaica isolate S13 ...   <a href = #2995764>452</a>  e-125
<a
href="http://www.ncbi.nlm.nih.gov:80/entrez/query.fcgi?cmd=Retrieve&db=Nucleotid
e&list_uids=02995762&dopt=GenBank">gb|AF053036.1|AF053036</a>  Panthera tigris
altaica isolate S12 ...   <a href = #2995762>452</a>  e-125
<a
href="http://www.ncbi.nlm.nih.gov:80/entrez/query.fcgi?cmd=Retrieve&db=Nucleotid
e&list_uids=02995760&dopt=GenBank">gb|AF053035.1|AF053035</a>  Panthera tigris
altaica isolate S11 ...   <a href = #2995760>452</a>  e-125
<a
href="http://www.ncbi.nlm.nih.gov:80/entrez/query.fcgi?cmd=Retrieve&db=Nucleotid
e&list_uids=02995758&dopt=GenBank">gb|AF053034.1|AF053034</a>  Panthera tigris
altaica isolate S10 ...   <a href = #2995758>452</a>  e-125
<a
href="http://www.ncbi.nlm.nih.gov:80/entrez/query.fcgi?cmd=Retrieve&db=Nucleotid
e&list_uids=02995756&dopt=GenBank">gb|AF053033.1|AF053033</a>  Panthera tigris
altaica isolate S8 c...   <a href = #2995756>452</a>  e-125
<a
href="http://www.ncbi.nlm.nih.gov:80/entrez/query.fcgi?cmd=Retrieve&db=Nucleotid
e&list_uids=02995754&dopt=GenBank">gb|AF053032.1|AF053032</a>  Panthera tigris
altaica isolate S7 c...   <a href = #2995754>452</a>  e-125
<a
href="http://www.ncbi.nlm.nih.gov:80/entrez/query.fcgi?cmd=Retrieve&db=Nucleotid
e&list_uids=02995752&dopt=GenBank">gb|AF053031.1|AF053031</a>  Panthera tigris
altaica isolate S6 c...   <a href = #2995752>452</a>  e-125
<a
href="http://www.ncbi.nlm.nih.gov:80/entrez/query.fcgi?cmd=Retrieve&db=Nucleotid
e&list_uids=02995750&dopt=GenBank">gb|AF053030.1|AF053030</a>  Panthera tigris
altaica isolate S5 c...   <a href = #2995750>452</a>  e-125
<a
href="http://www.ncbi.nlm.nih.gov:80/entrez/query.fcgi?cmd=Retrieve&db=Nucleotid
e&list_uids=02995748&dopt=GenBank">gb|AF053029.1|AF053029</a>  Panthera tigris
altaica isolate S4 c...   <a href = #2995748>452</a>  e-125
<a
href="http://www.ncbi.nlm.nih.gov:80/entrez/query.fcgi?cmd=Retrieve&db=Nucleotid
e&list_uids=02995746&dopt=GenBank">gb|AF053028.1|AF053028</a>  Panthera tigris
altaica isolate S3 c...   <a href = #2995746>452</a>  e-125
<a
href="http://www.ncbi.nlm.nih.gov:80/entrez/query.fcgi?cmd=Retrieve&db=Nucleotid
e&list_uids=02995744&dopt=GenBank">gb|AF053027.1|AF053027</a>  Panthera tigris
altaica isolate S2 c...   <a href = #2995744>452</a>  e-125
<a
href="http://www.ncbi.nlm.nih.gov:80/entrez/query.fcgi?cmd=Retrieve&db=Nucleotid
e&list_uids=02995742&dopt=GenBank">gb|AF053026.1|AF053026</a>  Panthera tigris
altaica isolate S1 c...   <a href = #2995742>452</a>  e-125
<a
href="http://www.ncbi.nlm.nih.gov:80/entrez/query.fcgi?cmd=Retrieve&db=Nucleotid
e&list_uids=02995730&dopt=GenBank">gb|AF053020.1|AF053020</a>  Panthera tigris
tigris isolate B4 cy...   <a href = #2995730>452</a>  e-125
<a
href="http://www.ncbi.nlm.nih.gov:80/entrez/query.fcgi?cmd=Retrieve&db=Nucleotid
```

```
e&list_uids=02995728&dopt=GenBank">gb|AF053019.1|AF053019</a>  Panthera tigris
tigris isolate B3 cy...    <a href = #2995728>452</a>   e-125
<a
href="http://www.ncbi.nlm.nih.gov:80/entrez/query.fcgi?cmd=Retrieve&db=Nucleotid
e&list_uids=02995776&dopt=GenBank">gb|AF053043.1|AF053043</a>  Panthera tigris
sumatrae isolate Su4...    <a href = #2995776>444</a>   e-122
<a
href="http://www.ncbi.nlm.nih.gov:80/entrez/query.fcgi?cmd=Retrieve&db=Nucleotid
e&list_uids=00693979&dopt=GenBank">emb|X82301.1|MIPTCYTB</a>  P.tigris
mitochondrial cytochrome b gene    <a href = #693979>444</a>   e-122
<a
href="http://www.ncbi.nlm.nih.gov:80/entrez/query.fcgi?cmd=Retrieve&db=Nucleotid
e&list_uids=02995794&dopt=GenBank">gb|AF053052.1|AF053052</a>  Panthera leo
cytochrome b (cytb) gen...    <a href = #2995794>440</a>   e-121
<a
href="http://www.ncbi.nlm.nih.gov:80/entrez/query.fcgi?cmd=Retrieve&db=Nucleotid
e&list_uids=00693977&dopt=GenBank">emb|X82300.1|MIPLCYTBG</a>  P.leo
mitochondrial cytochrome b gene    <a href = #693977>438</a>   e-121
<a
href="http://www.ncbi.nlm.nih.gov:80/entrez/query.fcgi?cmd=Retrieve&db=Nucleotid
e&list_uids=02575784&dopt=GenBank">dbj|AB004238.1|AB004238</a>  Felis catus
mitochondrial DNA for c...    <a href = #2575784>389</a>   e-106
<a
href="http://www.ncbi.nlm.nih.gov:80/entrez/query.fcgi?cmd=Retrieve&db=Nucleotid
e&list_uids=02575782&dopt=GenBank">dbj|AB004237.1|AB004237</a>  Felis catus
mitochondrial DNA for c...    <a href = #2575782>381</a>   e-103
<a
href="http://www.ncbi.nlm.nih.gov:80/entrez/query.fcgi?cmd=Retrieve&db=Nucleotid
e&list_uids=00693961&dopt=GenBank">emb|X82296.1|MIFDCYTB</a>  F.domesticus
mitochondrial cytochrome...    <a href = #693961>377</a>   e-102
<a
href="http://www.ncbi.nlm.nih.gov:80/entrez/query.fcgi?cmd=Retrieve&db=Nucleotid
e&list_uids=05835205&dopt=GenBank">ref|NC_001700.1|</a>  Felis catus
mitochondrion, complete genome    <a href = #5835205>365</a>   1e-98
<a
href="http://www.ncbi.nlm.nih.gov:80/entrez/query.fcgi?cmd=Retrieve&db=Nucleotid
e&list_uids=01098523&dopt=GenBank">gb|U20753.1|FCU20753</a>  Felis catus
mitochondrion, complete ge...    <a href = #1098523>365</a>   1e-98
<a
href="http://www.ncbi.nlm.nih.gov:80/entrez/query.fcgi?cmd=Retrieve&db=Nucleotid
e&list_uids=12619334&dopt=GenBank">gb|AF125145.1|AF125145</a>  Viverricula
indica cytochrome b gene...    <a href = #12619334>276</a>   7e-72
<a
href="http://www.ncbi.nlm.nih.gov:80/entrez/query.fcgi?cmd=Retrieve&db=Nucleotid
e&list_uids=12619332&dopt=GenBank">gb|AF125144.1|AF125144</a>  Chrotogale
owstoni cytochrome b gene...    <a href = #12619332>270</a>   4e-70
<a
href="http://www.ncbi.nlm.nih.gov:80/entrez/query.fcgi?cmd=Retrieve&db=Nucleotid
e&list_uids=06760027&dopt=GenBank">gb|AF154975.1|AF154975</a>  Martes martes
specimen_voucher AF175...    <a href = #6760027>256</a>   7e-66
<a
href="http://www.ncbi.nlm.nih.gov:80/entrez/query.fcgi?cmd=Retrieve&db=Nucleotid
e&list_uids=11275401&dopt=GenBank">dbj|AB051237.1|AB051237</a>  Martes martes
mitochondrial cytb ge...    <a href = #11275401>256</a>   7e-66
<a
href="http://www.ncbi.nlm.nih.gov:80/entrez/query.fcgi?cmd=Retrieve&db=Nucleotid
```

```
e&list_uids=12619342&dopt=GenBank">gb|AF125149.1|AF125149</a>  Viverra
tangalunga cytochrome b gene...    <a href = #12619342>246</a>  6e-63
</PRE>
<CENTER><b><FONT color="green">Alignments</FONT></b></CENTER>
<PRE>
tmpseq_0    1      tgaatctgaggaggcttctcagtagacaaagctaccctgacacgattctttgccttccac 60
<a name = 9795379></a><a
href=http://www.ncbi.nlm.nih.gov:80/entrez/query.fcgi?cmd=Retrieve&db=Nucleotide
&list_uids=09795379&dopt=GenBank>AY005809</a>   39
           ..........g.....................t....................... 98
<a name = 2995797></a><a
href=http://www.ncbi.nlm.nih.gov:80/entrez/query.fcgi?cmd=Retrieve&db=Nucleotide
&list_uids=02995797&dopt=GenBank>AF053054</a>   487
           ..........g.................c............................ 546
<a name = 2995796></a><a
href=http://www.ncbi.nlm.nih.gov:80/entrez/query.fcgi?cmd=Retrieve&db=Nucleotide
&list_uids=02995796&dopt=GenBank>AF053053</a>   487
           ..........g.................c............................ 546
<a name = 2995790></a><a
href=http://www.ncbi.nlm.nih.gov:80/entrez/query.fcgi?cmd=Retrieve&db=Nucleotide
&list_uids=02995790&dopt=GenBank>AF053050</a>   487
           ..........g..t............................................ 546
<a name = 2995788></a><a
href=http://www.ncbi.nlm.nih.gov:80/entrez/query.fcgi?cmd=Retrieve&db=Nucleotide
&list_uids=02995788&dopt=GenBank>AF053049</a>   487
           ..........g..t............................................ 546
<a name = 2995740></a><a
href=http://www.ncbi.nlm.nih.gov:80/entrez/query.fcgi?cmd=Retrieve&db=Nucleotide
&list_uids=02995740&dopt=GenBank>AF053025</a>   487
           ..........g..t............................................ 546
<a name = 2995738></a><a
href=http://www.ncbi.nlm.nih.gov:80/entrez/query.fcgi?cmd=Retrieve&db=Nucleotide
&list_uids=02995738&dopt=GenBank>AF053024</a>   487
           ..........g..t............................................ 546
<a name = 2995736></a><a
href=http://www.ncbi.nlm.nih.gov:80/entrez/query.fcgi?cmd=Retrieve&db=Nucleotide
&list_uids=02995736&dopt=GenBank>AF053023</a>   487
           ..........g..t............................................ 546
<a name = 2995734></a><a
href=http://www.ncbi.nlm.nih.gov:80/entrez/query.fcgi?cmd=Retrieve&db=Nucleotide
&list_uids=02995734&dopt=GenBank>AF053022</a>   487
           ..........g..t............................................ 546
<a name = 2995732></a><a
href=http://www.ncbi.nlm.nih.gov:80/entrez/query.fcgi?cmd=Retrieve&db=Nucleotide
&list_uids=02995732&dopt=GenBank>AF053021</a>   487
           ..........g..t............................................ 546
<a name = 2995726></a><a
href=http://www.ncbi.nlm.nih.gov:80/entrez/query.fcgi?cmd=Retrieve&db=Nucleotide
&list_uids=02995726&dopt=GenBank>AF053018</a>   487
           ..........g..t............................................ 546
<a name = 2995792></a><a
href=http://www.ncbi.nlm.nih.gov:80/entrez/query.fcgi?cmd=Retrieve&db=Nucleotide
&list_uids=02995792&dopt=GenBank>AF053051</a>   487
           ..........g..t............................................ 546
<a name = 2995786></a><a
href=http://www.ncbi.nlm.nih.gov:80/entrez/query.fcgi?cmd=Retrieve&db=Nucleotide
```

```
&list_uids=02995786&dopt=GenBank>AF053048</a>  487
..........g..t............................................. 546
<a name = 2995784></a><a
href=http://www.ncbi.nlm.nih.gov:80/entrez/query.fcgi?cmd=Retrieve&db=Nucleotide
&list_uids=02995784&dopt=GenBank>AF053047</a>  487
..........g..t............................................. 546
<a name = 2995782></a><a
href=http://www.ncbi.nlm.nih.gov:80/entrez/query.fcgi?cmd=Retrieve&db=Nucleotide
&list_uids=02995782&dopt=GenBank>AF053046</a>  487
..........g..t............................................. 546
<a name = 2995780></a><a
href=http://www.ncbi.nlm.nih.gov:80/entrez/query.fcgi?cmd=Retrieve&db=Nucleotide
&list_uids=02995780&dopt=GenBank>AF053045</a>  487
..........g..t............................................. 546
<a name = 2995778></a><a
href=http://www.ncbi.nlm.nih.gov:80/entrez/query.fcgi?cmd=Retrieve&db=Nucleotide
&list_uids=02995778&dopt=GenBank>AF053044</a>  487
..........g..t............................................. 546
<a name = 2995774></a><a
href=http://www.ncbi.nlm.nih.gov:80/entrez/query.fcgi?cmd=Retrieve&db=Nucleotide
&list_uids=02995774&dopt=GenBank>AF053042</a>  487
..........g..t............................................. 546
<a name = 2995772></a><a
href=http://www.ncbi.nlm.nih.gov:80/entrez/query.fcgi?cmd=Retrieve&db=Nucleotide
&list_uids=02995772&dopt=GenBank>AF053041</a>  487
..........g..t............................................. 546
<a name = 2995770></a><a
href=http://www.ncbi.nlm.nih.gov:80/entrez/query.fcgi?cmd=Retrieve&db=Nucleotide
&list_uids=02995770&dopt=GenBank>AF053040</a>  487
..........g..t............................................. 546
<a name = 2995768></a><a
href=http://www.ncbi.nlm.nih.gov:80/entrez/query.fcgi?cmd=Retrieve&db=Nucleotide
&list_uids=02995768&dopt=GenBank>AF053039</a>  487
..........g..t............................................. 546
<a name = 2995766></a><a
href=http://www.ncbi.nlm.nih.gov:80/entrez/query.fcgi?cmd=Retrieve&db=Nucleotide
&list_uids=02995766&dopt=GenBank>AF053038</a>  487
..........g..t............................................. 546
<a name = 2995764></a><a
href=http://www.ncbi.nlm.nih.gov:80/entrez/query.fcgi?cmd=Retrieve&db=Nucleotide
&list_uids=02995764&dopt=GenBank>AF053037</a>  487
..........g..t............................................. 546
<a name = 2995762></a><a
href=http://www.ncbi.nlm.nih.gov:80/entrez/query.fcgi?cmd=Retrieve&db=Nucleotide
&list_uids=02995762&dopt=GenBank>AF053036</a>  487
..........g..t............................................. 546
<a name = 2995760></a><a
href=http://www.ncbi.nlm.nih.gov:80/entrez/query.fcgi?cmd=Retrieve&db=Nucleotide
&list_uids=02995760&dopt=GenBank>AF053035</a>  487
..........g..t............................................. 546
<a name = 2995758></a><a
href=http://www.ncbi.nlm.nih.gov:80/entrez/query.fcgi?cmd=Retrieve&db=Nucleotide
&list_uids=02995758&dopt=GenBank>AF053034</a>  487
..........g..t............................................. 546
<a name = 2995756></a><a
href=http://www.ncbi.nlm.nih.gov:80/entrez/query.fcgi?cmd=Retrieve&db=Nucleotide
```

```
&list_uids=02995756&dopt=GenBank>AF053033</a>  487
..........g..t................................... 546
<a name = 2995754></a><a
href=http://www.ncbi.nlm.nih.gov:80/entrez/query.fcgi?cmd=Retrieve&db=Nucleotide
&list_uids=02995754&dopt=GenBank>AF053032</a>  487
..........g..t................................... 546
<a name = 2995752></a><a
href=http://www.ncbi.nlm.nih.gov:80/entrez/query.fcgi?cmd=Retrieve&db=Nucleotide
&list_uids=02995752&dopt=GenBank>AF053031</a>  487
..........g..t................................... 546
<a name = 2995750></a><a
href=http://www.ncbi.nlm.nih.gov:80/entrez/query.fcgi?cmd=Retrieve&db=Nucleotide
&list_uids=02995750&dopt=GenBank>AF053030</a>  487
..........g..t................................... 546
<a name = 2995748></a><a
href=http://www.ncbi.nlm.nih.gov:80/entrez/query.fcgi?cmd=Retrieve&db=Nucleotide
&list_uids=02995748&dopt=GenBank>AF053029</a>  487
..........g..t................................... 546
<a name = 2995746></a><a
href=http://www.ncbi.nlm.nih.gov:80/entrez/query.fcgi?cmd=Retrieve&db=Nucleotide
&list_uids=02995746&dopt=GenBank>AF053028</a>  487
..........g..t................................... 546
<a name = 2995744></a><a
href=http://www.ncbi.nlm.nih.gov:80/entrez/query.fcgi?cmd=Retrieve&db=Nucleotide
&list_uids=02995744&dopt=GenBank>AF053027</a>  487
..........g..t................................... 546
<a name = 2995742></a><a
href=http://www.ncbi.nlm.nih.gov:80/entrez/query.fcgi?cmd=Retrieve&db=Nucleotide
&list_uids=02995742&dopt=GenBank>AF053026</a>  487
..........g..t................................... 546
<a name = 2995730></a><a
href=http://www.ncbi.nlm.nih.gov:80/entrez/query.fcgi?cmd=Retrieve&db=Nucleotide
&list_uids=02995730&dopt=GenBank>AF053020</a>  487
..........g..t................................... 546
<a name = 2995728></a><a
href=http://www.ncbi.nlm.nih.gov:80/entrez/query.fcgi?cmd=Retrieve&db=Nucleotide
&list_uids=02995728&dopt=GenBank>AF053019</a>  487
..........g..t................................... 546
<a name = 2995776></a><a
href=http://www.ncbi.nlm.nih.gov:80/entrez/query.fcgi?cmd=Retrieve&db=Nucleotide
&list_uids=02995776&dopt=GenBank>AF053043</a>  487
..........g..t................................... 546
<a name = 693979></a><a
href=http://www.ncbi.nlm.nih.gov:80/entrez/query.fcgi?cmd=Retrieve&db=Nucleotide
&list_uids=00693979&dopt=GenBank>X82301</a>    487
..........g..t................................... 546
<a name = 2995794></a><a
href=http://www.ncbi.nlm.nih.gov:80/entrez/query.fcgi?cmd=Retrieve&db=Nucleotide
&list_uids=02995794&dopt=GenBank>AF053052</a>  487
........................c......................... 546
<a name = 693977></a><a
href=http://www.ncbi.nlm.nih.gov:80/entrez/query.fcgi?cmd=Retrieve&db=Nucleotide
&list_uids=00693977&dopt=GenBank>X82300</a>    490
.........................c......................... 546
<a name = 2575784></a><a
href=http://www.ncbi.nlm.nih.gov:80/entrez/query.fcgi?cmd=Retrieve&db=Nucleotide
```

```
&list_uids=02575784&dopt=GenBank>AB004238</a>  487
............g....................c.....a.................... 546
<a name = 2575782></a><a
href=http://www.ncbi.nlm.nih.gov:80/entrez/query.fcgi?cmd=Retrieve&db=Nucleotide
&list_uids=02575782&dopt=GenBank>AB004237</a>  487
............g....................c.....a...............t..... 546
<a name = 693961></a><a
href=http://www.ncbi.nlm.nih.gov:80/entrez/query.fcgi?cmd=Retrieve&db=Nucleotide
&list_uids=00693961&dopt=GenBank>X82296</a>  487
............g....................c.....a.................... 546
<a name = 5835205></a><a
href=http://www.ncbi.nlm.nih.gov:80/entrez/query.fcgi?cmd=Retrieve&db=Nucleotide
&list_uids=05835205&dopt=GenBank>NC_001700</a>  15524
............g..g.................c.....a.............g....... 15583
<a name = 1098523></a><a
href=http://www.ncbi.nlm.nih.gov:80/entrez/query.fcgi?cmd=Retrieve&db=Nucleotide
&list_uids=01098523&dopt=GenBank>U20753</a>  15524
............g..g.................c.....a.............g....... 15583
<a name = 12619334></a><a
href=http://www.ncbi.nlm.nih.gov:80/entrez/query.fcgi?cmd=Retrieve&db=Nucleotide
&list_uids=12619334&dopt=GenBank>AF125145</a>  357
.................t..............c...t.a...c........c......... 416
<a name = 12619332></a><a
href=http://www.ncbi.nlm.nih.gov:80/entrez/query.fcgi?cmd=Retrieve&db=Nucleotide
&list_uids=12619332&dopt=GenBank>AF125144</a>  357
.....t.....g.....t..............t.....c.....a.....c.......... 416
<a name = 6760027></a><a
href=http://www.ncbi.nlm.nih.gov:80/entrez/query.fcgi?cmd=Retrieve&db=Nucleotide
&list_uids=06760027&dopt=GenBank>AF154975</a>  487
............g.....g..............c.....a..g........c......... 546
<a name = 11275401></a><a
href=http://www.ncbi.nlm.nih.gov:80/entrez/query.fcgi?cmd=Retrieve&db=Nucleotide
&list_uids=11275401&dopt=GenBank>AB051237</a>  487
............g.....g..............c.....a..g........c......... 546
<a name = 12619342></a><a
href=http://www.ncbi.nlm.nih.gov:80/entrez/query.fcgi?cmd=Retrieve&db=Nucleotide
&list_uids=12619342&dopt=GenBank>AF125149</a>  357
............g.....t...........g..c...t.a..............t...... 416 tmpseq_0      61    ttcatccttccatttatcatctcagctctagcagcagtccacctcctattccttcacgag 120
<a
href=http://www.ncbi.nlm.nih.gov:80/entrez/query.fcgi?cmd=Retrieve&db=Nucleotide
&list_uids=09795379&dopt=GenBank>AY005809</a>  99
.............................................................t...... 158
<a
href=http://www.ncbi.nlm.nih.gov:80/entrez/query.fcgi?cmd=Retrieve&db=Nucleotide
&list_uids=02995797&dopt=GenBank>AF053054</a>  547
................................c........................c..t... 606
<a
href=http://www.ncbi.nlm.nih.gov:80/entrez/query.fcgi?cmd=Retrieve&db=Nucleotide
&list_uids=02995796&dopt=GenBank>AF053053</a>  547
................................c........................c..t... 606
<a
href=http://www.ncbi.nlm.nih.gov:80/entrez/query.fcgi?cmd=Retrieve&db=Nucleotide
&list_uids=02995790&dopt=GenBank>AF053050</a>  547
...........g.............c.................................a 606
```

```
<a
href=http://www.ncbi.nlm.nih.gov:80/entrez/query.fcgi?cmd=Retrieve&db=Nucleotide
&list_uids=02995788&dopt=GenBank>AF053049</a>   547
..........g......c...............................a 606
<a
href=http://www.ncbi.nlm.nih.gov:80/entrez/query.fcgi?cmd=Retrieve&db=Nucleotide
&list_uids=02995740&dopt=GenBank>AF053025</a>   547
..........g......g.......c........................a 606
<a
href=http://www.ncbi.nlm.nih.gov:80/entrez/query.fcgi?cmd=Retrieve&db=Nucleotide
&list_uids=02995738&dopt=GenBank>AF053024</a>   547
..........g......g.......c........................a 606
<a
href=http://www.ncbi.nlm.nih.gov:80/entrez/query.fcgi?cmd=Retrieve&db=Nucleotide
&list_uids=02995736&dopt=GenBank>AF053023</a>   547
..........g......g.......c........................a 606
<a
href=http://www.ncbi.nlm.nih.gov:80/entrez/query.fcgi?cmd=Retrieve&db=Nucleotide
&list_uids=02995734&dopt=GenBank>AF053022</a>   547
..........g......g.......c........................a 606
<a
href=http://www.ncbi.nlm.nih.gov:80/entrez/query.fcgi?cmd=Retrieve&db=Nucleotide
&list_uids=02995732&dopt=GenBank>AF053021</a>   547
..........g......g.......c........................a 606
<a
href=http://www.ncbi.nlm.nih.gov:80/entrez/query.fcgi?cmd=Retrieve&db=Nucleotide
&list_uids=02995726&dopt=GenBank>AF053018</a>   547
..................g.......c........................a 606
<a
href=http://www.ncbi.nlm.nih.gov:80/entrez/query.fcgi?cmd=Retrieve&db=Nucleotide
&list_uids=02995792&dopt=GenBank>AF053051</a>   547
..........g......g.......c........................a 606
<a
href=http://www.ncbi.nlm.nih.gov:80/entrez/query.fcgi?cmd=Retrieve&db=Nucleotide
&list_uids=02995786&dopt=GenBank>AF053048</a>   547
..........g......g.......c........................a 606
<a
href=http://www.ncbi.nlm.nih.gov:80/entrez/query.fcgi?cmd=Retrieve&db=Nucleotide
&list_uids=02995784&dopt=GenBank>AF053047</a>   547
..........g......g.......c........................a 606
<a
href=http://www.ncbi.nlm.nih.gov:80/entrez/query.fcgi?cmd=Retrieve&db=Nucleotide
&list_uids=02995782&dopt=GenBank>AF053046</a>   547
..........g......g.......c........................a 606
<a
href=http://www.ncbi.nlm.nih.gov:80/entrez/query.fcgi?cmd=Retrieve&db=Nucleotide
&list_uids=02995780&dopt=GenBank>AF053045</a>   547
..........g......g.......c........................a 606
<a
href=http://www.ncbi.nlm.nih.gov:80/entrez/query.fcgi?cmd=Retrieve&db=Nucleotide
&list_uids=02995778&dopt=GenBank>AF053044</a>   547
..........g......g.......c........................a 606
<a
href=http://www.ncbi.nlm.nih.gov:80/entrez/query.fcgi?cmd=Retrieve&db=Nucleotide
&list_uids=02995774&dopt=GenBank>AF053042</a>   547
..........g......g.......c........................a 606
```

```
<a
href=http://www.ncbi.nlm.nih.gov:80/entrez/query.fcgi?cmd=Retrieve&db=Nucleotide
&list_uids=02995772&dopt=GenBank>AF053041</a>  547
..........g......g.......c................................a 606
<a
href=http://www.ncbi.nlm.nih.gov:80/entrez/query.fcgi?cmd=Retrieve&db=Nucleotide
&list_uids=02995770&dopt=GenBank>AF053040</a>  547
..........g......g.......c................................a 606
<a
href=http://www.ncbi.nlm.nih.gov:80/entrez/query.fcgi?cmd=Retrieve&db=Nucleotide
&list_uids=02995768&dopt=GenBank>AF053039</a>  547
..........g......g.......c................................a 606
<a
href=http://www.ncbi.nlm.nih.gov:80/entrez/query.fcgi?cmd=Retrieve&db=Nucleotide
&list_uids=02995766&dopt=GenBank>AF053038</a>  547
..........g......g.......c................................a 606
<a
href=http://www.ncbi.nlm.nih.gov:80/entrez/query.fcgi?cmd=Retrieve&db=Nucleotide
&list_uids=02995764&dopt=GenBank>AF053037</a>  547
..........g......g.......c................................a 606
<a
href=http://www.ncbi.nlm.nih.gov:80/entrez/query.fcgi?cmd=Retrieve&db=Nucleotide
&list_uids=02995762&dopt=GenBank>AF053036</a>  547
..........g......g.......c................................a 606
<a
href=http://www.ncbi.nlm.nih.gov:80/entrez/query.fcgi?cmd=Retrieve&db=Nucleotide
&list_uids=02995760&dopt=GenBank>AF053035</a>  547
..........g......g.......c................................a 606
<a
href=http://www.ncbi.nlm.nih.gov:80/entrez/query.fcgi?cmd=Retrieve&db=Nucleotide
&list_uids=02995758&dopt=GenBank>AF053034</a>  547
..........g......g.......c................................a 606
<a
href=http://www.ncbi.nlm.nih.gov:80/entrez/query.fcgi?cmd=Retrieve&db=Nucleotide
&list_uids=02995756&dopt=GenBank>AF053033</a>  547
..........g......g.......c................................a 606
<a
href=http://www.ncbi.nlm.nih.gov:80/entrez/query.fcgi?cmd=Retrieve&db=Nucleotide
&list_uids=02995754&dopt=GenBank>AF053032</a>  547
..........g......g.......c................................a 606
<a
href=http://www.ncbi.nlm.nih.gov:80/entrez/query.fcgi?cmd=Retrieve&db=Nucleotide
&list_uids=02995752&dopt=GenBank>AF053031</a>  547
..........g......g.......c................................a 606
<a
href=http://www.ncbi.nlm.nih.gov:80/entrez/query.fcgi?cmd=Retrieve&db=Nucleotide
&list_uids=02995750&dopt=GenBank>AF053030</a>  547
..........g......g.......c................................a 606
<a
href=http://www.ncbi.nlm.nih.gov:80/entrez/query.fcgi?cmd=Retrieve&db=Nucleotide
&list_uids=02995748&dopt=GenBank>AF053029</a>  547
..........g......g.......c................................a 606
<a
href=http://www.ncbi.nlm.nih.gov:80/entrez/query.fcgi?cmd=Retrieve&db=Nucleotide
&list_uids=02995746&dopt=GenBank>AF053028</a>  547
..........g......g.......c................................a 606
```

```
<a
href=http://www.ncbi.nlm.nih.gov:80/entrez/query.fcgi?cmd=Retrieve&db=Nucleotide
&list_uids=02995744&dopt=GenBank>AF053027</a>   547
..........g......g.......c..................................a 606
<a
href=http://www.ncbi.nlm.nih.gov:80/entrez/query.fcgi?cmd=Retrieve&db=Nucleotide
&list_uids=02995742&dopt=GenBank>AF053026</a>   547
..........g......g.......c..................................a 606
<a
href=http://www.ncbi.nlm.nih.gov:80/entrez/query.fcgi?cmd=Retrieve&db=Nucleotide
&list_uids=02995730&dopt=GenBank>AF053020</a>   547
..........g......g.......c..................................a 606
<a
href=http://www.ncbi.nlm.nih.gov:80/entrez/query.fcgi?cmd=Retrieve&db=Nucleotide
&list_uids=02995728&dopt=GenBank>AF053019</a>   547
..........g......g.......c..................................a 606
<a
href=http://www.ncbi.nlm.nih.gov:80/entrez/query.fcgi?cmd=Retrieve&db=Nucleotide
&list_uids=02995776&dopt=GenBank>AF053043</a>   547
.....c......g......g.......c..................................a 606
<a
href=http://www.ncbi.nlm.nih.gov:80/entrez/query.fcgi?cmd=Retrieve&db=Nucleotide
&list_uids=00693979&dopt=GenBank>X82301</a>   547
.....c......g......g.......c..................................a 606
<a
href=http://www.ncbi.nlm.nih.gov:80/entrez/query.fcgi?cmd=Retrieve&db=Nucleotide
&list_uids=02995794&dopt=GenBank>AF053052</a>   547
........................c.....................g.....c..t..a 606
<a
href=http://www.ncbi.nlm.nih.gov:80/entrez/query.fcgi?cmd=Retrieve&db=Nucleotide
&list_uids=00693977&dopt=GenBank>X82300</a>   547
........................c.....................g.....c..t..a 606
<a
href=http://www.ncbi.nlm.nih.gov:80/entrez/query.fcgi?cmd=Retrieve&db=Nucleotide
&list_uids=02575784&dopt=GenBank>AB004238</a>   547
...............c..t........ct.......a......t..........t..a 606
<a
href=http://www.ncbi.nlm.nih.gov:80/entrez/query.fcgi?cmd=Retrieve&db=Nucleotide
&list_uids=02575782&dopt=GenBank>AB004237</a>   547
.....t........c..t........ct.......a......t..........t..a 606
<a
href=http://www.ncbi.nlm.nih.gov:80/entrez/query.fcgi?cmd=Retrieve&db=Nucleotide
&list_uids=00693961&dopt=GenBank>X82296</a>   547
.....t........c..t........ct.......a......t..........t..a 606
<a
href=http://www.ncbi.nlm.nih.gov:80/entrez/query.fcgi?cmd=Retrieve&db=Nucleotide
&list_uids=05835205&dopt=GenBank>NC_001700</a>   15584
.....t........c..t........ct......g...a......t..........t..a 15643
<a
href=http://www.ncbi.nlm.nih.gov:80/entrez/query.fcgi?cmd=Retrieve&db=Nucleotide
&list_uids=01098523&dopt=GenBank>U20753</a>   15584
.....t........c..t........ct......g...a......t..........t..a 15643
<a
href=http://www.ncbi.nlm.nih.gov:80/entrez/query.fcgi?cmd=Retrieve&db=Nucleotide
&list_uids=12619334&dopt=GenBank>AF125145</a>   417
..t....................c.........c..t..tt.a.........a.....a 476
```

```
<a
href=http://www.ncbi.nlm.nih.gov:80/entrez/query.fcgi?cmd=Retrieve&db=Nucleotide
&list_uids=12619332&dopt=GenBank>AF125144</a>   417
..t..t.....t..c.....t......c................t.a.....t..a.....a 476
<a
href=http://www.ncbi.nlm.nih.gov:80/entrez/query.fcgi?cmd=Retrieve&db=Nucleotide
&list_uids=06760027&dopt=GenBank>AF154975</a>   547
..t.....g........tg.......at..........a.....t.........c.....a 606
<a
href=http://www.ncbi.nlm.nih.gov:80/entrez/query.fcgi?cmd=Retrieve&db=Nucleotide
&list_uids=11275401&dopt=GenBank>AB051237</a>   547
..t.....g........tg.......at..........a.....t.........c.....a 606
<a
href=http://www.ncbi.nlm.nih.gov:80/entrez/query.fcgi?cmd=Retrieve&db=Nucleotide
&list_uids=12619342&dopt=GenBank>AF125149</a>   417
..............c..t.........c................t.at....t..a..t..a 476 tmpseq_0   121   acaggatctaacaacccctcaggaatagtatccgactcagacaaaattccattccaccca 180
<a
href=http://www.ncbi.nlm.nih.gov:80/entrez/query.fcgi?cmd=Retrieve&db=Nucleotide
&list_uids=09795379&dopt=GenBank>AY005809</a>   159
............................t............................... 218
<a
href=http://www.ncbi.nlm.nih.gov:80/entrez/query.fcgi?cmd=Retrieve&db=Nucleotide
&list_uids=02995797&dopt=GenBank>AF053054</a>   607
............................t...............c..g......... 666
<a
href=http://www.ncbi.nlm.nih.gov:80/entrez/query.fcgi?cmd=Retrieve&db=Nucleotide
&list_uids=02995796&dopt=GenBank>AF053053</a>   607
............................t...............c..g......... 666
<a
href=http://www.ncbi.nlm.nih.gov:80/entrez/query.fcgi?cmd=Retrieve&db=Nucleotide
&list_uids=02995790&dopt=GenBank>AF053050</a>   607
........c..t.................g..g............................ 666
<a
href=http://www.ncbi.nlm.nih.gov:80/entrez/query.fcgi?cmd=Retrieve&db=Nucleotide
&list_uids=02995788&dopt=GenBank>AF053049</a>   607
........c..t.................g..g............................ 666
<a
href=http://www.ncbi.nlm.nih.gov:80/entrez/query.fcgi?cmd=Retrieve&db=Nucleotide
&list_uids=02995740&dopt=GenBank>AF053025</a>   607
........c..t.................g..g.................c.......... 666
<a
href=http://www.ncbi.nlm.nih.gov:80/entrez/query.fcgi?cmd=Retrieve&db=Nucleotide
&list_uids=02995738&dopt=GenBank>AF053024</a>   607
........c..t.................g..g.................c.......... 666
<a
href=http://www.ncbi.nlm.nih.gov:80/entrez/query.fcgi?cmd=Retrieve&db=Nucleotide
&list_uids=02995736&dopt=GenBank>AF053023</a>   607
........c..t.................g..g.................c.......... 666
<a
href=http://www.ncbi.nlm.nih.gov:80/entrez/query.fcgi?cmd=Retrieve&db=Nucleotide
&list_uids=02995734&dopt=GenBank>AF053022</a>   607
........c..t.................g..g.................c.......... 666
<a
href=http://www.ncbi.nlm.nih.gov:80/entrez/query.fcgi?cmd=Retrieve&db=Nucleotide
```

```
<a
href=http://www.ncbi.nlm.nih.gov:80/entrez/query.fcgi?cmd=Retrieve&db=Nucleotide
&list_uids=02995732&dopt=GenBank>AF053021</a>   607
........c..t.............g..g..................c............  666
<a
href=http://www.ncbi.nlm.nih.gov:80/entrez/query.fcgi?cmd=Retrieve&db=Nucleotide
&list_uids=02995726&dopt=GenBank>AF053018</a>   607
........c..t.............g..g..................c............  666
<a
href=http://www.ncbi.nlm.nih.gov:80/entrez/query.fcgi?cmd=Retrieve&db=Nucleotide
&list_uids=02995792&dopt=GenBank>AF053051</a>   607
........c..t.............g..g..................c............  666
<a
href=http://www.ncbi.nlm.nih.gov:80/entrez/query.fcgi?cmd=Retrieve&db=Nucleotide
&list_uids=02995786&dopt=GenBank>AF053048</a>   607
........c..t.............g..g..................c............  666
<a
href=http://www.ncbi.nlm.nih.gov:80/entrez/query.fcgi?cmd=Retrieve&db=Nucleotide
&list_uids=02995784&dopt=GenBank>AF053047</a>   607
........c..t.............g..g..................c............  666
<a
href=http://www.ncbi.nlm.nih.gov:80/entrez/query.fcgi?cmd=Retrieve&db=Nucleotide
&list_uids=02995782&dopt=GenBank>AF053046</a>   607
........c..t.............g..g..................c............  666
<a
href=http://www.ncbi.nlm.nih.gov:80/entrez/query.fcgi?cmd=Retrieve&db=Nucleotide
&list_uids=02995780&dopt=GenBank>AF053045</a>   607
........c..t.............g..g..................c............  666
<a
href=http://www.ncbi.nlm.nih.gov:80/entrez/query.fcgi?cmd=Retrieve&db=Nucleotide
&list_uids=02995778&dopt=GenBank>AF053044</a>   607
........c..t.............g..g..................c............  666
<a
href=http://www.ncbi.nlm.nih.gov:80/entrez/query.fcgi?cmd=Retrieve&db=Nucleotide
&list_uids=02995774&dopt=GenBank>AF053042</a>   607
........c..t.............g..g..................c............  666
<a
href=http://www.ncbi.nlm.nih.gov:80/entrez/query.fcgi?cmd=Retrieve&db=Nucleotide
&list_uids=02995772&dopt=GenBank>AF053041</a>   607
........c..t.............g..g..................c............  666
<a
href=http://www.ncbi.nlm.nih.gov:80/entrez/query.fcgi?cmd=Retrieve&db=Nucleotide
&list_uids=02995770&dopt=GenBank>AF053040</a>   607
........c..t.............g..g..................c............  666
<a
href=http://www.ncbi.nlm.nih.gov:80/entrez/query.fcgi?cmd=Retrieve&db=Nucleotide
&list_uids=02995768&dopt=GenBank>AF053039</a>   607
........c..t.............g..g..................c............  666
<a
href=http://www.ncbi.nlm.nih.gov:80/entrez/query.fcgi?cmd=Retrieve&db=Nucleotide
&list_uids=02995766&dopt=GenBank>AF053038</a>   607
........c..t.............g..g..................c............  666
<a
href=http://www.ncbi.nlm.nih.gov:80/entrez/query.fcgi?cmd=Retrieve&db=Nucleotide
&list_uids=02995764&dopt=GenBank>AF053037</a>   607
........c..t.............g..g..................c............  666
<a
href=http://www.ncbi.nlm.nih.gov:80/entrez/query.fcgi?cmd=Retrieve&db=Nucleotide
```

```
&list_uids=02995762&dopt=GenBank>AF053036</a>  607
........c..t.............g..g...................c............ 666
<a
href=http://www.ncbi.nlm.nih.gov:80/entrez/query.fcgi?cmd=Retrieve&db=Nucleotide
&list_uids=02995760&dopt=GenBank>AF053035</a>  607
........c..t.............g..g...................c............ 666
<a
href=http://www.ncbi.nlm.nih.gov:80/entrez/query.fcgi?cmd=Retrieve&db=Nucleotide
&list_uids=02995758&dopt=GenBank>AF053034</a>  607
........c..t.............g..g...................c............ 666
<a
href=http://www.ncbi.nlm.nih.gov:80/entrez/query.fcgi?cmd=Retrieve&db=Nucleotide
&list_uids=02995756&dopt=GenBank>AF053033</a>  607
........c..t.............g..g...................c............ 666
<a
href=http://www.ncbi.nlm.nih.gov:80/entrez/query.fcgi?cmd=Retrieve&db=Nucleotide
&list_uids=02995754&dopt=GenBank>AF053032</a>  607
........c..t.............g..g...................c............ 666
<a
href=http://www.ncbi.nlm.nih.gov:80/entrez/query.fcgi?cmd=Retrieve&db=Nucleotide
&list_uids=02995752&dopt=GenBank>AF053031</a>  607
........c..t.............g..g...................c............ 666
<a
href=http://www.ncbi.nlm.nih.gov:80/entrez/query.fcgi?cmd=Retrieve&db=Nucleotide
&list_uids=02995750&dopt=GenBank>AF053030</a>  607
........c..t.............g..g...................c............ 666
<a
href=http://www.ncbi.nlm.nih.gov:80/entrez/query.fcgi?cmd=Retrieve&db=Nucleotide
&list_uids=02995748&dopt=GenBank>AF053029</a>  607
........c..t.............g..g...................c............ 666
<a
href=http://www.ncbi.nlm.nih.gov:80/entrez/query.fcgi?cmd=Retrieve&db=Nucleotide
&list_uids=02995746&dopt=GenBank>AF053028</a>  607
........c..t.............g..g...................c............ 666
<a
href=http://www.ncbi.nlm.nih.gov:80/entrez/query.fcgi?cmd=Retrieve&db=Nucleotide
&list_uids=02995744&dopt=GenBank>AF053027</a>  607
........c..t.............g..g...................c............ 666
<a
href=http://www.ncbi.nlm.nih.gov:80/entrez/query.fcgi?cmd=Retrieve&db=Nucleotide
&list_uids=02995742&dopt=GenBank>AF053026</a>  607
........c..t.............g..g...................c............ 666
<a
href=http://www.ncbi.nlm.nih.gov:80/entrez/query.fcgi?cmd=Retrieve&db=Nucleotide
&list_uids=02995730&dopt=GenBank>AF053020</a>  607
........c..t.............g..g...................c............ 666
<a
href=http://www.ncbi.nlm.nih.gov:80/entrez/query.fcgi?cmd=Retrieve&db=Nucleotide
&list_uids=02995728&dopt=GenBank>AF053019</a>  607
........c..t.............g..g...................c............ 666
<a
href=http://www.ncbi.nlm.nih.gov:80/entrez/query.fcgi?cmd=Retrieve&db=Nucleotide
&list_uids=02995776&dopt=GenBank>AF053043</a>  607
........c..t.............g..g...................c............ 666
<a
href=http://www.ncbi.nlm.nih.gov:80/entrez/query.fcgi?cmd=Retrieve&db=Nucleotide
```

```
&list_uids=00693979&dopt=GenBank>X82301</a>     607
........c..t.............g..g...............c............. 666
<a
href=http://www.ncbi.nlm.nih.gov:80/entrez/query.fcgi?cmd=Retrieve&db=Nucleotide
&list_uids=02995794&dopt=GenBank>AF053052</a>   607
............t.............g.....t.........t.....c.........t... 666
<a
href=http://www.ncbi.nlm.nih.gov:80/entrez/query.fcgi?cmd=Retrieve&db=Nucleotide
&list_uids=00693977&dopt=GenBank>X82300</a>     607
............t.............g.....t.........t.................t... 666
<a
href=http://www.ncbi.nlm.nih.gov:80/entrez/query.fcgi?cmd=Retrieve&db=Nucleotide
&list_uids=02575784&dopt=GenBank>AB004238</a>   607
........................tac.......t............c............. 666
<a
href=http://www.ncbi.nlm.nih.gov:80/entrez/query.fcgi?cmd=Retrieve&db=Nucleotide
&list_uids=02575782&dopt=GenBank>AB004237</a>   607
........................tac.......t............c............. 666
<a
href=http://www.ncbi.nlm.nih.gov:80/entrez/query.fcgi?cmd=Retrieve&db=Nucleotide
&list_uids=00693961&dopt=GenBank>X82296</a>     607
........................tac.......t............c............. 666
<a
href=http://www.ncbi.nlm.nih.gov:80/entrez/query.fcgi?cmd=Retrieve&db=Nucleotide
&list_uids=05835205&dopt=GenBank>NC_001700</a>  15644
........................tac.......t............c............. 15703
<a
href=http://www.ncbi.nlm.nih.gov:80/entrez/query.fcgi?cmd=Retrieve&db=Nucleotide
&list_uids=01098523&dopt=GenBank>U20753</a>     15644
........................tac.......t............c............. 15703
<a
href=http://www.ncbi.nlm.nih.gov:80/entrez/query.fcgi?cmd=Retrieve&db=Nucleotide
&list_uids=12619334&dopt=GenBank>AF125145</a>   477
........c.....t.............t..t............c............. 536
<a
href=http://www.ncbi.nlm.nih.gov:80/entrez/query.fcgi?cmd=Retrieve&db=Nucleotide
&list_uids=12619332&dopt=GenBank>AF125144</a>   477
..........t..t............ga....t.........t.................. 536
<a
href=http://www.ncbi.nlm.nih.gov:80/entrez/query.fcgi?cmd=Retrieve&db=Nucleotide
&list_uids=06760027&dopt=GenBank>AF154975</a>   607
............t.............cccc.........t.........c............. 666
<a
href=http://www.ncbi.nlm.nih.gov:80/entrez/query.fcgi?cmd=Retrieve&db=Nucleotide
&list_uids=11275401&dopt=GenBank>AB051237</a>   607
............t.............cccc.........t.........c............. 666
<a
href=http://www.ncbi.nlm.nih.gov:80/entrez/query.fcgi?cmd=Retrieve&db=Nucleotide
&list_uids=12619342&dopt=GenBank>AF125149</a>   477
........c..t..t.........g..a....t...............c...........g 536 tmpseq_0   181   tactacacaatcaaagatatcctgggccttctagtactaatcctagcactcatactactc 240
<a
href=http://www.ncbi.nlm.nih.gov:80/entrez/query.fcgi?cmd=Retrieve&db=Nucleotide
&list_uids=09795379&dopt=GenBank>AY005809</a>   219
...............................................t................. 278
```

```
<a href=http://www.ncbi.nlm.nih.gov:80/entrez/query.fcgi?cmd=Retrieve&db=Nucleotide
&list_uids=02995797&dopt=GenBank>AF053054</a>   667
................c.........................a.............. 726
<a href=http://www.ncbi.nlm.nih.gov:80/entrez/query.fcgi?cmd=Retrieve&db=Nucleotide
&list_uids=02995796&dopt=GenBank>AF053053</a>   667
................c.........................a.............. 726
<a href=http://www.ncbi.nlm.nih.gov:80/entrez/query.fcgi?cmd=Retrieve&db=Nucleotide
&list_uids=02995790&dopt=GenBank>AF053050</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995788&dopt=GenBank>AF053049</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995740&dopt=GenBank>AF053025</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995738&dopt=GenBank>AF053024</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995736&dopt=GenBank>AF053023</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995734&dopt=GenBank>AF053022</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995732&dopt=GenBank>AF053021</a>   667
..........t.........t.a.....ct..............a.c........... 726
<a href=http://www.ncbi.nlm.nih.gov:80/entrez/query.fcgi?cmd=Retrieve&db=Nucleotide
&list_uids=02995726&dopt=GenBank>AF053018</a>   667
..........t.........t.a.....ct..............a.c.....c..... 726
<a href=http://www.ncbi.nlm.nih.gov:80/entrez/query.fcgi?cmd=Retrieve&db=Nucleotide
&list_uids=02995792&dopt=GenBank>AF053051</a>   667
..........t.........t.a.....ct..............a.c.....c..... 726
<a href=http://www.ncbi.nlm.nih.gov:80/entrez/query.fcgi?cmd=Retrieve&db=Nucleotide
&list_uids=02995786&dopt=GenBank>AF053048</a>   667
..........t.........t.a.....ct........g.....a.c........... 726
<a href=http://www.ncbi.nlm.nih.gov:80/entrez/query.fcgi?cmd=Retrieve&db=Nucleotide
&list_uids=02995784&dopt=GenBank>AF053047</a>   667
..........t.........t.a.....ct........g.....a.c........... 726
<a href=http://www.ncbi.nlm.nih.gov:80/entrez/query.fcgi?cmd=Retrieve&db=Nucleotide
&list_uids=02995782&dopt=GenBank>AF053046</a>   667
..........t.........t.a.....ct........g.....a.c........... 726
```

```
<a
href=http://www.ncbi.nlm.nih.gov:80/entrez/query.fcgi?cmd=Retrieve&db=Nucleotide
&list_uids=02995780&dopt=GenBank>AF053045</a>   667
..........t.........t.a.....ct........g.....a.c............ 726
<a
href=http://www.ncbi.nlm.nih.gov:80/entrez/query.fcgi?cmd=Retrieve&db=Nucleotide
&list_uids=02995778&dopt=GenBank>AF053044</a>   667
..........t.........t.a.....ct........g.....a.c............ 726
<a
href=http://www.ncbi.nlm.nih.gov:80/entrez/query.fcgi?cmd=Retrieve&db=Nucleotide
&list_uids=02995774&dopt=GenBank>AF053042</a>   667
..........t.........t.a.....ct........g.....a.c............ 726
<a
href=http://www.ncbi.nlm.nih.gov:80/entrez/query.fcgi?cmd=Retrieve&db=Nucleotide
&list_uids=02995772&dopt=GenBank>AF053041</a>   667
..........t.........t.a.....ct........g.....a.c............ 726
<a
href=http://www.ncbi.nlm.nih.gov:80/entrez/query.fcgi?cmd=Retrieve&db=Nucleotide
&list_uids=02995770&dopt=GenBank>AF053040</a>   667
..........t.........t.a.....ct........g.....a.c............ 726
<a
href=http://www.ncbi.nlm.nih.gov:80/entrez/query.fcgi?cmd=Retrieve&db=Nucleotide
&list_uids=02995768&dopt=GenBank>AF053039</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995766&dopt=GenBank>AF053038</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995764&dopt=GenBank>AF053037</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995762&dopt=GenBank>AF053036</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995760&dopt=GenBank>AF053035</a>   667
..........t.........t.a.....ct..............a.c....c....... 726
<a
href=http://www.ncbi.nlm.nih.gov:80/entrez/query.fcgi?cmd=Retrieve&db=Nucleotide
&list_uids=02995758&dopt=GenBank>AF053034</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995756&dopt=GenBank>AF053033</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995754&dopt=GenBank>AF053032</a>   667
..........t.........t.a.....ct..............a.c.....c....... 726
<a
href=http://www.ncbi.nlm.nih.gov:80/entrez/query.fcgi?cmd=Retrieve&db=Nucleotide
&list_uids=02995752&dopt=GenBank>AF053031</a>   667
..........t.........t.a.....ct..............a.c.....c....... 726
```

```
<a
href=http://www.ncbi.nlm.nih.gov:80/entrez/query.fcgi?cmd=Retrieve&db=Nucleotide
&list_uids=02995750&dopt=GenBank>AF053030</a>  667
...........t.........t.a.....ct..............a.c.....c....... 726
<a
href=http://www.ncbi.nlm.nih.gov:80/entrez/query.fcgi?cmd=Retrieve&db=Nucleotide
&list_uids=02995748&dopt=GenBank>AF053029</a>  667
...........t.........t.a.....ct..............a.c.....c....... 726
<a
href=http://www.ncbi.nlm.nih.gov:80/entrez/query.fcgi?cmd=Retrieve&db=Nucleotide
&list_uids=02995746&dopt=GenBank>AF053028</a>  667
...........t.........t.a.....ct..............a.c.....c....... 726
<a
href=http://www.ncbi.nlm.nih.gov:80/entrez/query.fcgi?cmd=Retrieve&db=Nucleotide
&list_uids=02995744&dopt=GenBank>AF053027</a>  667
...........t.........t.a.....ct..............a.c.....c....... 726
<a
href=http://www.ncbi.nlm.nih.gov:80/entrez/query.fcgi?cmd=Retrieve&db=Nucleotide
&list_uids=02995742&dopt=GenBank>AF053026</a>  667
...........t.........t.a.....ct..............a.c.....c....., 726
<a
href=http://www.ncbi.nlm.nih.gov:80/entrez/query.fcgi?cmd=Retrieve&db=Nucleotide
&list_uids=02995730&dopt=GenBank>AF053020</a>  667
...........t.........t.a.....ct..............a.c.....c....... 726
<a
href=http://www.ncbi.nlm.nih.gov:80/entrez/query.fcgi?cmd=Retrieve&db=Nucleotide
&list_uids=02995728&dopt=GenBank>AF053019</a>  667
...........t.........t.a.....ct..............a.c.....c....... 726
<a
href=http://www.ncbi.nlm.nih.gov:80/entrez/query.fcgi?cmd=Retrieve&db=Nucleotide
&list_uids=02995776&dopt=GenBank>AF053043</a>  667
...........t.........t.a.....ct........g.....a.c............. 726
<a
href=http://www.ncbi.nlm.nih.gov:80/entrez/query.fcgi?cmd=Retrieve&db=Nucleotide
&list_uids=00693979&dopt=GenBank>X82301</a>  667
...........t.........t.a.....ct........g.....a.c............. 726
<a
href=http://www.ncbi.nlm.nih.gov:80/entrez/query.fcgi?cmd=Retrieve&db=Nucleotide
&list_uids=02995794&dopt=GenBank>AF053052</a>  667
.....t..............a..................t..a............... 726
<a
href=http://www.ncbi.nlm.nih.gov:80/entrez/query.fcgi?cmd=Retrieve&db=Nucleotide
&list_uids=00693977&dopt=GenBank>X82300</a>  667
.....t..............a..............t...t..a............... 726
<a
href=http://www.ncbi.nlm.nih.gov:80/entrez/query.fcgi?cmd=Retrieve&db=Nucleotide
&list_uids=02575784&dopt=GenBank>AB004238</a>  667
.....t..........c.....a..t............g.tt..a............... 726
<a
href=http://www.ncbi.nlm.nih.gov:80/entrez/query.fcgi?cmd=Retrieve&db=Nucleotide
&list_uids=02575782&dopt=GenBank>AB004237</a>  667
.....t..........c.....a..t............g.tt..a............... 726
<a
href=http://www.ncbi.nlm.nih.gov:80/entrez/query.fcgi?cmd=Retrieve&db=Nucleotide
&list_uids=00693961&dopt=GenBank>X82296</a>  667
.....t..........c.....a..t............g.tt..a......c....... 726
```

```
<a
href=http://www.ncbi.nlm.nih.gov:80/entrez/query.fcgi?cmd=Retrieve&db=Nucleotide
&list_uids=05835205&dopt=GenBank>NC_001700</a>  15704
.....t............c.....a..t............g.tt..a...............  15763
<a
href=http://www.ncbi.nlm.nih.gov:80/entrez/query.fcgi?cmd=Retrieve&db=Nucleotide
&list_uids=01098523&dopt=GenBank>U20753</a>  15704
.....t............c.....a..t............g.tt..a...............  15763
<a
href=http://www.ncbi.nlm.nih.gov:80/entrez/query.fcgi?cmd=Retrieve&db=Nucleotide
&list_uids=12619334&dopt=GenBank>AF125145</a>  537
.....t..............nt.a.....c...t.c.........at.t.a.....g..a  596
<a
href=http://www.ncbi.nlm.nih.gov:80/entrez/query.fcgi?cmd=Retrieve&db=Nucleotide
&list_uids=12619332&dopt=GenBank>AF125144</a>  537
.....t.................c.....gt..t.t..............a...t.g..a  596
<a
href=http://www.ncbi.nlm.nih.gov:80/entrez/query.fcgi?cmd=Retrieve&db=Nucleotide
&list_uids=06760027&dopt=GenBank>AF154975</a>  667
.........c.........c.....a...gcc...c.c...........tg......a....a  726
<a
href=http://www.ncbi.nlm.nih.gov:80/entrez/query.fcgi?cmd=Retrieve&db=Nucleotide
&list_uids=11275401&dopt=GenBank>AB051237</a>  667
.........c.........c.....a...gcc...t.c...........tg......a....a  726
<a
href=http://www.ncbi.nlm.nih.gov:80/entrez/query.fcgi?cmd=Retrieve&db=Nucleotide
&list_uids=12619342&dopt=GenBank>AF125149</a>  537
.....t.....t........t..a..t..c....t.c......t.....t.a.....gt.a  596 tmpseq_0   241  gtcctattctcaccagacctgttaggagaccccgataactacatccctgccaaccctcta  300
<a
href=http://www.ncbi.nlm.nih.gov:80/entrez/query.fcgi?cmd=Retrieve&db=Nucleotide
&list_uids=09795379&dopt=GenBank>AY005809</a>  279
............................t.........c.............  338
<a
href=http://www.ncbi.nlm.nih.gov:80/entrez/query.fcgi?cmd=Retrieve&db=Nucleotide
&list_uids=02995797&dopt=GenBank>AF053054</a>  727
....................a.....g....................c............  786
<a
href=http://www.ncbi.nlm.nih.gov:80/entrez/query.fcgi?cmd=Retrieve&db=Nucleotide
&list_uids=02995796&dopt=GenBank>AF053053</a>  727
....................a.....g....................c............  786
<a
href=http://www.ncbi.nlm.nih.gov:80/entrez/query.fcgi?cmd=Retrieve&db=Nucleotide
&list_uids=02995790&dopt=GenBank>AF053050</a>  727
....................a..........t...............c.........c...  786
<a
href=http://www.ncbi.nlm.nih.gov:80/entrez/query.fcgi?cmd=Retrieve&db=Nucleotide
&list_uids=02995788&dopt=GenBank>AF053049</a>  727
....................a..........t...............c.........c...  786
<a
href=http://www.ncbi.nlm.nih.gov:80/entrez/query.fcgi?cmd=Retrieve&db=Nucleotide
&list_uids=02995740&dopt=GenBank>AF053025</a>  727
....................a..........t...............c.........c...  786
<a
href=http://www.ncbi.nlm.nih.gov:80/entrez/query.fcgi?cmd=Retrieve&db=Nucleotide
```

```
&list_uids=02995738&dopt=GenBank>AF053024</a>   727
....................a..........t..............c........c... 786
<a
href=http://www.ncbi.nlm.nih.gov:80/entrez/query.fcgi?cmd=Retrieve&db=Nucleotide
&list_uids=02995736&dopt=GenBank>AF053023</a>   727
....................a..........t..............c........c... 786
<a
href=http://www.ncbi.nlm.nih.gov:80/entrez/query.fcgi?cmd=Retrieve&db=Nucleotide
&list_uids=02995734&dopt=GenBank>AF053022</a>   727
....................a..........t..............c........c... 786
<a
href=http://www.ncbi.nlm.nih.gov:80/entrez/query.fcgi?cmd=Retrieve&db=Nucleotide
&list_uids=02995732&dopt=GenBank>AF053021</a>   727
....................a..........t..............c........c... 786
<a
href=http://www.ncbi.nlm.nih.gov:80/entrez/query.fcgi?cmd=Retrieve&db=Nucleotide
&list_uids=02995726&dopt=GenBank>AF053018</a>   727
....................a..........t..............c........c... 786
<a
href=http://www.ncbi.nlm.nih.gov:80/entrez/query.fcgi?cmd=Retrieve&db=Nucleotide
&list_uids=02995792&dopt=GenBank>AF053051</a>   727
....................a..........t..............c........c... 786
<a
href=http://www.ncbi.nlm.nih.gov:80/entrez/query.fcgi?cmd=Retrieve&db=Nucleotide
&list_uids=02995786&dopt=GenBank>AF053048</a>   727
....................a..........t..............c........c... 786
<a
href=http://www.ncbi.nlm.nih.gov:80/entrez/query.fcgi?cmd=Retrieve&db=Nucleotide
&list_uids=02995784&dopt=GenBank>AF053047</a>   727
....................a..........t..............c........c... 786
<a
href=http://www.ncbi.nlm.nih.gov:80/entrez/query.fcgi?cmd=Retrieve&db=Nucleotide
&list_uids=02995782&dopt=GenBank>AF053046</a>   727
....................a..........t..............c........c... 786
<a
href=http://www.ncbi.nlm.nih.gov:80/entrez/query.fcgi?cmd=Retrieve&db=Nucleotide
&list_uids=02995780&dopt=GenBank>AF053045</a>   727
....................a..........t..............c........c... 786
<a
href=http://www.ncbi.nlm.nih.gov:80/entrez/query.fcgi?cmd=Retrieve&db=Nucleotide
&list_uids=02995778&dopt=GenBank>AF053044</a>   727
....................a..........t..............c........c... 786
<a
href=http://www.ncbi.nlm.nih.gov:80/entrez/query.fcgi?cmd=Retrieve&db=Nucleotide
&list_uids=02995774&dopt=GenBank>AF053042</a>   727
....................a..........t..............c........c... 786
<a
href=http://www.ncbi.nlm.nih.gov:80/entrez/query.fcgi?cmd=Retrieve&db=Nucleotide
&list_uids=02995772&dopt=GenBank>AF053041</a>   727
....................a..........t..............c........c... 786
<a
href=http://www.ncbi.nlm.nih.gov:80/entrez/query.fcgi?cmd=Retrieve&db=Nucleotide
&list_uids=02995770&dopt=GenBank>AF053040</a>   727
....................a..........t..............c........c... 786
<a
href=http://www.ncbi.nlm.nih.gov:80/entrez/query.fcgi?cmd=Retrieve&db=Nucleotide
```

```
&list_uids=02995768&dopt=GenBank>AF053039</a>  727
...................a...........t...............c.........c... 786
<a
href=http://www.ncbi.nlm.nih.gov:80/entrez/query.fcgi?cmd=Retrieve&db=Nucleotide
&list_uids=02995766&dopt=GenBank>AF053038</a>  727
...................a...........t...............c.........c... 786
<a
href=http://www.ncbi.nlm.nih.gov:80/entrez/query.fcgi?cmd=Retrieve&db=Nucleotide
&list_uids=02995764&dopt=GenBank>AF053037</a>  727
...................a...........t...............c.........c... 786
<a
href=http://www.ncbi.nlm.nih.gov:80/entrez/query.fcgi?cmd=Retrieve&db=Nucleotide
&list_uids=02995762&dopt=GenBank>AF053036</a>  727
...................a...........t...............c.........c... 786
<a
href=http://www.ncbi.nlm.nih.gov:80/entrez/query.fcgi?cmd=Retrieve&db=Nucleotide
&list_uids=02995760&dopt=GenBank>AF053035</a>  727
...................a...........t...............c.........c... 786
<a
href=http://www.ncbi.nlm.nih.gov:80/entrez/query.fcgi?cmd=Retrieve&db=Nucleotide
&list_uids=02995758&dopt=GenBank>AF053034</a>  727
...................a...........t...............c.........c... 786
<a
href=http://www.ncbi.nlm.nih.gov:80/entrez/query.fcgi?cmd=Retrieve&db=Nucleotide
&list_uids=02995756&dopt=GenBank>AF053033</a>  727
...................a...........t...............c.........c... 786
<a
href=http://www.ncbi.nlm.nih.gov:80/entrez/query.fcgi?cmd=Retrieve&db=Nucleotide
&list_uids=02995754&dopt=GenBank>AF053032</a>  727
...................a...........t...............c.........c... 786
<a
href=http://www.ncbi.nlm.nih.gov:80/entrez/query.fcgi?cmd=Retrieve&db=Nucleotide
&list_uids=02995752&dopt=GenBank>AF053031</a>  727
...................a...........t...............c.........c... 786
<a
href=http://www.ncbi.nlm.nih.gov:80/entrez/query.fcgi?cmd=Retrieve&db=Nucleotide
&list_uids=02995750&dopt=GenBank>AF053030</a>  727
...................a...........t...............c.........c... 786
<a
href=http://www.ncbi.nlm.nih.gov:80/entrez/query.fcgi?cmd=Retrieve&db=Nucleotide
&list_uids=02995748&dopt=GenBank>AF053029</a>  727
...................a...........t...............c.........c... 786
<a
href=http://www.ncbi.nlm.nih.gov:80/entrez/query.fcgi?cmd=Retrieve&db=Nucleotide
&list_uids=02995746&dopt=GenBank>AF053028</a>  727
...................a...........t...............c.........c... 786
<a
href=http://www.ncbi.nlm.nih.gov:80/entrez/query.fcgi?cmd=Retrieve&db=Nucleotide
&list_uids=02995744&dopt=GenBank>AF053027</a>  727
...................a...........t...............c.........c... 786
<a
href=http://www.ncbi.nlm.nih.gov:80/entrez/query.fcgi?cmd=Retrieve&db=Nucleotide
&list_uids=02995742&dopt=GenBank>AF053026</a>  727
...................a...........t...............c.........c... 786
<a
href=http://www.ncbi.nlm.nih.gov:80/entrez/query.fcgi?cmd=Retrieve&db=Nucleotide
```

```
<a href=http://www.ncbi.nlm.nih.gov:80/entrez/query.fcgi?cmd=Retrieve&db=Nucleotide
&list_uids=02995730&dopt=GenBank>AF053020</a>   727
.....................a...........t..............c.........c... 786
<a
href=http://www.ncbi.nlm.nih.gov:80/entrez/query.fcgi?cmd=Retrieve&db=Nucleotide
&list_uids=02995728&dopt=GenBank>AF053019</a>   727
.....................a...........t..............c.........c... 786
<a
href=http://www.ncbi.nlm.nih.gov:80/entrez/query.fcgi?cmd=Retrieve&db=Nucleotide
&list_uids=02995776&dopt=GenBank>AF053043</a>   727
.....................a...........t..............c.........c... 786
<a
href=http://www.ncbi.nlm.nih.gov:80/entrez/query.fcgi?cmd=Retrieve&db=Nucleotide
&list_uids=00693979&dopt=GenBank>X82301</a>     727
.....................a...........t..............c.........c... 786
<a
href=http://www.ncbi.nlm.nih.gov:80/entrez/query.fcgi?cmd=Retrieve&db=Nucleotide
&list_uids=02995794&dopt=GenBank>AF053052</a>   727
.....................a........t.....c.....t.c...c.....t...... 786
<a
href=http://www.ncbi.nlm.nih.gov:80/entrez/query.fcgi?cmd=Retrieve&db=Nucleotide
&list_uids=00693977&dopt=GenBank>X82300</a>     727
.....................a........t.....c.....t.c...c.....t...... 786
<a
href=http://www.ncbi.nlm.nih.gov:80/entrez/query.fcgi?cmd=Retrieve&db=Nucleotide
&list_uids=02575784&dopt=GenBank>AB004238</a>   727
........t.............c..........a..c.g.........a..........t.. 786
<a
href=http://www.ncbi.nlm.nih.gov:80/entrez/query.fcgi?cmd=Retrieve&db=Nucleotide
&list_uids=02575782&dopt=GenBank>AB004237</a>   727
........t.............c..........a..c............a..........t.. 786
<a
href=http://www.ncbi.nlm.nih.gov:80/entrez/query.fcgi?cmd=Retrieve&db=Nucleotide
&list_uids=00693961&dopt=GenBank>X82296</a>     727
.....r..t.............c..........a..c............a..........t.. 786
<a
href=http://www.ncbi.nlm.nih.gov:80/entrez/query.fcgi?cmd=Retrieve&db=Nucleotide
&list_uids=05835205&dopt=GenBank>NC_001700</a> 15764
........t.............c..........a..c............a..........t.. 15823
<a
href=http://www.ncbi.nlm.nih.gov:80/entrez/query.fcgi?cmd=Retrieve&db=Nucleotide
&list_uids=01098523&dopt=GenBank>U20753</a>    15764
........t.............c..........a..c............a..........t.. 15823
<a
href=http://www.ncbi.nlm.nih.gov:80/entrez/query.fcgi?cmd=Retrieve&db=Nucleotide
&list_uids=12619334&dopt=GenBank>AF125145</a>   597
...............t.....t...........a.....t.....t..c......    650
<a
href=http://www.ncbi.nlm.nih.gov:80/entrez/query.fcgi?cmd=Retrieve&db=Nucleotide
&list_uids=12619332&dopt=GenBank>AF125144</a>   597
..t.....t.....t.....t..........a..c........c......a......... 656
<a
href=http://www.ncbi.nlm.nih.gov:80/entrez/query.fcgi?cmd=Retrieve&db=Nucleotide
&list_uids=06760027&dopt=GenBank>AF154975</a>   727
..a...........c......c.g........a..c............c........a...c 786
<a
href=http://www.ncbi.nlm.nih.gov:80/entrez/query.fcgi?cmd=Retrieve&db=Nucleotide
```

```
&list_uids=11275401&dopt=GenBank>AB051237</a>  727
..a...........c......c.g........a..c............c........a..c 786
<a
href=http://www.ncbi.nlm.nih.gov:80/entrez/query.fcgi?cmd=Retrieve&db=Nucleotide
&list_uids=12619342&dopt=GenBank>AF125149</a>  597
..............t.....cc..........a.........t.c................ 656 tmpseq_0   301    aataccctccccatatcaagcctgaat 328
<a
href=http://www.ncbi.nlm.nih.gov:80/entrez/query.fcgi?cmd=Retrieve&db=Nucleotide
&list_uids=09795379&dopt=GenBank>AY005809</a>  339
........................... 366
<a
href=http://www.ncbi.nlm.nih.gov:80/entrez/query.fcgi?cmd=Retrieve&db=Nucleotide
&list_uids=02995797&dopt=GenBank>AF053054</a>  787    ..c..................
808
<a
href=http://www.ncbi.nlm.nih.gov:80/entrez/query.fcgi?cmd=Retrieve&db=Nucleotide
&list_uids=02995796&dopt=GenBank>AF053053</a>  787    ..c..................
808
<a
href=http://www.ncbi.nlm.nih.gov:80/entrez/query.fcgi?cmd=Retrieve&db=Nucleotide
&list_uids=02995790&dopt=GenBank>AF053050</a>  787
..................t......c.... 814
<a
href=http://www.ncbi.nlm.nih.gov:80/entrez/query.fcgi?cmd=Retrieve&db=Nucleotide
&list_uids=02995788&dopt=GenBank>AF053049</a>  787
..................t......c.... 814
<a
href=http://www.ncbi.nlm.nih.gov:80/entrez/query.fcgi?cmd=Retrieve&db=Nucleotide
&list_uids=02995740&dopt=GenBank>AF053025</a>  787
..................t......c.... 814
<a
href=http://www.ncbi.nlm.nih.gov:80/entrez/query.fcgi?cmd=Retrieve&db=Nucleotide
&list_uids=02995738&dopt=GenBank>AF053024</a>  787
..................t......c.... 814
<a
href=http://www.ncbi.nlm.nih.gov:80/entrez/query.fcgi?cmd=Retrieve&db=Nucleotide
&list_uids=02995736&dopt=GenBank>AF053023</a>  787
..................t......c.... 814
<a
href=http://www.ncbi.nlm.nih.gov:80/entrez/query.fcgi?cmd=Retrieve&db=Nucleotide
&list_uids=02995734&dopt=GenBank>AF053022</a>  787
..................t......c.... 814
<a
href=http://www.ncbi.nlm.nih.gov:80/entrez/query.fcgi?cmd=Retrieve&db=Nucleotide
&list_uids=02995732&dopt=GenBank>AF053021</a>  787
..................t......c.... 814
<a
href=http://www.ncbi.nlm.nih.gov:80/entrez/query.fcgi?cmd=Retrieve&db=Nucleotide
&list_uids=02995726&dopt=GenBank>AF053018</a>  787
..................t......c.... 814
<a
href=http://www.ncbi.nlm.nih.gov:80/entrez/query.fcgi?cmd=Retrieve&db=Nucleotide
&list_uids=02995792&dopt=GenBank>AF053051</a>  787
..................t......c.... 814
```

```
<a
href=http://www.ncbi.nlm.nih.gov:80/entrez/query.fcgi?cmd=Retrieve&db=Nucleotide
&list_uids=02995786&dopt=GenBank>AF053048</a>  787
.................t.....c....  814
<a
href=http://www.ncbi.nlm.nih.gov:80/entrez/query.fcgi?cmd=Retrieve&db=Nucleotide
&list_uids=02995784&dopt=GenBank>AF053047</a>  787
.................t.....c....  814
<a
href=http://www.ncbi.nlm.nih.gov:80/entrez/query.fcgi?cmd=Retrieve&db=Nucleotide
&list_uids=02995782&dopt=GenBank>AF053046</a>  787
.................t.....c....  814
<a
href=http://www.ncbi.nlm.nih.gov:80/entrez/query.fcgi?cmd=Retrieve&db=Nucleotide
&list_uids=02995780&dopt=GenBank>AF053045</a>  787
.................t.....c....  814
<a
href=http://www.ncbi.nlm.nih.gov:80/entrez/query.fcgi?cmd=Retrieve&db=Nucleotide
&list_uids=02995778&dopt=GenBank>AF053044</a>  787
.................t.....c....  814
<a
href=http://www.ncbi.nlm.nih.gov:80/entrez/query.fcgi?cmd=Retrieve&db=Nucleotide
&list_uids=02995774&dopt=GenBank>AF053042</a>  787
.................t.....c....  814
<a
href=http://www.ncbi.nlm.nih.gov:80/entrez/query.fcgi?cmd=Retrieve&db=Nucleotide
&list_uids=02995772&dopt=GenBank>AF053041</a>  787
.................t.....c....  814
<a
href=http://www.ncbi.nlm.nih.gov:80/entrez/query.fcgi?cmd=Retrieve&db=Nucleotide
&list_uids=02995770&dopt=GenBank>AF053040</a>  787
.................t.....c....  814
<a
href=http://www.ncbi.nlm.nih.gov:80/entrez/query.fcgi?cmd=Retrieve&db=Nucleotide
&list_uids=02995768&dopt=GenBank>AF053039</a>  787
.................t.....c....  814
<a
href=http://www.ncbi.nlm.nih.gov:80/entrez/query.fcgi?cmd=Retrieve&db=Nucleotide
&list_uids=02995766&dopt=GenBank>AF053038</a>  787
.................t.....c....  814
<a
href=http://www.ncbi.nlm.nih.gov:80/entrez/query.fcgi?cmd=Retrieve&db=Nucleotide
&list_uids=02995764&dopt=GenBank>AF053037</a>  787
.................t.....c....  814
<a
href=http://www.ncbi.nlm.nih.gov:80/entrez/query.fcgi?cmd=Retrieve&db=Nucleotide
&list_uids=02995762&dopt=GenBank>AF053036</a>  787
.................t.....c....  814
<a
href=http://www.ncbi.nlm.nih.gov:80/entrez/query.fcgi?cmd=Retrieve&db=Nucleotide
&list_uids=02995760&dopt=GenBank>AF053035</a>  787
.................t.....c....  814
<a
href=http://www.ncbi.nlm.nih.gov:80/entrez/query.fcgi?cmd=Retrieve&db=Nucleotide
&list_uids=02995758&dopt=GenBank>AF053034</a>  787
.................t.....c....  814
```

```
<a
href=http://www.ncbi.nlm.nih.gov:80/entrez/query.fcgi?cmd=Retrieve&db=Nucleotide
&list_uids=02995756&dopt=GenBank>AF053033</a>   787
..................t.....c....  814
<a
href=http://www.ncbi.nlm.nih.gov:80/entrez/query.fcgi?cmd=Retrieve&db=Nucleotide
&list_uids=02995754&dopt=GenBank>AF053032</a>   787
..................t.....c....  814
<a
href=http://www.ncbi.nlm.nih.gov:80/entrez/query.fcgi?cmd=Retrieve&db=Nucleotide
&list_uids=02995752&dopt=GenBank>AF053031</a>   787
..................t.....c....  814
<a
href=http://www.ncbi.nlm.nih.gov:80/entrez/query.fcgi?cmd=Retrieve&db=Nucleotide
&list_uids=02995750&dopt=GenBank>AF053030</a>   787
..................t.....c....  814
<a
href=http://www.ncbi.nlm.nih.gov:80/entrez/query.fcgi?cmd=Retrieve&db=Nucleotide
&list_uids=02995748&dopt=GenBank>AF053029</a>   787
..................t.....c....  814
<a
href=http://www.ncbi.nlm.nih.gov:80/entrez/query.fcgi?cmd=Retrieve&db=Nucleotide
&list_uids=02995746&dopt=GenBank>AF053028</a>   787
..................t.....c....  814
<a
href=http://www.ncbi.nlm.nih.gov:80/entrez/query.fcgi?cmd=Retrieve&db=Nucleotide
&list_uids=02995744&dopt=GenBank>AF053027</a>   787
..................t.....c....  814
<a
href=http://www.ncbi.nlm.nih.gov:80/entrez/query.fcgi?cmd=Retrieve&db=Nucleotide
&list_uids=02995742&dopt=GenBank>AF053026</a>   787
..................t.....c....  814
<a
href=http://www.ncbi.nlm.nih.gov:80/entrez/query.fcgi?cmd=Retrieve&db=Nucleotide
&list_uids=02995730&dopt=GenBank>AF053020</a>   787
..................t.....c....  814
<a
href=http://www.ncbi.nlm.nih.gov:80/entrez/query.fcgi?cmd=Retrieve&db=Nucleotide
&list_uids=02995728&dopt=GenBank>AF053019</a>   787
..................t.....c....  814
<a
href=http://www.ncbi.nlm.nih.gov:80/entrez/query.fcgi?cmd=Retrieve&db=Nucleotide
&list_uids=02995776&dopt=GenBank>AF053043</a>   787
..................t.....c....  814
<a
href=http://www.ncbi.nlm.nih.gov:80/entrez/query.fcgi?cmd=Retrieve&db=Nucleotide
&list_uids=00693979&dopt=GenBank>X82301</a>    787
..................t.....c....  814
<a
href=http://www.ncbi.nlm.nih.gov:80/entrez/query.fcgi?cmd=Retrieve&db=Nucleotide
&list_uids=02995794&dopt=GenBank>AF053052</a>   787   .gc................a.....
812
<a
href=http://www.ncbi.nlm.nih.gov:80/entrez/query.fcgi?cmd=Retrieve&db=Nucleotide
&list_uids=00693977&dopt=GenBank>X82300</a>    787
.gc................a.......  814
```

```
<a
href=http://www.ncbi.nlm.nih.gov:80/entrez/query.fcgi?cmd=Retrieve&db=Nucleotide
&list_uids=02575784&dopt=GenBank>AB004238</a>   787
................t..a....... 814
<a
href=http://www.ncbi.nlm.nih.gov:80/entrez/query.fcgi?cmd=Retrieve&db=Nucleotide
&list_uids=02575782&dopt=GenBank>AB004237</a>   787
................t..a....... 814
<a
href=http://www.ncbi.nlm.nih.gov:80/entrez/query.fcgi?cmd=Retrieve&db=Nucleotide
&list_uids=00693961&dopt=GenBank>X82296</a>   787
................t..a....... 814
<a
href=http://www.ncbi.nlm.nih.gov:80/entrez/query.fcgi?cmd=Retrieve&db=Nucleotide
&list_uids=05835205&dopt=GenBank>NC_001700</a>   15824
................t..a....... 15851
<a
href=http://www.ncbi.nlm.nih.gov:80/entrez/query.fcgi?cmd=Retrieve&db=Nucleotide
&list_uids=01098523&dopt=GenBank>U20753</a>   15824
................t..a....... 15851
<a
href=http://www.ncbi.nlm.nih.gov:80/entrez/query.fcgi?cmd=Retrieve&db=Nucleotide
&list_uids=12619332&dopt=GenBank>AF125144</a>   657    ..c.....
664
<a
href=http://www.ncbi.nlm.nih.gov:80/entrez/query.fcgi?cmd=Retrieve&db=Nucleotide
&list_uids=06760027&dopt=GenBank>AF154975</a>   787    ..c..a..a........
803
<a
href=http://www.ncbi.nlm.nih.gov:80/entrez/query.fcgi?cmd=Retrieve&db=Nucleotide
&list_uids=11275401&dopt=GenBank>AB051237</a>   787    ..c..a..a........
803
<a
href=http://www.ncbi.nlm.nih.gov:80/entrez/query.fcgi?cmd=Retrieve&db=Nucleotide
&list_uids=12619342&dopt=GenBank>AF125149</a>   657    ..c.....
664
</PRE>

<PRE>
  Database: nt
    Posted date:  Mar 2, 2001 12:20 AM
  Number of letters in database: 2,863,827,885
  Number of sequences in database:  807,597

Lambda     K        H
   1.37    0.711    1.31

Gapped
Lambda     K        H
   1.37    0.711    1.31

Matrix: blastn matrix:1 -3
Gap Penalties: Existence: 5, Extension: 2
Number of Hits to DB: 460542
Number of Sequences: 807597
Number of extensions: 460542
```

```
Number of successful extensions: 22671
Number of sequences better than 10.0: 6487
length of query: 328
length of database: 2,863,827,885
effective HSP length: 20
effective length of query: 308
effective length of database: 2,847,675,945
effective search space: 877084191060
effective search space used: 877084191060
T: 0
A: 30
X1: 6 (11.9 bits)
X2: 15 (29.7 bits)
S1: 12 (24.3 bits)
S2: 19 (38.2 bits)

</PRE>

</BODY>
</HTML>
</FORM>
</BODY>
</HTML>
```

Table 5. Reference animal belonging to family felidae selected for comparison with 'adil.flesh' to confirm the findings of BLAST analysis, results of which are mentioned in Table 3 and 4, respectively. The animals listed in SN. 1–21 represent different species of family felidae. SN. 22 and 23 are primate species taken for out-group comparisons. The samples started with the code 'bhz' were collected from Bhuvaneshwar zoo, the samples with code numbers 'gz' from Guwahati zoo, samples coded with the number 'darz' from Darjeeling zoo, and the samples coded as 'sbz' were collected from Sakkarbaug zoo, India.

TABLE 5

Reference animals and the allocated code numbers included in the study

| SN. | Code number | Name of the animal | Zoological name |
|---|---|---|---|
| 1 | bhz25t | Indian tiger | Panthera tigris tigris |
| 2 | bhz26t | Indian tiger | Panthera tigris tigris |
| 3 | bhz30t | Indian tiger | Panthera tigris tigris |
| 4 | bhz45t | Indian tiger | Panthera tigris tigris |
| 5 | bhz56t | Indian tiger | Panthera tigris tigris |
| 6 | bhz63t | Indian tiger | Panthera tigris tigris |
| 7 | bhz20wt | Indian white tiger | Panthera tigris bengalensis |
| 8 | bhz22wt | Indian white tiger | Panthera tigris bengalensis |
| 9 | bhz23wt | Indian white tiger | Panthera tigris bengalensis |
| 10 | bhz28wt | Indian white tiger | Panthera tigris bengalensis |
| 11 | gz11 | Normal leopard | Panthera pardus |
| 12 | gz21 | Normal leopard | Panthera pardus |
| 13 | gz31 | Normal leopard | Panthera pardus |
| 14 | gz21cl | Clouded leopard | Neofelis nebulosa |

TABLE 5-continued

Reference animals and the allocated code numbers included in the study

| SN. | Code number | Name of the animal | Zoological name |
|---|---|---|---|
| 15 | gz22cl | Clouded leopard | Neofelis nebulosa |
| 16 | darz14sl | Snow leopard | Panthera unicia |
| 17 | darz15sl | Snow leopard | Panthera unicia |
| 18 | darz16sl | Snow leopard | Panthera unicia |
| 19 | sbz22al | Asiatic lion | Panthera leo persica |
| 20 | sbz38al | Asiatic lion | Panthera leo persica |
| 21 | sbz39al | Asiatic lion | Panthera leo persica |
| 22 | humsk | Human | Homo sapiens sapiens |
| 23 | chimss | Chimpanzee | Pan troglodytes |

Table 6. Multiple sequence alignments of cytochrome b sequences (328 bp) revealed from 'adil.flesh' and reference animals listed in Table 5. The positions that have a common nucleotide in all the animal species under investigation are shown with a star (*) mark; however, the positions that are variable in any of the animals under investigation are unmarked. The nucleotides at these positions constitute the molecular signature of an individual species, which are unique and highly specific for its species. These signatures are the molecular basis of identification of individual animal species using our primers 'mcb398' and 'mcb869'.

TABLE 6

Multiple sequence alignments of the cytochrome b sequences of reference animals with the sequence obtained from confiscated animal remain

```
sbz22al      TGAATCTGAGGAGGCTTCTCAGTAGACAAAGCCACCCTGACACGATTCTTTGCCTTCCAC  60 sbz38al      TGAATCTGAGGAGGCTTCTCAGTAGACAAAGCCACCCTGACACGATTCTTTGCCTTCCAC  60 sbz39al      TGAATCTGAGGAGGCTTCTCAGTAGACAAAGCCACCCTGACACGATTCTTTGCCTTCCAC  60 adil.flesh   TGAATCTGAGGAGGCTTCTCAGTAGACAAAGCTACCCTGACACGATTCTTTGCCTTCCAC  60 gz1nl        TGAATCTGAGGAGGCTTCTCACTAGACAAAGCTACCTTGACACGATTCTTTGCCTTCCAC  60 gz2nl        TGAATCTGAGGAGGCTTCTCAGTAGACAAAGCTACCTTGACACGATTCTTTGCCTTCCAC  60 gz3nl        TGAATCTGAGGAGGCTTCTCAGTAGACAAAGCTACCTTGACACGATTCTTTGCCTTCCAC  60 bhz23wt      TGAATCTGAGGAGGCTTCTCAGTAGACAAAGCCACCCTGACACGATTCTTTGCCTTCCAC  60 bhz28wt      TGAATCTGAGGAGGCTTCTCAGTAGACAAAGCCACCCTGACACGATTCTTTGCCTTCCAC  60 bhz22wt      TGAATCTGAGGAGGCTTCTCAGTAGACAAAGCCACCCTGAGACGATTCTTTGCCTTCCAC  60 bhz20wt      TGAATCTGAGGAGGCTTCTCAGTAGACAAAGCCACCCTGACACGATTCTTTGCCTTCCAC  60 bhz63t       TGAATCTGAGGAGGCTTCTCAGTAGACAAAGCCACCCTGACACGATTCTTTGCCTTCCAC  60 bhz56t       TGAATCTGAGGAGGCTTCTCAGTAGACAAAGCCACCCTGACACGATTCTTTGCCTTCCAC  60 bhz26t       TGAATCTGACGAGGCTTCTCAGTAGACAAAGCCACCCTGACACGATTCTTTGCCTTCCAC  60 bhz30t       TGAATCTGAGGAGGCTTCTCAGTAGACAAAGCCACCCTGACACGATTCTTTGCCTTCCAC  60 bhz45t       TGAATCTGAGGAGGCTTCTCAGTAGACAAAGCCACCCTGACACGATTCTTTGCCTTCCAC  60 bhz25t       TGAATCTGAGGAGGCTTCTCAGTAGACAAAGCCACCCTGACACGATTCTTTGCCTTCCAC  60 dz14sl       TGAATCTGAGGAGGCTTCTCAGTACACAAAGCCACCCTGACACGATTCTTTGCCTTCCAC  60
```

TABLE 6-continued

Multiple sequence alignments of the cytochrome b sequences of reference
animals with the sequence obtained from confiscated animal remain

```
dz15sl      TGAATCTGAGGAGGCTTCTCAGTACACAAAGCCACCCTGACACGATTCTTTGCCTTCCAC  60
dz16sl      TGAATCTGAGGAGGCTTCTCAGTACACAAAGCCACCCTGACACGATTCTTTGCCTTCCAC  60
gz21cl      TGAATCTGAGGAGGCTTCTCAGTAGACAAAGCCACCCTGACACGATTTTTCGCCTTCCAC  60
gz22cl      TGAATCTGAGGAGGCTTCTCAGTAGACAAAGCCACCCTGACACGATTTTTCGCCTTCCAC  60
chimss      TGAATCTGAGGAGGCTACTCACTAGACAGCCCTACCCTTACACGATTCTTCACCTTCCAC  60
humsk       TGAATCTGACGAGGCTACTCAGTAGACAGTCCCACCCTCACACGATTCTTTACCTTTCAC  60
            **************  **  *    *  ***  *  ******      **  * sbz22al     TTCATCCTTCCATTTATCATCTCAGCCCTAGCAGCAGTCCACCTCCTGTTCCTCCATGAA 120
sbz38al     TTCATCCTTCCATTTATCATCTCAGCCCTAGCAGCAGTCCACCTCCTGTTCCTCGATGAA 120
sbz39al     TTCATCCTTCCATTTATCATCTCAGCCCTAGCAGCAGTCCACCTCCTGTTCCTCCATGAA 120
adil.flesh  TTCATCCTTCCATTTATGATCTCAGCTCTAGCAGCAGTCCACCTCCTATTCCTTCACGAG 120
gz1nl       TTCATCCTTCCATTTATCATCTCAGCTCTAGCAGCAGTCCACCTCCTATTCCTTCACGAG 120
gz2nl       TTCATCCTTCCATTTATCATCTCAGCTCTAGCAGCAGTCCACCTCCTATTCCTTCACGAG 120
gz3nl       TTCATCCTTCCATTTATCATCTCAGCTCTAGCAGCAGTCCACCTCCTATTCCTTCACGAG 120
bhz23wt     TTCATCCTTCCATTTATCATCTCAGCCCTAGCAGCAGTCCACCTCCTATTCCTCCATGAG 120
bhz28wt     TTCATCCTTCCATTTATCATCTCAGCCCTAGCAGCAGTCCACCTCCTATTCCTCCATGAG 120
bhz22wt     TTCATCCTTCCATTTATCATCTCAGCCCTAGCAGCAGTCCACCTCCTATTCCTCCATGAG 120
bhz20wt     TTCATCCTTCCATTTATCATCTCAGCCCTAGCAGCAGTGGACCTCCTATTCCTCCATGAG 120
bhz63t      TTCATCCTTCCATTTATCATCTCAGCCCTAGCAGCAGTCCACCTCCTATTCCTCCATGAG 120
bhz56t      TTCATCCTTCCATTTATCATCTCAGCCCTAGCAGCAGTCCACCTCCTATTCCTCCATGAG 120
bhz26t      TTCATCCTTCCATTTATCATCTCAGCCCTAGCAGCAGTCCACCTCCTATTCCTCCATGAG 120
bhz30t      TTCATCCTTCCATTTATCATCTCAGCCCTAGCAGCAGTCCACCTCCTATTCCTCCATGAG 120
bhz45t      TTCATCCTTCCATTTATCATCTCAGCCCTAGCAGCAGTCCACCTCCTATTCCTCCATGAG 120
bhz25t      TTCATCCTTCCATTTATCATCTCAGCGCTAGCAGCAGTCCACCTCCTATTCCTCCATGAG 120
dz14sl      TTCATCCTTCCATTTATCATCTCAGCCCTAGCAGCAGTCCACCTCCTATTCCTCCATGAG 120
dz15sl      TTCATCCTTCCATTTATCATCTCAGCCCTAGCAGCAGTCCACCTCCTATTCCTCCATGAG 120
dz16sl      TTCATCGTTCCATTTATCATCTCAGCCCTAGCAGCAGTCCACCTCCTATTCCTCCATGAG 120
gz21cl      TTCATCCTCCCATTTATCATCTCAGCCTTAGCAGCAGTTCACCTTCTATTTCTCCATGAA 120
gz22cl      TTCATCCTCCCATTTATCATCTCAGCCTTAGCAGCAGTTCACCTTCTATTTCTCCATGAA 120
chimss      TTTATCTTACCCTTCATTATCACAGCCCTAACAACACTTCATCTCCTATTCTTACACGAA 120
humsk       TTCATCTTGCCCTTCATTATTGCAGCCCTAGCAGCACTCCACCTCCTATTCTTGCACGAA 120
              *  *            **          *            * sbz22al     ACAGGATCTAATAACCCCTCAGGAATGGTATCTGACTCAGATAAAATTCCATTCCATCCA 180
sbz38al     ACAGGATCTAATAACCCCTCAGGAATGGTATCTGACTCAGATAAAATTCCATTCCATCCA 180
sbz39al     ACAGGATCTAACAACCCCTCAGGAATGGTATCTGACTCAGATAAAATTCCATTCCATCCA 180
adil.flesh  ACAGGATCTAACAACCCCTCAGGAATAGTATCCGACTCAGACAAAATTCCATTCCACCCA 180
gz1nl       ACAGGATCTAACAACCCCTCAGGAATAGTATCCGACTCAGACAAAATTCCATTCCACCCA 180
gz2nl       ACAGGATCTAACAACCCCTCAGGAATAGTATCTGACTCAGACAAAATTCCATTCCACCCA 180
```

TABLE 6-continued

Multiple sequence alignments of the cytochrome b sequences of reference animals with the sequence obtained from confiscated animal remain

| | | |
|---|---|---|
| gz3nl | ACAGGATCTAACAACCCCTCAGGAATAGTATCTGACTCAGACAAAATTCCATTCCACCCA | 180 |
| bhz23wt | ACAGGATCTAACAACCCCTCAGGAATAGTATCTGACTCAGACAAAATCCCGTTCCACCCA | 180 |
| bhz28wt | ACAGGATCTAACAACCCCTCAGGAATAGTATCTGACTCAGACAAAATCCCGTTCCACCCA | 180 |
| bhz22wt | ACAGGATCTAACAACCCCTCAGGAATAGTATCTGACTCAGACAAAATCCCGTTCCACCCA | 180 |
| bhz20wt | ACAGGATCTAACAACCCCTCAGGAATAGTATCTGACTCAGACAAAATCCCGTTCCACCCA | 180 |
| bhz63t | ACAGGATCTAACAACCCCTCAGGAATAGTATCTGACTCAGACAAAATCCCGTTCCACCCA | 180 |
| bhz56t | ACAGGATCTAACAACCCCTCAGGAATAGTATCTGACTCAGACAAAATCCCGTTCCACCCA | 180 |
| bhz26t | ACAGGATCTAACAACCCCTCAGGAATAGTATCTGACTCAGACAAAATCCCGTTCCACCCA | 180 |
| bhz30t | ACAGGATCTAACAACCCCTCAGGAATAGTATCTGACTCAGACAAAATCCCGTTCCACCCA | 180 |
| bhz45t | ACAGGATCTAACAACCCCTCAGGAATAGTATCTGACTCAGACAAAATCCCGTTCCACCCA | 180 |
| bhz25t | ACAGGATCTAACAACCCCTCAGGAATAGTATCTGACTCAGACAAAATCCCGTTCCACCCA | 180 |
| dz14sl | ACAGGATCTAACAACCCCTCAGGAATAGTATCTGACTCAGACAAAATCCCGTTCCACCCA | 180 |
| dz15sl | ACAGGATCTAACAACCCCTCAGGAATAGTATCTGACTCAGACAAAATCCCGTTCCACCCA | 180 |
| dz16sl | ACAGGATCTAACAACCCCTCAGGAATAGTATCTGACTCAGACAAAATCCCGTTCCACCCA | 180 |
| gz21cl | ACAGGATCCAATAACCCCTCAGGAATGGTATCCGATTCAGACAAAATCCCGTTCCACCCG | 180 |
| gz22cl | ACAGGATCCAATAACCCCTCAGGAATGGTATCCGATTCAGACAAAATCCCGTTCCACCCG | 180 |
| chimss | ACAGGATCAAATAACCCCCTGGGAATCACCTCCCACTCCGACAAAATTACCTTCCACCCC | 180 |
| humsk | ACGGGATCAAACAACCCCCTAGGAATCACCTCCCATTCCGATAAAATCATCTTCCACCCT | 180 |
| | ** ***** ** ******     *****     ** * ** ** *****    ***** ** | |
| sbz22al | TACTATACAATCAAAGATATCCTAGGCCTTCTAGTACTAATCTTAACACTCATACTACTC | 240 |
| sbz38al | TACTATACAATCAAAGATATCCTAGGCCTTCTAGTACTAATCTTAACACTCATACTACTC | 240 |
| sbz39al | TACTATACAATCAAAGATATCCTAGGCCTTCTAGTACTAATCTTAACACTCATACTACTC | 240 |
| adil.flesh | TACTACACAATCAAAGATATCCTGGGCCTTCTAGTACTAATCCTAGCACTCATACTACTC | 240 |
| gz1nl | TACTACACAATCAAAGATATCCTGGGCCTTCTAGTACTAATCCTAGCACTCATACTACTC | 240 |
| gz2nl | TACTACACAATCAAAGACATCCTGGGCCTTCTAGTACTAATCTTAGCACTCATACTACTC | 240 |
| gz3nl | TACTACACAATCAAAGACATCCTGGGCCTTCTAGTACTAATCTTAGCACTCATACTACTC | 240 |
| bhz23wt | TACTACACAATCAAAGACATCCTGGGCCTTCTAGTACTAATCCTAACACTCATACTACTC | 240 |
| bhz28wt | TACTACACAATCAAAGACATCCTGGGCCTTCTAGTACTAATCCTAACACTCATACTACTC | 240 |
| bhz22wt | TACTACACAATCAAAGACATCCTGGGCCTTCTAGTACTAATCCTAACACTCATACTACTC | 240 |
| bhz20wt | TACTACACAATCAAAGACATCCTGGGCCTTCTAGTACTAATCCTAACACTCATACTACTC | 240 |
| bhz63t | TACTACACAATCAAAGACATCCTGGGCCTTCTAGTACTAATCCTAACACTCATACTACTC | 240 |
| bhz56t | TACTACACAATCAAAGACATCCTGGGCCTTCTAGTACTAATCCTAACACTCATACTACTC | 240 |
| bhz26t | TACTACACAATCAAAGACATCCTGGGCCTTCTAGTACTAATCCTAACACTCATACTACTC | 240 |
| bhz30t | TACTACACAATCAAAGACATCCTGGGCCTTCTAGTACTAATCCTAACACTCATACTACTC | 240 |
| bhz45t | TACTACACAATCAAAGACATCCTGGGCCTTCTAGTACTAATCCTAACACTCATACTACTC | 240 |
| bhz25t | TACTACACAATCAAAGACATCCTGGGCCTTCTAGTACTAATCCTAACACTCATACTACTC | 240 |
| dz14sl | TACTACACAATCAAAGACATCCTCGGCCTTCTAGTACTAATCCTAACACTCATACTACTC | 240 |
| dz15sl | TACTACACAATCAAAGACATCCTGGGCCTTCTAGTACTAATCCTAACACTCATACTACTC | 240 |

TABLE 6-continued

Multiple sequence alignments of the cytochrome b sequences of reference animals with the sequence obtained from confiscated animal remain

```
dz16sl      TACTACACAATCAAAGACATCCTGGGCCTTCTAGTACTAATCCTAACACTCATACTACTC 240 gz21cl      TACTATACAATCAAAGATATCCTAGGCCTCCTAGTTCTAATTCTAGCGCTCACACTACTT 240 gz22cl      TACTATACAATCAAAGATATCCTAGGCCTCCTAGTTCTAATTCTAGCGCTCACACTACTT 240 chimss      TACTACACAATCAAAGATATCCTTGGCTTATTCCTTTTCCTCCTTATCCTAATGACATTA 240 humsk       TACTACACAATCAAAGACGCCCTCGGCTTACTTCTCTTCCTTCTCTCCTTAATGACATTA 240

***  ******   * ***  *   *   *    *    * *     *  * sbz22al     GTCCTATTCTCACCAGACCTATTAGGAGATCCCGACAACTATACCCCCGCCAATCCTCTA 300 sbz38al     GTCCTATTCTCACCAGACCTATTAGGAGATCCCGACAACTATACCCCCGCCAATCCTCTA 300 sbz39al     GTCCTATTCTCACCAGACCTATTAGGAGATCCCGACAACTATACCCCCGCCAATCCTCTA 300 adil.flesh  GTCCTATTCTCACCAGACCTGTTAGGAGACCCCGATAACTACATCCCTGCCAACCCTCTA 300 gz1nl       GTCCTATTCTCACCAGACCTGTTAGGAGACCCCGATAACTACATCCCTGCCAACCCTCTA 300 gz2nl       GTCCTATTCTCACCAGACCTGTTGGGAGACCCCGATAACTACATCCCCGCCAACCCTCTA 300 gz3nl       GTCCTATTCTCACCAGACCTGTTGGGAGACCCCGATAACTACATCCCCGCCAACCCTCTA 300 bhz23wt     GTCCTATTCTCACCAGAGCTATTAGGGGACCCCGATAACTACATCCCCGCCAACCCTCTA 300 bhz28wt     GTCCTATTCTCACCAGACCTATTAGGGGACCCCGATAACTACATCCCCGCCAACCCTCTA 300 bhz22wt     GTCCTATTCTCACCAGACCTATTAGGGGACCCCGATAACTACATCCCCGCCAACCCTCTA 300 bhz20wt     GTCCTATTCTCACCAGACCTATTAGGGGACCCCGATAACTACATCCCCGGCAACCCTCTA 300 bhz63t      GTCCTATTCTCACCAGACCTATTAGGGGACCCCGATAACTACATCCCCGCCAACCCTCTA 300 bhz56t      GTCCTATTCTCACCAGACCTATTAGGGGACCCCGATAACTACATCCCCGCCAACCCTCTA 300 bhz26t      GTCCTATTCTCACCAGACCTATTAGGGGACCCCGATAACTACATCCCCGCCAACCCTCTA 300 bhz30t      GTCCTATTCTCACCAGACCTATTAGGGGACCCCGATAACTACATCCCCGCCAACCCTCTA 300 bhz45t      GTCCTATTCTCACCAGACCTATTAGGGGACCCCGATAACTACATCCCCGCCAACCCTCTA 300 bhz25t      GTCCTATTCTCACCAGACCTATTAGGGGACCCCGATAACTACATCCCCGCCAACCCTCTA 300 dz14sl      GTCCTATTCTCACCAGACCTATTAGGGGACGCCGATAACTACATCCCCGCCAACCCTCTA 300 dz15sl      GTCCTATTCTCACCAGACCTATTAGGGGACGCCGATAACTACATCCCCGCCAACCCTCTA 300 dz16sl      GTCCTATTCTCACCAGACCTATTAGGGGACGCCGATAACTACATCCCCGCCAACCCTCTA 300 gz21cl      GTTCTATTCTCCCCAGACCTACTAGGAGACCCTGACAATTACACTCCCGCCAACCCTCTA 300 gz22cl      GTTCTATTCTCCCCAGACCTACTAGGAGACCCTGACAATTACACTCCCGCCAACCCTCTA 300 chimss      ACACTATTCTCACCAGACCTCCTGGGCGATCCAGACAACTATACCCTAGCTAACCCCCTA 300 humsk       ACACTATTCTCACCAGACCTCCTAGGCGACCCAGACAATTATACCCTAGCCAACCCCTTA 300

*****  *****  *         *      **  *       ** sbz22al     AGCACCCCTCCCCATATCAAACCTGAAT 328 sbz38al     AGCACCCCTCCCCATATCAAACCTGAAT 328 sbz39al     AGCACCCCTCCCCATATCAAACCTGAAT 328 adil.flesh  AATACCCCTCCCCATATCAAGCCTGAAT 328 gz1nl       AATACCCCTCCCCATATCAAGCCTGAAT 328 gz2nl       AATACCCCTCCCCATATCAAGCCTGAAT 328 gz3nl       AATACCCCTCCCCATATCAAGCCTGAAT 328
```

TABLE 6-continued

Multiple sequence alignments of the cytochrome b sequences of reference animals with the sequence obtained from confiscated animal remain

```
bhz23wt    AACACCCCTCCCCATATCAAGCGCGAAT 328 bhz28wt    AACACCCCTCCCCATATCAAGCGCGAAT 328 bhz22wt    AACACCCCTCCCCATATCAAGCGCGAAT 328 bhz20wt    AACACCCCTCCCCATATCAAGCGCGAAT 328 bhz63t     AACACCCCTCCCCATATCAAGCGCGAAT 328 bhz56t     AACACCCCTCCCCATATCAAGCGCGAAT 328 bhz26t     AACACCCCTCCCCATATCAAGCGCGAAT 328 bhz30t     AACACCCCTCCCCATATCAAGCGCGAAT 328 bhz45t     AACACCCCTCCCCATATCAAGCGCGAAT 328 bhz25t     AACACCCCTCCCCATATCAAGCGCGAAT 328 dz14sl     AACACCCCTCCCCATATCAAGCCCGAAT 328 dz15sl     AACACCCCTCCCCATATCAAGCCCGAAT 328 dz16sl     AACACCCCTCCCCATATCAAGCCCGAAT 328 gz21cl     AATACCCCTCCCCATATCAAGCCTGAAT 328 gz22cl     AATACCCCTCCCCATATCAACCCTGAAT 328 chimss     AACACCCCACCCCACATTAAACCCGAAT 328 humsk      AACACCCCTCCCCACATCAAGCCCGAAT 328

*  *** *  ** *  ****
```

Table 7 (Tables 7a, 7b, 7c and 7d). The comparison of the molecular signatures of different animal species investigated along with 'adil.flesh', the confiscated skin of unknown animal origin. This table demonstrates the variable positions (i.e. the positions which are not marked with star (*) symbol in Table 6), amongst the 328 bp fragment revealed from the animals listed in Table 5. The dot (.) mark represents the presence of the similar nucleotide as listed in lane 1 i.e. the sequence from "adil.flesh" at that position. It demonstrates that the signatures of each species are unique and specific to its species. The molecular signatures of 'adil.flesh' are comparable (except for position 37 which has a transition from 'T' to 'C') to the molecular signature of 'gz1L' i.e. the known leopard 'Panthera pardus' source, indicating the identity of the source of confiscated skin 'adil.flesh' as that of a leopard 'Panthera pardus' source. The nucleotide variations (at the positions 153, 198, 223, 264, among the known leopards, (i.e. gz1L, gz2L, and gz3L, respectively)), give an idea about the geographical habitat of each animals.

Various studies referring to molecular evolution of different animal species support this hypothesis[75]; however, it could further be confirmed by taking the reference animals from different geographical areas and analyzing by our primers 'mcb 398' and 'mcb869'. If we could generate the database of different haplotypes (i.e. habitat specific molecular signatures) of the animal species, it would also enable our primers to reveal the geographical location of the commitment of wildlife crime.

TABLE 7a

| Position | 17 | 25 | 29 | 30 | 31 | 33 | 37 | 39 | 48 | 51 | 52 | 57 | 63 | 67 | 69 | 72 |
|---|---|---|---|---|---|---|---|---|---|---|---|---|---|---|---|---|
| adil.flesh | T | G | A | A | G | T | C | G | C | T | G | C | C | C | T | A |
| gz1l | . | . | . | . | . | . | T | . | . | . | . | . | . | . | . | . |
| gz2l | . | . | . | . | . | . | T | . | . | . | . | . | . | . | . | . |
| gz3l | . | . | . | . | . | . | T | . | . | . | . | . | . | . | . | . |
| bhz25t | . | . | . | . | . | C | . | . | . | . | . | . | . | . | . | . |
| bhz26t | . | . | . | . | . | C | . | . | . | . | . | . | . | . | . | . |
| bhz30t | . | . | . | . | . | C | . | . | . | . | . | . | . | . | . | . |
| bhz45t | . | . | . | . | . | C | . | . | . | . | . | . | . | . | . | . |
| bhz56t | . | . | . | . | . | C | . | . | . | . | . | . | . | . | . | . |
| bhz20wt | . | . | . | . | . | C | . | . | . | . | . | . | . | . | . | . |
| bhz22wt | . | . | . | . | . | C | . | . | . | . | . | . | . | . | . | . |
| bhz23wt | . | . | . | . | . | C | . | . | . | . | . | . | . | . | . | . |
| dz14sl | . | C | . | . | . | C | . | . | . | . | . | . | . | . | . | . |

TABLE 7a-continued

| | | | | | | | | | | | | | | | | |
|---|---|---|---|---|---|---|---|---|---|---|---|---|---|---|---|---|
| dz15sl | . | C | . | . | . | C | . | . | . | . | . | . | . | . | . | . |
| sbz22al | . | . | . | . | . | C | . | . | . | . | . | . | . | . | . | . |
| sbz38al | . | . | . | . | . | C | . | . | . | . | . | . | . | . | . | . |
| gz21cl | . | . | . | . | . | C | . | . | T | C | . | . | . | . | C | . |
| gz22cl | . | . | . | . | . | C | . | . | T | C | . | . | . | . | C | . |
| chimss | A | . | G | C | C | . | . | T | . | C | A | . | T | T | A | C |
| humsk | A | . | G | T | C | C | . | C | . | . | A | T | . | T | G | C |

| | Position | 75 | 78 | 81 | 82 | 87 | 88 | 91 | 94 | 97 | 99 | 102 | 105 | 108 | 111 | 112 |
|---|---|---|---|---|---|---|---|---|---|---|---|---|---|---|---|---|
| | adil.flesh | T | C | C | T | T | C | G | G | G | C | C | C | A | C | C |
| | gz1l | . | . | . | . | . | . | . | . | . | . | . | . | . | . | . |
| | gz2l | . | . | . | . | . | . | . | . | . | . | . | . | . | . | . |
| | gz3l | . | . | . | . | . | . | . | . | . | . | . | . | . | . | . |
| | bhz25t | . | . | . | . | . | C | . | . | . | . | . | . | . | . | . |
| | bhz26t | . | . | . | . | . | C | . | . | . | . | . | . | . | . | . |
| | bhz30t | . | . | . | . | . | C | . | . | . | . | . | . | . | . | . |
| | bhz45t | . | . | . | . | . | C | . | . | . | . | . | . | . | . | . |
| | bhz56t | . | . | . | . | . | C | . | . | . | . | . | . | . | . | . |
| | bhz20wt | . | . | . | . | . | C | . | . | . | . | . | . | . | . | . |
| | bhz22wt | . | . | . | . | . | C | . | . | . | . | . | . | . | . | . |
| | bhz23wt | . | . | . | . | . | C | . | . | . | . | . | . | . | . | . |
| | dz14sl | . | . | . | . | . | C | . | . | . | . | . | . | . | . | . |
| | dz15sl | . | . | . | . | . | C | . | . | . | . | . | . | . | . | . |
| | sbz22al | . | . | . | . | . | C | . | . | . | . | . | . | G | . | . |
| | sbz38al | . | . | . | . | . | C | . | . | . | . | . | . | G | . | . |
| | gz21cl | . | . | . | . | . | C | T | . | . | . | T | . | T | . | T | . |
| | gz22cl | . | . | . | . | . | C | T | . | . | . | T | . | T | . | T | . |
| | chimss | C | T | . | A | C | . | A | A | C | T | T | . | . | . | T |
| | humsk | C | T | T | G | C | . | . | . | C | . | . | . | . | . | T |

TABLE 7b

| Position | 114 | 117 | 120 | 123 | 129 | 132 | 139 | 140 | 141 | 147 | 148 | 149 | 150 | 153 | 154 | 156 |
|---|---|---|---|---|---|---|---|---|---|---|---|---|---|---|---|---|
| adil.flesh | T | C | G | A | T | C | T | C | A | A | G | T | A | C | G | C |
| gz1l | . | . | . | . | . | . | . | . | . | . | . | . | . | . | . | . |
| gz2l | . | . | . | . | . | . | . | . | . | . | . | . | . | T | . | . |
| gz3l | . | . | . | . | . | . | . | . | . | . | . | . | . | T | . | . |
| bhz25t | C | T | . | . | . | . | . | . | . | . | . | . | . | T | . | . |
| bhz26t | C | T | . | . | . | . | . | . | . | . | . | . | . | T | . | . |
| bhz30t | C | T | . | . | . | . | . | . | . | . | . | . | . | T | . | . |
| bhz45t | C | T | . | . | . | . | . | . | . | . | . | . | . | T | . | . |
| bhz56t | C | T | . | . | . | . | . | . | . | . | . | . | . | T | . | . |
| bhz20wt | C | T | . | . | . | . | . | . | . | . | . | . | . | T | . | . |
| bhz22wt | C | T | . | . | . | . | . | . | . | . | . | . | . | T | . | . |
| bhz23wt | C | T | . | . | . | . | . | . | . | . | . | . | . | T | . | . |
| dz14sl | C | T | . | . | . | . | . | . | . | . | . | . | . | T | . | . |
| dz15sl | C | T | . | . | . | . | . | . | . | . | . | . | . | T | . | . |
| sbz22al | C | T | A | . | . | T | . | . | . | . | G | . | . | T | . | . |
| sbz38al | C | T | A | . | . | T | . | . | . | . | G | . | . | T | . | . |
| gz21cl | C | T | A | . | C | T | . | . | . | . | G | . | . | . | . | T |
| gz22cl | C | T | A | . | C | T | . | . | . | . | G | . | . | . | . | T |
| chimss | A | . | A | . | A | T | C | T | G | C | A | C | C | . | C | . |
| humsk | G | . | A | G | A | . | C | T | . | C | A | C | C | . | C | T |

| Position | 159 | 162 | 168 | 169 | 170 | 171 | 177 | 180 | 186 | 198 | 199 | 200 | 204 | 208 | 210 |
|---|---|---|---|---|---|---|---|---|---|---|---|---|---|---|---|
| adil.flesh | A | C | T | C | C | A | C | A | C | T | A | T | G | C | T |
| gz1l | . | . | . | . | . | . | . | . | . | . | . | . | . | . | . |
| gz2l | . | . | . | . | . | . | . | . | . | . | C | . | . | . | . |
| gz3l | . | . | . | . | . | . | . | . | . | . | C | . | . | . | . |
| bhz25t | . | . | C | . | . | G | . | . | . | . | C | . | . | . | . |
| bhz26t | . | . | C | . | . | G | . | . | . | . | C | . | . | . | . |
| bhz30t | . | . | C | . | . | G | . | . | . | . | C | . | . | . | . |
| bhz45t | . | . | C | . | . | G | . | . | . | . | C | . | . | . | . |
| bhz56t | . | . | C | . | . | G | . | . | . | . | C | . | . | . | . |
| bhz20wt | . | . | C | . | . | G | . | . | . | . | C | . | . | . | . |
| bhz22wt | . | . | C | . | . | G | . | . | . | . | C | . | . | . | . |
| bhz23wt | . | . | C | . | . | G | . | . | . | . | C | . | . | . | . |
| dz14sl | . | . | C | . | . | G | . | . | . | . | C | . | . | . | . |
| dz15sl | . | . | C | . | . | G | . | . | . | . | C | . | . | . | . |
| sbz22al | . | T | . | . | . | . | T | . | T | . | . | . | A | . | . |
| sbz38al | . | T | . | . | . | . | T | . | T | . | . | . | A | . | . |
| gz21cl | . | . | C | . | . | G | . | G | T | . | . | . | A | . | C |
| gz22cl | . | . | C | . | . | G | . | G | T | . | . | . | A | . | C |

TABLE 7b-continued

| | | | | | | | | | | | | | | |
|---|---|---|---|---|---|---|---|---|---|---|---|---|---|---|
| chimss | C | . | . | A | . | C | . | C | . | . | . | . | T | T | A |
| humsk | C | T | C | A | T | C | . | T | . | C | G | C | C | T | A |

TABLE 7c

| Position | 211 | 213 | 214 | 216 | 217 | 219 | 220 | 222 | 223 | 225 | 226 | 227 | 228 | 229 | 231 | 233 |
|---|---|---|---|---|---|---|---|---|---|---|---|---|---|---|---|---|
| adil.flesh | C | A | G | A | C | A | A | C | C | A | G | C | A | C | C | T |
| gz1l | . | . | . | . | . | . | . | . | . | . | . | . | . | . | . | . |
| gz2l | . | . | . | . | . | . | . | . | T | . | . | . | . | . | . | . |
| gz3l | . | . | . | . | . | . | . | . | T | . | . | . | . | . | . | . |
| bhz25t | . | . | . | . | . | . | . | . | . | . | A | . | . | . | . | . |
| bhz26t | . | . | . | . | . | . | . | . | . | . | A | . | . | . | . | . |
| bhz30t | . | . | . | . | . | . | . | . | . | . | A | . | . | . | . | . |
| bhz45t | . | . | . | . | . | . | . | . | . | . | A | . | . | . | . | . |
| bhz56t | . | . | . | . | . | . | . | . | . | . | A | . | . | . | . | . |
| bhz20wt | . | . | . | . | . | . | . | . | . | . | A | . | . | . | . | . |
| bhz22wt | . | . | . | . | . | . | . | . | . | . | A | . | . | . | . | . |
| bhz23wt | . | . | . | . | . | . | . | . | . | . | A | . | . | . | . | . |
| dz14sl | . | . | . | . | . | . | . | . | . | . | A | . | . | . | . | . |
| dz15sl | . | . | . | . | . | . | . | . | . | . | A | . | . | . | . | . |
| sbz22al | . | . | . | . | . | . | . | . | T | . | A | . | . | . | . | . |
| sbz38al | . | . | . | . | . | . | . | . | T | . | A | . | . | . | . | . |
| gz21cl | . | . | . | T | . | . | . | T | . | . | . | . | . | G | . | C |
| gz22cl | . | . | . | T | . | . | . | T | . | . | . | . | . | G | . | C |
| chimss | T | C | C | T | T | C | C | . | . | T | A | T | C | . | A | . |
| humsk | . | T | C | C | T | C | C | T | . | C | T | . | C | T | A | . |

| Position | 234 | 235 | 236 | 238 | 240 | 241 | 242 | 243 | 252 | 261 | 262 | 264 | 267 | 270 | 271 |
|---|---|---|---|---|---|---|---|---|---|---|---|---|---|---|---|
| adil.flesh | A | C | T | C | C | G | T | C | A | G | T | A | A | C | C |
| gz1l | . | . | . | . | . | . | . | . | . | . | . | . | . | . | . |
| gz2l | . | . | . | . | . | . | . | . | . | . | . | G | . | . | . |
| gz3l | . | . | . | . | . | . | . | . | . | . | . | G | . | . | . |
| bhz25t | . | . | . | . | . | . | . | . | . | A | . | . | G | . | . |
| bhz26t | . | . | . | . | . | . | . | . | . | A | . | . | G | . | . |
| bhz30t | . | . | . | . | . | . | . | . | . | A | . | . | G | . | . |
| bhz45t | . | . | . | . | . | . | . | . | . | A | . | . | G | . | . |
| bhz56t | . | . | . | . | . | . | . | . | . | A | . | . | G | . | . |
| bhz20wt | . | . | . | . | . | . | . | . | . | A | . | . | G | . | . |
| bhz22wt | . | . | . | . | . | . | . | . | . | A | . | . | G | . | . |
| bhz23wt | . | . | . | . | . | . | . | . | . | A | . | . | G | . | . |
| dz14sl | . | . | . | . | . | . | . | . | . | A | . | . | G | . | G |
| dz15sl | . | . | . | . | . | . | . | . | . | A | . | . | G | . | G |
| sbz22al | . | . | . | . | . | . | . | . | . | A | . | . | . | T | . |
| sbz38al | . | . | . | . | . | . | . | . | . | A | . | . | . | T | . |
| gz21cl | . | . | . | . | T | . | . | T | C | A | C | . | . | . | . |
| gz22cl | . | . | . | . | T | . | . | T | C | A | C | . | . | . | . |
| chimss | G | A | C | T | A | A | C | A | . | C | C | G | C | T | . |
| humsk | G | A | C | T | A | A | C | A | . | C | C | . | C | . | . |

TABLE 7d

| Position | 273 | 276 | 279 | 282 | 284 | 285 | 287 | 288 | 291 | 294 |
|---|---|---|---|---|---|---|---|---|---|---|
| adil.flesh | C | T | C | C | T | C | C | T | C | C |
| gz1l | . | . | . | . | . | . | . | . | . | . |
| gz2l | . | . | . | . | . | . | . | C | . | . |
| gz3l | . | . | . | . | . | . | . | C | . | . |
| bhz25t | . | . | . | . | . | . | . | C | . | . |
| bhz26t | . | . | . | . | . | . | . | C | . | . |
| bhz30t | . | . | . | . | . | . | . | C | . | . |
| bhz45t | . | . | . | . | . | . | . | C | . | . |
| bhz56t | . | . | . | . | . | . | . | C | . | . |
| bhz20wt | . | . | . | . | . | . | . | C | . | . |
| bhz22wt | . | . | . | . | . | . | . | C | . | . |
| bhz23wt | . | . | . | . | . | . | . | C | . | . |
| dz14sl | . | . | . | . | . | . | . | C | . | . |
| dz15sl | . | . | . | . | . | . | . | C | . | . |
| sbz22al | . | C | . | T | C | . | . | C | . | T |
| sbz38al | . | C | . | T | C | . | . | C | . | T |
| gz21cl | T | C | T | . | C | T | . | C | . | . |
| gz22cl | T | C | T | . | C | T | . | C | . | . |
| chimss | A | C | . | T | C | . | T | A | T | . |

TABLE 7d-continued

| humsk | A | C | T | T | C | . | T | A | . | . |
|---|---|---|---|---|---|---|---|---|---|---|
| Position | 297 | 298 | 302 | 303 | 309 | 315 | 318 | 321 | 323 | 324 |
| adil.flesh | T | C | A | T | T | T | C | G | C | T |
| gz1l | . | . | . | . | . | . | . | . | . | . |
| gz2l | . | . | . | . | . | . | . | . | . | . |
| gz3l | . | . | . | . | . | . | . | . | . | . |
| bhz25t | . | . | . | C | . | . | . | . | G | C |
| bhz26t | . | . | . | C | . | . | . | . | G | C |
| bhz30t | . | . | . | C | . | . | . | . | G | C |
| bhz45t | . | . | . | C | . | . | . | . | G | C |
| bhz56t | . | . | . | C | . | . | . | . | G | C |
| bhz20wt | . | . | . | C | . | . | . | . | G | C |
| bhz22wt | . | . | . | C | . | . | . | . | G | C |
| bhz23wt | . | . | . | C | . | . | . | . | G | C |
| dz14sl | . | . | . | C | . | . | . | . | . | C |
| dz15sl | . | . | . | C | . | . | . | . | . | C |
| sbz22al | . | . | G | C | . | . | . | A | . | . |
| sbz38al | . | . | G | C | . | . | . | A | . | . |
| gz21cl | . | . | . | . | . | . | . | . | . | . |
| gz22cl | . | . | . | . | . | . | . | . | . | . |
| chimss | C | . | . | C | A | C | T | A | . | C |
| humsk | C | T | . | C | . | C | . | . | . | C |

Table 8. Percent similarity matrix calculated by pair-vise comparisons of nucleotide sequences aligned (illustrated in Table 6). The cytochrome b gene sequence of DNA isolated from confiscated material had maximum similarity (99.7% and 98.2%, with the lineages of animals 'gz2L' and 'gz3L', respectively) with the sequences obtained from known normal leopard source, indicating its identity as that of a leopard origin. The similarity matrix has been calculated using the software PHYLIP (3.5).

TABLE 9

Animals selected for validation of minimum P'S score for efficient amplification of DNA templates in PCR

| SL. | Name | P,S/AFF | P,S/AFR |
|---|---|---|---|
| 1 | Indian black buck (*Antilope cervicapra*) | 97, 58 | 96, 54 |
| 2 | Sheep (*Ovis*) | 87, 53 | 96, 54 |
| 3 | Pig (*Sus scrofa*) | 87, 52 | 87, 41 |
| 4 | Fresh water dolphin (*Platanista gangetica*) | 86, 49 | 82, 47 |

TABLE 8

Percent similarity matrix calculated by pair-vise comparisons of cytochrome b gene sequences revealed from 'adil.flesh' and different felids

| | bhz20wt | bhz25t | dz14sl | humsk | chimss | sbz22al | gz1L | gz2L | gz3L | gz21cl | adil.flesh |
|---|---|---|---|---|---|---|---|---|---|---|---|
| bhz20wt | | 100 | 99.1 | 81.7 | 78.7 | 93.3 | 95.1 | 95.4 | 95.4 | 89.6 | 95.4 |
| bhz25t | 100 | | 99.1 | 81.7 | 78.7 | 93.3 | 95.1 | 95.4 | 95.4 | 89.6 | 95.4 |
| dz14sl | 99.1 | 99.1 | | 81.4 | 78.4 | 93 | 94.8 | 95.1 | 95.1 | 89.3 | 95.1 |
| humsk | 81.7 | 81.7 | 81.4 | | 86.9 | 79.6 | 81.1 | 80.2 | 80.2 | 79 | 81.4 |
| chimss | 78.7 | 78.7 | 78.4 | 86.9 | | 78.7 | 79.6 | 78.7 | 78.7 | 76.8 | 79.9 |
| sbz22al | 93.3 | 93.3 | 93 | 79.6 | 78.7 | | 92.1 | 92.4 | 92.4 | 89 | 92.4 |
| gz1L | 95.1 | 95.1 | 94.8 | 81.1 | 79.6 | 92.1 | | 98.5 | 98.5 | 89.3 | 99.7 |
| gz2L | 95.4 | 95.4 | 95.1 | 80.2 | 78.7 | 92.4 | 98.5 | | 100 | 88.1 | 98.2 |
| gz3L | 95.4 | 95.4 | 95.1 | 80.2 | 78.7 | 92.4 | 98.5 | 100 | | 88.1 | 98.2 |
| gz21cl | 89.6 | 89.6 | 89.3 | 79 | 76.8 | 89 | 89.3 | 88.1 | 88.1 | | 89.6 |
| adil.flesh | 95.4 | 95.4 | 95.1 | 81.4 | 79.9 | 92.4 | 99.7 | 98.2 | 98.2 | 89.6 | |

Table 9. Animals selected for validation of minimum P,S score for efficient amplification of cytochrome b gene of different origin by the primers 'mcb398' and 'mcb869'. P,S score of primers 'AFF' and 'AFR' for these animals are shown.

Table 10. BLAST analysis of primers 'mcb398' in nr database of NCBI. It demonstrates that the 3' end of this primer is highly conserved among a vast range of animal species. It also shows the significant homology among the primer and templates (i.e. the cytochrome b gene fragment of different animal species), confirming the universal nature of our primer

```
<p><!--
QBlastInfoBegin
        Status=READY
QBlastInfoEnd
--><p>
<TITLE>Results for RID 984591695-10075-13605 </TITLE>
<HTML>
<HEAD>
<TITLE>BLAST Search Results </TITLE>
</HEAD>
<BODY BGCOLOR="#FFFFFF" LINK="#0000FF" VLINK="#660099" ALINK="#660099">
<A HREF="http://www.ncbi.nlm.nih.gov/BLAST/blast_form.map"> <IMG
SRC="http://www.ncbi.nlm.nih.gov/BLAST/blast_results.gif" BORDER=0 ISMAP></A>
<BR><BR><PRE>
<b>BLASTN 2.1.2 [Nov-13-2000]</b>

<b><a href="http://www.ncbi.nlm.nih.gov/htbin-
post/Entrez/query?uid=9254694&form=6&db=m&Dopt=r">Reference</a>:</b>
Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs",  Nucleic Acids Res. 25:3389-3402.
<p>
RID: 984591695-10075-13605
<p>
<b>Query=</b>
         (25 letters)

<p>
<b>Database:</b> nt
           807,597 sequences; 2,863,827,885 total letters <p> <p>If you have any problems or questions with the results of this search
<br>please refer to the <b><a
href=http://www.ncbi.nlm.nih.gov/blast/blast_FAQs.html>BLAST FAQs</a></b><br><p>
<FORM NAME="BLASTFORM" METHOD="POST">
<a href="blast.cgi?RID=984591695-10075-13605&ALIGNMENT_VIEW=17" TARGET="Taxonomy
BLAST Results for 984591695-10075-13605">Taxonomy reports</a>
<BR>
</PRE>
<CENTER>
<H3><a href="/BLAST/newoptions.html#graphical-overview"> Distribution of 500
Blast Hits on the Query Sequence</a></H3>
<input name=defline size=80 value="Mouse-over to show defline and scores. Click
to show alignments">
</CENTER>
<map name=img_map>
<area shape=rect coords=62,101,509,106 href="#13171194"
ONMOUSEOVER='document.BLASTFORM.defline.value="AF231650   Strongylura notata
clone HB-159 cytochrome b oxidase (..S=50.1 E=2e-05"'
ONMOUSEOUT='document.BLASTFORM.defline.value="Mouse-over to show defline and
scores. Click to show alignments"' >
<area shape=rect coords=62,108,509,113 href="#13116556"
ONMOUSEOVER='document.BLASTFORM.defline.value="NC_002672   Dinornis giganteus
mitochondrion, complete genome..S=50.1 E=2e-05"'
```

```
ONMOUSEOUT='document.BLASTFORM.defline.value="Mouse-over to show defline and
scores. Click to show alignments"' >
<area shape=rect coords=62,115,509,120 href="#13116573"
ONMOUSEOVER='document.BLASTFORM.defline.value="NC_002673   Emeus crassus
mitochondrion, complete genome..S=50.1 E=2e-05"'
ONMOUSEOUT='document.BLASTFORM.defline.value="Mouse-over to show defline and
scores. Click to show alignments"' >
<area shape=rect coords=62,122,509,127 href="#13128885"
ONMOUSEOVER='document.BLASTFORM.defline.value="AF232015   Nothrotheriops
shastensis cytochrome b gene, partial c..S=50.1 E=2e-05"'
ONMOUSEOUT='document.BLASTFORM.defline.value="Mouse-over to show defline and
scores. Click to show alignments"' >
<area shape=rect coords=62,129,509,134 href="#13128881"
ONMOUSEOVER='document.BLASTFORM.defline.value="AF232013   Bradypus variegatus
cytochrome b gene, partial cds; mi..S=50.1 E=2e-05"'
ONMOUSEOUT='document.BLASTFORM.defline.value="Mouse-over to show defline and
scores. Click to show alignments"' >
<area shape=rect coords=62,136,509,141 href="#12957459"
ONMOUSEOVER='document.BLASTFORM.defline.value="AY016015   Emeus crassus
mitochondrion, complete genome..S=50.1 E=2e-05"'
ONMOUSEOUT='document.BLASTFORM.defline.value="Mouse-over to show defline and
scores. Click to show alignments"' >
<area shape=rect coords=62,143,509,148 href="#12957432"
ONMOUSEOVER='document.BLASTFORM.defline.value="AY016013   Dinornis giganteus
mitochondrion, complete genome..S=50.1 E=2e-05"'
ONMOUSEOUT='document.BLASTFORM.defline.value="Mouse-over to show defline and
scores. Click to show alignments"' >
<area shape=rect coords=62,150,509,155 href="#12957446"
ONMOUSEOVER='document.BLASTFORM.defline.value="AY016014   Dromaius
novaehollandiae mitochondrion, partial genome..S=50.1 E=2e-05"'
ONMOUSEOUT='document.BLASTFORM.defline.value="Mouse-over to show defline and
scores. Click to show alignments"' >
<area shape=rect coords=62,157,509,162 href="#6970176"
ONMOUSEOVER='document.BLASTFORM.defline.value="AF230167   Bonasa umbellus
cytochrome b (CYTB) gene, partial cds;..S=50.1 E=2e-05"'
ONMOUSEOUT='document.BLASTFORM.defline.value="Mouse-over to show defline and
scores. Click to show alignments"' >
<area shape=rect coords=62,164,509,169 href="#4336170"
ONMOUSEOVER='document.BLASTFORM.defline.value="AF074594   Baeolophus bicolor
cytochrome b gene, mitochondrial ge..S=50.1 E=2e-05"'
ONMOUSEOUT='document.BLASTFORM.defline.value="Mouse-over to show defline and
scores. Click to show alignments"' >
<area shape=rect coords=62,171,509,176 href="#12699071"
ONMOUSEOVER='document.BLASTFORM.defline.value="AY005210   Poospiza melanoleuca
isolate 3 cytochrome b (cytb) gen..S=50.1 E=2e-05"'
ONMOUSEOUT='document.BLASTFORM.defline.value="Mouse-over to show defline and
scores. Click to show alignments"' >
<area shape=rect coords=62,178,509,183 href="#12699069"
ONMOUSEOVER='document.BLASTFORM.defline.value="AY005209   Poospiza melanoleuca
isolate 2 cytochrome b (cytb) gen..S=50.1 E=2e-05"'
ONMOUSEOUT='document.BLASTFORM.defline.value="Mouse-over to show defline and
scores. Click to show alignments"' >
<area shape=rect coords=62,185,509,190 href="#12699067"
ONMOUSEOVER='document.BLASTFORM.defline.value="AY005208   Poospiza melanoleuca
isolate 1 cytochrome b (cytb) gen..S=50.1 E=2e-05"'
ONMOUSEOUT='document.BLASTFORM.defline.value="Mouse-over to show defline and
scores. Click to show alignments"' >
```

```
<area shape=rect coords=62,192,509,197 href="#12699061"
ONMOUSEOVER='document.BLASTFORM.defline.value="AY005205  Poospiza hispaniolensis
cytochrome b (cytb) gene, part..S=50.1 E=2e-05"'
ONMOUSEOUT='document.BLASTFORM.defline.value="Mouse-over to show defline and
scores. Click to show alignments"' >
<area shape=rect coords=62,199,509,204 href="#12699059"
ONMOUSEOVER='document.BLASTFORM.defline.value="AY005204  Poospiza garleppi
cytochrome b (cytb) gene, partial cd..S=50.1 E=2e-05"'
ONMOUSEOUT='document.BLASTFORM.defline.value="Mouse-over to show defline and
scores. Click to show alignments"' >
<area shape=rect coords=62,206,509,211 href="#12699057"
ONMOUSEOVER='document.BLASTFORM.defline.value="AY005203  Poospiza erythrophrys
cytochrome b (cytb) gene, partia..S=50.1 E=2e-05"'
ONMOUSEOUT='document.BLASTFORM.defline.value="Mouse-over to show defline and
scores. Click to show alignments"' >
<area shape=rect coords=62,213,509,218 href="#12699053"
ONMOUSEOVER='document.BLASTFORM.defline.value="AY005201  Poospiza boliviana
cytochrome b (cytb) gene, partial c..S=50.1 E=2e-05"'
ONMOUSEOUT='document.BLASTFORM.defline.value="Mouse-over to show defline and
scores. Click to show alignments"' >
<area shape=rect coords=62,220,509,225 href="#12699049"
ONMOUSEOVER='document.BLASTFORM.defline.value="AY005199  Poospiza alticola
isolate 2 cytochrome b (cytb) gene, ..S=50.1 E=2e-05"'
ONMOUSEOUT='document.BLASTFORM.defline.value="Mouse-over to show defline and
scores. Click to show alignments"' >
<area shape=rect coords=62,227,509,232 href="#12699047"
ONMOUSEOVER='document.BLASTFORM.defline.value="AY005198  Poospiza alticola
isolate 1 cytochrome b (cytb) gene, ..S=50.1 E=2e-05"'
ONMOUSEOUT='document.BLASTFORM.defline.value="Mouse-over to show defline and
scores. Click to show alignments"' >
<area shape=rect coords=62,234,509,239 href="#12581475"
ONMOUSEOVER='document.BLASTFORM.defline.value="AF155870  Heterocephalus glaber
cytochrome b (cyt b) gene, compl..S=50.1 E=2e-05"'
ONMOUSEOUT='document.BLASTFORM.defline.value="Mouse-over to show defline and
scores. Click to show alignments"' >
<area shape=rect coords=62,241,509,246 href="#10441566"
ONMOUSEOVER='document.BLASTFORM.defline.value="AF189123  Glyptotermes eukalypti
cytochrome b (Cytb) gene, parti..S=50.1 E=2e-05"'
ONMOUSEOUT='document.BLASTFORM.defline.value="Mouse-over to show defline and
scores. Click to show alignments"' >
<area shape=rect coords=62,248,509,253 href="#12024721"
ONMOUSEOVER='document.BLASTFORM.defline.value="AF102099  Criniferoides
leucogaster cytochrome b gene, partial c..S=50.1 E=2e-05"'
ONMOUSEOUT='document.BLASTFORM.defline.value="Mouse-over to show defline and
scores. Click to show alignments"' >
<area shape=rect coords=62,255,509,260 href="#12024713"
ONMOUSEOVER='document.BLASTFORM.defline.value="AF102095  Corythaixoides concolor
cytochrome b gene, partial seq..S=50.1 E=2e-05"'
ONMOUSEOUT='document.BLASTFORM.defline.value="Mouse-over to show defline and
scores. Click to show alignments"' >
<area shape=rect coords=62,262,509,267 href="#12006178"
ONMOUSEOVER='document.BLASTFORM.defline.value="AF271065  Mustela erminea
specimen-voucher AF16024 cytochrome b ..S=50.1 E=2e-05"'
ONMOUSEOUT='document.BLASTFORM.defline.value="Mouse-over to show defline and
scores. Click to show alignments"' >
<area shape=rect coords=62,269,509,274 href="#11995304"
ONMOUSEOVER='document.BLASTFORM.defline.value="AF243857  Strongylura notata
```

```
notata cytochrome b (cytb) gene, pa..S=50.1 E=2e-05"'
ONMOUSEOUT='document.BLASTFORM.defline.value="Mouse-over to show defline and
scores. Click to show alignments"' >
<area shape=rect coords=62,276,509,281 href="#11995302"
ONMOUSEOVER='document.BLASTFORM.defline.value="AF243856  Strongylura notata
forsythia cytochrome b (cytb) gene,..S=50.1 E=2e-05"'
ONMOUSEOUT='document.BLASTFORM.defline.value="Mouse-over to show defline and
scores. Click to show alignments"' >
<area shape=rect coords=62,283,509,288 href="#5834939"
ONMOUSEOVER='document.BLASTFORM.defline.value="NC_001567  Bos taurus
mitochondrion, complete genome..S=50.1 E=2e-05"'
ONMOUSEOUT='document.BLASTFORM.defline.value="Mouse-over to show defline and
scores. Click to show alignments"' >
<area shape=rect coords=62,290,509,295 href="#11993539"
ONMOUSEOVER='document.BLASTFORM.defline.value="AF306872  Brachyramphus
marmoratus haplotype MMB cytochrome b ge..S=50.1 E=2e-05"'
ONMOUSEOUT='document.BLASTFORM.defline.value="Mouse-over to show defline and
scores. Click to show alignments"' >
<area shape=rect coords=62,297,509,302 href="#11993537"
ONMOUSEOVER='document.BLASTFORM.defline.value="AF306871  Brachyramphus
marmoratus haplotype MMA cytochrome b ge..S=50.1 E=2e-05"'
ONMOUSEOUT='document.BLASTFORM.defline.value="Mouse-over to show defline and
scores. Click to show alignments"' >
<area shape=rect coords=62,304,509,309 href="#11993535"
ONMOUSEOVER='document.BLASTFORM.defline.value="AF306870  Brachyramphus
brevirostris haplotype KMC cytochrome b ..S=50.1 E=2e-05"'
ONMOUSEOUT='document.BLASTFORM.defline.value="Mouse-over to show defline and
scores. Click to show alignments"' >
<area shape=rect coords=62,311,509,316 href="#11993533"
ONMOUSEOVER='document.BLASTFORM.defline.value="AF306869  Brachyramphus
brevirostris haplotype KMB cytochrome b ..S=50.1 E=2e-05"'
ONMOUSEOUT='document.BLASTFORM.defline.value="Mouse-over to show defline and
scores. Click to show alignments"' >
<area shape=rect coords=62,318,509,323 href="#11993531"
ONMOUSEOVER='document.BLASTFORM.defline.value="AF306868  Brachyramphus
brevirostris haplotype KMA cytochrome b ..S=50.1 E=2e-05"'
ONMOUSEOUT='document.BLASTFORM.defline.value="Mouse-over to show defline and
scores. Click to show alignments"' >
<area shape=rect coords=62,325,509,330 href="#3445513"
ONMOUSEOVER='document.BLASTFORM.defline.value="AF010406  Ovis aries complete
mitochondrial genome..S=50.1 E=2e-05"'
ONMOUSEOUT='document.BLASTFORM.defline.value="Mouse-over to show defline and
scores. Click to show alignments"' >
<area shape=rect coords=62,332,509,337 href="#11141464"
ONMOUSEOVER='document.BLASTFORM.defline.value="AF248662  Gryllus campestris
haplotype 2 cytochrome b gene, part..S=50.1 E=2e-05"'
ONMOUSEOUT='document.BLASTFORM.defline.value="Mouse-over to show defline and
scores. Click to show alignments"' >
<area shape=rect coords=62,339,509,344 href="#11141462"
ONMOUSEOVER='document.BLASTFORM.defline.value="AF248661  Gryllus campestris
haplotype 1 cytochrome b gene, part..S=50.1 E=2e-05"'
ONMOUSEOUT='document.BLASTFORM.defline.value="Mouse-over to show defline and
scores. Click to show alignments"' >
<area shape=rect coords=62,346,509,351 href="#11139383"
ONMOUSEOVER='document.BLASTFORM.defline.value="AF096462  Rhipidura albicollis
cytochrome b gene, partial cds; m..S=50.1 E=2e-05"'
```

```
ONMOUSEOUT='document.BLASTFORM.defline.value="Mouse-over to show defline and
scores. Click to show alignments"' >
<area shape=rect coords=62,353,509,358 href="#11023426"
ONMOUSEOVER='document.BLASTFORM.defline.value="AF283644   Elaphe obsoleta
cytochrome b gene, complete cds; mitoc..S=50.1 E=2e-05"'
ONMOUSEOUT='document.BLASTFORM.defline.value="Mouse-over to show defline and
scores. Click to show alignments"' >
<area shape=rect coords=62,360,509,365 href="#11023424"
ONMOUSEOVER='document.BLASTFORM.defline.value="AF283643   Elaphe obsoleta
cytochrome b gene, complete cds; mitoc..S=50.1 E=2e-05"'
ONMOUSEOUT='document.BLASTFORM.defline.value="Mouse-over to show defline and
scores. Click to show alignments"' >
<area shape=rect coords=62,367,509,372 href="#11023422"
ONMOUSEOVER='document.BLASTFORM.defline.value="AF283642   Elaphe obsoleta
cytochrome b gene, complete cds; mitoc..S=50.1 E=2e-05"'
ONMOUSEOUT='document.BLASTFORM.defline.value="Mouse-over to show defline and
scores. Click to show alignments"' >
<area shape=rect coords=62,374,509,379 href="#11023420"
ONMOUSEOVER='document.BLASTFORM.defline.value="AF283641   Elaphe obsoleta
cytochrome b gene, complete cds; mitoc..S=50.1 E=2e-05"'
ONMOUSEOUT='document.BLASTFORM.defline.value="Mouse-over to show defline and
scores. Click to show alignments"' >
<area shape=rect coords=62,381,509,386 href="#11023418"
ONMOUSEOVER='document.BLASTFORM.defline.value="AF283640   Elaphe obsoleta
cytochrome b gene, complete cds; mitoc..S=50.1 E=2e-05"'
ONMOUSEOUT='document.BLASTFORM.defline.value="Mouse-over to show defline and
scores. Click to show alignments"' >
<area shape=rect coords=62,388,509,393 href="#11023416"
ONMOUSEOVER='document.BLASTFORM.defline.value="AF283639   Elaphe obsoleta
cytochrome b gene, complete cds; mitoc..S=50.1 E=2e-05"'
ONMOUSEOUT='document.BLASTFORM.defline.value="Mouse-over to show defline and
scores. Click to show alignments"' >
<area shape=rect coords=62,395,509,400 href="#11023412"
ONMOUSEOVER='document.BLASTFORM.defline.value="AF283637   Elaphe obsoleta LSUMZ
45359 cytochrome b gene, complet..S=50.1 E=2e-05"'
ONMOUSEOUT='document.BLASTFORM.defline.value="Mouse-over to show defline and
scores. Click to show alignments"' >
<area shape=rect coords=62,402,509,407 href="#11023410"
ONMOUSEOVER='document.BLASTFORM.defline.value="AF283636   Elaphe obsoleta LSUMZ
44662 cytochrome b gene, complet..S=50.1 E=2e-05"'
ONMOUSEOUT='document.BLASTFORM.defline.value="Mouse-over to show defline and
scores. Click to show alignments"' >
<area shape=rect coords=62,409,509,414 href="#11023408"
ONMOUSEOVER='document.BLASTFORM.defline.value="AF283635   Elaphe obsoleta LSUMZ
40443 cytochrome b gene, complet..S=50.1 E=2e-05"'
ONMOUSEOUT='document.BLASTFORM.defline.value="Mouse-over to show defline and
scores. Click to show alignments"' >
<area shape=rect coords=62,416,509,421 href="#11023406"
ONMOUSEOVER='document.BLASTFORM.defline.value="AF283634   Elaphe obsoleta LSUMZ
44335 cytochrome b gene, complet..S=50.1 E=2e-05"'
ONMOUSEOUT='document.BLASTFORM.defline.value="Mouse-over to show defline and
scores. Click to show alignments"' >
<area shape=rect coords=62,423,509,428 href="#11023404"
ONMOUSEOVER='document.BLASTFORM.defline.value="AF283633   Elaphe obsoleta LSUMZ
42624 cytochrome b gene, complet..S=50.1 E=2e-05"'
ONMOUSEOUT='document.BLASTFORM.defline.value="Mouse-over to show defline and
scores. Click to show alignments"' >
```

```
<area shape=rect coords=62,430,509,435 href="#11023402"
ONMOUSEOVER='document.BLASTFORM.defline.value="AF283632  Elaphe obsoleta LSUMZ
H1911 cytochrome b gene, complet..S=50.1 E=2e-05"'
ONMOUSEOUT='document.BLASTFORM.defline.value="Mouse-over to show defline and
scores. Click to show alignments"' >
<area shape=rect coords=62,437,509,442 href="#11023400"
ONMOUSEOVER='document.BLASTFORM.defline.value="AF283631  Elaphe obsoleta LSUMZ
41197 cytochrome b gene, complet..S=50.1 E=2e-05"'
ONMOUSEOUT='document.BLASTFORM.defline.value="Mouse-over to show defline and
scores. Click to show alignments"' >
<area shape=rect coords=62,444,509,449 href="#13171196"
ONMOUSEOVER='document.BLASTFORM.defline.value="AF231651  Strongylura notata
clone HB-82 cytochrome b oxidase (C..S=50.1 E=2e-05"'
ONMOUSEOUT='document.BLASTFORM.defline.value="Mouse-over to show defline and
scores. Click to show alignments"' >
</map>
<CENTER>
<IMG WIDTH=532 HEIGHT=451 USEMAP=#img_map BORDER=1 SRC="nph-
getgif.cgi?iblast11&207891705313935.gif" ISMAP></CENTER>
<HR>
<PRE>
<PRE>

Score     E
Sequences producing significant alignments:                     (bits)  Value <a
href="http://www.ncbi.nlm.nih.gov:80/entrez/query.fcgi?cmd=Retrieve&db=Nucleotid
e&list_uids=13171196&dopt=GenBank">gb|AF231651.1|AF231651</a>  Strongylura
notata clone HB-82 cytoc...    <a href = #13171196> 50</a>   2e-05
<a
href="http://www.ncbi.nlm.nih.gov:80/entrez/query.fcgi?cmd=Retrieve&db=Nucleotid
e&list_uids=13171194&dopt=GenBank">gb|AF231650.1|AF231650</a>  Strongylura
notata clone HB-159 cyto...    <a href = #13171194> 50</a>   2e-05
<a
href="http://www.ncbi.nlm.nih.gov:80/entrez/query.fcgi?cmd=Retrieve&db=Nucleotid
e&list_uids=13116556&dopt=GenBank">ref|NC_002672.1|</a>  Dinornis giganteus
mitochondrion, complete...    <a href = #13116556> 50</a>   2e-05
<a
href="http://www.ncbi.nlm.nih.gov:80/entrez/query.fcgi?cmd=Retrieve&db=Nucleotid
e&list_uids=13116573&dopt=GenBank">ref|NC_002673.1|</a>  Emeus crassus
mitochondrion, complete genome    <a href = #13116573> 50</a>   2e-05
<a
href="http://www.ncbi.nlm.nih.gov:80/entrez/query.fcgi?cmd=Retrieve&db=Nucleotid
e&list_uids=13128885&dopt=GenBank">gb|AF232015.1|AF232015</a>  Nothrotheriops
shastensis cytochrome...    <a href = #13128885> 50</a>   2e-05
<a
href="http://www.ncbi.nlm.nih.gov:80/entrez/query.fcgi?cmd=Retrieve&db=Nucleotid
e&list_uids=13128881&dopt=GenBank">gb|AF232013.1|AF232013</a>  Bradypus
variegatus cytochrome b gen...    <a href = #13128881> 50</a>   2e-05
<a
href="http://www.ncbi.nlm.nih.gov:80/entrez/query.fcgi?cmd=Retrieve&db=Nucleotid
e&list_uids=12957459&dopt=GenBank">gb|AY016015.1|</a>  Emeus crassus
mitochondrion, complete genome    <a href = #12957459> 50</a>   2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=12957432&dopt=GenBank">gb|AY016013.1|</a>  Dinornis giganteus
mitochondrion, complete g...   <a href = #12957432> 50</a>   2e-05
<a
href="http://www.ncbi.nlm.nih.gov:80/entrez/query.fcgi?cmd=Retrieve&db=Nucleotid
e&list_uids=12957446&dopt=GenBank">gb|AY016014.1|</a>  Dromaius novaehollandiae
mitochondrion, part...   <a href = #12957446> 50</a>   2e-05
<a
href="http://www.ncbi.nlm.nih.gov:80/entrez/query.fcgi?cmd=Retrieve&db=Nucleotid
e&list_uids=06970176&dopt=GenBank">gb|AF230167.1|AF230167</a>  Bonasa umbellus
cytochrome b (CYTB) ...   <a href = #6970176> 50</a>   2e-05
<a
href="http://www.ncbi.nlm.nih.gov:80/entrez/query.fcgi?cmd=Retrieve&db=Nucleotid
e&list_uids=04336170&dopt=GenBank">gb|AF074594.1|AF074594</a>  Baeolophus
bicolor cytochrome b gene...   <a href = #4336170> 50</a>   2e-05
<a
href="http://www.ncbi.nlm.nih.gov:80/entrez/query.fcgi?cmd=Retrieve&db=Nucleotid
e&list_uids=12699071&dopt=GenBank">gb|AY005210.1|</a>  Poospiza melanoleuca
isolate 3 cytochrome b ...   <a href = #12699071> 50</a>   2e-05
<a
href="http://www.ncbi.nlm.nih.gov:80/entrez/query.fcgi?cmd=Retrieve&db=Nucleotid
e&list_uids=12699069&dopt=GenBank">gb|AY005209.1|</a>  Poospiza melanoleuca
isolate 2 cytochrome b ...   <a href = #12699069> 50</a>   2e-05
<a
href="http://www.ncbi.nlm.nih.gov:80/entrez/query.fcgi?cmd=Retrieve&db=Nucleotid
e&list_uids=12699067&dopt=GenBank">gb|AY005208.1|</a>  Poospiza melanoleuca
isolate 1 cytochrome b ...   <a href = #12699067> 50</a>   2e-05
<a
href="http://www.ncbi.nlm.nih.gov:80/entrez/query.fcgi?cmd=Retrieve&db=Nucleotid
e&list_uids=12699061&dopt=GenBank">gb|AY005205.1|</a>  Poospiza hispaniolensis
cytochrome b (cytb) ...   <a href = #12699061> 50</a>   2e-05
<a
href="http://www.ncbi.nlm.nih.gov:80/entrez/query.fcgi?cmd=Retrieve&db=Nucleotid
e&list_uids=12699059&dopt=GenBank">gb|AY005204.1|</a>  Poospiza garleppi
cytochrome b (cytb) gene, ...   <a href = #12699059> 50</a>   2e-05
<a
href="http://www.ncbi.nlm.nih.gov:80/entrez/query.fcgi?cmd=Retrieve&db=Nucleotid
e&list_uids=12699057&dopt=GenBank">gb|AY005203.1|</a>  Poospiza erythrophrys
cytochrome b (cytb) ge...   <a href = #12699057> 50</a>   2e-05
<a
href="http://www.ncbi.nlm.nih.gov:80/entrez/query.fcgi?cmd=Retrieve&db=Nucleotid
e&list_uids=12699053&dopt=GenBank">gb|AY005201.1|</a>  Poospiza boliviana
cytochrome b (cytb) gene,...   <a href = #12699053> 50</a>   2e-05
<a
href="http://www.ncbi.nlm.nih.gov:80/entrez/query.fcgi?cmd=Retrieve&db=Nucleotid
e&list_uids=12699049&dopt=GenBank">gb|AY005199.1|</a>  Poospiza alticola isolate
2 cytochrome b (cy...   <a href = #12699049> 50</a>   2e-05
<a
href="http://www.ncbi.nlm.nih.gov:80/entrez/query.fcgi?cmd=Retrieve&db=Nucleotid
e&list_uids=12699047&dopt=GenBank">gb|AY005198.1|</a>  Poospiza alticola isolate
1 cytochrome b (cy...   <a href = #12699047> 50</a>   2e-05
<a
href="http://www.ncbi.nlm.nih.gov:80/entrez/query.fcgi?cmd=Retrieve&db=Nucleotid
e&list_uids=12581475&dopt=GenBank">gb|AF155870.1|AF155870</a>  Heterocephalus
glaber cytochrome b (...   <a href = #12581475> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotid
e&list_uids=10441566&dopt=GenBank">gb|AF189123.1|AF189123</a>   Glyptotermes
eukalypti cytochrome b ...    <a href = #10441566> 50</a>   2e-05
<a
href="http://www.ncbi.nlm.nih.gov:80/entrez/query.fcgi?cmd=Retrieve&db=Nucleotid
e&list_uids=12024721&dopt=GenBank">gb|AF102099.1|AF102099</a>   Criniferoides
leucogaster cytochrome...    <a href = #12024721> 50</a>   2e-05
<a
href="http://www.ncbi.nlm.nih.gov:80/entrez/query.fcgi?cmd=Retrieve&db=Nucleotid
e&list_uids=12024713&dopt=GenBank">gb|AF102095.1|AF102095S1</a>   Corythaixoides
concolor cytochrome...    <a href = #12024713> 50</a>   2e-05
<a
href="http://www.ncbi.nlm.nih.gov:80/entrez/query.fcgi?cmd=Retrieve&db=Nucleotid
e&list_uids=12006178&dopt=GenBank">gb|AF271065.1|AF271065</a>   Mustela erminea
specimen-voucher AF1...    <a href = #12006178> 50</a>   2e-05
<a
href="http://www.ncbi.nlm.nih.gov:80/entrez/query.fcgi?cmd=Retrieve&db=Nucleotid
e&list_uids=11995304&dopt=GenBank">gb|AF243857.1|AF243857</a>   Strongylura
notata notata cytochrome...    <a href = #11995304> 50</a>   2e-05
<a
href="http://www.ncbi.nlm.nih.gov:80/entrez/query.fcgi?cmd=Retrieve&db=Nucleotid
e&list_uids=11995302&dopt=GenBank">gb|AF243856.1|AF243856</a>   Strongylura
notata forsythia cytochr...    <a href = #11995302> 50</a>   2e-05
<a
href="http://www.ncbi.nlm.nih.gov:80/entrez/query.fcgi?cmd=Retrieve&db=Nucleotid
e&list_uids=05834939&dopt=GenBank">ref|NC_001567.1|</a>   Bos taurus
mitochondrion, complete genome    <a href = #5834939> 50</a>   2e-05
<a
href="http://www.ncbi.nlm.nih.gov:80/entrez/query.fcgi?cmd=Retrieve&db=Nucleotid
e&list_uids=11993539&dopt=GenBank">gb|AF306872.1|AF306872</a>   Brachyramphus
marmoratus haplotype M...    <a href = #11993539> 50</a>   2e-05
<a
href="http://www.ncbi.nlm.nih.gov:80/entrez/query.fcgi?cmd=Retrieve&db=Nucleotid
e&list_uids=11993537&dopt=GenBank">gb|AF306871.1|AF306871</a>   Brachyramphus
marmoratus haplotype M...    <a href = #11993537> 50</a>   2e-05
<a
href="http://www.ncbi.nlm.nih.gov:80/entrez/query.fcgi?cmd=Retrieve&db=Nucleotid
e&list_uids=11993535&dopt=GenBank">gb|AF306870.1|AF306870</a>   Brachyramphus
brevirostris haplotype...    <a href = #11993535> 50</a>   2e-05
<a
href="http://www.ncbi.nlm.nih.gov:80/entrez/query.fcgi?cmd=Retrieve&db=Nucleotid
e&list_uids=11993533&dopt=GenBank">gb|AF306869.1|AF306869</a>   Brachyramphus
brevirostris haplotype...    <a href = #11993533> 50</a>   2e-05
<a
href="http://www.ncbi.nlm.nih.gov:80/entrez/query.fcgi?cmd=Retrieve&db=Nucleotid
e&list_uids=11993531&dopt=GenBank">gb|AF306868.1|AF306868</a>   Brachyramphus
brevirostris haplotype...    <a href = #11993531> 50</a>   2e-05
<a
href="http://www.ncbi.nlm.nih.gov:80/entrez/query.fcgi?cmd=Retrieve&db=Nucleotid
e&list_uids=03445513&dopt=GenBank">gb|AF010406.1|AF010406</a>   Ovis aries
complete mitochondrial ge...    <a href = #3445513> 50</a>   2e-05
<a
href="http://www.ncbi.nlm.nih.gov:80/entrez/query.fcgi?cmd=Retrieve&db=Nucleotid
e&list_uids=11141464&dopt=GenBank">gb|AF248662.1|AF248662</a>   Gryllus
campestris haplotype 2 cytoc...    <a href = #11141464> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotide&list_uids=11141462&dopt=GenBank">gb|AF248661.1|AF248661</a>   Gryllus campestris haplotype 1 cytoc...   <a href = #11141462> 50</a>  2e-05
<a href="http://www.ncbi.nlm.nih.gov:80/entrez/query.fcgi?cmd=Retrieve&db=Nucleotide&list_uids=11139383&dopt=GenBank">gb|AF096462.1|AF096462</a>   Rhipidura albicollis cytochrome b ge...   <a href = #11139383> 50</a>  2e-05
<a href="http://www.ncbi.nlm.nih.gov:80/entrez/query.fcgi?cmd=Retrieve&db=Nucleotide&list_uids=11023426&dopt=GenBank">gb|AF283644.1|AF283644</a>   Elaphe obsoleta cytochrome b gene, c...   <a href = #11023426> 50</a>  2e-05
<a href="http://www.ncbi.nlm.nih.gov:80/entrez/query.fcgi?cmd=Retrieve&db=Nucleotide&list_uids=11023424&dopt=GenBank">gb|AF283643.1|AF283643</a>   Elaphe obsoleta cytochrome b gene, c...   <a href = #11023424> 50</a>  2e-05
<a href="http://www.ncbi.nlm.nih.gov:80/entrez/query.fcgi?cmd=Retrieve&db=Nucleotide&list_uids=11023422&dopt=GenBank">gb|AF283642.1|AF283642</a>   Elaphe obsoleta cytochrome b gene, c...   <a href = #11023422> 50</a>  2e-05
<a href="http://www.ncbi.nlm.nih.gov:80/entrez/query.fcgi?cmd=Retrieve&db=Nucleotide&list_uids=11023420&dopt=GenBank">gb|AF283641.1|AF283641</a>   Elaphe obsoleta cytochrome b gene, c...   <a href = #11023420> 50</a>  2e-05
<a href="http://www.ncbi.nlm.nih.gov:80/entrez/query.fcgi?cmd=Retrieve&db=Nucleotide&list_uids=11023418&dopt=GenBank">gb|AF283640.1|AF283640</a>   Elaphe obsoleta cytochrome b gene, c...   <a href = #11023418> 50</a>  2e-05
<a href="http://www.ncbi.nlm.nih.gov:80/entrez/query.fcgi?cmd=Retrieve&db=Nucleotide&list_uids=11023416&dopt=GenBank">gb|AF283639.1|AF283639</a>   Elaphe obsoleta cytochrome b gene, c...   <a href = #11023416> 50</a>  2e-05
<a href="http://www.ncbi.nlm.nih.gov:80/entrez/query.fcgi?cmd=Retrieve&db=Nucleotide&list_uids=11023412&dopt=GenBank">gb|AF283637.1|AF283637</a>   Elaphe obsoleta LSUMZ 45359 cytochro...   <a href = #11023412> 50</a>  2e-05
<a href="http://www.ncbi.nlm.nih.gov:80/entrez/query.fcgi?cmd=Retrieve&db=Nucleotide&list_uids=11023410&dopt=GenBank">gb|AF283636.1|AF283636</a>   Elaphe obsoleta LSUMZ 44662 cytochro...   <a href = #11023410> 50</a>  2e-05
<a href="http://www.ncbi.nlm.nih.gov:80/entrez/query.fcgi?cmd=Retrieve&db=Nucleotide&list_uids=11023408&dopt=GenBank">gb|AF283635.1|AF283635</a>   Elaphe obsoleta LSUMZ 40443 cytochro...   <a href = #11023408> 50</a>  2e-05
<a href="http://www.ncbi.nlm.nih.gov:80/entrez/query.fcgi?cmd=Retrieve&db=Nucleotide&list_uids=11023406&dopt=GenBank">gb|AF283634.1|AF283634</a>   Elaphe obsoleta LSUMZ 44335 cytochro...   <a href = #11023406> 50</a>  2e-05
<a href="http://www.ncbi.nlm.nih.gov:80/entrez/query.fcgi?cmd=Retrieve&db=Nucleotide&list_uids=11023404&dopt=GenBank">gb|AF283633.1|AF283633</a>   Elaphe obsoleta LSUMZ 42624 cytochro...   <a href = #11023404> 50</a>  2e-05
<a href="http://www.ncbi.nlm.nih.gov:80/entrez/query.fcgi?cmd=Retrieve&db=Nucleotide&list_uids=11023402&dopt=GenBank">gb|AF283632.1|AF283632</a>   Elaphe obsoleta LSUMZ H1911 cytochro...   <a href = #11023402> 50</a>  2e-05
<a href="http://www.ncbi.nlm.nih.gov:80/entrez/query.fcgi?cmd=Retrieve&db=Nucleotide
```

```
<a
href="http://www.ncbi.nlm.nih.gov:80/entrez/query.fcgi?cmd=Retrieve&db=Nucleotid
e&list_uids=11023400&dopt=GenBank">gb|AF283631.1|AF283631</a>   Elaphe obsoleta
LSUMZ 41197 cytochro...    <a href = #11023400> 50</a>   2e-05
<a
href="http://www.ncbi.nlm.nih.gov:80/entrez/query.fcgi?cmd=Retrieve&db=Nucleotid
e&list_uids=11023398&dopt=GenBank">gb|AF283630.1|AF283630</a>   Elaphe obsoleta
LSUMZ 41189 cytochro...    <a href = #11023398> 50</a>   2e-05
<a
href="http://www.ncbi.nlm.nih.gov:80/entrez/query.fcgi?cmd=Retrieve&db=Nucleotid
e&list_uids=11023396&dopt=GenBank">gb|AF283629.1|AF283629</a>   Elaphe obsoleta
LSUMZ 41188 cytochro...    <a href = #11023396> 50</a>   2e-05
<a
href="http://www.ncbi.nlm.nih.gov:80/entrez/query.fcgi?cmd=Retrieve&db=Nucleotid
e&list_uids=11023394&dopt=GenBank">gb|AF283628.1|AF283628</a>   Elaphe obsoleta
LSUMZ 41187 cytochro...    <a href = #11023394> 50</a>   2e-05
<a
href="http://www.ncbi.nlm.nih.gov:80/entrez/query.fcgi?cmd=Retrieve&db=Nucleotid
e&list_uids=11023392&dopt=GenBank">gb|AF283627.1|AF283627</a>   Elaphe obsoleta
LSUMZ 41186 cytochro...    <a href = #11023392> 50</a>   2e-05
<a
href="http://www.ncbi.nlm.nih.gov:80/entrez/query.fcgi?cmd=Retrieve&db=Nucleotid
e&list_uids=11023390&dopt=GenBank">gb|AF283626.1|AF283626</a>   Elaphe obsoleta
LSUMZ 40943 cytochro...    <a href = #11023390> 50</a>   2e-05
<a
href="http://www.ncbi.nlm.nih.gov:80/entrez/query.fcgi?cmd=Retrieve&db=Nucleotid
e&list_uids=11023388&dopt=GenBank">gb|AF283625.1|AF283625</a>   Elaphe obsoleta
LSUMZ 37499 cytochro...    <a href = #11023388> 50</a>   2e-05
<a
href="http://www.ncbi.nlm.nih.gov:80/entrez/query.fcgi?cmd=Retrieve&db=Nucleotid
e&list_uids=11023386&dopt=GenBank">gb|AF283624.1|AF283624</a>   Elaphe obsoleta
LSUMZ 44480 cytochro...    <a href = #11023386> 50</a>   2e-05
<a
href="http://www.ncbi.nlm.nih.gov:80/entrez/query.fcgi?cmd=Retrieve&db=Nucleotid
e&list_uids=11023384&dopt=GenBank">gb|AF283623.1|AF283623</a>   Elaphe obsoleta
LSUMZ 44451 cytochro...    <a href = #11023384> 50</a>   2e-05
<a
href="http://www.ncbi.nlm.nih.gov:80/entrez/query.fcgi?cmd=Retrieve&db=Nucleotid
e&list_uids=11023382&dopt=GenBank">gb|AF283622.1|AF283622</a>   Elaphe obsoleta
LSUMZ 40444 cytochro...    <a href = #11023382> 50</a>   2e-05
<a
href="http://www.ncbi.nlm.nih.gov:80/entrez/query.fcgi?cmd=Retrieve&db=Nucleotid
e&list_uids=11023380&dopt=GenBank">gb|AF283621.1|AF283621</a>   Elaphe obsoleta
LSUMZ 39925 cytochro...    <a href = #11023380> 50</a>   2e-05
<a
href="http://www.ncbi.nlm.nih.gov:80/entrez/query.fcgi?cmd=Retrieve&db=Nucleotid
e&list_uids=11023378&dopt=GenBank">gb|AF283620.1|AF283620</a>   Elaphe obsoleta
LSUMZ 39163 cytochro...    <a href = #11023378> 50</a>   2e-05
<a
href="http://www.ncbi.nlm.nih.gov:80/entrez/query.fcgi?cmd=Retrieve&db=Nucleotid
e&list_uids=11023376&dopt=GenBank">gb|AF283619.1|AF283619</a>   Elaphe obsoleta
LSUMZ39162 cytochrom...    <a href = #11023376> 50</a>   2e-05
<a
href="http://www.ncbi.nlm.nih.gov:80/entrez/query.fcgi?cmd=Retrieve&db=Nucleotid
e&list_uids=11023374&dopt=GenBank">gb|AF283618.1|AF283618</a>   Elaphe obsoleta
LSUMZ H15896 cytochr...    <a href = #11023374> 50</a>   2e-05
<a
href="http://www.ncbi.nlm.nih.gov:80/entrez/query.fcgi?cmd=Retrieve&db=Nucleotid
```

```
e&list_uids=11023372&dopt=GenBank">gb|AF283617.1|AF283617</a>   Elaphe obsoleta
LSUMZ H15892 cytochr...     <a href = #11023372> 50</a>    2e-05
<a
href="http://www.ncbi.nlm.nih.gov:80/entrez/query.fcgi?cmd=Retrieve&db=Nucleotid
e&list_uids=11023370&dopt=GenBank">gb|AF283616.1|AF283616</a>   Elaphe obsoleta
LSUMZ H15891 cytochro...    <a href = #11023370> 50</a>    2e-05
<a
href="http://www.ncbi.nlm.nih.gov:80/entrez/query.fcgi?cmd=Retrieve&db=Nucleotid
e&list_uids=11023368&dopt=GenBank">gb|AF283615.1|AF283615</a>   Elaphe obsoleta
LSUMZ H15890 cytochr...     <a href = #11023368> 50</a>    2e-05
<a
href="http://www.ncbi.nlm.nih.gov:80/entrez/query.fcgi?cmd=Retrieve&db=Nucleotid
e&list_uids=11023366&dopt=GenBank">gb|AF283614.1|AF283614</a>   Elaphe obsoleta
LSUMZ H15889 cytochr...     <a href = #11023366> 50</a>    2e-05
<a
href="http://www.ncbi.nlm.nih.gov:80/entrez/query.fcgi?cmd=Retrieve&db=Nucleotid
e&list_uids=11023364&dopt=GenBank">gb|AF283613.1|AF283613</a>   Elaphe obsoleta
LSUMZ H15888 cytochr...     <a href = #11023364> 50</a>    2e-05
<a
href="http://www.ncbi.nlm.nih.gov:80/entrez/query.fcgi?cmd=Retrieve&db=Nucleotid
e&list_uids=11023362&dopt=GenBank">gb|AF283612.1|AF283612</a>   Elaphe obsoleta
LSUMZ H15884 cytochr...     <a href = #11023362> 50</a>    2e-05
<a
href="http://www.ncbi.nlm.nih.gov:80/entrez/query.fcgi?cmd=Retrieve&db=Nucleotid
e&list_uids=11023360&dopt=GenBank">gb|AF283611.1|AF283611</a>   Elaphe obsoleta
LSUMZ H15031 cytochr...     <a href = #11023360> 50</a>    2e-05
<a
href="http://www.ncbi.nlm.nih.gov:80/entrez/query.fcgi?cmd=Retrieve&db=Nucleotid
e&list_uids=11023358&dopt=GenBank">gb|AF283610.1|AF283610</a>   Elaphe obsoleta
LSUMZ H15030 cytochr...     <a href = #11023358> 50</a>    2e-05
<a
href="http://www.ncbi.nlm.nih.gov:80/entrez/query.fcgi?cmd=Retrieve&db=Nucleotid
e&list_uids=11023356&dopt=GenBank">gb|AF283609.1|AF283609</a>   Elaphe obsoleta
CAS 169468 cytochrom...     <a href = #11023356> 50</a>    2e-05
<a
href="http://www.ncbi.nlm.nih.gov:80/entrez/query.fcgi?cmd=Retrieve&db=Nucleotid
e&list_uids=11023354&dopt=GenBank">gb|AF283608.1|AF283608</a>   Elaphe obsoleta
LSUMZ H14782 cytochr...     <a href = #11023354> 50</a>    2e-05
<a
href="http://www.ncbi.nlm.nih.gov:80/entrez/query.fcgi?cmd=Retrieve&db=Nucleotid
e&list_uids=11023352&dopt=GenBank">gb|AF283607.1|AF283607</a>   Elaphe obsoleta
LSUMZ H14781 cytochr...     <a href = #11023352> 50</a>    2e-05
<a
href="http://www.ncbi.nlm.nih.gov:80/entrez/query.fcgi?cmd=Retrieve&db=Nucleotid
e&list_uids=11023350&dopt=GenBank">gb|AF283606.1|AF283606</a>   Elaphe obsoleta
LSUMZ H14724 cytochr...     <a href = #11023350> 50</a>    2e-05
<a
href="http://www.ncbi.nlm.nih.gov:80/entrez/query.fcgi?cmd=Retrieve&db=Nucleotid
e&list_uids=11023348&dopt=GenBank">gb|AF283605.1|AF283605</a>   Elaphe obsoleta
cytochrome b gene, c...     <a href = #11023348> 50</a>    2e-05
<a
href="http://www.ncbi.nlm.nih.gov:80/entrez/query.fcgi?cmd=Retrieve&db=Nucleotid
e&list_uids=11023346&dopt=GenBank">gb|AF283604.1|AF283604</a>   Elaphe obsoleta
cytochrome b gene, c...     <a href = #11023346> 50</a>    2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=11023344&dopt=GenBank">gb|AF283603.1|AF283603</a>   Elaphe obsoleta
cytochrome b gene, c...      <a href = #11023344> 50</a>  2e-05
<a
href="http://www.ncbi.nlm.nih.gov:80/entrez/query.fcgi?cmd=Retrieve&db=Nucleotid
e&list_uids=11023342&dopt=GenBank">gb|AF283602.1|AF283602</a>   Elaphe obsoleta
LSUMZ H3388 cytochro...      <a href = #11023342> 50</a>  2e-05
<a
href="http://www.ncbi.nlm.nih.gov:80/entrez/query.fcgi?cmd=Retrieve&db=Nucleotid
e&list_uids=11023340&dopt=GenBank">gb|AF283601.1|AF283601</a>   Elaphe obsoleta
LSUMZ H3385 cytochro...      <a href = #11023340> 50</a>  2e-05
<a
href="http://www.ncbi.nlm.nih.gov:80/entrez/query.fcgi?cmd=Retrieve&db=Nucleotid
e&list_uids=11023338&dopt=GenBank">gb|AF283600.1|AF283600</a>   Elaphe obsoleta
LSUMZ H3384 cytochro...      <a href = #11023338> 50</a>  2e-05
<a
href="http://www.ncbi.nlm.nih.gov:80/entrez/query.fcgi?cmd=Retrieve&db=Nucleotid
e&list_uids=11023336&dopt=GenBank">gb|AF283599.1|AF283599</a>   Elaphe bairdi
LSUMZ H3382 cytochrome...    <a href = #11023336> 50</a>  2e-05
<a
href="http://www.ncbi.nlm.nih.gov:80/entrez/query.fcgi?cmd=Retrieve&db=Nucleotid
e&list_uids=11023334&dopt=GenBank">gb|AF283598.1|AF283598</a>   Elaphe bairdi
LSUMZ H3381 cytochrome...    <a href = #11023334> 50</a>  2e-05
<a
href="http://www.ncbi.nlm.nih.gov:80/entrez/query.fcgi?cmd=Retrieve&db=Nucleotid
e&list_uids=11023332&dopt=GenBank">gb|AF283597.1|AF283597</a>   Elaphe obsoleta
LSUMZ H3379 cytochro...      <a href = #11023332> 50</a>  2e-05
<a
href="http://www.ncbi.nlm.nih.gov:80/entrez/query.fcgi?cmd=Retrieve&db=Nucleotid
e&list_uids=11023330&dopt=GenBank">gb|AF283596.1|AF283596</a>   Elaphe obsoleta
LSUMZ 39816 cytochro...      <a href = #11023330> 50</a>  2e-05
<a
href="http://www.ncbi.nlm.nih.gov:80/entrez/query.fcgi?cmd=Retrieve&db=Nucleotid
e&list_uids=11023328&dopt=GenBank">gb|AF283595.1|AF283595</a>   Elaphe obsoleta
LSUMZ H3376 cytochro...      <a href = #11023328> 50</a>  2e-05
<a
href="http://www.ncbi.nlm.nih.gov:80/entrez/query.fcgi?cmd=Retrieve&db=Nucleotid
e&list_uids=11023326&dopt=GenBank">gb|AF283594.1|AF283594</a>   Elaphe obsoleta
LSUMZ H3345 cytochro...      <a href = #11023326> 50</a>  2e-05
<a
href="http://www.ncbi.nlm.nih.gov:80/entrez/query.fcgi?cmd=Retrieve&db=Nucleotid
e&list_uids=11023324&dopt=GenBank">gb|AF283593.1|AF283593</a>   Elaphe obsoleta
LSUMZ H3309 cytochro...      <a href = #11023324> 50</a>  2e-05
<a
href="http://www.ncbi.nlm.nih.gov:80/entrez/query.fcgi?cmd=Retrieve&db=Nucleotid
e&list_uids=11023322&dopt=GenBank">gb|AF283592.1|AF283592</a>   Elaphe obsoleta
LSUMZ H3306 cytochro...      <a href = #11023322> 50</a>  2e-05
<a
href="http://www.ncbi.nlm.nih.gov:80/entrez/query.fcgi?cmd=Retrieve&db=Nucleotid
e&list_uids=11023320&dopt=GenBank">gb|AF283591.1|AF283591</a>   Elaphe obsoleta
LSUMZ H3276 cytochro...      <a href = #11023320> 50</a>  2e-05
<a
href="http://www.ncbi.nlm.nih.gov:80/entrez/query.fcgi?cmd=Retrieve&db=Nucleotid
e&list_uids=11023318&dopt=GenBank">gb|AF283590.1|AF283590</a>   Elaphe obsoleta
LSUMZ H3246 cytochro...      <a href = #11023318> 50</a>  2e-05
<a
href="http://www.ncbi.nlm.nih.gov:80/entrez/query.fcgi?cmd=Retrieve&db=Nucleotid
```

```
e&list_uids=11023316&dopt=GenBank">gb|AF283589.1|AF283589</a>   Elaphe obsoleta
LSUMZ H3212 cytochro...    <a href = #11023316> 50</a>   2e-05
<a
href="http://www.ncbi.nlm.nih.gov:80/entrez/query.fcgi?cmd=Retrieve&db=Nucleotid
e&list_uids=11023314&dopt=GenBank">gb|AF283588.1|AF283588</a>   Elaphe obsoleta
LSUMZ H3209 cytochro...    <a href = #11023314> 50</a>   2e-05
<a
href="http://www.ncbi.nlm.nih.gov:80/entrez/query.fcgi?cmd=Retrieve&db=Nucleotid
e&list_uids=11023312&dopt=GenBank">gb|AF283587.1|AF283587</a>   Elaphe obsoleta
LSUMZ H3206 cytochro...    <a href = #11023312> 50</a>   2e-05
<a
href="http://www.ncbi.nlm.nih.gov:80/entrez/query.fcgi?cmd=Retrieve&db=Nucleotid
e&list_uids=11023310&dopt=GenBank">gb|AF283586.1|AF283586</a>   Elaphe obsoleta
LSUMZ H3191 cytochro...    <a href = #11023310> 50</a>   2e-05
<a
href="http://www.ncbi.nlm.nih.gov:80/entrez/query.fcgi?cmd=Retrieve&db=Nucleotid
e&list_uids=11023308&dopt=GenBank">gb|AF283585.1|AF283585</a>   Elaphe obsoleta
LSUMZ H3190 cytochro...    <a href = #11023308> 50</a>   2e-05
<a
href="http://www.ncbi.nlm.nih.gov:80/entrez/query.fcgi?cmd=Retrieve&db=Nucleotid
e&list_uids=11023306&dopt=GenBank">gb|AF283584.1|AF283584</a>   Elaphe obsoleta
LSUMZ H3189 cytochro...    <a href = #11023306> 50</a>   2e-05
<a
href="http://www.ncbi.nlm.nih.gov:80/entrez/query.fcgi?cmd=Retrieve&db=Nucleotid
e&list_uids=11023304&dopt=GenBank">gb|AF283583.1|AF283583</a>   Elaphe obsoleta
LSUMZ H3188 cytochro...    <a href = #11023304> 50</a>   2e-05
<a
href="http://www.ncbi.nlm.nih.gov:80/entrez/query.fcgi?cmd=Retrieve&db=Nucleotid
e&list_uids=11023302&dopt=GenBank">gb|AF283582.1|AF283582</a>   Elaphe obsoleta
LSUMZ H3186 cytochro...    <a href = #11023302> 50</a>   2e-05
<a
href="http://www.ncbi.nlm.nih.gov:80/entrez/query.fcgi?cmd=Retrieve&db=Nucleotid
e&list_uids=11023300&dopt=GenBank">gb|AF283581.1|AF283581</a>   Elaphe obsoleta
LSUMZ H3169 cytochro...    <a href = #11023300> 50</a>   2e-05
<a
href="http://www.ncbi.nlm.nih.gov:80/entrez/query.fcgi?cmd=Retrieve&db=Nucleotid
e&list_uids=11023298&dopt=GenBank">gb|AF283580.1|AF283580</a>   Elaphe obsoleta
CAS 203083 cytochrom...    <a href = #11023298> 50</a>   2e-05
<a
href="http://www.ncbi.nlm.nih.gov:80/entrez/query.fcgi?cmd=Retrieve&db=Nucleotid
e&list_uids=11023296&dopt=GenBank">gb|AF283579.1|AF283579</a>   Elaphe obsoleta
CAS 203079 cytochrom...    <a href = #11023296> 50</a>   2e-05
<a
href="http://www.ncbi.nlm.nih.gov:80/entrez/query.fcgi?cmd=Retrieve&db=Nucleotid
e&list_uids=11023294&dopt=GenBank">gb|AF283578.1|AF283578</a>   Elaphe obsoleta
LSUMZ H2286 cytochro...    <a href = #11023294> 50</a>   2e-05
<a
href="http://www.ncbi.nlm.nih.gov:80/entrez/query.fcgi?cmd=Retrieve&db=Nucleotid
e&list_uids=11023292&dopt=GenBank">gb|AF283577.1|AF283577</a>   Elaphe obsoleta
CAS 208631 cytochrom...    <a href = #11023292> 50</a>   2e-05
<a
href="http://www.ncbi.nlm.nih.gov:80/entrez/query.fcgi?cmd=Retrieve&db=Nucleotid
e&list_uids=11023290&dopt=GenBank">gb|AF283576.1|AF283576</a>   Elaphe obsoleta
LSUMZ H2229 cytochro...    <a href = #11023290> 50</a>   2e-05
<a
href="http://www.ncbi.nlm.nih.gov:80/entrez/query.fcgi?cmd=Retrieve&db=Nucleotid
```

```
e&list_uids=10998365&dopt=GenBank">gb|AF187030.1|AF187030</a>  Rhinophylla
pumilio isolate TK46001 ...    <a href = #10998365> 50</a>   2e-05
<a
href="http://www.ncbi.nlm.nih.gov:80/entrez/query.fcgi?cmd=Retrieve&db=Nucleotid
e&list_uids=10799225&dopt=GenBank">gb|AF310052.1|AF310052</a>  Poospiza
hispaneolensis cytochrome b...    <a href = #10799225> 50</a>   2e-05
<a
href="http://www.ncbi.nlm.nih.gov:80/entrez/query.fcgi?cmd=Retrieve&db=Nucleotid
e&list_uids=10799213&dopt=GenBank">gb|AF310046.1|AF310046</a>  Volatinia
jacarina cytochrome b gene...    <a href = #10799213> 50</a>   2e-05
<a
href="http://www.ncbi.nlm.nih.gov:80/entrez/query.fcgi?cmd=Retrieve&db=Nucleotid
e&list_uids=10443579&dopt=GenBank">gb|AF171919.1|AF171919</a>  Deinagkistrodon
acutus cytochrome b ...    <a href = #10443579> 50</a>   2e-05
<a
href="http://www.ncbi.nlm.nih.gov:80/entrez/query.fcgi?cmd=Retrieve&db=Nucleotid
e&list_uids=10443535&dopt=GenBank">gb|AF171897.1|AF171897</a>  Trimeresurus
mucrosquamatus cytb gen...    <a href = #10443535> 50</a>   2e-05
<a
href="http://www.ncbi.nlm.nih.gov:80/entrez/query.fcgi?cmd=Retrieve&db=Nucleotid
e&list_uids=09972117&dopt=GenBank">gb|AF290174.1|AF290174</a>  Agelaius cyanopus
cytochrome b (cytb...    <a href = #9972117> 50</a>   2e-05
<a
href="http://www.ncbi.nlm.nih.gov:80/entrez/query.fcgi?cmd=Retrieve&db=Nucleotid
e&list_uids=09972115&dopt=GenBank">gb|AF290173.1|AF290173</a>  Agelaius
phoeniceus cytochrome b (cy...    <a href = #9972115> 50</a>   2e-05
<a
href="http://www.ncbi.nlm.nih.gov:80/entrez/query.fcgi?cmd=Retrieve&db=Nucleotid
e&list_uids=09972111&dopt=GenBank">gb|AF290171.1|AF290171</a>  Quiscalus major
cytochrome b (cytb) ...    <a href = #9972111> 50</a>   2e-05
<a
href="http://www.ncbi.nlm.nih.gov:80/entrez/query.fcgi?cmd=Retrieve&db=Nucleotid
e&list_uids=09972109&dopt=GenBank">gb|AF290170.1|AF290170</a>  Amblycercus
holosericeus cytochrome ...    <a href = #9972109> 50</a>   2e-05
<a
href="http://www.ncbi.nlm.nih.gov:80/entrez/query.fcgi?cmd=Retrieve&db=Nucleotid
e&list_uids=09972069&dopt=GenBank">gb|AF290150.1|AF290150</a>  Volatinia
jacarina cytochrome b (cyt...    <a href = #9972069> 50</a>   2e-05
<a
href="http://www.ncbi.nlm.nih.gov:80/entrez/query.fcgi?cmd=Retrieve&db=Nucleotid
e&list_uids=09789155&dopt=GenBank">gb|AF176252.1|AF176252</a>  Reithrodontomys
zacatecae cytochrome...    <a href = #9789155> 50</a>   2e-05
<a
href="http://www.ncbi.nlm.nih.gov:80/entrez/query.fcgi?cmd=Retrieve&db=Nucleotid
e&list_uids=09789153&dopt=GenBank">gb|AF176251.1|AF176251</a>  Reithrodontomys
zacatecae cytochrome...    <a href = #9789153> 50</a>   2e-05
<a
href="http://www.ncbi.nlm.nih.gov:80/entrez/query.fcgi?cmd=Retrieve&db=Nucleotid
e&list_uids=06690577&dopt=GenBank">gb|AF163907.1|AF163907</a>  Microtus
xanthognathus cytochrome b ...    <a href = #6690577> 50</a>   2e-05
<a
href="http://www.ncbi.nlm.nih.gov:80/entrez/query.fcgi?cmd=Retrieve&db=Nucleotid
e&list_uids=06690574&dopt=GenBank">gb|AF163904.1|AF163904</a>  Microtus
pinetorum cytochrome b gene...    <a href = #6690574> 50</a>   2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=06690571&dopt=GenBank">gb|AF163901.1|AF163901</a>  Microtus
ochrogaster cytochrome b ge...    <a href = #6690571> 50</a>   2e-05
<a
href="http://www.ncbi.nlm.nih.gov:80/entrez/query.fcgi?cmd=Retrieve&db=Nucleotid
e&list_uids=06690569&dopt=GenBank">gb|AF163899.1|AF163899</a>  Microtus miurus
cytochrome b gene, c...    <a href = #6690569> 50</a>   2e-05
<a
href="http://www.ncbi.nlm.nih.gov:80/entrez/query.fcgi?cmd=Retrieve&db=Nucleotid
e&list_uids=09695295&dopt=GenBank">gb|AF163891.1|AF163891</a>  Microtus
californicus cytochrome B (...    <a href = #9695295> 50</a>   2e-05
<a
href="http://www.ncbi.nlm.nih.gov:80/entrez/query.fcgi?cmd=Retrieve&db=Nucleotid
e&list_uids=09695293&dopt=GenBank">gb|AF163890.1|AF163890</a>  Microtus
abbreviatus cytochrome B (c...    <a href = #9695293> 50</a>   2e-05
<a
href="http://www.ncbi.nlm.nih.gov:80/entrez/query.fcgi?cmd=Retrieve&db=Nucleotid
e&list_uids=09652375&dopt=GenBank">gb|AF288524.1|AF288524</a>  Dipsochelys
dussumieri isolate Germa...    <a href = #9652375> 50</a>   2e-05
<a
href="http://www.ncbi.nlm.nih.gov:80/entrez/query.fcgi?cmd=Retrieve&db=Nucleotid
e&list_uids=09652373&dopt=GenBank">gb|AF288523.1|AF288523</a>  Dipsochelys
dussumieri isolate white...    <a href = #9652373> 50</a>   2e-05
<a
href="http://www.ncbi.nlm.nih.gov:80/entrez/query.fcgi?cmd=Retrieve&db=Nucleotid
e&list_uids=09652371&dopt=GenBank">gb|AF288522.1|AF288522</a>  Dipsochelys
dussumieri isolate Aldy ...    <a href = #9652371> 50</a>   2e-05
<a
href="http://www.ncbi.nlm.nih.gov:80/entrez/query.fcgi?cmd=Retrieve&db=Nucleotid
e&list_uids=07573897&dopt=GenBank">gb|AF123530.1|AF123530</a>  Psilopogon
pyrolophus cytochrome b (...    <a href = #7573897> 50</a>   2e-05
<a
href="http://www.ncbi.nlm.nih.gov:80/entrez/query.fcgi?cmd=Retrieve&db=Nucleotid
e&list_uids=07573861&dopt=GenBank">gb|AF123512.1|AF123512</a>  Eubucco
bourcierii tucinkae cytochro...    <a href = #7573861> 50</a>   2e-05
<a
href="http://www.ncbi.nlm.nih.gov:80/entrez/query.fcgi?cmd=Retrieve&db=Nucleotid
e&list_uids=07861886&dopt=GenBank">gb|AF206548.1|AF206548</a>  Adolfus
vauereselli cytochrome b gen...    <a href = #7861886> 50</a>   2e-05
<a
href="http://www.ncbi.nlm.nih.gov:80/entrez/query.fcgi?cmd=Retrieve&db=Nucleotid
e&list_uids=06469790&dopt=GenBank">gb|AF197867.1|AF197867</a>  Gymnorhina
tibicen cytochrome b gene...    <a href = #6469790> 50</a>   2e-05
<a
href="http://www.ncbi.nlm.nih.gov:80/entrez/query.fcgi?cmd=Retrieve&db=Nucleotid
e&list_uids=07690342&dopt=GenBank">gb|U63397.2|SEU63397</a>  Sitta europaea
cytochrome b gene, part...    <a href = #7690342> 50</a>   2e-05
<a
href="http://www.ncbi.nlm.nih.gov:80/entrez/query.fcgi?cmd=Retrieve&db=Nucleotid
e&list_uids=05835568&dopt=GenBank">ref|NC_001945.1|</a>  Dinodon semicarinatus
mitochondrion, compl...    <a href = #5835568> 50</a>   2e-05
<a
href="http://www.ncbi.nlm.nih.gov:80/entrez/query.fcgi?cmd=Retrieve&db=Nucleotid
e&list_uids=05835429&dopt=GenBank">ref|NC_001821.1|</a>  Dasypus novemcinctus
mitochondrion, comple...    <a href = #5835429> 50</a>   2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=07648602&dopt=GenBank">gb|AF141217.1|AF141217</a>    Dasymys incomtus
country Tanzania cy...      <a href = #7648602> 50</a>   2e-05
<a
href="http://www.ncbi.nlm.nih.gov:80/entrez/query.fcgi?cmd=Retrieve&db=Nucleotid
e&list_uids=07243470&dopt=GenBank">gb|AF201615.1|AF201615</a>    Pantodon
buchholzi cyotchrome b gene...      <a href = #7243470> 50</a>   2e-05
<a
href="http://www.ncbi.nlm.nih.gov:80/entrez/query.fcgi?cmd=Retrieve&db=Nucleotid
e&list_uids=05596403&dopt=GenBank">gb|AF077920.1|AF077920</a>    Bombus nevadensis
cytochrome b gene,...      <a href = #5596403> 50</a>   2e-05
<a
href="http://www.ncbi.nlm.nih.gov:80/entrez/query.fcgi?cmd=Retrieve&db=Nucleotid
e&list_uids=07406984&dopt=GenBank">gb|AF190632.1|AF190632</a>    Oreamnos
americanus cytochrome b (cy...      <a href = #7406984> 50</a>   2e-05
<a
href="http://www.ncbi.nlm.nih.gov:80/entrez/query.fcgi?cmd=Retrieve&db=Nucleotid
e&list_uids=00336430&dopt=GenBank">gb|J01394.1|BOVMT</a>    Bos taurus
mitochondrion, complete genome      <a href = #336430> 50</a>   2e-05
<a
href="http://www.ncbi.nlm.nih.gov:80/entrez/query.fcgi?cmd=Retrieve&db=Nucleotid
e&list_uids=07208260&dopt=GenBank">gb|AF193830.1|AF193830</a>    Cochlearius
cochlearius cytochrome b...      <a href = #7208260> 50</a>   2e-05
<a
href="http://www.ncbi.nlm.nih.gov:80/entrez/query.fcgi?cmd=Retrieve&db=Nucleotid
e&list_uids=04099741&dopt=GenBank">gb|U89181.1|CAU89181</a>    Chlorostilbon
aureoventris cytochrome ...      <a href = #4099741> 50</a>   2e-05
<a
href="http://www.ncbi.nlm.nih.gov:80/entrez/query.fcgi?cmd=Retrieve&db=Nucleotid
e&list_uids=04099727&dopt=GenBank">gb|U89171.1|AFU89171</a>    Asio flammeus
cytochrome b (cytb) gene...      <a href = #4099727> 50</a>   2e-05
<a
href="http://www.ncbi.nlm.nih.gov:80/entrez/query.fcgi?cmd=Retrieve&db=Nucleotid
e&list_uids=07141212&dopt=GenBank">gb|AF217833.1|AF217833</a>    Homoroselaps
lacteus cytochrome b ge...      <a href = #7141212> 50</a>   2e-05
<a
href="http://www.ncbi.nlm.nih.gov:80/entrez/query.fcgi?cmd=Retrieve&db=Nucleotid
e&list_uids=07141190&dopt=GenBank">gb|AF217822.1|AF217822</a>    Hydrophis semperi
cytochrome b gene,...      <a href = #7141190> 50</a>   2e-05
<a
href="http://www.ncbi.nlm.nih.gov:80/entrez/query.fcgi?cmd=Retrieve&db=Nucleotid
e&list_uids=07141172&dopt=GenBank">gb|AF217813.1|AF217813</a>    Acanthophis
antarcticus cytochrome b...      <a href = #7141172> 50</a>   2e-05
<a
href="http://www.ncbi.nlm.nih.gov:80/entrez/query.fcgi?cmd=Retrieve&db=Nucleotid
e&list_uids=07021371&dopt=GenBank">gb|AF220408.1|AF220408</a>    Calliophis
kelloggi cytochrome b (cy...      <a href = #7021371> 50</a>   2e-05
<a
href="http://www.ncbi.nlm.nih.gov:80/entrez/query.fcgi?cmd=Retrieve&db=Nucleotid
e&list_uids=06689885&dopt=GenBank">gb|AF126430.1|AF126430</a>    Ellobius
fuscocapillus cytochrome b ...      <a href = #6689885> 50</a>   2e-05
<a
href="http://www.ncbi.nlm.nih.gov:80/entrez/query.fcgi?cmd=Retrieve&db=Nucleotid
e&list_uids=04887659&dopt=GenBank">gb|AF090337.1|AF090337</a>    Aythya americana
mitochondrion, comp...      <a href = #4887659> 50</a>   2e-05
<a
href="http://www.ncbi.nlm.nih.gov:80/entrez/query.fcgi?cmd=Retrieve&db=Nucleotid
```

```
e&list_uids=03088771&dopt=GenBank">gb|AF059111.1|AF059111</a>    Sarkidiornis
melanotos cytochrome b ...    <a href = #3088771> 50</a>    2e-05
<a
href="http://www.ncbi.nlm.nih.gov:80/entrez/query.fcgi?cmd=Retrieve&db=Nucleotid
e&list_uids=03088655&dopt=GenBank">gb|AF059053.1|AF059053</a>    Aix sponsa
cytochrome b gene, partia...    <a href = #3088655> 50</a>    2e-05
<a
href="http://www.ncbi.nlm.nih.gov:80/entrez/query.fcgi?cmd=Retrieve&db=Nucleotid
e&list_uids=06062907&dopt=GenBank">gb|AF099308.1|AF099308</a>    Icterus wagleri
wagleri cytochrome b...    <a href = #6062907> 50</a>    2e-05
<a
href="http://www.ncbi.nlm.nih.gov:80/entrez/query.fcgi?cmd=Retrieve&db=Nucleotid
e&list_uids=06062894&dopt=GenBank">gb|AF099295.1|AF099295</a>    Icterus gularis
yucatanensis cytochr...    <a href = #6062894> 50</a>    2e-05
<a
href="http://www.ncbi.nlm.nih.gov:80/entrez/query.fcgi?cmd=Retrieve&db=Nucleotid
e&list_uids=06062893&dopt=GenBank">gb|AF099294.1|AF099294</a>    Icterus gularis
tamaulipensis cytoch...    <a href = #6062893> 50</a>    2e-05
<a
href="http://www.ncbi.nlm.nih.gov:80/entrez/query.fcgi?cmd=Retrieve&db=Nucleotid
e&list_uids=06062892&dopt=GenBank">gb|AF099293.1|AF099293</a>    Icterus gularis
gularis cytochrome b...    <a href = #6062892> 50</a>    2e-05
<a
href="http://www.ncbi.nlm.nih.gov:80/entrez/query.fcgi?cmd=Retrieve&db=Nucleotid
e&list_uids=06524786&dopt=GenBank">gb|AF160610.1|AF160610</a>    Cricetomys emini
Cemi636 cytochrome ...    <a href = #6524786> 50</a>    2e-05
<a
href="http://www.ncbi.nlm.nih.gov:80/entrez/query.fcgi?cmd=Retrieve&db=Nucleotid
e&list_uids=05777921&dopt=GenBank">gb|AF036280.1|AF036280</a>    Tragelaphus
strepsiceros cytochrome ...    <a href = #5777921> 50</a>    2e-05
<a
href="http://www.ncbi.nlm.nih.gov:80/entrez/query.fcgi?cmd=Retrieve&db=Nucleotid
e&list_uids=05777915&dopt=GenBank">gb|AF036277.1|AF036277</a>    Tragelaphus
scriptus cytochrome b (c...    <a href = #5777915> 50</a>    2e-05
<a
href="http://www.ncbi.nlm.nih.gov:80/entrez/query.fcgi?cmd=Retrieve&db=Nucleotid
e&list_uids=05777909&dopt=GenBank">gb|AF036274.1|</a>    Tetracerus quadricornis
cytochrome b (cytb) ...    <a href = #5777909> 50</a>    2e-05
<a
href="http://www.ncbi.nlm.nih.gov:80/entrez/query.fcgi?cmd=Retrieve&db=Nucleotid
e&list_uids=06456620&dopt=GenBank">gb|AF194218.1|AF194218</a>    Phrynosoma
platyrhinos cytochrome b ...    <a href = #6456620> 50</a>    2e-05
<a
href="http://www.ncbi.nlm.nih.gov:80/entrez/query.fcgi?cmd=Retrieve&db=Nucleotid
e&list_uids=06456618&dopt=GenBank">gb|AF194216.1|AF194216</a>    Urosaurus ornatus
cytochrome b gene,...    <a href = #6456618> 50</a>    2e-05
<a
href="http://www.ncbi.nlm.nih.gov:80/entrez/query.fcgi?cmd=Retrieve&db=Nucleotid
e&list_uids=05835666&dopt=GenBank">ref|NC_002009.1|</a>    Artibeus jamaicensis
mitochondrion, comple...    <a href = #5835666> 50</a>    2e-05
<a
href="http://www.ncbi.nlm.nih.gov:80/entrez/query.fcgi?cmd=Retrieve&db=Nucleotid
e&list_uids=05835554&dopt=GenBank">ref|NC_001941.1|</a>    Ovis aries
mitochondrion, complete genome    <a href = #5835554> 50</a>    2e-05
<a
href="http://www.ncbi.nlm.nih.gov:80/entrez/query.fcgi?cmd=Retrieve&db=Nucleotid
```

```
e&list_uids=05835932&dopt=GenBank">ref|NC_000877.1|</a>  Aythya americana
mitochondrion, complete g...    <a href = #5835932> 50</a>  2e-05
<a
href="http://www.ncbi.nlm.nih.gov:80/entrez/query.fcgi?cmd=Retrieve&db=Nucleotid
e&list_uids=05835498&dopt=GenBank">ref|NC_000846.1|</a>  Rhea americana
mitochondrion, complete genome   <a href = #5835498> 50</a>  2e-05
<a
href="http://www.ncbi.nlm.nih.gov:80/entrez/query.fcgi?cmd=Retrieve&db=Nucleotid
e&list_uids=00896416&dopt=GenBank">gb|U27551.1|GCU27551</a>  Grus canadensis
tabida cytochrome b (c...    <a href = #896416> 50</a>  2e-05
<a
href="http://www.ncbi.nlm.nih.gov:80/entrez/query.fcgi?cmd=Retrieve&db=Nucleotid
e&list_uids=06048478&dopt=GenBank">gb|AF089058.1|AF089058</a>  Quiscalus
quiscula cytochrome b (cyt...    <a href = #6048478> 50</a>  2e-05
<a
href="http://www.ncbi.nlm.nih.gov:80/entrez/query.fcgi?cmd=Retrieve&db=Nucleotid
e&list_uids=06048475&dopt=GenBank">gb|AF089055.1|AF089055</a>  Quiscalus major
cytochrome b (cytb) ...    <a href = #6048475> 50</a>  2e-05
<a
href="http://www.ncbi.nlm.nih.gov:80/entrez/query.fcgi?cmd=Retrieve&db=Nucleotid
e&list_uids=06048474&dopt=GenBank">gb|AF089054.1|AF089054</a>  Quiscalus
lugubris cytochrome b (cyt...    <a href = #6048474> 50</a>  2e-05
<a
href="http://www.ncbi.nlm.nih.gov:80/entrez/query.fcgi?cmd=Retrieve&db=Nucleotid
e&list_uids=06048466&dopt=GenBank">gb|AF089046.1|AF089046</a>  Oreopsar
bolivianus cytochrome b (cy...    <a href = #6048466> 50</a>  2e-05
<a
href="http://www.ncbi.nlm.nih.gov:80/entrez/query.fcgi?cmd=Retrieve&db=Nucleotid
e&list_uids=06048462&dopt=GenBank">gb|AF089042.1|AF089042</a>  Molothrus badius
cytochrome b (cytb)...    <a href = #6048462> 50</a>  2e-05
<a
href="http://www.ncbi.nlm.nih.gov:80/entrez/query.fcgi?cmd=Retrieve&db=Nucleotid
e&list_uids=06048459&dopt=GenBank">gb|AF089039.1|AF089039</a>  Macroagelaius
imthurni cytochrome b ...    <a href = #6048459> 50</a>  2e-05
<a
href="http://www.ncbi.nlm.nih.gov:80/entrez/query.fcgi?cmd=Retrieve&db=Nucleotid
e&list_uids=06048457&dopt=GenBank">gb|AF089037.1|AF089037</a>  Lampropsar
tanagrinus cytochrome b (...    <a href = #6048457> 50</a>  2e-05
<a
href="http://www.ncbi.nlm.nih.gov:80/entrez/query.fcgi?cmd=Retrieve&db=Nucleotid
e&list_uids=06048446&dopt=GenBank">gb|AF089026.1|AF089026</a>  Gymnomystax
mexicanus cytochrome b (...    <a href = #6048446> 50</a>  2e-05
<a
href="http://www.ncbi.nlm.nih.gov:80/entrez/query.fcgi?cmd=Retrieve&db=Nucleotid
e&list_uids=06048445&dopt=GenBank">gb|AF089025.1|AF089025</a>  Gnorimopsar chopi
cytochrome b (cytb...    <a href = #6048445> 50</a>  2e-05
<a
href="http://www.ncbi.nlm.nih.gov:80/entrez/query.fcgi?cmd=Retrieve&db=Nucleotid
e&list_uids=06048444&dopt=GenBank">gb|AF089024.1|AF089024</a>  Euphagus
cyanocephalus cytochrome b ...    <a href = #6048444> 50</a>  2e-05
<a
href="http://www.ncbi.nlm.nih.gov:80/entrez/query.fcgi?cmd=Retrieve&db=Nucleotid
e&list_uids=06048443&dopt=GenBank">gb|AF089023.1|AF089023</a>  Euphagus
carolinus cytochrome b (cyt...    <a href = #6048443> 50</a>  2e-05
<a
href="http://www.ncbi.nlm.nih.gov:80/entrez/query.fcgi?cmd=Retrieve&db=Nucleotid
```

```
e&list_uids=06048441&dopt=GenBank">gb|AF089021.1|AF089021</a>  Dives
warszwewiczi cytochrome b (cyt...    <a href = #6048441> 50</a>   2e-05
<a
href="http://www.ncbi.nlm.nih.gov:80/entrez/query.fcgi?cmd=Retrieve&db=Nucleotid
e&list_uids=06048440&dopt=GenBank">gb|AF089020.1|AF089020</a>  Curaeus curaeus
cytochrome b (cytb) ...    <a href = #6048440> 50</a>   2e-05
<a
href="http://www.ncbi.nlm.nih.gov:80/entrez/query.fcgi?cmd=Retrieve&db=Nucleotid
e&list_uids=06048436&dopt=GenBank">gb|AF089016.1|AF089016</a>  Amblycercus
holosericeus cytochrome ...    <a href = #6048436> 50</a>   2e-05
<a
href="http://www.ncbi.nlm.nih.gov:80/entrez/query.fcgi?cmd=Retrieve&db=Nucleotid
e&list_uids=06048433&dopt=GenBank">gb|AF089013.1|AF089013</a>  Agelaius
xanthophthalmus cytochrome ...    <a href = #6048433> 50</a>   2e-05
<a
href="http://www.ncbi.nlm.nih.gov:80/entrez/query.fcgi?cmd=Retrieve&db=Nucleotid
e&list_uids=06048432&dopt=GenBank">gb|AF089012.1|AF089012</a>  Agelaius
xanthomus cytochrome b (cyt...    <a href = #6048432> 50</a>   2e-05
<a
href="http://www.ncbi.nlm.nih.gov:80/entrez/query.fcgi?cmd=Retrieve&db=Nucleotid
e&list_uids=06048428&dopt=GenBank">gb|AF089008.1|AF089008</a>  Agelaius
phoeniceus sub-species phoe...    <a href = #6048428> 50</a>   2e-05
<a
href="http://www.ncbi.nlm.nih.gov:80/entrez/query.fcgi?cmd=Retrieve&db=Nucleotid
e&list_uids=06048426&dopt=GenBank">gb|AF089006.1|AF089006</a>  Agelaius
humeralis cytochrome b (cyt...    <a href = #6048426> 50</a>   2e-05
<a
href="http://www.ncbi.nlm.nih.gov:80/entrez/query.fcgi?cmd=Retrieve&db=Nucleotid
e&list_uids=06048425&dopt=GenBank">gb|AF089005.1|AF089005</a>  Agelaius cyanopus
cytochrome b (cytb...    <a href = #6048425> 50</a>   2e-05
<a
href="http://www.ncbi.nlm.nih.gov:80/entrez/query.fcgi?cmd=Retrieve&db=Nucleotid
e&list_uids=05579169&dopt=GenBank">gb|AF108696.1|AF108696</a>  Scolomys
juruaense cytochrome B (cyt...    <a href = #5579169> 50</a>   2e-05
<a
href="http://www.ncbi.nlm.nih.gov:80/entrez/query.fcgi?cmd=Retrieve&db=Nucleotid
e&list_uids=05579158&dopt=GenBank">gb|AF108685.1|AF108685</a>  Wiedomys
pyrrhorhinos cytochrome B (...    <a href = #5579158> 50</a>   2e-05
<a
href="http://www.ncbi.nlm.nih.gov:80/entrez/query.fcgi?cmd=Retrieve&db=Nucleotid
e&list_uids=05579150&dopt=GenBank">gb|AF108677.1|AF108677</a>  Thomasomys oreas
cytochrome B (cytB)...    <a href = #5579150> 50</a>   2e-05
<a
href="http://www.ncbi.nlm.nih.gov:80/entrez/query.fcgi?cmd=Retrieve&db=Nucleotid
e&list_uids=05918591&dopt=GenBank">gb|AF145531.1|AF145531</a>  Melanoplus foedus
cytochrome b gene,...    <a href = #5918591> 50</a>   2e-05
<a
href="http://www.ncbi.nlm.nih.gov:80/entrez/query.fcgi?cmd=Retrieve&db=Nucleotid
e&list_uids=05918571&dopt=GenBank">gb|AF145511.1|AF145511</a>  Melanoplus
angustipennis cytochrome ...    <a href = #5918571> 50</a>   2e-05
<a
href="http://www.ncbi.nlm.nih.gov:80/entrez/query.fcgi?cmd=Retrieve&db=Nucleotid
e&list_uids=02351722&dopt=GenBank">gb|U89627.1|BMU89627</a>  Bolitoglossa
marmorea cytochrome b (cy...    <a href = #2351722> 50</a>   2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=02351726&dopt=GenBank">gb|U89623.1|BPU89623</a>   Batrachoseps
pacificus cytochrome b (c...    <a href = #2351726> 50</a>    2e-05
<a
href="http://www.ncbi.nlm.nih.gov:80/entrez/query.fcgi?cmd=Retrieve&db=Nucleotid
e&list_uids=05853310&dopt=GenBank">gb|AF181470.1|AF181470</a>   Okapia johnstoni
cytochrome b gene, ...    <a href = #5853310> 50</a>    2e-05
<a
href="http://www.ncbi.nlm.nih.gov:80/entrez/query.fcgi?cmd=Retrieve&db=Nucleotid
e&list_uids=05870028&dopt=GenBank">gb|AF084075.1|AF084075</a>   Lagenorhynchus
acutus cytochrome b g...    <a href = #5870028> 50</a>    2e-05
<a
href="http://www.ncbi.nlm.nih.gov:80/entrez/query.fcgi?cmd=Retrieve&db=Nucleotid
e&list_uids=01899215&dopt=GenBank">gb|U90303.1|OMU90303</a>   Ovibos moschatus
cytochrome b (cytb) g...    <a href = #1899215> 50</a>    2e-05
<a
href="http://www.ncbi.nlm.nih.gov:80/entrez/query.fcgi?cmd=Retrieve&db=Nucleotid
e&list_uids=01899213&dopt=GenBank">gb|U90302.1|OMU90302</a>   Ovibos moschatus
cytochrome b (cytb) g...    <a href = #1899213> 50</a>    2e-05
<a
href="http://www.ncbi.nlm.nih.gov:80/entrez/query.fcgi?cmd=Retrieve&db=Nucleotid
e&list_uids=01899211&dopt=GenBank">gb|U90301.1|OMU90301</a>   Ovibos moschatus
cytochrome b (cytb) g...    <a href = #1899211> 50</a>    2e-05
<a
href="http://www.ncbi.nlm.nih.gov:80/entrez/query.fcgi?cmd=Retrieve&db=Nucleotid
e&list_uids=01899209&dopt=GenBank">gb|U90300.1|OMU90300</a>   Ovibos moschatus
cytochrome b (cytb) g...    <a href = #1899209> 50</a>    2e-05
<a
href="http://www.ncbi.nlm.nih.gov:80/entrez/query.fcgi?cmd=Retrieve&db=Nucleotid
e&list_uids=03510549&dopt=GenBank">gb|AF038883.1|AF038883</a>   Deinagkistrodon
acutus cytochrome b ...    <a href = #3510549> 50</a>    2e-05
<a
href="http://www.ncbi.nlm.nih.gov:80/entrez/query.fcgi?cmd=Retrieve&db=Nucleotid
e&list_uids=03510575&dopt=GenBank">gb|AF039268.1|AF039268</a>   Agkistrodon
contortrix cytochrome b ...    <a href = #3510575> 50</a>    2e-05
<a
href="http://www.ncbi.nlm.nih.gov:80/entrez/query.fcgi?cmd=Retrieve&db=Nucleotid
e&list_uids=03510573&dopt=GenBank">gb|AF039267.1|AF039267</a>   Boa constrictor
cytochrome b (cytb) ...    <a href = #3510573> 50</a>    2e-05
<a
href="http://www.ncbi.nlm.nih.gov:80/entrez/query.fcgi?cmd=Retrieve&db=Nucleotid
e&list_uids=00259294&dopt=GenBank">gb|S49215.1|S49215</a>   apocytochrome b
[sheep, domestic, Merino...    <a href = #259294> 50</a>    2e-05
<a
href="http://www.ncbi.nlm.nih.gov:80/entrez/query.fcgi?cmd=Retrieve&db=Nucleotid
e&list_uids=05616280&dopt=GenBank">gb|AF158698.1|AF158698</a>   Geomys pinetis
cytochrome b gene, co...    <a href = #5616280> 50</a>    2e-05
<a
href="http://www.ncbi.nlm.nih.gov:80/entrez/query.fcgi?cmd=Retrieve&db=Nucleotid
e&list_uids=05616266&dopt=GenBank">gb|AF158692.1|AF158692</a>   Geomys bursarius
jugossicularis cyto...    <a href = #5616266> 50</a>    2e-05
<a
href="http://www.ncbi.nlm.nih.gov:80/entrez/query.fcgi?cmd=Retrieve&db=Nucleotid
e&list_uids=03834418&dopt=GenBank">gb|AF068193.1|AF068193</a>   Ithaginis
cruentus cytochrome b (cyt...    <a href = #3834418> 50</a>    2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=05359509&dopt=GenBank">gb|AF091629.1|AF091629</a>   Antilocapra
americana cytochrome b (...    <a href = #5359509> 50</a>   2e-05
<a
href="http://www.ncbi.nlm.nih.gov:80/entrez/query.fcgi?cmd=Retrieve&db=Nucleotid
e&list_uids=04103301&dopt=GenBank">gb|AF022063.1|</a>   Tragelaphus strepsiceros
cytochrome b (cytb)...    <a href = #4103301> 50</a>   2e-05
<a
href="http://www.ncbi.nlm.nih.gov:80/entrez/query.fcgi?cmd=Retrieve&db=Nucleotid
e&list_uids=04103299&dopt=GenBank">gb|AF022062.1|</a>   Tragelaphus derbianus
cytochrome b (cytb) ge...    <a href = #4103299> 50</a>   2e-05
<a
href="http://www.ncbi.nlm.nih.gov:80/entrez/query.fcgi?cmd=Retrieve&db=Nucleotid
e&list_uids=04103295&dopt=GenBank">gb|AF022060.1|</a>   Hippotragus equinus
cytochrome b (cytb) gene...    <a href = #4103295> 50</a>   2e-05
<a
href="http://www.ncbi.nlm.nih.gov:80/entrez/query.fcgi?cmd=Retrieve&db=Nucleotid
e&list_uids=04103289&dopt=GenBank">gb|AF022057.1|</a>   Tragelaphus oryx
cytochrome b (cytb) gene, m...    <a href = #4103289> 50</a>   2e-05
<a
href="http://www.ncbi.nlm.nih.gov:80/entrez/query.fcgi?cmd=Retrieve&db=Nucleotid
e&list_uids=04559243&dopt=GenBank">gb|AF113500.1|AF113500</a>   Lagenorhynchus
acutus isolate LACU94...    <a href = #4559243> 50</a>   2e-05
<a
href="http://www.ncbi.nlm.nih.gov:80/entrez/query.fcgi?cmd=Retrieve&db=Nucleotid
e&list_uids=04559242&dopt=GenBank">gb|AF113499.1|AF113499</a>   Lagenorhynchus
acutus isolate LACU93...    <a href = #4559242> 50</a>   2e-05
<a
href="http://www.ncbi.nlm.nih.gov:80/entrez/query.fcgi?cmd=Retrieve&db=Nucleotid
e&list_uids=02843024&dopt=GenBank">gb|U69845.1|LBU69845</a>   Loxocemus bicolor
cytochrome b (cytb) ...    <a href = #2843024> 50</a>   2e-05
<a
href="http://www.ncbi.nlm.nih.gov:80/entrez/query.fcgi?cmd=Retrieve&db=Nucleotid
e&list_uids=02842972&dopt=GenBank">gb|U69810.1|ENU69810</a>   Eunectes notaeus
cytochrome b (cytb) g...    <a href = #2842972> 50</a>   2e-05
<a
href="http://www.ncbi.nlm.nih.gov:80/entrez/query.fcgi?cmd=Retrieve&db=Nucleotid
e&list_uids=02842962&dopt=GenBank">gb|U69808.1|EMU69808</a>   Eunectes murinus
cytochrome b (cytb) g...    <a href = #2842962> 50</a>   2e-05
<a
href="http://www.ncbi.nlm.nih.gov:80/entrez/query.fcgi?cmd=Retrieve&db=Nucleotid
e&list_uids=02842988&dopt=GenBank">gb|U69799.1|ESU69799</a>   Epicrates striatus
fosteri cytochrome ...    <a href = #2842988> 50</a>   2e-05
<a
href="http://www.ncbi.nlm.nih.gov:80/entrez/query.fcgi?cmd=Retrieve&db=Nucleotid
e&list_uids=02842982&dopt=GenBank">gb|U69796.1|ESU69796</a>   Epicrates striatus
strigilatus cytochr...    <a href = #2842982> 50</a>   2e-05
<a
href="http://www.ncbi.nlm.nih.gov:80/entrez/query.fcgi?cmd=Retrieve&db=Nucleotid
e&list_uids=02842980&dopt=GenBank">gb|U69795.1|ESU69795</a>   Epicrates striatus
strigilatus cytochr...    <a href = #2842980> 50</a>   2e-05
<a
href="http://www.ncbi.nlm.nih.gov:80/entrez/query.fcgi?cmd=Retrieve&db=Nucleotid
e&list_uids=02842978&dopt=GenBank">gb|U69794.1|ESU69794</a>   Epicrates striatus
mccraniei cytochrom...    <a href = #2842978> 50</a>   2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=02842976&dopt=GenBank">gb|U69793.1|ESU69793</a>  Epicrates striatus
mccraniei cytochrom...     <a href = #2842976> 50</a>   2e-05
<a
href="http://www.ncbi.nlm.nih.gov:80/entrez/query.fcgi?cmd=Retrieve&db=Nucleotid
e&list_uids=02842960&dopt=GenBank">gb|U69792.1|EMU69792</a>  Epicrates monensis
cytochrome b (cytb)...     <a href = #2842960> 50</a>   2e-05
<a
href="http://www.ncbi.nlm.nih.gov:80/entrez/query.fcgi?cmd=Retrieve&db=Nucleotid
e&list_uids=02842958&dopt=GenBank">gb|U69790.1|EMU69790</a>  Epicrates monensis
cytochrome b (cytb)...     <a href = #2842958> 50</a>   2e-05
<a
href="http://www.ncbi.nlm.nih.gov:80/entrez/query.fcgi?cmd=Retrieve&db=Nucleotid
e&list_uids=02842942&dopt=GenBank">gb|U69786.1|EFU69786</a>  Epicrates fordi
cytochrome b (cytb) ge...     <a href = #2842942> 50</a>   2e-05
<a
href="http://www.ncbi.nlm.nih.gov:80/entrez/query.fcgi?cmd=Retrieve&db=Nucleotid
e&list_uids=02842938&dopt=GenBank">gb|U69784.1|EFU69784</a>  Epicrates fordi
cytochrome b (cytb) ge...     <a href = #2842938> 50</a>   2e-05
<a
href="http://www.ncbi.nlm.nih.gov:80/entrez/query.fcgi?cmd=Retrieve&db=Nucleotid
e&list_uids=02842910&dopt=GenBank">gb|U69779.1|ECU69779</a>  Epicrates cenchria
cytochrome b (cytb)...     <a href = #2842910> 50</a>   2e-05
<a
href="http://www.ncbi.nlm.nih.gov:80/entrez/query.fcgi?cmd=Retrieve&db=Nucleotid
e&list_uids=02842906&dopt=GenBank">gb|U69777.1|ECU69777</a>  Epicrates cenchria
cytochrome b (cytb)...     <a href = #2842906> 50</a>   2e-05
<a
href="http://www.ncbi.nlm.nih.gov:80/entrez/query.fcgi?cmd=Retrieve&db=Nucleotid
e&list_uids=02842904&dopt=GenBank">gb|U69776.1|EAU69776</a>  Epicrates angulifer
cytochrome b (cytb...     <a href = #2842904> 50</a>   2e-05
<a
href="http://www.ncbi.nlm.nih.gov:80/entrez/query.fcgi?cmd=Retrieve&db=Nucleotid
e&list_uids=02842900&dopt=GenBank">gb|U69774.1|EAU69774</a>  Epicrates angulifer
cytochrome b (cytb...     <a href = #2842900> 50</a>   2e-05
<a
href="http://www.ncbi.nlm.nih.gov:80/entrez/query.fcgi?cmd=Retrieve&db=Nucleotid
e&list_uids=02842888&dopt=GenBank">gb|U69772.1|CEU69772</a>  Corallus enydris
cytochrome b (cytb) g...     <a href = #2842888> 50</a>   2e-05
<a
href="http://www.ncbi.nlm.nih.gov:80/entrez/query.fcgi?cmd=Retrieve&db=Nucleotid
e&list_uids=02842886&dopt=GenBank">gb|U69771.1|CEU69771</a>  Corallus enydris
cytochrome b (cytb) g...     <a href = #2842886> 50</a>   2e-05
<a
href="http://www.ncbi.nlm.nih.gov:80/entrez/query.fcgi?cmd=Retrieve&db=Nucleotid
e&list_uids=02842884&dopt=GenBank">gb|U69770.1|CEU69770</a>  Corallus enydris
cytochrome b (cytb) g...     <a href = #2842884> 50</a>   2e-05
<a
href="http://www.ncbi.nlm.nih.gov:80/entrez/query.fcgi?cmd=Retrieve&db=Nucleotid
e&list_uids=02842882&dopt=GenBank">gb|U69769.1|CEU69769</a>  Corallus enydris
cytochrome b (cytb) g...     <a href = #2842882> 50</a>   2e-05
<a
href="http://www.ncbi.nlm.nih.gov:80/entrez/query.fcgi?cmd=Retrieve&db=Nucleotid
e&list_uids=02842856&dopt=GenBank">gb|U69752.1|CAU69752</a>  Candoia aspera
cytochrome b (cytb) gen...     <a href = #2842856> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotide&list_uids=02842844&dopt=GenBank">gb|U69746.1|BCU69746</a>   Boa constrictor
cytochrome b (cytb) ge...    <a href = #2842844> 50</a>   2e-05
<a href="http://www.ncbi.nlm.nih.gov:80/entrez/query.fcgi?cmd=Retrieve&db=Nucleotide&list_uids=02842834&dopt=GenBank">gb|U69740.1|BCU69740</a>   Boa constrictor
cytochrome b (cytb) ge...    <a href = #2842834> 50</a>   2e-05
<a href="http://www.ncbi.nlm.nih.gov:80/entrez/query.fcgi?cmd=Retrieve&db=Nucleotide&list_uids=04894935&dopt=GenBank">gb|AF139057.1|AF139057</a>   Isoodon macrourus
cytochrome b gene,...    <a href = #4894935> 50</a>   2e-05
<a href="http://www.ncbi.nlm.nih.gov:80/entrez/query.fcgi?cmd=Retrieve&db=Nucleotide&list_uids=04894475&dopt=GenBank">gb|AF090339.1|AF090339</a>   Rhea americana
mitochondrion, comple...    <a href = #4894475> 50</a>   2e-05
<a href="http://www.ncbi.nlm.nih.gov:80/entrez/query.fcgi?cmd=Retrieve&db=Nucleotide&list_uids=04565839&dopt=GenBank">gb|AF006275.1|AF006275</a>   Cnemidophorus
tigris strain Isla Ang...    <a href = #4565839> 50</a>   2e-05
<a href="http://www.ncbi.nlm.nih.gov:80/entrez/query.fcgi?cmd=Retrieve&db=Nucleotide&list_uids=04565823&dopt=GenBank">gb|AF006267.1|AF006267</a>   Cnemidophorus
tigris strain Isla Smi...    <a href = #4565823> 50</a>   2e-05
<a href="http://www.ncbi.nlm.nih.gov:80/entrez/query.fcgi?cmd=Retrieve&db=Nucleotide&list_uids=02660921&dopt=GenBank">gb|AF034969.1|AF034969</a>   Connochaetes
taurinus cytochrome b g...    <a href = #2660921> 50</a>   2e-05
<a href="http://www.ncbi.nlm.nih.gov:80/entrez/query.fcgi?cmd=Retrieve&db=Nucleotide&list_uids=02605884&dopt=GenBank">gb|AF028822.1|AF028822</a>   Alcelaphus
buselaphus cytochrome b g...    <a href = #2605884> 50</a>   2e-05
<a href="http://www.ncbi.nlm.nih.gov:80/entrez/query.fcgi?cmd=Retrieve&db=Nucleotide&list_uids=02605882&dopt=GenBank">gb|AF028821.1|AF028821</a>   Damaliscus
lunatus cytochrome b gene...    <a href = #2605882> 50</a>   2e-05
<a href="http://www.ncbi.nlm.nih.gov:80/entrez/query.fcgi?cmd=Retrieve&db=Nucleotide&list_uids=04164474&dopt=GenBank">gb|AF061340.1|AF061340</a>   Artibeus
jamaicensis mitochondrial D...    <a href = #4164474> 50</a>   2e-05
<a href="http://www.ncbi.nlm.nih.gov:80/entrez/query.fcgi?cmd=Retrieve&db=Nucleotide&list_uids=03420708&dopt=GenBank">gb|AF076093.1|AF076093</a>   Thalassarche
impavida cytochrome b (...    <a href = #3420708> 50</a>   2e-05
<a href="http://www.ncbi.nlm.nih.gov:80/entrez/query.fcgi?cmd=Retrieve&db=Nucleotide&list_uids=03420704&dopt=GenBank">gb|AF076091.1|AF076091</a>   Thalassarche
carteri cytochrome b (c...    <a href = #3420704> 50</a>   2e-05
<a href="http://www.ncbi.nlm.nih.gov:80/entrez/query.fcgi?cmd=Retrieve&db=Nucleotide&list_uids=03420666&dopt=GenBank">gb|AF076072.1|AF076072</a>   Pelagodroma
marina cytochrome b (cyt...    <a href = #3420666> 50</a>   2e-05
<a href="http://www.ncbi.nlm.nih.gov:80/entrez/query.fcgi?cmd=Retrieve&db=Nucleotide&list_uids=03420648&dopt=GenBank">gb|AF076063.1|AF076063</a>   Oceanodroma
furcata cytochrome b (cy...    <a href = #3420648> 50</a>   2e-05
<a href="http://www.ncbi.nlm.nih.gov:80/entrez/query.fcgi?cmd=Retrieve&db=Nucleotide
```

```
<a
href="http://www.ncbi.nlm.nih.gov:80/entrez/query.fcgi?cmd=Retrieve&db=Nucleotid
e&list_uids=03420640&dopt=GenBank">gb|AF076059.1|AF076059</a>   Hydrobates
pelagicus cytochrome b (c...    <a href = #3420640> 50</a>   2e-05
<a
href="http://www.ncbi.nlm.nih.gov:80/entrez/query.fcgi?cmd=Retrieve&db=Nucleotid
e&list_uids=03420634&dopt=GenBank">gb|AF076056.1|AF076056</a>   Garrodia nereis
cytochrome b (cytb) ...    <a href = #3420634> 50</a>   2e-05
<a
href="http://www.ncbi.nlm.nih.gov:80/entrez/query.fcgi?cmd=Retrieve&db=Nucleotid
e&list_uids=03420628&dopt=GenBank">gb|AF076053.1|AF076053</a>   Fregetta tropica
cytochrome b (cytb)...    <a href = #3420628> 50</a>   2e-05
<a
href="http://www.ncbi.nlm.nih.gov:80/entrez/query.fcgi?cmd=Retrieve&db=Nucleotid
e&list_uids=03420622&dopt=GenBank">gb|AF076050.1|AF076050</a>   Diomedea gibsoni
cytochrome b (cytb)...    <a href = #3420622> 50</a>   2e-05
<a
href="http://www.ncbi.nlm.nih.gov:80/entrez/query.fcgi?cmd=Retrieve&db=Nucleotid
e&list_uids=03420620&dopt=GenBank">gb|AF076049.1|AF076049</a>   Diomedea
epomophora cytochrome b (cy...    <a href = #3420620> 50</a>   2e-05
<a
href="http://www.ncbi.nlm.nih.gov:80/entrez/query.fcgi?cmd=Retrieve&db=Nucleotid
e&list_uids=03420618&dopt=GenBank">gb|AF076048.1|AF076048</a>   Diomedea
chionoptera cytochrome b (c...    <a href = #3420618> 50</a>   2e-05
<a
href="http://www.ncbi.nlm.nih.gov:80/entrez/query.fcgi?cmd=Retrieve&db=Nucleotid
e&list_uids=03420616&dopt=GenBank">gb|AF076047.1|AF076047</a>   Diomedea
antipodensis cytochrome b (...    <a href = #3420616> 50</a>   2e-05
<a
href="http://www.ncbi.nlm.nih.gov:80/entrez/query.fcgi?cmd=Retrieve&db=Nucleotid
e&list_uids=02231527&dopt=GenBank">gb|U83314.1|MSU83314</a>   Micrastur
semitorquatus cytochrome b (...    <a href = #2231527> 50</a>   2e-05
<a
href="http://www.ncbi.nlm.nih.gov:80/entrez/query.fcgi?cmd=Retrieve&db=Nucleotid
e&list_uids=02231523&dopt=GenBank">gb|U83318.1|MEU83318</a>   Microhierax
erythrogenys cytochrome b ...    <a href = #2231523> 50</a>   2e-05
<a
href="http://www.ncbi.nlm.nih.gov:80/entrez/query.fcgi?cmd=Retrieve&db=Nucleotid
e&list_uids=01255763&dopt=GenBank">gb|U37303.1|SAU37303</a>   Synthliboramphus
antiquus cytochrome b...    <a href = #1255763> 50</a>   2e-05
<a
href="http://www.ncbi.nlm.nih.gov:80/entrez/query.fcgi?cmd=Retrieve&db=Nucleotid
e&list_uids=01255761&dopt=GenBank">gb|U37302.1|PAU37302</a>   Ptychoramphus
aleuticus cytochrome b g...    <a href = #1255761> 50</a>   2e-05
<a
href="http://www.ncbi.nlm.nih.gov:80/entrez/query.fcgi?cmd=Retrieve&db=Nucleotid
e&list_uids=01255749&dopt=GenBank">gb|U37296.1|CPU37296</a>   Cyclorrhynchus
psittacula cytochrome b...    <a href = #1255749> 50</a>   2e-05
<a
href="http://www.ncbi.nlm.nih.gov:80/entrez/query.fcgi?cmd=Retrieve&db=Nucleotid
e&list_uids=01255735&dopt=GenBank">gb|U37289.1|BBU37289</a>   Brachyramphus
brevirostris cytochrome ...    <a href = #1255735> 50</a>   2e-05
<a
href="http://www.ncbi.nlm.nih.gov:80/entrez/query.fcgi?cmd=Retrieve&db=Nucleotid
e&list_uids=01255731&dopt=GenBank">gb|U37286.1|APU37286</a>   Aethia pygmaea
cytochrome b gene, mito...    <a href = #1255731> 50</a>   2e-05
<a
href="http://www.ncbi.nlm.nih.gov:80/entrez/query.fcgi?cmd=Retrieve&db=Nucleotid
```

```
e&list_uids=01143282&dopt=GenBank">gb|U37104.1|APU37104</a>   Aethia pusilla
cytochrome b gene, mito...     <a href = #1143282> 50</a>   2e-05
<a
href="http://www.ncbi.nlm.nih.gov:80/entrez/query.fcgi?cmd=Retrieve&db=Nucleotid
e&list_uids=01143280&dopt=GenBank">gb|U37087.1|ACU37087</a>   Aethia cristatella
cytochrome b gene, ...     <a href = #1143280> 50</a>   2e-05
<a
href="http://www.ncbi.nlm.nih.gov:80/entrez/query.fcgi?cmd=Retrieve&db=Nucleotid
e&list_uids=02239314&dopt=GenBank">gb|U87525.1|HGU87525</a>   Heterocephalus
glaber cytochrome-b gen...     <a href = #2239314> 50</a>   2e-05
<a
href="http://www.ncbi.nlm.nih.gov:80/entrez/query.fcgi?cmd=Retrieve&db=Nucleotid
e&list_uids=02239312&dopt=GenBank">gb|U87524.1|HGU87524</a>   Heterocephalus
glaber cytochrome-b gen...     <a href = #2239312> 50</a>   2e-05
<a
href="http://www.ncbi.nlm.nih.gov:80/entrez/query.fcgi?cmd=Retrieve&db=Nucleotid
e&list_uids=02239310&dopt=GenBank">gb|U87523.1|HGU87523</a>   Heterocephalus
glaber cytochrome-b gen...     <a href = #2239310> 50</a>   2e-05
<a
href="http://www.ncbi.nlm.nih.gov:80/entrez/query.fcgi?cmd=Retrieve&db=Nucleotid
e&list_uids=02239308&dopt=GenBank">gb|U87522.1|HGU87522</a>   Heterocephalus
glaber cytochrome-b gen...     <a href = #2239308> 50</a>   2e-05
<a
href="http://www.ncbi.nlm.nih.gov:80/entrez/query.fcgi?cmd=Retrieve&db=Nucleotid
e&list_uids=00604335&dopt=GenBank">gb|U17864.1|STU17864</a>   Saiga tatarica
cytochrome b gene, mito...     <a href = #604335> 50</a>   2e-05
<a
href="http://www.ncbi.nlm.nih.gov:80/entrez/query.fcgi?cmd=Retrieve&db=Nucleotid
e&list_uids=00604333&dopt=GenBank">gb|U17863.1|OAU17863</a>   Oreamnos americanus
cytochrome b gene,...     <a href = #604333> 50</a>   2e-05
<a
href="http://www.ncbi.nlm.nih.gov:80/entrez/query.fcgi?cmd=Retrieve&db=Nucleotid
e&list_uids=00604331&dopt=GenBank">gb|U17862.1|OMU17862</a>   Ovibos moschatus
moschatus cytochrome ...     <a href = #604331> 50</a>   2e-05
<a
href="http://www.ncbi.nlm.nih.gov:80/entrez/query.fcgi?cmd=Retrieve&db=Nucleotid
e&list_uids=00604327&dopt=GenBank">gb|U17860.1|ODU17860</a>   Ovis dalli
cytochrome b gene, mitochon...     <a href = #604327> 50</a>   2e-05
<a
href="http://www.ncbi.nlm.nih.gov:80/entrez/query.fcgi?cmd=Retrieve&db=Nucleotid
e&list_uids=00604325&dopt=GenBank">gb|U17859.1|OCU17859</a>   Ovis canadensis
cytochrome b gene, mit...     <a href = #604325> 50</a>   2e-05
<a
href="http://www.ncbi.nlm.nih.gov:80/entrez/query.fcgi?cmd=Retrieve&db=Nucleotid
e&list_uids=02894743&dopt=GenBank">gb|U65274.1|TBU65274</a>   Thomomys bottae
cytochrome b (cytb) ge...     <a href = #2894743> 50</a>   2e-05
<a
href="http://www.ncbi.nlm.nih.gov:80/entrez/query.fcgi?cmd=Retrieve&db=Nucleotid
e&list_uids=02894729&dopt=GenBank">gb|U65267.1|TBU65267</a>   Thomomys bottae
cytochrome b (cytb) ge...     <a href = #2894729> 50</a>   2e-05
<a
href="http://www.ncbi.nlm.nih.gov:80/entrez/query.fcgi?cmd=Retrieve&db=Nucleotid
e&list_uids=02894715&dopt=GenBank">gb|U65260.1|TBU65260</a>   Thomomys bottae
cytochrome b (cytb) ge...     <a href = #2894715> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotid
e&list_uids=02894685&dopt=GenBank">gb|U65301.1|PAU65301</a>   Perognathus amplus
cytochrome b (cytb)...    <a href = #2894685> 50</a>   2e-05
<a
href="http://www.ncbi.nlm.nih.gov:80/entrez/query.fcgi?cmd=Retrieve&db=Nucleotid
e&list_uids=03417594&dopt=GenBank">gb|AF034739.1|AF034739</a>   Capra aegagrus
cytochrome b (cytb) g...    <a href = #3417594> 50</a>   2e-05
<a
href="http://www.ncbi.nlm.nih.gov:80/entrez/query.fcgi?cmd=Retrieve&db=Nucleotid
e&list_uids=03417592&dopt=GenBank">gb|AF034738.1|</a>   Capra caucasica
cytochrome b (cytb) gene, mi...    <a href = #3417592> 50</a>   2e-05
<a
href="http://www.ncbi.nlm.nih.gov:80/entrez/query.fcgi?cmd=Retrieve&db=Nucleotid
e&list_uids=03417590&dopt=GenBank">gb|AF034737.1|</a>   Capra cylindricornis
cytochrome b (cytb) gen...    <a href = #3417590> 50</a>   2e-05
<a
href="http://www.ncbi.nlm.nih.gov:80/entrez/query.fcgi?cmd=Retrieve&db=Nucleotid
e&list_uids=03417588&dopt=GenBank">gb|AF034736.1|AF034736</a>   Capra falconeri
cytochrome b (cytb) ...    <a href = #3417588> 50</a>   2e-05
<a
href="http://www.ncbi.nlm.nih.gov:80/entrez/query.fcgi?cmd=Retrieve&db=Nucleotid
e&list_uids=03417586&dopt=GenBank">gb|AF034735.1|</a>   Capra ibex cytochrome b
(cytb) gene, mitocho...    <a href = #3417586> 50</a>   2e-05
<a
href="http://www.ncbi.nlm.nih.gov:80/entrez/query.fcgi?cmd=Retrieve&db=Nucleotid
e&list_uids=03417576&dopt=GenBank">gb|AF034730.1|AF034730</a>   Ovis aries
cytochrome b (cytb) gene,...    <a href = #3417576> 50</a>   2e-05
<a
href="http://www.ncbi.nlm.nih.gov:80/entrez/query.fcgi?cmd=Retrieve&db=Nucleotid
e&list_uids=03417574&dopt=GenBank">gb|AF034729.1|AF034729</a>   Ovis vignei
cytochrome b (cytb) gene...    <a href = #3417574> 50</a>   2e-05
<a
href="http://www.ncbi.nlm.nih.gov:80/entrez/query.fcgi?cmd=Retrieve&db=Nucleotid
e&list_uids=03417572&dopt=GenBank">gb|AF034728.1|</a>   Ovis dalli dalli
cytochrome b (cytb) gene, m...    <a href = #3417572> 50</a>   2e-05
<a
href="http://www.ncbi.nlm.nih.gov:80/entrez/query.fcgi?cmd=Retrieve&db=Nucleotid
e&list_uids=03417570&dopt=GenBank">gb|AF034727.1|</a>   Ovis ammon darwini
cytochrome b (cytb) gene,...    <a href = #3417570> 50</a>   2e-05
<a
href="http://www.ncbi.nlm.nih.gov:80/entrez/query.fcgi?cmd=Retrieve&db=Nucleotid
e&list_uids=03417564&dopt=GenBank">gb|AF034724.1|AF034724</a>   Pantholops
hodgsoni cytochrome b (cy...    <a href = #3417564> 50</a>   2e-05
<a
href="http://www.ncbi.nlm.nih.gov:80/entrez/query.fcgi?cmd=Retrieve&db=Nucleotid
e&list_uids=03511111&dopt=GenBank">gb|AF057132.1|AF057132</a>   Taxidea taxus
cytochrome b (cytb) ge...    <a href = #3511111> 50</a>   2e-05
<a
href="http://www.ncbi.nlm.nih.gov:80/entrez/query.fcgi?cmd=Retrieve&db=Nucleotid
e&list_uids=03452043&dopt=GenBank">gb|U94805.1|TMU94805</a>   Trogon melanurus
cytochrome b gene, mi...    <a href = #3452043> 50</a>   2e-05
<a
href="http://www.ncbi.nlm.nih.gov:80/entrez/query.fcgi?cmd=Retrieve&db=Nucleotid
e&list_uids=03452040&dopt=GenBank">gb|U94804.1|TCU94804</a>   Trogon comptus
cytochrome b gene, mito...    <a href = #3452040> 50</a>   2e-05
<a
href="http://www.ncbi.nlm.nih.gov:80/entrez/query.fcgi?cmd=Retrieve&db=Nucleotid
```

```
e&list_uids=03452037&dopt=GenBank">gb|U94803.1|TVU94803</a>   Trogon viridis
cytochrome b gene, mito...    <a href = #3452037>  50</a>   2e-05
<a
href="http://www.ncbi.nlm.nih.gov:80/entrez/query.fcgi?cmd=Retrieve&db=Nucleotid
e&list_uids=02935116&dopt=GenBank">gb|AF006251.1|AF006251</a>   Sericossypha
albocristata cytochrome...    <a href = #2935116>  50</a>   2e-05
<a
href="http://www.ncbi.nlm.nih.gov:80/entrez/query.fcgi?cmd=Retrieve&db=Nucleotid
e&list_uids=02935112&dopt=GenBank">gb|AF006249.1|AF006249</a>   Pyrrhocoma
ruficeps cytochrome b (cy...    <a href = #2935112>  50</a>   2e-05
<a
href="http://www.ncbi.nlm.nih.gov:80/entrez/query.fcgi?cmd=Retrieve&db=Nucleotid
e&list_uids=02935090&dopt=GenBank">gb|AF006238.1|AF006238</a>   Lamprospiza
melanoleuca cytochrome b...    <a href = #2935090>  50</a>   2e-05
<a
href="http://www.ncbi.nlm.nih.gov:80/entrez/query.fcgi?cmd=Retrieve&db=Nucleotid
e&list_uids=02935082&dopt=GenBank">gb|AF006234.1|AF006234</a>   Hemispingus
atropileus cytochrome b ...    <a href = #2935082>  50</a>   2e-05
<a
href="http://www.ncbi.nlm.nih.gov:80/entrez/query.fcgi?cmd=Retrieve&db=Nucleotid
e&list_uids=02935066&dopt=GenBank">gb|AF006226.1|AF006226</a>   Cypsnagra
hirundinacea cytochrome b ...    <a href = #2935066>  50</a>   2e-05
<a
href="http://www.ncbi.nlm.nih.gov:80/entrez/query.fcgi?cmd=Retrieve&db=Nucleotid
e&list_uids=02935044&dopt=GenBank">gb|AF006215.1|AF006215</a>   Chlorophanes
spiza cytochrome b (cyt...    <a href = #2935044>  50</a>   2e-05
<a
href="http://www.ncbi.nlm.nih.gov:80/entrez/query.fcgi?cmd=Retrieve&db=Nucleotid
e&list_uids=02935042&dopt=GenBank">gb|AF006214.1|AF006214</a>   Chlorochrysa
calliparaea cytochrome ...    <a href = #2935042>  50</a>   2e-05
<a
href="http://www.ncbi.nlm.nih.gov:80/entrez/query.fcgi?cmd=Retrieve&db=Nucleotid
e&list_uids=02935040&dopt=GenBank">gb|AF006213.1|AF006213</a>   Calochaetes
coccineus cytochrome b (...    <a href = #2935040>  50</a>   2e-05
<a
href="http://www.ncbi.nlm.nih.gov:80/entrez/query.fcgi?cmd=Retrieve&db=Nucleotid
e&list_uids=02935038&dopt=GenBank">gb|AF006212.1|AF006212</a>   Buthraupis
montana cytochrome b (cyt...    <a href = #2935038>  50</a>   2e-05
<a
href="http://www.ncbi.nlm.nih.gov:80/entrez/query.fcgi?cmd=Retrieve&db=Nucleotid
e&list_uids=11071919&dopt=GenBank">emb|AJ293419.1|RRU293419</a>   Rupicapra
rupicapra rupicapra mito...    <a href = #11071919>  50</a>   2e-05
<a
href="http://www.ncbi.nlm.nih.gov:80/entrez/query.fcgi?cmd=Retrieve&db=Nucleotid
e&list_uids=11071915&dopt=GenBank">emb|AJ293416.1|RPY293416</a>   Rupicapra
pyrenaica pyrenaica mito...    <a href = #11071915>  50</a>   2e-05
<a
href="http://www.ncbi.nlm.nih.gov:80/entrez/query.fcgi?cmd=Retrieve&db=Nucleotid
e&list_uids=11071913&dopt=GenBank">emb|AJ293415.1|RPY293415</a>   Rupicapra
pyrenaica parva mitochon...    <a href = #11071913>  50</a>   2e-05
<a
href="http://www.ncbi.nlm.nih.gov:80/entrez/query.fcgi?cmd=Retrieve&db=Nucleotid
e&list_uids=11071911&dopt=GenBank">emb|AJ293414.1|RPY293414</a>   Rupicapra
pyrenaica ornata mitocho...    <a href = #11071911>  50</a>   2e-05
<a
href="http://www.ncbi.nlm.nih.gov:80/entrez/query.fcgi?cmd=Retrieve&db=Nucleotid
```

```
&list_uids=00624181&dopt=GenBank>U18257</a>   169  ........................
193
<a name = 624173></a><a
href=http://www.ncbi.nlm.nih.gov:80/entrez/query.fcgi?cmd=Retrieve&db=Nucleotide
&list_uids=00624173&dopt=GenBank>U18253</a>   169  ........................
193
<a name = 624167></a><a
href=http://www.ncbi.nlm.nih.gov:80/entrez/query.fcgi?cmd=Retrieve&db=Nucleotide
&list_uids=00624167&dopt=GenBank>U18250</a>   169  ........................
193
<a name = 601796></a><a
href=http://www.ncbi.nlm.nih.gov:80/entrez/query.fcgi?cmd=Retrieve&db=Nucleotide
&list_uids=00601796&dopt=GenBank>U17904</a>   169  ........................
193
<a name = 1256162></a><a
href=http://www.ncbi.nlm.nih.gov:80/entrez/query.fcgi?cmd=Retrieve&db=Nucleotide
&list_uids=01256162&dopt=GenBank>D84202</a>   398  ........................
422
<a name = 1813356></a><a
href=http://www.ncbi.nlm.nih.gov:80/entrez/query.fcgi?cmd=Retrieve&db=Nucleotide
&list_uids=01813356&dopt=GenBank>D82889</a>   398  ........................
422
<a name = 516676></a><a
href=http://www.ncbi.nlm.nih.gov:80/entrez/query.fcgi?cmd=Retrieve&db=Nucleotide
&list_uids=00516676&dopt=GenBank>D32195</a>   243  ........................
267
<a name = 516672></a><a
href=http://www.ncbi.nlm.nih.gov:80/entrez/query.fcgi?cmd=Retrieve&db=Nucleotide
&list_uids=00516672&dopt=GenBank>D32191</a>   398  ........................
422
<a name = 5811559></a><a
href=http://www.ncbi.nlm.nih.gov:80/entrez/query.fcgi?cmd=Retrieve&db=Nucleotide
&list_uids=05811559&dopt=GenBank>AB021098</a> 398  ........................
422
<a name = 5811557></a><a
href=http://www.ncbi.nlm.nih.gov:80/entrez/query.fcgi?cmd=Retrieve&db=Nucleotide
&list_uids=05811557&dopt=GenBank>AB021097</a> 398  ........................
422
<a name = 5811553></a><a
href=http://www.ncbi.nlm.nih.gov:80/entrez/query.fcgi?cmd=Retrieve&db=Nucleotide
&list_uids=05811553&dopt=GenBank>AB021095</a> 398  ........................
422
<a name = 5811551></a><a
href=http://www.ncbi.nlm.nih.gov:80/entrez/query.fcgi?cmd=Retrieve&db=Nucleotide
&list_uids=05811551&dopt=GenBank>AB021094</a> 398  ........................
422
<a name = 5811547></a><a
href=http://www.ncbi.nlm.nih.gov:80/entrez/query.fcgi?cmd=Retrieve&db=Nucleotide
&list_uids=05811547&dopt=GenBank>AB021092</a> 398  ........................
422
<a name = 5811545></a><a
href=http://www.ncbi.nlm.nih.gov:80/entrez/query.fcgi?cmd=Retrieve&db=Nucleotide
&list_uids=05811545&dopt=GenBank>AB021091</a> 398  ........................
422
<a name = 1881395></a><a
href=http://www.ncbi.nlm.nih.gov:80/entrez/query.fcgi?cmd=Retrieve&db=Nucleotide
```

```
&list_uids=01881395&dopt=GenBank>AB001612</a>   398   ..........................
422
<a name = 1256201></a><a
href=http://www.ncbi.nlm.nih.gov:80/entrez/query.fcgi?cmd=Retrieve&db=Nucleotide
&list_uids=01256201&dopt=GenBank>D84205</a>   398   ..........................
422
<a name = 1256199></a><a
href=http://www.ncbi.nlm.nih.gov:80/entrez/query.fcgi?cmd=Retrieve&db=Nucleotide
&list_uids=01256199&dopt=GenBank>D84203</a>   398   ..........................
422
<a name = 516663></a><a
href=http://www.ncbi.nlm.nih.gov:80/entrez/query.fcgi?cmd=Retrieve&db=Nucleotide
&list_uids=00516663&dopt=GenBank>D34636</a>   398   ..........................
422
<a name = 516661></a><a
href=http://www.ncbi.nlm.nih.gov:80/entrez/query.fcgi?cmd=Retrieve&db=Nucleotide
&list_uids=00516661&dopt=GenBank>D34635</a>   398   ..........................
422
<a name = 516821></a><a
href=http://www.ncbi.nlm.nih.gov:80/entrez/query.fcgi?cmd=Retrieve&db=Nucleotide
&list_uids=00516821&dopt=GenBank>D32198</a>   243   ..........................
267
<a name = 516816></a><a
href=http://www.ncbi.nlm.nih.gov:80/entrez/query.fcgi?cmd=Retrieve&db=Nucleotide
&list_uids=00516816&dopt=GenBank>D32196</a>   243   ..........................
267
<a name = 516678></a><a
href=http://www.ncbi.nlm.nih.gov:80/entrez/query.fcgi?cmd=Retrieve&db=Nucleotide
&list_uids=00516678&dopt=GenBank>D32192</a>   398   ..........................
422
<a name = 5811561></a><a
href=http://www.ncbi.nlm.nih.gov:80/entrez/query.fcgi?cmd=Retrieve&db=Nucleotide
&list_uids=05811561&dopt=GenBank>AB021099</a>   398   ..........................
422
<a name = 5811555></a><a
href=http://www.ncbi.nlm.nih.gov:80/entrez/query.fcgi?cmd=Retrieve&db=Nucleotide
&list_uids=05811555&dopt=GenBank>AB021096</a>   398   ..........................
422
<a name = 5811549></a><a
href=http://www.ncbi.nlm.nih.gov:80/entrez/query.fcgi?cmd=Retrieve&db=Nucleotide
&list_uids=05811549&dopt=GenBank>AB021093</a>   398   ..........................
422
<a name = 5811543></a><a
href=http://www.ncbi.nlm.nih.gov:80/entrez/query.fcgi?cmd=Retrieve&db=Nucleotide
&list_uids=05811543&dopt=GenBank>AB021090</a>   398   ..........................
422
<a name = 3582121></a><a
href=http://www.ncbi.nlm.nih.gov:80/entrez/query.fcgi?cmd=Retrieve&db=Nucleotide
&list_uids=03582121&dopt=GenBank>AB008539</a>   15302   ..........................
15326
<a name = 2351091></a><a
href=http://www.ncbi.nlm.nih.gov:80/entrez/query.fcgi?cmd=Retrieve&db=Nucleotide
&list_uids=02351091&dopt=GenBank>AB006800</a>   398   ..........................
422
<a name = 308874></a><a
href=http://www.ncbi.nlm.nih.gov:80/entrez/query.fcgi?cmd=Retrieve&db=Nucleotide
```

```
&list_uids=00308874&dopt=GenBank>L12763</a>    260   ........................
284
<a name = 336659></a><a
href=http://www.ncbi.nlm.nih.gov:80/entrez/query.fcgi?cmd=Retrieve&db=Nucleotide
&list_uids=00336659&dopt=GenBank>L08032</a>    401   ........................
425
<a name = 455382></a><a
href=http://www.ncbi.nlm.nih.gov:80/entrez/query.fcgi?cmd=Retrieve&db=Nucleotide
&list_uids=00455382&dopt=GenBank>L28941</a>    398   ........................
422
<a name = 455130></a><a
href=http://www.ncbi.nlm.nih.gov:80/entrez/query.fcgi?cmd=Retrieve&db=Nucleotide
&list_uids=00455130&dopt=GenBank>L28937</a>    398   ........................
422
<a name = 3549827></a><a
href=http://www.ncbi.nlm.nih.gov:80/entrez/query.fcgi?cmd=Retrieve&db=Nucleotide
&list_uids=03549827&dopt=GenBank>AJ010056</a>  269   ........................
293
<a name = 3549825></a><a
href=http://www.ncbi.nlm.nih.gov:80/entrez/query.fcgi?cmd=Retrieve&db=Nucleotide
&list_uids=03549825&dopt=GenBank>AJ010054</a>  269   ........................
293
<a name = 3549823></a><a
href=http://www.ncbi.nlm.nih.gov:80/entrez/query.fcgi?cmd=Retrieve&db=Nucleotide
&list_uids=03549823&dopt=GenBank>AJ010053</a>  269   ........................
293
<a name = 3549821></a><a
href=http://www.ncbi.nlm.nih.gov:80/entrez/query.fcgi?cmd=Retrieve&db=Nucleotide
&list_uids=03549821&dopt=GenBank>AJ010052</a>  269   ........................
293
<a name = 3549819></a><a
href=http://www.ncbi.nlm.nih.gov:80/entrez/query.fcgi?cmd=Retrieve&db=Nucleotide
&list_uids=03549819&dopt=GenBank>AJ010051</a>  269   ........................
293
<a name = 3549817></a><a
href=http://www.ncbi.nlm.nih.gov:80/entrez/query.fcgi?cmd=Retrieve&db=Nucleotide
&list_uids=03549817&dopt=GenBank>AJ010050</a>  269   ........................
293
<a name = 3549815></a><a
href=http://www.ncbi.nlm.nih.gov:80/entrez/query.fcgi?cmd=Retrieve&db=Nucleotide
&list_uids=03549815&dopt=GenBank>AJ010049</a>  269   ........................
293
<a name = 3549813></a><a
href=http://www.ncbi.nlm.nih.gov:80/entrez/query.fcgi?cmd=Retrieve&db=Nucleotide
&list_uids=03549813&dopt=GenBank>AJ010048</a>  269   ........................
293
<a name = 3549811></a><a
href=http://www.ncbi.nlm.nih.gov:80/entrez/query.fcgi?cmd=Retrieve&db=Nucleotide
&list_uids=03549811&dopt=GenBank>AJ010047</a>  269   ........................
293
<a name = 1261899></a><a
href=http://www.ncbi.nlm.nih.gov:80/entrez/query.fcgi?cmd=Retrieve&db=Nucleotide
&list_uids=01261899&dopt=GenBank>X95777</a>    407   ........................
431
<a name = 3549805></a><a
href=http://www.ncbi.nlm.nih.gov:80/entrez/query.fcgi?cmd=Retrieve&db=Nucleotide
```

```
&list_uids=03549805&dopt=GenBank>AJ009879</a>  269  .........................
293
<a name = 3549779></a><a
href=http://www.ncbi.nlm.nih.gov:80/entrez/query.fcgi?cmd=Retrieve&db=Nucleotide
&list_uids=03549779&dopt=GenBank>AJ010055</a>  269  .........................
293
<a name = 482869></a><a
href=http://www.ncbi.nlm.nih.gov:80/entrez/query.fcgi?cmd=Retrieve&db=Nucleotide
&list_uids=00482869&dopt=GenBank>U08946</a>  303  .........................
327
<a name = 482867></a><a
href=http://www.ncbi.nlm.nih.gov:80/entrez/query.fcgi?cmd=Retrieve&db=Nucleotide
&list_uids=00482867&dopt=GenBank>U08945</a>  303  .........................
327
<a name = 482865></a><a
href=http://www.ncbi.nlm.nih.gov:80/entrez/query.fcgi?cmd=Retrieve&db=Nucleotide
&list_uids=00482865&dopt=GenBank>U08944</a>  303  .........................
327
<a name = 482859></a><a
href=http://www.ncbi.nlm.nih.gov:80/entrez/query.fcgi?cmd=Retrieve&db=Nucleotide
&list_uids=00482859&dopt=GenBank>U08941</a>  303  .........................
327
<a name = 482857></a><a
href=http://www.ncbi.nlm.nih.gov:80/entrez/query.fcgi?cmd=Retrieve&db=Nucleotide
&list_uids=00482857&dopt=GenBank>U08940</a>  303  .........................
327
<a name = 1261861></a><a
href=http://www.ncbi.nlm.nih.gov:80/entrez/query.fcgi?cmd=Retrieve&db=Nucleotide
&list_uids=01261861&dopt=GenBank>X95775</a>  303  .........................
327
<a name = 1261860></a><a
href=http://www.ncbi.nlm.nih.gov:80/entrez/query.fcgi?cmd=Retrieve&db=Nucleotide
&list_uids=01261860&dopt=GenBank>X95774</a>  303  .........................
327
<a name = 1204043></a><a
href=http://www.ncbi.nlm.nih.gov:80/entrez/query.fcgi?cmd=Retrieve&db=Nucleotide
&list_uids=01204043&dopt=GenBank>X95764</a>  303  .........................
327
<a name = 4104825></a><a
href=http://www.ncbi.nlm.nih.gov:80/entrez/query.fcgi?cmd=Retrieve&db=Nucleotide
&list_uids=04104825&dopt=GenBank>AF040383</a>  287  .........................
310
<a name = 13128900></a><a
href=http://www.ncbi.nlm.nih.gov:80/entrez/query.fcgi?cmd=Retrieve&db=Nucleotide
&list_uids=13128900&dopt=GenBank>AF232023</a>  400  .........................
422
<a name = 13128899></a><a
href=http://www.ncbi.nlm.nih.gov:80/entrez/query.fcgi?cmd=Retrieve&db=Nucleotide
&list_uids=13128899&dopt=GenBank>AF232022</a>  400  .........................
422
<a name = 13128897></a><a
href=http://www.ncbi.nlm.nih.gov:80/entrez/query.fcgi?cmd=Retrieve&db=Nucleotide
&list_uids=13128897&dopt=GenBank>AF232021</a>  400  .........................
422
<a name = 5596617></a><a
href=http://www.ncbi.nlm.nih.gov:80/entrez/query.fcgi?cmd=Retrieve&db=Nucleotide
```

```
&list_uids=05596617&dopt=GenBank>AF157466</a>   322   ........................
344
<a name = 5596615></a><a
href=http://www.ncbi.nlm.nih.gov:80/entrez/query.fcgi?cmd=Retrieve&db=Nucleotide
&list_uids=05596615&dopt=GenBank>AF157465</a>   324   ........................
346
<a name = 5596613></a><a
href=http://www.ncbi.nlm.nih.gov:80/entrez/query.fcgi?cmd=Retrieve&db=Nucleotide
&list_uids=05596613&dopt=GenBank>AF157464</a>   324   ........................
346
<a name = 5596611></a><a
href=http://www.ncbi.nlm.nih.gov:80/entrez/query.fcgi?cmd=Retrieve&db=Nucleotide
&list_uids=05596611&dopt=GenBank>AF157463</a>   324   ........................
346
<a name = 5596605></a><a
href=http://www.ncbi.nlm.nih.gov:80/entrez/query.fcgi?cmd=Retrieve&db=Nucleotide
&list_uids=05596605&dopt=GenBank>AF157460</a>   321   ........................
343
<a name = 13171222></a><a
href=http://www.ncbi.nlm.nih.gov:80/entrez/query.fcgi?cmd=Retrieve&db=Nucleotide
&list_uids=13171222&dopt=GenBank>AF231664</a>   400   ........................
422
<a name = 13171220></a><a
href=http://www.ncbi.nlm.nih.gov:80/entrez/query.fcgi?cmd=Retrieve&db=Nucleotide
&list_uids=13171220&dopt=GenBank>AF231663</a>   400   ........................
422
<a name = 13171218></a><a
href=http://www.ncbi.nlm.nih.gov:80/entrez/query.fcgi?cmd=Retrieve&db=Nucleotide
&list_uids=13171218&dopt=GenBank>AF231662</a>   400   ........................
422
<a name = 13171214></a><a
href=http://www.ncbi.nlm.nih.gov:80/entrez/query.fcgi?cmd=Retrieve&db=Nucleotide
&list_uids=13171214&dopt=GenBank>AF231660</a>   400   ........................
422
<a name = 13171212></a><a
href=http://www.ncbi.nlm.nih.gov:80/entrez/query.fcgi?cmd=Retrieve&db=Nucleotide
&list_uids=13171212&dopt=GenBank>AF231659</a>   400   ........................
422
<a name = 13171210></a><a
href=http://www.ncbi.nlm.nih.gov:80/entrez/query.fcgi?cmd=Retrieve&db=Nucleotide
&list_uids=13171210&dopt=GenBank>AF231658</a>   400   ........................
422
<a name = 13171208></a><a
href=http://www.ncbi.nlm.nih.gov:80/entrez/query.fcgi?cmd=Retrieve&db=Nucleotide
&list_uids=13171208&dopt=GenBank>AF231657</a>   400   ........................
422
<a name = 13171206></a><a
href=http://www.ncbi.nlm.nih.gov:80/entrez/query.fcgi?cmd=Retrieve&db=Nucleotide
&list_uids=13171206&dopt=GenBank>AF231656</a>   400   ........................
422
<a name = 13171182></a><a
href=http://www.ncbi.nlm.nih.gov:80/entrez/query.fcgi?cmd=Retrieve&db=Nucleotide
&list_uids=13171182&dopt=GenBank>AF231644</a>   400   ........................
422
<a name = 13171172></a><a
href=http://www.ncbi.nlm.nih.gov:80/entrez/query.fcgi?cmd=Retrieve&db=Nucleotide
```

```
&list_uids=13171172&dopt=GenBank>AF231639</a>  400  .......................
422
<a name = 13128893></a><a
href=http://www.ncbi.nlm.nih.gov:80/entrez/query.fcgi?cmd=Retrieve&db=Nucleotide
&list_uids=13128893&dopt=GenBank>AF232019</a>  400  .......................
422
<a name = 13128889></a><a
href=http://www.ncbi.nlm.nih.gov:80/entrez/query.fcgi?cmd=Retrieve&db=Nucleotide
&list_uids=13128889&dopt=GenBank>AF232017</a>  400  .......................
422
<a name = 13128883></a><a
href=http://www.ncbi.nlm.nih.gov:80/entrez/query.fcgi?cmd=Retrieve&db=Nucleotide
&list_uids=13128883&dopt=GenBank>AF232014</a>  400  .......................
422
<a name = 13123638></a><a
href=http://www.ncbi.nlm.nih.gov:80/entrez/query.fcgi?cmd=Retrieve&db=Nucleotide
&list_uids=13123638&dopt=GenBank>AF318564</a>  345  .......................
367
<a name = 13123636></a><a
href=http://www.ncbi.nlm.nih.gov:80/entrez/query.fcgi?cmd=Retrieve&db=Nucleotide
&list_uids=13123636&dopt=GenBank>AF318563</a>  345  .......................
367
<a name = 13123634></a><a
href=http://www.ncbi.nlm.nih.gov:80/entrez/query.fcgi?cmd=Retrieve&db=Nucleotide
&list_uids=13123634&dopt=GenBank>AF318562</a>  344  .......................
366
<a name = 13123632></a><a
href=http://www.ncbi.nlm.nih.gov:80/entrez/query.fcgi?cmd=Retrieve&db=Nucleotide
&list_uids=13123632&dopt=GenBank>AF318561</a>  344  .......................
366
<a name = 13123630></a><a
href=http://www.ncbi.nlm.nih.gov:80/entrez/query.fcgi?cmd=Retrieve&db=Nucleotide
&list_uids=13123630&dopt=GenBank>AF318560</a>  344  .......................
366
<a name = 13123628></a><a
href=http://www.ncbi.nlm.nih.gov:80/entrez/query.fcgi?cmd=Retrieve&db=Nucleotide
&list_uids=13123628&dopt=GenBank>AF318559</a>  344  .......................
366
<a name = 13123626></a><a
href=http://www.ncbi.nlm.nih.gov:80/entrez/query.fcgi?cmd=Retrieve&db=Nucleotide
&list_uids=13123626&dopt=GenBank>AF318558</a>  344  .......................
366
<a name = 13123624></a><a
href=http://www.ncbi.nlm.nih.gov:80/entrez/query.fcgi?cmd=Retrieve&db=Nucleotide
&list_uids=13123624&dopt=GenBank>AF318557</a>  381  .......................
403
<a name = 13123622></a><a
href=http://www.ncbi.nlm.nih.gov:80/entrez/query.fcgi?cmd=Retrieve&db=Nucleotide
&list_uids=13123622&dopt=GenBank>AF318556</a>  381  .......................
403
<a name = 13123620></a><a
href=http://www.ncbi.nlm.nih.gov:80/entrez/query.fcgi?cmd=Retrieve&db=Nucleotide
&list_uids=13123620&dopt=GenBank>AF318555</a>  381  .......................
403
<a name = 13123618></a><a
href=http://www.ncbi.nlm.nih.gov:80/entrez/query.fcgi?cmd=Retrieve&db=Nucleotide
```

```
&list_uids=13123618&dopt=GenBank>AF318554</a>  381     ........................
403
<a name = 13123616></a><a
href=http://www.ncbi.nlm.nih.gov:80/entrez/query.fcgi?cmd=Retrieve&db=Nucleotide
&list_uids=13123616&dopt=GenBank>AF318553</a>  381     ........................
403
<a name = 13123614></a><a
href=http://www.ncbi.nlm.nih.gov:80/entrez/query.fcgi?cmd=Retrieve&db=Nucleotide
&list_uids=13123614&dopt=GenBank>AF318552</a>  381     ........................
403
<a name = 13123612></a><a
href=http://www.ncbi.nlm.nih.gov:80/entrez/query.fcgi?cmd=Retrieve&db=Nucleotide
&list_uids=13123612&dopt=GenBank>AF318551</a>  381     ........................
403
<a name = 13123610></a><a
href=http://www.ncbi.nlm.nih.gov:80/entrez/query.fcgi?cmd=Retrieve&db=Nucleotide
&list_uids=13123610&dopt=GenBank>AF318550</a>  381     ........................
403
<a name = 13123608></a><a
href=http://www.ncbi.nlm.nih.gov:80/entrez/query.fcgi?cmd=Retrieve&db=Nucleotide
&list_uids=13123608&dopt=GenBank>AF318549</a>  381     ........................
403
<a name = 13123606></a><a
href=http://www.ncbi.nlm.nih.gov:80/entrez/query.fcgi?cmd=Retrieve&db=Nucleotide
&list_uids=13123606&dopt=GenBank>AF318548</a>  381     ........................
403
<a name = 13122454></a><a
href=http://www.ncbi.nlm.nih.gov:80/entrez/query.fcgi?cmd=Retrieve&db=Nucleotide
&list_uids=13122454&dopt=GenBank>AF238041</a>  400     ........................
422
<a name = 12083042></a><a
href=http://www.ncbi.nlm.nih.gov:80/entrez/query.fcgi?cmd=Retrieve&db=Nucleotide
&list_uids=12083042&dopt=GenBank>AF326272</a>  400     ........................
422
<a name = 12083040></a><a
href=http://www.ncbi.nlm.nih.gov:80/entrez/query.fcgi?cmd=Retrieve&db=Nucleotide
&list_uids=12083040&dopt=GenBank>AF326271</a>  400     ........................
422
<a name = 12083038></a><a
href=http://www.ncbi.nlm.nih.gov:80/entrez/query.fcgi?cmd=Retrieve&db=Nucleotide
&list_uids=12083038&dopt=GenBank>AF326270</a>  400     ........................
422
<a name = 12083030></a><a
href=http://www.ncbi.nlm.nih.gov:80/entrez/query.fcgi?cmd=Retrieve&db=Nucleotide
&list_uids=12083030&dopt=GenBank>AF326266</a>  400     ........................
422
<a name = 9967766></a><a
href=http://www.ncbi.nlm.nih.gov:80/entrez/query.fcgi?cmd=Retrieve&db=Nucleotide
&list_uids=09967766&dopt=GenBank>AJ004340</a>  302     ....n...................
326
<a name = 9967734></a><a
href=http://www.ncbi.nlm.nih.gov:80/entrez/query.fcgi?cmd=Retrieve&db=Nucleotide
&list_uids=09967734&dopt=GenBank>AJ004264</a>  302     ....n...................
326
</PRE>

<PRE>
```

```
Database: nt
  Posted date:  Mar 2, 2001 12:20 AM
Number of letters in database: 2,863,827,885
Number of sequences in database:  807,597

Lambda     K      H
   1.37    0.711   1.31

Gapped
Lambda     K      H
   1.37    0.711   1.31

Matrix: blastn matrix:1 -3
Gap Penalties: Existence: 5, Extension: 2
Number of Hits to DB: 39355
Number of Sequences: 807597
Number of extensions: 39355
Number of successful extensions: 15066
Number of sequences better than 10.0: 5706
length of query: 25
length of database: 2,863,827,885
effective HSP length: 17
effective length of query: 8
effective length of database: 2,850,098,736
effective search space: 22800789888
effective search space used: 22800789888
T: 0
A: 30
X1: 6 (11.9 bits)
X2: 15 (29.7 bits)
S1: 12 (24.3 bits)
S2: 16 (32.2 bits)

</PRE>

</BODY>
</HTML>
</FORM>
</BODY>
</HTML>
```

```
<a
href="http://www.ncbi.nlm.nih.gov:80/entrez/query.fcgi?cmd=Retrieve&db=Nucleotid
e&list_uids=11071907&dopt=GenBank">emb|AJ293412.1|RRU293412</a>  Rupicapra
rupicapra rupicapra mito...    <a href = #11071907> 50</a>   2e-05
<a
href="http://www.ncbi.nlm.nih.gov:80/entrez/query.fcgi?cmd=Retrieve&db=Nucleotid
e&list_uids=11071724&dopt=GenBank">emb|AJ293418.1|CFA293418</a>  Capra falconeri
mitochondrial part...    <a href = #11071724> 50</a>   2e-05
<a
href="http://www.ncbi.nlm.nih.gov:80/entrez/query.fcgi?cmd=Retrieve&db=Nucleotid
e&list_uids=02677641&dopt=GenBank">gb|U07578.1|DCU07578</a>  Dasycercus
cristicauda mitochondrion c...    <a href = #2677641> 50</a>   2e-05
<a
href="http://www.ncbi.nlm.nih.gov:80/entrez/query.fcgi?cmd=Retrieve&db=Nucleotid
e&list_uids=09998754&dopt=GenBank">emb|AJ004180.1|HPAJ4180</a>  Hydrobates
pelagicus mitochondrial ...    <a href = #9998754> 50</a>   2e-05
<a
href="http://www.ncbi.nlm.nih.gov:80/entrez/query.fcgi?cmd=Retrieve&db=Nucleotid
e&list_uids=09968729&dopt=GenBank">emb|Y15695.1|SMY15695</a>  Schilbe mystus
mitochondrial cytb gen...    <a href = #9968729> 50</a>   2e-05
<a
href="http://www.ncbi.nlm.nih.gov:80/entrez/query.fcgi?cmd=Retrieve&db=Nucleotid
e&list_uids=09967851&dopt=GenBank">emb|Y15697.1|EDY15697</a>  Eutropius
depressirostris mitochondri...    <a href = #9967851> 50</a>   2e-05
<a
href="http://www.ncbi.nlm.nih.gov:80/entrez/query.fcgi?cmd=Retrieve&db=Nucleotid
e&list_uids=09967849&dopt=GenBank">emb|Y15696.1|EDY15696</a>  Eutropius
depressirostris mitochondri...    <a href = #9967849> 50</a>   2e-05
<a
href="http://www.ncbi.nlm.nih.gov:80/entrez/query.fcgi?cmd=Retrieve&db=Nucleotid
e&list_uids=02394147&dopt=GenBank">gb|AF015035.1|AF015035</a>  Steatocranus
casuarinus 20 cytochrom...    <a href = #2394147> 50</a>   2e-05
<a
href="http://www.ncbi.nlm.nih.gov:80/entrez/query.fcgi?cmd=Retrieve&db=Nucleotid
e&list_uids=02367574&dopt=GenBank">gb|AF015761.1|AF015761</a>  Palmeria dolei
cytochrome b (Cytb) g...    <a href = #2367574> 50</a>   2e-05
<a
href="http://www.ncbi.nlm.nih.gov:80/entrez/query.fcgi?cmd=Retrieve&db=Nucleotid
e&list_uids=02367568&dopt=GenBank">gb|AF015758.1|AF015758</a>  Oreomystis mana
cytochrome b (Cytb) ...    <a href = #2367568> 50</a>   2e-05
<a
href="http://www.ncbi.nlm.nih.gov:80/entrez/query.fcgi?cmd=Retrieve&db=Nucleotid
e&list_uids=02367564&dopt=GenBank">gb|AF015756.1|AF015756</a>  Vestiaria
coccinea cytochrome b (Cyt...    <a href = #2367564> 50</a>   2e-05
<a
href="http://www.ncbi.nlm.nih.gov:80/entrez/query.fcgi?cmd=Retrieve&db=Nucleotid
e&list_uids=02367560&dopt=GenBank">gb|AF015754.1|AF015754</a>  Himatione
sanguinea cytochrome b (Cy...    <a href = #2367560> 50</a>   2e-05
<a
href="http://www.ncbi.nlm.nih.gov:80/entrez/query.fcgi?cmd=Retrieve&db=Nucleotid
e&list_uids=02198698&dopt=GenBank">gb|U76052.1|DNU76052</a>  Dromaius
novaehollandiae cytochrome b ...    <a href = #2198698> 50</a>   2e-05
<a
href="http://www.ncbi.nlm.nih.gov:80/entrez/query.fcgi?cmd=Retrieve&db=Nucleotid
e&list_uids=08052194&dopt=GenBank">emb|AJ236834.1|CGL236834</a>  Clethrionomys
glareolus mitochondr...    <a href = #8052194> 50</a>   2e-05
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=02149204&dopt=GenBank">gb|U83158.1|POU83158</a>  Pelecanus
onocrotalus cytochrome B gen...   <a href = #2149204> 50</a>   2e-05
<a
href="http://www.ncbi.nlm.nih.gov:80/entrez/query.fcgi?cmd=Retrieve&db=Nucleotid
e&list_uids=02149202&dopt=GenBank">gb|U83157.1|POU83157</a>  Pelecanus
onocrotalus cytochrome B gen...   <a href = #2149202> 50</a>   2e-05
<a
href="http://www.ncbi.nlm.nih.gov:80/entrez/query.fcgi?cmd=Retrieve&db=Nucleotid
e&list_uids=02149182&dopt=GenBank">gb|U83156.1|AAU83156</a>  Anhinga anhinga
cytochrome B gene, mit...   <a href = #2149182> 50</a>   2e-05
<a
href="http://www.ncbi.nlm.nih.gov:80/entrez/query.fcgi?cmd=Retrieve&db=Nucleotid
e&list_uids=02149180&dopt=GenBank">gb|U83155.1|AAU83155</a>  Anhinga anhinga
cytochrome B gene, mit...   <a href = #2149180> 50</a>   2e-05
<a
href="http://www.ncbi.nlm.nih.gov:80/entrez/query.fcgi?cmd=Retrieve&db=Nucleotid
e&list_uids=02149178&dopt=GenBank">gb|U83154.1|AAU83154</a>  Anhinga anhinga
cytochrome B gene, mit...   <a href = #2149178> 50</a>   2e-05
<a
href="http://www.ncbi.nlm.nih.gov:80/entrez/query.fcgi?cmd=Retrieve&db=Nucleotid
e&list_uids=02098654&dopt=GenBank">gb|U81356.1|CLU81356</a>  Chelodina
longicollis cytochrome b gen...   <a href = #2098654> 50</a>   2e-05
<a
href="http://www.ncbi.nlm.nih.gov:80/entrez/query.fcgi?cmd=Retrieve&db=Nucleotid
e&list_uids=07671584&dopt=GenBank">emb|AJ277676.1|ESC277676</a>  Elaphe scalaris
mitochondrial part...   <a href = #7671584> 50</a>   2e-05
<a
href="http://www.ncbi.nlm.nih.gov:80/entrez/query.fcgi?cmd=Retrieve&db=Nucleotid
e&list_uids=07671582&dopt=GenBank">emb|AJ277675.1|ESC277675</a>  Elaphe scalaris
mitochondrial part...   <a href = #7671582> 50</a>   2e-05
<a
href="http://www.ncbi.nlm.nih.gov:80/entrez/query.fcgi?cmd=Retrieve&db=Nucleotid
e&list_uids=07671550&dopt=GenBank">emb|AJ277672.1|ELO277672</a>  Elaphe
longissima mitochondrial pa...   <a href = #7671550> 50</a>   2e-05
<a
href="http://www.ncbi.nlm.nih.gov:80/entrez/query.fcgi?cmd=Retrieve&db=Nucleotid
e&list_uids=07671548&dopt=GenBank">emb|AJ277671.1|ELO277671</a>  Elaphe
longissima mitochondrial pa...   <a href = #7671548> 50</a>   2e-05
<a
href="http://www.ncbi.nlm.nih.gov:80/entrez/query.fcgi?cmd=Retrieve&db=Nucleotid
e&list_uids=02252500&dopt=GenBank">emb|Y11832.1|MTDNCOMGN</a>  Dasypus
novemcinctus complete mitoch...   <a href = #2252500> 50</a>   2e-05
<a
href="http://www.ncbi.nlm.nih.gov:80/entrez/query.fcgi?cmd=Retrieve&db=Nucleotid
e&list_uids=06522826&dopt=GenBank">emb|AJ388467.1|NBA388467</a>  Nemacheilus
barbatulus mitochondria...   <a href = #6522826> 50</a>   2e-05
<a
href="http://www.ncbi.nlm.nih.gov:80/entrez/query.fcgi?cmd=Retrieve&db=Nucleotid
e&list_uids=06522795&dopt=GenBank">emb|AJ388468.1|IME388468</a>  Ictalurus melas
mitchondrial cyt b...   <a href = #6522795> 50</a>   2e-05
<a
href="http://www.ncbi.nlm.nih.gov:80/entrez/query.fcgi?cmd=Retrieve&db=Nucleotid
e&list_uids=06522793&dopt=GenBank">emb|AJ388459.1|LDE388459</a>  Leucaspius
delineatus mitochondrial...   <a href = #6522793> 50</a>   2e-05
<a
href="http://www.ncbi.nlm.nih.gov:80/entrez/query.fcgi?cmd=Retrieve&db=Nucleotid
```

```
e&list_uids=01184332&dopt=GenBank">gb|U46167.1|SCU46167</a>   Sciurus
carolinensis cytochrome b gene...    <a href = #1184332> 50</a>   2e-05
<a
href="http://www.ncbi.nlm.nih.gov:80/entrez/query.fcgi?cmd=Retrieve&db=Nucleotid
e&list_uids=05731956&dopt=GenBank">emb|AJ245673.1|SIN245673</a>   Schilbe
intermedius partial mitoch...    <a href = #5731956> 50</a>   2e-05
<a
href="http://www.ncbi.nlm.nih.gov:80/entrez/query.fcgi?cmd=Retrieve&db=Nucleotid
e&list_uids=05731954&dopt=GenBank">emb|AJ245638.1|SIN245638</a>   Schilbe
intermedius partial mitoch...    <a href = #5731954> 50</a>   2e-05
<a
href="http://www.ncbi.nlm.nih.gov:80/entrez/query.fcgi?cmd=Retrieve&db=Nucleotid
e&list_uids=05731784&dopt=GenBank">emb|AJ245678.1|EDE245678</a>   Eutropius
depressirostris partial ...    <a href = #5731784> 50</a>   2e-05
<a
href="http://www.ncbi.nlm.nih.gov:80/entrez/query.fcgi?cmd=Retrieve&db=Nucleotid
e&list_uids=05731782&dopt=GenBank">emb|AJ245677.1|EDE245677</a>   Eutropius
depressirostris partial ...    <a href = #5731782> 50</a>   2e-05
<a
href="http://www.ncbi.nlm.nih.gov:80/entrez/query.fcgi?cmd=Retrieve&db=Nucleotid
e&list_uids=05731780&dopt=GenBank">emb|AJ245676.1|EDE245676</a>   Eutropius
depressirostris partial ...    <a href = #5731780> 50</a>   2e-05
<a
href="http://www.ncbi.nlm.nih.gov:80/entrez/query.fcgi?cmd=Retrieve&db=Nucleotid
e&list_uids=05731778&dopt=GenBank">emb|AJ245675.1|EDE245675</a>   Eutropius
depressirostris partial ...    <a href = #5731778> 50</a>   2e-05
<a
href="http://www.ncbi.nlm.nih.gov:80/entrez/query.fcgi?cmd=Retrieve&db=Nucleotid
e&list_uids=05731776&dopt=GenBank">emb|AJ245674.1|EDE245674</a>   Eutropius
depressirostris partial ...    <a href = #5731776> 50</a>   2e-05
<a
href="http://www.ncbi.nlm.nih.gov:80/entrez/query.fcgi?cmd=Retrieve&db=Nucleotid
e&list_uids=05541879&dopt=GenBank">emb|Y16884.3|MTRACOMPL</a>   Rhea americana
complete mitochondria...    <a href = #5541879> 50</a>   2e-05
<a
href="http://www.ncbi.nlm.nih.gov:80/entrez/query.fcgi?cmd=Retrieve&db=Nucleotid
e&list_uids=01674455&dopt=GenBank">gb|U60768.1|PCU60768</a>   Parus cinctus
cytochrome b gene, mitoc...    <a href = #1674455> 50</a>   2e-05
<a
href="http://www.ncbi.nlm.nih.gov:80/entrez/query.fcgi?cmd=Retrieve&db=Nucleotid
e&list_uids=01657738&dopt=GenBank">gb|U48955.1|TMU48955</a>   Thalassarche
melanophris melanophris c...    <a href = #1657738> 50</a>   2e-05
<a
href="http://www.ncbi.nlm.nih.gov:80/entrez/query.fcgi?cmd=Retrieve&db=Nucleotid
e&list_uids=01657736&dopt=GenBank">gb|U48954.1|TCU48954</a>   Thalassarche
chrysostoma cytochrome b ...    <a href = #1657736> 50</a>   2e-05
<a
href="http://www.ncbi.nlm.nih.gov:80/entrez/query.fcgi?cmd=Retrieve&db=Nucleotid
e&list_uids=01657732&dopt=GenBank">gb|U48944.1|TCU48944</a>   Thalassarche
chlororhynchos chlororhyn...    <a href = #1657732> 50</a>   2e-05
<a
href="http://www.ncbi.nlm.nih.gov:80/entrez/query.fcgi?cmd=Retrieve&db=Nucleotid
e&list_uids=01657728&dopt=GenBank">gb|U48943.1|PPU48943</a>   Phoebetria
palpebrata cytochrome b (cy...    <a href = #1657728> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotid
e&list_uids=01657720&dopt=GenBank">gb|U48942.1|PFU48942</a>   Phoebetria fusca
cytochrome b (cytb) g...    <a href = #1657720> 50</a>   2e-05
<a
href="http://www.ncbi.nlm.nih.gov:80/entrez/query.fcgi?cmd=Retrieve&db=Nucleotid
e&list_uids=01657714&dopt=GenBank">gb|U48941.1|MGU48941</a>   Macronectes
giganteus cytochrome b (cy...    <a href = #1657714> 50</a>   2e-05
<a
href="http://www.ncbi.nlm.nih.gov:80/entrez/query.fcgi?cmd=Retrieve&db=Nucleotid
e&list_uids=01657712&dopt=GenBank">gb|U48947.1|DEU48947</a>   Diomedea exulans
dabbenena cytochrome ...    <a href = #1657712> 50</a>   2e-05
<a
href="http://www.ncbi.nlm.nih.gov:80/entrez/query.fcgi?cmd=Retrieve&db=Nucleotid
e&list_uids=01657710&dopt=GenBank">gb|U48946.1|DEU48946</a>   Diomedea epomophora
sanfordi cytochrom...    <a href = #1657710> 50</a>   2e-05
<a
href="http://www.ncbi.nlm.nih.gov:80/entrez/query.fcgi?cmd=Retrieve&db=Nucleotid
e&list_uids=01657708&dopt=GenBank">gb|U48948.1|DAU48948</a>   Diomedea
amsterdamensis cytochrome b (...    <a href = #1657708> 50</a>   2e-05
<a
href="http://www.ncbi.nlm.nih.gov:80/entrez/query.fcgi?cmd=Retrieve&db=Nucleotid
e&list_uids=01256221&dopt=GenBank">gb|U15725.1|PRU15725</a>   Piranga rubra
cytochrome b gene, mitoc...    <a href = #1256221> 50</a>   2e-05
<a
href="http://www.ncbi.nlm.nih.gov:80/entrez/query.fcgi?cmd=Retrieve&db=Nucleotid
e&list_uids=01513285&dopt=GenBank">gb|U66508.1|APU66508</a>   Artibeus
planirostris cytochrome b (cy...    <a href = #1513285> 50</a>   2e-05
<a
href="http://www.ncbi.nlm.nih.gov:80/entrez/query.fcgi?cmd=Retrieve&db=Nucleotid
e&list_uids=01513283&dopt=GenBank">gb|U66507.1|AOU66507</a>   Artibeus obscurus
cytochrome b (cytb) ...    <a href = #1513283> 50</a>   2e-05
<a
href="http://www.ncbi.nlm.nih.gov:80/entrez/query.fcgi?cmd=Retrieve&db=Nucleotid
e&list_uids=01513281&dopt=GenBank">gb|U66506.1|AOU66506</a>   Artibeus obscurus
cytochrome b (cytb) ...    <a href = #1513281> 50</a>   2e-05
<a
href="http://www.ncbi.nlm.nih.gov:80/entrez/query.fcgi?cmd=Retrieve&db=Nucleotid
e&list_uids=01513279&dopt=GenBank">gb|U66505.1|ALU66505</a>   Artibeus lituratus
cytochrome b (cytb)...    <a href = #1513279> 50</a>   2e-05
<a
href="http://www.ncbi.nlm.nih.gov:80/entrez/query.fcgi?cmd=Retrieve&db=Nucleotid
e&list_uids=01513277&dopt=GenBank">gb|U66504.1|AJU66504</a>   Artibeus
jamaicensis cytochrome b (cyt...    <a href = #1513277> 50</a>   2e-05
<a
href="http://www.ncbi.nlm.nih.gov:80/entrez/query.fcgi?cmd=Retrieve&db=Nucleotid
e&list_uids=01513275&dopt=GenBank">gb|U66503.1|AJU66503</a>   Artibeus
jamaicensis cytochrome b (cyt...    <a href = #1513275> 50</a>   2e-05
<a
href="http://www.ncbi.nlm.nih.gov:80/entrez/query.fcgi?cmd=Retrieve&db=Nucleotid
e&list_uids=01513273&dopt=GenBank">gb|U66502.1|AIU66502</a>   Artibeus
intermedius cytochrome b (cyt...    <a href = #1513273> 50</a>   2e-05
<a
href="http://www.ncbi.nlm.nih.gov:80/entrez/query.fcgi?cmd=Retrieve&db=Nucleotid
e&list_uids=01513271&dopt=GenBank">gb|U66501.1|AIU66501</a>   Artibeus inopinatus
cytochrome b (cytb...    <a href = #1513271> 50</a>   2e-05
<a
href="http://www.ncbi.nlm.nih.gov:80/entrez/query.fcgi?cmd=Retrieve&db=Nucleotid
```

```
e&list_uids=01513267&dopt=GenBank">gb|U66500.1|AHU66500</a>   Artibeus hirsutus
cytochrome b (cytb) ...    <a href = #1513267> 50</a>   2e-05
<a
href="http://www.ncbi.nlm.nih.gov:80/entrez/query.fcgi?cmd=Retrieve&db=Nucleotid
e&list_uids=01513259&dopt=GenBank">gb|U66499.1|AFU66499</a>   Artibeus
fraterculus cytochrome b (cyt...    <a href = #1513259> 50</a>   2e-05
<a
href="http://www.ncbi.nlm.nih.gov:80/entrez/query.fcgi?cmd=Retrieve&db=Nucleotid
e&list_uids=01513257&dopt=GenBank">gb|U66498.1|AFU66498</a>   Artibeus fimbriatus
cytochrome b (cytb...    <a href = #1513257> 50</a>   2e-05
<a
href="http://www.ncbi.nlm.nih.gov:80/entrez/query.fcgi?cmd=Retrieve&db=Nucleotid
e&list_uids=01458165&dopt=GenBank">gb|U63061.1|BBU63061</a>   Brachyramphus
brevirostris cytochrome ...    <a href = #1458165> 50</a>   2e-05
<a
href="http://www.ncbi.nlm.nih.gov:80/entrez/query.fcgi?cmd=Retrieve&db=Nucleotid
e&list_uids=01458163&dopt=GenBank">gb|U63060.1|BBU63060</a>   Brachyramphus
brevirostris cytochrome ...    <a href = #1458163> 50</a>   2e-05
<a
href="http://www.ncbi.nlm.nih.gov:80/entrez/query.fcgi?cmd=Retrieve&db=Nucleotid
e&list_uids=01458161&dopt=GenBank">gb|U63059.1|BBU63059</a>   Brachyramphus
brevirostris cytochrome ...    <a href = #1458161> 50</a>   2e-05
<a
href="http://www.ncbi.nlm.nih.gov:80/entrez/query.fcgi?cmd=Retrieve&db=Nucleotid
e&list_uids=01458159&dopt=GenBank">gb|U63058.1|BBU63058</a>   Brachyramphus
brevirostris cytochrome ...    <a href = #1458159> 50</a>   2e-05
<a
href="http://www.ncbi.nlm.nih.gov:80/entrez/query.fcgi?cmd=Retrieve&db=Nucleotid
e&list_uids=01381629&dopt=GenBank">gb|U58386.1|SJU58386</a>   Scolomys juruaense
cytochrome b (cyt-b...    <a href = #1381629> 50</a>   2e-05
<a
href="http://www.ncbi.nlm.nih.gov:80/entrez/query.fcgi?cmd=Retrieve&db=Nucleotid
e&list_uids=00336482&dopt=GenBank">gb|L11905.1|CGYMTCYTBD</a>   Cratogeomys
gymnurus mitochondrial c...    <a href = #336482> 50</a>   2e-05
<a
href="http://www.ncbi.nlm.nih.gov:80/entrez/query.fcgi?cmd=Retrieve&db=Nucleotid
e&list_uids=01041855&dopt=GenBank">gb|U34672.1|MNU34672</a>   Metachirus
nudicaudatus cytochrome b l...    <a href = #1041855> 50</a>   2e-05
<a
href="http://www.ncbi.nlm.nih.gov:80/entrez/query.fcgi?cmd=Retrieve&db=Nucleotid
e&list_uids=01041853&dopt=GenBank">gb|U34671.1|MNU34671</a>   Metachirus
nudicaudatus cytochrome b l...    <a href = #1041853> 50</a>   2e-05
<a
href="http://www.ncbi.nlm.nih.gov:80/entrez/query.fcgi?cmd=Retrieve&db=Nucleotid
e&list_uids=02440142&dopt=GenBank">emb|Y14951.1|MTY14951</a>   Capreolus
capreolus mitochondrial cyt...    <a href = #2440142> 50</a>   2e-05
<a
href="http://www.ncbi.nlm.nih.gov:80/entrez/query.fcgi?cmd=Retrieve&db=Nucleotid
e&list_uids=02315216&dopt=GenBank">emb|Y14371.1|MTCCCYTB</a>   Capreolus
capreolus mitochondrial cyt...    <a href = #2315216> 50</a>   2e-05
<a
href="http://www.ncbi.nlm.nih.gov:80/entrez/query.fcgi?cmd=Retrieve&db=Nucleotid
e&list_uids=00336490&dopt=GenBank">gb|L11909.1|CGYMTCYTBH</a>   Cratogeomys
tylorhinus mitochondrial...    <a href = #336490> 50</a>   2e-05
<a
href="http://www.ncbi.nlm.nih.gov:80/entrez/query.fcgi?cmd=Retrieve&db=Nucleotid
```

```
e&list_uids=00343117&dopt=GenBank">gb|L11901.1|PPGMTCYTBB</a>  Geomys bursarius
juggosicularis mito...    <a href = #343117> 50</a>   2e-05
<a
href="http://www.ncbi.nlm.nih.gov:80/entrez/query.fcgi?cmd=Retrieve&db=Nucleotid
e&list_uids=00336480&dopt=GenBank">gb|L11904.1|CGYMTCYTBC</a>  Cratogeomys
goldmani goldmani mitoch...    <a href = #336480> 50</a>   2e-05
<a
href="http://www.ncbi.nlm.nih.gov:80/entrez/query.fcgi?cmd=Retrieve&db=Nucleotid
e&list_uids=01289306&dopt=GenBank">emb|X94928.1|SPCYTB</a>  S.putorius
mitochondrial DNA for cytoch...    <a href = #1289306> 50</a>   2e-05
<a
href="http://www.ncbi.nlm.nih.gov:80/entrez/query.fcgi?cmd=Retrieve&db=Nucleotid
e&list_uids=01197608&dopt=GenBank">gb|U46770.1|ARU46770</a>  Anthus richardi
cytochrome b gene, mit...    <a href = #1197608> 50</a>   2e-05
<a
href="http://www.ncbi.nlm.nih.gov:80/entrez/query.fcgi?cmd=Retrieve&db=Nucleotid
e&list_uids=01197598&dopt=GenBank">gb|U46769.1|ABU46769</a>  Anthus berthelotii
cytochrome b gene, ...    <a href = #1197598> 50</a>   2e-05
<a
href="http://www.ncbi.nlm.nih.gov:80/entrez/query.fcgi?cmd=Retrieve&db=Nucleotid
e&list_uids=01184364&dopt=GenBank">gb|U46183.1|SSU46183</a>  Sciurus stramineus
cytochrome b gene, ...    <a href = #1184364> 50</a>   2e-05
<a
href="http://www.ncbi.nlm.nih.gov:80/entrez/query.fcgi?cmd=Retrieve&db=Nucleotid
e&list_uids=02407991&dopt=GenBank">emb|Y10728.1|PSMY10728</a>   P.schwarzi
mitochondrial cytb gene, ...    <a href = #2407991> 50</a>   2e-05
<a
href="http://www.ncbi.nlm.nih.gov:80/entrez/query.fcgi?cmd=Retrieve&db=Nucleotid
e&list_uids=01204134&dopt=GenBank">emb|X95768.1|NLMCB</a>  N.leucopterus
mitochondrial cytochrome b...    <a href = #1204134> 50</a>   2e-05
<a
href="http://www.ncbi.nlm.nih.gov:80/entrez/query.fcgi?cmd=Retrieve&db=Nucleotid
e&list_uids=01261958&dopt=GenBank">emb|X95767.1|NGRIMCB</a>  N.griseus
mitochondrial cytochrome b gene    <a href = #1261958> 50</a>   2e-05
<a
href="http://www.ncbi.nlm.nih.gov:80/entrez/query.fcgi?cmd=Retrieve&db=Nucleotid
e&list_uids=01050714&dopt=GenBank">emb|X86763.1|MTVGCYT26</a>  V.gryphus
mitochondrial cytb gene         <a href = #1050714> 50</a>   2e-05
<a
href="http://www.ncbi.nlm.nih.gov:80/entrez/query.fcgi?cmd=Retrieve&db=Nucleotid
e&list_uids=01050648&dopt=GenBank">emb|X86754.1|MTLCCYT17</a>  L.crumeniferus
mitochondrial cytb gene     <a href = #1050648> 50</a>   2e-05
<a
href="http://www.ncbi.nlm.nih.gov:80/entrez/query.fcgi?cmd=Retrieve&db=Nucleotid
e&list_uids=01050586&dopt=GenBank">emb|X86743.1|MTCACYT6</a>  C.aura
mitochondrial cytb gene            <a href = #1050586> 50</a>   2e-05
<a
href="http://www.ncbi.nlm.nih.gov:80/entrez/query.fcgi?cmd=Retrieve&db=Nucleotid
e&list_uids=11862859&dopt=GenBank">dbj|AB035242.1|AB035242</a>  Pantodon
buchholzi mitochondrial cy...    <a href = #11862859> 50</a>   2e-05
<a
href="http://www.ncbi.nlm.nih.gov:80/entrez/query.fcgi?cmd=Retrieve&db=Nucleotid
e&list_uids=00013749&dopt=GenBank">emb|X60946.1|MITDCB33</a>  T. dorbignyi
mitochondrial gene for c...    <a href = #13749> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotid
e&list_uids=02959918&dopt=GenBank">emb|AJ000029.1|MIRTCYB29</a>   Rangifer
tarandus mitochondrial cy...      <a href = #2959918>  50</a>     2e-05
<a
href="http://www.ncbi.nlm.nih.gov:80/entrez/query.fcgi?cmd=Retrieve&db=Nucleotid
e&list_uids=00693969&dopt=GenBank">emb|X82302.1|MIPFCYTBG</a>   P.fasciata
mitochondrial cytochrome ...     <a href = #693969>  50</a>     2e-05
<a
href="http://www.ncbi.nlm.nih.gov:80/entrez/query.fcgi?cmd=Retrieve&db=Nucleotid
e&list_uids=00013198&dopt=GenBank">emb|X56291.1|MIOHCYTB</a>   O.hemionus
mitochondrion cytb gene fo...    <a href = #13198>  50</a>     2e-05
<a
href="http://www.ncbi.nlm.nih.gov:80/entrez/query.fcgi?cmd=Retrieve&db=Nucleotid
e&list_uids=00013156&dopt=GenBank">emb|X56284.1|MIOACYTB</a>   O.aries
mitochondrion cytb gene for c...    <a href = #13156>  50</a>     2e-05
<a
href="http://www.ncbi.nlm.nih.gov:80/entrez/query.fcgi?cmd=Retrieve&db=Nucleotid
e&list_uids=02959904&dopt=GenBank">emb|AJ000022.1|MIMSCYB22</a>   Dama dama
mitochondrial cytb gene         <a href = #2959904>  50</a>     2e-05
<a
href="http://www.ncbi.nlm.nih.gov:80/entrez/query.fcgi?cmd=Retrieve&db=Nucleotid
e&list_uids=00414771&dopt=GenBank">emb|X72005.1|MILWCYTB</a>   L.weddelli
mitochondrial gene for cyt...     <a href = #414771>  50</a>     2e-05
<a
href="http://www.ncbi.nlm.nih.gov:80/entrez/query.fcgi?cmd=Retrieve&db=Nucleotid
e&list_uids=02154895&dopt=GenBank">emb|Y08814.1|MIHLCYTBG</a>   H.liberiensis
mitochondrial cytochro...     <a href = #2154895>  50</a>     2e-05
<a
href="http://www.ncbi.nlm.nih.gov:80/entrez/query.fcgi?cmd=Retrieve&db=Nucleotid
e&list_uids=00012981&dopt=GenBank">emb|X60942.1|MIGTCB33</a>   Gymnorhina tibicen
mitochondrial gene...     <a href = #12981>  50</a>     2e-05
<a
href="http://www.ncbi.nlm.nih.gov:80/entrez/query.fcgi?cmd=Retrieve&db=Nucleotid
e&list_uids=00012907&dopt=GenBank">emb|X56290.1|MIDDCYTB</a>   D.dama
mitochondrion cytb gene for cy...    <a href = #12907>  50</a>     2e-05
<a
href="http://www.ncbi.nlm.nih.gov:80/entrez/query.fcgi?cmd=Retrieve&db=Nucleotid
e&list_uids=02959902&dopt=GenBank">emb|AJ000021.1|MICECYB21</a>   Cervus elaphus
mitochondrial cytb ...     <a href = #2959902>  50</a>     2e-05
<a
href="http://www.ncbi.nlm.nih.gov:80/entrez/query.fcgi?cmd=Retrieve&db=Nucleotid
e&list_uids=02959908&dopt=GenBank">emb|AJ000024.1|MICCCYB24</a>   Capreolus
capreolus mitochondrial ...     <a href = #2959908>  50</a>     2e-05
<a
href="http://www.ncbi.nlm.nih.gov:80/entrez/query.fcgi?cmd=Retrieve&db=Nucleotid
e&list_uids=00012800&dopt=GenBank">emb|V00654.1|MIBTXX</a>   Bos taurus complete
mitochondrial genome        <a href = #12800>  50</a>     2e-05
<a
href="http://www.ncbi.nlm.nih.gov:80/entrez/query.fcgi?cmd=Retrieve&db=Nucleotid
e&list_uids=00012624&dopt=GenBank">emb|X56286.1|MIAACYTBA</a>   A.americana
mitochondrion cytb gene ...     <a href = #12624>  50</a>     2e-05
<a
href="http://www.ncbi.nlm.nih.gov:80/entrez/query.fcgi?cmd=Retrieve&db=Nucleotid
e&list_uids=00304034&dopt=GenBank">gb|L19718.1|AIUMTCYTB</a>   Artibeus lituratus
mitochondrial cyto...     <a href = #304034>  50</a>     2e-05
<a
href="http://www.ncbi.nlm.nih.gov:80/entrez/query.fcgi?cmd=Retrieve&db=Nucleotid
```

```
e&list_uids=00896408&dopt=GenBank">gb|U27543.1|BRU27543</a>  Balearica regulorum
cytochrome b (cytb...    <a href = #896408> 50</a>   2e-05
<a
href="http://www.ncbi.nlm.nih.gov:80/entrez/query.fcgi?cmd=Retrieve&db=Nucleotid
e&list_uids=09845006&dopt=GenBank">dbj|AB030025.1|AB030025</a>  Sciurus
stramineus mitochondrial cy...    <a href = #9845006> 50</a>   2e-05
<a
href="http://www.ncbi.nlm.nih.gov:80/entrez/query.fcgi?cmd=Retrieve&db=Nucleotid
e&list_uids=00624183&dopt=GenBank">gb|U18258.1|SCU18258</a>  Spharagemon
campestris cytochrome b ge...    <a href = #624183> 50</a>   2e-05
<a
href="http://www.ncbi.nlm.nih.gov:80/entrez/query.fcgi?cmd=Retrieve&db=Nucleotid
e&list_uids=00624181&dopt=GenBank">gb|U18257.1|SCU18257</a>  Spharagemon collare
cytochrome b gene,...    <a href = #624181> 50</a>   2e-05
<a
href="http://www.ncbi.nlm.nih.gov:80/entrez/query.fcgi?cmd=Retrieve&db=Nucleotid
e&list_uids=00624173&dopt=GenBank">gb|U18253.1|TPU18253</a>  Trimerotropis
pistrinaria cytochrome b...    <a href = #624173> 50</a>   2e-05
<a
href="http://www.ncbi.nlm.nih.gov:80/entrez/query.fcgi?cmd=Retrieve&db=Nucleotid
e&list_uids=00624167&dopt=GenBank">gb|U18250.1|CPU18250</a>  Camnula pellucida
cytochrome b gene, m...    <a href = #624167> 50</a>   2e-05
<a
href="http://www.ncbi.nlm.nih.gov:80/entrez/query.fcgi?cmd=Retrieve&db=Nucleotid
e&list_uids=00601796&dopt=GenBank">gb|U17904.1|CCU17904</a>  Circotettix
carlinianus mitochondrion ...    <a href = #601796> 50</a>   2e-05
<a
href="http://www.ncbi.nlm.nih.gov:80/entrez/query.fcgi?cmd=Retrieve&db=Nucleotid
e&list_uids=01256162&dopt=GenBank">dbj|D84202.1|GOTMTCBB</a>  Capra falconeri
mitochondrial DNA for...    <a href = #1256162> 50</a>   2e-05
<a
href="http://www.ncbi.nlm.nih.gov:80/entrez/query.fcgi?cmd=Retrieve&db=Nucleotid
e&list_uids=01813356&dopt=GenBank">dbj|D82889.1|D82889</a>  Bos javanicus
mitochondrial DNA for cyt...    <a href = #1813356> 50</a>   2e-05
<a
href="http://www.ncbi.nlm.nih.gov:80/entrez/query.fcgi?cmd=Retrieve&db=Nucleotid
e&list_uids=00516676&dopt=GenBank">dbj|D32195.1|CCRMTCB25</a>  Capricornis
sumatrensis mitochodrial...    <a href = #516676> 50</a>   2e-05
<a
href="http://www.ncbi.nlm.nih.gov:80/entrez/query.fcgi?cmd=Retrieve&db=Nucleotid
e&list_uids=00516672&dopt=GenBank">dbj|D32191.1|CCRMTCB21</a>  Capricornis
crispus mitochondrial ge...    <a href = #516672> 50</a>   2e-05
<a
href="http://www.ncbi.nlm.nih.gov:80/entrez/query.fcgi?cmd=Retrieve&db=Nucleotid
e&list_uids=05811559&dopt=GenBank">dbj|AB021098.1|AB021098</a>  Cervus elaphus
kansuensis mitochond...    <a href = #5811559> 50</a>   2e-05
<a
href="http://www.ncbi.nlm.nih.gov:80/entrez/query.fcgi?cmd=Retrieve&db=Nucleotid
e&list_uids=05811557&dopt=GenBank">dbj|AB021097.1|AB021097</a>  Cervus elaphus
xanthopygus mitochon...    <a href = #5811557> 50</a>   2e-05
<a
href="http://www.ncbi.nlm.nih.gov:80/entrez/query.fcgi?cmd=Retrieve&db=Nucleotid
e&list_uids=05811553&dopt=GenBank">dbj|AB021095.1|AB021095</a>  Cervus nippon
yesoensis mitochondri...    <a href = #5811553> 50</a>   2e-05
<a
href="http://www.ncbi.nlm.nih.gov:80/entrez/query.fcgi?cmd=Retrieve&db=Nucleotid
```

```
e&list_uids=05811551&dopt=GenBank">dbj|AB021094.1|AB021094</a>  Cervus nippon
centralis mitochondri...    <a href = #5811551> 50</a>   2e-05
<a
href="http://www.ncbi.nlm.nih.gov:80/entrez/query.fcgi?cmd=Retrieve&db=Nucleotid
e&list_uids=05811547&dopt=GenBank">dbj|AB021092.1|AB021092</a>  Cervus nippon
mageshimae mitochondr...    <a href = #5811547> 50</a>   2e-05
<a
href="http://www.ncbi.nlm.nih.gov:80/entrez/query.fcgi?cmd=Retrieve&db=Nucleotid
e&list_uids=05811545&dopt=GenBank">dbj|AB021091.1|AB021091</a>  Cervus nippon
keramae mitochondrial...    <a href = #5811545> 50</a>   2e-05
<a
href="http://www.ncbi.nlm.nih.gov:80/entrez/query.fcgi?cmd=Retrieve&db=Nucleotid
e&list_uids=01881395&dopt=GenBank">dbj|AB001612.1|AB001612</a>  Cervus elaphus
mitochondrial DNA fo...    <a href = #1881395> 50</a>   2e-05
<a
href="http://www.ncbi.nlm.nih.gov:80/entrez/query.fcgi?cmd=Retrieve&db=Nucleotid
e&list_uids=01256201&dopt=GenBank">dbj|D84205.1|SHPMTCBE</a>  Sheep
mitochondrial DNA for cytochrom...    <a href = #1256201> 50</a>   2e-05
<a
href="http://www.ncbi.nlm.nih.gov:80/entrez/query.fcgi?cmd=Retrieve&db=Nucleotid
e&list_uids=01256199&dopt=GenBank">dbj|D84203.1|SHPMTCBC</a>  Ovis musimon
mitochondrial DNA for cy...    <a href = #1256199> 50</a>   2e-05
<a
href="http://www.ncbi.nlm.nih.gov:80/entrez/query.fcgi?cmd=Retrieve&db=Nucleotid
e&list_uids=00516663&dopt=GenBank">dbj|D34636.1|BOVMTCBB</a>  Bos javanicus
mitochondrial gene for ...    <a href = #516663> 50</a>   2e-05
<a
href="http://www.ncbi.nlm.nih.gov:80/entrez/query.fcgi?cmd=Retrieve&db=Nucleotid
e&list_uids=00516661&dopt=GenBank">dbj|D34635.1|BOVMTCBA</a>  Bovine
mitochondrial gene for cytochr...    <a href = #516661> 50</a>   2e-05
<a
href="http://www.ncbi.nlm.nih.gov:80/entrez/query.fcgi?cmd=Retrieve&db=Nucleotid
e&list_uids=00516821&dopt=GenBank">dbj|D32198.1|ORMMTCB28</a>  Oreamnos
americanus mitochondrial ge...    <a href = #516821> 50</a>   2e-05
<a
href="http://www.ncbi.nlm.nih.gov:80/entrez/query.fcgi?cmd=Retrieve&db=Nucleotid
e&list_uids=00516816&dopt=GenBank">dbj|D32196.1|NAGMTCB26</a>  Nemorhaedus goral
mitochondrial gene...    <a href = #516816> 50</a>   2e-05
<a
href="http://www.ncbi.nlm.nih.gov:80/entrez/query.fcgi?cmd=Retrieve&db=Nucleotid
e&list_uids=00516678&dopt=GenBank">dbj|D32192.1|CEUMTCB22</a>  Cervus nippon
mitochondrial gene for...    <a href = #516678> 50</a>   2e-05
<a
href="http://www.ncbi.nlm.nih.gov:80/entrez/query.fcgi?cmd=Retrieve&db=Nucleotid
e&list_uids=05811561&dopt=GenBank">dbj|AB021099.1|AB021099</a>  Cervus elaphus
scoticus mitochondri...    <a href = #5811561> 50</a>   2e-05
<a
href="http://www.ncbi.nlm.nih.gov:80/entrez/query.fcgi?cmd=Retrieve&db=Nucleotid
e&list_uids=05811555&dopt=GenBank">dbj|AB021096.1|AB021096</a>  Cervus elaphus
canadensis mitochond...    <a href = #5811555> 50</a>   2e-05
<a
href="http://www.ncbi.nlm.nih.gov:80/entrez/query.fcgi?cmd=Retrieve&db=Nucleotid
e&list_uids=05811549&dopt=GenBank">dbj|AB021093.1|AB021093</a>  Cervus nippon
nippon mitochondrial ...    <a href = #5811549> 50</a>   2e-05
<a
href="http://www.ncbi.nlm.nih.gov:80/entrez/query.fcgi?cmd=Retrieve&db=Nucleotid
```

```
e&list_uids=05811543&dopt=GenBank">dbj|AB021090.1|AB021090</a>   Cervus nippon
pulchellus mitochondr...     <a href = #5811543> 50</a>   2e-05
<a
href="http://www.ncbi.nlm.nih.gov:80/entrez/query.fcgi?cmd=Retrieve&db=Nucleotid
e&list_uids=03582121&dopt=GenBank">dbj|AB008539.1|AB008539</a>   Dinodon
semicarinatus mitochondrial...     <a href = #3582121> 50</a>   2e-05
<a
href="http://www.ncbi.nlm.nih.gov:80/entrez/query.fcgi?cmd=Retrieve&db=Nucleotid
e&list_uids=02351091&dopt=GenBank">dbj|AB006800.1|AB006800</a>   Ovis aries
mitochondrial DNA for cy...     <a href = #2351091> 50</a>   2e-05
<a
href="http://www.ncbi.nlm.nih.gov:80/entrez/query.fcgi?cmd=Retrieve&db=Nucleotid
e&list_uids=00308874&dopt=GenBank">gb|L12763.1|LDHMTCYTB</a>   Lepidochelys kempi
(LK-3) mitochondri...     <a href = #308874> 50</a>   2e-05
<a
href="http://www.ncbi.nlm.nih.gov:80/entrez/query.fcgi?cmd=Retrieve&db=Nucleotid
e&list_uids=00336659&dopt=GenBank">gb|L08032.1|CPLMTCYTBA</a>   Carcharhinus
plumbeus mitochondrial ...     <a href = #336659> 50</a>   2e-05
<a
href="http://www.ncbi.nlm.nih.gov:80/entrez/query.fcgi?cmd=Retrieve&db=Nucleotid
e&list_uids=00455382&dopt=GenBank">gb|L28941.1|URRCYB</a>   Uroderma bilobatum
cytochrome b gene, 5'...     <a href = #455382> 50</a>   2e-05
<a
href="http://www.ncbi.nlm.nih.gov:80/entrez/query.fcgi?cmd=Retrieve&db=Nucleotid
e&list_uids=00455130&dopt=GenBank">gb|L28937.1|CDECYB</a>   Chiroderma doriae
cytochrome b gene, 5' end     <a href = #455130> 50</a>   2e-05
<a
href="http://www.ncbi.nlm.nih.gov:80/entrez/query.fcgi?cmd=Retrieve&db=Nucleotid
e&list_uids=03549827&dopt=GenBank">emb|AJ010056.1|CPY010056</a>   Capra pyrenaica
(individual 12) mi...     <a href = #3549827> 50</a>   2e-05
<a
href="http://www.ncbi.nlm.nih.gov:80/entrez/query.fcgi?cmd=Retrieve&db=Nucleotid
e&list_uids=03549825&dopt=GenBank">emb|AJ010054.1|CPY010054</a>   Capra pyrenaica
(individual 11) mi...     <a href = #3549825> 50</a>   2e-05
<a
href="http://www.ncbi.nlm.nih.gov:80/entrez/query.fcgi?cmd=Retrieve&db=Nucleotid
e&list_uids=03549823&dopt=GenBank">emb|AJ010053.1|CPY010053</a>   Capra pyrenaica
(individual 10) mi...     <a href = #3549823> 50</a>   2e-05
<a
href="http://www.ncbi.nlm.nih.gov:80/entrez/query.fcgi?cmd=Retrieve&db=Nucleotid
e&list_uids=03549821&dopt=GenBank">emb|AJ010052.1|CPY010052</a>   Capra pyrenaica
(individual 9) mit...     <a href = #3549821> 50</a>   2e-05
<a
href="http://www.ncbi.nlm.nih.gov:80/entrez/query.fcgi?cmd=Retrieve&db=Nucleotid
e&list_uids=03549819&dopt=GenBank">emb|AJ010051.1|CPY010051</a>   Capra pyrenaica
(individual 8) mit...     <a href = #3549819> 50</a>   2e-05
<a
href="http://www.ncbi.nlm.nih.gov:80/entrez/query.fcgi?cmd=Retrieve&db=Nucleotid
e&list_uids=03549817&dopt=GenBank">emb|AJ010050.1|CPY010050</a>   Capra pyrenaica
(individual 7) mit...     <a href = #3549817> 50</a>   2e-05
<a
href="http://www.ncbi.nlm.nih.gov:80/entrez/query.fcgi?cmd=Retrieve&db=Nucleotid
e&list_uids=03549815&dopt=GenBank">emb|AJ010049.1|CPY010049</a>   Capra pyrenaica
(individual 6) mit...     <a href = #3549815> 50</a>   2e-05
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotid
e&list_uids=03549813&dopt=GenBank">emb|AJ010048.1|CPY010048</a>   Capra pyrenaica
(individual 5) mit...    <a href = #3549813> 50</a>   2e-05
<a
href="http://www.ncbi.nlm.nih.gov:80/entrez/query.fcgi?cmd=Retrieve&db=Nucleotid
e&list_uids=03549811&dopt=GenBank">emb|AJ010047.1|CPY010047</a>   Capra pyrenaica
(individual 4) mit...    <a href = #3549811> 50</a>   2e-05
<a
href="http://www.ncbi.nlm.nih.gov:80/entrez/query.fcgi?cmd=Retrieve&db=Nucleotid
e&list_uids=01261899&dopt=GenBank">emb|X95777.1|CLMCB</a>   C.longirostris
mitochondrial cytochrome ...    <a href = #1261899> 50</a>   2e-05
<a
href="http://www.ncbi.nlm.nih.gov:80/entrez/query.fcgi?cmd=Retrieve&db=Nucleotid
e&list_uids=03549805&dopt=GenBank">emb|AJ009879.1|CIB9879</a>   Capra ibex
nubiana mitochondrial cyt...    <a href = #3549805> 50</a>   2e-05
<a
href="http://www.ncbi.nlm.nih.gov:80/entrez/query.fcgi?cmd=Retrieve&db=Nucleotid
e&list_uids=03549779&dopt=GenBank">emb|AJ010055.1|CIB010055</a>   Capra ibex
(individual 1) ibex mit...    <a href = #3549779> 50</a>   2e-05
<a
href="http://www.ncbi.nlm.nih.gov:80/entrez/query.fcgi?cmd=Retrieve&db=Nucleotid
e&list_uids=00482869&dopt=GenBank">gb|U08946.1|CAU08946</a>   Coragyps atratus
mitochondrion cytochr...    <a href = #482869> 50</a>   2e-05
<a
href="http://www.ncbi.nlm.nih.gov:80/entrez/query.fcgi?cmd=Retrieve&db=Nucleotid
e&list_uids=00482867&dopt=GenBank">gb|U08945.1|CBU08945</a>   Cathartes
burrovianus mitochondrion cy...    <a href = #482867> 50</a>   2e-05
<a
href="http://www.ncbi.nlm.nih.gov:80/entrez/query.fcgi?cmd=Retrieve&db=Nucleotid
e&list_uids=00482865&dopt=GenBank">gb|U08944.1|VGU08944</a>   Vultur gryphus
mitochondrion cytochrom...    <a href = #482865> 50</a>   2e-05
<a
href="http://www.ncbi.nlm.nih.gov:80/entrez/query.fcgi?cmd=Retrieve&db=Nucleotid
e&list_uids=00482859&dopt=GenBank">gb|U08941.1|PAU08941</a>   Platalea alba
mitochondrion cytochrome...    <a href = #482859> 50</a>   2e-05
<a
href="http://www.ncbi.nlm.nih.gov:80/entrez/query.fcgi?cmd=Retrieve&db=Nucleotid
e&list_uids=00482857&dopt=GenBank">gb|U08940.1|PRU08940</a>   Phoenicopterus
ruber mitochondrion cyt...    <a href = #482857> 50</a>   2e-05
<a
href="http://www.ncbi.nlm.nih.gov:80/entrez/query.fcgi?cmd=Retrieve&db=Nucleotid
e&list_uids=01261861&dopt=GenBank">emb|X95775.1|ACMCB</a>   A.cristatus
mitochondrial cytochrome b gene    <a href = #1261861> 50</a>   2e-05
<a
href="http://www.ncbi.nlm.nih.gov:80/entrez/query.fcgi?cmd=Retrieve&db=Nucleotid
e&list_uids=01261860&dopt=GenBank">emb|X95774.1|ABMCB</a>   A.bennettii
mitochondrial cytochrome b gene    <a href = #1261860> 50</a>   2e-05
<a
href="http://www.ncbi.nlm.nih.gov:80/entrez/query.fcgi?cmd=Retrieve&db=Nucleotid
e&list_uids=01204043&dopt=GenBank">emb|X95764.1|AAMCB</a>   A.albertisi
mitochondrial cytochrome b gene    <a href = #1204043> 50</a>   2e-05
<a
href="http://www.ncbi.nlm.nih.gov:80/entrez/query.fcgi?cmd=Retrieve&db=Nucleotid
e&list_uids=04104825&dopt=GenBank">gb|AF040383.1|AF040383</a>   Alces alces
cytochrome b (cytb) gene...    <a href = #4104825> 48</a>   8e-05
<a
href="http://www.ncbi.nlm.nih.gov:80/entrez/query.fcgi?cmd=Retrieve&db=Nucleotid
```

```
e&list_uids=13128900&dopt=GenBank">gb|AF232023.1|AF232023</a>   Tamandua
tetradactyla clone 7 cytoch...   <a href = #13128900> 46</a>   3e-04
<a
href="http://www.ncbi.nlm.nih.gov:80/entrez/query.fcgi?cmd=Retrieve&db=Nucleotid
e&list_uids=13128899&dopt=GenBank">gb|AF232022.1|AF232022</a>   Tamandua
tetradactyla clone 6 mitoch...   <a href = #13128899> 46</a>   3e-04
<a
href="http://www.ncbi.nlm.nih.gov:80/entrez/query.fcgi?cmd=Retrieve&db=Nucleotid
e&list_uids=13128897&dopt=GenBank">gb|AF232021.1|AF232021</a>   Tamandua
tetradactyla clone 5 cytoch...   <a href = #13128897> 46</a>   3e-04
<a
href="http://www.ncbi.nlm.nih.gov:80/entrez/query.fcgi?cmd=Retrieve&db=Nucleotid
e&list_uids=05596617&dopt=GenBank">gb|AF157466.1|AF157466</a>   Lepus timidus
cytochrome b (Cyb) gen...   <a href = #5596617> 46</a>   3e-04
<a
href="http://www.ncbi.nlm.nih.gov:80/entrez/query.fcgi?cmd=Retrieve&db=Nucleotid
e&list_uids=05596615&dopt=GenBank">gb|AF157465.1|AF157465</a>   Lepus granatensis
cytochrome b (Cyb)...   <a href = #5596615> 46</a>   3e-04
<a
href="http://www.ncbi.nlm.nih.gov:80/entrez/query.fcgi?cmd=Retrieve&db=Nucleotid
e&list_uids=05596613&dopt=GenBank">gb|AF157464.1|AF157464</a>   Lepus corsicanus
haplotype 1 cytochr...   <a href = #5596613> 46</a>   3e-04
<a
href="http://www.ncbi.nlm.nih.gov:80/entrez/query.fcgi?cmd=Retrieve&db=Nucleotid
e&list_uids=05596611&dopt=GenBank">gb|AF157463.1|AF157463</a>   Lepus corsicanus
haplotype 3 cytochr...   <a href = #5596611> 46</a>   3e-04
<a
href="http://www.ncbi.nlm.nih.gov:80/entrez/query.fcgi?cmd=Retrieve&db=Nucleotid
e&list_uids=05596605&dopt=GenBank">gb|AF157460.1|AF157460</a>   Lepus europaeus
cytochrome b (Cyb) g...   <a href = #5596605> 46</a>   3e-04
<a
href="http://www.ncbi.nlm.nih.gov:80/entrez/query.fcgi?cmd=Retrieve&db=Nucleotid
e&list_uids=13171222&dopt=GenBank">gb|AF231664.1|AF231664</a>   Tylosurus
crocodilus crocodilus cyto...   <a href = #13171222> 46</a>   3e-04
<a
href="http://www.ncbi.nlm.nih.gov:80/entrez/query.fcgi?cmd=Retrieve&db=Nucleotid
e&list_uids=13171220&dopt=GenBank">gb|AF231663.1|AF231663</a>   Tylosurus
crocodilus clone STRI-3837...   <a href = #13171220> 46</a>   3e-04
<a
href="http://www.ncbi.nlm.nih.gov:80/entrez/query.fcgi?cmd=Retrieve&db=Nucleotid
e&list_uids=13171218&dopt=GenBank">gb|AF231662.1|AF231662</a>   Tylosurus
crocodilus clone HB-166 cy...   <a href = #13171218> 46</a>   3e-04
<a
href="http://www.ncbi.nlm.nih.gov:80/entrez/query.fcgi?cmd=Retrieve&db=Nucleotid
e&list_uids=13171214&dopt=GenBank">gb|AF231660.1|AF231660</a>   Tylosurus acus
pacificus cytochrome ...   <a href = #13171214> 46</a>   3e-04
<a
href="http://www.ncbi.nlm.nih.gov:80/entrez/query.fcgi?cmd=Retrieve&db=Nucleotid
e&list_uids=13171212&dopt=GenBank">gb|AF231659.1|AF231659</a>   Tylosurus acus
melanotus clone STRI-...   <a href = #13171212> 46</a>   3e-04
<a
href="http://www.ncbi.nlm.nih.gov:80/entrez/query.fcgi?cmd=Retrieve&db=Nucleotid
e&list_uids=13171210&dopt=GenBank">gb|AF231658.1|AF231658</a>   Tylosurus acus
melanotus clone STRI-...   <a href = #13171210> 46</a>   3e-04
<a
href="http://www.ncbi.nlm.nih.gov:80/entrez/query.fcgi?cmd=Retrieve&db=Nucleotid
```

```
e&list_uids=13171208&dopt=GenBank">gb|AF231657.1|AF231657</a>  Tylosurus acus
imperialis cytochrome...    <a href = #13171208> 46</a>   3e-04
<a
href="http://www.ncbi.nlm.nih.gov:80/entrez/query.fcgi?cmd=Retrieve&db=Nucleotid
e&list_uids=13171206&dopt=GenBank">gb|AF231656.1|AF231656</a>  Tylosurus acus
acus cytochrome b oxi...    <a href = #13171206> 46</a>   3e-04
<a
href="http://www.ncbi.nlm.nih.gov:80/entrez/query.fcgi?cmd=Retrieve&db=Nucleotid
e&list_uids=13171182&dopt=GenBank">gb|AF231644.1|AF231644</a>  Strongylura
hubbsi cytochrome b oxid...    <a href = #13171182> 46</a>   3e-04
<a
href="http://www.ncbi.nlm.nih.gov:80/entrez/query.fcgi?cmd=Retrieve&db=Nucleotid
e&list_uids=13171172&dopt=GenBank">gb|AF231639.1|AF231639</a>  Ablennes hians
cytochrome b oxidase ...    <a href = #13171172> 46</a>   3e-04
<a
href="http://www.ncbi.nlm.nih.gov:80/entrez/query.fcgi?cmd=Retrieve&db=Nucleotid
e&list_uids=13128893&dopt=GenBank">gb|AF232019.1|AF232019</a>  Tamandua
tetradactyla clone 3 cytoch...    <a href = #13128893> 46</a>   3e-04
<a
href="http://www.ncbi.nlm.nih.gov:80/entrez/query.fcgi?cmd=Retrieve&db=Nucleotid
e&list_uids=13128889&dopt=GenBank">gb|AF232017.1|AF232017</a>  Tamandua
tetradactyla clone 1 cytoch...    <a href = #13128889> 46</a>   3e-04
<a
href="http://www.ncbi.nlm.nih.gov:80/entrez/query.fcgi?cmd=Retrieve&db=Nucleotid
e&list_uids=13128883&dopt=GenBank">gb|AF232014.1|AF232014</a>  Mylodon darwinii
cytochrome b gene, ...    <a href = #13128883> 46</a>   3e-04
<a
href="http://www.ncbi.nlm.nih.gov:80/entrez/query.fcgi?cmd=Retrieve&db=Nucleotid
e&list_uids=13123638&dopt=GenBank">gb|AF318564.1|AF318564</a>  Alligator
mississippiensis isolate S...    <a href = #13123638> 46</a>   3e-04
<a
href="http://www.ncbi.nlm.nih.gov:80/entrez/query.fcgi?cmd=Retrieve&db=Nucleotid
e&list_uids=13123636&dopt=GenBank">gb|AF318563.1|AF318563</a>  Alligator
mississippiensis isolate S...    <a href = #13123636> 46</a>   3e-04
<a
href="http://www.ncbi.nlm.nih.gov:80/entrez/query.fcgi?cmd=Retrieve&db=Nucleotid
e&list_uids=13123634&dopt=GenBank">gb|AF318562.1|AF318562</a>  Alligator
mississippiensis isolate S...    <a href = #13123634> 46</a>   3e-04
<a
href="http://www.ncbi.nlm.nih.gov:80/entrez/query.fcgi?cmd=Retrieve&db=Nucleotid
e&list_uids=13123632&dopt=GenBank">gb|AF318561.1|AF318561</a>  Alligator
mississippiensis isolate G...    <a href = #13123632> 46</a>   3e-04
<a
href="http://www.ncbi.nlm.nih.gov:80/entrez/query.fcgi?cmd=Retrieve&db=Nucleotid
e&list_uids=13123630&dopt=GenBank">gb|AF318560.1|AF318560</a>  Alligator
mississippiensis isolate G...    <a href = #13123630> 46</a>   3e-04
<a
href="http://www.ncbi.nlm.nih.gov:80/entrez/query.fcgi?cmd=Retrieve&db=Nucleotid
e&list_uids=13123628&dopt=GenBank">gb|AF318559.1|AF318559</a>  Alligator
mississippiensis isolate A...    <a href = #13123628> 46</a>   3e-04
<a
href="http://www.ncbi.nlm.nih.gov:80/entrez/query.fcgi?cmd=Retrieve&db=Nucleotid
e&list_uids=13123626&dopt=GenBank">gb|AF318558.1|AF318558</a>  Alligator
mississippiensis isolate A...    <a href = #13123626> 46</a>   3e-04
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=13123624&dopt=GenBank">gb|AF318557.1|AF318557</a>  Alligator
mississippiensis isolate S...    <a href = #13123624> 46</a>  3e-04
<a
href="http://www.ncbi.nlm.nih.gov:80/entrez/query.fcgi?cmd=Retrieve&db=Nucleotid
e&list_uids=13123622&dopt=GenBank">gb|AF318556.1|AF318556</a>  Alligator
mississippiensis isolate S...    <a href = #13123622> 46</a>  3e-04
<a
href="http://www.ncbi.nlm.nih.gov:80/entrez/query.fcgi?cmd=Retrieve&db=Nucleotid
e&list_uids=13123620&dopt=GenBank">gb|AF318555.1|AF318555</a>  Alligator
mississippiensis isolate S...    <a href = #13123620> 46</a>  3e-04
<a
href="http://www.ncbi.nlm.nih.gov:80/entrez/query.fcgi?cmd=Retrieve&db=Nucleotid
e&list_uids=13123618&dopt=GenBank">gb|AF318554.1|AF318554</a>  Alligator
mississippiensis isolate S...    <a href = #13123618> 46</a>  3e-04
<a
href="http://www.ncbi.nlm.nih.gov:80/entrez/query.fcgi?cmd=Retrieve&db=Nucleotid
e&list_uids=13123616&dopt=GenBank">gb|AF318553.1|AF318553</a>  Alligator
mississippiensis isolate L...    <a href = #13123616> 46</a>  3e-04
<a
href="http://www.ncbi.nlm.nih.gov:80/entrez/query.fcgi?cmd=Retrieve&db=Nucleotid
e&list_uids=13123614&dopt=GenBank">gb|AF318552.1|AF318552</a>  Alligator
mississippiensis isolate L...    <a href = #13123614> 46</a>  3e-04
<a
href="http://www.ncbi.nlm.nih.gov:80/entrez/query.fcgi?cmd=Retrieve&db=Nucleotid
e&list_uids=13123612&dopt=GenBank">gb|AF318551.1|AF318551</a>  Alligator
mississippiensis isolate L...    <a href = #13123612> 46</a>  3e-04
<a
href="http://www.ncbi.nlm.nih.gov:80/entrez/query.fcgi?cmd=Retrieve&db=Nucleotid
e&list_uids=13123610&dopt=GenBank">gb|AF318550.1|AF318550</a>  Alligator
mississippiensis isolate F...    <a href = #13123610> 46</a>  3e-04
<a
href="http://www.ncbi.nlm.nih.gov:80/entrez/query.fcgi?cmd=Retrieve&db=Nucleotid
e&list_uids=13123608&dopt=GenBank">gb|AF318549.1|AF318549</a>  Alligator
mississippiensis isolate F...    <a href = #13123608> 46</a>  3e-04
<a
href="http://www.ncbi.nlm.nih.gov:80/entrez/query.fcgi?cmd=Retrieve&db=Nucleotid
e&list_uids=13123606&dopt=GenBank">gb|AF318548.1|AF318548</a>  Alligator
mississippiensis isolate F...    <a href = #13123606> 46</a>  3e-04
<a
href="http://www.ncbi.nlm.nih.gov:80/entrez/query.fcgi?cmd=Retrieve&db=Nucleotid
e&list_uids=13122454&dopt=GenBank">gb|AF238041.1|AF238041</a>  Sorex monticolus
specimen-voucher AF...    <a href = #13122454> 46</a>  3e-04
<a
href="http://www.ncbi.nlm.nih.gov:80/entrez/query.fcgi?cmd=Retrieve&db=Nucleotid
e&list_uids=12083042&dopt=GenBank">gb|AF326272.1|AF326272</a>  Myospalax
myospalax cytochrome b (cy...    <a href = #12083042> 46</a>  3e-04
<a
href="http://www.ncbi.nlm.nih.gov:80/entrez/query.fcgi?cmd=Retrieve&db=Nucleotid
e&list_uids=12083040&dopt=GenBank">gb|AF326271.1|AF326271</a>  Myospalax
psilurus isolate 2 cytochr...    <a href = #12083040> 46</a>  3e-04
<a
href="http://www.ncbi.nlm.nih.gov:80/entrez/query.fcgi?cmd=Retrieve&db=Nucleotid
e&list_uids=12083038&dopt=GenBank">gb|AF326270.1|AF326270</a>  Myospalax
psilurus isolate 1 cytochr...    <a href = #12083038> 46</a>  3e-04
<a
href="http://www.ncbi.nlm.nih.gov:80/entrez/query.fcgi?cmd=Retrieve&db=Nucleotid
```

```
e&list_uids=12083030&dopt=GenBank">gb|AF326266.1|AF326266</a>  Eospalax
fontanierii isolate 4 cytoc...    <a href = #12083030> 46</a>   3e-04
<a
href="http://www.ncbi.nlm.nih.gov:80/entrez/query.fcgi?cmd=Retrieve&db=Nucleotid
e&list_uids=09967766&dopt=GenBank">emb|AJ004340.1|ADAJ4340</a>  Acrocephalus
dumetorum mitochondria...    <a href = #9967766> 44</a>   0.001
<a
href="http://www.ncbi.nlm.nih.gov:80/entrez/query.fcgi?cmd=Retrieve&db=Nucleotid
e&list_uids=09967734&dopt=GenBank">emb|AJ004264.1|ADAJ4264</a>  Acrocephalus
dumetorum mitochondria...    <a href = #9967734> 44</a>   0.001
</PRE>
<CENTER><b><FONT color="green">Alignments</FONT></b></CENTER>
<PRE>
tmpseq_0  1    taccatgaggacaaatatcattctg 25
<a name = 13171196></a><a
href=http://www.ncbi.nlm.nih.gov:80/entrez/query.fcgi?cmd=Retrieve&db=Nucleotide
&list_uids=13171196&dopt=GenBank>AF231651</a>  398  ..........................
422
<a name = 13171194></a><a
href=http://www.ncbi.nlm.nih.gov:80/entrez/query.fcgi?cmd=Retrieve&db=Nucleotide
&list_uids=13171194&dopt=GenBank>AF231650</a>  398  ..........................
422
<a name = 13116556></a><a
href=http://www.ncbi.nlm.nih.gov:80/entrez/query.fcgi?cmd=Retrieve&db=Nucleotide
&list_uids=13116556&dopt=GenBank>NC_002672</a>  15560  ..........................
15584
<a name = 13116573></a><a
href=http://www.ncbi.nlm.nih.gov:80/entrez/query.fcgi?cmd=Retrieve&db=Nucleotide
&list_uids=13116573&dopt=GenBank>NC_002673</a>  15552  ..........................
15576
<a name = 13128885></a><a
href=http://www.ncbi.nlm.nih.gov:80/entrez/query.fcgi?cmd=Retrieve&db=Nucleotide
&list_uids=13128885&dopt=GenBank>AF232015</a>  398  ..........................
422
<a name = 13128881></a><a
href=http://www.ncbi.nlm.nih.gov:80/entrez/query.fcgi?cmd=Retrieve&db=Nucleotide
&list_uids=13128881&dopt=GenBank>AF232013</a>  398  ..........................
422
<a name = 12957459></a><a
href=http://www.ncbi.nlm.nih.gov:80/entrez/query.fcgi?cmd=Retrieve&db=Nucleotide
&list_uids=12957459&dopt=GenBank>AY016015</a>  15552  ..........................
15576
<a name = 12957432></a><a
href=http://www.ncbi.nlm.nih.gov:80/entrez/query.fcgi?cmd=Retrieve&db=Nucleotide
&list_uids=12957432&dopt=GenBank>AY016013</a>  15560  ..........................
15584
<a name = 12957446></a><a
href=http://www.ncbi.nlm.nih.gov:80/entrez/query.fcgi?cmd=Retrieve&db=Nucleotide
&list_uids=12957446&dopt=GenBank>AY016014</a>  11516  ..........................
11540
<a name = 6970176></a><a
href=http://www.ncbi.nlm.nih.gov:80/entrez/query.fcgi?cmd=Retrieve&db=Nucleotide
&list_uids=06970176&dopt=GenBank>AF230167</a>  266  ..........................
290
<a name = 4336170></a><a
href=http://www.ncbi.nlm.nih.gov:80/entrez/query.fcgi?cmd=Retrieve&db=Nucleotide
```

```
&list_uids=04336170&dopt=GenBank>AF074594</a>   206   ........................
230
<a name = 12699071></a><a
href=http://www.ncbi.nlm.nih.gov:80/entrez/query.fcgi?cmd=Retrieve&db=Nucleotide
&list_uids=12699071&dopt=GenBank>AY005210</a>   290   ........................
314
<a name = 12699069></a><a
href=http://www.ncbi.nlm.nih.gov:80/entrez/query.fcgi?cmd=Retrieve&db=Nucleotide
&list_uids=12699069&dopt=GenBank>AY005209</a>   290   ........................
314
<a name = 12699067></a><a
href=http://www.ncbi.nlm.nih.gov:80/entrez/query.fcgi?cmd=Retrieve&db=Nucleotide
&list_uids=12699067&dopt=GenBank>AY005208</a>   290   ........................
314
<a name = 12699061></a><a
href=http://www.ncbi.nlm.nih.gov:80/entrez/query.fcgi?cmd=Retrieve&db=Nucleotide
&list_uids=12699061&dopt=GenBank>AY005205</a>   290   ........................
314
<a name = 12699059></a><a
href=http://www.ncbi.nlm.nih.gov:80/entrez/query.fcgi?cmd=Retrieve&db=Nucleotide
&list_uids=12699059&dopt=GenBank>AY005204</a>   290   ........................
314
<a name = 12699057></a><a
href=http://www.ncbi.nlm.nih.gov:80/entrez/query.fcgi?cmd=Retrieve&db=Nucleotide
&list_uids=12699057&dopt=GenBank>AY005203</a>   290   ........................
314
<a name = 12699053></a><a
href=http://www.ncbi.nlm.nih.gov:80/entrez/query.fcgi?cmd=Retrieve&db=Nucleotide
&list_uids=12699053&dopt=GenBank>AY005201</a>   290   ........................
314
<a name = 12699049></a><a
href=http://www.ncbi.nlm.nih.gov:80/entrez/query.fcgi?cmd=Retrieve&db=Nucleotide
&list_uids=12699049&dopt=GenBank>AY005199</a>   290   ........................
314
<a name = 12699047></a><a
href=http://www.ncbi.nlm.nih.gov:80/entrez/query.fcgi?cmd=Retrieve&db=Nucleotide
&list_uids=12699047&dopt=GenBank>AY005198</a>   290   ........................
314
<a name = 12581475></a><a
href=http://www.ncbi.nlm.nih.gov:80/entrez/query.fcgi?cmd=Retrieve&db=Nucleotide
&list_uids=12581475&dopt=GenBank>AF155870</a>   398   ........................
422
<a name = 10441566></a><a
href=http://www.ncbi.nlm.nih.gov:80/entrez/query.fcgi?cmd=Retrieve&db=Nucleotide
&list_uids=10441566&dopt=GenBank>AF189123</a>   326   ........................
350
<a name = 12024721></a><a
href=http://www.ncbi.nlm.nih.gov:80/entrez/query.fcgi?cmd=Retrieve&db=Nucleotide
&list_uids=12024721&dopt=GenBank>AF102099</a>   215   ........................
239
<a name = 12024713></a><a
href=http://www.ncbi.nlm.nih.gov:80/entrez/query.fcgi?cmd=Retrieve&db=Nucleotide
&list_uids=12024713&dopt=GenBank>AF102095</a>   208   ........................
232
<a name = 12006178></a><a
href=http://www.ncbi.nlm.nih.gov:80/entrez/query.fcgi?cmd=Retrieve&db=Nucleotide
```

```
&list_uids=12006178&dopt=GenBank>AF271065</a>  398 ........................
422
<a name = 11995304></a><a
href=http://www.ncbi.nlm.nih.gov:80/entrez/query.fcgi?cmd=Retrieve&db=Nucleotide
&list_uids=11995304&dopt=GenBank>AF243857</a>  275 ........................
299
<a name = 11995302></a><a
href=http://www.ncbi.nlm.nih.gov:80/entrez/query.fcgi?cmd=Retrieve&db=Nucleotide
&list_uids=11995302&dopt=GenBank>AF243856</a>  275 ........................
299
<a name = 5834939></a><a
href=http://www.ncbi.nlm.nih.gov:80/entrez/query.fcgi?cmd=Retrieve&db=Nucleotide
&list_uids=05834939&dopt=GenBank>NC_001567</a>  14911 ........................
14935
<a name = 11993539></a><a
href=http://www.ncbi.nlm.nih.gov:80/entrez/query.fcgi?cmd=Retrieve&db=Nucleotide
&list_uids=11993539&dopt=GenBank>AF306872</a>  302 ........................
326
<a name = 11993537></a><a
href=http://www.ncbi.nlm.nih.gov:80/entrez/query.fcgi?cmd=Retrieve&db=Nucleotide
&list_uids=11993537&dopt=GenBank>AF306871</a>  302 ........................
326
<a name = 11993535></a><a
href=http://www.ncbi.nlm.nih.gov:80/entrez/query.fcgi?cmd=Retrieve&db=Nucleotide
&list_uids=11993535&dopt=GenBank>AF306870</a>  302 ........................
326
<a name = 11993533></a><a
href=http://www.ncbi.nlm.nih.gov:80/entrez/query.fcgi?cmd=Retrieve&db=Nucleotide
&list_uids=11993533&dopt=GenBank>AF306869</a>  302 ........................
326
<a name = 11993531></a><a
href=http://www.ncbi.nlm.nih.gov:80/entrez/query.fcgi?cmd=Retrieve&db=Nucleotide
&list_uids=11993531&dopt=GenBank>AF306868</a>  302 ........................
326
<a name = 3445513></a><a
href=http://www.ncbi.nlm.nih.gov:80/entrez/query.fcgi?cmd=Retrieve&db=Nucleotide
&list_uids=03445513&dopt=GenBank>AF010406</a>  14556 ........................
14580
<a name = 11141464></a><a
href=http://www.ncbi.nlm.nih.gov:80/entrez/query.fcgi?cmd=Retrieve&db=Nucleotide
&list_uids=11141464&dopt=GenBank>AF248662</a>  303 ........................
327
<a name = 11141462></a><a
href=http://www.ncbi.nlm.nih.gov:80/entrez/query.fcgi?cmd=Retrieve&db=Nucleotide
&list_uids=11141462&dopt=GenBank>AF248661</a>  303 ........................
327
<a name = 11139383></a><a
href=http://www.ncbi.nlm.nih.gov:80/entrez/query.fcgi?cmd=Retrieve&db=Nucleotide
&list_uids=11139383&dopt=GenBank>AF096462</a>  264 ........................
288
<a name = 11023426></a><a
href=http://www.ncbi.nlm.nih.gov:80/entrez/query.fcgi?cmd=Retrieve&db=Nucleotide
&list_uids=11023426&dopt=GenBank>AF283644</a>  374 ........................
398
<a name = 11023424></a><a
href=http://www.ncbi.nlm.nih.gov:80/entrez/query.fcgi?cmd=Retrieve&db=Nucleotide
```

```
&list_uids=11023424&dopt=GenBank>AF283643</a> 374 ........................
398
<a name = 11023422></a><a
href=http://www.ncbi.nlm.nih.gov:80/entrez/query.fcgi?cmd=Retrieve&db=Nucleotide
&list_uids=11023422&dopt=GenBank>AF283642</a> 374 ........................
398
<a name = 11023420></a><a
href=http://www.ncbi.nlm.nih.gov:80/entrez/query.fcgi?cmd=Retrieve&db=Nucleotide
&list_uids=11023420&dopt=GenBank>AF283641</a> 374 ........................
398
<a name = 11023418></a><a
href=http://www.ncbi.nlm.nih.gov:80/entrez/query.fcgi?cmd=Retrieve&db=Nucleotide
&list_uids=11023418&dopt=GenBank>AF283640</a> 374 ........................
398
<a name = 11023416></a><a
href=http://www.ncbi.nlm.nih.gov:80/entrez/query.fcgi?cmd=Retrieve&db=Nucleotide
&list_uids=11023416&dopt=GenBank>AF283639</a> 374 ........................
398
<a name = 11023412></a><a
href=http://www.ncbi.nlm.nih.gov:80/entrez/query.fcgi?cmd=Retrieve&db=Nucleotide
&list_uids=11023412&dopt=GenBank>AF283637</a> 374 ........................
398
<a name = 11023410></a><a
href=http://www.ncbi.nlm.nih.gov:80/entrez/query.fcgi?cmd=Retrieve&db=Nucleotide
&list_uids=11023410&dopt=GenBank>AF283636</a> 374 ........................
398
<a name = 11023408></a><a
href=http://www.ncbi.nlm.nih.gov:80/entrez/query.fcgi?cmd=Retrieve&db=Nucleotide
&list_uids=11023408&dopt=GenBank>AF283635</a> 374 ........................
398
<a name = 11023406></a><a
href=http://www.ncbi.nlm.nih.gov:80/entrez/query.fcgi?cmd=Retrieve&db=Nucleotide
&list_uids=11023406&dopt=GenBank>AF283634</a> 374 ........................
398
<a name = 11023404></a><a
href=http://www.ncbi.nlm.nih.gov:80/entrez/query.fcgi?cmd=Retrieve&db=Nucleotide
&list_uids=11023404&dopt=GenBank>AF283633</a> 374 ........................
398
<a name = 11023402></a><a
href=http://www.ncbi.nlm.nih.gov:80/entrez/query.fcgi?cmd=Retrieve&db=Nucleotide
&list_uids=11023402&dopt=GenBank>AF283632</a> 374 ........................
398
<a name = 11023400></a><a
href=http://www.ncbi.nlm.nih.gov:80/entrez/query.fcgi?cmd=Retrieve&db=Nucleotide
&list_uids=11023400&dopt=GenBank>AF283631</a> 374 ........................
398
<a name = 11023398></a><a
href=http://www.ncbi.nlm.nih.gov:80/entrez/query.fcgi?cmd=Retrieve&db=Nucleotide
&list_uids=11023398&dopt=GenBank>AF283630</a> 374 ........................
398
<a name = 11023396></a><a
href=http://www.ncbi.nlm.nih.gov:80/entrez/query.fcgi?cmd=Retrieve&db=Nucleotide
&list_uids=11023396&dopt=GenBank>AF283629</a> 374 ........................
398
<a name = 11023394></a><a
href=http://www.ncbi.nlm.nih.gov:80/entrez/query.fcgi?cmd=Retrieve&db=Nucleotide
```

```
&list_uids=11023394&dopt=GenBank>AF283628</a>  374  ........................
398
<a name = 11023392></a><a
href=http://www.ncbi.nlm.nih.gov:80/entrez/query.fcgi?cmd=Retrieve&db=Nucleotide
&list_uids=11023392&dopt=GenBank>AF283627</a>  374  ........................
398
<a name = 11023390></a><a
href=http://www.ncbi.nlm.nih.gov:80/entrez/query.fcgi?cmd=Retrieve&db=Nucleotide
&list_uids=11023390&dopt=GenBank>AF283626</a>  374  ........................
398
<a name = 11023388></a><a
href=http://www.ncbi.nlm.nih.gov:80/entrez/query.fcgi?cmd=Retrieve&db=Nucleotide
&list_uids=11023388&dopt=GenBank>AF283625</a>  374  ........................
398
<a name = 11023386></a><a
href=http://www.ncbi.nlm.nih.gov:80/entrez/query.fcgi?cmd=Retrieve&db=Nucleotide
&list_uids=11023386&dopt=GenBank>AF283624</a>  374  ........................
398
<a name = 11023384></a><a
href=http://www.ncbi.nlm.nih.gov:80/entrez/query.fcgi?cmd=Retrieve&db=Nucleotide
&list_uids=11023384&dopt=GenBank>AF283623</a>  374  ........................
398
<a name = 11023382></a><a
href=http://www.ncbi.nlm.nih.gov:80/entrez/query.fcgi?cmd=Retrieve&db=Nucleotide
&list_uids=11023382&dopt=GenBank>AF283622</a>  374  ........................
398
<a name = 11023380></a><a
href=http://www.ncbi.nlm.nih.gov:80/entrez/query.fcgi?cmd=Retrieve&db=Nucleotide
&list_uids=11023380&dopt=GenBank>AF283621</a>  374  ........................
398
<a name = 11023378></a><a
href=http://www.ncbi.nlm.nih.gov:80/entrez/query.fcgi?cmd=Retrieve&db=Nucleotide
&list_uids=11023378&dopt=GenBank>AF283620</a>  374  ........................
398
<a name = 11023376></a><a
href=http://www.ncbi.nlm.nih.gov:80/entrez/query.fcgi?cmd=Retrieve&db=Nucleotide
&list_uids=11023376&dopt=GenBank>AF283619</a>  374  ........................
398
<a name = 11023374></a><a
href=http://www.ncbi.nlm.nih.gov:80/entrez/query.fcgi?cmd=Retrieve&db=Nucleotide
&list_uids=11023374&dopt=GenBank>AF283618</a>  374  ........................
398
<a name = 11023372></a><a
href=http://www.ncbi.nlm.nih.gov:80/entrez/query.fcgi?cmd=Retrieve&db=Nucleotide
&list_uids=11023372&dopt=GenBank>AF283617</a>  374  ........................
398
<a name = 11023370></a><a
href=http://www.ncbi.nlm.nih.gov:80/entrez/query.fcgi?cmd=Retrieve&db=Nucleotide
&list_uids=11023370&dopt=GenBank>AF283616</a>  374  ........................
398
<a name = 11023368></a><a
href=http://www.ncbi.nlm.nih.gov:80/entrez/query.fcgi?cmd=Retrieve&db=Nucleotide
&list_uids=11023368&dopt=GenBank>AF283615</a>  374  ........................
398
<a name = 11023366></a><a
href=http://www.ncbi.nlm.nih.gov:80/entrez/query.fcgi?cmd=Retrieve&db=Nucleotide
```

```
&list_uids=11023366&dopt=GenBank>AF283614</a>   374   ........................
398
<a name = 11023364></a><a
href=http://www.ncbi.nlm.nih.gov:80/entrez/query.fcgi?cmd=Retrieve&db=Nucleotide
&list_uids=11023364&dopt=GenBank>AF283613</a>   374   ........................
398
<a name = 11023362></a><a
href=http://www.ncbi.nlm.nih.gov:80/entrez/query.fcgi?cmd=Retrieve&db=Nucleotide
&list_uids=11023362&dopt=GenBank>AF283612</a>   374   ........................
398
<a name = 11023360></a><a
href=http://www.ncbi.nlm.nih.gov:80/entrez/query.fcgi?cmd=Retrieve&db=Nucleotide
&list_uids=11023360&dopt=GenBank>AF283611</a>   374   ........................
398
<a name = 11023358></a><a
href=http://www.ncbi.nlm.nih.gov:80/entrez/query.fcgi?cmd=Retrieve&db=Nucleotide
&list_uids=11023358&dopt=GenBank>AF283610</a>   374   ........................
398
<a name = 11023356></a><a
href=http://www.ncbi.nlm.nih.gov:80/entrez/query.fcgi?cmd=Retrieve&db=Nucleotide
&list_uids=11023356&dopt=GenBank>AF283609</a>   374   ........................
398
<a name = 11023354></a><a
href=http://www.ncbi.nlm.nih.gov:80/entrez/query.fcgi?cmd=Retrieve&db=Nucleotide
&list_uids=11023354&dopt=GenBank>AF283608</a>   374   ........................
398
<a name = 11023352></a><a
href=http://www.ncbi.nlm.nih.gov:80/entrez/query.fcgi?cmd=Retrieve&db=Nucleotide
&list_uids=11023352&dopt=GenBank>AF283607</a>   374   ........................
398
<a name = 11023350></a><a
href=http://www.ncbi.nlm.nih.gov:80/entrez/query.fcgi?cmd=Retrieve&db=Nucleotide
&list_uids=11023350&dopt=GenBank>AF283606</a>   374   ........................
398
<a name = 11023348></a><a
href=http://www.ncbi.nlm.nih.gov:80/entrez/query.fcgi?cmd=Retrieve&db=Nucleotide
&list_uids=11023348&dopt=GenBank>AF283605</a>   374   ........................
398
<a name = 11023346></a><a
href=http://www.ncbi.nlm.nih.gov:80/entrez/query.fcgi?cmd=Retrieve&db=Nucleotide
&list_uids=11023346&dopt=GenBank>AF283604</a>   374   ........................
398
<a name = 11023344></a><a
href=http://www.ncbi.nlm.nih.gov:80/entrez/query.fcgi?cmd=Retrieve&db=Nucleotide
&list_uids=11023344&dopt=GenBank>AF283603</a>   374   ........................
398
<a name = 11023342></a><a
href=http://www.ncbi.nlm.nih.gov:80/entrez/query.fcgi?cmd=Retrieve&db=Nucleotide
&list_uids=11023342&dopt=GenBank>AF283602</a>   374   ........................
398
<a name = 11023340></a><a
href=http://www.ncbi.nlm.nih.gov:80/entrez/query.fcgi?cmd=Retrieve&db=Nucleotide
&list_uids=11023340&dopt=GenBank>AF283601</a>   374   ........................
398
<a name = 11023338></a><a
href=http://www.ncbi.nlm.nih.gov:80/entrez/query.fcgi?cmd=Retrieve&db=Nucleotide
```

```
&list_uids=11023338&dopt=GenBank>AF283600</a>  374  . . . . . . . . . . . . . . . . . . . . . . . .
398
<a name = 11023336></a><a
href=http://www.ncbi.nlm.nih.gov:80/entrez/query.fcgi?cmd=Retrieve&db=Nucleotide
&list_uids=11023336&dopt=GenBank>AF283599</a>  374  . . . . . . . . . . . . . . . . . . . . . . . .
398
<a name = 11023334></a><a
href=http://www.ncbi.nlm.nih.gov:80/entrez/query.fcgi?cmd=Retrieve&db=Nucleotide
&list_uids=11023334&dopt=GenBank>AF283598</a>  374  . . . . . . . . . . . . . . . . . . . . . . . .
398
<a name = 11023332></a><a
href=http://www.ncbi.nlm.nih.gov:80/entrez/query.fcgi?cmd=Retrieve&db=Nucleotide
&list_uids=11023332&dopt=GenBank>AF283597</a>  374  . . . . . . . . . . . . . . . . . . . . . . . .
398
<a name = 11023330></a><a
href=http://www.ncbi.nlm.nih.gov:80/entrez/query.fcgi?cmd=Retrieve&db=Nucleotide
&list_uids=11023330&dopt=GenBank>AF283596</a>  374  . . . . . . . . . . . . . . . . . . . . . . . .
398
<a name = 11023328></a><a
href=http://www.ncbi.nlm.nih.gov:80/entrez/query.fcgi?cmd=Retrieve&db=Nucleotide
&list_uids=11023328&dopt=GenBank>AF283595</a>  374  . . . . . . . . . . . . . . . . . . . . . . . .
398
<a name = 11023326></a><a
href=http://www.ncbi.nlm.nih.gov:80/entrez/query.fcgi?cmd=Retrieve&db=Nucleotide
&list_uids=11023326&dopt=GenBank>AF283594</a>  374  . . . . . . . . . . . . . . . . . . . . . . . .
398
<a name = 11023324></a><a
href=http://www.ncbi.nlm.nih.gov:80/entrez/query.fcgi?cmd=Retrieve&db=Nucleotide
&list_uids=11023324&dopt=GenBank>AF283593</a>  374  . . . . . . . . . . . . . . . . . . . . . . . .
398
<a name = 11023322></a><a
href=http://www.ncbi.nlm.nih.gov:80/entrez/query.fcgi?cmd=Retrieve&db=Nucleotide
&list_uids=11023322&dopt=GenBank>AF283592</a>  374  . . . . . . . . . . . . . . . . . . . . . . . .
398
<a name = 11023320></a><a
href=http://www.ncbi.nlm.nih.gov:80/entrez/query.fcgi?cmd=Retrieve&db=Nucleotide
&list_uids=11023320&dopt=GenBank>AF283591</a>  374  . . . . . . . . . . . . . . . . . . . . . . . .
398
<a name = 11023318></a><a
href=http://www.ncbi.nlm.nih.gov:80/entrez/query.fcgi?cmd=Retrieve&db=Nucleotide
&list_uids=11023318&dopt=GenBank>AF283590</a>  374  . . . . . . . . . . . . . . . . . . . . . . . .
398
<a name = 11023316></a><a
href=http://www.ncbi.nlm.nih.gov:80/entrez/query.fcgi?cmd=Retrieve&db=Nucleotide
&list_uids=11023316&dopt=GenBank>AF283589</a>  374  . . . . . . . . . . . . . . . . . . . . . . . .
398
<a name = 11023314></a><a
href=http://www.ncbi.nlm.nih.gov:80/entrez/query.fcgi?cmd=Retrieve&db=Nucleotide
&list_uids=11023314&dopt=GenBank>AF283588</a>  374  . . . . . . . . . . . . . . . . . . . . . . . .
398
<a name = 11023312></a><a
href=http://www.ncbi.nlm.nih.gov:80/entrez/query.fcgi?cmd=Retrieve&db=Nucleotide
&list_uids=11023312&dopt=GenBank>AF283587</a>  374  . . . . . . . . . . . . . . . . . . . . . . . .
398
<a name = 11023310></a><a
href=http://www.ncbi.nlm.nih.gov:80/entrez/query.fcgi?cmd=Retrieve&db=Nucleotide
```

```
<a name = 11023310></a><a
href=http://www.ncbi.nlm.nih.gov:80/entrez/query.fcgi?cmd=Retrieve&db=Nucleotide
&list_uids=11023310&dopt=GenBank>AF283586</a>  374  ........................
398
<a name = 11023308></a><a
href=http://www.ncbi.nlm.nih.gov:80/entrez/query.fcgi?cmd=Retrieve&db=Nucleotide
&list_uids=11023308&dopt=GenBank>AF283585</a>  374  ........................
398
<a name = 11023306></a><a
href=http://www.ncbi.nlm.nih.gov:80/entrez/query.fcgi?cmd=Retrieve&db=Nucleotide
&list_uids=11023306&dopt=GenBank>AF283584</a>  374  ........................
398
<a name = 11023304></a><a
href=http://www.ncbi.nlm.nih.gov:80/entrez/query.fcgi?cmd=Retrieve&db=Nucleotide
&list_uids=11023304&dopt=GenBank>AF283583</a>  374  ........................
398
<a name = 11023302></a><a
href=http://www.ncbi.nlm.nih.gov:80/entrez/query.fcgi?cmd=Retrieve&db=Nucleotide
&list_uids=11023302&dopt=GenBank>AF283582</a>  374  ........................
398
<a name = 11023300></a><a
href=http://www.ncbi.nlm.nih.gov:80/entrez/query.fcgi?cmd=Retrieve&db=Nucleotide
&list_uids=11023300&dopt=GenBank>AF283581</a>  374  ........................
398
<a name = 11023298></a><a
href=http://www.ncbi.nlm.nih.gov:80/entrez/query.fcgi?cmd=Retrieve&db=Nucleotide
&list_uids=11023298&dopt=GenBank>AF283580</a>  374  ........................
398
<a name = 11023296></a><a
href=http://www.ncbi.nlm.nih.gov:80/entrez/query.fcgi?cmd=Retrieve&db=Nucleotide
&list_uids=11023296&dopt=GenBank>AF283579</a>  374  ........................
398
<a name = 11023294></a><a
href=http://www.ncbi.nlm.nih.gov:80/entrez/query.fcgi?cmd=Retrieve&db=Nucleotide
&list_uids=11023294&dopt=GenBank>AF283578</a>  374  ........................
398
<a name = 11023292></a><a
href=http://www.ncbi.nlm.nih.gov:80/entrez/query.fcgi?cmd=Retrieve&db=Nucleotide
&list_uids=11023292&dopt=GenBank>AF283577</a>  374  ........................
398
<a name = 11023290></a><a
href=http://www.ncbi.nlm.nih.gov:80/entrez/query.fcgi?cmd=Retrieve&db=Nucleotide
&list_uids=11023290&dopt=GenBank>AF283576</a>  374  ........................
398
<a name = 10998365></a><a
href=http://www.ncbi.nlm.nih.gov:80/entrez/query.fcgi?cmd=Retrieve&db=Nucleotide
&list_uids=10998365&dopt=GenBank>AF187030</a>  398  ........................
422
<a name = 10799225></a><a
href=http://www.ncbi.nlm.nih.gov:80/entrez/query.fcgi?cmd=Retrieve&db=Nucleotide
&list_uids=10799225&dopt=GenBank>AF310052</a>  299  ........................
323
<a name = 10799213></a><a
href=http://www.ncbi.nlm.nih.gov:80/entrez/query.fcgi?cmd=Retrieve&db=Nucleotide
&list_uids=10799213&dopt=GenBank>AF310046</a>  299  ........................
323
<a name = 10443579></a><a
href=http://www.ncbi.nlm.nih.gov:80/entrez/query.fcgi?cmd=Retrieve&db=Nucleotide
```

```
&list_uids=10443579&dopt=GenBank>AF171919</a>  302  ........................
326
<a name = 10443535></a><a
href=http://www.ncbi.nlm.nih.gov:80/entrez/query.fcgi?cmd=Retrieve&db=Nucleotide
&list_uids=10443535&dopt=GenBank>AF171897</a>  297  ........................
321
<a name = 9972117></a><a
href=http://www.ncbi.nlm.nih.gov:80/entrez/query.fcgi?cmd=Retrieve&db=Nucleotide
&list_uids=09972117&dopt=GenBank>AF290174</a>  281  ........................
305
<a name = 9972115></a><a
href=http://www.ncbi.nlm.nih.gov:80/entrez/query.fcgi?cmd=Retrieve&db=Nucleotide
&list_uids=09972115&dopt=GenBank>AF290173</a>  281  ........................
305
<a name = 9972111></a><a
href=http://www.ncbi.nlm.nih.gov:80/entrez/query.fcgi?cmd=Retrieve&db=Nucleotide
&list_uids=09972111&dopt=GenBank>AF290171</a>  281  ........................
305
<a name = 9972109></a><a
href=http://www.ncbi.nlm.nih.gov:80/entrez/query.fcgi?cmd=Retrieve&db=Nucleotide
&list_uids=09972109&dopt=GenBank>AF290170</a>  281  ........................
305
<a name = 9972069></a><a
href=http://www.ncbi.nlm.nih.gov:80/entrez/query.fcgi?cmd=Retrieve&db=Nucleotide
&list_uids=09972069&dopt=GenBank>AF290150</a>  281  ........................
305
<a name = 9789155></a><a
href=http://www.ncbi.nlm.nih.gov:80/entrez/query.fcgi?cmd=Retrieve&db=Nucleotide
&list_uids=09789155&dopt=GenBank>AF176252</a>  398  ........................
422
<a name = 9789153></a><a
href=http://www.ncbi.nlm.nih.gov:80/entrez/query.fcgi?cmd=Retrieve&db=Nucleotide
&list_uids=09789153&dopt=GenBank>AF176251</a>  398  ........................
422
<a name = 6690577></a><a
href=http://www.ncbi.nlm.nih.gov:80/entrez/query.fcgi?cmd=Retrieve&db=Nucleotide
&list_uids=06690577&dopt=GenBank>AF163907</a>  398  ........................
422
<a name = 6690574></a><a
href=http://www.ncbi.nlm.nih.gov:80/entrez/query.fcgi?cmd=Retrieve&db=Nucleotide
&list_uids=06690574&dopt=GenBank>AF163904</a>  398  ........................
422
<a name = 6690571></a><a
href=http://www.ncbi.nlm.nih.gov:80/entrez/query.fcgi?cmd=Retrieve&db=Nucleotide
&list_uids=06690571&dopt=GenBank>AF163901</a>  398  ........................
422
<a name = 6690569></a><a
href=http://www.ncbi.nlm.nih.gov:80/entrez/query.fcgi?cmd=Retrieve&db=Nucleotide
&list_uids=06690569&dopt=GenBank>AF163899</a>  398  ........................
422
<a name = 9695295></a><a
href=http://www.ncbi.nlm.nih.gov:80/entrez/query.fcgi?cmd=Retrieve&db=Nucleotide
&list_uids=09695295&dopt=GenBank>AF163891</a>  398  ........................
422
<a name = 9695293></a><a
href=http://www.ncbi.nlm.nih.gov:80/entrez/query.fcgi?cmd=Retrieve&db=Nucleotide
```

```
&list_uids=09695293&dopt=GenBank>AF163890</a>  398  ..........................
422
<a name = 9652375></a><a
href=http://www.ncbi.nlm.nih.gov:80/entrez/query.fcgi?cmd=Retrieve&db=Nucleotide
&list_uids=09652375&dopt=GenBank>AF288524</a>  401  ..........................
425
<a name = 9652373></a><a
href=http://www.ncbi.nlm.nih.gov:80/entrez/query.fcgi?cmd=Retrieve&db=Nucleotide
&list_uids=09652373&dopt=GenBank>AF288523</a>  401  ..........................
425
<a name = 9652371></a><a
href=http://www.ncbi.nlm.nih.gov:80/entrez/query.fcgi?cmd=Retrieve&db=Nucleotide
&list_uids=09652371&dopt=GenBank>AF288522</a>  401  ..........................
425
<a name = 7573897></a><a
href=http://www.ncbi.nlm.nih.gov:80/entrez/query.fcgi?cmd=Retrieve&db=Nucleotide
&list_uids=07573897&dopt=GenBank>AF123530</a>  303  ..........................
327
<a name = 7573861></a><a
href=http://www.ncbi.nlm.nih.gov:80/entrez/query.fcgi?cmd=Retrieve&db=Nucleotide
&list_uids=07573861&dopt=GenBank>AF123512</a>  303  ..........................
327
<a name = 7861886></a><a
href=http://www.ncbi.nlm.nih.gov:80/entrez/query.fcgi?cmd=Retrieve&db=Nucleotide
&list_uids=07861886&dopt=GenBank>AF206548</a>  303  ..........................
327
<a name = 6469790></a><a
href=http://www.ncbi.nlm.nih.gov:80/entrez/query.fcgi?cmd=Retrieve&db=Nucleotide
&list_uids=06469790&dopt=GenBank>AF197867</a>  401  ..........................
425
<a name = 7690342></a><a
href=http://www.ncbi.nlm.nih.gov:80/entrez/query.fcgi?cmd=Retrieve&db=Nucleotide
&list_uids=07690342&dopt=GenBank>U63397</a>    303  ..........................
327
<a name = 5835568></a><a
href=http://www.ncbi.nlm.nih.gov:80/entrez/query.fcgi?cmd=Retrieve&db=Nucleotide
&list_uids=05835568&dopt=GenBank>NC_001945</a> 15302 ..........................
15326
<a name = 5835429></a><a
href=http://www.ncbi.nlm.nih.gov:80/entrez/query.fcgi?cmd=Retrieve&db=Nucleotide
&list_uids=05835429&dopt=GenBank>NC_001821</a> 14568 ..........................
14592
<a name = 7648602></a><a
href=http://www.ncbi.nlm.nih.gov:80/entrez/query.fcgi?cmd=Retrieve&db=Nucleotide
&list_uids=07648602&dopt=GenBank>AF141217</a>  398  ..........................
422
<a name = 7243470></a><a
href=http://www.ncbi.nlm.nih.gov:80/entrez/query.fcgi?cmd=Retrieve&db=Nucleotide
&list_uids=07243470&dopt=GenBank>AF201615</a>  385  ..........................
409
<a name = 5596403></a><a
href=http://www.ncbi.nlm.nih.gov:80/entrez/query.fcgi?cmd=Retrieve&db=Nucleotide
&list_uids=05596403&dopt=GenBank>AF077920</a>  154  ..........................
178
<a name = 7406984></a><a
href=http://www.ncbi.nlm.nih.gov:80/entrez/query.fcgi?cmd=Retrieve&db=Nucleotide
```

```
&list_uids=07406984&dopt=GenBank>AF190632</a>  398  ..........................
422
<a name = 336430></a><a
href=http://www.ncbi.nlm.nih.gov:80/entrez/query.fcgi?cmd=Retrieve&db=Nucleotide
&list_uids=00336430&dopt=GenBank>J01394</a>    14911 ..........................
14935
<a name = 7208260></a><a
href=http://www.ncbi.nlm.nih.gov:80/entrez/query.fcgi?cmd=Retrieve&db=Nucleotide
&list_uids=07208260&dopt=GenBank>AF193830</a>  302  ..........................
326
<a name = 4099741></a><a
href=http://www.ncbi.nlm.nih.gov:80/entrez/query.fcgi?cmd=Retrieve&db=Nucleotide
&list_uids=04099741&dopt=GenBank>U89181</a>    401  ..........................
425
<a name = 4099727></a><a
href=http://www.ncbi.nlm.nih.gov:80/entrez/query.fcgi?cmd=Retrieve&db=Nucleotide
&list_uids=04099727&dopt=GenBank>U89171</a>    401  ..........................
425
<a name = 7141212></a><a
href=http://www.ncbi.nlm.nih.gov:80/entrez/query.fcgi?cmd=Retrieve&db=Nucleotide
&list_uids=07141212&dopt=GenBank>AF217833</a>  371  ..........................
395
<a name = 7141190></a><a
href=http://www.ncbi.nlm.nih.gov:80/entrez/query.fcgi?cmd=Retrieve&db=Nucleotide
&list_uids=07141190&dopt=GenBank>AF217822</a>  374  ..........................
398
<a name = 7141172></a><a
href=http://www.ncbi.nlm.nih.gov:80/entrez/query.fcgi?cmd=Retrieve&db=Nucleotide
&list_uids=07141172&dopt=GenBank>AF217813</a>  374  ..........................
398
<a name = 7021371></a><a
href=http://www.ncbi.nlm.nih.gov:80/entrez/query.fcgi?cmd=Retrieve&db=Nucleotide
&list_uids=07021371&dopt=GenBank>AF220408</a>  413  ..........................
437
<a name = 6689885></a><a
href=http://www.ncbi.nlm.nih.gov:80/entrez/query.fcgi?cmd=Retrieve&db=Nucleotide
&list_uids=06689885&dopt=GenBank>AF126430</a>  398  ..........................
422
<a name = 4887659></a><a
href=http://www.ncbi.nlm.nih.gov:80/entrez/query.fcgi?cmd=Retrieve&db=Nucleotide
&list_uids=04887659&dopt=GenBank>AF090337</a>  15123 ..........................
15147
<a name = 3088771></a><a
href=http://www.ncbi.nlm.nih.gov:80/entrez/query.fcgi?cmd=Retrieve&db=Nucleotide
&list_uids=03088771&dopt=GenBank>AF059111</a>  305  ..........................
329
<a name = 3088655></a><a
href=http://www.ncbi.nlm.nih.gov:80/entrez/query.fcgi?cmd=Retrieve&db=Nucleotide
&list_uids=03088655&dopt=GenBank>AF059053</a>  305  ..........................
329
<a name = 6062907></a><a
href=http://www.ncbi.nlm.nih.gov:80/entrez/query.fcgi?cmd=Retrieve&db=Nucleotide
&list_uids=06062907&dopt=GenBank>AF099308</a>  303  ..........................
327
<a name = 6062894></a><a
href=http://www.ncbi.nlm.nih.gov:80/entrez/query.fcgi?cmd=Retrieve&db=Nucleotide
```

```
&list_uids=06062894&dopt=GenBank>AF099295</a>  303  ..........................
327
<a name = 6062893></a><a
href=http://www.ncbi.nlm.nih.gov:80/entrez/query.fcgi?cmd=Retrieve&db=Nucleotide
&list_uids=06062893&dopt=GenBank>AF099294</a>  303  ..........................
327
<a name = 6062892></a><a
href=http://www.ncbi.nlm.nih.gov:80/entrez/query.fcgi?cmd=Retrieve&db=Nucleotide
&list_uids=06062892&dopt=GenBank>AF099293</a>  303  ..........................
327
<a name = 6524786></a><a
href=http://www.ncbi.nlm.nih.gov:80/entrez/query.fcgi?cmd=Retrieve&db=Nucleotide
&list_uids=06524786&dopt=GenBank>AF160610</a>  398  ..........................
422
<a name = 5777921></a><a
href=http://www.ncbi.nlm.nih.gov:80/entrez/query.fcgi?cmd=Retrieve&db=Nucleotide
&list_uids=05777921&dopt=GenBank>AF036280</a>  398  ..........................
422
<a name = 5777915></a><a
href=http://www.ncbi.nlm.nih.gov:80/entrez/query.fcgi?cmd=Retrieve&db=Nucleotide
&list_uids=05777915&dopt=GenBank>AF036277</a>  398  ..........................
422
<a name = 5777909></a><a
href=http://www.ncbi.nlm.nih.gov:80/entrez/query.fcgi?cmd=Retrieve&db=Nucleotide
&list_uids=05777909&dopt=GenBank>AF036274</a>  398  ..........................
422
<a name = 6456620></a><a
href=http://www.ncbi.nlm.nih.gov:80/entrez/query.fcgi?cmd=Retrieve&db=Nucleotide
&list_uids=06456620&dopt=GenBank>AF194218</a>  302  ..........................
326
<a name = 6456618></a><a
href=http://www.ncbi.nlm.nih.gov:80/entrez/query.fcgi?cmd=Retrieve&db=Nucleotide
&list_uids=06456618&dopt=GenBank>AF194216</a>  302  ..........................
326
<a name = 5835666></a><a
href=http://www.ncbi.nlm.nih.gov:80/entrez/query.fcgi?cmd=Retrieve&db=Nucleotide
&list_uids=05835666&dopt=GenBank>NC_002009</a>  14547  ..........................
14571
<a name = 5835554></a><a
href=http://www.ncbi.nlm.nih.gov:80/entrez/query.fcgi?cmd=Retrieve&db=Nucleotide
&list_uids=05835554&dopt=GenBank>NC_001941</a>  14556  ..........................
14580
<a name = 5835932></a><a
href=http://www.ncbi.nlm.nih.gov:80/entrez/query.fcgi?cmd=Retrieve&db=Nucleotide
&list_uids=05835932&dopt=GenBank>NC_000877</a>  15123  ..........................
15147
<a name = 5835498></a><a
href=http://www.ncbi.nlm.nih.gov:80/entrez/query.fcgi?cmd=Retrieve&db=Nucleotide
&list_uids=05835498&dopt=GenBank>NC_000846</a>  14038  ..........................
14062
<a name = 896416></a><a
href=http://www.ncbi.nlm.nih.gov:80/entrez/query.fcgi?cmd=Retrieve&db=Nucleotide
&list_uids=00896416&dopt=GenBank>U27551</a>     401  ..........................
425
<a name = 6048478></a><a
href=http://www.ncbi.nlm.nih.gov:80/entrez/query.fcgi?cmd=Retrieve&db=Nucleotide
```

```
&list_uids=06048478&dopt=GenBank>AF089058</a>  281  ........................
305
<a name = 6048475></a><a
href=http://www.ncbi.nlm.nih.gov:80/entrez/query.fcgi?cmd=Retrieve&db=Nucleotide
&list_uids=06048475&dopt=GenBank>AF089055</a>  281  ........................
305
<a name = 6048474></a><a
href=http://www.ncbi.nlm.nih.gov:80/entrez/query.fcgi?cmd=Retrieve&db=Nucleotide
&list_uids=06048474&dopt=GenBank>AF089054</a>  281  ........................
305
<a name = 6048466></a><a
href=http://www.ncbi.nlm.nih.gov:80/entrez/query.fcgi?cmd=Retrieve&db=Nucleotide
&list_uids=06048466&dopt=GenBank>AF089046</a>  281  ........................
305
<a name = 6048462></a><a
href=http://www.ncbi.nlm.nih.gov:80/entrez/query.fcgi?cmd=Retrieve&db=Nucleotide
&list_uids=06048462&dopt=GenBank>AF089042</a>  272  ........................
296
<a name = 6048459></a><a
href=http://www.ncbi.nlm.nih.gov:80/entrez/query.fcgi?cmd=Retrieve&db=Nucleotide
&list_uids=06048459&dopt=GenBank>AF089039</a>  281  ........................
305
<a name = 6048457></a><a
href=http://www.ncbi.nlm.nih.gov:80/entrez/query.fcgi?cmd=Retrieve&db=Nucleotide
&list_uids=06048457&dopt=GenBank>AF089037</a>  281  ........................
305
<a name = 6048446></a><a
href=http://www.ncbi.nlm.nih.gov:80/entrez/query.fcgi?cmd=Retrieve&db=Nucleotide
&list_uids=06048446&dopt=GenBank>AF089026</a>  281  ........................
305
<a name = 6048445></a><a
href=http://www.ncbi.nlm.nih.gov:80/entrez/query.fcgi?cmd=Retrieve&db=Nucleotide
&list_uids=06048445&dopt=GenBank>AF089025</a>  281  ........................
305
<a name = 6048444></a><a
href=http://www.ncbi.nlm.nih.gov:80/entrez/query.fcgi?cmd=Retrieve&db=Nucleotide
&list_uids=06048444&dopt=GenBank>AF089024</a>  281  ........................
305
<a name = 6048443></a><a
href=http://www.ncbi.nlm.nih.gov:80/entrez/query.fcgi?cmd=Retrieve&db=Nucleotide
&list_uids=06048443&dopt=GenBank>AF089023</a>  281  ........................
305
<a name = 6048441></a><a
href=http://www.ncbi.nlm.nih.gov:80/entrez/query.fcgi?cmd=Retrieve&db=Nucleotide
&list_uids=06048441&dopt=GenBank>AF089021</a>  281  ........................
305
<a name = 6048440></a><a
href=http://www.ncbi.nlm.nih.gov:80/entrez/query.fcgi?cmd=Retrieve&db=Nucleotide
&list_uids=06048440&dopt=GenBank>AF089020</a>  281  ........................
305
<a name = 6048436></a><a
href=http://www.ncbi.nlm.nih.gov:80/entrez/query.fcgi?cmd=Retrieve&db=Nucleotide
&list_uids=06048436&dopt=GenBank>AF089016</a>  281  ........................
305
<a name = 6048433></a><a
href=http://www.ncbi.nlm.nih.gov:80/entrez/query.fcgi?cmd=Retrieve&db=Nucleotide
```

```
&list_uids=06048433&dopt=GenBank>AF089013</a>  281  ........................
305
<a name = 6048432></a><a
href=http://www.ncbi.nlm.nih.gov:80/entrez/query.fcgi?cmd=Retrieve&db=Nucleotide
&list_uids=06048432&dopt=GenBank>AF089012</a>  281  ........................
305
<a name = 6048428></a><a
href=http://www.ncbi.nlm.nih.gov:80/entrez/query.fcgi?cmd=Retrieve&db=Nucleotide
&list_uids=06048428&dopt=GenBank>AF089008</a>  281  ........................
305
<a name = 6048426></a><a
href=http://www.ncbi.nlm.nih.gov:80/entrez/query.fcgi?cmd=Retrieve&db=Nucleotide
&list_uids=06048426&dopt=GenBank>AF089006</a>  257  ........................
281
<a name = 6048425></a><a
href=http://www.ncbi.nlm.nih.gov:80/entrez/query.fcgi?cmd=Retrieve&db=Nucleotide
&list_uids=06048425&dopt=GenBank>AF089005</a>  281  ........................
305
<a name = 5579169></a><a
href=http://www.ncbi.nlm.nih.gov:80/entrez/query.fcgi?cmd=Retrieve&db=Nucleotide
&list_uids=05579169&dopt=GenBank>AF108696</a>  398  ........................
422
<a name = 5579158></a><a
href=http://www.ncbi.nlm.nih.gov:80/entrez/query.fcgi?cmd=Retrieve&db=Nucleotide
&list_uids=05579158&dopt=GenBank>AF108685</a>  392  ........................
416
<a name = 5579150></a><a
href=http://www.ncbi.nlm.nih.gov:80/entrez/query.fcgi?cmd=Retrieve&db=Nucleotide
&list_uids=05579150&dopt=GenBank>AF108677</a>  398  ........................
422
<a name = 5918591></a><a
href=http://www.ncbi.nlm.nih.gov:80/entrez/query.fcgi?cmd=Retrieve&db=Nucleotide
&list_uids=05918591&dopt=GenBank>AF145531</a>  169  ........................
193
<a name = 5918571></a><a
href=http://www.ncbi.nlm.nih.gov:80/entrez/query.fcgi?cmd=Retrieve&db=Nucleotide
&list_uids=05918571&dopt=GenBank>AF145511</a>  169  ........................
193
<a name = 2351722></a><a
href=http://www.ncbi.nlm.nih.gov:80/entrez/query.fcgi?cmd=Retrieve&db=Nucleotide
&list_uids=02351722&dopt=GenBank>U89627</a>    360  ........................
384
<a name = 2351726></a><a
href=http://www.ncbi.nlm.nih.gov:80/entrez/query.fcgi?cmd=Retrieve&db=Nucleotide
&list_uids=02351726&dopt=GenBank>U89623</a>    360  ........................
384
<a name = 5853310></a><a
href=http://www.ncbi.nlm.nih.gov:80/entrez/query.fcgi?cmd=Retrieve&db=Nucleotide
&list_uids=05853310&dopt=GenBank>AF181470</a>  303  ........................
327
<a name = 5870028></a><a
href=http://www.ncbi.nlm.nih.gov:80/entrez/query.fcgi?cmd=Retrieve&db=Nucleotide
&list_uids=05870028&dopt=GenBank>AF084075</a>  398  ........................
422
<a name = 1899215></a><a
href=http://www.ncbi.nlm.nih.gov:80/entrez/query.fcgi?cmd=Retrieve&db=Nucleotide
```

```
&list_uids=01899215&dopt=GenBank>U90303</a>    398 ........................
422
<a name = 1899213></a><a
href=http://www.ncbi.nlm.nih.gov:80/entrez/query.fcgi?cmd=Retrieve&db=Nucleotide
&list_uids=01899213&dopt=GenBank>U90302</a>    398 ........................
422
<a name = 1899211></a><a
href=http://www.ncbi.nlm.nih.gov:80/entrez/query.fcgi?cmd=Retrieve&db=Nucleotide
&list_uids=01899211&dopt=GenBank>U90301</a>    398 ........................
422
<a name = 1899209></a><a
href=http://www.ncbi.nlm.nih.gov:80/entrez/query.fcgi?cmd=Retrieve&db=Nucleotide
&list_uids=01899209&dopt=GenBank>U90300</a>    398 ........................
422
<a name = 3510549></a><a
href=http://www.ncbi.nlm.nih.gov:80/entrez/query.fcgi?cmd=Retrieve&db=Nucleotide
&list_uids=03510549&dopt=GenBank>AF038883</a>    392 ........................
416
<a name = 3510575></a><a
href=http://www.ncbi.nlm.nih.gov:80/entrez/query.fcgi?cmd=Retrieve&db=Nucleotide
&list_uids=03510575&dopt=GenBank>AF039268</a>    392 ........................
416
<a name = 3510573></a><a
href=http://www.ncbi.nlm.nih.gov:80/entrez/query.fcgi?cmd=Retrieve&db=Nucleotide
&list_uids=03510573&dopt=GenBank>AF039267</a>    392 ........................
416
<a name = 259294></a><a
href=http://www.ncbi.nlm.nih.gov:80/entrez/query.fcgi?cmd=Retrieve&db=Nucleotide
&list_uids=00259294&dopt=GenBank>S49215</a>    56 ........................
80
<a name = 5616280></a><a
href=http://www.ncbi.nlm.nih.gov:80/entrez/query.fcgi?cmd=Retrieve&db=Nucleotide
&list_uids=05616280&dopt=GenBank>AF158698</a>    398 ........................
422
<a name = 5616266></a><a
href=http://www.ncbi.nlm.nih.gov:80/entrez/query.fcgi?cmd=Retrieve&db=Nucleotide
&list_uids=05616266&dopt=GenBank>AF158692</a>    398 ........................
422
<a name = 3834418></a><a
href=http://www.ncbi.nlm.nih.gov:80/entrez/query.fcgi?cmd=Retrieve&db=Nucleotide
&list_uids=03834418&dopt=GenBank>AF068193</a>    401 ........................
425
<a name = 5359509></a><a
href=http://www.ncbi.nlm.nih.gov:80/entrez/query.fcgi?cmd=Retrieve&db=Nucleotide
&list_uids=05359509&dopt=GenBank>AF091629</a>    398 ........................
422
<a name = 4103301></a><a
href=http://www.ncbi.nlm.nih.gov:80/entrez/query.fcgi?cmd=Retrieve&db=Nucleotide
&list_uids=04103301&dopt=GenBank>AF022063</a>    398 ........................
422
<a name = 4103299></a><a
href=http://www.ncbi.nlm.nih.gov:80/entrez/query.fcgi?cmd=Retrieve&db=Nucleotide
&list_uids=04103299&dopt=GenBank>AF022062</a>    398 ........................
422
<a name = 4103295></a><a
href=http://www.ncbi.nlm.nih.gov:80/entrez/query.fcgi?cmd=Retrieve&db=Nucleotide
```

```
&list_uids=04103295&dopt=GenBank>AF022060</a>  398  ..........................
422
<a name = 4103289></a><a
href=http://www.ncbi.nlm.nih.gov:80/entrez/query.fcgi?cmd=Retrieve&db=Nucleotide
&list_uids=04103289&dopt=GenBank>AF022057</a>  398  ..........................
422
<a name = 4559243></a><a
href=http://www.ncbi.nlm.nih.gov:80/entrez/query.fcgi?cmd=Retrieve&db=Nucleotide
&list_uids=04559243&dopt=GenBank>AF113500</a>  384  ..........................
408
<a name = 4559242></a><a
href=http://www.ncbi.nlm.nih.gov:80/entrez/query.fcgi?cmd=Retrieve&db=Nucleotide
&list_uids=04559242&dopt=GenBank>AF113499</a>  363  ..........................
387
<a name = 2843024></a><a
href=http://www.ncbi.nlm.nih.gov:80/entrez/query.fcgi?cmd=Retrieve&db=Nucleotide
&list_uids=02843024&dopt=GenBank>U69845</a>    374  ..........................
398
<a name = 2842972></a><a
href=http://www.ncbi.nlm.nih.gov:80/entrez/query.fcgi?cmd=Retrieve&db=Nucleotide
&list_uids=02842972&dopt=GenBank>U69810</a>    374  ..........................
398
<a name = 2842962></a><a
href=http://www.ncbi.nlm.nih.gov:80/entrez/query.fcgi?cmd=Retrieve&db=Nucleotide
&list_uids=02842962&dopt=GenBank>U69808</a>    374  ..........................
398
<a name = 2842988></a><a
href=http://www.ncbi.nlm.nih.gov:80/entrez/query.fcgi?cmd=Retrieve&db=Nucleotide
&list_uids=02842988&dopt=GenBank>U69799</a>    374  ..........................
398
<a name = 2842982></a><a
href=http://www.ncbi.nlm.nih.gov:80/entrez/query.fcgi?cmd=Retrieve&db=Nucleotide
&list_uids=02842982&dopt=GenBank>U69796</a>    374  ..........................
398
<a name = 2842980></a><a
href=http://www.ncbi.nlm.nih.gov:80/entrez/query.fcgi?cmd=Retrieve&db=Nucleotide
&list_uids=02842980&dopt=GenBank>U69795</a>    374  ..........................
398
<a name = 2842978></a><a
href=http://www.ncbi.nlm.nih.gov:80/entrez/query.fcgi?cmd=Retrieve&db=Nucleotide
&list_uids=02842978&dopt=GenBank>U69794</a>    374  ..........................
398
<a name = 2842976></a><a
href=http://www.ncbi.nlm.nih.gov:80/entrez/query.fcgi?cmd=Retrieve&db=Nucleotide
&list_uids=02842976&dopt=GenBank>U69793</a>    374  ..........................
398
<a name = 2842960></a><a
href=http://www.ncbi.nlm.nih.gov:80/entrez/query.fcgi?cmd=Retrieve&db=Nucleotide
&list_uids=02842960&dopt=GenBank>U69792</a>    374  ..........................
398
<a name = 2842958></a><a
href=http://www.ncbi.nlm.nih.gov:80/entrez/query.fcgi?cmd=Retrieve&db=Nucleotide
&list_uids=02842958&dopt=GenBank>U69790</a>    374  ..........................
398
<a name = 2842942></a><a
href=http://www.ncbi.nlm.nih.gov:80/entrez/query.fcgi?cmd=Retrieve&db=Nucleotide
```

```
&list_uids=02842942&dopt=GenBank>U69786</a>   374   ..........................
398
<a name = 2842938></a><a
href=http://www.ncbi.nlm.nih.gov:80/entrez/query.fcgi?cmd=Retrieve&db=Nucleotide
&list_uids=02842938&dopt=GenBank>U69784</a>   374   ..........................
398
<a name = 2842910></a><a
href=http://www.ncbi.nlm.nih.gov:80/entrez/query.fcgi?cmd=Retrieve&db=Nucleotide
&list_uids=02842910&dopt=GenBank>U69779</a>   374   ..........................
398
<a name = 2842906></a><a
href=http://www.ncbi.nlm.nih.gov:80/entrez/query.fcgi?cmd=Retrieve&db=Nucleotide
&list_uids=02842906&dopt=GenBank>U69777</a>   374   ..........................
398
<a name = 2842904></a><a
href=http://www.ncbi.nlm.nih.gov:80/entrez/query.fcgi?cmd=Retrieve&db=Nucleotide
&list_uids=02842904&dopt=GenBank>U69776</a>   374   ..........................
398
<a name = 2842900></a><a
href=http://www.ncbi.nlm.nih.gov:80/entrez/query.fcgi?cmd=Retrieve&db=Nucleotide
&list_uids=02842900&dopt=GenBank>U69774</a>   374   ..........................
398
<a name = 2842888></a><a
href=http://www.ncbi.nlm.nih.gov:80/entrez/query.fcgi?cmd=Retrieve&db=Nucleotide
&list_uids=02842888&dopt=GenBank>U69772</a>   374   ..........................
398
<a name = 2842886></a><a
href=http://www.ncbi.nlm.nih.gov:80/entrez/query.fcgi?cmd=Retrieve&db=Nucleotide
&list_uids=02842886&dopt=GenBank>U69771</a>   374   ..........................
398
<a name = 2842884></a><a
href=http://www.ncbi.nlm.nih.gov:80/entrez/query.fcgi?cmd=Retrieve&db=Nucleotide
&list_uids=02842884&dopt=GenBank>U69770</a>   374   ..........................
398
<a name = 2842882></a><a
href=http://www.ncbi.nlm.nih.gov:80/entrez/query.fcgi?cmd=Retrieve&db=Nucleotide
&list_uids=02842882&dopt=GenBank>U69769</a>   374   ..........................
398
<a name = 2842856></a><a
href=http://www.ncbi.nlm.nih.gov:80/entrez/query.fcgi?cmd=Retrieve&db=Nucleotide
&list_uids=02842856&dopt=GenBank>U69752</a>   74    ..........................
98
<a name = 2842844></a><a
href=http://www.ncbi.nlm.nih.gov:80/entrez/query.fcgi?cmd=Retrieve&db=Nucleotide
&list_uids=02842844&dopt=GenBank>U69746</a>   374   ..........................
398
<a name = 2842834></a><a
href=http://www.ncbi.nlm.nih.gov:80/entrez/query.fcgi?cmd=Retrieve&db=Nucleotide
&list_uids=02842834&dopt=GenBank>U69740</a>   374   ..........................
398
<a name = 4894935></a><a
href=http://www.ncbi.nlm.nih.gov:80/entrez/query.fcgi?cmd=Retrieve&db=Nucleotide
&list_uids=04894935&dopt=GenBank>AF139057</a> 398   ..........................
422
<a name = 4894475></a><a
href=http://www.ncbi.nlm.nih.gov:80/entrez/query.fcgi?cmd=Retrieve&db=Nucleotide
```

```
&list_uids=04894475&dopt=GenBank>AF090339</a>  15199 .......................
15223
<a name = 4565839></a><a
href=http://www.ncbi.nlm.nih.gov:80/entrez/query.fcgi?cmd=Retrieve&db=Nucleotide
&list_uids=04565839&dopt=GenBank>AF006275</a>  475 .........................
499
<a name = 4565823></a><a
href=http://www.ncbi.nlm.nih.gov:80/entrez/query.fcgi?cmd=Retrieve&db=Nucleotide
&list_uids=04565823&dopt=GenBank>AF006267</a>  475 .........................
499
<a name = 2660921></a><a
href=http://www.ncbi.nlm.nih.gov:80/entrez/query.fcgi?cmd=Retrieve&db=Nucleotide
&list_uids=02660921&dopt=GenBank>AF034969</a>  398 .........................
422
<a name = 2605884></a><a
href=http://www.ncbi.nlm.nih.gov:80/entrez/query.fcgi?cmd=Retrieve&db=Nucleotide
&list_uids=02605884&dopt=GenBank>AF028822</a>  398 .........................
422
<a name = 2605882></a><a
href=http://www.ncbi.nlm.nih.gov:80/entrez/query.fcgi?cmd=Retrieve&db=Nucleotide
&list_uids=02605882&dopt=GenBank>AF028821</a>  398 .........................
422
<a name = 4164474></a><a
href=http://www.ncbi.nlm.nih.gov:80/entrez/query.fcgi?cmd=Retrieve&db=Nucleotide
&list_uids=04164474&dopt=GenBank>AF061340</a>  14547 .......................
14571
<a name = 3420708></a><a
href=http://www.ncbi.nlm.nih.gov:80/entrez/query.fcgi?cmd=Retrieve&db=Nucleotide
&list_uids=03420708&dopt=GenBank>AF076093</a>  401 .........................
425
<a name = 3420704></a><a
href=http://www.ncbi.nlm.nih.gov:80/entrez/query.fcgi?cmd=Retrieve&db=Nucleotide
&list_uids=03420704&dopt=GenBank>AF076091</a>  401 .........................
425
<a name = 3420666></a><a
href=http://www.ncbi.nlm.nih.gov:80/entrez/query.fcgi?cmd=Retrieve&db=Nucleotide
&list_uids=03420666&dopt=GenBank>AF076072</a>  401 .........................
425
<a name = 3420648></a><a
href=http://www.ncbi.nlm.nih.gov:80/entrez/query.fcgi?cmd=Retrieve&db=Nucleotide
&list_uids=03420648&dopt=GenBank>AF076063</a>  401 .........................
425
<a name = 3420640></a><a
href=http://www.ncbi.nlm.nih.gov:80/entrez/query.fcgi?cmd=Retrieve&db=Nucleotide
&list_uids=03420640&dopt=GenBank>AF076059</a>  401 .........................
425
<a name = 3420634></a><a
href=http://www.ncbi.nlm.nih.gov:80/entrez/query.fcgi?cmd=Retrieve&db=Nucleotide
&list_uids=03420634&dopt=GenBank>AF076056</a>  401 .........................
425
<a name = 3420628></a><a
href=http://www.ncbi.nlm.nih.gov:80/entrez/query.fcgi?cmd=Retrieve&db=Nucleotide
&list_uids=03420628&dopt=GenBank>AF076053</a>  401 .........................
425
<a name = 3420622></a><a
href=http://www.ncbi.nlm.nih.gov:80/entrez/query.fcgi?cmd=Retrieve&db=Nucleotide
```

```
&list_uids=03420622&dopt=GenBank>AF076050</a>   401   .........................
425
<a name = 3420620></a><a
href=http://www.ncbi.nlm.nih.gov:80/entrez/query.fcgi?cmd=Retrieve&db=Nucleotide
&list_uids=03420620&dopt=GenBank>AF076049</a>   401   .........................
425
<a name = 3420618></a><a
href=http://www.ncbi.nlm.nih.gov:80/entrez/query.fcgi?cmd=Retrieve&db=Nucleotide
&list_uids=03420618&dopt=GenBank>AF076048</a>   401   .........................
425
<a name = 3420616></a><a
href=http://www.ncbi.nlm.nih.gov:80/entrez/query.fcgi?cmd=Retrieve&db=Nucleotide
&list_uids=03420616&dopt=GenBank>AF076047</a>   401   .........................
425
<a name = 2231527></a><a
href=http://www.ncbi.nlm.nih.gov:80/entrez/query.fcgi?cmd=Retrieve&db=Nucleotide
&list_uids=02231527&dopt=GenBank>U83314</a>   401   .........................
425
<a name = 2231523></a><a
href=http://www.ncbi.nlm.nih.gov:80/entrez/query.fcgi?cmd=Retrieve&db=Nucleotide
&list_uids=02231523&dopt=GenBank>U83318</a>   401   .........................
425
<a name = 1255763></a><a
href=http://www.ncbi.nlm.nih.gov:80/entrez/query.fcgi?cmd=Retrieve&db=Nucleotide
&list_uids=01255763&dopt=GenBank>U37303</a>   303   .........................
327
<a name = 1255761></a><a
href=http://www.ncbi.nlm.nih.gov:80/entrez/query.fcgi?cmd=Retrieve&db=Nucleotide
&list_uids=01255761&dopt=GenBank>U37302</a>   303   .........................
327
<a name = 1255749></a><a
href=http://www.ncbi.nlm.nih.gov:80/entrez/query.fcgi?cmd=Retrieve&db=Nucleotide
&list_uids=01255749&dopt=GenBank>U37296</a>   303   .........................
327
<a name = 1255735></a><a
href=http://www.ncbi.nlm.nih.gov:80/entrez/query.fcgi?cmd=Retrieve&db=Nucleotide
&list_uids=01255735&dopt=GenBank>U37289</a>   303   .........................
327
<a name = 1255731></a><a
href=http://www.ncbi.nlm.nih.gov:80/entrez/query.fcgi?cmd=Retrieve&db=Nucleotide
&list_uids=01255731&dopt=GenBank>U37286</a>   303   .........................
327
<a name = 1143282></a><a
href=http://www.ncbi.nlm.nih.gov:80/entrez/query.fcgi?cmd=Retrieve&db=Nucleotide
&list_uids=01143282&dopt=GenBank>U37104</a>   303   .........................
327
<a name = 1143280></a><a
href=http://www.ncbi.nlm.nih.gov:80/entrez/query.fcgi?cmd=Retrieve&db=Nucleotide
&list_uids=01143280&dopt=GenBank>U37087</a>   303   .........................
327
<a name = 2239314></a><a
href=http://www.ncbi.nlm.nih.gov:80/entrez/query.fcgi?cmd=Retrieve&db=Nucleotide
&list_uids=02239314&dopt=GenBank>U87525</a>   380   .........................
404
<a name = 2239312></a><a
href=http://www.ncbi.nlm.nih.gov:80/entrez/query.fcgi?cmd=Retrieve&db=Nucleotide
```

```
&list_uids=02239312&dopt=GenBank>U87524</a>     385   ........................
409
<a name = 2239310></a><a
href=http://www.ncbi.nlm.nih.gov:80/entrez/query.fcgi?cmd=Retrieve&db=Nucleotide
&list_uids=02239310&dopt=GenBank>U87523</a>     354   ........................
378
<a name = 2239308></a><a
href=http://www.ncbi.nlm.nih.gov:80/entrez/query.fcgi?cmd=Retrieve&db=Nucleotide
&list_uids=02239308&dopt=GenBank>U87522</a>     379   ........................
403
<a name = 604335></a><a
href=http://www.ncbi.nlm.nih.gov:80/entrez/query.fcgi?cmd=Retrieve&db=Nucleotide
&list_uids=00604335&dopt=GenBank>U17864</a>     398   ........................
422
<a name = 604333></a><a
href=http://www.ncbi.nlm.nih.gov:80/entrez/query.fcgi?cmd=Retrieve&db=Nucleotide
&list_uids=00604333&dopt=GenBank>U17863</a>     329   ........................
353
<a name = 604331></a><a
href=http://www.ncbi.nlm.nih.gov:80/entrez/query.fcgi?cmd=Retrieve&db=Nucleotide
&list_uids=00604331&dopt=GenBank>U17862</a>     398   ........................
422
<a name = 604327></a><a
href=http://www.ncbi.nlm.nih.gov:80/entrez/query.fcgi?cmd=Retrieve&db=Nucleotide
&list_uids=00604327&dopt=GenBank>U17860</a>     398   ........................
422
<a name = 604325></a><a
href=http://www.ncbi.nlm.nih.gov:80/entrez/query.fcgi?cmd=Retrieve&db=Nucleotide
&list_uids=00604325&dopt=GenBank>U17859</a>     329   ........................
353
<a name = 2894743></a><a
href=http://www.ncbi.nlm.nih.gov:80/entrez/query.fcgi?cmd=Retrieve&db=Nucleotide
&list_uids=02894743&dopt=GenBank>U65274</a>     398   ........................
422
<a name = 2894729></a><a
href=http://www.ncbi.nlm.nih.gov:80/entrez/query.fcgi?cmd=Retrieve&db=Nucleotide
&list_uids=02894729&dopt=GenBank>U65267</a>     398   ........................
422
<a name = 2894715></a><a
href=http://www.ncbi.nlm.nih.gov:80/entrez/query.fcgi?cmd=Retrieve&db=Nucleotide
&list_uids=02894715&dopt=GenBank>U65260</a>     398   ........................
422
<a name = 2894685></a><a
href=http://www.ncbi.nlm.nih.gov:80/entrez/query.fcgi?cmd=Retrieve&db=Nucleotide
&list_uids=02894685&dopt=GenBank>U65301</a>     398   ........................
422
<a name = 3417594></a><a
href=http://www.ncbi.nlm.nih.gov:80/entrez/query.fcgi?cmd=Retrieve&db=Nucleotide
&list_uids=03417594&dopt=GenBank>AF034739</a>   398   ........................
422
<a name = 3417592></a><a
href=http://www.ncbi.nlm.nih.gov:80/entrez/query.fcgi?cmd=Retrieve&db=Nucleotide
&list_uids=03417592&dopt=GenBank>AF034738</a>   398   ........................
422
<a name = 3417590></a><a
href=http://www.ncbi.nlm.nih.gov:80/entrez/query.fcgi?cmd=Retrieve&db=Nucleotide
```

```
&list_uids=03417590&dopt=GenBank>AF034737</a>   398   ..........................
422
<a name = 3417588></a><a
href=http://www.ncbi.nlm.nih.gov:80/entrez/query.fcgi?cmd=Retrieve&db=Nucleotide
&list_uids=03417588&dopt=GenBank>AF034736</a>   398   ..........................
422
<a name = 3417586></a><a
href=http://www.ncbi.nlm.nih.gov:80/entrez/query.fcgi?cmd=Retrieve&db=Nucleotide
&list_uids=03417586&dopt=GenBank>AF034735</a>   398   ..........................
422
<a name = 3417576></a><a
href=http://www.ncbi.nlm.nih.gov:80/entrez/query.fcgi?cmd=Retrieve&db=Nucleotide
&list_uids=03417576&dopt=GenBank>AF034730</a>   398   ..........................
422
<a name = 3417574></a><a
href=http://www.ncbi.nlm.nih.gov:80/entrez/query.fcgi?cmd=Retrieve&db=Nucleotide
&list_uids=03417574&dopt=GenBank>AF034729</a>   398   ..........................
422
<a name = 3417572></a><a
href=http://www.ncbi.nlm.nih.gov:80/entrez/query.fcgi?cmd=Retrieve&db=Nucleotide
&list_uids=03417572&dopt=GenBank>AF034728</a>   398   ..........................
422
<a name = 3417570></a><a
href=http://www.ncbi.nlm.nih.gov:80/entrez/query.fcgi?cmd=Retrieve&db=Nucleotide
&list_uids=03417570&dopt=GenBank>AF034727</a>   398   ..........................
422
<a name = 3417564></a><a
href=http://www.ncbi.nlm.nih.gov:80/entrez/query.fcgi?cmd=Retrieve&db=Nucleotide
&list_uids=03417564&dopt=GenBank>AF034724</a>   398   ..........................
422
<a name = 3511111></a><a
href=http://www.ncbi.nlm.nih.gov:80/entrez/query.fcgi?cmd=Retrieve&db=Nucleotide
&list_uids=03511111&dopt=GenBank>AF057132</a>   398   ..........................
422
<a name = 3452043></a><a
href=http://www.ncbi.nlm.nih.gov:80/entrez/query.fcgi?cmd=Retrieve&db=Nucleotide
&list_uids=03452043&dopt=GenBank>U94805</a>    401   ..........................
425
<a name = 3452040></a><a
href=http://www.ncbi.nlm.nih.gov:80/entrez/query.fcgi?cmd=Retrieve&db=Nucleotide
&list_uids=03452040&dopt=GenBank>U94804</a>    401   ..........................
425
<a name = 3452037></a><a
href=http://www.ncbi.nlm.nih.gov:80/entrez/query.fcgi?cmd=Retrieve&db=Nucleotide
&list_uids=03452037&dopt=GenBank>U94803</a>    401   ..........................
425
<a name = 2935116></a><a
href=http://www.ncbi.nlm.nih.gov:80/entrez/query.fcgi?cmd=Retrieve&db=Nucleotide
&list_uids=02935116&dopt=GenBank>AF006251</a>   303   ..........................
327
<a name = 2935112></a><a
href=http://www.ncbi.nlm.nih.gov:80/entrez/query.fcgi?cmd=Retrieve&db=Nucleotide
&list_uids=02935112&dopt=GenBank>AF006249</a>   303   ..........................
327
<a name = 2935090></a><a
href=http://www.ncbi.nlm.nih.gov:80/entrez/query.fcgi?cmd=Retrieve&db=Nucleotide
```

```
<a name = 2935090></a><a
href=http://www.ncbi.nlm.nih.gov:80/entrez/query.fcgi?cmd=Retrieve&db=Nucleotide
&list_uids=02935090&dopt=GenBank>AF006238</a>  303  ........................
327
<a name = 2935082></a><a
href=http://www.ncbi.nlm.nih.gov:80/entrez/query.fcgi?cmd=Retrieve&db=Nucleotide
&list_uids=02935082&dopt=GenBank>AF006234</a>  303  ........................
327
<a name = 2935066></a><a
href=http://www.ncbi.nlm.nih.gov:80/entrez/query.fcgi?cmd=Retrieve&db=Nucleotide
&list_uids=02935066&dopt=GenBank>AF006226</a>  303  ........................
327
<a name = 2935044></a><a
href=http://www.ncbi.nlm.nih.gov:80/entrez/query.fcgi?cmd=Retrieve&db=Nucleotide
&list_uids=02935044&dopt=GenBank>AF006215</a>  303  ........................
327
<a name = 2935042></a><a
href=http://www.ncbi.nlm.nih.gov:80/entrez/query.fcgi?cmd=Retrieve&db=Nucleotide
&list_uids=02935042&dopt=GenBank>AF006214</a>  303  ........................
327
<a name = 2935040></a><a
href=http://www.ncbi.nlm.nih.gov:80/entrez/query.fcgi?cmd=Retrieve&db=Nucleotide
&list_uids=02935040&dopt=GenBank>AF006213</a>  303  ........................
327
<a name = 2935038></a><a
href=http://www.ncbi.nlm.nih.gov:80/entrez/query.fcgi?cmd=Retrieve&db=Nucleotide
&list_uids=02935038&dopt=GenBank>AF006212</a>  303  ........................
327
<a name = 11071919></a><a
href=http://www.ncbi.nlm.nih.gov:80/entrez/query.fcgi?cmd=Retrieve&db=Nucleotide
&list_uids=11071919&dopt=GenBank>AJ293419</a>  398  ........................
422
<a name = 11071915></a><a
href=http://www.ncbi.nlm.nih.gov:80/entrez/query.fcgi?cmd=Retrieve&db=Nucleotide
&list_uids=11071915&dopt=GenBank>AJ293416</a>  398  ........................
422
<a name = 11071913></a><a
href=http://www.ncbi.nlm.nih.gov:80/entrez/query.fcgi?cmd=Retrieve&db=Nucleotide
&list_uids=11071913&dopt=GenBank>AJ293415</a>  398  ........................
422
<a name = 11071911></a><a
href=http://www.ncbi.nlm.nih.gov:80/entrez/query.fcgi?cmd=Retrieve&db=Nucleotide
&list_uids=11071911&dopt=GenBank>AJ293414</a>  398  ........................
422
<a name = 11071907></a><a
href=http://www.ncbi.nlm.nih.gov:80/entrez/query.fcgi?cmd=Retrieve&db=Nucleotide
&list_uids=11071907&dopt=GenBank>AJ293412</a>  398  ........................
422
<a name = 11071724></a><a
href=http://www.ncbi.nlm.nih.gov:80/entrez/query.fcgi?cmd=Retrieve&db=Nucleotide
&list_uids=11071724&dopt=GenBank>AJ293418</a>  398  ........................
422
<a name = 2677641></a><a
href=http://www.ncbi.nlm.nih.gov:80/entrez/query.fcgi?cmd=Retrieve&db=Nucleotide
&list_uids=02677641&dopt=GenBank>U07578</a>    398  ........................
422
<a name = 9998754></a><a
href=http://www.ncbi.nlm.nih.gov:80/entrez/query.fcgi?cmd=Retrieve&db=Nucleotide
```

```
&list_uids=09998754&dopt=GenBank>AJ004180</a>   302  .........................
326
<a name = 9968729></a><a
href=http://www.ncbi.nlm.nih.gov:80/entrez/query.fcgi?cmd=Retrieve&db=Nucleotide
&list_uids=09968729&dopt=GenBank>Y15695</a>    432  .........................
456
<a name = 9967851></a><a
href=http://www.ncbi.nlm.nih.gov:80/entrez/query.fcgi?cmd=Retrieve&db=Nucleotide
&list_uids=09967851&dopt=GenBank>Y15697</a>    432  .........................
456
<a name = 9967849></a><a
href=http://www.ncbi.nlm.nih.gov:80/entrez/query.fcgi?cmd=Retrieve&db=Nucleotide
&list_uids=09967849&dopt=GenBank>Y15696</a>    432  .........................
456
<a name = 2394147></a><a
href=http://www.ncbi.nlm.nih.gov:80/entrez/query.fcgi?cmd=Retrieve&db=Nucleotide
&list_uids=02394147&dopt=GenBank>AF015035</a>   448  .........................
472
<a name = 2367574></a><a
href=http://www.ncbi.nlm.nih.gov:80/entrez/query.fcgi?cmd=Retrieve&db=Nucleotide
&list_uids=02367574&dopt=GenBank>AF015761</a>   303  .........................
327
<a name = 2367568></a><a
href=http://www.ncbi.nlm.nih.gov:80/entrez/query.fcgi?cmd=Retrieve&db=Nucleotide
&list_uids=02367568&dopt=GenBank>AF015758</a>   303  .........................
327
<a name = 2367564></a><a
href=http://www.ncbi.nlm.nih.gov:80/entrez/query.fcgi?cmd=Retrieve&db=Nucleotide
&list_uids=02367564&dopt=GenBank>AF015756</a>   303  .........................
327
<a name = 2367560></a><a
href=http://www.ncbi.nlm.nih.gov:80/entrez/query.fcgi?cmd=Retrieve&db=Nucleotide
&list_uids=02367560&dopt=GenBank>AF015754</a>   303  .........................
327
<a name = 2198698></a><a
href=http://www.ncbi.nlm.nih.gov:80/entrez/query.fcgi?cmd=Retrieve&db=Nucleotide
&list_uids=02198698&dopt=GenBank>U76052</a>    401  .........................
425
<a name = 8052194></a><a
href=http://www.ncbi.nlm.nih.gov:80/entrez/query.fcgi?cmd=Retrieve&db=Nucleotide
&list_uids=08052194&dopt=GenBank>AJ236834</a>   398  .........................
422
<a name = 2149204></a><a
href=http://www.ncbi.nlm.nih.gov:80/entrez/query.fcgi?cmd=Retrieve&db=Nucleotide
&list_uids=02149204&dopt=GenBank>U83158</a>    302  .........................
326
<a name = 2149202></a><a
href=http://www.ncbi.nlm.nih.gov:80/entrez/query.fcgi?cmd=Retrieve&db=Nucleotide
&list_uids=02149202&dopt=GenBank>U83157</a>    304  .........................
328
<a name = 2149182></a><a
href=http://www.ncbi.nlm.nih.gov:80/entrez/query.fcgi?cmd=Retrieve&db=Nucleotide
&list_uids=02149182&dopt=GenBank>U83156</a>    302  .........................
326
<a name = 2149180></a><a
href=http://www.ncbi.nlm.nih.gov:80/entrez/query.fcgi?cmd=Retrieve&db=Nucleotide
```

```
&list_uids=02149180&dopt=GenBank>U83155</a>    303    ..........................
327
<a name = 2149178></a><a
href=http://www.ncbi.nlm.nih.gov:80/entrez/query.fcgi?cmd=Retrieve&db=Nucleotide
&list_uids=02149178&dopt=GenBank>U83154</a>    300    ..........................
324
<a name = 2098654></a><a
href=http://www.ncbi.nlm.nih.gov:80/entrez/query.fcgi?cmd=Retrieve&db=Nucleotide
&list_uids=02098654&dopt=GenBank>U81356</a>    320    ..........................
344
<a name = 7671584></a><a
href=http://www.ncbi.nlm.nih.gov:80/entrez/query.fcgi?cmd=Retrieve&db=Nucleotide
&list_uids=07671584&dopt=GenBank>AJ277676</a>  299    ..........................
323
<a name = 7671582></a><a
href=http://www.ncbi.nlm.nih.gov:80/entrez/query.fcgi?cmd=Retrieve&db=Nucleotide
&list_uids=07671582&dopt=GenBank>AJ277675</a>  299    ..........................
323
<a name = 7671550></a><a
href=http://www.ncbi.nlm.nih.gov:80/entrez/query.fcgi?cmd=Retrieve&db=Nucleotide
&list_uids=07671550&dopt=GenBank>AJ277672</a>  299    ..........................
323
<a name = 7671548></a><a
href=http://www.ncbi.nlm.nih.gov:80/entrez/query.fcgi?cmd=Retrieve&db=Nucleotide
&list_uids=07671548&dopt=GenBank>AJ277671</a>  299    ..........................
323
<a name = 2252500></a><a
href=http://www.ncbi.nlm.nih.gov:80/entrez/query.fcgi?cmd=Retrieve&db=Nucleotide
&list_uids=02252500&dopt=GenBank>Y11832</a>    14568  ..........................
14592
<a name = 6522826></a><a
href=http://www.ncbi.nlm.nih.gov:80/entrez/query.fcgi?cmd=Retrieve&db=Nucleotide
&list_uids=06522826&dopt=GenBank>AJ388467</a>  305    ..........................
329
<a name = 6522795></a><a
href=http://www.ncbi.nlm.nih.gov:80/entrez/query.fcgi?cmd=Retrieve&db=Nucleotide
&list_uids=06522795&dopt=GenBank>AJ388468</a>  305    ..........................
329
<a name = 6522793></a><a
href=http://www.ncbi.nlm.nih.gov:80/entrez/query.fcgi?cmd=Retrieve&db=Nucleotide
&list_uids=06522793&dopt=GenBank>AJ388459</a>  305    ..........................
329
<a name = 1184332></a><a
href=http://www.ncbi.nlm.nih.gov:80/entrez/query.fcgi?cmd=Retrieve&db=Nucleotide
&list_uids=01184332&dopt=GenBank>U46167</a>    398    ..........................
422
<a name = 5731956></a><a
href=http://www.ncbi.nlm.nih.gov:80/entrez/query.fcgi?cmd=Retrieve&db=Nucleotide
&list_uids=05731956&dopt=GenBank>AJ245673</a>  400    ..........................
424
<a name = 5731954></a><a
href=http://www.ncbi.nlm.nih.gov:80/entrez/query.fcgi?cmd=Retrieve&db=Nucleotide
&list_uids=05731954&dopt=GenBank>AJ245638</a>  400    ..........................
424
<a name = 5731784></a><a
href=http://www.ncbi.nlm.nih.gov:80/entrez/query.fcgi?cmd=Retrieve&db=Nucleotide
```

```
&list_uids=05731784&dopt=GenBank>AJ245678</a>  400  ........................
424
<a name = 5731782></a><a
href=http://www.ncbi.nlm.nih.gov:80/entrez/query.fcgi?cmd=Retrieve&db=Nucleotide
&list_uids=05731782&dopt=GenBank>AJ245677</a>  400  ........................
424
<a name = 5731780></a><a
href=http://www.ncbi.nlm.nih.gov:80/entrez/query.fcgi?cmd=Retrieve&db=Nucleotide
&list_uids=05731780&dopt=GenBank>AJ245676</a>  400  ........................
424
<a name = 5731778></a><a
href=http://www.ncbi.nlm.nih.gov:80/entrez/query.fcgi?cmd=Retrieve&db=Nucleotide
&list_uids=05731778&dopt=GenBank>AJ245675</a>  400  ........................
424
<a name = 5731776></a><a
href=http://www.ncbi.nlm.nih.gov:80/entrez/query.fcgi?cmd=Retrieve&db=Nucleotide
&list_uids=05731776&dopt=GenBank>AJ245674</a>  400  ........................
424
<a name = 5541879></a><a
href=http://www.ncbi.nlm.nih.gov:80/entrez/query.fcgi?cmd=Retrieve&db=Nucleotide
&list_uids=05541879&dopt=GenBank>Y16884</a>   14038  ........................
14062
<a name = 1674455></a><a
href=http://www.ncbi.nlm.nih.gov:80/entrez/query.fcgi?cmd=Retrieve&db=Nucleotide
&list_uids=01674455&dopt=GenBank>U60768</a>   243  ........................
267
<a name = 1657738></a><a
href=http://www.ncbi.nlm.nih.gov:80/entrez/query.fcgi?cmd=Retrieve&db=Nucleotide
&list_uids=01657738&dopt=GenBank>U48955</a>   401  ........................
425
<a name = 1657736></a><a
href=http://www.ncbi.nlm.nih.gov:80/entrez/query.fcgi?cmd=Retrieve&db=Nucleotide
&list_uids=01657736&dopt=GenBank>U48954</a>   401  ........................
425
<a name = 1657732></a><a
href=http://www.ncbi.nlm.nih.gov:80/entrez/query.fcgi?cmd=Retrieve&db=Nucleotide
&list_uids=01657732&dopt=GenBank>U48944</a>   401  ........................
425
<a name = 1657728></a><a
href=http://www.ncbi.nlm.nih.gov:80/entrez/query.fcgi?cmd=Retrieve&db=Nucleotide
&list_uids=01657728&dopt=GenBank>U48943</a>   401  ........................
425
<a name = 1657720></a><a
href=http://www.ncbi.nlm.nih.gov:80/entrez/query.fcgi?cmd=Retrieve&db=Nucleotide
&list_uids=01657720&dopt=GenBank>U48942</a>   401  ........................
425
<a name = 1657714></a><a
href=http://www.ncbi.nlm.nih.gov:80/entrez/query.fcgi?cmd=Retrieve&db=Nucleotide
&list_uids=01657714&dopt=GenBank>U48941</a>   401  ........................
425
<a name = 1657712></a><a
href=http://www.ncbi.nlm.nih.gov:80/entrez/query.fcgi?cmd=Retrieve&db=Nucleotide
&list_uids=01657712&dopt=GenBank>U48947</a>   401  ........................
425
<a name = 1657710></a><a
href=http://www.ncbi.nlm.nih.gov:80/entrez/query.fcgi?cmd=Retrieve&db=Nucleotide
```

```
&list_uids=01657710&dopt=GenBank>U48946</a>    401  ........................
425
<a name = 1657708></a><a
href=http://www.ncbi.nlm.nih.gov:80/entrez/query.fcgi?cmd=Retrieve&db=Nucleotide
&list_uids=01657708&dopt=GenBank>U48948</a>    401  ........................
425
<a name = 1256221></a><a
href=http://www.ncbi.nlm.nih.gov:80/entrez/query.fcgi?cmd=Retrieve&db=Nucleotide
&list_uids=01256221&dopt=GenBank>U15725</a>    303  ........................
327
<a name = 1513285></a><a
href=http://www.ncbi.nlm.nih.gov:80/entrez/query.fcgi?cmd=Retrieve&db=Nucleotide
&list_uids=01513285&dopt=GenBank>U66508</a>    398  ........................
422
<a name = 1513283></a><a
href=http://www.ncbi.nlm.nih.gov:80/entrez/query.fcgi?cmd=Retrieve&db=Nucleotide
&list_uids=01513283&dopt=GenBank>U66507</a>    398  ........................
422
<a name = 1513281></a><a
href=http://www.ncbi.nlm.nih.gov:80/entrez/query.fcgi?cmd=Retrieve&db=Nucleotide
&list_uids=01513281&dopt=GenBank>U66506</a>    398  ........................
422
<a name = 1513279></a><a
href=http://www.ncbi.nlm.nih.gov:80/entrez/query.fcgi?cmd=Retrieve&db=Nucleotide
&list_uids=01513279&dopt=GenBank>U66505</a>    398  ........................
422
<a name = 1513277></a><a
href=http://www.ncbi.nlm.nih.gov:80/entrez/query.fcgi?cmd=Retrieve&db=Nucleotide
&list_uids=01513277&dopt=GenBank>U66504</a>    398  ........................
422
<a name = 1513275></a><a
href=http://www.ncbi.nlm.nih.gov:80/entrez/query.fcgi?cmd=Retrieve&db=Nucleotide
&list_uids=01513275&dopt=GenBank>U66503</a>    398  ........................
422
<a name = 1513273></a><a
href=http://www.ncbi.nlm.nih.gov:80/entrez/query.fcgi?cmd=Retrieve&db=Nucleotide
&list_uids=01513273&dopt=GenBank>U66502</a>    398  ........................
422
<a name = 1513271></a><a
href=http://www.ncbi.nlm.nih.gov:80/entrez/query.fcgi?cmd=Retrieve&db=Nucleotide
&list_uids=01513271&dopt=GenBank>U66501</a>    398  ........................
422
<a name = 1513267></a><a
href=http://www.ncbi.nlm.nih.gov:80/entrez/query.fcgi?cmd=Retrieve&db=Nucleotide
&list_uids=01513267&dopt=GenBank>U66500</a>    398  ........................
422
<a name = 1513259></a><a
href=http://www.ncbi.nlm.nih.gov:80/entrez/query.fcgi?cmd=Retrieve&db=Nucleotide
&list_uids=01513259&dopt=GenBank>U66499</a>    398  ........................
422
<a name = 1513257></a><a
href=http://www.ncbi.nlm.nih.gov:80/entrez/query.fcgi?cmd=Retrieve&db=Nucleotide
&list_uids=01513257&dopt=GenBank>U66498</a>    398  ........................
422
<a name = 1458165></a><a
href=http://www.ncbi.nlm.nih.gov:80/entrez/query.fcgi?cmd=Retrieve&db=Nucleotide
```

```
&list_uids=01458165&dopt=GenBank>U63061</a>    302    ........................
326
<a name = 1458163></a><a
href=http://www.ncbi.nlm.nih.gov:80/entrez/query.fcgi?cmd=Retrieve&db=Nucleotide
&list_uids=01458163&dopt=GenBank>U63060</a>    302    ........................
326
<a name = 1458161></a><a
href=http://www.ncbi.nlm.nih.gov:80/entrez/query.fcgi?cmd=Retrieve&db=Nucleotide
&list_uids=01458161&dopt=GenBank>U63059</a>    302    ........................
326
<a name = 1458159></a><a
href=http://www.ncbi.nlm.nih.gov:80/entrez/query.fcgi?cmd=Retrieve&db=Nucleotide
&list_uids=01458159&dopt=GenBank>U63058</a>    302    ........................
326
<a name = 1381629></a><a
href=http://www.ncbi.nlm.nih.gov:80/entrez/query.fcgi?cmd=Retrieve&db=Nucleotide
&list_uids=01381629&dopt=GenBank>U58386</a>    398    ........................
422
<a name = 336482></a><a
href=http://www.ncbi.nlm.nih.gov:80/entrez/query.fcgi?cmd=Retrieve&db=Nucleotide
&list_uids=00336482&dopt=GenBank>L11905</a>    398    ........................
422
<a name = 1041855></a><a
href=http://www.ncbi.nlm.nih.gov:80/entrez/query.fcgi?cmd=Retrieve&db=Nucleotide
&list_uids=01041855&dopt=GenBank>U34672</a>    398    ........................
422
<a name = 1041853></a><a
href=http://www.ncbi.nlm.nih.gov:80/entrez/query.fcgi?cmd=Retrieve&db=Nucleotide
&list_uids=01041853&dopt=GenBank>U34671</a>    398    ........................
422
<a name = 2440142></a><a
href=http://www.ncbi.nlm.nih.gov:80/entrez/query.fcgi?cmd=Retrieve&db=Nucleotide
&list_uids=02440142&dopt=GenBank>Y14951</a>    398    ........................
422
<a name = 2315216></a><a
href=http://www.ncbi.nlm.nih.gov:80/entrez/query.fcgi?cmd=Retrieve&db=Nucleotide
&list_uids=02315216&dopt=GenBank>Y14371</a>    398    ........................
422
<a name = 336490></a><a
href=http://www.ncbi.nlm.nih.gov:80/entrez/query.fcgi?cmd=Retrieve&db=Nucleotide
&list_uids=00336490&dopt=GenBank>L11909</a>    398    ........................
422
<a name = 343117></a><a
href=http://www.ncbi.nlm.nih.gov:80/entrez/query.fcgi?cmd=Retrieve&db=Nucleotide
&list_uids=00343117&dopt=GenBank>L11901</a>    398    ........................
422
<a name = 336480></a><a
href=http://www.ncbi.nlm.nih.gov:80/entrez/query.fcgi?cmd=Retrieve&db=Nucleotide
&list_uids=00336480&dopt=GenBank>L11904</a>    398    ........................
422
<a name = 1289306></a><a
href=http://www.ncbi.nlm.nih.gov:80/entrez/query.fcgi?cmd=Retrieve&db=Nucleotide
&list_uids=01289306&dopt=GenBank>X94928</a>    398    ........................
422
<a name = 1197608></a><a
href=http://www.ncbi.nlm.nih.gov:80/entrez/query.fcgi?cmd=Retrieve&db=Nucleotide
```

```
&list_uids=01197608&dopt=GenBank>U46770</a>    302   .........................
326
<a name = 1197598></a><a
href=http://www.ncbi.nlm.nih.gov:80/entrez/query.fcgi?cmd=Retrieve&db=Nucleotide
&list_uids=01197598&dopt=GenBank>U46769</a>    302   .........................
326
<a name = 1184364></a><a
href=http://www.ncbi.nlm.nih.gov:80/entrez/query.fcgi?cmd=Retrieve&db=Nucleotide
&list_uids=01184364&dopt=GenBank>U46183</a>    398   .........................
422
<a name = 2407991></a><a
href=http://www.ncbi.nlm.nih.gov:80/entrez/query.fcgi?cmd=Retrieve&db=Nucleotide
&list_uids=02407991&dopt=GenBank>Y10728</a>    299   .........................
323
<a name = 1204134></a><a
href=http://www.ncbi.nlm.nih.gov:80/entrez/query.fcgi?cmd=Retrieve&db=Nucleotide
&list_uids=01204134&dopt=GenBank>X95768</a>    303   .........................
327
<a name = 1261958></a><a
href=http://www.ncbi.nlm.nih.gov:80/entrez/query.fcgi?cmd=Retrieve&db=Nucleotide
&list_uids=01261958&dopt=GenBank>X95767</a>    303   .........................
327
<a name = 1050714></a><a
href=http://www.ncbi.nlm.nih.gov:80/entrez/query.fcgi?cmd=Retrieve&db=Nucleotide
&list_uids=01050714&dopt=GenBank>X86763</a>    299   .........................
323
<a name = 1050648></a><a
href=http://www.ncbi.nlm.nih.gov:80/entrez/query.fcgi?cmd=Retrieve&db=Nucleotide
&list_uids=01050648&dopt=GenBank>X86754</a>    299   .........................
323
<a name = 1050586></a><a
href=http://www.ncbi.nlm.nih.gov:80/entrez/query.fcgi?cmd=Retrieve&db=Nucleotide
&list_uids=01050586&dopt=GenBank>X86743</a>    299   .........................
323
<a name = 11862859></a><a
href=http://www.ncbi.nlm.nih.gov:80/entrez/query.fcgi?cmd=Retrieve&db=Nucleotide
&list_uids=11862859&dopt=GenBank>AB035242</a>  398   .........................
422
<a name = 13749></a><a
href=http://www.ncbi.nlm.nih.gov:80/entrez/query.fcgi?cmd=Retrieve&db=Nucleotide
&list_uids=00013749&dopt=GenBank>X60946</a>    302   .........................
326
<a name = 2959918></a><a
href=http://www.ncbi.nlm.nih.gov:80/entrez/query.fcgi?cmd=Retrieve&db=Nucleotide
&list_uids=02959918&dopt=GenBank>AJ000029</a>  398   .........................
422
<a name = 693969></a><a
href=http://www.ncbi.nlm.nih.gov:80/entrez/query.fcgi?cmd=Retrieve&db=Nucleotide
&list_uids=00693969&dopt=GenBank>X82302</a>    398   .........................
422
<a name = 13198></a><a
href=http://www.ncbi.nlm.nih.gov:80/entrez/query.fcgi?cmd=Retrieve&db=Nucleotide
&list_uids=00013198&dopt=GenBank>X56291</a>    398   .........................
422
<a name = 13156></a><a
href=http://www.ncbi.nlm.nih.gov:80/entrez/query.fcgi?cmd=Retrieve&db=Nucleotide
```

```
<a name = 00013156></a><a
href=http://www.ncbi.nlm.nih.gov:80/entrez/query.fcgi?cmd=Retrieve&db=Nucleotide
&list_uids=00013156&dopt=GenBank>X56284</a>    398  ........................
422
<a name = 2959904></a><a
href=http://www.ncbi.nlm.nih.gov:80/entrez/query.fcgi?cmd=Retrieve&db=Nucleotide
&list_uids=02959904&dopt=GenBank>AJ000022</a>   398  ........................
422
<a name = 414771></a><a
href=http://www.ncbi.nlm.nih.gov:80/entrez/query.fcgi?cmd=Retrieve&db=Nucleotide
&list_uids=00414771&dopt=GenBank>X72005</a>     398  ........................
422
<a name = 2154895></a><a
href=http://www.ncbi.nlm.nih.gov:80/entrez/query.fcgi?cmd=Retrieve&db=Nucleotide
&list_uids=02154895&dopt=GenBank>Y08814</a>     398  ........................
422
<a name = 12981></a><a
href=http://www.ncbi.nlm.nih.gov:80/entrez/query.fcgi?cmd=Retrieve&db=Nucleotide
&list_uids=00012981&dopt=GenBank>X60942</a>     302  ........................
326
<a name = 12907></a><a
href=http://www.ncbi.nlm.nih.gov:80/entrez/query.fcgi?cmd=Retrieve&db=Nucleotide
&list_uids=00012907&dopt=GenBank>X56290</a>     398  ........................
422
<a name = 2959902></a><a
href=http://www.ncbi.nlm.nih.gov:80/entrez/query.fcgi?cmd=Retrieve&db=Nucleotide
&list_uids=02959902&dopt=GenBank>AJ000021</a>   398  ........................
422
<a name = 2959908></a><a
href=http://www.ncbi.nlm.nih.gov:80/entrez/query.fcgi?cmd=Retrieve&db=Nucleotide
&list_uids=02959908&dopt=GenBank>AJ000024</a>   398  ........................
422
<a name = 12800></a><a
href=http://www.ncbi.nlm.nih.gov:80/entrez/query.fcgi?cmd=Retrieve&db=Nucleotide
&list_uids=00012800&dopt=GenBank>V00654</a>     14911 ........................
14935
<a name = 12624></a><a
href=http://www.ncbi.nlm.nih.gov:80/entrez/query.fcgi?cmd=Retrieve&db=Nucleotide
&list_uids=00012624&dopt=GenBank>X56286</a>     398  ........................
422
<a name = 304034></a><a
href=http://www.ncbi.nlm.nih.gov:80/entrez/query.fcgi?cmd=Retrieve&db=Nucleotide
&list_uids=00304034&dopt=GenBank>L19718</a>     398  ........................
422
<a name = 896408></a><a
href=http://www.ncbi.nlm.nih.gov:80/entrez/query.fcgi?cmd=Retrieve&db=Nucleotide
&list_uids=00896408&dopt=GenBank>U27543</a>     401  ........................
425
<a name = 9845006></a><a
href=http://www.ncbi.nlm.nih.gov:80/entrez/query.fcgi?cmd=Retrieve&db=Nucleotide
&list_uids=09845006&dopt=GenBank>AB030025</a>   343  ........................
367
<a name = 624183></a><a
href=http://www.ncbi.nlm.nih.gov:80/entrez/query.fcgi?cmd=Retrieve&db=Nucleotide
&list_uids=00624183&dopt=GenBank>U18258</a>     169  ........................
193
<a name = 624181></a><a
href=http://www.ncbi.nlm.nih.gov:80/entrez/query.fcgi?cmd=Retrieve&db=Nucleotide
```

```
<p><!--
QBlastInfoBegin
        Status=READY
QBlastInfoEnd
--><p>
<TITLE>Results for RID 984593033-24247-14777 </TITLE>
<HTML>
<HEAD>
<TITLE>BLAST Search Results </TITLE>
</HEAD>
<BODY BGCOLOR="#FFFFFF" LINK="#0000FF" VLINK="#660099" ALINK="#660099">
<A HREF="http://www.ncbi.nlm.nih.gov/BLAST/blast_form.map"> <IMG
SRC="http://www.ncbi.nlm.nih.gov/BLAST/blast_results.gif" BORDER=0 ISMAP></A>
<BR><BR><PRE>
<b>BLASTN 2.1.2 [Nov-13-2000]</b>

<b><a href="http://www.ncbi.nlm.nih.gov/htbin-
post/Entrez/query?uid=9254694&form=6&db=m&Dopt=r">Reference</a>:</b>
Altschul, Stephen F., Thomas L. Madden, Alejandro A. Schäffer,
Jinghui Zhang, Zheng Zhang, Webb Miller, and David J. Lipman (1997),
"Gapped BLAST and PSI-BLAST: a new generation of protein database search
programs",  Nucleic Acids Res. 25:3389-3402.
<p>
RID: 984593033-24247-14777
<p>
<b>Query=</b>
         (26 letters)

<p>
<b>Database:</b> nt
           807,597 sequences; 2,863,827,885 total letters <p> <p>If you have any problems or questions with the results of this search
<br>please refer to the <b><a
href=http://www.ncbi.nlm.nih.gov/blast/blast_FAQs.html>BLAST FAQs</a></b><br><p>
<FORM NAME="BLASTFORM" METHOD="POST">
<a href="blast.cgi?RID=984593033-24247-14777&ALIGNMENT_VIEW=17" TARGET="Taxonomy
BLAST Results for 984593033-24247-14777">Taxonomy reports</a>
<BR>
</PRE>
<CENTER>
<H3><a href="/BLAST/newoptions.html#graphical-overview"> Distribution of 500
Blast Hits on the Query Sequence</a></H3>
<input name=defline size=80 value="Mouse-over to show defline and scores. Click
to show alignments">
</CENTER>
<map name=img_map>
<area shape=rect coords=62,101,510,106 href="#4127784"
ONMOUSEOVER='document.BLASTFORM.defline.value="AJ225116   Dryomys nitedula
mitochondrial gene for cytochrome b..S=52.0 E=6e-06"'
ONMOUSEOUT='document.BLASTFORM.defline.value="Mouse-over to show defline and
scores. Click to show alignments"' >
<area shape=rect coords=62,108,510,113 href="#2677639"
ONMOUSEOVER='document.BLASTFORM.defline.value="U07577   Antechinus melanurus
mitochondrion cytochrome b gene, co..S=52.0 E=6e-06"'
```

```
ONMOUSEOUT='document.BLASTFORM.defline.value="Mouse-over to show defline and
scores. Click to show alignments"' >
<area shape=rect coords=62,115,510,120 href="#5359509"
ONMOUSEOVER='document.BLASTFORM.defline.value="AF091629  Antilocapra americana
cytochrome b (cytb) gene, comple..S=52.0 E=6e-06"'
ONMOUSEOUT='document.BLASTFORM.defline.value="Mouse-over to show defline and
scores. Click to show alignments"' >
<area shape=rect coords=62,122,510,127 href="#10441542"
ONMOUSEOVER='document.BLASTFORM.defline.value="AF189111  Cryptotermes austrinus
cytochrome b (Cytb) gene, parti..S=52.0 E=6e-06"'
ONMOUSEOUT='document.BLASTFORM.defline.value="Mouse-over to show defline and
scores. Click to show alignments"' >
<area shape=rect coords=62,129,510,134 href="#3098363"
ONMOUSEOVER='document.BLASTFORM.defline.value="AF038290  Antechinus sp.
cytochrome b gene, mitochondrial gene e..S=52.0 E=6e-06"'
ONMOUSEOUT='document.BLASTFORM.defline.value="Mouse-over to show defline and
scores. Click to show alignments"' >
<area shape=rect coords=62,136,510,141 href="#2098650"
ONMOUSEOVER='document.BLASTFORM.defline.value="U81343  Chelus fimbriata
cytochrome b gene, mitochondrial gene e..S=52.0 E=6e-06"'
ONMOUSEOUT='document.BLASTFORM.defline.value="Mouse-over to show defline and
scores. Click to show alignments"' >
<area shape=rect coords=62,143,510,148 href="#12624"
ONMOUSEOVER='document.BLASTFORM.defline.value="X56286  A.americana mitochondrion
cytb gene for cytochrome b..S=52.0 E=6e-06"'
ONMOUSEOUT='document.BLASTFORM.defline.value="Mouse-over to show defline and
scores. Click to show alignments"' >
<area shape=rect coords=62,150,510,155 href="#840940"
ONMOUSEOVER='document.BLASTFORM.defline.value="U15204  Paradisaea raggiana
mitochondrion cytochrome b gene, com..S=52.0 E=6e-06"'
ONMOUSEOUT='document.BLASTFORM.defline.value="Mouse-over to show defline and
scores. Click to show alignments"' >
<area shape=rect coords=62,157,510,162 href="#2660917"
ONMOUSEOVER='document.BLASTFORM.defline.value="AF034967  Sigmoceros
lichtensteinii cytochrome b gene, mitochond..S=52.0 E=6e-06"'
ONMOUSEOUT='document.BLASTFORM.defline.value="Mouse-over to show defline and
scores. Click to show alignments"' >
<area shape=rect coords=62,164,510,169 href="#5713297"
ONMOUSEOVER='document.BLASTFORM.defline.value="AF009931  Archocentrus
centrarchus cytochrome b (cytb) gene, mit..S=52.0 E=6e-06"'
ONMOUSEOUT='document.BLASTFORM.defline.value="Mouse-over to show defline and
scores. Click to show alignments"' >
<area shape=rect coords=62,171,510,176 href="#1778694"
ONMOUSEOVER='document.BLASTFORM.defline.value="M99464  Planigale sp. cytochrome
b gene, complete cds..S=52.0 E=6e-06"'
ONMOUSEOUT='document.BLASTFORM.defline.value="Mouse-over to show defline and
scores. Click to show alignments"' >
<area shape=rect coords=62,178,510,183 href="#3483067"
ONMOUSEOVER='document.BLASTFORM.defline.value="AJ222681  Alcelaphus buselaphus
mitochondrial cytochrome b gene,..S=52.0 E=6e-06"'
ONMOUSEOUT='document.BLASTFORM.defline.value="Mouse-over to show defline and
scores. Click to show alignments"' >
<area shape=rect coords=62,185,510,190 href="#1707347"
ONMOUSEOVER='document.BLASTFORM.defline.value="D88639  Anoa depressicornis
mitochondrial DNA for cytochrome b, ..S=52.0 E=6e-06"'
ONMOUSEOUT='document.BLASTFORM.defline.value="Mouse-over to show defline and
scores. Click to show alignments"' >
```

```
<area shape=rect coords=62,192,510,197 href="#7141202"
ONMOUSEOVER='document.BLASTFORM.defline.value="AF217828  Aspidelaps scutatus
cytochrome b gene, complete cds; m..S=52.0 E=6e-06"'
ONMOUSEOUT='document.BLASTFORM.defline.value="Mouse-over to show defline and
scores. Click to show alignments"' >
<area shape=rect coords=62,199,510,204 href="#8050348"
ONMOUSEOVER='document.BLASTFORM.defline.value="AF123617  Pipreola arcuata
cytochrome b gene, partial cds; mitoc..S=52.0 E=6e-06"'
ONMOUSEOUT='document.BLASTFORM.defline.value="Mouse-over to show defline and
scores. Click to show alignments"' >
<area shape=rect coords=62,206,510,211 href="#1813358"
ONMOUSEOVER='document.BLASTFORM.defline.value="D82890  Bubalus depressicornis
mitochondrial DNA for cytochrome ..S=52.0 E=6e-06"'
ONMOUSEOUT='document.BLASTFORM.defline.value="Mouse-over to show defline and
scores. Click to show alignments"' >
<area shape=rect coords=62,213,510,218 href="#4218914"
ONMOUSEOVER='document.BLASTFORM.defline.value="U86834  Phyllotis wolffsohni MSB
67270 cytochrome b (cytb) gene,..S=52.0 E=6e-06"'
ONMOUSEOUT='document.BLASTFORM.defline.value="Mouse-over to show defline and
scores. Click to show alignments"' >
<area shape=rect coords=62,220,510,225 href="#12907"
ONMOUSEOVER='document.BLASTFORM.defline.value="X56290  D.dama mitochondrion cytb
gene for cytochrome b..S=52.0 E=6e-06"'
ONMOUSEOUT='document.BLASTFORM.defline.value="Mouse-over to show defline and
scores. Click to show alignments"' >
<area shape=rect coords=62,227,510,232 href="#7715727"
ONMOUSEOVER='document.BLASTFORM.defline.value="AF127202  Hylopezus fulviventris
cytochrome b gene, partial cds;..S=52.0 E=6e-06"'
ONMOUSEOUT='document.BLASTFORM.defline.value="Mouse-over to show defline and
scores. Click to show alignments"' >
<area shape=rect coords=62,234,510,239 href="#840936"
ONMOUSEOVER='document.BLASTFORM.defline.value="U15202  Seleucidis melanoleuca
mitochondrion cytochrome b gene, ..S=52.0 E=6e-06"'
ONMOUSEOUT='document.BLASTFORM.defline.value="Mouse-over to show defline and
scores. Click to show alignments"' >
<area shape=rect coords=62,241,510,246 href="#841451"
ONMOUSEOVER='document.BLASTFORM.defline.value="U25736  Paradisaea rubra
cytochrome b gene, mitochondrial gene e..S=52.0 E=6e-06"'
ONMOUSEOUT='document.BLASTFORM.defline.value="Mouse-over to show defline and
scores. Click to show alignments"' >
<area shape=rect coords=62,248,510,253 href="#841455"
ONMOUSEOVER='document.BLASTFORM.defline.value="U25738  Paradisaea raggiana
cytochrome b gene, mitochondrial gen..S=52.0 E=6e-06"'
ONMOUSEOUT='document.BLASTFORM.defline.value="Mouse-over to show defline and
scores. Click to show alignments"' >
<area shape=rect coords=62,255,510,260 href="#8050379"
ONMOUSEOVER='document.BLASTFORM.defline.value="AF123633  Perissocephalus
tricolor cytochrome b gene, partial cd..S=52.0 E=6e-06"'
ONMOUSEOUT='document.BLASTFORM.defline.value="Mouse-over to show defline and
scores. Click to show alignments"' >
<area shape=rect coords=62,262,510,267 href="#6524754"
ONMOUSEOVER='document.BLASTFORM.defline.value="AF160578  Hypogeomys antimena
Hant555 cytochrome b (cytb) gene, ..S=52.0 E=6e-06"'
ONMOUSEOUT='document.BLASTFORM.defline.value="Mouse-over to show defline and
scores. Click to show alignments"' >
<area shape=rect coords=62,269,510,274 href="#7715712"
ONMOUSEOVER='document.BLASTFORM.defline.value="AF127194  Grallaria guatimalensis
```

```
cytochrome b gene, partial cds..S=52.0 E=6e-06"'
ONMOUSEOUT='document.BLASTFORM.defline.value="Mouse-over to show defline and
scores. Click to show alignments"' >
<area shape=rect coords=62,276,456,281 href="#1488224"
ONMOUSEOVER='document.BLASTFORM.defline.value="U62685   Charadrius bicinctus
cytochrome b (cyt b) gene, mitochon..S=46.1 E=3e-04"'
ONMOUSEOUT='document.BLASTFORM.defline.value="Mouse-over to show defline and
scores. Click to show alignments"' >
<area shape=rect coords=62,283,456,288 href="#2052291"
ONMOUSEOVER='document.BLASTFORM.defline.value="U62687   Charadrius collaris
cytochrome b (cytb) gene, 3- region,..S=46.1 E=3e-04"'
ONMOUSEOUT='document.BLASTFORM.defline.value="Mouse-over to show defline and
scores. Click to show alignments"' >
<area shape=rect coords=62,290,456,295 href="#5478447"
ONMOUSEOVER='document.BLASTFORM.defline.value="AF119261   Peromyscus maniculatus
cytochrome b gene, partial cds;..S=46.1 E=3e-04"'
ONMOUSEOUT='document.BLASTFORM.defline.value="Mouse-over to show defline and
scores. Click to show alignments"' >
<area shape=rect coords=62,297,456,302 href="#8272431"
ONMOUSEOVER='document.BLASTFORM.defline.value="AB036400   Rana porosa brevipoda
mitochondrial DNA, cytochrome b ..S=46.1 E=3e-04"'
ONMOUSEOUT='document.BLASTFORM.defline.value="Mouse-over to show defline and
scores. Click to show alignments"' >
<area shape=rect coords=62,304,456,309 href="#8272434"
ONMOUSEOVER='document.BLASTFORM.defline.value="AB036402   Rana porosa brevipoda
mitochondrial DNA, cytochrome b ..S=46.1 E=3e-04"'
ONMOUSEOUT='document.BLASTFORM.defline.value="Mouse-over to show defline and
scores. Click to show alignments"' >
<area shape=rect coords=62,311,456,316 href="#8272437"
ONMOUSEOVER='document.BLASTFORM.defline.value="AB036404   Rana porosa brevipoda
mitochondrial DNA, cytochrome b ..S=46.1 E=3e-04"'
ONMOUSEOUT='document.BLASTFORM.defline.value="Mouse-over to show defline and
scores. Click to show alignments"' >
<area shape=rect coords=62,318,456,323 href="#1458193"
ONMOUSEOVER='document.BLASTFORM.defline.value="U63057   Brachyramphus marmoratus
perdix cytochrome b gene, mitoc..S=46.1 E=3e-04"'
ONMOUSEOUT='document.BLASTFORM.defline.value="Mouse-over to show defline and
scores. Click to show alignments"' >
<area shape=rect coords=62,325,456,330 href="#1890874"
ONMOUSEOVER='document.BLASTFORM.defline.value="U90001   Morus bassanus cytochrome
b gene, mitochondrial gene enc..S=46.1 E=3e-04"'
ONMOUSEOUT='document.BLASTFORM.defline.value="Mouse-over to show defline and
scores. Click to show alignments"' >
<area shape=rect coords=62,332,456,337 href="#2290368"
ONMOUSEOVER='document.BLASTFORM.defline.value="U88865   Pomacentrus sp.
cytochrome b (cytb) gene, mitochondrial ..S=46.1 E=3e-04"'
ONMOUSEOUT='document.BLASTFORM.defline.value="Mouse-over to show defline and
scores. Click to show alignments"' >
<area shape=rect coords=62,339,456,344 href="#9971120"
ONMOUSEOVER='document.BLASTFORM.defline.value="AJ004232   Sula bassana
mitochondrial cytb gene, partial (isolate..S=46.1 E=3e-04"'
ONMOUSEOUT='document.BLASTFORM.defline.value="Mouse-over to show defline and
scores. Click to show alignments"' >
<area shape=rect coords=62,346,456,351 href="#9998872"
ONMOUSEOVER='document.BLASTFORM.defline.value="AJ004230   Sula bassana
mitochondrial cytb gene, partial (isolate..S=46.1 E=3e-04"'
```

```
ONMOUSEOUT='document.BLASTFORM.defline.value="Mouse-over to show defline and
scores. Click to show alignments"' >
<area shape=rect coords=62,353,456,358 href="#9998874"
ONMOUSEOVER='document.BLASTFORM.defline.value="AJ004231  Sula bassana
mitochondrial cytb gene, partial (isolate..S=46.1 E=3e-04"'
ONMOUSEOUT='document.BLASTFORM.defline.value="Mouse-over to show defline and
scores. Click to show alignments"' >
<area shape=rect coords=62,360,456,365 href="#2642615"
ONMOUSEOVER='document.BLASTFORM.defline.value="AF031908  Geopsittacus
occidentalis cytochrome b (cytb) gene, mi..S=46.1 E=3e-04"'
ONMOUSEOUT='document.BLASTFORM.defline.value="Mouse-over to show defline and
scores. Click to show alignments"' >
<area shape=rect coords=62,367,456,372 href="#2677641"
ONMOUSEOVER='document.BLASTFORM.defline.value="U07578  Dasycercus cristicauda
mitochondrion cytochrome b gene, ..S=46.1 E=3e-04"'
ONMOUSEOUT='document.BLASTFORM.defline.value="Mouse-over to show defline and
scores. Click to show alignments"' >
<area shape=rect coords=62,374,456,379 href="#3211690"
ONMOUSEOVER='document.BLASTFORM.defline.value="U72770  Jabiru mycteria
cytochrome b gene, mitochondrial gene en..S=46.1 E=3e-04"'
ONMOUSEOUT='document.BLASTFORM.defline.value="Mouse-over to show defline and
scores. Click to show alignments"' >
<area shape=rect coords=62,381,456,386 href="#1255739"
ONMOUSEOVER='document.BLASTFORM.defline.value="U37291  Brachyramphus marmoratus
perdix cytochrome b gene, mitoc..S=46.1 E=3e-04"'
ONMOUSEOUT='document.BLASTFORM.defline.value="Mouse-over to show defline and
scores. Click to show alignments"' >
<area shape=rect coords=62,388,456,393 href="#9998870"
ONMOUSEOVER='document.BLASTFORM.defline.value="AJ004229  Sula bassana
mitochondrial cytb gene, partial (isolate..S=46.1 E=3e-04"'
ONMOUSEOUT='document.BLASTFORM.defline.value="Mouse-over to show defline and
scores. Click to show alignments"' >
<area shape=rect coords=62,395,456,400 href="#1255741"
ONMOUSEOVER='document.BLASTFORM.defline.value="U37292  Cepphus carbo cytochrome
b gene, mitochondrial gene enco..S=46.1 E=3e-04"'
ONMOUSEOUT='document.BLASTFORM.defline.value="Mouse-over to show defline and
scores. Click to show alignments"' >
<area shape=rect coords=62,402,456,407 href="#1255743"
ONMOUSEOVER='document.BLASTFORM.defline.value="U37293  Cepphus columba
cytochrome b gene, mitochondrial gene en..S=46.1 E=3e-04"'
ONMOUSEOUT='document.BLASTFORM.defline.value="Mouse-over to show defline and
scores. Click to show alignments"' >
<area shape=rect coords=62,409,456,414 href="#2231533"
ONMOUSEOVER='document.BLASTFORM.defline.value="U83317  Polihierax semitorquatus
cytochrome b (cytb) gene, mitoc..S=46.1 E=3e-04"'
ONMOUSEOUT='document.BLASTFORM.defline.value="Mouse-over to show defline and
scores. Click to show alignments"' >
<area shape=rect coords=115,416,510,421 href="#4103317"
ONMOUSEOVER='document.BLASTFORM.defline.value="AF022071  Madoqua guentheri
cytochrome b (cytb) gene, mitochondr..S=46.1 E=3e-04"'
ONMOUSEOUT='document.BLASTFORM.defline.value="Mouse-over to show defline and
scores. Click to show alignments"' >
<area shape=rect coords=115,423,510,428 href="#6524779"
ONMOUSEOVER='document.BLASTFORM.defline.value="AF160603  Apodemus sylvaticus
Asyl588 cytochrome b (cytb) gene, ..S=46.1 E=3e-04"'
ONMOUSEOUT='document.BLASTFORM.defline.value="Mouse-over to show defline and
scores. Click to show alignments"' >
```

```
<area shape=rect coords=115,430,510,435 href="#8050344"
ONMOUSEOVER='document.BLASTFORM.defline.value="AF123615  Rupicola rupicola
cytochrome b gene, partial cds; mito..S=46.1 E=3e-04"'
ONMOUSEOUT='document.BLASTFORM.defline.value="Mouse-over to show defline and
scores. Click to show alignments"' >
<area shape=rect coords=115,437,510,442 href="#3551896"
ONMOUSEOVER='document.BLASTFORM.defline.value="AF082055  Rupicola rupicola
cytochrome b gene, partial cds; tRNA..S=46.1 E=3e-04"'
ONMOUSEOUT='document.BLASTFORM.defline.value="Mouse-over to show defline and
scores. Click to show alignments"' >
<area shape=rect coords=115,444,510,449 href="#4103315"
ONMOUSEOVER='document.BLASTFORM.defline.value="AF022070  Madoqua kirkii
cytochrome b (cytb) gene, mitochondrial..S=46.1 E=3e-04"'
ONMOUSEOUT='document.BLASTFORM.defline.value="Mouse-over to show defline and
scores. Click to show alignments"' >
</map>
<CENTER>
<IMG WIDTH=532 HEIGHT=451 USEMAP=#img_map BORDER=1 SRC="nph-
getgif.cgi?iblast11&20789170531424.gif" ISMAP></CENTER>
<HR>
<PRE>
<PRE>

Score     E
Sequences producing significant alignments:                           (bits)   Value <a
href="http://www.ncbi.nlm.nih.gov:80/entrez/query.fcgi?cmd=Retrieve&db=Nucleotid
e&list_uids=10441542&dopt=GenBank">gb|AF189111.1|AF189111</a>  Cryptotermes
austrinus cytochrome b ...    <a href = #10441542> 52</a>   6e-06
<a
href="http://www.ncbi.nlm.nih.gov:80/entrez/query.fcgi?cmd=Retrieve&db=Nucleotid
e&list_uids=04218914&dopt=GenBank">gb|U86834.1|U86834</a>  Phyllotis wolffsohni
MSB 67270 cytochrom...    <a href = #4218914> 52</a>   6e-06
<a
href="http://www.ncbi.nlm.nih.gov:80/entrez/query.fcgi?cmd=Retrieve&db=Nucleotid
e&list_uids=08050379&dopt=GenBank">gb|AF123633.1|AF123633</a>  Perissocephalus
tricolor cytochrome ...    <a href = #8050379> 52</a>   6e-06
<a
href="http://www.ncbi.nlm.nih.gov:80/entrez/query.fcgi?cmd=Retrieve&db=Nucleotid
e&list_uids=08050348&dopt=GenBank">gb|AF123617.1|AF123617</a>  Pipreola arcuata
cytochrome b gene, ...    <a href = #8050348> 52</a>   6e-06
<a
href="http://www.ncbi.nlm.nih.gov:80/entrez/query.fcgi?cmd=Retrieve&db=Nucleotid
e&list_uids=07715727&dopt=GenBank">gb|AF127202.1|AF127202</a>  Hylopezus
fulviventris cytochrome b ...    <a href = #7715727> 52</a>   6e-06
<a
href="http://www.ncbi.nlm.nih.gov:80/entrez/query.fcgi?cmd=Retrieve&db=Nucleotid
e&list_uids=07715712&dopt=GenBank">gb|AF127194.1|AF127194</a>  Grallaria
guatimalensis cytochrome b...    <a href = #7715712> 52</a>   6e-06
<a
href="http://www.ncbi.nlm.nih.gov:80/entrez/query.fcgi?cmd=Retrieve&db=Nucleotid
e&list_uids=07141202&dopt=GenBank">gb|AF217828.1|AF217828</a>  Aspidelaps
scutatus cytochrome b gen...    <a href = #7141202> 52</a>   6e-06
<a
href="http://www.ncbi.nlm.nih.gov:80/entrez/query.fcgi?cmd=Retrieve&db=Nucleotid
```

```
e&list_uids=06524754&dopt=GenBank">gb|AF160578.1|AF160578</a>  Hypogeomys
antimena Hant555 cytochro...    <a href = #6524754> 52</a>   6e-06
<a
href="http://www.ncbi.nlm.nih.gov:80/entrez/query.fcgi?cmd=Retrieve&db=Nucleotid
e&list_uids=05713297&dopt=GenBank">gb|AF009931.2|AF009931</a>  Archocentrus
centrarchus cytochrome ...    <a href = #5713297> 52</a>   6e-06
<a
href="http://www.ncbi.nlm.nih.gov:80/entrez/query.fcgi?cmd=Retrieve&db=Nucleotid
e&list_uids=05359509&dopt=GenBank">gb|AF091629.1|AF091629</a>  Antilocapra
americana cytochrome b (...    <a href = #5359509> 52</a>   6e-06
<a
href="http://www.ncbi.nlm.nih.gov:80/entrez/query.fcgi?cmd=Retrieve&db=Nucleotid
e&list_uids=02660917&dopt=GenBank">gb|AF034967.1|</a>  Sigmoceros lichtensteinii
cytochrome b gene,...    <a href = #2660917> 52</a>   6e-06
<a
href="http://www.ncbi.nlm.nih.gov:80/entrez/query.fcgi?cmd=Retrieve&db=Nucleotid
e&list_uids=03098363&dopt=GenBank">gb|AF038290.1|AF038290</a>  Antechinus sp.
cytochrome b gene, mi...    <a href = #3098363> 52</a>   6e-06
<a
href="http://www.ncbi.nlm.nih.gov:80/entrez/query.fcgi?cmd=Retrieve&db=Nucleotid
e&list_uids=02677639&dopt=GenBank">gb|U07577.1|AMU07577</a>  Antechinus
melanurus mitochondrion cyt...    <a href = #2677639> 52</a>   6e-06
<a
href="http://www.ncbi.nlm.nih.gov:80/entrez/query.fcgi?cmd=Retrieve&db=Nucleotid
e&list_uids=02098650&dopt=GenBank">gb|U81343.1|CFU81343</a>  Chelus fimbriata
cytochrome b gene, mi...    <a href = #2098650> 52</a>   6e-06
<a
href="http://www.ncbi.nlm.nih.gov:80/entrez/query.fcgi?cmd=Retrieve&db=Nucleotid
e&list_uids=03483067&dopt=GenBank">emb|AJ222681.1|ABCYTOB</a>  Alcelaphus
buselaphus mitochondrial ...    <a href = #3483067> 52</a>   6e-06
<a
href="http://www.ncbi.nlm.nih.gov:80/entrez/query.fcgi?cmd=Retrieve&db=Nucleotid
e&list_uids=01778694&dopt=GenBank">gb|M99464.1|PNZMTCYTB</a>  Planigale sp.
cytochrome b gene, comp...    <a href = #1778694> 52</a>   6e-06
<a
href="http://www.ncbi.nlm.nih.gov:80/entrez/query.fcgi?cmd=Retrieve&db=Nucleotid
e&list_uids=04127784&dopt=GenBank">emb|AJ225116.1|DNJ225116</a>  Dryomys
nitedula mitochondrial gen...    <a href = #4127784> 52</a>   6e-06
<a
href="http://www.ncbi.nlm.nih.gov:80/entrez/query.fcgi?cmd=Retrieve&db=Nucleotid
e&list_uids=00841455&dopt=GenBank">gb|U25738.1|PRU25738</a>  Paradisaea raggiana
cytochrome b gene,...    <a href = #841455> 52</a>   6e-06
<a
href="http://www.ncbi.nlm.nih.gov:80/entrez/query.fcgi?cmd=Retrieve&db=Nucleotid
e&list_uids=00841451&dopt=GenBank">gb|U25736.1|PRU25736</a>  Paradisaea rubra
cytochrome b gene, mi...    <a href = #841451> 52</a>   6e-06
<a
href="http://www.ncbi.nlm.nih.gov:80/entrez/query.fcgi?cmd=Retrieve&db=Nucleotid
e&list_uids=00840936&dopt=GenBank">gb|U15202.1|SMU15202</a>  Seleucidis
melanoleuca mitochondrion c...    <a href = #840936> 52</a>   6e-06
<a
href="http://www.ncbi.nlm.nih.gov:80/entrez/query.fcgi?cmd=Retrieve&db=Nucleotid
e&list_uids=00840940&dopt=GenBank">gb|U15204.1|PR15204</a>  Paradisaea raggiana
mitochondrion cytoc...    <a href = #840940> 52</a>   6e-06
<a
href="http://www.ncbi.nlm.nih.gov:80/entrez/query.fcgi?cmd=Retrieve&db=Nucleotid
```

```
e&list_uids=00012907&dopt=GenBank">emb|X56290.1|MIDDCYTB</a>   D.dama
mitochondrion cytb gene for cy...    <a href = #12907>  52</a>   6e-06
<a
href="http://www.ncbi.nlm.nih.gov:80/entrez/query.fcgi?cmd=Retrieve&db=Nucleotid
e&list_uids=00012624&dopt=GenBank">emb|X56286.1|MIAACYTBA</a>   A.americana
mitochondrion cytb gene ...    <a href = #12624>  52</a>   6e-06
<a
href="http://www.ncbi.nlm.nih.gov:80/entrez/query.fcgi?cmd=Retrieve&db=Nucleotid
e&list_uids=01707347&dopt=GenBank">dbj|D88639.1|D88639</a>   Anoa depressicornis
mitochondrial DNA f...    <a href = #1707347>  52</a>   6e-06
<a
href="http://www.ncbi.nlm.nih.gov:80/entrez/query.fcgi?cmd=Retrieve&db=Nucleotid
e&list_uids=01813358&dopt=GenBank">dbj|D82890.1|D82890</a>   Bubalus
depressicornis mitochondrial DN...    <a href = #1813358>  52</a>   6e-06
<a
href="http://www.ncbi.nlm.nih.gov:80/entrez/query.fcgi?cmd=Retrieve&db=Nucleotid
e&list_uids=05478447&dopt=GenBank">gb|AF119261.1|AF119261</a>   Peromyscus
maniculatus cytochrome b ...    <a href = #5478447>  46</a>   3e-04
<a
href="http://www.ncbi.nlm.nih.gov:80/entrez/query.fcgi?cmd=Retrieve&db=Nucleotid
e&list_uids=08050344&dopt=GenBank">gb|AF123615.1|AF123615</a>   Rupicola rupicola
cytochrome b gene,...    <a href = #8050344>  46</a>   3e-04
<a
href="http://www.ncbi.nlm.nih.gov:80/entrez/query.fcgi?cmd=Retrieve&db=Nucleotid
e&list_uids=06524779&dopt=GenBank">gb|AF160603.1|AF160603</a>   Apodemus
sylvaticus Asyl588 cytochro...    <a href = #6524779>  46</a>   3e-04
<a
href="http://www.ncbi.nlm.nih.gov:80/entrez/query.fcgi?cmd=Retrieve&db=Nucleotid
e&list_uids=02052291&dopt=GenBank">gb|U62687.1|CCOLCYTB2</a>   Charadrius
collaris cytochrome b (cyt...    <a href = #2052291>  46</a>   3e-04
<a
href="http://www.ncbi.nlm.nih.gov:80/entrez/query.fcgi?cmd=Retrieve&db=Nucleotid
e&list_uids=01488224&dopt=GenBank">gb|U62685.1|CBICCYTB2</a>   Charadrius
bicinctus cytochrome b (cy...    <a href = #1488224>  46</a>   3e-04
<a
href="http://www.ncbi.nlm.nih.gov:80/entrez/query.fcgi?cmd=Retrieve&db=Nucleotid
e&list_uids=04103317&dopt=GenBank">gb|AF022071.1|</a>   Madoqua guentheri
cytochrome b (cytb) gene, ...    <a href = #4103317>  46</a>   3e-04
<a
href="http://www.ncbi.nlm.nih.gov:80/entrez/query.fcgi?cmd=Retrieve&db=Nucleotid
e&list_uids=04103315&dopt=GenBank">gb|AF022070.1|</a>   Madoqua kirkii cytochrome
b (cytb) gene, mit...    <a href = #4103315>  46</a>   3e-04
<a
href="http://www.ncbi.nlm.nih.gov:80/entrez/query.fcgi?cmd=Retrieve&db=Nucleotid
e&list_uids=02231533&dopt=GenBank">gb|U83317.1|PSU83317</a>   Polihierax
semitorquatus cytochrome b ...    <a href = #2231533>  46</a>   3e-04
<a
href="http://www.ncbi.nlm.nih.gov:80/entrez/query.fcgi?cmd=Retrieve&db=Nucleotid
e&list_uids=01255743&dopt=GenBank">gb|U37293.1|CCU37293</a>   Cepphus columba
cytochrome b gene, mit...    <a href = #1255743>  46</a>   3e-04
<a
href="http://www.ncbi.nlm.nih.gov:80/entrez/query.fcgi?cmd=Retrieve&db=Nucleotid
e&list_uids=01255741&dopt=GenBank">gb|U37292.1|CCU37292</a>   Cepphus carbo
cytochrome b gene, mitoc...    <a href = #1255741>  46</a>   3e-04
<a
href="http://www.ncbi.nlm.nih.gov:80/entrez/query.fcgi?cmd=Retrieve&db=Nucleotid
```

```
e&list_uids=01255739&dopt=GenBank">gb|U37291.1|BMU37291</a>  Brachyramphus
marmoratus perdix cytoch...    <a href = #1255739> 46</a>   3e-04
<a
href="http://www.ncbi.nlm.nih.gov:80/entrez/query.fcgi?cmd=Retrieve&db=Nucleotid
e&list_uids=03551896&dopt=GenBank">gb|AF082055.1|AF082055</a>  Rupicola rupicola
cytochrome b gene,...    <a href = #3551896> 46</a>   3e-04
<a
href="http://www.ncbi.nlm.nih.gov:80/entrez/query.fcgi?cmd=Retrieve&db=Nucleotid
e&list_uids=03211690&dopt=GenBank">gb|U72770.1|JMU72770</a>  Jabiru mycteria
cytochrome b gene, mit...    <a href = #3211690> 46</a>   3e-04
<a
href="http://www.ncbi.nlm.nih.gov:80/entrez/query.fcgi?cmd=Retrieve&db=Nucleotid
e&list_uids=02677641&dopt=GenBank">gb|U07578.1|DCU07578</a>  Dasycercus
cristicauda mitochondrion c...    <a href = #2677641> 46</a>   3e-04
<a
href="http://www.ncbi.nlm.nih.gov:80/entrez/query.fcgi?cmd=Retrieve&db=Nucleotid
e&list_uids=02642615&dopt=GenBank">gb|AF031908.1|GOCCCYTB3</a>  Geopsittacus
occidentalis cytochrom...    <a href = #2642615> 46</a>   3e-04
<a
href="http://www.ncbi.nlm.nih.gov:80/entrez/query.fcgi?cmd=Retrieve&db=Nucleotid
e&list_uids=09998874&dopt=GenBank">emb|AJ004231.1|SBAJ4231</a>  Sula bassana
mitochondrial cytb gen...    <a href = #9998874> 46</a>   3e-04
<a
href="http://www.ncbi.nlm.nih.gov:80/entrez/query.fcgi?cmd=Retrieve&db=Nucleotid
e&list_uids=09998872&dopt=GenBank">emb|AJ004230.1|SBAJ4230</a>  Sula bassana
mitochondrial cytb gen...    <a href = #9998872> 46</a>   3e-04
<a
href="http://www.ncbi.nlm.nih.gov:80/entrez/query.fcgi?cmd=Retrieve&db=Nucleotid
e&list_uids=09998870&dopt=GenBank">emb|AJ004229.1|SBAJ4229</a>  Sula bassana
mitochondrial cytb gen...    <a href = #9998870> 46</a>   3e-04
<a
href="http://www.ncbi.nlm.nih.gov:80/entrez/query.fcgi?cmd=Retrieve&db=Nucleotid
e&list_uids=09971120&dopt=GenBank">emb|AJ004232.1|SBAJ4232</a>  Sula bassana
mitochondrial cytb gen...    <a href = #9971120> 46</a>   3e-04
<a
href="http://www.ncbi.nlm.nih.gov:80/entrez/query.fcgi?cmd=Retrieve&db=Nucleotid
e&list_uids=02290368&dopt=GenBank">gb|U88865.1|</a>  Pomacentrus sp. cytochrome
b (cytb) gene, mito...    <a href = #2290368> 46</a>   3e-04
<a
href="http://www.ncbi.nlm.nih.gov:80/entrez/query.fcgi?cmd=Retrieve&db=Nucleotid
e&list_uids=01890874&dopt=GenBank">gb|U90001.1|MBU90001</a>  Morus bassanus
cytochrome b gene, mito...    <a href = #1890874> 46</a>   3e-04
<a
href="http://www.ncbi.nlm.nih.gov:80/entrez/query.fcgi?cmd=Retrieve&db=Nucleotid
e&list_uids=01458193&dopt=GenBank">gb|U63057.1|BMU63057</a>  Brachyramphus
marmoratus perdix cytoch...    <a href = #1458193> 46</a>   3e-04
<a
href="http://www.ncbi.nlm.nih.gov:80/entrez/query.fcgi?cmd=Retrieve&db=Nucleotid
e&list_uids=08272437&dopt=GenBank">dbj|AB036404.1|AB036404</a>  Rana porosa
brevipoda mitochondrial...    <a href = #8272437> 46</a>   3e-04
<a
href="http://www.ncbi.nlm.nih.gov:80/entrez/query.fcgi?cmd=Retrieve&db=Nucleotid
e&list_uids=08272434&dopt=GenBank">dbj|AB036402.1|AB036402</a>  Rana porosa
brevipoda mitochondrial...    <a href = #8272434> 46</a>   3e-04
<a
href="http://www.ncbi.nlm.nih.gov:80/entrez/query.fcgi?cmd=Retrieve&db=Nucleotid
```

```
e&list_uids=08272431&dopt=GenBank">dbj|AB036400.1|AB036400</a>  Rana porosa
brevipoda mitochondrial...    <a href = #8272431> 46</a>  3e-04
<a
href="http://www.ncbi.nlm.nih.gov:80/entrez/query.fcgi?cmd=Retrieve&db=Nucleotid
e&list_uids=08272428&dopt=GenBank">dbj|AB036398.1|AB036398</a>  Rana porosa
porosa mitochondrial DN...    <a href = #8272428> 46</a>  3e-04
<a
href="http://www.ncbi.nlm.nih.gov:80/entrez/query.fcgi?cmd=Retrieve&db=Nucleotid
e&list_uids=00642546&dopt=GenBank">gb|U19611.1|JMU19611</a>  Jabiru mycteria
cytochrome b gene, mit...    <a href = #642546> 46</a>  3e-04
<a
href="http://www.ncbi.nlm.nih.gov:80/entrez/query.fcgi?cmd=Retrieve&db=Nucleotid
e&list_uids=01199822&dopt=GenBank">emb|X92539.1|HACYTB</a>  H.ampullatus
cytochrome b gene (complet...    <a href = #1199822> 46</a>  3e-04
<a
href="http://www.ncbi.nlm.nih.gov:80/entrez/query.fcgi?cmd=Retrieve&db=Nucleotid
e&list_uids=00336992&dopt=GenBank">gb|L08034.1|GAEMTCYTBA</a>  Galeocerdo cuvier
mitochondrial cyto...    <a href = #336992> 46</a>  3e-04
<a
href="http://www.ncbi.nlm.nih.gov:80/entrez/query.fcgi?cmd=Retrieve&db=Nucleotid
e&list_uids=00336661&dopt=GenBank">gb|L08033.1|CPLMTCYTBB</a>  Carcharhinus
porosus mitochondrial c...    <a href = #336661> 46</a>  3e-04
<a
href="http://www.ncbi.nlm.nih.gov:80/entrez/query.fcgi?cmd=Retrieve&db=Nucleotid
e&list_uids=12957419&dopt=GenBank">gb|AY016012.1|</a>  Crypturellus tataupa
mitochondrion, partial ...    <a href = #12957419> 44</a>  0.001
<a
href="http://www.ncbi.nlm.nih.gov:80/entrez/query.fcgi?cmd=Retrieve&db=Nucleotid
e&list_uids=04336167&dopt=GenBank">gb|AF074591.1|AF074591</a>  Petrochelidon
pyrrhonota cytochrome ...    <a href = #4336167> 44</a>  0.001
<a
href="http://www.ncbi.nlm.nih.gov:80/entrez/query.fcgi?cmd=Retrieve&db=Nucleotid
e&list_uids=12699075&dopt=GenBank">gb|AY005212.1|</a>  Poospiza whitii isolate 2
cytochrome b (cytb...    <a href = #12699075> 44</a>  0.001
<a
href="http://www.ncbi.nlm.nih.gov:80/entrez/query.fcgi?cmd=Retrieve&db=Nucleotid
e&list_uids=12699073&dopt=GenBank">gb|AY005211.1|</a>  Poospiza whitii isolate 1
cytochrome b (cytb...    <a href = #12699073> 44</a>  0.001
<a
href="http://www.ncbi.nlm.nih.gov:80/entrez/query.fcgi?cmd=Retrieve&db=Nucleotid
e&list_uids=10441564&dopt=GenBank">gb|AF189122.1|AF189122</a>  Cryptotermes
tropicalis cytochrome b...    <a href = #10441564> 44</a>  0.001
<a
href="http://www.ncbi.nlm.nih.gov:80/entrez/query.fcgi?cmd=Retrieve&db=Nucleotid
e&list_uids=10441560&dopt=GenBank">gb|AF189120.1|AF189120</a>  Cryptotermes
secundus cytochrome b (...    <a href = #10441560> 44</a>  0.001
<a
href="http://www.ncbi.nlm.nih.gov:80/entrez/query.fcgi?cmd=Retrieve&db=Nucleotid
e&list_uids=10441556&dopt=GenBank">gb|AF189118.1|AF189118</a>  Cryptotermes
primus isolate 2 cytoch...    <a href = #10441556> 44</a>  0.001
<a
href="http://www.ncbi.nlm.nih.gov:80/entrez/query.fcgi?cmd=Retrieve&db=Nucleotid
e&list_uids=10441554&dopt=GenBank">gb|AF189117.1|AF189117</a>  Cryptotermes
primus isolate 1 cytoch...    <a href = #10441554> 44</a>  0.001
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotide&list_uids=10441552&dopt=GenBank">gb|AF189116.1|AF189116</a>   Cryptotermes dudlyi cytochrome b (Cy...    <a href = #10441552> 44</a>   0.001
<a href="http://www.ncbi.nlm.nih.gov:80/entrez/query.fcgi?cmd=Retrieve&db=Nucleotide&list_uids=12275815&dopt=GenBank">gb|AF112140.1|AF112140</a>   Ovis canadensis cytochrome b gene, p...    <a href = #12275815> 44</a>   0.001
<a href="http://www.ncbi.nlm.nih.gov:80/entrez/query.fcgi?cmd=Retrieve&db=Nucleotide&list_uids=12275813&dopt=GenBank">gb|AF112139.1|AF112139</a>   Ovis canadensis canadensis cytochrom...    <a href = #12275813> 44</a>   0.001
<a href="http://www.ncbi.nlm.nih.gov:80/entrez/query.fcgi?cmd=Retrieve&db=Nucleotide&list_uids=12275811&dopt=GenBank">gb|AF112138.1|AF112138</a>   Ovis canadensis nelsoni cytochrome b...    <a href = #12275811> 44</a>   0.001
<a href="http://www.ncbi.nlm.nih.gov:80/entrez/query.fcgi?cmd=Retrieve&db=Nucleotide&list_uids=03676623&dopt=GenBank">gb|AF081990.1|AF081990</a>   Vireo cassinii cassinii specimen-vou...    <a href = #3676623> 44</a>   0.001
<a href="http://www.ncbi.nlm.nih.gov:80/entrez/query.fcgi?cmd=Retrieve&db=Nucleotide&list_uids=03676621&dopt=GenBank">gb|AF081989.1|AF081989</a>   Vireo cassinii cassinii specimen-vou...    <a href = #3676621> 44</a>   0.001
<a href="http://www.ncbi.nlm.nih.gov:80/entrez/query.fcgi?cmd=Retrieve&db=Nucleotide&list_uids=03676619&dopt=GenBank">gb|AF081988.1|AF081988</a>   Vireo cassinii cassinii specimen-vou...    <a href = #3676619> 44</a>   0.001
<a href="http://www.ncbi.nlm.nih.gov:80/entrez/query.fcgi?cmd=Retrieve&db=Nucleotide&list_uids=03676617&dopt=GenBank">gb|AF081987.1|AF081987</a>   Vireo cassinii cassinii specimen-vou...    <a href = #3676617> 44</a>   0.001
<a href="http://www.ncbi.nlm.nih.gov:80/entrez/query.fcgi?cmd=Retrieve&db=Nucleotide&list_uids=03676615&dopt=GenBank">gb|AF081986.1|AF081986</a>   Vireo cassinii cassinii specimen-vou...    <a href = #3676615> 44</a>   0.001
<a href="http://www.ncbi.nlm.nih.gov:80/entrez/query.fcgi?cmd=Retrieve&db=Nucleotide&list_uids=03676613&dopt=GenBank">gb|AF081985.1|AF081985</a>   Vireo cassinii cassinii specimen-vou...    <a href = #3676613> 44</a>   0.001
<a href="http://www.ncbi.nlm.nih.gov:80/entrez/query.fcgi?cmd=Retrieve&db=Nucleotide&list_uids=03676611&dopt=GenBank">gb|AF081984.1|AF081984</a>   Vireo cassinii cassinii specimen-vou...    <a href = #3676611> 44</a>   0.001
<a href="http://www.ncbi.nlm.nih.gov:80/entrez/query.fcgi?cmd=Retrieve&db=Nucleotide&list_uids=03676609&dopt=GenBank">gb|AF081983.1|AF081983</a>   Vireo cassinii cassinii specimen-vou...    <a href = #3676609> 44</a>   0.001
<a href="http://www.ncbi.nlm.nih.gov:80/entrez/query.fcgi?cmd=Retrieve&db=Nucleotide&list_uids=03676607&dopt=GenBank">gb|AF081982.1|AF081982</a>   Vireo cassinii cassinii specimen-vou...    <a href = #3676607> 44</a>   0.001
<a href="http://www.ncbi.nlm.nih.gov:80/entrez/query.fcgi?cmd=Retrieve&db=Nucleotide&list_uids=03676605&dopt=GenBank">gb|AF081981.1|AF081981</a>   Vireo cassinii cassinii specimen-vou...    <a href = #3676605> 44</a>   0.001
<a href="http://www.ncbi.nlm.nih.gov:80/entrez/query.fcgi?cmd=Retrieve&db=Nucleotid
``` e&list_uids=03676603&dopt=GenBank">gb|AF081980.1|AF081980</a>   Vireo cassinii
cassinii specimen-vou...    <a href = #3676603> 44</a>   0.001
<a
href="http://www.ncbi.nlm.nih.gov:80/entrez/query.fcgi?cmd=Retrieve&db=Nucleotid
e&list_uids=03676601&dopt=GenBank">gb|AF081979.1|AF081979</a>   Vireo cassinii
cassinii specimen-vou...    <a href = #3676601> 44</a>   0.001
<a
href="http://www.ncbi.nlm.nih.gov:80/entrez/query.fcgi?cmd=Retrieve&db=Nucleotid
e&list_uids=03676599&dopt=GenBank">gb|AF081978.1|AF081978</a>   Vireo cassinii
cassinii specimen-vou...    <a href = #3676599> 44</a>   0.001
<a
href="http://www.ncbi.nlm.nih.gov:80/entrez/query.fcgi?cmd=Retrieve&db=Nucleotid
e&list_uids=03676597&dopt=GenBank">gb|AF081977.1|AF081977</a>   Vireo cassinii
cassinii specimen-vou...    <a href = #3676597> 44</a>   0.001
<a
href="http://www.ncbi.nlm.nih.gov:80/entrez/query.fcgi?cmd=Retrieve&db=Nucleotid
e&list_uids=03676595&dopt=GenBank">gb|AF081976.1|AF081976</a>   Vireo cassinii
cassinii specimen-vou...    <a href = #3676595> 44</a>   0.001
<a
href="http://www.ncbi.nlm.nih.gov:80/entrez/query.fcgi?cmd=Retrieve&db=Nucleotid
e&list_uids=03676593&dopt=GenBank">gb|AF081975.1|AF081975</a>   Vireo cassinii
cassinii specimen-vou...    <a href = #3676593> 44</a>   0.001
<a
href="http://www.ncbi.nlm.nih.gov:80/entrez/query.fcgi?cmd=Retrieve&db=Nucleotid
e&list_uids=03676591&dopt=GenBank">gb|AF081974.1|AF081974</a>   Vireo cassinii
cassinii specimen-vou...    <a href = #3676591> 44</a>   0.001
<a
href="http://www.ncbi.nlm.nih.gov:80/entrez/query.fcgi?cmd=Retrieve&db=Nucleotid
e&list_uids=03676589&dopt=GenBank">gb|AF081973.1|AF081973</a>   Vireo cassinii
cassinii specimen-vou...    <a href = #3676589> 44</a>   0.001
<a
href="http://www.ncbi.nlm.nih.gov:80/entrez/query.fcgi?cmd=Retrieve&db=Nucleotid
e&list_uids=03676587&dopt=GenBank">gb|AF081972.1|AF081972</a>   Vireo cassinii
cassinii specimen-vou...    <a href = #3676587> 44</a>   0.001
<a
href="http://www.ncbi.nlm.nih.gov:80/entrez/query.fcgi?cmd=Retrieve&db=Nucleotid
e&list_uids=03676585&dopt=GenBank">gb|AF081971.1|AF081971</a>   Vireo cassinii
cassinii specimen-vou...    <a href = #3676585> 44</a>   0.001
<a
href="http://www.ncbi.nlm.nih.gov:80/entrez/query.fcgi?cmd=Retrieve&db=Nucleotid
e&list_uids=03676583&dopt=GenBank">gb|AF081970.1|AF081970</a>   Vireo solitarius
alticola country US...    <a href = #3676583> 44</a>   0.001
<a
href="http://www.ncbi.nlm.nih.gov:80/entrez/query.fcgi?cmd=Retrieve&db=Nucleotid
e&list_uids=03676581&dopt=GenBank">gb|AF081969.1|AF081969</a>   Vireo solitarius
alticola country US...    <a href = #3676581> 44</a>   0.001
<a
href="http://www.ncbi.nlm.nih.gov:80/entrez/query.fcgi?cmd=Retrieve&db=Nucleotid
e&list_uids=03676579&dopt=GenBank">gb|AF081968.1|AF081968</a>   Vireo solitarius
alticola country US...    <a href = #3676579> 44</a>   0.001
<a
href="http://www.ncbi.nlm.nih.gov:80/entrez/query.fcgi?cmd=Retrieve&db=Nucleotid
e&list_uids=03676577&dopt=GenBank">gb|AF081967.1|AF081967</a>   Vireo solitarius
alticola country US...    <a href = #3676577> 44</a>   0.001
<a
href="http://www.ncbi.nlm.nih.gov:80/entrez/query.fcgi?cmd=Retrieve&db=Nucleotid

```
e&list_uids=03676575&dopt=GenBank">gb|AF081966.1|AF081966</a>  Vireo solitarius
solitarius specimen...   <a href = #3676575> 44</a>   0.001
<a
href="http://www.ncbi.nlm.nih.gov:80/entrez/query.fcgi?cmd=Retrieve&db=Nucleotid
e&list_uids=03676573&dopt=GenBank">gb|AF081965.1|AF081965</a>  Vireo solitarius
solitarius specimen...   <a href = #3676573> 44</a>   0.001
<a
href="http://www.ncbi.nlm.nih.gov:80/entrez/query.fcgi?cmd=Retrieve&db=Nucleotid
e&list_uids=03676571&dopt=GenBank">gb|AF081964.1|AF081964</a>  Vireo solitarius
solitarius specimen...   <a href = #3676571> 44</a>   0.001
<a
href="http://www.ncbi.nlm.nih.gov:80/entrez/query.fcgi?cmd=Retrieve&db=Nucleotid
e&list_uids=03676567&dopt=GenBank">gb|AF081962.1|AF081962</a>  Vireo flavifrons
specimen-voucher LS...   <a href = #3676567> 44</a>   0.001
<a
href="http://www.ncbi.nlm.nih.gov:80/entrez/query.fcgi?cmd=Retrieve&db=Nucleotid
e&list_uids=03676565&dopt=GenBank">gb|AF081961.1|AF081961</a>  Vireo flavifrons
specimen-voucher LS...   <a href = #3676565> 44</a>   0.001
<a
href="http://www.ncbi.nlm.nih.gov:80/entrez/query.fcgi?cmd=Retrieve&db=Nucleotid
e&list_uids=03676563&dopt=GenBank">gb|AF081960.1|AF081960</a>  Vireo leucophrys
leucophrys specimen...   <a href = #3676563> 44</a>   0.001
<a
href="http://www.ncbi.nlm.nih.gov:80/entrez/query.fcgi?cmd=Retrieve&db=Nucleotid
e&list_uids=03676561&dopt=GenBank">gb|AF081959.1|AF081959</a>  Vireolanius
leucotis leucotis cytoch...   <a href = #3676561> 44</a>   0.001
<a
href="http://www.ncbi.nlm.nih.gov:80/entrez/query.fcgi?cmd=Retrieve&db=Nucleotid
e&list_uids=12050550&dopt=GenBank">gb|AF112405.2|AF112405</a>  Barbus anoplus
cytochrome b (cytb) g...   <a href = #12050550> 44</a>   0.001
<a
href="http://www.ncbi.nlm.nih.gov:80/entrez/query.fcgi?cmd=Retrieve&db=Nucleotid
e&list_uids=12002328&dopt=GenBank">gb|AF144317.1|AF144317</a>  Amphiprion
ocellaris isolate 3 haplo...   <a href = #12002328> 44</a>   0.001
<a
href="http://www.ncbi.nlm.nih.gov:80/entrez/query.fcgi?cmd=Retrieve&db=Nucleotid
e&list_uids=12002326&dopt=GenBank">gb|AF144316.1|AF144316</a>  Amphiprion
ocellaris haplotype 3DH11...   <a href = #12002326> 44</a>   0.001
<a
href="http://www.ncbi.nlm.nih.gov:80/entrez/query.fcgi?cmd=Retrieve&db=Nucleotid
e&list_uids=12002324&dopt=GenBank">gb|AF144315.1|AF144315</a>  Amphiprion
ocellaris haplotype 3DH15...   <a href = #12002324> 44</a>   0.001
<a
href="http://www.ncbi.nlm.nih.gov:80/entrez/query.fcgi?cmd=Retrieve&db=Nucleotid
e&list_uids=12002322&dopt=GenBank">gb|AF144314.1|AF144314</a>  Amphiprion
ocellaris isolate 2 haplo...   <a href = #12002322> 44</a>   0.001
<a
href="http://www.ncbi.nlm.nih.gov:80/entrez/query.fcgi?cmd=Retrieve&db=Nucleotid
e&list_uids=12002320&dopt=GenBank">gb|AF144313.1|AF144313</a>  Amphiprion
ocellaris isolate 1 haplo...   <a href = #12002320> 44</a>   0.001
<a
href="http://www.ncbi.nlm.nih.gov:80/entrez/query.fcgi?cmd=Retrieve&db=Nucleotid
e&list_uids=12002318&dopt=GenBank">gb|AF144312.1|AF144312</a>  Amphiprion
ocellaris haplotype 3DH12...   <a href = #12002318> 44</a>   0.001
<a
href="http://www.ncbi.nlm.nih.gov:80/entrez/query.fcgi?cmd=Retrieve&db=Nucleotid
```

```
e&list_uids=12002316&dopt=GenBank">gb|AF144311.1|AF144311</a>  Amphiprion
ocellaris haplotype 3DH1 ...    <a href = #12002316> 44</a>  0.001
<a
href="http://www.ncbi.nlm.nih.gov:80/entrez/query.fcgi?cmd=Retrieve&db=Nucleotid
e&list_uids=12002314&dopt=GenBank">gb|AF144310.1|AF144310</a>  Amphiprion
ocellaris isolate 2 haplo...    <a href = #12002314> 44</a>  0.001
<a
href="http://www.ncbi.nlm.nih.gov:80/entrez/query.fcgi?cmd=Retrieve&db=Nucleotid
e&list_uids=12002312&dopt=GenBank">gb|AF144309.1|AF144309</a>  Amphiprion
ocellaris isolate 1 haplo...    <a href = #12002312> 44</a>  0.001
<a
href="http://www.ncbi.nlm.nih.gov:80/entrez/query.fcgi?cmd=Retrieve&db=Nucleotid
e&list_uids=05834939&dopt=GenBank">ref|NC_001567.1|</a>  Bos taurus
mitochondrion, complete genome      <a href = #5834939> 44</a>  0.001
<a
href="http://www.ncbi.nlm.nih.gov:80/entrez/query.fcgi?cmd=Retrieve&db=Nucleotid
e&list_uids=11991819&dopt=GenBank">gb|AF212124.1|AF212124</a>  Anolis schwartzi
cytochrome b gene, ...    <a href = #11991819> 44</a>  0.001
<a
href="http://www.ncbi.nlm.nih.gov:80/entrez/query.fcgi?cmd=Retrieve&db=Nucleotid
e&list_uids=07262982&dopt=GenBank">gb|AF182706.1|AF182706</a>  Phapitreron
amethystina cytochrome b...    <a href = #7262982> 44</a>  0.001
<a
href="http://www.ncbi.nlm.nih.gov:80/entrez/query.fcgi?cmd=Retrieve&db=Nucleotid
e&list_uids=03445513&dopt=GenBank">gb|AF010406.1|AF010406</a>  Ovis aries
complete mitochondrial ge...    <a href = #3445513> 44</a>  0.001
<a
href="http://www.ncbi.nlm.nih.gov:80/entrez/query.fcgi?cmd=Retrieve&db=Nucleotid
e&list_uids=11139363&dopt=GenBank">gb|AF096452.1|AF096452</a>  Platysteira
cyanea cytochrome b gene...    <a href = #11139363> 44</a>  0.001
<a
href="http://www.ncbi.nlm.nih.gov:80/entrez/query.fcgi?cmd=Retrieve&db=Nucleotid
e&list_uids=11023376&dopt=GenBank">gb|AF283619.1|AF283619</a>  Elaphe obsoleta
LSUMZ39162 cytochrom...    <a href = #11023376> 44</a>  0.001
<a
href="http://www.ncbi.nlm.nih.gov:80/entrez/query.fcgi?cmd=Retrieve&db=Nucleotid
e&list_uids=11023374&dopt=GenBank">gb|AF283618.1|AF283618</a>  Elaphe obsoleta
LSUMZ H15896 cytochr...    <a href = #11023374> 44</a>  0.001
<a
href="http://www.ncbi.nlm.nih.gov:80/entrez/query.fcgi?cmd=Retrieve&db=Nucleotid
e&list_uids=11023354&dopt=GenBank">gb|AF283608.1|AF283608</a>  Elaphe obsoleta
LSUMZ H14782 cytochr...    <a href = #11023354> 44</a>  0.001
<a
href="http://www.ncbi.nlm.nih.gov:80/entrez/query.fcgi?cmd=Retrieve&db=Nucleotid
e&list_uids=11023342&dopt=GenBank">gb|AF283602.1|AF283602</a>  Elaphe obsoleta
LSUMZ H3388 cytochro...    <a href = #11023342> 44</a>  0.001
<a
href="http://www.ncbi.nlm.nih.gov:80/entrez/query.fcgi?cmd=Retrieve&db=Nucleotid
e&list_uids=10799259&dopt=GenBank">gb|AF310069.1|AF310069</a>  Elaenia martinica
cytochrome b gene,...    <a href = #10799259> 44</a>  0.001
<a
href="http://www.ncbi.nlm.nih.gov:80/entrez/query.fcgi?cmd=Retrieve&db=Nucleotid
e&list_uids=10440971&dopt=GenBank">gb|AF146616.1|AF146616</a>  Actophilornis
africanus cytochrome b...    <a href = #10440971> 44</a>  0.001
<a
href="http://www.ncbi.nlm.nih.gov:80/entrez/query.fcgi?cmd=Retrieve&db=Nucleotid
``` e&list_uids=10442514&dopt=GenBank">gb|AF271410.1|AF271410</a>  Galago moholi cytochrome b (cyt b) g...    <a href = #10442514> 44</a>   0.001
<a href="http://www.ncbi.nlm.nih.gov:80/entrez/query.fcgi?cmd=Retrieve&db=Nucleotide&list_uids=09972047&dopt=GenBank">gb|AF290139.1|AF290139</a>  Peucedramus taeniatus cytochrome b (...    <a href = #9972047> 44</a>   0.001
<a href="http://www.ncbi.nlm.nih.gov:80/entrez/query.fcgi?cmd=Retrieve&db=Nucleotide&list_uids=09755345&dopt=GenBank">ref|NC_002504.1|</a>  Lama pacos mitochondrion, complete genome       <a href = #9755345> 44</a>   0.001
<a href="http://www.ncbi.nlm.nih.gov:80/entrez/query.fcgi?cmd=Retrieve&db=Nucleotide&list_uids=06690571&dopt=GenBank">gb|AF163901.1|AF163901</a>  Microtus ochrogaster cytochrome b ge...    <a href = #6690571> 44</a>   0.001
<a href="http://www.ncbi.nlm.nih.gov:80/entrez/query.fcgi?cmd=Retrieve&db=Nucleotide&list_uids=05478451&dopt=GenBank">gb|AF119263.1|AF119263</a>  Myopus schisticolor cytochrome b gen...    <a href = #5478451> 44</a>   0.001
<a href="http://www.ncbi.nlm.nih.gov:80/entrez/query.fcgi?cmd=Retrieve&db=Nucleotide&list_uids=05478441&dopt=GenBank">gb|AF119259.1|AF119259</a>  Synaptomys borealis cytochrome b gen...    <a href = #5478441> 44</a>   0.001
<a href="http://www.ncbi.nlm.nih.gov:80/entrez/query.fcgi?cmd=Retrieve&db=Nucleotide&list_uids=09664890&dopt=GenBank">gb|AF288454.1|AF288454</a>  Nyctereutes procyonoides koreensis c...    <a href = #9664890> 44</a>   0.001
<a href="http://www.ncbi.nlm.nih.gov:80/entrez/query.fcgi?cmd=Retrieve&db=Nucleotide&list_uids=09695303&dopt=GenBank">gb|AF163895.1|AF163895</a>  Microtus gregalis cytochrome B (cytB...    <a href = #9695303> 44</a>   0.001
<a href="http://www.ncbi.nlm.nih.gov:80/entrez/query.fcgi?cmd=Retrieve&db=Nucleotide&list_uids=08050411&dopt=GenBank">gb|AF123649.1|AF123649</a>  Machaeropterus regulus striolatus cy...    <a href = #8050411> 44</a>   0.001
<a href="http://www.ncbi.nlm.nih.gov:80/entrez/query.fcgi?cmd=Retrieve&db=Nucleotide&list_uids=08050407&dopt=GenBank">gb|AF123647.1|AF123647</a>  Machaeropterus pyrocephalus cytochro...    <a href = #8050407> 44</a>   0.001
<a href="http://www.ncbi.nlm.nih.gov:80/entrez/query.fcgi?cmd=Retrieve&db=Nucleotide&list_uids=08050405&dopt=GenBank">gb|AF123646.1|AF123646</a>  Xenopipo atronitens cytochrome b gen...    <a href = #8050405> 44</a>   0.001
<a href="http://www.ncbi.nlm.nih.gov:80/entrez/query.fcgi?cmd=Retrieve&db=Nucleotide&list_uids=08050403&dopt=GenBank">gb|AF123645.1|AF123645</a>  Pipra fasciicauda cytochrome b gene,...    <a href = #8050403> 44</a>   0.001
<a href="http://www.ncbi.nlm.nih.gov:80/entrez/query.fcgi?cmd=Retrieve&db=Nucleotide&list_uids=08050381&dopt=GenBank">gb|AF123634.1|AF123634</a>  Pyroderus scutatus cytochrome b gene...    <a href = #8050381> 44</a>   0.001
<a href="http://www.ncbi.nlm.nih.gov:80/entrez/query.fcgi?cmd=Retrieve&db=Nucleotide&list_uids=08050377&dopt=GenBank">gb|AF123632.1|AF123632</a>  Cephalopterus ornatus cytochrome b g...    <a href = #8050377> 44</a>   0.001
<a href="http://www.ncbi.nlm.nih.gov:80/entrez/query.fcgi?cmd=Retrieve&db=Nucleotid

```
<a href="http://www.ncbi.nlm.nih.gov:80/entrez/query.fcgi?cmd=Retrieve&db=Nucleotid
e&list_uids=08050369&dopt=GenBank">gb|AF123628.1|AF123628</a>  Turdampelis
cryptolophus cytochrome ...    <a href = #8050369> 44</a>   0.001
<a
href="http://www.ncbi.nlm.nih.gov:80/entrez/query.fcgi?cmd=Retrieve&db=Nucleotid
e&list_uids=08050356&dopt=GenBank">gb|AF123621.1|AF123621</a>  Porphyrolaema
porphyrolaema cytochro...    <a href = #8050356> 44</a>   0.001
<a
href="http://www.ncbi.nlm.nih.gov:80/entrez/query.fcgi?cmd=Retrieve&db=Nucleotid
e&list_uids=08050352&dopt=GenBank">gb|AF123619.1|AF123619</a>  Ampelioides
tschudii cytochrome b ge...    <a href = #8050352> 44</a>   0.001
<a
href="http://www.ncbi.nlm.nih.gov:80/entrez/query.fcgi?cmd=Retrieve&db=Nucleotid
e&list_uids=08050350&dopt=GenBank">gb|AF123618.1|AF123618</a>  Pipreola
chlorolepidota cytochrome b...    <a href = #8050350> 44</a>   0.001
<a
href="http://www.ncbi.nlm.nih.gov:80/entrez/query.fcgi?cmd=Retrieve&db=Nucleotid
e&list_uids=08050342&dopt=GenBank">gb|AF123614.1|AF123614</a>  Rupicola
peruviana cytochrome b gene...    <a href = #8050342> 44</a>   0.001
<a
href="http://www.ncbi.nlm.nih.gov:80/entrez/query.fcgi?cmd=Retrieve&db=Nucleotid
e&list_uids=08050340&dopt=GenBank">gb|AF123613.1|AF123613</a>  Doliornis
sclateri cytochrome b gene...    <a href = #8050340> 44</a>   0.001
<a
href="http://www.ncbi.nlm.nih.gov:80/entrez/query.fcgi?cmd=Retrieve&db=Nucleotid
e&list_uids=07715725&dopt=GenBank">gb|AF127201.1|AF127201</a>  Myrmothera
campanisona cytochrome b ...    <a href = #7715725> 44</a>   0.001
<a
href="http://www.ncbi.nlm.nih.gov:80/entrez/query.fcgi?cmd=Retrieve&db=Nucleotid
e&list_uids=07715708&dopt=GenBank">gb|AF127192.1|AF127192</a>  Grallaria
ruficapilla cytochrome b g...    <a href = #7715708> 44</a>   0.001
<a
href="http://www.ncbi.nlm.nih.gov:80/entrez/query.fcgi?cmd=Retrieve&db=Nucleotid
e&list_uids=07715702&dopt=GenBank">gb|AF127189.1|AF127189</a>  Grallaria varia
cytochrome b gene, p...    <a href = #7715702> 44</a>   0.001
<a
href="http://www.ncbi.nlm.nih.gov:80/entrez/query.fcgi?cmd=Retrieve&db=Nucleotid
e&list_uids=06469754&dopt=GenBank">gb|AF197849.1|AF197849</a>  Sericornis
frontalis cytochrome b ge...    <a href = #6469754> 44</a>   0.001
<a
href="http://www.ncbi.nlm.nih.gov:80/entrez/query.fcgi?cmd=Retrieve&db=Nucleotid
e&list_uids=06469750&dopt=GenBank">gb|AF197847.1|AF197847</a>  Pardalotus
striatus cytochrome b gen...    <a href = #6469750> 44</a>   0.001
<a
href="http://www.ncbi.nlm.nih.gov:80/entrez/query.fcgi?cmd=Retrieve&db=Nucleotid
e&list_uids=05836030&dopt=GenBank">ref|NC_000889.1|</a>  Hippopotamus amphibius
mitochondrion, comp...    <a href = #5836030> 44</a>   0.001
<a
href="http://www.ncbi.nlm.nih.gov:80/entrez/query.fcgi?cmd=Retrieve&db=Nucleotid
e&list_uids=05835778&dopt=GenBank">ref|NC_002079.1|</a>  Carassius auratus
mitochondrion, complete ...    <a href = #5835778> 44</a>   0.001
<a
href="http://www.ncbi.nlm.nih.gov:80/entrez/query.fcgi?cmd=Retrieve&db=Nucleotid
e&list_uids=05835359&dopt=GenBank">ref|NC_001794.1|</a>  Macropus robustus
mitochondrion, complete ...    <a href = #5835359> 44</a>   0.001
<a
href="http://www.ncbi.nlm.nih.gov:80/entrez/query.fcgi?cmd=Retrieve&db=Nucleotid
```

```
e&list_uids=05835037&dopt=GenBank">ref|NC_001610.1|</a>  Didelphis virginiana
mitochondrion, comple...    <a href = #5835037> 44</a>  0.001
<a
href="http://www.ncbi.nlm.nih.gov:80/entrez/query.fcgi?cmd=Retrieve&db=Nucleotid
e&list_uids=07243464&dopt=GenBank">gb|AF201612.1|AF201612</a>  Stomatorhinus sp.
CU79703 cyotchrome...    <a href = #7243464> 44</a>  0.001
<a
href="http://www.ncbi.nlm.nih.gov:80/entrez/query.fcgi?cmd=Retrieve&db=Nucleotid
e&list_uids=07546722&dopt=GenBank">gb|AF097931.1|AF097931</a>  Amphiprion
clarkii cytochrome b gene...    <a href = #7546722> 44</a>  0.001
<a
href="http://www.ncbi.nlm.nih.gov:80/entrez/query.fcgi?cmd=Retrieve&db=Nucleotid
e&list_uids=07546714&dopt=GenBank">gb|AF097927.1|AF097927</a>  Amphiprion
ocellaris cytochrome b ge...    <a href = #7546714> 44</a>  0.001
<a
href="http://www.ncbi.nlm.nih.gov:80/entrez/query.fcgi?cmd=Retrieve&db=Nucleotid
e&list_uids=00336430&dopt=GenBank">gb|J01394.1|BOVMT</a>  Bos taurus
mitochondrion, complete genome      <a href = #336430> 44</a>  0.001
<a
href="http://www.ncbi.nlm.nih.gov:80/entrez/query.fcgi?cmd=Retrieve&db=Nucleotid
e&list_uids=05764440&dopt=GenBank">gb|AF168760.1|AF168760</a>  Apalone spinifera
isolate TXsc cytoc...    <a href = #5764440> 44</a>  0.001
<a
href="http://www.ncbi.nlm.nih.gov:80/entrez/query.fcgi?cmd=Retrieve&db=Nucleotid
e&list_uids=05764438&dopt=GenBank">gb|AF168759.1|AF168759</a>  Apalone spinifera
isolate TXki cytoc...    <a href = #5764438> 44</a>  0.001
<a
href="http://www.ncbi.nlm.nih.gov:80/entrez/query.fcgi?cmd=Retrieve&db=Nucleotid
e&list_uids=05764436&dopt=GenBank">gb|AF168758.1|AF168758</a>  Apalone spinifera
isolate TXcc cytoc...    <a href = #5764436> 44</a>  0.001
<a
href="http://www.ncbi.nlm.nih.gov:80/entrez/query.fcgi?cmd=Retrieve&db=Nucleotid
e&list_uids=05764432&dopt=GenBank">gb|AF168756.1|AF168756</a>  Apalone spinifera
isolate NMrg cytoc...    <a href = #5764432> 44</a>  0.001
<a
href="http://www.ncbi.nlm.nih.gov:80/entrez/query.fcgi?cmd=Retrieve&db=Nucleotid
e&list_uids=06063112&dopt=GenBank">gb|AF182381.1|AF182381</a>  Petrochelidon
rufocollaris isolate E...    <a href = #6063112> 44</a>  0.001
<a
href="http://www.ncbi.nlm.nih.gov:80/entrez/query.fcgi?cmd=Retrieve&db=Nucleotid
e&list_uids=06063111&dopt=GenBank">gb|AF182380.1|AF182380</a>  Petrochelidon
rufocollaris isolate E...    <a href = #6063111> 44</a>  0.001
<a
href="http://www.ncbi.nlm.nih.gov:80/entrez/query.fcgi?cmd=Retrieve&db=Nucleotid
e&list_uids=04099753&dopt=GenBank">gb|U89187.1|MMU89187</a>  Momotus mexicanus
cytochrome b (cytb) ...    <a href = #4099753> 44</a>  0.001
<a
href="http://www.ncbi.nlm.nih.gov:80/entrez/query.fcgi?cmd=Retrieve&db=Nucleotid
e&list_uids=07208266&dopt=GenBank">gb|AF193833.1|AF193833</a>  Botaurus
lentiginosus cytochrome b g...    <a href = #7208266> 44</a>  0.001
<a
href="http://www.ncbi.nlm.nih.gov:80/entrez/query.fcgi?cmd=Retrieve&db=Nucleotid
e&list_uids=07208244&dopt=GenBank">gb|AF193822.1|AF193822</a>  Ardea alba
cytochrome b gene, partia...    <a href = #7208244> 44</a>  0.001
<a
href="http://www.ncbi.nlm.nih.gov:80/entrez/query.fcgi?cmd=Retrieve&db=Nucleotid
```

```
<a href="http://www.ncbi.nlm.nih.gov:80/entrez/query.fcgi?cmd=Retrieve&db=Nucleotid
e&list_uids=07208242&dopt=GenBank">gb|AF193821.1|AF193821</a>  Ardea herodias
cytochrome b gene, pa...    <a href = #7208242> 44</a>   0.001
<a
href="http://www.ncbi.nlm.nih.gov:80/entrez/query.fcgi?cmd=Retrieve&db=Nucleotid
e&list_uids=07141220&dopt=GenBank">gb|AF217837.1|AF217837</a>  Paranaja
multifasciata cytochrome b ...    <a href = #7141220> 44</a>   0.001
<a
href="http://www.ncbi.nlm.nih.gov:80/entrez/query.fcgi?cmd=Retrieve&db=Nucleotid
e&list_uids=07141216&dopt=GenBank">gb|AF217835.1|AF217835</a>  Naja kaouthia
cytochrome b gene, com...    <a href = #7141216> 44</a>   0.001
<a
href="http://www.ncbi.nlm.nih.gov:80/entrez/query.fcgi?cmd=Retrieve&db=Nucleotid
e&list_uids=07141214&dopt=GenBank">gb|AF217834.1|AF217834</a>  Laticauda
colubrina cytochrome b gen...    <a href = #7141214> 44</a>   0.001
<a
href="http://www.ncbi.nlm.nih.gov:80/entrez/query.fcgi?cmd=Retrieve&db=Nucleotid
e&list_uids=07141208&dopt=GenBank">gb|AF217831.1|AF217831</a>  Calliophis
japonicus cytochrome b ge...    <a href = #7141208> 44</a>   0.001
<a
href="http://www.ncbi.nlm.nih.gov:80/entrez/query.fcgi?cmd=Retrieve&db=Nucleotid
e&list_uids=07141192&dopt=GenBank">gb|AF217823.1|AF217823</a>  Micruroides
euryxanthus cytochrome b...    <a href = #7141192> 44</a>   0.001
<a
href="http://www.ncbi.nlm.nih.gov:80/entrez/query.fcgi?cmd=Retrieve&db=Nucleotid
e&list_uids=07141184&dopt=GenBank">gb|AF217819.1|AF217819</a>  Drysdalia
coronata cytochrome b gene...    <a href = #7141184> 44</a>   0.001
<a
href="http://www.ncbi.nlm.nih.gov:80/entrez/query.fcgi?cmd=Retrieve&db=Nucleotid
e&list_uids=07141176&dopt=GenBank">gb|AF217815.1|AF217815</a>  Austrelaps
superbus cytochrome b gen...    <a href = #7141176> 44</a>   0.001
<a
href="http://www.ncbi.nlm.nih.gov:80/entrez/query.fcgi?cmd=Retrieve&db=Nucleotid
e&list_uids=06650839&dopt=GenBank">gb|AF118156.1|AF118156</a>  Terenura
humeralis specimen-voucher ...    <a href = #6650839> 44</a>   0.001
<a
href="http://www.ncbi.nlm.nih.gov:80/entrez/query.fcgi?cmd=Retrieve&db=Nucleotid
e&list_uids=06715327&dopt=GenBank">gb|AF209938.1|AF209938</a>  Euura atra
isolate 62 cytochrome b g...    <a href = #6715327> 44</a>   0.001
<a
href="http://www.ncbi.nlm.nih.gov:80/entrez/query.fcgi?cmd=Retrieve&db=Nucleotid
e&list_uids=06715322&dopt=GenBank">gb|AF209933.1|AF209933</a>  Euura atra
isolate C cytochrome b ge...    <a href = #6715322> 44</a>   0.001
<a
href="http://www.ncbi.nlm.nih.gov:80/entrez/query.fcgi?cmd=Retrieve&db=Nucleotid
e&list_uids=03088757&dopt=GenBank">gb|AF059104.1|AF059104</a>  Marmaronetta
angustirostris cytochro...    <a href = #3088757> 44</a>   0.001
<a
href="http://www.ncbi.nlm.nih.gov:80/entrez/query.fcgi?cmd=Retrieve&db=Nucleotid
e&list_uids=03088753&dopt=GenBank">gb|AF059102.1|AF059102</a>  Lophonetta
specularoides cytochrome ...    <a href = #3088753> 44</a>   0.001
<a
href="http://www.ncbi.nlm.nih.gov:80/entrez/query.fcgi?cmd=Retrieve&db=Nucleotid
e&list_uids=03088657&dopt=GenBank">gb|AF059054.1|AF059054</a>  Amazonetta
brasiliensis cytochrome b...    <a href = #3088657> 44</a>   0.001
<a
href="http://www.ncbi.nlm.nih.gov:80/entrez/query.fcgi?cmd=Retrieve&db=Nucleotid
```

```
e&list_uids=06539763&dopt=GenBank">gb|AF192646.1|AF192646</a>  Hippocampus
barbouri haplotype PH.22...    <a href = #6539763> 44</a>   0.001
<a
href="http://www.ncbi.nlm.nih.gov:80/entrez/query.fcgi?cmd=Retrieve&db=Nucleotid
e&list_uids=06539762&dopt=GenBank">gb|AF192645.1|AF192645</a>  Hippocampus
barbouri haplotype PH.13...    <a href = #6539762> 44</a>   0.001
<a
href="http://www.ncbi.nlm.nih.gov:80/entrez/query.fcgi?cmd=Retrieve&db=Nucleotid
e&list_uids=06524790&dopt=GenBank">gb|AF160614.1|AF160614</a>  Cricetomys
gambianus Cgam518 cytochr...    <a href = #6524790> 44</a>   0.001
<a
href="http://www.ncbi.nlm.nih.gov:80/entrez/query.fcgi?cmd=Retrieve&db=Nucleotid
e&list_uids=06524789&dopt=GenBank">gb|AF160613.1|AF160613</a>  Cricetomys emini
Cemi531 cytochrome ...    <a href = #6524789> 44</a>   0.001
<a
href="http://www.ncbi.nlm.nih.gov:80/entrez/query.fcgi?cmd=Retrieve&db=Nucleotid
e&list_uids=06524788&dopt=GenBank">gb|AF160612.1|AF160612</a>  Cricetomys emini
Cemi530 cytochrome ...    <a href = #6524788> 44</a>   0.001
<a
href="http://www.ncbi.nlm.nih.gov:80/entrez/query.fcgi?cmd=Retrieve&db=Nucleotid
e&list_uids=06524787&dopt=GenBank">gb|AF160611.1|AF160611</a>  Cricetomys emini
Cemi637 cytochrome ...    <a href = #6524787> 44</a>   0.001
<a
href="http://www.ncbi.nlm.nih.gov:80/entrez/query.fcgi?cmd=Retrieve&db=Nucleotid
e&list_uids=06524786&dopt=GenBank">gb|AF160610.1|AF160610</a>  Cricetomys emini
Cemi636 cytochrome ...    <a href = #6524786> 44</a>   0.001
<a
href="http://www.ncbi.nlm.nih.gov:80/entrez/query.fcgi?cmd=Retrieve&db=Nucleotid
e&list_uids=06524780&dopt=GenBank">gb|AF160604.1|AF160604</a>  Calomyscus
bailwardi Cbal576 cytochr...    <a href = #6524780> 44</a>   0.001
<a
href="http://www.ncbi.nlm.nih.gov:80/entrez/query.fcgi?cmd=Retrieve&db=Nucleotid
e&list_uids=06524736&dopt=GenBank">gb|AF160560.1|AF160560</a>  Eliurus majori
Emaj642 cytochrome b ...    <a href = #6524736> 44</a>   0.001
<a
href="http://www.ncbi.nlm.nih.gov:80/entrez/query.fcgi?cmd=Retrieve&db=Nucleotid
e&list_uids=06524735&dopt=GenBank">gb|AF160559.1|AF160559</a>  Eliurus majori
Emaj641 cytochrome b ...    <a href = #6524735> 44</a>   0.001
<a
href="http://www.ncbi.nlm.nih.gov:80/entrez/query.fcgi?cmd=Retrieve&db=Nucleotid
e&list_uids=06524734&dopt=GenBank">gb|AF160558.1|AF160558</a>  Eliurus majori
Emaj639 cytochrome b ...    <a href = #6524734> 44</a>   0.001
<a
href="http://www.ncbi.nlm.nih.gov:80/entrez/query.fcgi?cmd=Retrieve&db=Nucleotid
e&list_uids=06524733&dopt=GenBank">gb|AF160557.1|AF160557</a>  Eliurus majori
Emaj638 cytochrome b ...    <a href = #6524733> 44</a>   0.001
<a
href="http://www.ncbi.nlm.nih.gov:80/entrez/query.fcgi?cmd=Retrieve&db=Nucleotid
e&list_uids=06524731&dopt=GenBank">gb|AF160555.1|AF160555</a>  Eliurus majori
Emaj614 cytochrome b ...    <a href = #6524731> 44</a>   0.001
<a
href="http://www.ncbi.nlm.nih.gov:80/entrez/query.fcgi?cmd=Retrieve&db=Nucleotid
e&list_uids=06524730&dopt=GenBank">gb|AF160554.1|AF160554</a>  Eliurus majori
Emaj617 cytochrome b ...    <a href = #6524730> 44</a>   0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=06524729&dopt=GenBank">gb|AF160553.1|AF160553</a>   Eliurus majori
Emaj573 cytochrome b ...    <a href = #6524729>  44</a>   0.001
<a
href="http://www.ncbi.nlm.nih.gov:80/entrez/query.fcgi?cmd=Retrieve&db=Nucleotid
e&list_uids=06524728&dopt=GenBank">gb|AF160552.1|AF160552</a>   Eliurus majori
Emaj556 cytochrome b ...    <a href = #6524728>  44</a>   0.001
<a
href="http://www.ncbi.nlm.nih.gov:80/entrez/query.fcgi?cmd=Retrieve&db=Nucleotid
e&list_uids=06524727&dopt=GenBank">gb|AF160551.1|AF160551</a>   Eliurus majori
Emaj561 cytochrome b ...    <a href = #6524727>  44</a>   0.001
<a
href="http://www.ncbi.nlm.nih.gov:80/entrez/query.fcgi?cmd=Retrieve&db=Nucleotid
e&list_uids=06524726&dopt=GenBank">gb|AF160550.1|AF160550</a>   Eliurus majori
Emaj443 cytochrome b ...    <a href = #6524726>  44</a>   0.001
<a
href="http://www.ncbi.nlm.nih.gov:80/entrez/query.fcgi?cmd=Retrieve&db=Nucleotid
e&list_uids=06524725&dopt=GenBank">gb|AF160549.1|AF160549</a>   Eliurus majori
Emaj444 cytochrome b ...    <a href = #6524725>  44</a>   0.001
<a
href="http://www.ncbi.nlm.nih.gov:80/entrez/query.fcgi?cmd=Retrieve&db=Nucleotid
e&list_uids=05777935&dopt=GenBank">gb|AF036287.1|AF036287</a>   Damaliscus
pygargus cytochrome b (cy...   <a href = #5777935>  44</a>   0.001
<a
href="http://www.ncbi.nlm.nih.gov:80/entrez/query.fcgi?cmd=Retrieve&db=Nucleotid
e&list_uids=05777933&dopt=GenBank">gb|AF036286.1|AF036286</a>   Oryx leucoryx
cytochrome b (cytb) ge...    <a href = #5777933>  44</a>   0.001
<a
href="http://www.ncbi.nlm.nih.gov:80/entrez/query.fcgi?cmd=Retrieve&db=Nucleotid
e&list_uids=05777927&dopt=GenBank">gb|AF036283.1|AF036283</a>   Antilope
cervicapra cytochrome b (cy...   <a href = #5777927>  44</a>   0.001
<a
href="http://www.ncbi.nlm.nih.gov:80/entrez/query.fcgi?cmd=Retrieve&db=Nucleotid
e&list_uids=05777923&dopt=GenBank">gb|AF036281.1|AF036281</a>   Antidorcas
marsupialis cytochrome b ...    <a href = #5777923>  44</a>   0.001
<a
href="http://www.ncbi.nlm.nih.gov:80/entrez/query.fcgi?cmd=Retrieve&db=Nucleotid
e&list_uids=05777917&dopt=GenBank">gb|AF036278.1|AF036278</a>   Tragelaphus oryx
cytochrome b (cytb)...    <a href = #5777917>  44</a>   0.001
<a
href="http://www.ncbi.nlm.nih.gov:80/entrez/query.fcgi?cmd=Retrieve&db=Nucleotid
e&list_uids=05777913&dopt=GenBank">gb|AF036276.1|AF036276</a>   Tragelaphus
euryceros cytochrome b (...    <a href = #5777913>  44</a>   0.001
<a
href="http://www.ncbi.nlm.nih.gov:80/entrez/query.fcgi?cmd=Retrieve&db=Nucleotid
e&list_uids=05777909&dopt=GenBank">gb|AF036274.1|</a>   Tetracerus quadricornis
cytochrome b (cytb) ...    <a href = #5777909>  44</a>   0.001
<a
href="http://www.ncbi.nlm.nih.gov:80/entrez/query.fcgi?cmd=Retrieve&db=Nucleotid
e&list_uids=05835554&dopt=GenBank">ref|NC_001941.1|</a>   Ovis aries
mitochondrion, complete genome       <a href = #5835554>  44</a>   0.001
<a
href="http://www.ncbi.nlm.nih.gov:80/entrez/query.fcgi?cmd=Retrieve&db=Nucleotid
e&list_uids=05579171&dopt=GenBank">gb|AF108698.1|AF108698</a>   Microryzomys
minutus cytochrome B (c...    <a href = #5579171>  44</a>   0.001
<a
href="http://www.ncbi.nlm.nih.gov:80/entrez/query.fcgi?cmd=Retrieve&db=Nucleotid
``` e&list_uids=05579155&dopt=GenBank">gb|AF108682.1|AF108682</a> Rhipidomys nitela cytochrome B (cytB... <a href = #5579155> 44</a> 0.001
<a href="http://www.ncbi.nlm.nih.gov:80/entrez/query.fcgi?cmd=Retrieve&db=Nucleotide&list_uids=05579146&dopt=GenBank">gb|AF108673.1|AF108673</a> Thomasomys daphne cytochrome B (cytB... <a href = #5579146> 44</a> 0.001
<a href="http://www.ncbi.nlm.nih.gov:80/entrez/query.fcgi?cmd=Retrieve&db=Nucleotide&list_uids=05579142&dopt=GenBank">gb|AF108669.1|AF108669</a> Scapteromys tumidus cytochrome B (cy... <a href = #5579142> 44</a> 0.001
<a href="http://www.ncbi.nlm.nih.gov:80/entrez/query.fcgi?cmd=Retrieve&db=Nucleotide&list_uids=05910972&dopt=GenBank">gb|AF042720.1|AF042720</a> Megamuntiacus vuquangensis cytochrom... <a href = #5910972> 44</a> 0.001
<a href="http://www.ncbi.nlm.nih.gov:80/entrez/query.fcgi?cmd=Retrieve&db=Nucleotide&list_uids=05910968&dopt=GenBank">gb|AF042718.1|</a> Muntiacus muntjak cytochrome b gene, mitocho... <a href = #5910968> 44</a> 0.001
<a href="http://www.ncbi.nlm.nih.gov:80/entrez/query.fcgi?cmd=Retrieve&db=Nucleotide&list_uids=05870035&dopt=GenBank">gb|AF084082.1|AF084082</a> Stenella coeruleoalba cytochrome b g... <a href = #5870035> 44</a> 0.001
<a href="http://www.ncbi.nlm.nih.gov:80/entrez/query.fcgi?cmd=Retrieve&db=Nucleotide&list_uids=05870034&dopt=GenBank">gb|AF084081.1|AF084081</a> Stenella coeruleoalba cytochrome b g... <a href = #5870034> 44</a> 0.001
<a href="http://www.ncbi.nlm.nih.gov:80/entrez/query.fcgi?cmd=Retrieve&db=Nucleotide&list_uids=05870027&dopt=GenBank">gb|AF084074.1|AF084074</a> Lagenorhynchus albirostris cytochrom... <a href = #5870027> 44</a> 0.001
<a href="http://www.ncbi.nlm.nih.gov:80/entrez/query.fcgi?cmd=Retrieve&db=Nucleotide&list_uids=05832998&dopt=GenBank">gb|AF090750.1|AF090750</a> Gobio gobio balcanicus cytochrome b ... <a href = #5832998> 44</a> 0.001
<a href="http://www.ncbi.nlm.nih.gov:80/entrez/query.fcgi?cmd=Retrieve&db=Nucleotide&list_uids=05737944&dopt=GenBank">gb|AF157939.1|AF157939</a> Spermophilus columbianus columbianus... <a href = #5737944> 44</a> 0.001
<a href="http://www.ncbi.nlm.nih.gov:80/entrez/query.fcgi?cmd=Retrieve&db=Nucleotide&list_uids=05737942&dopt=GenBank">gb|AF157937.1|AF157937</a> Spermophilus washingtoni isolate S89... <a href = #5737942> 44</a> 0.001
<a href="http://www.ncbi.nlm.nih.gov:80/entrez/query.fcgi?cmd=Retrieve&db=Nucleotide&list_uids=05737941&dopt=GenBank">gb|AF157936.1|AF157936</a> Spermophilus washingtoni isolate S88... <a href = #5737941> 44</a> 0.001
<a href="http://www.ncbi.nlm.nih.gov:80/entrez/query.fcgi?cmd=Retrieve&db=Nucleotide&list_uids=05737920&dopt=GenBank">gb|AF157915.1|AF157915</a> Spermophilus richardsoni isolate S63... <a href = #5737920> 44</a> 0.001
<a href="http://www.ncbi.nlm.nih.gov:80/entrez/query.fcgi?cmd=Retrieve&db=Nucleotide&list_uids=05737919&dopt=GenBank">gb|AF157914.1|AF157914</a> Spermophilus richardsoni isolate S62... <a href = #5737919> 44</a> 0.001
<a href="http://www.ncbi.nlm.nih.gov:80/entrez/query.fcgi?cmd=Retrieve&db=Nucleotid

```
e&list_uids=05737917&dopt=GenBank">gb|AF157912.1|AF157912</a>   Spermophilus
undulatus isolate S60 c...    <a href = #5737917>  44</a>    0.001
<a
href="http://www.ncbi.nlm.nih.gov:80/entrez/query.fcgi?cmd=Retrieve&db=Nucleotid
e&list_uids=05737911&dopt=GenBank">gb|AF157906.1|AF157906</a>   Spermophilus
undulatus isolate S55 c...    <a href = #5737911>  44</a>    0.001
<a
href="http://www.ncbi.nlm.nih.gov:80/entrez/query.fcgi?cmd=Retrieve&db=Nucleotid
e&list_uids=05737896&dopt=GenBank">gb|AF157891.1|AF157891</a>   Spermophilus
elegans elegans isolate...    <a href = #5737896>  44</a>    0.001
<a
href="http://www.ncbi.nlm.nih.gov:80/entrez/query.fcgi?cmd=Retrieve&db=Nucleotid
e&list_uids=05737887&dopt=GenBank">gb|AF157882.1|AF157882</a>   Spermophilus
columbianus columbianus...    <a href = #5737887>  44</a>    0.001
<a
href="http://www.ncbi.nlm.nih.gov:80/entrez/query.fcgi?cmd=Retrieve&db=Nucleotid
e&list_uids=05737864&dopt=GenBank">gb|AF157859.1|AF157859</a>   Spermophilus
citellus isolate S118 c...    <a href = #5737864>  44</a>    0.001
<a
href="http://www.ncbi.nlm.nih.gov:80/entrez/query.fcgi?cmd=Retrieve&db=Nucleotid
e&list_uids=05737863&dopt=GenBank">gb|AF157858.1|AF157858</a>   Spermophilus
citellus isolate S117 c...    <a href = #5737863>  44</a>    0.001
<a
href="http://www.ncbi.nlm.nih.gov:80/entrez/query.fcgi?cmd=Retrieve&db=Nucleotid
e&list_uids=05737844&dopt=GenBank">gb|AF157839.1|AF157839</a>   Spermophilus
elegans elegans isolate...    <a href = #5737844>  44</a>    0.001
<a
href="http://www.ncbi.nlm.nih.gov:80/entrez/query.fcgi?cmd=Retrieve&db=Nucleotid
e&list_uids=02674125&dopt=GenBank">gb|AF030497.1|AF030497</a>   Crocidura brunnea
cytochrome b (cyt ...    <a href = #2674125>  44</a>    0.001
<a
href="http://www.ncbi.nlm.nih.gov:80/entrez/query.fcgi?cmd=Retrieve&db=Nucleotid
e&list_uids=05453528&dopt=GenBank">gb|U03541.2|LAU03541</a>   Lenoxus apicalis
cytochrome b gene, pa...    <a href = #5453528>  44</a>    0.001
<a
href="http://www.ncbi.nlm.nih.gov:80/entrez/query.fcgi?cmd=Retrieve&db=Nucleotid
e&list_uids=05713307&dopt=GenBank">gb|AF009951.2|AF009951</a>   Heros
appendiculatus cytochrome b (c...    <a href = #5713307>  44</a>    0.001
<a
href="http://www.ncbi.nlm.nih.gov:80/entrez/query.fcgi?cmd=Retrieve&db=Nucleotid
e&list_uids=02281562&dopt=GenBank">gb|AF009941.1|AF009941</a>   Tomocichla tuba
cytochrome b (cytb) ...    <a href = #2281562>  44</a>    0.001
<a
href="http://www.ncbi.nlm.nih.gov:80/entrez/query.fcgi?cmd=Retrieve&db=Nucleotid
e&list_uids=02281530&dopt=GenBank">gb|AF009925.1|AF009925</a>   Archocentrus
sajica cytochrome b (cy...    <a href = #2281530>  44</a>    0.001
<a
href="http://www.ncbi.nlm.nih.gov:80/entrez/query.fcgi?cmd=Retrieve&db=Nucleotid
e&list_uids=05712261&dopt=GenBank">gb|AF094633.1|AF094633</a>   Stachyris
whiteheadi cytochrome b ge...    <a href = #5712261>  44</a>    0.001
<a
href="http://www.ncbi.nlm.nih.gov:80/entrez/query.fcgi?cmd=Retrieve&db=Nucleotid
e&list_uids=05712237&dopt=GenBank">gb|AF094621.1|AF094621</a>   Eminia lepida
cytochrome b gene, par...    <a href = #5712237>  44</a>    0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=05712231&dopt=GenBank">gb|AF094618.1|AF094618</a>  Hypergerus
atriceps cytochrome b gen...    <a href = #5712231>  44</a>   0.001
<a
href="http://www.ncbi.nlm.nih.gov:80/entrez/query.fcgi?cmd=Retrieve&db=Nucleotid
e&list_uids=05616507&dopt=GenBank">gb|AF166348.1|AF166348</a>  Phascolarctos
cinereus cytochrome b ...    <a href = #5616507>  44</a>   0.001
<a
href="http://www.ncbi.nlm.nih.gov:80/entrez/query.fcgi?cmd=Retrieve&db=Nucleotid
e&list_uids=05616278&dopt=GenBank">gb|AF158697.1|AF158697</a>  Geomys bursarius
ozarkensis cytochro...    <a href = #5616278>  44</a>   0.001
<a
href="http://www.ncbi.nlm.nih.gov:80/entrez/query.fcgi?cmd=Retrieve&db=Nucleotid
e&list_uids=05616271&dopt=GenBank">gb|AF158694.1|AF158694</a>  Geomys bursarius
majusculus cytochro...    <a href = #5616271>  44</a>   0.001
<a
href="http://www.ncbi.nlm.nih.gov:80/entrez/query.fcgi?cmd=Retrieve&db=Nucleotid
e&list_uids=05616268&dopt=GenBank">gb|AF158693.1|AF158693</a>  Geomys bursarius
bursarius cytochrom...    <a href = #5616268>  44</a>   0.001
<a
href="http://www.ncbi.nlm.nih.gov:80/entrez/query.fcgi?cmd=Retrieve&db=Nucleotid
e&list_uids=05616256&dopt=GenBank">gb|AF158688.1|AF158688</a>  Geomys bursarius
missouriensis cytoc...    <a href = #5616256>  44</a>   0.001
<a
href="http://www.ncbi.nlm.nih.gov:80/entrez/query.fcgi?cmd=Retrieve&db=Nucleotid
e&list_uids=05565802&dopt=GenBank">gb|AF100720.1|AF100720</a>  Spermophilus
citellus cytochrome b (...    <a href = #5565802>  44</a>   0.001
<a
href="http://www.ncbi.nlm.nih.gov:80/entrez/query.fcgi?cmd=Retrieve&db=Nucleotid
e&list_uids=05359515&dopt=GenBank">gb|AF091632.1|AF091632</a>  Bubalus
depressicornis cytochrome b ...    <a href = #5359515>  44</a>   0.001
<a
href="http://www.ncbi.nlm.nih.gov:80/entrez/query.fcgi?cmd=Retrieve&db=Nucleotid
e&list_uids=04324400&dopt=GenBank">gb|AF102815.1|AF102815</a>  Dromiciops
gliroides cytochrome b ge...    <a href = #4324400>  44</a>   0.001
<a
href="http://www.ncbi.nlm.nih.gov:80/entrez/query.fcgi?cmd=Retrieve&db=Nucleotid
e&list_uids=04324399&dopt=GenBank">gb|AF102814.1|AF102814</a>  Vombatus ursinus
cytochrome b gene, ...    <a href = #4324399>  44</a>   0.001
<a
href="http://www.ncbi.nlm.nih.gov:80/entrez/query.fcgi?cmd=Retrieve&db=Nucleotid
e&list_uids=04103305&dopt=GenBank">gb|AF022065.1|</a>  Tragelaphus euryceros
cytochrome b (cytb) ge...    <a href = #4103305>  44</a>   0.001
<a
href="http://www.ncbi.nlm.nih.gov:80/entrez/query.fcgi?cmd=Retrieve&db=Nucleotid
e&list_uids=04103293&dopt=GenBank">gb|AF022059.1|</a>  Kobus ellipsiprymnus
cytochrome b (cytb) gen...    <a href = #4103293>  44</a>   0.001
<a
href="http://www.ncbi.nlm.nih.gov:80/entrez/query.fcgi?cmd=Retrieve&db=Nucleotid
e&list_uids=04103291&dopt=GenBank">gb|AF022058.1|</a>  Antilope cervicapra
cytochrome b (cytb) gene...    <a href = #4103291>  44</a>   0.001
<a
href="http://www.ncbi.nlm.nih.gov:80/entrez/query.fcgi?cmd=Retrieve&db=Nucleotid
e&list_uids=04103289&dopt=GenBank">gb|AF022057.1|</a>  Tragelaphus oryx
cytochrome b (cytb) gene, m...    <a href = #4103289>  44</a>   0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=04103283&dopt=GenBank">gb|AF022054.1|</a>   Antidorcas marsupialis
cytochrome b (cytb) g...    <a href = #4103283> 44</a>   0.001
<a
href="http://www.ncbi.nlm.nih.gov:80/entrez/query.fcgi?cmd=Retrieve&db=Nucleotid
e&list_uids=04102850&dopt=GenBank">gb|AF016637.1|AF016637</a>   Connochaetes gnou
cytochrome b (cytb...    <a href = #4102850> 44</a>   0.001
<a
href="http://www.ncbi.nlm.nih.gov:80/entrez/query.fcgi?cmd=Retrieve&db=Nucleotid
e&list_uids=02843078&dopt=GenBank">gb|U69863.1|PSU69863</a>   Python sebae
cytochrome b (cytb) gene,...    <a href = #2843078> 44</a>   0.001
<a
href="http://www.ncbi.nlm.nih.gov:80/entrez/query.fcgi?cmd=Retrieve&db=Nucleotid
e&list_uids=02843040&dopt=GenBank">gb|U69844.1|LTU69844</a>   Lichanura
trivirgata cytochrome b (cyt...    <a href = #2843040> 44</a>   0.001
<a
href="http://www.ncbi.nlm.nih.gov:80/entrez/query.fcgi?cmd=Retrieve&db=Nucleotid
e&list_uids=05070473&dopt=GenBank">gb|AF143193.1|AF143193</a>   Epinephelus sp.
cytochrome b (cytb) ...    <a href = #5070473> 44</a>   0.001
<a
href="http://www.ncbi.nlm.nih.gov:80/entrez/query.fcgi?cmd=Retrieve&db=Nucleotid
e&list_uids=04903279&dopt=GenBank">gb|AF121222.1|AF121222</a>   Amphiprion
ocellaris isolate 8 cytoc...    <a href = #4903279> 44</a>   0.001
<a
href="http://www.ncbi.nlm.nih.gov:80/entrez/query.fcgi?cmd=Retrieve&db=Nucleotid
e&list_uids=04689176&dopt=GenBank">gb|AF096625.1|AF096625</a>   Kobus
ellipsiprymnus defassa cytochr...    <a href = #4689176> 44</a>   0.001
<a
href="http://www.ncbi.nlm.nih.gov:80/entrez/query.fcgi?cmd=Retrieve&db=Nucleotid
e&list_uids=04689174&dopt=GenBank">gb|AF096624.1|AF096624</a>   Kobus
ellipsiprymnus ellipsiprymus c...    <a href = #4689174> 44</a>   0.001
<a
href="http://www.ncbi.nlm.nih.gov:80/entrez/query.fcgi?cmd=Retrieve&db=Nucleotid
e&list_uids=04235321&dopt=GenBank">gb|AF081052.1|AF081052</a>   Eulemur
rubriventer cytochrome b (cy...    <a href = #4235321> 44</a>   0.001
<a
href="http://www.ncbi.nlm.nih.gov:80/entrez/query.fcgi?cmd=Retrieve&db=Nucleotid
e&list_uids=04235315&dopt=GenBank">gb|AF081049.1|AF081049</a>   Eulemur macaco
macaco cytochrome b (...    <a href = #4235315> 44</a>   0.001
<a
href="http://www.ncbi.nlm.nih.gov:80/entrez/query.fcgi?cmd=Retrieve&db=Nucleotid
e&list_uids=04235313&dopt=GenBank">gb|AF081048.1|AF081048</a>   Eulemur fulvus
albifrons cytochrome ...    <a href = #4235313> 44</a>   0.001
<a
href="http://www.ncbi.nlm.nih.gov:80/entrez/query.fcgi?cmd=Retrieve&db=Nucleotid
e&list_uids=03551922&dopt=GenBank">gb|AF082063.1|AF082063</a>   Elminia
longicauda cytochrome b gene...    <a href = #3551922> 44</a>   0.001
<a
href="http://www.ncbi.nlm.nih.gov:80/entrez/query.fcgi?cmd=Retrieve&db=Nucleotid
e&list_uids=04127863&dopt=GenBank">emb|AJ010957.1|HAAJ10957</a>   Hippopotamus
amphibius complete mi...    <a href = #4127863> 44</a>   0.001
<a
href="http://www.ncbi.nlm.nih.gov:80/entrez/query.fcgi?cmd=Retrieve&db=Nucleotid
e&list_uids=04098265&dopt=GenBank">gb|U76506.1|CLU76506</a>   Chlamydera
lauterbachii cytochrome b g...    <a href = #4098265> 44</a>   0.001
<a
href="http://www.ncbi.nlm.nih.gov:80/entrez/query.fcgi?cmd=Retrieve&db=Nucleotid
```

```
e&list_uids=04098261&dopt=GenBank">gb|U76504.1|CCU76504</a>   Chlamydera
cerviniventris cytochrome b...    <a href = #4098261> 44</a>   0.001
<a
href="http://www.ncbi.nlm.nih.gov:80/entrez/query.fcgi?cmd=Retrieve&db=Nucleotid
e&list_uids=04098259&dopt=GenBank">gb|U76505.1|ASU76505</a>   Amblyornis
subalaris cytochrome b gene...    <a href = #4098259> 44</a>   0.001
<a
href="http://www.ncbi.nlm.nih.gov:80/entrez/query.fcgi?cmd=Retrieve&db=Nucleotid
e&list_uids=04098257&dopt=GenBank">gb|U76503.1|APU76503</a>   Archboldia
papuensis cytochrome b gene...    <a href = #4098257> 44</a>   0.001
<a
href="http://www.ncbi.nlm.nih.gov:80/entrez/query.fcgi?cmd=Retrieve&db=Nucleotid
e&list_uids=04098255&dopt=GenBank">gb|U76508.1|AIU76508</a>   Amblyornis
inornatus cytochrome b gene...    <a href = #4098255> 44</a>   0.001
<a
href="http://www.ncbi.nlm.nih.gov:80/entrez/query.fcgi?cmd=Retrieve&db=Nucleotid
e&list_uids=02660921&dopt=GenBank">gb|AF034969.1|AF034969</a>   Connochaetes
taurinus cytochrome b g...    <a href = #2660921> 44</a>   0.001
<a
href="http://www.ncbi.nlm.nih.gov:80/entrez/query.fcgi?cmd=Retrieve&db=Nucleotid
e&list_uids=04079773&dopt=GenBank">gb|AF051876.1|AF051876</a>   Rhodeus ocellatus
cytochrome b (cytb...    <a href = #4079773> 44</a>   0.001
<a
href="http://www.ncbi.nlm.nih.gov:80/entrez/query.fcgi?cmd=Retrieve&db=Nucleotid
e&list_uids=03676657&dopt=GenBank">gb|AF082007.1|AF082007</a>   Vireo plumbeus
plumbeus specimen-vou...    <a href = #3676657> 44</a>   0.001
<a
href="http://www.ncbi.nlm.nih.gov:80/entrez/query.fcgi?cmd=Retrieve&db=Nucleotid
e&list_uids=03676655&dopt=GenBank">gb|AF082006.1|AF082006</a>   Vireo plumbeus
plumbeus specimen-vou...    <a href = #3676655> 44</a>   0.001
<a
href="http://www.ncbi.nlm.nih.gov:80/entrez/query.fcgi?cmd=Retrieve&db=Nucleotid
e&list_uids=03676653&dopt=GenBank">gb|AF082005.1|AF082005</a>   Vireo plumbeus
plumbeus specimen-vou...    <a href = #3676653> 44</a>   0.001
<a
href="http://www.ncbi.nlm.nih.gov:80/entrez/query.fcgi?cmd=Retrieve&db=Nucleotid
e&list_uids=03676651&dopt=GenBank">gb|AF082004.1|AF082004</a>   Vireo plumbeus
plumbeus specimen-vou...    <a href = #3676651> 44</a>   0.001
<a
href="http://www.ncbi.nlm.nih.gov:80/entrez/query.fcgi?cmd=Retrieve&db=Nucleotid
e&list_uids=03676649&dopt=GenBank">gb|AF082003.1|AF082003</a>   Vireo plumbeus
plumbeus specimen-vou...    <a href = #3676649> 44</a>   0.001
<a
href="http://www.ncbi.nlm.nih.gov:80/entrez/query.fcgi?cmd=Retrieve&db=Nucleotid
e&list_uids=03676647&dopt=GenBank">gb|AF082002.1|AF082002</a>   Vireo plumbeus
plumbeus specimen-vou...    <a href = #3676647> 44</a>   0.001
<a
href="http://www.ncbi.nlm.nih.gov:80/entrez/query.fcgi?cmd=Retrieve&db=Nucleotid
e&list_uids=03676645&dopt=GenBank">gb|AF082001.1|AF082001</a>   Vireo plumbeus
plumbeus specimen-vou...    <a href = #3676645> 44</a>   0.001
<a
href="http://www.ncbi.nlm.nih.gov:80/entrez/query.fcgi?cmd=Retrieve&db=Nucleotid
e&list_uids=03676643&dopt=GenBank">gb|AF082000.1|AF082000</a>   Vireo plumbeus
plumbeus specimen-vou...    <a href = #3676643> 44</a>   0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=03676641&dopt=GenBank">gb|AF081999.1|AF081999</a>   Vireo plumbeus
plumbeus specimen-vou...    <a href = #3676641> 44</a>   0.001
<a
href="http://www.ncbi.nlm.nih.gov:80/entrez/query.fcgi?cmd=Retrieve&db=Nucleotid
e&list_uids=03676639&dopt=GenBank">gb|AF081998.1|AF081998</a>   Vireo plumbeus
plumbeus specimen-vou...    <a href = #3676639> 44</a>   0.001
<a
href="http://www.ncbi.nlm.nih.gov:80/entrez/query.fcgi?cmd=Retrieve&db=Nucleotid
e&list_uids=03676637&dopt=GenBank">gb|AF081997.1|AF081997</a>   Vireo plumbeus
plumbeus specimen-vou...    <a href = #3676637> 44</a>   0.001
<a
href="http://www.ncbi.nlm.nih.gov:80/entrez/query.fcgi?cmd=Retrieve&db=Nucleotid
e&list_uids=03676635&dopt=GenBank">gb|AF081996.1|AF081996</a>   Vireo plumbeus
plumbeus specimen-vou...    <a href = #3676635> 44</a>   0.001
<a
href="http://www.ncbi.nlm.nih.gov:80/entrez/query.fcgi?cmd=Retrieve&db=Nucleotid
e&list_uids=03676633&dopt=GenBank">gb|AF081995.1|AF081995</a>   Vireo plumbeus
plumbeus specimen-vou...    <a href = #3676633> 44</a>   0.001
<a
href="http://www.ncbi.nlm.nih.gov:80/entrez/query.fcgi?cmd=Retrieve&db=Nucleotid
e&list_uids=03676631&dopt=GenBank">gb|AF081994.1|AF081994</a>   Vireo plumbeus
plumbeus specimen-vou...    <a href = #3676631> 44</a>   0.001
<a
href="http://www.ncbi.nlm.nih.gov:80/entrez/query.fcgi?cmd=Retrieve&db=Nucleotid
e&list_uids=03676629&dopt=GenBank">gb|AF081993.1|AF081993</a>   Vireo plumbeus
plumbeus specimen-vou...    <a href = #3676629> 44</a>   0.001
<a
href="http://www.ncbi.nlm.nih.gov:80/entrez/query.fcgi?cmd=Retrieve&db=Nucleotid
e&list_uids=03676627&dopt=GenBank">gb|AF081992.1|AF081992</a>   Vireo plumbeus
plumbeus specimen-vou...    <a href = #3676627> 44</a>   0.001
<a
href="http://www.ncbi.nlm.nih.gov:80/entrez/query.fcgi?cmd=Retrieve&db=Nucleotid
e&list_uids=03676625&dopt=GenBank">gb|AF081991.1|AF081991</a>   Vireo plumbeus
plumbeus specimen-vou...    <a href = #3676625> 44</a>   0.001
<a
href="http://www.ncbi.nlm.nih.gov:80/entrez/query.fcgi?cmd=Retrieve&db=Nucleotid
e&list_uids=00639944&dopt=GenBank">gb|S73150.1|S73150</a>   cytochrome b
[Spermophilus richardsonii=...    <a href = #639944> 44</a>   0.001
<a
href="http://www.ncbi.nlm.nih.gov:80/entrez/query.fcgi?cmd=Retrieve&db=Nucleotid
e&list_uids=02581990&dopt=GenBank">gb|AF012235.1|AF012235</a>   Cryptomys
hottentotus natalensis cyt...    <a href = #2581990> 44</a>   0.001
<a
href="http://www.ncbi.nlm.nih.gov:80/entrez/query.fcgi?cmd=Retrieve&db=Nucleotid
e&list_uids=01374743&dopt=GenBank">gb|U53580.1|NCU53580</a>   Nycticebus coucang
cytochrome b (cyt b...    <a href = #1374743> 44</a>   0.001
<a
href="http://www.ncbi.nlm.nih.gov:80/entrez/query.fcgi?cmd=Retrieve&db=Nucleotid
e&list_uids=01374731&dopt=GenBank">gb|U53577.1|EFU53577</a>   Eulemur fulvus
rufus cytochrome b (cyt...    <a href = #1374731> 44</a>   0.001
<a
href="http://www.ncbi.nlm.nih.gov:80/entrez/query.fcgi?cmd=Retrieve&db=Nucleotid
e&list_uids=01374729&dopt=GenBank">gb|U53576.1|EFU53576</a>   Eulemur fulvus
collaris cytochrome b (...    <a href = #1374729> 44</a>   0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=02253669&dopt=GenBank">gb|U95512.1|ESERCYTB2</a>   Eptesicus
serotinus 3' cytochrome b (...    <a href = #2253669> 44</a>   0.001
<a
href="http://www.ncbi.nlm.nih.gov:80/entrez/query.fcgi?cmd=Retrieve&db=Nucleotid
e&list_uids=02253659&dopt=GenBank">gb|U95508.1|PKUHLCYTB2</a>   Pipistrellus
kuhli 5' cytochrome b (...    <a href = #2253659> 44</a>   0.001
<a
href="http://www.ncbi.nlm.nih.gov:80/entrez/query.fcgi?cmd=Retrieve&db=Nucleotid
e&list_uids=01504122&dopt=GenBank">gb|U17868.1|BTU17868</a>   Budorcas taxicolor
taxicolor cytochrom...    <a href = #1504122> 44</a>   0.001
<a
href="http://www.ncbi.nlm.nih.gov:80/entrez/query.fcgi?cmd=Retrieve&db=Nucleotid
e&list_uids=01504120&dopt=GenBank">gb|U17867.1|BTU17867</a>   Budorcas taxicolor
bedfordi cytochrome...    <a href = #1504120> 44</a>   0.001
<a
href="http://www.ncbi.nlm.nih.gov:80/entrez/query.fcgi?cmd=Retrieve&db=Nucleotid
e&list_uids=00604327&dopt=GenBank">gb|U17860.1|ODU17860</a>   Ovis dalli
cytochrome b gene, mitochon...    <a href = #604327> 44</a>   0.001
<a
href="http://www.ncbi.nlm.nih.gov:80/entrez/query.fcgi?cmd=Retrieve&db=Nucleotid
e&list_uids=00604325&dopt=GenBank">gb|U17859.1|OCU17859</a>   Ovis canadensis
cytochrome b gene, mit...    <a href = #604325> 44</a>   0.001
<a
href="http://www.ncbi.nlm.nih.gov:80/entrez/query.fcgi?cmd=Retrieve&db=Nucleotid
e&list_uids=04127373&dopt=GenBank">emb|AJ010556.1|ASP010556</a>   Acomys
spinosissimus mitochondrial...    <a href = #4127373> 44</a>   0.001
<a
href="http://www.ncbi.nlm.nih.gov:80/entrez/query.fcgi?cmd=Retrieve&db=Nucleotid
e&list_uids=03417588&dopt=GenBank">gb|AF034736.1|AF034736</a>   Capra falconeri
cytochrome b (cytb) ...    <a href = #3417588> 44</a>   0.001
<a
href="http://www.ncbi.nlm.nih.gov:80/entrez/query.fcgi?cmd=Retrieve&db=Nucleotid
e&list_uids=03417576&dopt=GenBank">gb|AF034730.1|AF034730</a>   Ovis aries
cytochrome b (cytb) gene,...    <a href = #3417576> 44</a>   0.001
<a
href="http://www.ncbi.nlm.nih.gov:80/entrez/query.fcgi?cmd=Retrieve&db=Nucleotid
e&list_uids=03417574&dopt=GenBank">gb|AF034729.1|AF034729</a>   Ovis vignei
cytochrome b (cytb) gene...    <a href = #3417574> 44</a>   0.001
<a
href="http://www.ncbi.nlm.nih.gov:80/entrez/query.fcgi?cmd=Retrieve&db=Nucleotid
e&list_uids=03417572&dopt=GenBank">gb|AF034728.1|</a>   Ovis dalli dalli
cytochrome b (cytb) gene, m...    <a href = #3417572> 44</a>   0.001
<a
href="http://www.ncbi.nlm.nih.gov:80/entrez/query.fcgi?cmd=Retrieve&db=Nucleotid
e&list_uids=03417570&dopt=GenBank">gb|AF034727.1|</a>   Ovis ammon darwini
cytochrome b (cytb) gene,...    <a href = #3417570> 44</a>   0.001
<a
href="http://www.ncbi.nlm.nih.gov:80/entrez/query.fcgi?cmd=Retrieve&db=Nucleotid
e&list_uids=03417564&dopt=GenBank">gb|AF034724.1|AF034724</a>   Pantholops
hodgsoni cytochrome b (cy...    <a href = #3417564> 44</a>   0.001
<a
href="http://www.ncbi.nlm.nih.gov:80/entrez/query.fcgi?cmd=Retrieve&db=Nucleotid
e&list_uids=03417560&dopt=GenBank">gb|AF034722.1|AF034722</a>   Addax
nasomaculatus cytochrome b (cy...    <a href = #3417560> 44</a>   0.001
<a
href="http://www.ncbi.nlm.nih.gov:80/entrez/query.fcgi?cmd=Retrieve&db=Nucleotid
```

```
e&list_uids=01695902&dopt=GenBank">gb|U72038.1|MMU72038</a>   Monodon monoceros
cytochrome b (cytb),...    <a href = #1695902> 44</a>   0.001
<a
href="http://www.ncbi.nlm.nih.gov:80/entrez/query.fcgi?cmd=Retrieve&db=Nucleotid
e&list_uids=01695900&dopt=GenBank">gb|U72037.1|DLU72037</a>   Delphinapterus
leucas cytochrome b (cy...    <a href = #1695900> 44</a>   0.001
<a
href="http://www.ncbi.nlm.nih.gov:80/entrez/query.fcgi?cmd=Retrieve&db=Nucleotid
e&list_uids=01778700&dopt=GenBank">gb|M99455.1|MUXMTCYTB</a>   Murexia
longicaudata cytochrome b gen...    <a href = #1778700> 44</a>   0.001
<a
href="http://www.ncbi.nlm.nih.gov:80/entrez/query.fcgi?cmd=Retrieve&db=Nucleotid
e&list_uids=00456705&dopt=GenBank">gb|L29055.1|SHPMTDLOOP</a>   Sheep
mitochondrial cytochrome b (Cy...    <a href = #456705> 44</a>   0.001
<a
href="http://www.ncbi.nlm.nih.gov:80/entrez/query.fcgi?cmd=Retrieve&db=Nucleotid
e&list_uids=03551884&dopt=GenBank">gb|AF082047.1|AF082047</a>   Coccyzus
americanus cytochrome b gen...    <a href = #3551884> 44</a>   0.001
<a
href="http://www.ncbi.nlm.nih.gov:80/entrez/query.fcgi?cmd=Retrieve&db=Nucleotid
e&list_uids=03098355&dopt=GenBank">gb|AF038286.1|AF038286</a>   Antechinus
minimus cytochrome b gene...    <a href = #3098355> 44</a>   0.001
<a
href="http://www.ncbi.nlm.nih.gov:80/entrez/query.fcgi?cmd=Retrieve&db=Nucleotid
e&list_uids=03098351&dopt=GenBank">gb|AF038284.1|AF038284</a>   Antechinus
swainsonii cytochrome b g...    <a href = #3098351> 44</a>   0.001
<a
href="http://www.ncbi.nlm.nih.gov:80/entrez/query.fcgi?cmd=Retrieve&db=Nucleotid
e&list_uids=03088735&dopt=GenBank">gb|AF059093.1|AF059093</a>   Anas undulata
cytochrome b gene, par...    <a href = #3088735> 44</a>   0.001
<a
href="http://www.ncbi.nlm.nih.gov:80/entrez/query.fcgi?cmd=Retrieve&db=Nucleotid
e&list_uids=03088733&dopt=GenBank">gb|AF059092.1|AF059092</a>   Anas superciliosa
rogersi cytochrome...    <a href = #3088733> 44</a>   0.001
<a
href="http://www.ncbi.nlm.nih.gov:80/entrez/query.fcgi?cmd=Retrieve&db=Nucleotid
e&list_uids=03088731&dopt=GenBank">gb|AF059091.1|AF059091</a>   Anas sparsa
cytochrome b gene, parti...    <a href = #3088731> 44</a>   0.001
<a
href="http://www.ncbi.nlm.nih.gov:80/entrez/query.fcgi?cmd=Retrieve&db=Nucleotid
e&list_uids=03088709&dopt=GenBank">gb|AF059080.1|AF059080</a>   Anas melleri
cytochrome b gene, part...    <a href = #3088709> 44</a>   0.001
<a
href="http://www.ncbi.nlm.nih.gov:80/entrez/query.fcgi?cmd=Retrieve&db=Nucleotid
e&list_uids=03088705&dopt=GenBank">gb|AF059078.1|AF059078</a>   Anas laysanensis
cytochrome b gene, ...    <a href = #3088705> 44</a>   0.001
<a
href="http://www.ncbi.nlm.nih.gov:80/entrez/query.fcgi?cmd=Retrieve&db=Nucleotid
e&list_uids=02970664&dopt=GenBank">gb|AF052240.1|AF052240</a>   Anairetes
flavirostris cytochrome b ...    <a href = #2970664> 44</a>   0.001
<a
href="http://www.ncbi.nlm.nih.gov:80/entrez/query.fcgi?cmd=Retrieve&db=Nucleotid
e&list_uids=02935094&dopt=GenBank">gb|AF006240.1|AF006240</a>   Mitrospingus
cassinii cytochrome b (...    <a href = #2935094> 44</a>   0.001
<a
href="http://www.ncbi.nlm.nih.gov:80/entrez/query.fcgi?cmd=Retrieve&db=Nucleotid
```

```
e&list_uids=02935068&dopt=GenBank">gb|AF006227.1|AF006227</a>   Dacnis cayana
cytochrome b (cytb) ge...    <a href = #2935068> 44</a>   0.001
<a
href="http://www.ncbi.nlm.nih.gov:80/entrez/query.fcgi?cmd=Retrieve&db=Nucleotid
e&list_uids=02921858&dopt=GenBank">gb|AF047447.1|AF047447</a>   Oryx leucoryx
cytochrome b gene, mit...    <a href = #2921858> 44</a>   0.001
<a
href="http://www.ncbi.nlm.nih.gov:80/entrez/query.fcgi?cmd=Retrieve&db=Nucleotid
e&list_uids=02905822&dopt=GenBank">gb|U07576.1|AHU07576</a>   Antechinus habbema
mitochondrion cytoc...    <a href = #2905822> 44</a>   0.001
<a
href="http://www.ncbi.nlm.nih.gov:80/entrez/query.fcgi?cmd=Retrieve&db=Nucleotid
e&list_uids=02828646&dopt=GenBank">gb|AF028180.1|AF028180</a>   Urocyon
cinereoargenteus cytochrome ...    <a href = #2828646> 44</a>   0.001
<a
href="http://www.ncbi.nlm.nih.gov:80/entrez/query.fcgi?cmd=Retrieve&db=Nucleotid
e&list_uids=02828644&dopt=GenBank">gb|AF028178.1|AF028178</a>   Pseudalopex
sechurae cytochrome b (c...    <a href = #2828644> 44</a>   0.001
<a
href="http://www.ncbi.nlm.nih.gov:80/entrez/query.fcgi?cmd=Retrieve&db=Nucleotid
e&list_uids=02828638&dopt=GenBank">gb|AF028170.1|AF028170</a>   Vulpes zerda
cytochrome b (cytb) gen...    <a href = #2828638> 44</a>   0.001
<a
href="http://www.ncbi.nlm.nih.gov:80/entrez/query.fcgi?cmd=Retrieve&db=Nucleotid
e&list_uids=01773228&dopt=GenBank">gb|M99454.1|ASWMTSCYTB</a>   Antechinus
stuartii cytochrome b gen...    <a href = #1773228> 44</a>   0.001
<a
href="http://www.ncbi.nlm.nih.gov:80/entrez/query.fcgi?cmd=Retrieve&db=Nucleotid
e&list_uids=01773232&dopt=GenBank">gb|M99453.1|ASWMTCYTB</a>   Antechinus
swainsonii cytochrome b ge...    <a href = #1773232> 44</a>   0.001
<a
href="http://www.ncbi.nlm.nih.gov:80/entrez/query.fcgi?cmd=Retrieve&db=Nucleotid
e&list_uids=02689878&dopt=GenBank">gb|U23461.1|ANU23461</a>   Antechinus naso
cytochrome b gene, mit...    <a href = #2689878> 44</a>   0.001
<a
href="http://www.ncbi.nlm.nih.gov:80/entrez/query.fcgi?cmd=Retrieve&db=Nucleotid
e&list_uids=02149540&dopt=GenBank">gb|U87138.1|TVU87138</a>   Trichosurus
vulpecula cytochrome b (cy...    <a href = #2149540> 44</a>   0.001
<a
href="http://www.ncbi.nlm.nih.gov:80/entrez/query.fcgi?cmd=Retrieve&db=Nucleotid
e&list_uids=02677661&dopt=GenBank">gb|U07590.1|PMU07590</a>   Planigale maculata
mitochondrion cytoc...    <a href = #2677661> 44</a>   0.001
<a
href="http://www.ncbi.nlm.nih.gov:80/entrez/query.fcgi?cmd=Retrieve&db=Nucleotid
e&list_uids=09998878&dopt=GenBank">emb|AJ004326.1|PTAJ4326</a>   Phylloscopus
trochilus mitochondria...    <a href = #9998878> 44</a>   0.001
<a
href="http://www.ncbi.nlm.nih.gov:80/entrez/query.fcgi?cmd=Retrieve&db=Nucleotid
e&list_uids=02444366&dopt=GenBank">gb|AF020255.1|AF020255</a>   Cyclura nubila
cytochrome b (cytb) g...    <a href = #2444366> 44</a>   0.001
<a
href="http://www.ncbi.nlm.nih.gov:80/entrez/query.fcgi?cmd=Retrieve&db=Nucleotid
e&list_uids=09558343&dopt=GenBank">emb|Y19184.1|LPA19184</a>   Lama pacos
complete mitochondrial genome    <a href = #9558343> 44</a>   0.001
<a
href="http://www.ncbi.nlm.nih.gov:80/entrez/query.fcgi?cmd=Retrieve&db=Nucleotid
```

```
e&list_uids=02290362&dopt=GenBank">gb|U88862.1|</a>  Amphilophus citrinellum
cytochrome b (cytb) ge...    <a href = #2290362> 44</a>   0.001
<a
href="http://www.ncbi.nlm.nih.gov:80/entrez/query.fcgi?cmd=Retrieve&db=Nucleotid
e&list_uids=02290356&dopt=GenBank">gb|U88859.1|</a>  Thorichthys aureum
cytochrome b (cytb) gene, m...    <a href = #2290356> 44</a>   0.001
<a
href="http://www.ncbi.nlm.nih.gov:80/entrez/query.fcgi?cmd=Retrieve&db=Nucleotid
e&list_uids=02290354&dopt=GenBank">gb|U88858.1|</a>  Thorichthys cf. aureum
cytochrome b (cytb) gen...    <a href = #2290354> 44</a>   0.001
<a
href="http://www.ncbi.nlm.nih.gov:80/entrez/query.fcgi?cmd=Retrieve&db=Nucleotid
e&list_uids=02290352&dopt=GenBank">gb|U88857.1|</a>  Herichthys labridens
cytochrome b (cytb) gene,...    <a href = #2290352> 44</a>   0.001
<a
href="http://www.ncbi.nlm.nih.gov:80/entrez/query.fcgi?cmd=Retrieve&db=Nucleotid
e&list_uids=02290350&dopt=GenBank">gb|U88856.1|</a>  Herichthys carpintis
cytochrome b (cytb) gene,...    <a href = #2290350> 44</a>   0.001
<a
href="http://www.ncbi.nlm.nih.gov:80/entrez/query.fcgi?cmd=Retrieve&db=Nucleotid
e&list_uids=01850861&dopt=GenBank">emb|Y10524.1|MIMRGEN</a>  Macropus robustus
complete mitochondri...    <a href = #1850861> 44</a>   0.001
<a
href="http://www.ncbi.nlm.nih.gov:80/entrez/query.fcgi?cmd=Retrieve&db=Nucleotid
e&list_uids=02098662&dopt=GenBank">gb|U81357.1|CSU81357</a>  Chelydra serpentina
cytochrome b gene,...    <a href = #2098662> 44</a>   0.001
<a
href="http://www.ncbi.nlm.nih.gov:80/entrez/query.fcgi?cmd=Retrieve&db=Nucleotid
e&list_uids=02098654&dopt=GenBank">gb|U81356.1|CLU81356</a>  Chelodina
longicollis cytochrome b gen...    <a href = #2098654> 44</a>   0.001
<a
href="http://www.ncbi.nlm.nih.gov:80/entrez/query.fcgi?cmd=Retrieve&db=Nucleotid
e&list_uids=01923224&dopt=GenBank">gb|U75354.1|LUU75354</a>  Leptomyrmex
unicolor cytochrome b gene...    <a href = #1923224> 44</a>   0.001
<a
href="http://www.ncbi.nlm.nih.gov:80/entrez/query.fcgi?cmd=Retrieve&db=Nucleotid
e&list_uids=01841718&dopt=GenBank">gb|U77332.1|GCU77332</a>  Gymnorhinus
cyanocephala cytochrome-b ...    <a href = #1841718> 44</a>   0.001
<a
href="http://www.ncbi.nlm.nih.gov:80/entrez/query.fcgi?cmd=Retrieve&db=Nucleotid
e&list_uids=00452251&dopt=GenBank">emb|Z29573.1|DVMTGNME</a>  Didelphis
virginiana complete mitocho...    <a href = #452251> 44</a>   0.001
<a
href="http://www.ncbi.nlm.nih.gov:80/entrez/query.fcgi?cmd=Retrieve&db=Nucleotid
e&list_uids=03483071&dopt=GenBank">emb|AJ222679.1|BTCYTOB</a>  Boselaphus
tragocamelus mitochondria...    <a href = #3483071> 44</a>   0.001
<a
href="http://www.ncbi.nlm.nih.gov:80/entrez/query.fcgi?cmd=Retrieve&db=Nucleotid
e&list_uids=03492812&dopt=GenBank">emb|AJ222680.1|TSCYTOB</a>  Tragelaphus
spekii mitochondrial cyt...    <a href = #3492812> 44</a>   0.001
<a
href="http://www.ncbi.nlm.nih.gov:80/entrez/query.fcgi?cmd=Retrieve&db=Nucleotid
e&list_uids=03492814&dopt=GenBank">emb|AJ222685.1|ODCYTOB</a>  Oryx dammah
mitochondrial cytochrome...    <a href = #3492814> 44</a>   0.001
<a
href="http://www.ncbi.nlm.nih.gov:80/entrez/query.fcgi?cmd=Retrieve&db=Nucleotid
```

```
e&list_uids=01778698&dopt=GenBank">gb|M99466.1|PMLMTCYTB</a>   Perameles nasuta
cytochrome b gene, c...    <a href = #1778698> 44</a>   0.001
<a
href="http://www.ncbi.nlm.nih.gov:80/entrez/query.fcgi?cmd=Retrieve&db=Nucleotid
e&list_uids=01778696&dopt=GenBank">gb|M99452.1|THNMTCYTB</a>   Thylacinus
cyncocephalus cytochrome b...    <a href = #1778696> 44</a>   0.001
<a
href="http://www.ncbi.nlm.nih.gov:80/entrez/query.fcgi?cmd=Retrieve&db=Nucleotid
e&list_uids=01777381&dopt=GenBank">gb|M99460.1|DAVMTCYTB</a>   Dasyurus
hallucatus cytochrome b gene...    <a href = #1777381> 44</a>   0.001
<a
href="http://www.ncbi.nlm.nih.gov:80/entrez/query.fcgi?cmd=Retrieve&db=Nucleotid
e&list_uids=00841453&dopt=GenBank">gb|U25737.1|PMU25737</a>   Paradisaea minor
cytochrome b gene, mi...    <a href = #841453> 44</a>   0.001
<a
href="http://www.ncbi.nlm.nih.gov:80/entrez/query.fcgi?cmd=Retrieve&db=Nucleotid
e&list_uids=00840938&dopt=GenBank">gb|U15203.1|PRU15203</a>   Paradisaea rudolphi
mitochondrion cyto...    <a href = #840938> 44</a>   0.001
<a
href="http://www.ncbi.nlm.nih.gov:80/entrez/query.fcgi?cmd=Retrieve&db=Nucleotid
e&list_uids=00840942&dopt=GenBank">gb|U15205.1|EAU15205</a>   Epimachus albertisi
mitochondrion cyto...    <a href = #840942> 44</a>   0.001
<a
href="http://www.ncbi.nlm.nih.gov:80/entrez/query.fcgi?cmd=Retrieve&db=Nucleotid
e&list_uids=00840932&dopt=GenBank">gb|U15200.1|DRU15200</a>   Diphyllodes
respublica mitochondrion c...    <a href = #840932> 44</a>   0.001
<a
href="http://www.ncbi.nlm.nih.gov:80/entrez/query.fcgi?cmd=Retrieve&db=Nucleotid
e&list_uids=03320079&dopt=GenBank">emb|AJ000424.1|STAJ424</a>   Sorex tundrensis
partial mitochondri...    <a href = #3320079> 44</a>   0.001
<a
href="http://www.ncbi.nlm.nih.gov:80/entrez/query.fcgi?cmd=Retrieve&db=Nucleotid
e&list_uids=03327022&dopt=GenBank">emb|AJ000423.1|STAJ423</a>   Sorex tundrensis
partial mitochondri...    <a href = #3327022> 44</a>   0.001
<a
href="http://www.ncbi.nlm.nih.gov:80/entrez/query.fcgi?cmd=Retrieve&db=Nucleotid
e&list_uids=03320026&dopt=GenBank">emb|AJ000438.1|SIAJ438</a>   Sorex isodon
partial mitochondrial c...    <a href = #3320026> 44</a>   0.001
<a
href="http://www.ncbi.nlm.nih.gov:80/entrez/query.fcgi?cmd=Retrieve&db=Nucleotid
e&list_uids=03320024&dopt=GenBank">emb|AJ000437.1|SIAJ437</a>   Sorex isodon
partial mitochondrial c...    <a href = #3320024> 44</a>   0.001
<a
href="http://www.ncbi.nlm.nih.gov:80/entrez/query.fcgi?cmd=Retrieve&db=Nucleotid
e&list_uids=03320001&dopt=GenBank">emb|AJ000428.1|SAAJ428</a>   Sorex arcticus
partial mitochondrial...    <a href = #3320001> 44</a>   0.001
<a
href="http://www.ncbi.nlm.nih.gov:80/entrez/query.fcgi?cmd=Retrieve&db=Nucleotid
e&list_uids=03319999&dopt=GenBank">emb|AJ000427.1|SAAJ427</a>   Sorex arcticus
ssp. maritimensis par...    <a href = #3319999> 44</a>   0.001
<a
href="http://www.ncbi.nlm.nih.gov:80/entrez/query.fcgi?cmd=Retrieve&db=Nucleotid
e&list_uids=03319997&dopt=GenBank">emb|AJ000426.1|SAAJ426</a>   Sorex asper
partial mitochondrial cy...    <a href = #3319997> 44</a>   0.001
<a
href="http://www.ncbi.nlm.nih.gov:80/entrez/query.fcgi?cmd=Retrieve&db=Nucleotid
```

```
e&list_uids=03319995&dopt=GenBank">emb|AJ000425.1|SAAJ425</a>   Sorex asper
partial mitochondrial cy...    <a href = #3319995> 44</a>   0.001
<a
href="http://www.ncbi.nlm.nih.gov:80/entrez/query.fcgi?cmd=Retrieve&db=Nucleotid
e&list_uids=03320014&dopt=GenBank">emb|AJ000418.1|SGAJ418</a>   Sorex granarius
partial mitochondria...    <a href = #3320014> 44</a>   0.001
<a
href="http://www.ncbi.nlm.nih.gov:80/entrez/query.fcgi?cmd=Retrieve&db=Nucleotid
e&list_uids=03320012&dopt=GenBank">emb|AJ000417.1|SGAJ417</a>   Sorex granarius
partial mitochondria...    <a href = #3320012> 44</a>   0.001
<a
href="http://www.ncbi.nlm.nih.gov:80/entrez/query.fcgi?cmd=Retrieve&db=Nucleotid
e&list_uids=03319993&dopt=GenBank">emb|AJ000416.1|SAAJ416</a>   Sorex araneus
partial mitochondrial ...    <a href = #3319993> 44</a>   0.001
<a
href="http://www.ncbi.nlm.nih.gov:80/entrez/query.fcgi?cmd=Retrieve&db=Nucleotid
e&list_uids=04691252&dopt=GenBank">emb|AJ004793.1|HCAJ4793</a>   Hippolais
caligata ssp. caligata mi...    <a href = #4691252> 44</a>   0.001
<a
href="http://www.ncbi.nlm.nih.gov:80/entrez/query.fcgi?cmd=Retrieve&db=Nucleotid
e&list_uids=04691250&dopt=GenBank">emb|AJ004792.1|HCAJ4792</a>   Hippolais
caligata ssp. rama mitoch...    <a href = #4691250> 44</a>   0.001
<a
href="http://www.ncbi.nlm.nih.gov:80/entrez/query.fcgi?cmd=Retrieve&db=Nucleotid
e&list_uids=01256207&dopt=GenBank">gb|U15718.1|RSU15718</a>   Ramphocelus
sanguinolentus cytochrome ...    <a href = #1256207> 44</a>   0.001
<a
href="http://www.ncbi.nlm.nih.gov:80/entrez/query.fcgi?cmd=Retrieve&db=Nucleotid
e&list_uids=00336482&dopt=GenBank">gb|L11905.1|CGYMTCYTBD</a>   Cratogeomys
gymnurus mitochondrial c...    <a href = #336482> 44</a>   0.001
<a
href="http://www.ncbi.nlm.nih.gov:80/entrez/query.fcgi?cmd=Retrieve&db=Nucleotid
e&list_uids=01041865&dopt=GenBank">gb|U34679.1|POU34679</a>   Philander opossum
cytochrome b light s...    <a href = #1041865> 44</a>   0.001
<a
href="http://www.ncbi.nlm.nih.gov:80/entrez/query.fcgi?cmd=Retrieve&db=Nucleotid
e&list_uids=00336486&dopt=GenBank">gb|L11907.1|CGYMTCYTBF</a>   Cratogeomys
goldmani rubellus mitoch...    <a href = #336486> 44</a>   0.001
<a
href="http://www.ncbi.nlm.nih.gov:80/entrez/query.fcgi?cmd=Retrieve&db=Nucleotid
e&list_uids=00336484&dopt=GenBank">gb|L11906.1|CGYMTCYTBE</a>   Cratogeomys
merriami mitochondrial c...    <a href = #336484> 44</a>   0.001
<a
href="http://www.ncbi.nlm.nih.gov:80/entrez/query.fcgi?cmd=Retrieve&db=Nucleotid
e&list_uids=00336476&dopt=GenBank">gb|L11902.1|CGYMTCYTBA</a>   Cratogeomys
castanops castanops mito...    <a href = #336476> 44</a>   0.001
<a
href="http://www.ncbi.nlm.nih.gov:80/entrez/query.fcgi?cmd=Retrieve&db=Nucleotid
e&list_uids=01199854&dopt=GenBank">emb|X92524.1|SLCYTB</a>   S.longirostris
cytochrome b gene (compl...    <a href = #1199854> 44</a>   0.001
<a
href="http://www.ncbi.nlm.nih.gov:80/entrez/query.fcgi?cmd=Retrieve&db=Nucleotid
e&list_uids=01197600&dopt=GenBank">gb|U46771.1|ACU46771</a>   Anthus campestris
cytochrome b gene, m...    <a href = #1197600> 44</a>   0.001
<a
href="http://www.ncbi.nlm.nih.gov:80/entrez/query.fcgi?cmd=Retrieve&db=Nucleotid
```

```
e&list_uids=12248822&dopt=GenBank">dbj|AB021773.1|AB021773</a>  Anguilla
interioris mitochondrial c...    <a href = #12248822>  44</a>   0.001
<a
href="http://www.ncbi.nlm.nih.gov:80/entrez/query.fcgi?cmd=Retrieve&db=Nucleotid
e&list_uids=03288686&dopt=GenBank">dbj|AB006953.1|AB006953</a>  Carassius
auratus langsdorfi mitoch...    <a href = #3288686>  44</a>   0.001
<a
href="http://www.ncbi.nlm.nih.gov:80/entrez/query.fcgi?cmd=Retrieve&db=Nucleotid
e&list_uids=01332568&dopt=GenBank">emb|Z73492.1|MTPTRCYTB</a>  P.trochilus
mitochondrial cytochrome...    <a href = #1332568>  44</a>   0.001
<a
href="http://www.ncbi.nlm.nih.gov:80/entrez/query.fcgi?cmd=Retrieve&db=Nucleotid
e&list_uids=11862853&dopt=GenBank">dbj|AB035239.1|AB035239</a>  Osteoglossum
ferreirai mitochondria...    <a href = #11862853>  44</a>   0.001
<a
href="http://www.ncbi.nlm.nih.gov:80/entrez/query.fcgi?cmd=Retrieve&db=Nucleotid
e&list_uids=01199828&dopt=GenBank">emb|X92532.1|MMCYTB2</a>  M.monoceros
cytochrome b gene (complet...    <a href = #1199828>  44</a>   0.001
<a
href="http://www.ncbi.nlm.nih.gov:80/entrez/query.fcgi?cmd=Retrieve&db=Nucleotid
e&list_uids=00396737&dopt=GenBank">emb|X74260.1|MIVOCYTB</a>  V.olivaceus
mitochondrion gene for cy...    <a href = #396737>  44</a>   0.001
<a
href="http://www.ncbi.nlm.nih.gov:80/entrez/query.fcgi?cmd=Retrieve&db=Nucleotid
e&list_uids=00013628&dopt=GenBank">emb|X56293.1|MISLCYTBB</a>  S.longiroshis
mitochondrion cytb gen...    <a href = #13628>  44</a>   0.001
<a
href="http://www.ncbi.nlm.nih.gov:80/entrez/query.fcgi?cmd=Retrieve&db=Nucleotid
e&list_uids=00013626&dopt=GenBank">emb|X56292.1|MISLCYTBA</a>  S.longirostris
mitochondrion cytb ge...    <a href = #13626>  44</a>   0.001
<a
href="http://www.ncbi.nlm.nih.gov:80/entrez/query.fcgi?cmd=Retrieve&db=Nucleotid
e&list_uids=00396735&dopt=GenBank">emb|X74256.1|MIPVCYTB</a>  P.violaceus
mitochondrion gene for cy...    <a href = #396735>  44</a>   0.001
<a
href="http://www.ncbi.nlm.nih.gov:80/entrez/query.fcgi?cmd=Retrieve&db=Nucleotid
e&list_uids=00693973&dopt=GenBank">emb|X82304.1|MIPHCYTBG</a>  P.hispida
mitochondrial cytochrome b...    <a href = #693973>  44</a>   0.001
<a
href="http://www.ncbi.nlm.nih.gov:80/entrez/query.fcgi?cmd=Retrieve&db=Nucleotid
e&list_uids=00693969&dopt=GenBank">emb|X82302.1|MIPFCYTBG</a>  P.fasciata
mitochondrial cytochrome ...    <a href = #693969>  44</a>   0.001
<a
href="http://www.ncbi.nlm.nih.gov:80/entrez/query.fcgi?cmd=Retrieve&db=Nucleotid
e&list_uids=00013156&dopt=GenBank">emb|X56284.1|MIOACYTB</a>  O.aries
mitochondrion cytb gene for c...    <a href = #13156>  44</a>   0.001
<a
href="http://www.ncbi.nlm.nih.gov:80/entrez/query.fcgi?cmd=Retrieve&db=Nucleotid
e&list_uids=00396731&dopt=GenBank">emb|X74252.1|MIMKCYTB</a>  M.keraudrenii
mitochondrion gene for ...    <a href = #396731>  44</a>   0.001
<a
href="http://www.ncbi.nlm.nih.gov:80/entrez/query.fcgi?cmd=Retrieve&db=Nucleotid
e&list_uids=00414771&dopt=GenBank">emb|X72005.1|MILWCYTB</a>  L.weddelli
mitochondrial gene for cyt...    <a href = #414771>  44</a>   0.001
<a
href="http://www.ncbi.nlm.nih.gov:80/entrez/query.fcgi?cmd=Retrieve&db=Nucleotid
```

```
e&list_uids=00396729&dopt=GenBank">emb|X74259.1|MILLCYTB</a>  L.ludovicianus
mitochondrion gene for...    <a href = #396729> 44</a>   0.001
<a
href="http://www.ncbi.nlm.nih.gov:80/entrez/query.fcgi?cmd=Retrieve&db=Nucleotid
e&list_uids=02154895&dopt=GenBank">emb|Y08814.1|MIHLCYTBG</a>  H.liberiensis
mitochondrial cytochro...    <a href = #2154895> 44</a>   0.001
<a
href="http://www.ncbi.nlm.nih.gov:80/entrez/query.fcgi?cmd=Retrieve&db=Nucleotid
e&list_uids=02154892&dopt=GenBank">emb|Y08813.1|MIHACYTB</a>  H.amphibius
mitochondrial cytochrome ...    <a href = #2154892> 44</a>   0.001
<a
href="http://www.ncbi.nlm.nih.gov:80/entrez/query.fcgi?cmd=Retrieve&db=Nucleotid
e&list_uids=00012951&dopt=GenBank">emb|X56287.1|MIGCCYTB</a>  G.camelopardalis
mitochondrion cytb g...    <a href = #12951> 44</a>   0.001
<a
href="http://www.ncbi.nlm.nih.gov:80/entrez/query.fcgi?cmd=Retrieve&db=Nucleotid
e&list_uids=00396725&dopt=GenBank">emb|X74253.1|MIEFCYTB</a>  E.fastuosus
mitochondrion gene for cy...    <a href = #396725> 44</a>   0.001
<a
href="http://www.ncbi.nlm.nih.gov:80/entrez/query.fcgi?cmd=Retrieve&db=Nucleotid
e&list_uids=00012941&dopt=GenBank">emb|X60941.1|MIEACB33</a>  Epimachus
albertisii mitochondrial ge...    <a href = #12941> 44</a>   0.001
<a
href="http://www.ncbi.nlm.nih.gov:80/entrez/query.fcgi?cmd=Retrieve&db=Nucleotid
e&list_uids=00396723&dopt=GenBank">emb|X74255.1|MIDMCYTB</a>  D.magnificus
mitochondrion gene for c...    <a href = #396723> 44</a>   0.001
<a
href="http://www.ncbi.nlm.nih.gov:80/entrez/query.fcgi?cmd=Retrieve&db=Nucleotid
e&list_uids=00012871&dopt=GenBank">emb|X56289.1|MICHCYTB</a>  C.hircus
mitochondrion cytb gene for ...    <a href = #12871> 44</a>   0.001
<a
href="http://www.ncbi.nlm.nih.gov:80/entrez/query.fcgi?cmd=Retrieve&db=Nucleotid
e&list_uids=00012800&dopt=GenBank">emb|V00654.1|MIBTXX</a>  Bos taurus complete
mitochondrial genome      <a href = #12800> 44</a>   0.001
<a
href="http://www.ncbi.nlm.nih.gov:80/entrez/query.fcgi?cmd=Retrieve&db=Nucleotid
e&list_uids=00012683&dopt=GenBank">emb|X60940.1|MIAMCB33</a>  A.macgregoriae
mitochondrial gene for...    <a href = #12683> 44</a>   0.001
<a
href="http://www.ncbi.nlm.nih.gov:80/entrez/query.fcgi?cmd=Retrieve&db=Nucleotid
e&list_uids=01199826&dopt=GenBank">emb|X92530.1|LACYTB</a>  L.albirostris
cytochrome b gene (comple...    <a href = #1199826> 44</a>   0.001
<a
href="http://www.ncbi.nlm.nih.gov:80/entrez/query.fcgi?cmd=Retrieve&db=Nucleotid
e&list_uids=00487613&dopt=GenBank">gb|U09265.1|CAU09265</a>  Coccyzus americanus
mitochondrion cyto...    <a href = #487613> 44</a>   0.001
<a
href="http://www.ncbi.nlm.nih.gov:80/entrez/query.fcgi?cmd=Retrieve&db=Nucleotid
e&list_uids=09844992&dopt=GenBank">dbj|AB023906.1|AB023906</a>  Petaurista
leucogenys mitochondrial...    <a href = #9844992> 44</a>   0.001
<a
href="http://www.ncbi.nlm.nih.gov:80/entrez/query.fcgi?cmd=Retrieve&db=Nucleotid
e&list_uids=09844990&dopt=GenBank">dbj|AB023905.1|AB023905</a>  Petaurista
leucogenys mitochondrial...    <a href = #9844990> 44</a>   0.001
<a
href="http://www.ncbi.nlm.nih.gov:80/entrez/query.fcgi?cmd=Retrieve&db=Nucleotid
```

```
e&list_uids=09844988&dopt=GenBank">dbj|AB023904.1|AB023904</a>  Petaurista
leucogenys mitochondrial...    <a href = #9844988> 44</a>   0.001
<a
href="http://www.ncbi.nlm.nih.gov:80/entrez/query.fcgi?cmd=Retrieve&db=Nucleotid
e&list_uids=09844986&dopt=GenBank">dbj|AB023903.1|AB023903</a>  Petaurista
leucogenys mitochondrial...    <a href = #9844986> 44</a>   0.001
<a
href="http://www.ncbi.nlm.nih.gov:80/entrez/query.fcgi?cmd=Retrieve&db=Nucleotid
e&list_uids=01695710&dopt=GenBank">dbj|D88983.1|D88983</a>  Bubalus bubalis
mitochondrial DNA for c...    <a href = #1695710> 44</a>   0.001
<a
href="http://www.ncbi.nlm.nih.gov:80/entrez/query.fcgi?cmd=Retrieve&db=Nucleotid
e&list_uids=01707345&dopt=GenBank">dbj|D88638.1|D88638</a>  Bubalus bubalis
mitochondrial DNA for c...    <a href = #1707345> 44</a>   0.001
<a
href="http://www.ncbi.nlm.nih.gov:80/entrez/query.fcgi?cmd=Retrieve&db=Nucleotid
e&list_uids=01707341&dopt=GenBank">dbj|D88636.1|D88636</a>  Bubalus bubalis
mitochondrial DNA for c...    <a href = #1707341> 44</a>   0.001
<a
href="http://www.ncbi.nlm.nih.gov:80/entrez/query.fcgi?cmd=Retrieve&db=Nucleotid
e&list_uids=01707339&dopt=GenBank">dbj|D88635.1|D88635</a>  Bubalus bubalis
mitochondrial DNA for c...    <a href = #1707339> 44</a>   0.001
<a
href="http://www.ncbi.nlm.nih.gov:80/entrez/query.fcgi?cmd=Retrieve&db=Nucleotid
e&list_uids=01707335&dopt=GenBank">dbj|D88633.1|D88633</a>  Bubalus bubalis
mitochondrial DNA for c...    <a href = #1707335> 44</a>   0.001
<a
href="http://www.ncbi.nlm.nih.gov:80/entrez/query.fcgi?cmd=Retrieve&db=Nucleotid
e&list_uids=01707333&dopt=GenBank">dbj|D88632.1|D88632</a>  Bubalus bubalis
mitochondrial DNA for c...    <a href = #1707333> 44</a>   0.001
<a
href="http://www.ncbi.nlm.nih.gov:80/entrez/query.fcgi?cmd=Retrieve&db=Nucleotid
e&list_uids=01707329&dopt=GenBank">dbj|D88630.1|D88630</a>  Bubalus bubalis
mitochondrial DNA for c...    <a href = #1707329> 44</a>   0.001
<a
href="http://www.ncbi.nlm.nih.gov:80/entrez/query.fcgi?cmd=Retrieve&db=Nucleotid
e&list_uids=01707325&dopt=GenBank">dbj|D88628.1|D88628</a>  Bubalus bubalis
mitochondrial DNA for c...    <a href = #1707325> 44</a>   0.001
<a
href="http://www.ncbi.nlm.nih.gov:80/entrez/query.fcgi?cmd=Retrieve&db=Nucleotid
e&list_uids=01707323&dopt=GenBank">dbj|D88627.1|D88627</a>  Bubalus bubalis
mitochondrial DNA for c...    <a href = #1707323> 44</a>   0.001
<a
href="http://www.ncbi.nlm.nih.gov:80/entrez/query.fcgi?cmd=Retrieve&db=Nucleotid
e&list_uids=01256164&dopt=GenBank">dbj|D84204.1|GOTMTCBD</a>  Capra aegagrus
mitochondrial DNA for ...    <a href = #1256164> 44</a>   0.001
<a
href="http://www.ncbi.nlm.nih.gov:80/entrez/query.fcgi?cmd=Retrieve&db=Nucleotid
e&list_uids=01256162&dopt=GenBank">dbj|D84202.1|GOTMTCBB</a>  Capra falconeri
mitochondrial DNA for...    <a href = #1256162> 44</a>   0.001
<a
href="http://www.ncbi.nlm.nih.gov:80/entrez/query.fcgi?cmd=Retrieve&db=Nucleotid
e&list_uids=01813364&dopt=GenBank">dbj|D82893.1|D82893</a>  Bubalus bubalis
mitochondrial DNA for c...    <a href = #1813364> 44</a>   0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=01813362&dopt=GenBank">dbj|D82892.1|D82892</a>  Bubalus bubalis
mitochondrial DNA for c...    <a href = #1813362> 44</a>   0.001
<a
href="http://www.ncbi.nlm.nih.gov:80/entrez/query.fcgi?cmd=Retrieve&db=Nucleotid
e&list_uids=01813356&dopt=GenBank">dbj|D82889.1|D82889</a>  Bos javanicus
mitochondrial DNA for cyt...    <a href = #1813356> 44</a>   0.001
<a
href="http://www.ncbi.nlm.nih.gov:80/entrez/query.fcgi?cmd=Retrieve&db=Nucleotid
e&list_uids=00516653&dopt=GenBank">dbj|D32193.1|BBUMTCB23</a>  Bubalus arnee
bubalis mitochondrial ...    <a href = #516653> 44</a>   0.001
<a
href="http://www.ncbi.nlm.nih.gov:80/entrez/query.fcgi?cmd=Retrieve&db=Nucleotid
e&list_uids=00517076&dopt=GenBank">dbj|D34637.1|BBUMTCBA</a>  Bubalus bubalis
mitochondrial gene fo...    <a href = #517076> 44</a>   0.001
<a
href="http://www.ncbi.nlm.nih.gov:80/entrez/query.fcgi?cmd=Retrieve&db=Nucleotid
e&list_uids=02189986&dopt=GenBank">dbj|AB004074.1|AB004074</a>  Capra hircus
mitochondrial DNA for ...    <a href = #2189986> 44</a>   0.001
<a
href="http://www.ncbi.nlm.nih.gov:80/entrez/query.fcgi?cmd=Retrieve&db=Nucleotid
e&list_uids=02189984&dopt=GenBank">dbj|AB004072.1|AB004072</a>  Capra hircus
mitochondrial DNA for ...    <a href = #2189984> 44</a>   0.001
<a
href="http://www.ncbi.nlm.nih.gov:80/entrez/query.fcgi?cmd=Retrieve&db=Nucleotid
e&list_uids=02189983&dopt=GenBank">dbj|AB004071.1|AB004071</a>  Capra hircus
mitochondrial DNA for ...    <a href = #2189983> 44</a>   0.001
<a
href="http://www.ncbi.nlm.nih.gov:80/entrez/query.fcgi?cmd=Retrieve&db=Nucleotid
e&list_uids=02189981&dopt=GenBank">dbj|AB004069.1|AB004069</a>  Capra aegagrus
mitochondrial DNA fo...    <a href = #2189981> 44</a>   0.001
<a
href="http://www.ncbi.nlm.nih.gov:80/entrez/query.fcgi?cmd=Retrieve&db=Nucleotid
e&list_uids=01707349&dopt=GenBank">dbj|D88640.1|D88640</a>  Anoa depressicornis
mitochondrial DNA f...    <a href = #1707349> 44</a>   0.001
<a
href="http://www.ncbi.nlm.nih.gov:80/entrez/query.fcgi?cmd=Retrieve&db=Nucleotid
e&list_uids=01707343&dopt=GenBank">dbj|D88637.1|D88637</a>  Bubalus bubalis
mitochondrial DNA for c...    <a href = #1707343> 44</a>   0.001
<a
href="http://www.ncbi.nlm.nih.gov:80/entrez/query.fcgi?cmd=Retrieve&db=Nucleotid
e&list_uids=01707337&dopt=GenBank">dbj|D88634.1|D88634</a>  Bubalus bubalis
mitochondrial DNA for c...    <a href = #1707337> 44</a>   0.001
<a
href="http://www.ncbi.nlm.nih.gov:80/entrez/query.fcgi?cmd=Retrieve&db=Nucleotid
e&list_uids=01707331&dopt=GenBank">dbj|D88631.1|D88631</a>  Bubalus bubalis
mitochondrial DNA for c...    <a href = #1707331> 44</a>   0.001
<a
href="http://www.ncbi.nlm.nih.gov:80/entrez/query.fcgi?cmd=Retrieve&db=Nucleotid
e&list_uids=01707327&dopt=GenBank">dbj|D88629.1|D88629</a>  Bubalus bubalis
mitochondrial DNA for c...    <a href = #1707327> 44</a>   0.001
<a
href="http://www.ncbi.nlm.nih.gov:80/entrez/query.fcgi?cmd=Retrieve&db=Nucleotid
e&list_uids=01256201&dopt=GenBank">dbj|D84205.1|SHPMTCBE</a>  Sheep
mitochondrial DNA for cytochrom...    <a href = #1256201> 44</a>   0.001
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=01256199&dopt=GenBank">dbj|D84203.1|SHPMTCBC</a>   Ovis musimon
mitochondrial DNA for cy...    <a href = #1256199> 44</a>   0.001
<a
href="http://www.ncbi.nlm.nih.gov:80/entrez/query.fcgi?cmd=Retrieve&db=Nucleotid
e&list_uids=01256160&dopt=GenBank">dbj|D84201.1|GOTMTCBA</a>   Goat mitochondrial
DNA for cytochrome...    <a href = #1256160> 44</a>   0.001
<a
href="http://www.ncbi.nlm.nih.gov:80/entrez/query.fcgi?cmd=Retrieve&db=Nucleotid
e&list_uids=01813366&dopt=GenBank">dbj|D82894.1|D82894</a>   Bubalus bubalis
mitochondrial DNA for c...    <a href = #1813366> 44</a>   0.001
<a
href="http://www.ncbi.nlm.nih.gov:80/entrez/query.fcgi?cmd=Retrieve&db=Nucleotid
e&list_uids=01813360&dopt=GenBank">dbj|D82891.1|D82891</a>   Bubalus quarlesi
mitochondrial DNA for ...    <a href = #1813360> 44</a>   0.001
<a
href="http://www.ncbi.nlm.nih.gov:80/entrez/query.fcgi?cmd=Retrieve&db=Nucleotid
e&list_uids=00517078&dopt=GenBank">dbj|D34638.1|BBUMTCBB</a>   Bubalus bubalis
mitochondrial gene fo...    <a href = #517078> 44</a>   0.001
<a
href="http://www.ncbi.nlm.nih.gov:80/entrez/query.fcgi?cmd=Retrieve&db=Nucleotid
e&list_uids=00516663&dopt=GenBank">dbj|D34636.1|BOVMTCBB</a>   Bos javanicus
mitochondrial gene for ...    <a href = #516663> 44</a>   0.001
<a
href="http://www.ncbi.nlm.nih.gov:80/entrez/query.fcgi?cmd=Retrieve&db=Nucleotid
e&list_uids=06906755&dopt=GenBank">dbj|AB037602.1|AB037602</a>   Talpa altaica
mitochondrial cytb ge...    <a href = #6906755> 44</a>   0.001
<a
href="http://www.ncbi.nlm.nih.gov:80/entrez/query.fcgi?cmd=Retrieve&db=Nucleotid
e&list_uids=06682770&dopt=GenBank">dbj|AB018985.1|AB018985</a>   Cichlasoma
citrinellum mitochondria...    <a href = #6682770> 44</a>   0.001
<a
href="http://www.ncbi.nlm.nih.gov:80/entrez/query.fcgi?cmd=Retrieve&db=Nucleotid
e&list_uids=02189987&dopt=GenBank">dbj|AB004075.1|AB004075</a>   Capra hircus
mitochondrial DNA for ...    <a href = #2189987> 44</a>   0.001
<a
href="http://www.ncbi.nlm.nih.gov:80/entrez/query.fcgi?cmd=Retrieve&db=Nucleotid
e&list_uids=02189985&dopt=GenBank">dbj|AB004073.1|AB004073</a>   Capra hircus
mitochondrial DNA for ...    <a href = #2189985> 44</a>   0.001
<a
href="http://www.ncbi.nlm.nih.gov:80/entrez/query.fcgi?cmd=Retrieve&db=Nucleotid
e&list_uids=02189982&dopt=GenBank">dbj|AB004070.1|AB004070</a>   Capra hircus
mitochondrial DNA for ...    <a href = #2189982> 44</a>   0.001
<a
href="http://www.ncbi.nlm.nih.gov:80/entrez/query.fcgi?cmd=Retrieve&db=Nucleotid
e&list_uids=01199512&dopt=GenBank">emb|X92531.1|DLCYTB</a>   D.leucas cytochrome
b gene (complete se...    <a href = #1199512> 44</a>   0.001
<a
href="http://www.ncbi.nlm.nih.gov:80/entrez/query.fcgi?cmd=Retrieve&db=Nucleotid
e&list_uids=00511676&dopt=GenBank">gb|U07565.1|HAU07565</a>   Hippopotamus
amphibius mitochondrion c...    <a href = #511676> 44</a>   0.001
<a
href="http://www.ncbi.nlm.nih.gov:80/entrez/query.fcgi?cmd=Retrieve&db=Nucleotid
e&list_uids=00501121&dopt=GenBank">gb|U10367.1|PVU10367</a>   Ptilonorhynchus
violaceus mitochondrio...    <a href = #501121> 44</a>   0.001
<a
href="http://www.ncbi.nlm.nih.gov:80/entrez/query.fcgi?cmd=Retrieve&db=Nucleotid
```

```
e&list_uids=00501117&dopt=GenBank">gb|U10364.1|CMU10364</a>  Chlamydera maculata
mitochondrion cyto...    <a href = #501117> 44</a>  0.001
<a
href="http://www.ncbi.nlm.nih.gov:80/entrez/query.fcgi?cmd=Retrieve&db=Nucleotid
e&list_uids=02924255&dopt=GenBank">emb|Z96068.1|ASZ96068</a>  Acomys
spinosissimus DNA for mitochon...    <a href = #2924255> 44</a>  0.001
<a
href="http://www.ncbi.nlm.nih.gov:80/entrez/query.fcgi?cmd=Retrieve&db=Nucleotid
e&list_uids=04098253&dopt=GenBank">gb|U76507.1|AIU76507</a>  Amblyornis
inornatus cytochrome b gene...    <a href = #4098253> 42</a>  0.005
<a
href="http://www.ncbi.nlm.nih.gov:80/entrez/query.fcgi?cmd=Retrieve&db=Nucleotid
e&list_uids=05596617&dopt=GenBank">gb|AF157466.1|AF157466</a>  Lepus timidus
cytochrome b (Cyb) gen...    <a href = #5596617> 40</a>  0.021
<a
href="http://www.ncbi.nlm.nih.gov:80/entrez/query.fcgi?cmd=Retrieve&db=Nucleotid
e&list_uids=05596613&dopt=GenBank">gb|AF157464.1|AF157464</a>  Lepus corsicanus
haplotype 1 cytochr...    <a href = #5596613> 40</a>  0.021
<a
href="http://www.ncbi.nlm.nih.gov:80/entrez/query.fcgi?cmd=Retrieve&db=Nucleotid
e&list_uids=05596611&dopt=GenBank">gb|AF157463.1|AF157463</a>  Lepus corsicanus
haplotype 3 cytochr...    <a href = #5596611> 40</a>  0.021
<a
href="http://www.ncbi.nlm.nih.gov:80/entrez/query.fcgi?cmd=Retrieve&db=Nucleotid
e&list_uids=13096063&dopt=GenBank">gb|AY016019.1|AY016018S3</a>  Mullerornis
agilis cytochrome b ge...    <a href = #13096063> 40</a>  0.021
<a
href="http://www.ncbi.nlm.nih.gov:80/entrez/query.fcgi?cmd=Retrieve&db=Nucleotid
e&list_uids=04590012&dopt=GenBank">gb|AF027330.1|</a>  Akodon olivaceus
canescens museum catalog nu...    <a href = #4590012> 40</a>  0.021
<a
href="http://www.ncbi.nlm.nih.gov:80/entrez/query.fcgi?cmd=Retrieve&db=Nucleotid
e&list_uids=04590011&dopt=GenBank">gb|AF027329.1|</a>  Akodon olivaceus
canescens museum catalog nu...    <a href = #4590011> 40</a>  0.021
<a
href="http://www.ncbi.nlm.nih.gov:80/entrez/query.fcgi?cmd=Retrieve&db=Nucleotid
e&list_uids=04590010&dopt=GenBank">gb|AF027328.1|</a>  Akodon olivaceus
canescens museum catalog nu...    <a href = #4590010> 40</a>  0.021
<a
href="http://www.ncbi.nlm.nih.gov:80/entrez/query.fcgi?cmd=Retrieve&db=Nucleotid
e&list_uids=04590009&dopt=GenBank">gb|AF027327.1|</a>  Akodon olivaceus
canescens museum catalog nu...    <a href = #4590009> 40</a>  0.021
<a
href="http://www.ncbi.nlm.nih.gov:80/entrez/query.fcgi?cmd=Retrieve&db=Nucleotid
e&list_uids=04590008&dopt=GenBank">gb|AF027326.1|</a>  Akodon olivaceus
canescens museum catalog nu...    <a href = #4590008> 40</a>  0.021
<a
href="http://www.ncbi.nlm.nih.gov:80/entrez/query.fcgi?cmd=Retrieve&db=Nucleotid
e&list_uids=04590007&dopt=GenBank">gb|AF027325.1|</a>  Akodon olivaceus
canescens museum catalog nu...    <a href = #4590007> 40</a>  0.021
<a
href="http://www.ncbi.nlm.nih.gov:80/entrez/query.fcgi?cmd=Retrieve&db=Nucleotid
e&list_uids=04590006&dopt=GenBank">gb|AF027324.1|</a>  Akodon olivaceus
canescens museum catalog nu...    <a href = #4590006> 40</a>  0.021
<a
href="http://www.ncbi.nlm.nih.gov:80/entrez/query.fcgi?cmd=Retrieve&db=Nucleotid
```

```
<a
href="http://www.ncbi.nlm.nih.gov:80/entrez/query.fcgi?cmd=Retrieve&db=Nucleotid
e&list_uids=04590005&dopt=GenBank">gb|AF027323.1|</a>   Akodon olivaceus
canescens museum catalog nu...    <a href = #4590005>  40</a>   0.021
<a
href="http://www.ncbi.nlm.nih.gov:80/entrez/query.fcgi?cmd=Retrieve&db=Nucleotid
e&list_uids=04590004&dopt=GenBank">gb|AF027322.1|</a>   Akodon olivaceus beatus
museum catalog numbe...    <a href = #4590004>  40</a>   0.021
<a
href="http://www.ncbi.nlm.nih.gov:80/entrez/query.fcgi?cmd=Retrieve&db=Nucleotid
e&list_uids=04590003&dopt=GenBank">gb|AF027321.1|</a>   Akodon olivaceus beatus
museum catalog numbe...    <a href = #4590003>  40</a>   0.021
<a
href="http://www.ncbi.nlm.nih.gov:80/entrez/query.fcgi?cmd=Retrieve&db=Nucleotid
e&list_uids=04590002&dopt=GenBank">gb|AF027320.1|</a>   Akodon olivaceus beatus
museum catalog numbe...    <a href = #4590002>  40</a>   0.021
<a
href="http://www.ncbi.nlm.nih.gov:80/entrez/query.fcgi?cmd=Retrieve&db=Nucleotid
e&list_uids=04590001&dopt=GenBank">gb|AF027319.1|</a>   Akodon olivaceus beatus
museum catalog numbe...    <a href = #4590001>  40</a>   0.021
<a
href="http://www.ncbi.nlm.nih.gov:80/entrez/query.fcgi?cmd=Retrieve&db=Nucleotid
e&list_uids=04590000&dopt=GenBank">gb|AF027318.1|</a>   Akodon olivaceus beatus
museum catalog numbe...    <a href = #4590000>  40</a>   0.021
<a
href="http://www.ncbi.nlm.nih.gov:80/entrez/query.fcgi?cmd=Retrieve&db=Nucleotid
e&list_uids=04589999&dopt=GenBank">gb|AF027317.1|</a>   Akodon olivaceus beatus
museum catalog numbe...    <a href = #4589999>  40</a>   0.021
<a
href="http://www.ncbi.nlm.nih.gov:80/entrez/query.fcgi?cmd=Retrieve&db=Nucleotid
e&list_uids=04589998&dopt=GenBank">gb|AF027316.1|</a>   Akodon olivaceus beatus
museum catalog numbe...    <a href = #4589998>  40</a>   0.021
<a
href="http://www.ncbi.nlm.nih.gov:80/entrez/query.fcgi?cmd=Retrieve&db=Nucleotid
e&list_uids=04589997&dopt=GenBank">gb|AF027315.1|</a>   Akodon olivaceus beatus
museum catalog numbe...    <a href = #4589997>  40</a>   0.021
<a
href="http://www.ncbi.nlm.nih.gov:80/entrez/query.fcgi?cmd=Retrieve&db=Nucleotid
e&list_uids=04589996&dopt=GenBank">gb|AF027314.1|</a>   Akodon olivaceus beatus
museum catalog numbe...    <a href = #4589996>  40</a>   0.021
<a
href="http://www.ncbi.nlm.nih.gov:80/entrez/query.fcgi?cmd=Retrieve&db=Nucleotid
e&list_uids=04589995&dopt=GenBank">gb|AF027313.1|</a>   Akodon olivaceus beatus
museum catalog numbe...    <a href = #4589995>  40</a>   0.021
<a
href="http://www.ncbi.nlm.nih.gov:80/entrez/query.fcgi?cmd=Retrieve&db=Nucleotid
e&list_uids=04589994&dopt=GenBank">gb|AF027312.1|</a>   Akodon olivaceus beatus
museum catalog numbe...    <a href = #4589994>  40</a>   0.021
<a
href="http://www.ncbi.nlm.nih.gov:80/entrez/query.fcgi?cmd=Retrieve&db=Nucleotid
e&list_uids=04589993&dopt=GenBank">gb|AF027311.1|</a>   Akodon olivaceus
brachiotis museum catalog n...    <a href = #4589993>  40</a>   0.021
<a
href="http://www.ncbi.nlm.nih.gov:80/entrez/query.fcgi?cmd=Retrieve&db=Nucleotid
e&list_uids=04589992&dopt=GenBank">gb|AF027310.1|</a>   Akodon olivaceus
brachiotis museum catalog n...    <a href = #4589992>  40</a>   0.021
<a
href="http://www.ncbi.nlm.nih.gov:80/entrez/query.fcgi?cmd=Retrieve&db=Nucleotid
```

```
e&list_uids=04589991&dopt=GenBank">gb|AF027309.1|</a>  Akodon olivaceus
brachiotis museum catalog n...    <a href = #4589991>  40</a>   0.021
<a
href="http://www.ncbi.nlm.nih.gov:80/entrez/query.fcgi?cmd=Retrieve&db=Nucleotid
e&list_uids=04589990&dopt=GenBank">gb|AF027308.1|</a>  Akodon olivaceus
brachiotis museum catalog n...    <a href = #4589990>  40</a>   0.021
<a
href="http://www.ncbi.nlm.nih.gov:80/entrez/query.fcgi?cmd=Retrieve&db=Nucleotid
e&list_uids=04589989&dopt=GenBank">gb|AF027307.1|</a>  Akodon olivaceus
brachiotis museum catalog n...    <a href = #4589989>  40</a>   0.021
<a
href="http://www.ncbi.nlm.nih.gov:80/entrez/query.fcgi?cmd=Retrieve&db=Nucleotid
e&list_uids=10121656&dopt=GenBank">gb|AF266188.1|AF266188</a>  Gillichthys
mirabilis cytochrome b m...    <a href = #10121656>  40</a>   0.021
<a
href="http://www.ncbi.nlm.nih.gov:80/entrez/query.fcgi?cmd=Retrieve&db=Nucleotid
e&list_uids=13095017&dopt=GenBank">gb|AF324034.1|AF324034</a>  Phyllobates
aurotaenia isolate Quebr...    <a href = #13095017>  40</a>   0.021
<a
href="http://www.ncbi.nlm.nih.gov:80/entrez/query.fcgi?cmd=Retrieve&db=Nucleotid
e&list_uids=12006255&dopt=GenBank">gb|AF272639.1|AF272639</a>  Clethrionomys
gapperi specimen-vouch...    <a href = #12006255>  40</a>   0.021
<a
href="http://www.ncbi.nlm.nih.gov:80/entrez/query.fcgi?cmd=Retrieve&db=Nucleotid
e&list_uids=12006249&dopt=GenBank">gb|AF272636.1|AF272636</a>  Clethrionomys
gapperi specimen-vouch...    <a href = #12006249>  40</a>   0.021
<a
href="http://www.ncbi.nlm.nih.gov:80/entrez/query.fcgi?cmd=Retrieve&db=Nucleotid
e&list_uids=12006245&dopt=GenBank">gb|AF272634.1|AF272634</a>  Clethrionomys
gapperi specimen-vouch...    <a href = #12006245>  40</a>   0.021
<a
href="http://www.ncbi.nlm.nih.gov:80/entrez/query.fcgi?cmd=Retrieve&db=Nucleotid
e&list_uids=12006243&dopt=GenBank">gb|AF272633.1|AF272633</a>  Clethrionomys
gapperi specimen-vouch...    <a href = #12006243>  40</a>   0.021
<a
href="http://www.ncbi.nlm.nih.gov:80/entrez/query.fcgi?cmd=Retrieve&db=Nucleotid
e&list_uids=07262992&dopt=GenBank">gb|AF182711.1|AF182711</a>  Geopelia cuneata
cytochrome b gene, ...    <a href = #7262992>  40</a>   0.021
<a
href="http://www.ncbi.nlm.nih.gov:80/entrez/query.fcgi?cmd=Retrieve&db=Nucleotid
e&list_uids=07262944&dopt=GenBank">gb|AF182687.1|AF182687</a>  Columbina picui
cytochrome b gene, p...    <a href = #7262944>  40</a>   0.021
<a
href="http://www.ncbi.nlm.nih.gov:80/entrez/query.fcgi?cmd=Retrieve&db=Nucleotid
e&list_uids=08698642&dopt=GenBank">gb|AF155422.1|AF155422</a>  Sigmodon
ochrognathus cytochrome b (...    <a href = #8698642>  40</a>   0.021
<a
href="http://www.ncbi.nlm.nih.gov:80/entrez/query.fcgi?cmd=Retrieve&db=Nucleotid
e&list_uids=05410547&dopt=GenBank">gb|AF155400.1|AF155400</a>  Peromyscus
pectoralis laceianus cyto...    <a href = #5410547>  40</a>   0.021
<a
href="http://www.ncbi.nlm.nih.gov:80/entrez/query.fcgi?cmd=Retrieve&db=Nucleotid
e&list_uids=05410532&dopt=GenBank">gb|AF155385.1|AF155385</a>  Peromyscus
attwateri isolate 1b cyto...    <a href = #5410532>  40</a>   0.021
<a
href="http://www.ncbi.nlm.nih.gov:80/entrez/query.fcgi?cmd=Retrieve&db=Nucleotid
```

```
e&list_uids=05410531&dopt=GenBank">gb|AF155384.1|AF155384</a>  Peromyscus
attwateri isolate 1a cyto...    <a href = #5410531> 40</a>  0.021
<a
href="http://www.ncbi.nlm.nih.gov:80/entrez/query.fcgi?cmd=Retrieve&db=Nucleotid
e&list_uids=08885870&dopt=GenBank">gb|AF155592.1|AF155592</a>  Sigmodon
ochrognathus isolate ArizAC...    <a href = #8885870> 40</a>  0.021
<a
href="http://www.ncbi.nlm.nih.gov:80/entrez/query.fcgi?cmd=Retrieve&db=Nucleotid
e&list_uids=08885868&dopt=GenBank">gb|AF155591.1|AF155591</a>  Sigmodon
ochrognathus isolate MtLiv7...    <a href = #8885868> 40</a>  0.021
<a
href="http://www.ncbi.nlm.nih.gov:80/entrez/query.fcgi?cmd=Retrieve&db=Nucleotid
e&list_uids=08885866&dopt=GenBank">gb|AF155590.1|AF155590</a>  Sigmodon
ochrognathus isolate Duran4...    <a href = #8885866> 40</a>  0.021
<a
href="http://www.ncbi.nlm.nih.gov:80/entrez/query.fcgi?cmd=Retrieve&db=Nucleotid
e&list_uids=08885864&dopt=GenBank">gb|AF155589.1|AF155589</a>  Sigmodon
ochrognathus isolate EleMt8...    <a href = #8885864> 40</a>  0.021
<a
href="http://www.ncbi.nlm.nih.gov:80/entrez/query.fcgi?cmd=Retrieve&db=Nucleotid
e&list_uids=08885862&dopt=GenBank">gb|AF155588.1|AF155588</a>  Sigmodon
ochrognathus isolate Bbend4...    <a href = #8885862> 40</a>  0.021
<a
href="http://www.ncbi.nlm.nih.gov:80/entrez/query.fcgi?cmd=Retrieve&db=Nucleotid
e&list_uids=07573899&dopt=GenBank">gb|AF123531.1|AF123531</a>  Trachyphonus
darnaudii cytochrome b ...    <a href = #7573899> 40</a>  0.021
<a
href="http://www.ncbi.nlm.nih.gov:80/entrez/query.fcgi?cmd=Retrieve&db=Nucleotid
e&list_uids=08308177&dopt=GenBank">gb|AF264047.1|AF264047</a>  Ursus spelaeus
cytochrome b gene, co...    <a href = #8308177> 40</a>  0.021
<a
href="http://www.ncbi.nlm.nih.gov:80/entrez/query.fcgi?cmd=Retrieve&db=Nucleotid
e&list_uids=07861845&dopt=GenBank">gb|AF206531.1|AF206531</a>  Podarcis sicula
cytochrome b gene, p...    <a href = #7861845> 40</a>  0.021
<a
href="http://www.ncbi.nlm.nih.gov:80/entrez/query.fcgi?cmd=Retrieve&db=Nucleotid
e&list_uids=06539823&dopt=GenBank">gb|AF192706.1|AF192706</a>  Hippocampus
zosterae haplotype FK.14...    <a href = #6539823> 40</a>  0.021
<a
href="http://www.ncbi.nlm.nih.gov:80/entrez/query.fcgi?cmd=Retrieve&db=Nucleotid
e&list_uids=05835988&dopt=GenBank">ref|NC_000884.1|</a>  Cavia porcellus
complete mitochondrial genome    <a href = #5835988> 40</a>  0.021
<a
href="http://www.ncbi.nlm.nih.gov:80/entrez/query.fcgi?cmd=Retrieve&db=Nucleotid
e&list_uids=02921010&dopt=GenBank">gb|AF004572.1|AF004572</a>  Arvicanthis
niloticus cytochrome b (...    <a href = #2921010> 40</a>  0.021
<a
href="http://www.ncbi.nlm.nih.gov:80/entrez/query.fcgi?cmd=Retrieve&db=Nucleotid
e&list_uids=05052150&dopt=GenBank">gb|AF088932.1|AF088932</a>  Sminthopsis
psammophila cytochrome b...    <a href = #5052150> 40</a>  0.021
<a
href="http://www.ncbi.nlm.nih.gov:80/entrez/query.fcgi?cmd=Retrieve&db=Nucleotid
e&list_uids=02052316&dopt=GenBank">gb|U62697.1|ORUCYTB2</a>  Oreopholus
ruficollis cytochrome b (cy...    <a href = #2052316> 40</a>  0.021
<a
href="http://www.ncbi.nlm.nih.gov:80/entrez/query.fcgi?cmd=Retrieve&db=Nucleotid
```

```
e&list_uids=01488214&dopt=GenBank">gb|U62681.1|CACYTB2</a>  Charadrius australis
cytochrome b (cyt ...    <a href = #1488214> 40</a>  0.021
<a
href="http://www.ncbi.nlm.nih.gov:80/entrez/query.fcgi?cmd=Retrieve&db=Nucleotid
e&list_uids=02052341&dopt=GenBank">gb|U62707.1|CVERCYTB2</a>  Charadrius veredus
cytochrome b (cytb...    <a href = #2052341> 38</a>  0.084
<a
href="http://www.ncbi.nlm.nih.gov:80/entrez/query.fcgi?cmd=Retrieve&db=Nucleotid
e&list_uids=09967917&dopt=GenBank">emb|AJ004315.1|HCAJ4315</a>  Hippolais
caligata mitochondrial cy...    <a href = #9967917> 38</a>  0.084
</PRE>
<CENTER><b><FONT color="green">Alignments</FONT></b></CENTER>
<PRE>
tmpseq_0  1    cctcctagtttgttagggattgatcg 26
<a name = 10441542></a><a
href=http://www.ncbi.nlm.nih.gov:80/entrez/query.fcgi?cmd=Retrieve&db=Nucleotide
&list_uids=10441542&dopt=GenBank>AF189111</a>  797 ..........................
772
<a name = 4218914></a><a
href=http://www.ncbi.nlm.nih.gov:80/entrez/query.fcgi?cmd=Retrieve&db=Nucleotide
&list_uids=04218914&dopt=GenBank>U86834</a>  858 ..........................
833
<a name = 8050379></a><a
href=http://www.ncbi.nlm.nih.gov:80/entrez/query.fcgi?cmd=Retrieve&db=Nucleotide
&list_uids=08050379&dopt=GenBank>AF123633</a>  56 ..........................
31
<a name = 8050348></a><a
href=http://www.ncbi.nlm.nih.gov:80/entrez/query.fcgi?cmd=Retrieve&db=Nucleotide
&list_uids=08050348&dopt=GenBank>AF123617</a>  104 ..........................
79
<a name = 7715727></a><a
href=http://www.ncbi.nlm.nih.gov:80/entrez/query.fcgi?cmd=Retrieve&db=Nucleotide
&list_uids=07715727&dopt=GenBank>AF127202</a>  107 ..........................
82
<a name = 7715712></a><a
href=http://www.ncbi.nlm.nih.gov:80/entrez/query.fcgi?cmd=Retrieve&db=Nucleotide
&list_uids=07715712&dopt=GenBank>AF127194</a>  107 ..........................
82
<a name = 7141202></a><a
href=http://www.ncbi.nlm.nih.gov:80/entrez/query.fcgi?cmd=Retrieve&db=Nucleotide
&list_uids=07141202&dopt=GenBank>AF217828</a>  845 ..........................
820
<a name = 6524754></a><a
href=http://www.ncbi.nlm.nih.gov:80/entrez/query.fcgi?cmd=Retrieve&db=Nucleotide
&list_uids=06524754&dopt=GenBank>AF160578</a>  869 ..........................
844
<a name = 5713297></a><a
href=http://www.ncbi.nlm.nih.gov:80/entrez/query.fcgi?cmd=Retrieve&db=Nucleotide
&list_uids=05713297&dopt=GenBank>AF009931</a>  869 ..........................
844
<a name = 5359509></a><a
href=http://www.ncbi.nlm.nih.gov:80/entrez/query.fcgi?cmd=Retrieve&db=Nucleotide
&list_uids=05359509&dopt=GenBank>AF091629</a>  869 ..........................
844
<a name = 2660917></a><a
href=http://www.ncbi.nlm.nih.gov:80/entrez/query.fcgi?cmd=Retrieve&db=Nucleotide
```

```
&list_uids=02660917&dopt=GenBank>AF034967</a>  869  ..........................
844
<a name = 3098363></a><a
href=http://www.ncbi.nlm.nih.gov:80/entrez/query.fcgi?cmd=Retrieve&db=Nucleotide
&list_uids=03098363&dopt=GenBank>AF038290</a>  869  ..........................
844
<a name = 2677639></a><a
href=http://www.ncbi.nlm.nih.gov:80/entrez/query.fcgi?cmd=Retrieve&db=Nucleotide
&list_uids=02677639&dopt=GenBank>U07577</a>   869  ..........................
844
<a name = 2098650></a><a
href=http://www.ncbi.nlm.nih.gov:80/entrez/query.fcgi?cmd=Retrieve&db=Nucleotide
&list_uids=02098650&dopt=GenBank>U81343</a>    791  ..........................
766
<a name = 3483067></a><a
href=http://www.ncbi.nlm.nih.gov:80/entrez/query.fcgi?cmd=Retrieve&db=Nucleotide
&list_uids=03483067&dopt=GenBank>AJ222681</a>  869  ..........................
844
<a name = 1778694></a><a
href=http://www.ncbi.nlm.nih.gov:80/entrez/query.fcgi?cmd=Retrieve&db=Nucleotide
&list_uids=01778694&dopt=GenBank>M99464</a>   869  ..........................
844
<a name = 4127784></a><a
href=http://www.ncbi.nlm.nih.gov:80/entrez/query.fcgi?cmd=Retrieve&db=Nucleotide
&list_uids=04127784&dopt=GenBank>AJ225116</a>  869  ..........................
844
<a name = 841455></a><a
href=http://www.ncbi.nlm.nih.gov:80/entrez/query.fcgi?cmd=Retrieve&db=Nucleotide
&list_uids=00841455&dopt=GenBank>U25738</a>   872  ..........................
847
<a name = 841451></a><a
href=http://www.ncbi.nlm.nih.gov:80/entrez/query.fcgi?cmd=Retrieve&db=Nucleotide
&list_uids=00841451&dopt=GenBank>U25736</a>   872  ..........................
847
<a name = 840936></a><a
href=http://www.ncbi.nlm.nih.gov:80/entrez/query.fcgi?cmd=Retrieve&db=Nucleotide
&list_uids=00840936&dopt=GenBank>U15202</a>   872  ..........................
847
<a name = 840940></a><a
href=http://www.ncbi.nlm.nih.gov:80/entrez/query.fcgi?cmd=Retrieve&db=Nucleotide
&list_uids=00840940&dopt=GenBank>U15204</a>   872  ..........................
847
<a name = 12907></a><a
href=http://www.ncbi.nlm.nih.gov:80/entrez/query.fcgi?cmd=Retrieve&db=Nucleotide
&list_uids=00012907&dopt=GenBank>X56290</a>   869  ..........................
844
<a name = 12624></a><a
href=http://www.ncbi.nlm.nih.gov:80/entrez/query.fcgi?cmd=Retrieve&db=Nucleotide
&list_uids=00012624&dopt=GenBank>X56286</a>   869  ..........................
844
<a name = 1707347></a><a
href=http://www.ncbi.nlm.nih.gov:80/entrez/query.fcgi?cmd=Retrieve&db=Nucleotide
&list_uids=01707347&dopt=GenBank>D88639</a>   869  ..........................
844
<a name = 1813358></a><a
href=http://www.ncbi.nlm.nih.gov:80/entrez/query.fcgi?cmd=Retrieve&db=Nucleotide
```

```
&list_uids=01813358&dopt=GenBank>D82890</a>    869  ........................
844
<a name = 5478447></a><a
href=http://www.ncbi.nlm.nih.gov:80/entrez/query.fcgi?cmd=Retrieve&db=Nucleotide
&list_uids=05478447&dopt=GenBank>AF119261</a>  869  ........................
847
<a name = 8050344></a><a
href=http://www.ncbi.nlm.nih.gov:80/entrez/query.fcgi?cmd=Retrieve&db=Nucleotide
&list_uids=08050344&dopt=GenBank>AF123615</a>  101  ........................
79
<a name = 6524779></a><a
href=http://www.ncbi.nlm.nih.gov:80/entrez/query.fcgi?cmd=Retrieve&db=Nucleotide
&list_uids=06524779&dopt=GenBank>AF160603</a>  866  ........................
844
<a name = 2052291></a><a
href=http://www.ncbi.nlm.nih.gov:80/entrez/query.fcgi?cmd=Retrieve&db=Nucleotide
&list_uids=02052291&dopt=GenBank>U62687</a>    179  ........................
157
<a name = 1488224></a><a
href=http://www.ncbi.nlm.nih.gov:80/entrez/query.fcgi?cmd=Retrieve&db=Nucleotide
&list_uids=01488224&dopt=GenBank>U62685</a>    179  ........................
157
<a name = 4103317></a><a
href=http://www.ncbi.nlm.nih.gov:80/entrez/query.fcgi?cmd=Retrieve&db=Nucleotide
&list_uids=04103317&dopt=GenBank>AF022071</a>  866  ........................
844
<a name = 4103315></a><a
href=http://www.ncbi.nlm.nih.gov:80/entrez/query.fcgi?cmd=Retrieve&db=Nucleotide
&list_uids=04103315&dopt=GenBank>AF022070</a>  866  ........................
844
<a name = 2231533></a><a
href=http://www.ncbi.nlm.nih.gov:80/entrez/query.fcgi?cmd=Retrieve&db=Nucleotide
&list_uids=02231533&dopt=GenBank>U83317</a>    872  ........................
850
<a name = 1255743></a><a
href=http://www.ncbi.nlm.nih.gov:80/entrez/query.fcgi?cmd=Retrieve&db=Nucleotide
&list_uids=01255743&dopt=GenBank>U37293</a>    774  ........................
752
<a name = 1255741></a><a
href=http://www.ncbi.nlm.nih.gov:80/entrez/query.fcgi?cmd=Retrieve&db=Nucleotide
&list_uids=01255741&dopt=GenBank>U37292</a>    774  ........................
752
<a name = 1255739></a><a
href=http://www.ncbi.nlm.nih.gov:80/entrez/query.fcgi?cmd=Retrieve&db=Nucleotide
&list_uids=01255739&dopt=GenBank>U37291</a>    774  ........................
752
<a name = 3551896></a><a
href=http://www.ncbi.nlm.nih.gov:80/entrez/query.fcgi?cmd=Retrieve&db=Nucleotide
&list_uids=03551896&dopt=GenBank>AF082055</a>  51   ........................
29
<a name = 3211690></a><a
href=http://www.ncbi.nlm.nih.gov:80/entrez/query.fcgi?cmd=Retrieve&db=Nucleotide
&list_uids=03211690&dopt=GenBank>U72770</a>    798  ........................
776
<a name = 2677641></a><a
href=http://www.ncbi.nlm.nih.gov:80/entrez/query.fcgi?cmd=Retrieve&db=Nucleotide
```

```
<a name = 2677641></a><a
href=http://www.ncbi.nlm.nih.gov:80/entrez/query.fcgi?cmd=Retrieve&db=Nucleotide
&list_uids=02677641&dopt=GenBank>U07578</a>    869    ......................
847
<a name = 2642615></a><a
href=http://www.ncbi.nlm.nih.gov:80/entrez/query.fcgi?cmd=Retrieve&db=Nucleotide
&list_uids=02642615&dopt=GenBank>AF031908</a>  187    ......................
165
<a name = 9998874></a><a
href=http://www.ncbi.nlm.nih.gov:80/entrez/query.fcgi?cmd=Retrieve&db=Nucleotide
&list_uids=09998874&dopt=GenBank>AJ004231</a>  773    ......................
751
<a name = 9998872></a><a
href=http://www.ncbi.nlm.nih.gov:80/entrez/query.fcgi?cmd=Retrieve&db=Nucleotide
&list_uids=09998872&dopt=GenBank>AJ004230</a>  773    ......................
751
<a name = 9998870></a><a
href=http://www.ncbi.nlm.nih.gov:80/entrez/query.fcgi?cmd=Retrieve&db=Nucleotide
&list_uids=09998870&dopt=GenBank>AJ004229</a>  773    ......................
751
<a name = 9971120></a><a
href=http://www.ncbi.nlm.nih.gov:80/entrez/query.fcgi?cmd=Retrieve&db=Nucleotide
&list_uids=09971120&dopt=GenBank>AJ004232</a>  773    ......................
751
<a name = 2290368></a><a
href=http://www.ncbi.nlm.nih.gov:80/entrez/query.fcgi?cmd=Retrieve&db=Nucleotide
&list_uids=02290368&dopt=GenBank>U88865</a>    850    ......................
828
<a name = 1890874></a><a
href=http://www.ncbi.nlm.nih.gov:80/entrez/query.fcgi?cmd=Retrieve&db=Nucleotide
&list_uids=01890874&dopt=GenBank>U90001</a>    536    ......................
514
<a name = 1458193></a><a
href=http://www.ncbi.nlm.nih.gov:80/entrez/query.fcgi?cmd=Retrieve&db=Nucleotide
&list_uids=01458193&dopt=GenBank>U63057</a>    773    ......................
751
<a name = 8272437></a><a
href=http://www.ncbi.nlm.nih.gov:80/entrez/query.fcgi?cmd=Retrieve&db=Nucleotide
&list_uids=08272437&dopt=GenBank>AB036404</a>  173    ......................
151
<a name = 8272434></a><a
href=http://www.ncbi.nlm.nih.gov:80/entrez/query.fcgi?cmd=Retrieve&db=Nucleotide
&list_uids=08272434&dopt=GenBank>AB036402</a>  173    ......................
151
<a name = 8272431></a><a
href=http://www.ncbi.nlm.nih.gov:80/entrez/query.fcgi?cmd=Retrieve&db=Nucleotide
&list_uids=08272431&dopt=GenBank>AB036400</a>  173    ......................
151
<a name = 8272428></a><a
href=http://www.ncbi.nlm.nih.gov:80/entrez/query.fcgi?cmd=Retrieve&db=Nucleotide
&list_uids=08272428&dopt=GenBank>AB036398</a>  173    ......................
151
<a name = 642546></a><a
href=http://www.ncbi.nlm.nih.gov:80/entrez/query.fcgi?cmd=Retrieve&db=Nucleotide
&list_uids=00642546&dopt=GenBank>U19611</a>    774    ......................
752
<a name = 1199822></a><a
href=http://www.ncbi.nlm.nih.gov:80/entrez/query.fcgi?cmd=Retrieve&db=Nucleotide
```

```
&list_uids=01199822&dopt=GenBank>X92539</a>   869   ....................
847
<a name = 336992></a><a
href=http://www.ncbi.nlm.nih.gov:80/entrez/query.fcgi?cmd=Retrieve&db=Nucleotide
&list_uids=00336992&dopt=GenBank>L08034</a>   872   ....................
850
<a name = 336661></a><a
href=http://www.ncbi.nlm.nih.gov:80/entrez/query.fcgi?cmd=Retrieve&db=Nucleotide
&list_uids=00336661&dopt=GenBank>L08033</a>   872   ....................
850
<a name = 12957419></a><a
href=http://www.ncbi.nlm.nih.gov:80/entrez/query.fcgi?cmd=Retrieve&db=Nucleotide
&list_uids=12957419&dopt=GenBank>AY016012</a>  11937 ...................a.....
11912
<a name = 4336167></a><a
href=http://www.ncbi.nlm.nih.gov:80/entrez/query.fcgi?cmd=Retrieve&db=Nucleotide
&list_uids=04336167&dopt=GenBank>AF074591</a>  677   ..............t...........
652
<a name = 12699075></a><a
href=http://www.ncbi.nlm.nih.gov:80/entrez/query.fcgi?cmd=Retrieve&db=Nucleotide
&list_uids=12699075&dopt=GenBank>AY005212</a>  761   ....................g.....
736
<a name = 12699073></a><a
href=http://www.ncbi.nlm.nih.gov:80/entrez/query.fcgi?cmd=Retrieve&db=Nucleotide
&list_uids=12699073&dopt=GenBank>AY005211</a>  761   ....................g.....
736
<a name = 10441564></a><a
href=http://www.ncbi.nlm.nih.gov:80/entrez/query.fcgi?cmd=Retrieve&db=Nucleotide
&list_uids=10441564&dopt=GenBank>AF189122</a>  797   ......c...................
772
<a name = 10441560></a><a
href=http://www.ncbi.nlm.nih.gov:80/entrez/query.fcgi?cmd=Retrieve&db=Nucleotide
&list_uids=10441560&dopt=GenBank>AF189120</a>  797   ...............t...........
772
<a name = 10441556></a><a
href=http://www.ncbi.nlm.nih.gov:80/entrez/query.fcgi?cmd=Retrieve&db=Nucleotide
&list_uids=10441556&dopt=GenBank>AF189118</a>  797   .......a.................
772
<a name = 10441554></a><a
href=http://www.ncbi.nlm.nih.gov:80/entrez/query.fcgi?cmd=Retrieve&db=Nucleotide
&list_uids=10441554&dopt=GenBank>AF189117</a>  797   .......a.................
772
<a name = 10441552></a><a
href=http://www.ncbi.nlm.nih.gov:80/entrez/query.fcgi?cmd=Retrieve&db=Nucleotide
&list_uids=10441552&dopt=GenBank>AF189116</a>  797   ..............g..........
772
<a name = 12275815></a><a
href=http://www.ncbi.nlm.nih.gov:80/entrez/query.fcgi?cmd=Retrieve&db=Nucleotide
&list_uids=12275815&dopt=GenBank>AF112140</a>  310   ..............g..........
285
<a name = 12275813></a><a
href=http://www.ncbi.nlm.nih.gov:80/entrez/query.fcgi?cmd=Retrieve&db=Nucleotide
&list_uids=12275813&dopt=GenBank>AF112139</a>  310   ..............g..........
285
<a name = 12275811></a><a
href=http://www.ncbi.nlm.nih.gov:80/entrez/query.fcgi?cmd=Retrieve&db=Nucleotide
```

```
&list_uids=12275811&dopt=GenBank>AF112138</a>   310       .............g..........
285
<a name = 3676623></a><a
href=http://www.ncbi.nlm.nih.gov:80/entrez/query.fcgi?cmd=Retrieve&db=Nucleotide
&list_uids=03676623&dopt=GenBank>AF081990</a>   872       ..............t..........
847
<a name = 3676621></a><a
href=http://www.ncbi.nlm.nih.gov:80/entrez/query.fcgi?cmd=Retrieve&db=Nucleotide
&list_uids=03676621&dopt=GenBank>AF081989</a>   872       ..............t..........
847
<a name = 3676619></a><a
href=http://www.ncbi.nlm.nih.gov:80/entrez/query.fcgi?cmd=Retrieve&db=Nucleotide
&list_uids=03676619&dopt=GenBank>AF081988</a>   872       ..............t..........
847
<a name = 3676617></a><a
href=http://www.ncbi.nlm.nih.gov:80/entrez/query.fcgi?cmd=Retrieve&db=Nucleotide
&list_uids=03676617&dopt=GenBank>AF081987</a>   872       ..............t..........
847
<a name = 3676615></a><a
href=http://www.ncbi.nlm.nih.gov:80/entrez/query.fcgi?cmd=Retrieve&db=Nucleotide
&list_uids=03676615&dopt=GenBank>AF081986</a>   872       ..............t..........
847
<a name = 3676613></a><a
href=http://www.ncbi.nlm.nih.gov:80/entrez/query.fcgi?cmd=Retrieve&db=Nucleotide
&list_uids=03676613&dopt=GenBank>AF081985</a>   872       ..............t..........
847
<a name = 3676611></a><a
href=http://www.ncbi.nlm.nih.gov:80/entrez/query.fcgi?cmd=Retrieve&db=Nucleotide
&list_uids=03676611&dopt=GenBank>AF081984</a>   872       ..............t..........
847
<a name = 3676609></a><a
href=http://www.ncbi.nlm.nih.gov:80/entrez/query.fcgi?cmd=Retrieve&db=Nucleotide
&list_uids=03676609&dopt=GenBank>AF081983</a>   872       ..............t..........
847
<a name = 3676607></a><a
href=http://www.ncbi.nlm.nih.gov:80/entrez/query.fcgi?cmd=Retrieve&db=Nucleotide
&list_uids=03676607&dopt=GenBank>AF081982</a>   872       ..............t..........
847
<a name = 3676605></a><a
href=http://www.ncbi.nlm.nih.gov:80/entrez/query.fcgi?cmd=Retrieve&db=Nucleotide
&list_uids=03676605&dopt=GenBank>AF081981</a>   872       ..............t..........
847
<a name = 3676603></a><a
href=http://www.ncbi.nlm.nih.gov:80/entrez/query.fcgi?cmd=Retrieve&db=Nucleotide
&list_uids=03676603&dopt=GenBank>AF081980</a>   872       ..............t..........
847
<a name = 3676601></a><a
href=http://www.ncbi.nlm.nih.gov:80/entrez/query.fcgi?cmd=Retrieve&db=Nucleotide
&list_uids=03676601&dopt=GenBank>AF081979</a>   872       ..............t..........
847
<a name = 3676599></a><a
href=http://www.ncbi.nlm.nih.gov:80/entrez/query.fcgi?cmd=Retrieve&db=Nucleotide
&list_uids=03676599&dopt=GenBank>AF081978</a>   872       ..............t..........
847
<a name = 3676597></a><a
href=http://www.ncbi.nlm.nih.gov:80/entrez/query.fcgi?cmd=Retrieve&db=Nucleotide
```

```
&list_uids=03676597&dopt=GenBank>AF081977</a>   872       ...............t...........
847
<a name = 3676595></a><a
href=http://www.ncbi.nlm.nih.gov:80/entrez/query.fcgi?cmd=Retrieve&db=Nucleotide
&list_uids=03676595&dopt=GenBank>AF081976</a>   872       ...............t...........
847
<a name = 3676593></a><a
href=http://www.ncbi.nlm.nih.gov:80/entrez/query.fcgi?cmd=Retrieve&db=Nucleotide
&list_uids=03676593&dopt=GenBank>AF081975</a>   872       ...............t...........
847
<a name = 3676591></a><a
href=http://www.ncbi.nlm.nih.gov:80/entrez/query.fcgi?cmd=Retrieve&db=Nucleotide
&list_uids=03676591&dopt=GenBank>AF081974</a>   872       ...............t...........
847
<a name = 3676589></a><a
href=http://www.ncbi.nlm.nih.gov:80/entrez/query.fcgi?cmd=Retrieve&db=Nucleotide
&list_uids=03676589&dopt=GenBank>AF081973</a>   872       ...............t...........
847
<a name = 3676587></a><a
href=http://www.ncbi.nlm.nih.gov:80/entrez/query.fcgi?cmd=Retrieve&db=Nucleotide
&list_uids=03676587&dopt=GenBank>AF081972</a>   872       ...............t...........
847
<a name = 3676585></a><a
href=http://www.ncbi.nlm.nih.gov:80/entrez/query.fcgi?cmd=Retrieve&db=Nucleotide
&list_uids=03676585&dopt=GenBank>AF081971</a>   872       ...............t...........
847
<a name = 3676583></a><a
href=http://www.ncbi.nlm.nih.gov:80/entrez/query.fcgi?cmd=Retrieve&db=Nucleotide
&list_uids=03676583&dopt=GenBank>AF081970</a>   872       ...............t...........
847
<a name = 3676581></a><a
href=http://www.ncbi.nlm.nih.gov:80/entrez/query.fcgi?cmd=Retrieve&db=Nucleotide
&list_uids=03676581&dopt=GenBank>AF081969</a>   872       ...............t...........
847
<a name = 3676579></a><a
href=http://www.ncbi.nlm.nih.gov:80/entrez/query.fcgi?cmd=Retrieve&db=Nucleotide
&list_uids=03676579&dopt=GenBank>AF081968</a>   872       ...............t...........
847
<a name = 3676577></a><a
href=http://www.ncbi.nlm.nih.gov:80/entrez/query.fcgi?cmd=Retrieve&db=Nucleotide
&list_uids=03676577&dopt=GenBank>AF081967</a>   872       ...............t...........
847
<a name = 3676575></a><a
href=http://www.ncbi.nlm.nih.gov:80/entrez/query.fcgi?cmd=Retrieve&db=Nucleotide
&list_uids=03676575&dopt=GenBank>AF081966</a>   872       ...............t...........
847
<a name = 3676573></a><a
href=http://www.ncbi.nlm.nih.gov:80/entrez/query.fcgi?cmd=Retrieve&db=Nucleotide
&list_uids=03676573&dopt=GenBank>AF081965</a>   872       ...............t...........
847
<a name = 3676571></a><a
href=http://www.ncbi.nlm.nih.gov:80/entrez/query.fcgi?cmd=Retrieve&db=Nucleotide
&list_uids=03676571&dopt=GenBank>AF081964</a>   872       ...............t...........
847
<a name = 3676567></a><a
href=http://www.ncbi.nlm.nih.gov:80/entrez/query.fcgi?cmd=Retrieve&db=Nucleotide
```

```
&list_uids=03676567&dopt=GenBank>AF081962</a>  754        ................t............
729
<a name = 3676565></a><a
href=http://www.ncbi.nlm.nih.gov:80/entrez/query.fcgi?cmd=Retrieve&db=Nucleotide
&list_uids=03676565&dopt=GenBank>AF081961</a>  872        ................t............
847
<a name = 3676563></a><a
href=http://www.ncbi.nlm.nih.gov:80/entrez/query.fcgi?cmd=Retrieve&db=Nucleotide
&list_uids=03676563&dopt=GenBank>AF081960</a>  872        ................g............
847
<a name = 3676561></a><a
href=http://www.ncbi.nlm.nih.gov:80/entrez/query.fcgi?cmd=Retrieve&db=Nucleotide
&list_uids=03676561&dopt=GenBank>AF081959</a>  872        ................t............
847
<a name = 12050550></a><a
href=http://www.ncbi.nlm.nih.gov:80/entrez/query.fcgi?cmd=Retrieve&db=Nucleotide
&list_uids=12050550&dopt=GenBank>AF112405</a>  869        ......................c......
844
<a name = 12002328></a><a
href=http://www.ncbi.nlm.nih.gov:80/entrez/query.fcgi?cmd=Retrieve&db=Nucleotide
&list_uids=12002328&dopt=GenBank>AF144317</a>  161        ......................g......
136
<a name = 12002326></a><a
href=http://www.ncbi.nlm.nih.gov:80/entrez/query.fcgi?cmd=Retrieve&db=Nucleotide
&list_uids=12002326&dopt=GenBank>AF144316</a>  161        ......................g......
136
<a name = 12002324></a><a
href=http://www.ncbi.nlm.nih.gov:80/entrez/query.fcgi?cmd=Retrieve&db=Nucleotide
&list_uids=12002324&dopt=GenBank>AF144315</a>  161        ......................g......
136
<a name = 12002322></a><a
href=http://www.ncbi.nlm.nih.gov:80/entrez/query.fcgi?cmd=Retrieve&db=Nucleotide
&list_uids=12002322&dopt=GenBank>AF144314</a>  161        ......................g......
136
<a name = 12002320></a><a
href=http://www.ncbi.nlm.nih.gov:80/entrez/query.fcgi?cmd=Retrieve&db=Nucleotide
&list_uids=12002320&dopt=GenBank>AF144313</a>  161        ......................g......
136
<a name = 12002318></a><a
href=http://www.ncbi.nlm.nih.gov:80/entrez/query.fcgi?cmd=Retrieve&db=Nucleotide
&list_uids=12002318&dopt=GenBank>AF144312</a>  161        ......................g......
136
<a name = 12002316></a><a
href=http://www.ncbi.nlm.nih.gov:80/entrez/query.fcgi?cmd=Retrieve&db=Nucleotide
&list_uids=12002316&dopt=GenBank>AF144311</a>  161        ......................g......
136
<a name = 12002314></a><a
href=http://www.ncbi.nlm.nih.gov:80/entrez/query.fcgi?cmd=Retrieve&db=Nucleotide
&list_uids=12002314&dopt=GenBank>AF144310</a>  161        ......................g......
136
<a name = 12002312></a><a
href=http://www.ncbi.nlm.nih.gov:80/entrez/query.fcgi?cmd=Retrieve&db=Nucleotide
&list_uids=12002312&dopt=GenBank>AF144309</a>  161        ......................g......
136
<a name = 5834939></a><a
href=http://www.ncbi.nlm.nih.gov:80/entrez/query.fcgi?cmd=Retrieve&db=Nucleotide
```

```
&list_uids=05834939&dopt=GenBank>NC_001567</a>  15382  .............g..........
15357
<a name = 11991819></a><a
href=http://www.ncbi.nlm.nih.gov:80/entrez/query.fcgi?cmd=Retrieve&db=Nucleotide
&list_uids=11991819&dopt=GenBank>AF212124</a>  425  ..............t...........
400
<a name = 7262982></a><a
href=http://www.ncbi.nlm.nih.gov:80/entrez/query.fcgi?cmd=Retrieve&db=Nucleotide
&list_uids=07262982&dopt=GenBank>AF182706</a>  739  ....................a.....
714
<a name = 3445513></a><a
href=http://www.ncbi.nlm.nih.gov:80/entrez/query.fcgi?cmd=Retrieve&db=Nucleotide
&list_uids=03445513&dopt=GenBank>AF010406</a>  15027  ...........a..............
15002
<a name = 11139363></a><a
href=http://www.ncbi.nlm.nih.gov:80/entrez/query.fcgi?cmd=Retrieve&db=Nucleotide
&list_uids=11139363&dopt=GenBank>AF096452</a>  735  ..............t...........
710
<a name = 11023376></a><a
href=http://www.ncbi.nlm.nih.gov:80/entrez/query.fcgi?cmd=Retrieve&db=Nucleotide
&list_uids=11023376&dopt=GenBank>AF283619</a>  845  ...........a..............
820
<a name = 11023374></a><a
href=http://www.ncbi.nlm.nih.gov:80/entrez/query.fcgi?cmd=Retrieve&db=Nucleotide
&list_uids=11023374&dopt=GenBank>AF283618</a>  845  ...........a..............
820
<a name = 11023354></a><a
href=http://www.ncbi.nlm.nih.gov:80/entrez/query.fcgi?cmd=Retrieve&db=Nucleotide
&list_uids=11023354&dopt=GenBank>AF283608</a>  845  ...........a..............
820
<a name = 11023342></a><a
href=http://www.ncbi.nlm.nih.gov:80/entrez/query.fcgi?cmd=Retrieve&db=Nucleotide
&list_uids=11023342&dopt=GenBank>AF283602</a>  845  ...........a..............
820
<a name = 10799259></a><a
href=http://www.ncbi.nlm.nih.gov:80/entrez/query.fcgi?cmd=Retrieve&db=Nucleotide
&list_uids=10799259&dopt=GenBank>AF310069</a>  770  ................a.........
745
<a name = 10440971></a><a
href=http://www.ncbi.nlm.nih.gov:80/entrez/query.fcgi?cmd=Retrieve&db=Nucleotide
&list_uids=10440971&dopt=GenBank>AF146616</a>  95  ..............g...........
70
<a name = 10442514></a><a
href=http://www.ncbi.nlm.nih.gov:80/entrez/query.fcgi?cmd=Retrieve&db=Nucleotide
&list_uids=10442514&dopt=GenBank>AF271410</a>  869  ..............g...........
844
<a name = 9972047></a><a
href=http://www.ncbi.nlm.nih.gov:80/entrez/query.fcgi?cmd=Retrieve&db=Nucleotide
&list_uids=09972047&dopt=GenBank>AF290139</a>  752  ....................g.....
727
<a name = 9755345></a><a
href=http://www.ncbi.nlm.nih.gov:80/entrez/query.fcgi?cmd=Retrieve&db=Nucleotide
&list_uids=09755345&dopt=GenBank>NC_002504</a>  15022  .............g..........
14997
<a name = 6690571></a><a
href=http://www.ncbi.nlm.nih.gov:80/entrez/query.fcgi?cmd=Retrieve&db=Nucleotide
```

```
&list_uids=06690571&dopt=GenBank>AF163901</a>  869          .................g.....
844
<a name = 5478451></a><a
href=http://www.ncbi.nlm.nih.gov:80/entrez/query.fcgi?cmd=Retrieve&db=Nucleotide
&list_uids=05478451&dopt=GenBank>AF119263</a>  869          ..............g..........
844
<a name = 5478441></a><a
href=http://www.ncbi.nlm.nih.gov:80/entrez/query.fcgi?cmd=Retrieve&db=Nucleotide
&list_uids=05478441&dopt=GenBank>AF119259</a>  869          ....................g.....
844
<a name = 9664890></a><a
href=http://www.ncbi.nlm.nih.gov:80/entrez/query.fcgi?cmd=Retrieve&db=Nucleotide
&list_uids=09664890&dopt=GenBank>AF288454</a>  91           ..................a........
66
<a name = 9695303></a><a
href=http://www.ncbi.nlm.nih.gov:80/entrez/query.fcgi?cmd=Retrieve&db=Nucleotide
&list_uids=09695303&dopt=GenBank>AF163895</a>  869          ....................c......
844
<a name = 8050411></a><a
href=http://www.ncbi.nlm.nih.gov:80/entrez/query.fcgi?cmd=Retrieve&db=Nucleotide
&list_uids=08050411&dopt=GenBank>AF123649</a>  68           ..............g...........
43
<a name = 8050407></a><a
href=http://www.ncbi.nlm.nih.gov:80/entrez/query.fcgi?cmd=Retrieve&db=Nucleotide
&list_uids=08050407&dopt=GenBank>AF123647</a>  68           ..............g...........
43
<a name = 8050405></a><a
href=http://www.ncbi.nlm.nih.gov:80/entrez/query.fcgi?cmd=Retrieve&db=Nucleotide
&list_uids=08050405&dopt=GenBank>AF123646</a>  104          ..............g...........
79
<a name = 8050403></a><a
href=http://www.ncbi.nlm.nih.gov:80/entrez/query.fcgi?cmd=Retrieve&db=Nucleotide
&list_uids=08050403&dopt=GenBank>AF123645</a>  68           ..............g...........
43
<a name = 8050381></a><a
href=http://www.ncbi.nlm.nih.gov:80/entrez/query.fcgi?cmd=Retrieve&db=Nucleotide
&list_uids=08050381&dopt=GenBank>AF123634</a>  84           ..............g...........
59
<a name = 8050377></a><a
href=http://www.ncbi.nlm.nih.gov:80/entrez/query.fcgi?cmd=Retrieve&db=Nucleotide
&list_uids=08050377&dopt=GenBank>AF123632</a>  104          .....c....................
79
<a name = 8050369></a><a
href=http://www.ncbi.nlm.nih.gov:80/entrez/query.fcgi?cmd=Retrieve&db=Nucleotide
&list_uids=08050369&dopt=GenBank>AF123628</a>  104          ..............g...........
79
<a name = 8050356></a><a
href=http://www.ncbi.nlm.nih.gov:80/entrez/query.fcgi?cmd=Retrieve&db=Nucleotide
&list_uids=08050356&dopt=GenBank>AF123621</a>  85           ....................g......
60
<a name = 8050352></a><a
href=http://www.ncbi.nlm.nih.gov:80/entrez/query.fcgi?cmd=Retrieve&db=Nucleotide
&list_uids=08050352&dopt=GenBank>AF123619</a>  104          ..............g...........
79
<a name = 8050350></a><a
href=http://www.ncbi.nlm.nih.gov:80/entrez/query.fcgi?cmd=Retrieve&db=Nucleotide
```

```
&list_uids=08050350&dopt=GenBank>AF123618</a>  104         ................g.....
79
<a name = 8050342></a><a
href=http://www.ncbi.nlm.nih.gov:80/entrez/query.fcgi?cmd=Retrieve&db=Nucleotide
&list_uids=08050342&dopt=GenBank>AF123614</a>  104         ...............g...........
79
<a name = 8050340></a><a
href=http://www.ncbi.nlm.nih.gov:80/entrez/query.fcgi?cmd=Retrieve&db=Nucleotide
&list_uids=08050340&dopt=GenBank>AF123613</a>  101         ...............g...........
76
<a name = 7715725></a><a
href=http://www.ncbi.nlm.nih.gov:80/entrez/query.fcgi?cmd=Retrieve&db=Nucleotide
&list_uids=07715725&dopt=GenBank>AF127201</a>  107         ...............g...........
82
<a name = 7715708></a><a
href=http://www.ncbi.nlm.nih.gov:80/entrez/query.fcgi?cmd=Retrieve&db=Nucleotide
&list_uids=07715708&dopt=GenBank>AF127192</a>  107         ...............t...........
82
<a name = 7715702></a><a
href=http://www.ncbi.nlm.nih.gov:80/entrez/query.fcgi?cmd=Retrieve&db=Nucleotide
&list_uids=07715702&dopt=GenBank>AF127189</a>  107         ...............g...........
82
<a name = 6469754></a><a
href=http://www.ncbi.nlm.nih.gov:80/entrez/query.fcgi?cmd=Retrieve&db=Nucleotide
&list_uids=06469754&dopt=GenBank>AF197849</a>  872         ....................g.....
847
<a name = 6469750></a><a
href=http://www.ncbi.nlm.nih.gov:80/entrez/query.fcgi?cmd=Retrieve&db=Nucleotide
&list_uids=06469750&dopt=GenBank>AF197847</a>  872         ...............t...........
847
<a name = 5836030></a><a
href=http://www.ncbi.nlm.nih.gov:80/entrez/query.fcgi?cmd=Retrieve&db=Nucleotide
&list_uids=05836030&dopt=GenBank>NC_000889</a> 15040       ...............g...........
15015
<a name = 5835778></a><a
href=http://www.ncbi.nlm.nih.gov:80/entrez/query.fcgi?cmd=Retrieve&db=Nucleotide
&list_uids=05835778&dopt=GenBank>NC_002079</a> 16164       ...............g...........
16139
<a name = 5835359></a><a
href=http://www.ncbi.nlm.nih.gov:80/entrez/query.fcgi?cmd=Retrieve&db=Nucleotide
&list_uids=05835359&dopt=GenBank>NC_001794</a> 15052       .....................a.....
15027
<a name = 5835037></a><a
href=http://www.ncbi.nlm.nih.gov:80/entrez/query.fcgi?cmd=Retrieve&db=Nucleotide
&list_uids=05835037&dopt=GenBank>NC_001610</a> 15045       ...............t...........
15020
<a name = 7243464></a><a
href=http://www.ncbi.nlm.nih.gov:80/entrez/query.fcgi?cmd=Retrieve&db=Nucleotide
&list_uids=07243464&dopt=GenBank>AF201612</a>  520         ...............t...........
495
<a name = 7546722></a><a
href=http://www.ncbi.nlm.nih.gov:80/entrez/query.fcgi?cmd=Retrieve&db=Nucleotide
&list_uids=07546722&dopt=GenBank>AF097931</a>  869         ...................a.......
844
<a name = 7546714></a><a
href=http://www.ncbi.nlm.nih.gov:80/entrez/query.fcgi?cmd=Retrieve&db=Nucleotide
```

```
&list_uids=07546714&dopt=GenBank>AF097927</a>  869  .....................g.....
844
<a name = 336430></a><a
href=http://www.ncbi.nlm.nih.gov:80/entrez/query.fcgi?cmd=Retrieve&db=Nucleotide
&list_uids=00336430&dopt=GenBank>J01394</a>   15382  ..............g...........
15357
<a name = 5764440></a><a
href=http://www.ncbi.nlm.nih.gov:80/entrez/query.fcgi?cmd=Retrieve&db=Nucleotide
&list_uids=05764440&dopt=GenBank>AF168760</a>  507  .....................a......
482
<a name = 5764438></a><a
href=http://www.ncbi.nlm.nih.gov:80/entrez/query.fcgi?cmd=Retrieve&db=Nucleotide
&list_uids=05764438&dopt=GenBank>AF168759</a>  507  .....................a......
482
<a name = 5764436></a><a
href=http://www.ncbi.nlm.nih.gov:80/entrez/query.fcgi?cmd=Retrieve&db=Nucleotide
&list_uids=05764436&dopt=GenBank>AF168758</a>  507  .....................a......
482
<a name = 5764432></a><a
href=http://www.ncbi.nlm.nih.gov:80/entrez/query.fcgi?cmd=Retrieve&db=Nucleotide
&list_uids=05764432&dopt=GenBank>AF168756</a>  507  .....................a......
482
<a name = 6063112></a><a
href=http://www.ncbi.nlm.nih.gov:80/entrez/query.fcgi?cmd=Retrieve&db=Nucleotide
&list_uids=06063112&dopt=GenBank>AF182381</a>  692  ...............t...........
667
<a name = 6063111></a><a
href=http://www.ncbi.nlm.nih.gov:80/entrez/query.fcgi?cmd=Retrieve&db=Nucleotide
&list_uids=06063111&dopt=GenBank>AF182380</a>  692  ...............t...........
667
<a name = 4099753></a><a
href=http://www.ncbi.nlm.nih.gov:80/entrez/query.fcgi?cmd=Retrieve&db=Nucleotide
&list_uids=04099753&dopt=GenBank>U89187</a>   872  ..................a........
847
<a name = 7208266></a><a
href=http://www.ncbi.nlm.nih.gov:80/entrez/query.fcgi?cmd=Retrieve&db=Nucleotide
&list_uids=07208266&dopt=GenBank>AF193833</a>  773  ...............g...........
748
<a name = 7208244></a><a
href=http://www.ncbi.nlm.nih.gov:80/entrez/query.fcgi?cmd=Retrieve&db=Nucleotide
&list_uids=07208244&dopt=GenBank>AF193822</a>  773  .....................g......
748
<a name = 7208242></a><a
href=http://www.ncbi.nlm.nih.gov:80/entrez/query.fcgi?cmd=Retrieve&db=Nucleotide
&list_uids=07208242&dopt=GenBank>AF193821</a>  773  .....................a......
748
<a name = 7141220></a><a
href=http://www.ncbi.nlm.nih.gov:80/entrez/query.fcgi?cmd=Retrieve&db=Nucleotide
&list_uids=07141220&dopt=GenBank>AF217837</a>  845  ...............t...........
820
<a name = 7141216></a><a
href=http://www.ncbi.nlm.nih.gov:80/entrez/query.fcgi?cmd=Retrieve&db=Nucleotide
&list_uids=07141216&dopt=GenBank>AF217835</a>  845  ...............t...........
820
<a name = 7141214></a><a
href=http://www.ncbi.nlm.nih.gov:80/entrez/query.fcgi?cmd=Retrieve&db=Nucleotide
```

```
&list_uids=07141214&dopt=GenBank>AF217834</a>  845       .......a.................
820
<a name = 7141208></a><a
href=http://www.ncbi.nlm.nih.gov:80/entrez/query.fcgi?cmd=Retrieve&db=Nucleotide
&list_uids=07141208&dopt=GenBank>AF217831</a>  845       .............g...........
820
<a name = 7141192></a><a
href=http://www.ncbi.nlm.nih.gov:80/entrez/query.fcgi?cmd=Retrieve&db=Nucleotide
&list_uids=07141192&dopt=GenBank>AF217823</a>  845       .......a.................
820
<a name = 7141184></a><a
href=http://www.ncbi.nlm.nih.gov:80/entrez/query.fcgi?cmd=Retrieve&db=Nucleotide
&list_uids=07141184&dopt=GenBank>AF217819</a>  845       .....a...................
820
<a name = 7141176></a><a
href=http://www.ncbi.nlm.nih.gov:80/entrez/query.fcgi?cmd=Retrieve&db=Nucleotide
&list_uids=07141176&dopt=GenBank>AF217815</a>  845       .............c...........
820
<a name = 6650839></a><a
href=http://www.ncbi.nlm.nih.gov:80/entrez/query.fcgi?cmd=Retrieve&db=Nucleotide
&list_uids=06650839&dopt=GenBank>AF118156</a>  101       .............g...........
76
<a name = 6715327></a><a
href=http://www.ncbi.nlm.nih.gov:80/entrez/query.fcgi?cmd=Retrieve&db=Nucleotide
&list_uids=06715327&dopt=GenBank>AF209938</a>  418       ............a............
393
<a name = 6715322></a><a
href=http://www.ncbi.nlm.nih.gov:80/entrez/query.fcgi?cmd=Retrieve&db=Nucleotide
&list_uids=06715322&dopt=GenBank>AF209933</a>  418       ............a............
393
<a name = 3088757></a><a
href=http://www.ncbi.nlm.nih.gov:80/entrez/query.fcgi?cmd=Retrieve&db=Nucleotide
&list_uids=03088757&dopt=GenBank>AF059104</a>  776       .....c...................
751
<a name = 3088753></a><a
href=http://www.ncbi.nlm.nih.gov:80/entrez/query.fcgi?cmd=Retrieve&db=Nucleotide
&list_uids=03088753&dopt=GenBank>AF059102</a>  776       ..............c..........
751
<a name = 3088657></a><a
href=http://www.ncbi.nlm.nih.gov:80/entrez/query.fcgi?cmd=Retrieve&db=Nucleotide
&list_uids=03088657&dopt=GenBank>AF059054</a>  776       ..............c..........
751
<a name = 6539763></a><a
href=http://www.ncbi.nlm.nih.gov:80/entrez/query.fcgi?cmd=Retrieve&db=Nucleotide
&list_uids=06539763&dopt=GenBank>AF192646</a>  869       ..............t..........
844
<a name = 6539762></a><a
href=http://www.ncbi.nlm.nih.gov:80/entrez/query.fcgi?cmd=Retrieve&db=Nucleotide
&list_uids=06539762&dopt=GenBank>AF192645</a>  869       ..............t..........
844
<a name = 6524790></a><a
href=http://www.ncbi.nlm.nih.gov:80/entrez/query.fcgi?cmd=Retrieve&db=Nucleotide
&list_uids=06524790&dopt=GenBank>AF160614</a>  869       ..............g..........
844
<a name = 6524789></a><a
href=http://www.ncbi.nlm.nih.gov:80/entrez/query.fcgi?cmd=Retrieve&db=Nucleotide
```

```
&list_uids=06524789&dopt=GenBank>AF160613</a>  869  ..............g............
844
<a name = 6524788></a><a
href=http://www.ncbi.nlm.nih.gov:80/entrez/query.fcgi?cmd=Retrieve&db=Nucleotide
&list_uids=06524788&dopt=GenBank>AF160612</a>  869  .....................g.....
844
<a name = 6524787></a><a
href=http://www.ncbi.nlm.nih.gov:80/entrez/query.fcgi?cmd=Retrieve&db=Nucleotide
&list_uids=06524787&dopt=GenBank>AF160611</a>  238  .....................g.....
213
<a name = 6524786></a><a
href=http://www.ncbi.nlm.nih.gov:80/entrez/query.fcgi?cmd=Retrieve&db=Nucleotide
&list_uids=06524786&dopt=GenBank>AF160610</a>  869  .....................g.....
844
<a name = 6524780></a><a
href=http://www.ncbi.nlm.nih.gov:80/entrez/query.fcgi?cmd=Retrieve&db=Nucleotide
&list_uids=06524780&dopt=GenBank>AF160604</a>  869  .....................g.....
844
<a name = 6524736></a><a
href=http://www.ncbi.nlm.nih.gov:80/entrez/query.fcgi?cmd=Retrieve&db=Nucleotide
&list_uids=06524736&dopt=GenBank>AF160560</a>  869  .....................a.....
844
<a name = 6524735></a><a
href=http://www.ncbi.nlm.nih.gov:80/entrez/query.fcgi?cmd=Retrieve&db=Nucleotide
&list_uids=06524735&dopt=GenBank>AF160559</a>  869  .....................a.....
844
<a name = 6524734></a><a
href=http://www.ncbi.nlm.nih.gov:80/entrez/query.fcgi?cmd=Retrieve&db=Nucleotide
&list_uids=06524734&dopt=GenBank>AF160558</a>  869  .....................a.....
844
<a name = 6524733></a><a
href=http://www.ncbi.nlm.nih.gov:80/entrez/query.fcgi?cmd=Retrieve&db=Nucleotide
&list_uids=06524733&dopt=GenBank>AF160557</a>  869  .....................a.....
844
<a name = 6524731></a><a
href=http://www.ncbi.nlm.nih.gov:80/entrez/query.fcgi?cmd=Retrieve&db=Nucleotide
&list_uids=06524731&dopt=GenBank>AF160555</a>  869  .....................a.....
844
<a name = 6524730></a><a
href=http://www.ncbi.nlm.nih.gov:80/entrez/query.fcgi?cmd=Retrieve&db=Nucleotide
&list_uids=06524730&dopt=GenBank>AF160554</a>  869  .....................a.....
844
<a name = 6524729></a><a
href=http://www.ncbi.nlm.nih.gov:80/entrez/query.fcgi?cmd=Retrieve&db=Nucleotide
&list_uids=06524729&dopt=GenBank>AF160553</a>  869  .....................a.....
844
<a name = 6524728></a><a
href=http://www.ncbi.nlm.nih.gov:80/entrez/query.fcgi?cmd=Retrieve&db=Nucleotide
&list_uids=06524728&dopt=GenBank>AF160552</a>  869  .....................a.....
844
<a name = 6524727></a><a
href=http://www.ncbi.nlm.nih.gov:80/entrez/query.fcgi?cmd=Retrieve&db=Nucleotide
&list_uids=06524727&dopt=GenBank>AF160551</a>  869  .....................a.....
844
<a name = 6524726></a><a
href=http://www.ncbi.nlm.nih.gov:80/entrez/query.fcgi?cmd=Retrieve&db=Nucleotide
```

```
&list_uids=06524726&dopt=GenBank>AF160550</a>  869       ....................a.....
844
<a name = 6524725></a><a
href=http://www.ncbi.nlm.nih.gov:80/entrez/query.fcgi?cmd=Retrieve&db=Nucleotide
&list_uids=06524725&dopt=GenBank>AF160549</a>  869       ....................a.....
844
<a name = 5777935></a><a
href=http://www.ncbi.nlm.nih.gov:80/entrez/query.fcgi?cmd=Retrieve&db=Nucleotide
&list_uids=05777935&dopt=GenBank>AF036287</a>  869       ..............g...........
844
<a name = 5777933></a><a
href=http://www.ncbi.nlm.nih.gov:80/entrez/query.fcgi?cmd=Retrieve&db=Nucleotide
&list_uids=05777933&dopt=GenBank>AF036286</a>  869       ..............g...........
844
<a name = 5777927></a><a
href=http://www.ncbi.nlm.nih.gov:80/entrez/query.fcgi?cmd=Retrieve&db=Nucleotide
&list_uids=05777927&dopt=GenBank>AF036283</a>  869       ..................a........
844
<a name = 5777923></a><a
href=http://www.ncbi.nlm.nih.gov:80/entrez/query.fcgi?cmd=Retrieve&db=Nucleotide
&list_uids=05777923&dopt=GenBank>AF036281</a>  869       ..................a........
844
<a name = 5777917></a><a
href=http://www.ncbi.nlm.nih.gov:80/entrez/query.fcgi?cmd=Retrieve&db=Nucleotide
&list_uids=05777917&dopt=GenBank>AF036278</a>  869       ..............g...........
844
<a name = 5777913></a><a
href=http://www.ncbi.nlm.nih.gov:80/entrez/query.fcgi?cmd=Retrieve&db=Nucleotide
&list_uids=05777913&dopt=GenBank>AF036276</a>  869       ...........a...............
844
<a name = 5777909></a><a
href=http://www.ncbi.nlm.nih.gov:80/entrez/query.fcgi?cmd=Retrieve&db=Nucleotide
&list_uids=05777909&dopt=GenBank>AF036274</a>  869       ..............g...........
844
<a name = 5835554></a><a
href=http://www.ncbi.nlm.nih.gov:80/entrez/query.fcgi?cmd=Retrieve&db=Nucleotide
&list_uids=05835554&dopt=GenBank>NC_001941</a> 15027     ...........a...............
15002
<a name = 5579171></a><a
href=http://www.ncbi.nlm.nih.gov:80/entrez/query.fcgi?cmd=Retrieve&db=Nucleotide
&list_uids=05579171&dopt=GenBank>AF108698</a>  869       ....................a.....
844
<a name = 5579155></a><a
href=http://www.ncbi.nlm.nih.gov:80/entrez/query.fcgi?cmd=Retrieve&db=Nucleotide
&list_uids=05579155&dopt=GenBank>AF108682</a>  869       ....................a.....
844
<a name = 5579146></a><a
href=http://www.ncbi.nlm.nih.gov:80/entrez/query.fcgi?cmd=Retrieve&db=Nucleotide
&list_uids=05579146&dopt=GenBank>AF108673</a>  869       ....................g.....
844
<a name = 5579142></a><a
href=http://www.ncbi.nlm.nih.gov:80/entrez/query.fcgi?cmd=Retrieve&db=Nucleotide
&list_uids=05579142&dopt=GenBank>AF108669</a>  857       ..............g...........
832
<a name = 5910972></a><a
href=http://www.ncbi.nlm.nih.gov:80/entrez/query.fcgi?cmd=Retrieve&db=Nucleotide
```

```
&list_uids=05910972&dopt=GenBank>AF042720</a> 869          .........a..........
844
<a name = 5910968></a><a
href=http://www.ncbi.nlm.nih.gov:80/entrez/query.fcgi?cmd=Retrieve&db=Nucleotide
&list_uids=05910968&dopt=GenBank>AF042718</a> 869          ................a........
844
<a name = 5870035></a><a
href=http://www.ncbi.nlm.nih.gov:80/entrez/query.fcgi?cmd=Retrieve&db=Nucleotide
&list_uids=05870035&dopt=GenBank>AF084082</a> 869          .....a....................
844
<a name = 5870034></a><a
href=http://www.ncbi.nlm.nih.gov:80/entrez/query.fcgi?cmd=Retrieve&db=Nucleotide
&list_uids=05870034&dopt=GenBank>AF084081</a> 869          .....a....................
844
<a name = 5870027></a><a
href=http://www.ncbi.nlm.nih.gov:80/entrez/query.fcgi?cmd=Retrieve&db=Nucleotide
&list_uids=05870027&dopt=GenBank>AF084074</a> 869          .....a....................
844
<a name = 5832998></a><a
href=http://www.ncbi.nlm.nih.gov:80/entrez/query.fcgi?cmd=Retrieve&db=Nucleotide
&list_uids=05832998&dopt=GenBank>AF090750</a> 869          ....................a.....
844
<a name = 5737944></a><a
href=http://www.ncbi.nlm.nih.gov:80/entrez/query.fcgi?cmd=Retrieve&db=Nucleotide
&list_uids=05737944&dopt=GenBank>AF157939</a> 869          ....................a.....
844
<a name = 5737942></a><a
href=http://www.ncbi.nlm.nih.gov:80/entrez/query.fcgi?cmd=Retrieve&db=Nucleotide
&list_uids=05737942&dopt=GenBank>AF157937</a> 869          ....................a.....
844
<a name = 5737941></a><a
href=http://www.ncbi.nlm.nih.gov:80/entrez/query.fcgi?cmd=Retrieve&db=Nucleotide
&list_uids=05737941&dopt=GenBank>AF157936</a> 869          ....................a.....
844
<a name = 5737920></a><a
href=http://www.ncbi.nlm.nih.gov:80/entrez/query.fcgi?cmd=Retrieve&db=Nucleotide
&list_uids=05737920&dopt=GenBank>AF157915</a> 869          ....................a.....
844
<a name = 5737919></a><a
href=http://www.ncbi.nlm.nih.gov:80/entrez/query.fcgi?cmd=Retrieve&db=Nucleotide
&list_uids=05737919&dopt=GenBank>AF157914</a> 869          ....................a.....
844
<a name = 5737917></a><a
href=http://www.ncbi.nlm.nih.gov:80/entrez/query.fcgi?cmd=Retrieve&db=Nucleotide
&list_uids=05737917&dopt=GenBank>AF157912</a> 869          ....................g.....
844
<a name = 5737911></a><a
href=http://www.ncbi.nlm.nih.gov:80/entrez/query.fcgi?cmd=Retrieve&db=Nucleotide
&list_uids=05737911&dopt=GenBank>AF157906</a> 869          ....................g.....
844
<a name = 5737896></a><a
href=http://www.ncbi.nlm.nih.gov:80/entrez/query.fcgi?cmd=Retrieve&db=Nucleotide
&list_uids=05737896&dopt=GenBank>AF157891</a> 869          ....................g.....
844
<a name = 5737887></a><a
href=http://www.ncbi.nlm.nih.gov:80/entrez/query.fcgi?cmd=Retrieve&db=Nucleotide
```

```
&list_uids=05737887&dopt=GenBank>AF157882</a>  869    .................a.....
844
<a name = 5737864></a><a
href=http://www.ncbi.nlm.nih.gov:80/entrez/query.fcgi?cmd=Retrieve&db=Nucleotide
&list_uids=05737864&dopt=GenBank>AF157859</a>  869    .................a.....
844
<a name = 5737863></a><a
href=http://www.ncbi.nlm.nih.gov:80/entrez/query.fcgi?cmd=Retrieve&db=Nucleotide
&list_uids=05737863&dopt=GenBank>AF157858</a>  869    .................a.....
844
<a name = 5737844></a><a
href=http://www.ncbi.nlm.nih.gov:80/entrez/query.fcgi?cmd=Retrieve&db=Nucleotide
&list_uids=05737844&dopt=GenBank>AF157839</a>  869    .................g.....
844
<a name = 2674125></a><a
href=http://www.ncbi.nlm.nih.gov:80/entrez/query.fcgi?cmd=Retrieve&db=Nucleotide
&list_uids=02674125&dopt=GenBank>AF030497</a>  50     .....a..................
25
<a name = 5453528></a><a
href=http://www.ncbi.nlm.nih.gov:80/entrez/query.fcgi?cmd=Retrieve&db=Nucleotide
&list_uids=05453528&dopt=GenBank>U03541</a>    869    .................g.....
844
<a name = 5713307></a><a
href=http://www.ncbi.nlm.nih.gov:80/entrez/query.fcgi?cmd=Retrieve&db=Nucleotide
&list_uids=05713307&dopt=GenBank>AF009951</a>  866    ................a........
841
<a name = 2281562></a><a
href=http://www.ncbi.nlm.nih.gov:80/entrez/query.fcgi?cmd=Retrieve&db=Nucleotide
&list_uids=02281562&dopt=GenBank>AF009941</a>  869    ............g...........
844
<a name = 2281530></a><a
href=http://www.ncbi.nlm.nih.gov:80/entrez/query.fcgi?cmd=Retrieve&db=Nucleotide
&list_uids=02281530&dopt=GenBank>AF009925</a>  869    ...............a........
844
<a name = 5712261></a><a
href=http://www.ncbi.nlm.nih.gov:80/entrez/query.fcgi?cmd=Retrieve&db=Nucleotide
&list_uids=05712261&dopt=GenBank>AF094633</a>  737    ..................g.....
712
<a name = 5712237></a><a
href=http://www.ncbi.nlm.nih.gov:80/entrez/query.fcgi?cmd=Retrieve&db=Nucleotide
&list_uids=05712237&dopt=GenBank>AF094621</a>  737    ..............t..........
712
<a name = 5712231></a><a
href=http://www.ncbi.nlm.nih.gov:80/entrez/query.fcgi?cmd=Retrieve&db=Nucleotide
&list_uids=05712231&dopt=GenBank>AF094618</a>  737    ..............t..........
712
<a name = 5616507></a><a
href=http://www.ncbi.nlm.nih.gov:80/entrez/query.fcgi?cmd=Retrieve&db=Nucleotide
&list_uids=05616507&dopt=GenBank>AF166348</a>  869    ..............g..........
844
<a name = 5616278></a><a
href=http://www.ncbi.nlm.nih.gov:80/entrez/query.fcgi?cmd=Retrieve&db=Nucleotide
&list_uids=05616278&dopt=GenBank>AF158697</a>  869    ............a...........
844
<a name = 5616271></a><a
href=http://www.ncbi.nlm.nih.gov:80/entrez/query.fcgi?cmd=Retrieve&db=Nucleotide
```

```
&list_uids=05616271&dopt=GenBank>AF158694</a>   869        ..........a..............
844
<a name = 5616268></a><a
href=http://www.ncbi.nlm.nih.gov:80/entrez/query.fcgi?cmd=Retrieve&db=Nucleotide
&list_uids=05616268&dopt=GenBank>AF158693</a>   869        ..........a..............
844
<a name = 5616256></a><a
href=http://www.ncbi.nlm.nih.gov:80/entrez/query.fcgi?cmd=Retrieve&db=Nucleotide
&list_uids=05616256&dopt=GenBank>AF158688</a>   869        ..........a..............
844
<a name = 5565802></a><a
href=http://www.ncbi.nlm.nih.gov:80/entrez/query.fcgi?cmd=Retrieve&db=Nucleotide
&list_uids=05565802&dopt=GenBank>AF100720</a>   869        ....................a.....
844
<a name = 5359515></a><a
href=http://www.ncbi.nlm.nih.gov:80/entrez/query.fcgi?cmd=Retrieve&db=Nucleotide
&list_uids=05359515&dopt=GenBank>AF091632</a>   869        ................a.........
844
<a name = 4324400></a><a
href=http://www.ncbi.nlm.nih.gov:80/entrez/query.fcgi?cmd=Retrieve&db=Nucleotide
&list_uids=04324400&dopt=GenBank>AF102815</a>   869        ....................a......
844
<a name = 4324399></a><a
href=http://www.ncbi.nlm.nih.gov:80/entrez/query.fcgi?cmd=Retrieve&db=Nucleotide
&list_uids=04324399&dopt=GenBank>AF102814</a>   869        ..............t............
844
<a name = 4103305></a><a
href=http://www.ncbi.nlm.nih.gov:80/entrez/query.fcgi?cmd=Retrieve&db=Nucleotide
&list_uids=04103305&dopt=GenBank>AF022065</a>   869        ..........a..............
844
<a name = 4103293></a><a
href=http://www.ncbi.nlm.nih.gov:80/entrez/query.fcgi?cmd=Retrieve&db=Nucleotide
&list_uids=04103293&dopt=GenBank>AF022059</a>   869        ..............g............
844
<a name = 4103291></a><a
href=http://www.ncbi.nlm.nih.gov:80/entrez/query.fcgi?cmd=Retrieve&db=Nucleotide
&list_uids=04103291&dopt=GenBank>AF022058</a>   869        ................a........
844
<a name = 4103289></a><a
href=http://www.ncbi.nlm.nih.gov:80/entrez/query.fcgi?cmd=Retrieve&db=Nucleotide
&list_uids=04103289&dopt=GenBank>AF022057</a>   869        ..............g............
844
<a name = 4103283></a><a
href=http://www.ncbi.nlm.nih.gov:80/entrez/query.fcgi?cmd=Retrieve&db=Nucleotide
&list_uids=04103283&dopt=GenBank>AF022054</a>   869        ................a........
844
<a name = 4102850></a><a
href=http://www.ncbi.nlm.nih.gov:80/entrez/query.fcgi?cmd=Retrieve&db=Nucleotide
&list_uids=04102850&dopt=GenBank>AF016637</a>   869        ..........c..............
844
<a name = 2843078></a><a
href=http://www.ncbi.nlm.nih.gov:80/entrez/query.fcgi?cmd=Retrieve&db=Nucleotide
&list_uids=02843078&dopt=GenBank>U69863</a>     845        ..............t............
820
<a name = 2843040></a><a
href=http://www.ncbi.nlm.nih.gov:80/entrez/query.fcgi?cmd=Retrieve&db=Nucleotide
```

```
&list_uids=02843040&dopt=GenBank>U69844</a>    845   .............t............
820
<a name = 5070473></a><a
href=http://www.ncbi.nlm.nih.gov:80/entrez/query.fcgi?cmd=Retrieve&db=Nucleotide
&list_uids=05070473&dopt=GenBank>AF143193</a>  869   ....................a......
844
<a name = 4903279></a><a
href=http://www.ncbi.nlm.nih.gov:80/entrez/query.fcgi?cmd=Retrieve&db=Nucleotide
&list_uids=04903279&dopt=GenBank>AF121222</a>  140   ....................g......
115
<a name = 4689176></a><a
href=http://www.ncbi.nlm.nih.gov:80/entrez/query.fcgi?cmd=Retrieve&db=Nucleotide
&list_uids=04689176&dopt=GenBank>AF096625</a>  869   ..............g...........
844
<a name = 4689174></a><a
href=http://www.ncbi.nlm.nih.gov:80/entrez/query.fcgi?cmd=Retrieve&db=Nucleotide
&list_uids=04689174&dopt=GenBank>AF096624</a>  869   ..............g...........
844
<a name = 4235321></a><a
href=http://www.ncbi.nlm.nih.gov:80/entrez/query.fcgi?cmd=Retrieve&db=Nucleotide
&list_uids=04235321&dopt=GenBank>AF081052</a>  869   ....................a......
844
<a name = 4235315></a><a
href=http://www.ncbi.nlm.nih.gov:80/entrez/query.fcgi?cmd=Retrieve&db=Nucleotide
&list_uids=04235315&dopt=GenBank>AF081049</a>  869   ....................a......
844
<a name = 4235313></a><a
href=http://www.ncbi.nlm.nih.gov:80/entrez/query.fcgi?cmd=Retrieve&db=Nucleotide
&list_uids=04235313&dopt=GenBank>AF081048</a>  869   ....................g......
844
<a name = 3551922></a><a
href=http://www.ncbi.nlm.nih.gov:80/entrez/query.fcgi?cmd=Retrieve&db=Nucleotide
&list_uids=03551922&dopt=GenBank>AF082063</a>  54    ....................g......
29
<a name = 4127863></a><a
href=http://www.ncbi.nlm.nih.gov:80/entrez/query.fcgi?cmd=Retrieve&db=Nucleotide
&list_uids=04127863&dopt=GenBank>AJ010957</a>  15040 ..............g...........
15015
<a name = 4098265></a><a
href=http://www.ncbi.nlm.nih.gov:80/entrez/query.fcgi?cmd=Retrieve&db=Nucleotide
&list_uids=04098265&dopt=GenBank>U76506</a>    773   ..............g...........
748
<a name = 4098261></a><a
href=http://www.ncbi.nlm.nih.gov:80/entrez/query.fcgi?cmd=Retrieve&db=Nucleotide
&list_uids=04098261&dopt=GenBank>U76504</a>    773   ..............g...........
748
<a name = 4098259></a><a
href=http://www.ncbi.nlm.nih.gov:80/entrez/query.fcgi?cmd=Retrieve&db=Nucleotide
&list_uids=04098259&dopt=GenBank>U76505</a>    773   ..............t...........
748
<a name = 4098257></a><a
href=http://www.ncbi.nlm.nih.gov:80/entrez/query.fcgi?cmd=Retrieve&db=Nucleotide
&list_uids=04098257&dopt=GenBank>U76503</a>    773   ..............t...........
748
<a name = 4098255></a><a
href=http://www.ncbi.nlm.nih.gov:80/entrez/query.fcgi?cmd=Retrieve&db=Nucleotide
```

```
&list_uids=04098255&dopt=GenBank>U76508</a>    773   ................t............
748
<a name = 2660921></a><a
href=http://www.ncbi.nlm.nih.gov:80/entrez/query.fcgi?cmd=Retrieve&db=Nucleotide
&list_uids=02660921&dopt=GenBank>AF034969</a>   869   ...............g............
844
<a name = 4079773></a><a
href=http://www.ncbi.nlm.nih.gov:80/entrez/query.fcgi?cmd=Retrieve&db=Nucleotide
&list_uids=04079773&dopt=GenBank>AF051876</a>   869   ...............t............
844
<a name = 3676657></a><a
href=http://www.ncbi.nlm.nih.gov:80/entrez/query.fcgi?cmd=Retrieve&db=Nucleotide
&list_uids=03676657&dopt=GenBank>AF082007</a>   872   ...............t............
847
<a name = 3676655></a><a
href=http://www.ncbi.nlm.nih.gov:80/entrez/query.fcgi?cmd=Retrieve&db=Nucleotide
&list_uids=03676655&dopt=GenBank>AF082006</a>   872   ...............t............
847
<a name = 3676653></a><a
href=http://www.ncbi.nlm.nih.gov:80/entrez/query.fcgi?cmd=Retrieve&db=Nucleotide
&list_uids=03676653&dopt=GenBank>AF082005</a>   872   ...............t............
847
<a name = 3676651></a><a
href=http://www.ncbi.nlm.nih.gov:80/entrez/query.fcgi?cmd=Retrieve&db=Nucleotide
&list_uids=03676651&dopt=GenBank>AF082004</a>   872   ...............t............
847
<a name = 3676649></a><a
href=http://www.ncbi.nlm.nih.gov:80/entrez/query.fcgi?cmd=Retrieve&db=Nucleotide
&list_uids=03676649&dopt=GenBank>AF082003</a>   872   ...............t............
847
<a name = 3676647></a><a
href=http://www.ncbi.nlm.nih.gov:80/entrez/query.fcgi?cmd=Retrieve&db=Nucleotide
&list_uids=03676647&dopt=GenBank>AF082002</a>   872   ...............t............
847
<a name = 3676645></a><a
href=http://www.ncbi.nlm.nih.gov:80/entrez/query.fcgi?cmd=Retrieve&db=Nucleotide
&list_uids=03676645&dopt=GenBank>AF082001</a>   872   ...............t............
847
<a name = 3676643></a><a
href=http://www.ncbi.nlm.nih.gov:80/entrez/query.fcgi?cmd=Retrieve&db=Nucleotide
&list_uids=03676643&dopt=GenBank>AF082000</a>   872   ...............t............
847
<a name = 3676641></a><a
href=http://www.ncbi.nlm.nih.gov:80/entrez/query.fcgi?cmd=Retrieve&db=Nucleotide
&list_uids=03676641&dopt=GenBank>AF081999</a>   872   ...............t............
847
<a name = 3676639></a><a
href=http://www.ncbi.nlm.nih.gov:80/entrez/query.fcgi?cmd=Retrieve&db=Nucleotide
&list_uids=03676639&dopt=GenBank>AF081998</a>   872   ...............t............
847
<a name = 3676637></a><a
href=http://www.ncbi.nlm.nih.gov:80/entrez/query.fcgi?cmd=Retrieve&db=Nucleotide
&list_uids=03676637&dopt=GenBank>AF081997</a>   872   ...............t............
847
<a name = 3676635></a><a
href=http://www.ncbi.nlm.nih.gov:80/entrez/query.fcgi?cmd=Retrieve&db=Nucleotide
```

```
&list_uids=03676635&dopt=GenBank>AF081996</a>  872          ...............t...........
847
<a name = 3676633></a><a
href=http://www.ncbi.nlm.nih.gov:80/entrez/query.fcgi?cmd=Retrieve&db=Nucleotide
&list_uids=03676633&dopt=GenBank>AF081995</a>  872          ...............t...........
847
<a name = 3676631></a><a
href=http://www.ncbi.nlm.nih.gov:80/entrez/query.fcgi?cmd=Retrieve&db=Nucleotide
&list_uids=03676631&dopt=GenBank>AF081994</a>  872          ...............t...........
847
<a name = 3676629></a><a
href=http://www.ncbi.nlm.nih.gov:80/entrez/query.fcgi?cmd=Retrieve&db=Nucleotide
&list_uids=03676629&dopt=GenBank>AF081993</a>  872          ...............t...........
847
<a name = 3676627></a><a
href=http://www.ncbi.nlm.nih.gov:80/entrez/query.fcgi?cmd=Retrieve&db=Nucleotide
&list_uids=03676627&dopt=GenBank>AF081992</a>  872          ...............t...........
847
<a name = 3676625></a><a
href=http://www.ncbi.nlm.nih.gov:80/entrez/query.fcgi?cmd=Retrieve&db=Nucleotide
&list_uids=03676625&dopt=GenBank>AF081991</a>  872          ...............t...........
847
<a name = 639944></a><a
href=http://www.ncbi.nlm.nih.gov:80/entrez/query.fcgi?cmd=Retrieve&db=Nucleotide
&list_uids=00639944&dopt=GenBank>S73150</a>  869          ....................a......
844
<a name = 2581990></a><a
href=http://www.ncbi.nlm.nih.gov:80/entrez/query.fcgi?cmd=Retrieve&db=Nucleotide
&list_uids=02581990&dopt=GenBank>AF012235</a>  860          ....................a......
835
<a name = 1374743></a><a
href=http://www.ncbi.nlm.nih.gov:80/entrez/query.fcgi?cmd=Retrieve&db=Nucleotide
&list_uids=01374743&dopt=GenBank>U53580</a>  869          ...............g...........
844
<a name = 1374731></a><a
href=http://www.ncbi.nlm.nih.gov:80/entrez/query.fcgi?cmd=Retrieve&db=Nucleotide
&list_uids=01374731&dopt=GenBank>U53577</a>  869          ....................g......
844
<a name = 1374729></a><a
href=http://www.ncbi.nlm.nih.gov:80/entrez/query.fcgi?cmd=Retrieve&db=Nucleotide
&list_uids=01374729&dopt=GenBank>U53576</a>  869          ....................a......
844
<a name = 2253669></a><a
href=http://www.ncbi.nlm.nih.gov:80/entrez/query.fcgi?cmd=Retrieve&db=Nucleotide
&list_uids=02253669&dopt=GenBank>U95512</a>  31           ....................g......
6
<a name = 2253659></a><a
href=http://www.ncbi.nlm.nih.gov:80/entrez/query.fcgi?cmd=Retrieve&db=Nucleotide
&list_uids=02253659&dopt=GenBank>U95508</a>  31           ...........a...............
6
<a name = 1504122></a><a
href=http://www.ncbi.nlm.nih.gov:80/entrez/query.fcgi?cmd=Retrieve&db=Nucleotide
&list_uids=01504122&dopt=GenBank>U17868</a>  869          ...............g...........
844
<a name = 1504120></a><a
href=http://www.ncbi.nlm.nih.gov:80/entrez/query.fcgi?cmd=Retrieve&db=Nucleotide
```

```
&list_uids=01504120&dopt=GenBank>U17867</a>    869    ...............g...........
844
<a name = 604327></a><a
href=http://www.ncbi.nlm.nih.gov:80/entrez/query.fcgi?cmd=Retrieve&db=Nucleotide
&list_uids=00604327&dopt=GenBank>U17860</a>    869    ...............g...........
844
<a name = 604325></a><a
href=http://www.ncbi.nlm.nih.gov:80/entrez/query.fcgi?cmd=Retrieve&db=Nucleotide
&list_uids=00604325&dopt=GenBank>U17859</a>    800    ...............g...........
775
<a name = 4127373></a><a
href=http://www.ncbi.nlm.nih.gov:80/entrez/query.fcgi?cmd=Retrieve&db=Nucleotide
&list_uids=04127373&dopt=GenBank>AJ010556</a>  869    .....................g.....
844
<a name = 3417588></a><a
href=http://www.ncbi.nlm.nih.gov:80/entrez/query.fcgi?cmd=Retrieve&db=Nucleotide
&list_uids=03417588&dopt=GenBank>AF034736</a>  869    ...............g...........
844
<a name = 3417576></a><a
href=http://www.ncbi.nlm.nih.gov:80/entrez/query.fcgi?cmd=Retrieve&db=Nucleotide
&list_uids=03417576&dopt=GenBank>AF034730</a>  869    ............a..............
844
<a name = 3417574></a><a
href=http://www.ncbi.nlm.nih.gov:80/entrez/query.fcgi?cmd=Retrieve&db=Nucleotide
&list_uids=03417574&dopt=GenBank>AF034729</a>  869    ............a..............
844
<a name = 3417572></a><a
href=http://www.ncbi.nlm.nih.gov:80/entrez/query.fcgi?cmd=Retrieve&db=Nucleotide
&list_uids=03417572&dopt=GenBank>AF034728</a>  869    ...............g...........
844
<a name = 3417570></a><a
href=http://www.ncbi.nlm.nih.gov:80/entrez/query.fcgi?cmd=Retrieve&db=Nucleotide
&list_uids=03417570&dopt=GenBank>AF034727</a>  869    ............a..............
844
<a name = 3417564></a><a
href=http://www.ncbi.nlm.nih.gov:80/entrez/query.fcgi?cmd=Retrieve&db=Nucleotide
&list_uids=03417564&dopt=GenBank>AF034724</a>  869    ...............g...........
844
<a name = 3417560></a><a
href=http://www.ncbi.nlm.nih.gov:80/entrez/query.fcgi?cmd=Retrieve&db=Nucleotide
&list_uids=03417560&dopt=GenBank>AF034722</a>  869    ...............g...........
844
<a name = 1695902></a><a
href=http://www.ncbi.nlm.nih.gov:80/entrez/query.fcgi?cmd=Retrieve&db=Nucleotide
&list_uids=01695902&dopt=GenBank>U72038</a>    869    ...............g...........
844
<a name = 1695900></a><a
href=http://www.ncbi.nlm.nih.gov:80/entrez/query.fcgi?cmd=Retrieve&db=Nucleotide
&list_uids=01695900&dopt=GenBank>U72037</a>    869    ...............g...........
844
<a name = 1778700></a><a
href=http://www.ncbi.nlm.nih.gov:80/entrez/query.fcgi?cmd=Retrieve&db=Nucleotide
&list_uids=01778700&dopt=GenBank>M99455</a>    869    ............a..............
844
<a name = 456705></a><a
href=http://www.ncbi.nlm.nih.gov:80/entrez/query.fcgi?cmd=Retrieve&db=Nucleotide
```

```
&list_uids=00456705&dopt=GenBank>L29055</a>   260       ...........a.............
235
<a name = 3551884></a><a
href=http://www.ncbi.nlm.nih.gov:80/entrez/query.fcgi?cmd=Retrieve&db=Nucleotide
&list_uids=03551884&dopt=GenBank>AF082047</a>   54       .....................g.....
29
<a name = 3098355></a><a
href=http://www.ncbi.nlm.nih.gov:80/entrez/query.fcgi?cmd=Retrieve&db=Nucleotide
&list_uids=03098355&dopt=GenBank>AF038286</a>   869      ...............t...........
844
<a name = 3098351></a><a
href=http://www.ncbi.nlm.nih.gov:80/entrez/query.fcgi?cmd=Retrieve&db=Nucleotide
&list_uids=03098351&dopt=GenBank>AF038284</a>   869      ...............t...........
844
<a name = 3088735></a><a
href=http://www.ncbi.nlm.nih.gov:80/entrez/query.fcgi?cmd=Retrieve&db=Nucleotide
&list_uids=03088735&dopt=GenBank>AF059093</a>   776      ................t...........
751
<a name = 3088733></a><a
href=http://www.ncbi.nlm.nih.gov:80/entrez/query.fcgi?cmd=Retrieve&db=Nucleotide
&list_uids=03088733&dopt=GenBank>AF059092</a>   776      ................t...........
751
<a name = 3088731></a><a
href=http://www.ncbi.nlm.nih.gov:80/entrez/query.fcgi?cmd=Retrieve&db=Nucleotide
&list_uids=03088731&dopt=GenBank>AF059091</a>   776      ................t...........
751
<a name = 3088709></a><a
href=http://www.ncbi.nlm.nih.gov:80/entrez/query.fcgi?cmd=Retrieve&db=Nucleotide
&list_uids=03088709&dopt=GenBank>AF059080</a>   776      ................t...........
751
<a name = 3088705></a><a
href=http://www.ncbi.nlm.nih.gov:80/entrez/query.fcgi?cmd=Retrieve&db=Nucleotide
&list_uids=03088705&dopt=GenBank>AF059078</a>   776      ................t...........
751
<a name = 2970664></a><a
href=http://www.ncbi.nlm.nih.gov:80/entrez/query.fcgi?cmd=Retrieve&db=Nucleotide
&list_uids=02970664&dopt=GenBank>AF052240</a>   61       .....................a......
36
<a name = 2935094></a><a
href=http://www.ncbi.nlm.nih.gov:80/entrez/query.fcgi?cmd=Retrieve&db=Nucleotide
&list_uids=02935094&dopt=GenBank>AF006240</a>   774      ................t...........
749
<a name = 2935068></a><a
href=http://www.ncbi.nlm.nih.gov:80/entrez/query.fcgi?cmd=Retrieve&db=Nucleotide
&list_uids=02935068&dopt=GenBank>AF006227</a>   774      .....................g.....
749
<a name = 2921858></a><a
href=http://www.ncbi.nlm.nih.gov:80/entrez/query.fcgi?cmd=Retrieve&db=Nucleotide
&list_uids=02921858&dopt=GenBank>AF047447</a>   41       ...............g...........
16
<a name = 2905822></a><a
href=http://www.ncbi.nlm.nih.gov:80/entrez/query.fcgi?cmd=Retrieve&db=Nucleotide
&list_uids=02905822&dopt=GenBank>U07576</a>   869        ..............g...........
844
<a name = 2828646></a><a
href=http://www.ncbi.nlm.nih.gov:80/entrez/query.fcgi?cmd=Retrieve&db=Nucleotide
```

```
&list_uids=02828646&dopt=GenBank>AF028180</a>  65          ..............g..........
40
<a name = 2828644></a><a
href=http://www.ncbi.nlm.nih.gov:80/entrez/query.fcgi?cmd=Retrieve&db=Nucleotide
&list_uids=02828644&dopt=GenBank>AF028178</a>  69          .....................g.....
44
<a name = 2828638></a><a
href=http://www.ncbi.nlm.nih.gov:80/entrez/query.fcgi?cmd=Retrieve&db=Nucleotide
&list_uids=02828638&dopt=GenBank>AF028170</a>  77          .....................g.....
52
<a name = 1773228></a><a
href=http://www.ncbi.nlm.nih.gov:80/entrez/query.fcgi?cmd=Retrieve&db=Nucleotide
&list_uids=01773228&dopt=GenBank>M99454</a>   869         ..................a.........
844
<a name = 1773232></a><a
href=http://www.ncbi.nlm.nih.gov:80/entrez/query.fcgi?cmd=Retrieve&db=Nucleotide
&list_uids=01773232&dopt=GenBank>M99453</a>   869         ...............t............
844
<a name = 2689878></a><a
href=http://www.ncbi.nlm.nih.gov:80/entrez/query.fcgi?cmd=Retrieve&db=Nucleotide
&list_uids=02689878&dopt=GenBank>U23461</a>   869         ........c...................
844
<a name = 2149540></a><a
href=http://www.ncbi.nlm.nih.gov:80/entrez/query.fcgi?cmd=Retrieve&db=Nucleotide
&list_uids=02149540&dopt=GenBank>U87138</a>   869         ...............g............
844
<a name = 2677661></a><a
href=http://www.ncbi.nlm.nih.gov:80/entrez/query.fcgi?cmd=Retrieve&db=Nucleotide
&list_uids=02677661&dopt=GenBank>U07590</a>   869         .....................g.....
844
<a name = 9998878></a><a
href=http://www.ncbi.nlm.nih.gov:80/entrez/query.fcgi?cmd=Retrieve&db=Nucleotide
&list_uids=09998878&dopt=GenBank>AJ004326</a>  773         ......c.....................
748
<a name = 2444366></a><a
href=http://www.ncbi.nlm.nih.gov:80/entrez/query.fcgi?cmd=Retrieve&db=Nucleotide
&list_uids=02444366&dopt=GenBank>AF020255</a>  819         .....................g.....
794
<a name = 9558343></a><a
href=http://www.ncbi.nlm.nih.gov:80/entrez/query.fcgi?cmd=Retrieve&db=Nucleotide
&list_uids=09558343&dopt=GenBank>Y19184</a>   15022  ..............g............
14997
<a name = 2290362></a><a
href=http://www.ncbi.nlm.nih.gov:80/entrez/query.fcgi?cmd=Retrieve&db=Nucleotide
&list_uids=02290362&dopt=GenBank>U88862</a>   843         ..................a.........
818
<a name = 2290356></a><a
href=http://www.ncbi.nlm.nih.gov:80/entrez/query.fcgi?cmd=Retrieve&db=Nucleotide
&list_uids=02290356&dopt=GenBank>U88859</a>   867         ...............g............
842
<a name = 2290354></a><a
href=http://www.ncbi.nlm.nih.gov:80/entrez/query.fcgi?cmd=Retrieve&db=Nucleotide
&list_uids=02290354&dopt=GenBank>U88858</a>   843         ........c...................
818
<a name = 2290352></a><a
href=http://www.ncbi.nlm.nih.gov:80/entrez/query.fcgi?cmd=Retrieve&db=Nucleotide
```

```
&list_uids=02290352&dopt=GenBank>U88857</a>    863    ..............g..........
838
<a name = 2290350></a><a
href=http://www.ncbi.nlm.nih.gov:80/entrez/query.fcgi?cmd=Retrieve&db=Nucleotide
&list_uids=02290350&dopt=GenBank>U88856</a>    867    ..............g..........
842
<a name = 1850861></a><a
href=http://www.ncbi.nlm.nih.gov:80/entrez/query.fcgi?cmd=Retrieve&db=Nucleotide
&list_uids=01850861&dopt=GenBank>Y10524</a>    15052   ....................a.....
15027
<a name = 2098662></a><a
href=http://www.ncbi.nlm.nih.gov:80/entrez/query.fcgi?cmd=Retrieve&db=Nucleotide
&list_uids=02098662&dopt=GenBank>U81357</a>    791    ..............t...........
766
<a name = 2098654></a><a
href=http://www.ncbi.nlm.nih.gov:80/entrez/query.fcgi?cmd=Retrieve&db=Nucleotide
&list_uids=02098654&dopt=GenBank>U81356</a>    791    ...........a..............
766
<a name = 1923224></a><a
href=http://www.ncbi.nlm.nih.gov:80/entrez/query.fcgi?cmd=Retrieve&db=Nucleotide
&list_uids=01923224&dopt=GenBank>U75354</a>    452    ...................a........
427
<a name = 1841718></a><a
href=http://www.ncbi.nlm.nih.gov:80/entrez/query.fcgi?cmd=Retrieve&db=Nucleotide
&list_uids=01841718&dopt=GenBank>U77332</a>    872    .....................g.....
847
<a name = 452251></a><a
href=http://www.ncbi.nlm.nih.gov:80/entrez/query.fcgi?cmd=Retrieve&db=Nucleotide
&list_uids=00452251&dopt=GenBank>Z29573</a>    15045   ..............t...........
15020
<a name = 3483071></a><a
href=http://www.ncbi.nlm.nih.gov:80/entrez/query.fcgi?cmd=Retrieve&db=Nucleotide
&list_uids=03483071&dopt=GenBank>AJ222679</a>  869    ..............g...........
844
<a name = 3492812></a><a
href=http://www.ncbi.nlm.nih.gov:80/entrez/query.fcgi?cmd=Retrieve&db=Nucleotide
&list_uids=03492812&dopt=GenBank>AJ222680</a>  869    ............a...............
844
<a name = 3492814></a><a
href=http://www.ncbi.nlm.nih.gov:80/entrez/query.fcgi?cmd=Retrieve&db=Nucleotide
&list_uids=03492814&dopt=GenBank>AJ222685</a>  869    ..............g...........
844
<a name = 1778698></a><a
href=http://www.ncbi.nlm.nih.gov:80/entrez/query.fcgi?cmd=Retrieve&db=Nucleotide
&list_uids=01778698&dopt=GenBank>M99466</a>    869    .................a.........
844
<a name = 1778696></a><a
href=http://www.ncbi.nlm.nih.gov:80/entrez/query.fcgi?cmd=Retrieve&db=Nucleotide
&list_uids=01778696&dopt=GenBank>M99452</a>    869    ..............t...........
844
<a name = 1777381></a><a
href=http://www.ncbi.nlm.nih.gov:80/entrez/query.fcgi?cmd=Retrieve&db=Nucleotide
&list_uids=01777381&dopt=GenBank>M99460</a>    869    .....................g.....
844
<a name = 841453></a><a
href=http://www.ncbi.nlm.nih.gov:80/entrez/query.fcgi?cmd=Retrieve&db=Nucleotide
```

```
&list_uids=00841453&dopt=GenBank>U25737</a>    872    ..................a........
847
<a name = 840938></a><a
href=http://www.ncbi.nlm.nih.gov:80/entrez/query.fcgi?cmd=Retrieve&db=Nucleotide
&list_uids=00840938&dopt=GenBank>U15203</a>    872    ...............t...........
847
<a name = 840942></a><a
href=http://www.ncbi.nlm.nih.gov:80/entrez/query.fcgi?cmd=Retrieve&db=Nucleotide
&list_uids=00840942&dopt=GenBank>U15205</a>    872    .....c.....................
847
<a name = 840932></a><a
href=http://www.ncbi.nlm.nih.gov:80/entrez/query.fcgi?cmd=Retrieve&db=Nucleotide
&list_uids=00840932&dopt=GenBank>U15200</a>    872    ...............g...........
847
<a name = 3320079></a><a
href=http://www.ncbi.nlm.nih.gov:80/entrez/query.fcgi?cmd=Retrieve&db=Nucleotide
&list_uids=03320079&dopt=GenBank>AJ000424</a>   740    ....................g.....
715
<a name = 3327022></a><a
href=http://www.ncbi.nlm.nih.gov:80/entrez/query.fcgi?cmd=Retrieve&db=Nucleotide
&list_uids=03327022&dopt=GenBank>AJ000423</a>   740    ....................g.....
715
<a name = 3320026></a><a
href=http://www.ncbi.nlm.nih.gov:80/entrez/query.fcgi?cmd=Retrieve&db=Nucleotide
&list_uids=03320026&dopt=GenBank>AJ000438</a>   740    ................a........
715
<a name = 3320024></a><a
href=http://www.ncbi.nlm.nih.gov:80/entrez/query.fcgi?cmd=Retrieve&db=Nucleotide
&list_uids=03320024&dopt=GenBank>AJ000437</a>   740    ................a........
715
<a name = 3320001></a><a
href=http://www.ncbi.nlm.nih.gov:80/entrez/query.fcgi?cmd=Retrieve&db=Nucleotide
&list_uids=03320001&dopt=GenBank>AJ000428</a>   740    ....................a.....
715
<a name = 3319999></a><a
href=http://www.ncbi.nlm.nih.gov:80/entrez/query.fcgi?cmd=Retrieve&db=Nucleotide
&list_uids=03319999&dopt=GenBank>AJ000427</a>   740    ....................a.....
715
<a name = 3319997></a><a
href=http://www.ncbi.nlm.nih.gov:80/entrez/query.fcgi?cmd=Retrieve&db=Nucleotide
&list_uids=03319997&dopt=GenBank>AJ000426</a>   740    ....................g.....
715
<a name = 3319995></a><a
href=http://www.ncbi.nlm.nih.gov:80/entrez/query.fcgi?cmd=Retrieve&db=Nucleotide
&list_uids=03319995&dopt=GenBank>AJ000425</a>   740    ....................g.....
715
<a name = 3320014></a><a
href=http://www.ncbi.nlm.nih.gov:80/entrez/query.fcgi?cmd=Retrieve&db=Nucleotide
&list_uids=03320014&dopt=GenBank>AJ000418</a>   740    ....................a.....
715
<a name = 3320012></a><a
href=http://www.ncbi.nlm.nih.gov:80/entrez/query.fcgi?cmd=Retrieve&db=Nucleotide
&list_uids=03320012&dopt=GenBank>AJ000417</a>   740    ....................a.....
715
<a name = 3319993></a><a
href=http://www.ncbi.nlm.nih.gov:80/entrez/query.fcgi?cmd=Retrieve&db=Nucleotide
```

```
&list_uids=03319993&dopt=GenBank>AJ000416</a>  740   ....................a.....
715
<a name = 4691252></a><a
href=http://www.ncbi.nlm.nih.gov:80/entrez/query.fcgi?cmd=Retrieve&db=Nucleotide
&list_uids=04691252&dopt=GenBank>AJ004793</a>  770   ..............t...........
745
<a name = 4691250></a><a
href=http://www.ncbi.nlm.nih.gov:80/entrez/query.fcgi?cmd=Retrieve&db=Nucleotide
&list_uids=04691250&dopt=GenBank>AJ004792</a>  770   ..............t...........
745
<a name = 1256207></a><a
href=http://www.ncbi.nlm.nih.gov:80/entrez/query.fcgi?cmd=Retrieve&db=Nucleotide
&list_uids=01256207&dopt=GenBank>U15718</a>    774   ..............t...........
749
<a name = 336482></a><a
href=http://www.ncbi.nlm.nih.gov:80/entrez/query.fcgi?cmd=Retrieve&db=Nucleotide
&list_uids=00336482&dopt=GenBank>L11905</a>    869   ...........a..............
844
<a name = 1041865></a><a
href=http://www.ncbi.nlm.nih.gov:80/entrez/query.fcgi?cmd=Retrieve&db=Nucleotide
&list_uids=01041865&dopt=GenBank>U34679</a>    869   ..............t...........
844
<a name = 336486></a><a
href=http://www.ncbi.nlm.nih.gov:80/entrez/query.fcgi?cmd=Retrieve&db=Nucleotide
&list_uids=00336486&dopt=GenBank>L11907</a>    869   ...........a..............
844
<a name = 336484></a><a
href=http://www.ncbi.nlm.nih.gov:80/entrez/query.fcgi?cmd=Retrieve&db=Nucleotide
&list_uids=00336484&dopt=GenBank>L11906</a>    869   ...........a..............
844
<a name = 336476></a><a
href=http://www.ncbi.nlm.nih.gov:80/entrez/query.fcgi?cmd=Retrieve&db=Nucleotide
&list_uids=00336476&dopt=GenBank>L11902</a>    869   ...........a..............
844
<a name = 1199854></a><a
href=http://www.ncbi.nlm.nih.gov:80/entrez/query.fcgi?cmd=Retrieve&db=Nucleotide
&list_uids=01199854&dopt=GenBank>X92524</a>    869   .....a....................
844
<a name = 1197600></a><a
href=http://www.ncbi.nlm.nih.gov:80/entrez/query.fcgi?cmd=Retrieve&db=Nucleotide
&list_uids=01197600&dopt=GenBank>U46771</a>    773   .....................g....
748
<a name = 12248822></a><a
href=http://www.ncbi.nlm.nih.gov:80/entrez/query.fcgi?cmd=Retrieve&db=Nucleotide
&list_uids=12248822&dopt=GenBank>AB021773</a>  869   .....a....................
844
<a name = 3288686></a><a
href=http://www.ncbi.nlm.nih.gov:80/entrez/query.fcgi?cmd=Retrieve&db=Nucleotide
&list_uids=03288686&dopt=GenBank>AB006953</a>  16164 ..............g...........
16139
<a name = 1332568></a><a
href=http://www.ncbi.nlm.nih.gov:80/entrez/query.fcgi?cmd=Retrieve&db=Nucleotide
&list_uids=01332568&dopt=GenBank>Z73492</a>    770   .....c....................
745
<a name = 11862853></a><a
href=http://www.ncbi.nlm.nih.gov:80/entrez/query.fcgi?cmd=Retrieve&db=Nucleotide
```

```
<a name = 11862853></a><a href=http://www.ncbi.nlm.nih.gov:80/entrez/query.fcgi?cmd=Retrieve&db=Nucleotide
&list_uids=11862853&dopt=GenBank>AB035239</a>   869        ...............t..........
844
<a name = 1199828></a><a
href=http://www.ncbi.nlm.nih.gov:80/entrez/query.fcgi?cmd=Retrieve&db=Nucleotide
&list_uids=01199828&dopt=GenBank>X92532</a>      869        ...............g..........
844
<a name = 396737></a><a
href=http://www.ncbi.nlm.nih.gov:80/entrez/query.fcgi?cmd=Retrieve&db=Nucleotide
&list_uids=00396737&dopt=GenBank>X74260</a>      872        ...............g..........
847
<a name = 13628></a><a
href=http://www.ncbi.nlm.nih.gov:80/entrez/query.fcgi?cmd=Retrieve&db=Nucleotide
&list_uids=00013628&dopt=GenBank>X56293</a>      869        .....a....................
844
<a name = 13626></a><a
href=http://www.ncbi.nlm.nih.gov:80/entrez/query.fcgi?cmd=Retrieve&db=Nucleotide
&list_uids=00013626&dopt=GenBank>X56292</a>      869        .....a....................
844
<a name = 396735></a><a
href=http://www.ncbi.nlm.nih.gov:80/entrez/query.fcgi?cmd=Retrieve&db=Nucleotide
&list_uids=00396735&dopt=GenBank>X74256</a>      872        ...............g..........
847
<a name = 693973></a><a
href=http://www.ncbi.nlm.nih.gov:80/entrez/query.fcgi?cmd=Retrieve&db=Nucleotide
&list_uids=00693973&dopt=GenBank>X82304</a>      869        ....................g.....
844
<a name = 693969></a><a
href=http://www.ncbi.nlm.nih.gov:80/entrez/query.fcgi?cmd=Retrieve&db=Nucleotide
&list_uids=00693969&dopt=GenBank>X82302</a>      869        ...............g..........
844
<a name = 13156></a><a
href=http://www.ncbi.nlm.nih.gov:80/entrez/query.fcgi?cmd=Retrieve&db=Nucleotide
&list_uids=00013156&dopt=GenBank>X56284</a>      869        ............a.............
844
<a name = 396731></a><a
href=http://www.ncbi.nlm.nih.gov:80/entrez/query.fcgi?cmd=Retrieve&db=Nucleotide
&list_uids=00396731&dopt=GenBank>X74252</a>      872        ...............g..........
847
<a name = 414771></a><a
href=http://www.ncbi.nlm.nih.gov:80/entrez/query.fcgi?cmd=Retrieve&db=Nucleotide
&list_uids=00414771&dopt=GenBank>X72005</a>      869        ....................g.....
844
<a name = 396729></a><a
href=http://www.ncbi.nlm.nih.gov:80/entrez/query.fcgi?cmd=Retrieve&db=Nucleotide
&list_uids=00396729&dopt=GenBank>X74259</a>      872        ...............g..........
847
<a name = 2154895></a><a
href=http://www.ncbi.nlm.nih.gov:80/entrez/query.fcgi?cmd=Retrieve&db=Nucleotide
&list_uids=02154895&dopt=GenBank>Y08814</a>      869        .....c....................
844
<a name = 2154892></a><a
href=http://www.ncbi.nlm.nih.gov:80/entrez/query.fcgi?cmd=Retrieve&db=Nucleotide
&list_uids=02154892&dopt=GenBank>Y08813</a>      869        ...............g..........
844
<a name = 12951></a><a
href=http://www.ncbi.nlm.nih.gov:80/entrez/query.fcgi?cmd=Retrieve&db=Nucleotide
```

```
&list_uids=00012951&dopt=GenBank>X56287</a>      869     ..............g...........
844
<a name = 396725></a><a
href=http://www.ncbi.nlm.nih.gov:80/entrez/query.fcgi?cmd=Retrieve&db=Nucleotide
&list_uids=00396725&dopt=GenBank>X74253</a>      872     ..............g...........
847
<a name = 12941></a><a
href=http://www.ncbi.nlm.nih.gov:80/entrez/query.fcgi?cmd=Retrieve&db=Nucleotide
&list_uids=00012941&dopt=GenBank>X60941</a>      773     .....c....................
748
<a name = 396723></a><a
href=http://www.ncbi.nlm.nih.gov:80/entrez/query.fcgi?cmd=Retrieve&db=Nucleotide
&list_uids=00396723&dopt=GenBank>X74255</a>      872     ..............g...........
847
<a name = 12871></a><a
href=http://www.ncbi.nlm.nih.gov:80/entrez/query.fcgi?cmd=Retrieve&db=Nucleotide
&list_uids=00012871&dopt=GenBank>X56289</a>      869     ..............g...........
844
<a name = 12800></a><a
href=http://www.ncbi.nlm.nih.gov:80/entrez/query.fcgi?cmd=Retrieve&db=Nucleotide
&list_uids=00012800&dopt=GenBank>V00654</a>      15382   ..............g...........
15357
<a name = 12683></a><a
href=http://www.ncbi.nlm.nih.gov:80/entrez/query.fcgi?cmd=Retrieve&db=Nucleotide
&list_uids=00012683&dopt=GenBank>X60940</a>      773     ..............t...........
748
<a name = 1199826></a><a
href=http://www.ncbi.nlm.nih.gov:80/entrez/query.fcgi?cmd=Retrieve&db=Nucleotide
&list_uids=01199826&dopt=GenBank>X92530</a>      869     .....a....................
844
<a name = 487613></a><a
href=http://www.ncbi.nlm.nih.gov:80/entrez/query.fcgi?cmd=Retrieve&db=Nucleotide
&list_uids=00487613&dopt=GenBank>U09265</a>      774     ....................g.....
749
<a name = 9844992></a><a
href=http://www.ncbi.nlm.nih.gov:80/entrez/query.fcgi?cmd=Retrieve&db=Nucleotide
&list_uids=09844992&dopt=GenBank>AB023906</a>    842     ....................a.....
817
<a name = 9844990></a><a
href=http://www.ncbi.nlm.nih.gov:80/entrez/query.fcgi?cmd=Retrieve&db=Nucleotide
&list_uids=09844990&dopt=GenBank>AB023905</a>    842     ....................a.....
817
<a name = 9844988></a><a
href=http://www.ncbi.nlm.nih.gov:80/entrez/query.fcgi?cmd=Retrieve&db=Nucleotide
&list_uids=09844988&dopt=GenBank>AB023904</a>    842     ....................a.....
817
<a name = 9844986></a><a
href=http://www.ncbi.nlm.nih.gov:80/entrez/query.fcgi?cmd=Retrieve&db=Nucleotide
&list_uids=09844986&dopt=GenBank>AB023903</a>    842     ....................a.....
817
<a name = 1695710></a><a
href=http://www.ncbi.nlm.nih.gov:80/entrez/query.fcgi?cmd=Retrieve&db=Nucleotide
&list_uids=01695710&dopt=GenBank>D88983</a>      869     ................a.........
844
<a name = 1707345></a><a
href=http://www.ncbi.nlm.nih.gov:80/entrez/query.fcgi?cmd=Retrieve&db=Nucleotide
```

```
&list_uids=01707345&dopt=GenBank>D88638</a>    869   .................a........
844
<a name = 1707341></a><a
href=http://www.ncbi.nlm.nih.gov:80/entrez/query.fcgi?cmd=Retrieve&db=Nucleotide
&list_uids=01707341&dopt=GenBank>D88636</a>    869   .................a........
844
<a name = 1707339></a><a
href=http://www.ncbi.nlm.nih.gov:80/entrez/query.fcgi?cmd=Retrieve&db=Nucleotide
&list_uids=01707339&dopt=GenBank>D88635</a>    869   .................a........
844
<a name = 1707335></a><a
href=http://www.ncbi.nlm.nih.gov:80/entrez/query.fcgi?cmd=Retrieve&db=Nucleotide
&list_uids=01707335&dopt=GenBank>D88633</a>    869   .................a........
844
<a name = 1707333></a><a
href=http://www.ncbi.nlm.nih.gov:80/entrez/query.fcgi?cmd=Retrieve&db=Nucleotide
&list_uids=01707333&dopt=GenBank>D88632</a>    869   .................a........
844
<a name = 1707329></a><a
href=http://www.ncbi.nlm.nih.gov:80/entrez/query.fcgi?cmd=Retrieve&db=Nucleotide
&list_uids=01707329&dopt=GenBank>D88630</a>    869   .................a........
844
<a name = 1707325></a><a
href=http://www.ncbi.nlm.nih.gov:80/entrez/query.fcgi?cmd=Retrieve&db=Nucleotide
&list_uids=01707325&dopt=GenBank>D88628</a>    869   .................a........
844
<a name = 1707323></a><a
href=http://www.ncbi.nlm.nih.gov:80/entrez/query.fcgi?cmd=Retrieve&db=Nucleotide
&list_uids=01707323&dopt=GenBank>D88627</a>    869   .................a........
844
<a name = 1256164></a><a
href=http://www.ncbi.nlm.nih.gov:80/entrez/query.fcgi?cmd=Retrieve&db=Nucleotide
&list_uids=01256164&dopt=GenBank>D84204</a>    869   ...............g............
844
<a name = 1256162></a><a
href=http://www.ncbi.nlm.nih.gov:80/entrez/query.fcgi?cmd=Retrieve&db=Nucleotide
&list_uids=01256162&dopt=GenBank>D84202</a>    869   ...............g............
844
<a name = 1813364></a><a
href=http://www.ncbi.nlm.nih.gov:80/entrez/query.fcgi?cmd=Retrieve&db=Nucleotide
&list_uids=01813364&dopt=GenBank>D82893</a>    869   .................a........
844
<a name = 1813362></a><a
href=http://www.ncbi.nlm.nih.gov:80/entrez/query.fcgi?cmd=Retrieve&db=Nucleotide
&list_uids=01813362&dopt=GenBank>D82892</a>    869   .................a........
844
<a name = 1813356></a><a
href=http://www.ncbi.nlm.nih.gov:80/entrez/query.fcgi?cmd=Retrieve&db=Nucleotide
&list_uids=01813356&dopt=GenBank>D82889</a>    869   ...............g............
844
<a name = 516653></a><a
href=http://www.ncbi.nlm.nih.gov:80/entrez/query.fcgi?cmd=Retrieve&db=Nucleotide
&list_uids=00516653&dopt=GenBank>D32193</a>    869   .................a........
844
<a name = 517076></a><a
href=http://www.ncbi.nlm.nih.gov:80/entrez/query.fcgi?cmd=Retrieve&db=Nucleotide
```

```
&list_uids=00517076&dopt=GenBank>D34637</a>    869         ................a........
844
<a name = 2189986></a><a
href=http://www.ncbi.nlm.nih.gov:80/entrez/query.fcgi?cmd=Retrieve&db=Nucleotide
&list_uids=02189986&dopt=GenBank>AB004074</a>   869         ...............g...........
844
<a name = 2189984></a><a
href=http://www.ncbi.nlm.nih.gov:80/entrez/query.fcgi?cmd=Retrieve&db=Nucleotide
&list_uids=02189984&dopt=GenBank>AB004072</a>   869         ...............g...........
844
<a name = 2189983></a><a
href=http://www.ncbi.nlm.nih.gov:80/entrez/query.fcgi?cmd=Retrieve&db=Nucleotide
&list_uids=02189983&dopt=GenBank>AB004071</a>   869         ...............g...........
844
<a name = 2189981></a><a
href=http://www.ncbi.nlm.nih.gov:80/entrez/query.fcgi?cmd=Retrieve&db=Nucleotide
&list_uids=02189981&dopt=GenBank>AB004069</a>   869         ...............g...........
844
<a name = 1707349></a><a
href=http://www.ncbi.nlm.nih.gov:80/entrez/query.fcgi?cmd=Retrieve&db=Nucleotide
&list_uids=01707349&dopt=GenBank>D88640</a>    869         ................a........
844
<a name = 1707343></a><a
href=http://www.ncbi.nlm.nih.gov:80/entrez/query.fcgi?cmd=Retrieve&db=Nucleotide
&list_uids=01707343&dopt=GenBank>D88637</a>    869         ................a........
844
<a name = 1707337></a><a
href=http://www.ncbi.nlm.nih.gov:80/entrez/query.fcgi?cmd=Retrieve&db=Nucleotide
&list_uids=01707337&dopt=GenBank>D88634</a>    869         ................a........
844
<a name = 1707331></a><a
href=http://www.ncbi.nlm.nih.gov:80/entrez/query.fcgi?cmd=Retrieve&db=Nucleotide
&list_uids=01707331&dopt=GenBank>D88631</a>    869         ................a........
844
<a name = 1707327></a><a
href=http://www.ncbi.nlm.nih.gov:80/entrez/query.fcgi?cmd=Retrieve&db=Nucleotide
&list_uids=01707327&dopt=GenBank>D88629</a>    869         ................a........
844
<a name = 1256201></a><a
href=http://www.ncbi.nlm.nih.gov:80/entrez/query.fcgi?cmd=Retrieve&db=Nucleotide
&list_uids=01256201&dopt=GenBank>D84205</a>    869         ............a...............
844
<a name = 1256199></a><a
href=http://www.ncbi.nlm.nih.gov:80/entrez/query.fcgi?cmd=Retrieve&db=Nucleotide
&list_uids=01256199&dopt=GenBank>D84203</a>    869         ............a...............
844
<a name = 1256160></a><a
href=http://www.ncbi.nlm.nih.gov:80/entrez/query.fcgi?cmd=Retrieve&db=Nucleotide
&list_uids=01256160&dopt=GenBank>D84201</a>    869         ...............g...........
844
<a name = 1813366></a><a
href=http://www.ncbi.nlm.nih.gov:80/entrez/query.fcgi?cmd=Retrieve&db=Nucleotide
&list_uids=01813366&dopt=GenBank>D82894</a>    869         ................a........
844
<a name = 1813360></a><a
href=http://www.ncbi.nlm.nih.gov:80/entrez/query.fcgi?cmd=Retrieve&db=Nucleotide
```

```
&list_uids=01813360&dopt=GenBank>D82891</a>    869    ................a........
844
<a name = 517078></a><a
href=http://www.ncbi.nlm.nih.gov:80/entrez/query.fcgi?cmd=Retrieve&db=Nucleotide
&list_uids=00517078&dopt=GenBank>D34638</a>    869    ................a........
844
<a name = 516663></a><a
href=http://www.ncbi.nlm.nih.gov:80/entrez/query.fcgi?cmd=Retrieve&db=Nucleotide
&list_uids=00516663&dopt=GenBank>D34636</a>    869    ...............g.............
844
<a name = 6906755></a><a
href=http://www.ncbi.nlm.nih.gov:80/entrez/query.fcgi?cmd=Retrieve&db=Nucleotide
&list_uids=06906755&dopt=GenBank>AB037602</a>  869    ............a...............
844
<a name = 6682770></a><a
href=http://www.ncbi.nlm.nih.gov:80/entrez/query.fcgi?cmd=Retrieve&db=Nucleotide
&list_uids=06682770&dopt=GenBank>AB018985</a>  869    ................a.......
844
<a name = 2189987></a><a
href=http://www.ncbi.nlm.nih.gov:80/entrez/query.fcgi?cmd=Retrieve&db=Nucleotide
&list_uids=02189987&dopt=GenBank>AB004075</a>  869    ...............g.............
844
<a name = 2189985></a><a
href=http://www.ncbi.nlm.nih.gov:80/entrez/query.fcgi?cmd=Retrieve&db=Nucleotide
&list_uids=02189985&dopt=GenBank>AB004073</a>  869    ...............g.............
844
<a name = 2189982></a><a
href=http://www.ncbi.nlm.nih.gov:80/entrez/query.fcgi?cmd=Retrieve&db=Nucleotide
&list_uids=02189982&dopt=GenBank>AB004070</a>  869    ...............g.............
844
<a name = 1199512></a><a
href=http://www.ncbi.nlm.nih.gov:80/entrez/query.fcgi?cmd=Retrieve&db=Nucleotide
&list_uids=01199512&dopt=GenBank>X92531</a>    869    ...............g.............
844
<a name = 511676></a><a
href=http://www.ncbi.nlm.nih.gov:80/entrez/query.fcgi?cmd=Retrieve&db=Nucleotide
&list_uids=00511676&dopt=GenBank>U07565</a>    869    ...............g............
844
<a name = 501121></a><a
href=http://www.ncbi.nlm.nih.gov:80/entrez/query.fcgi?cmd=Retrieve&db=Nucleotide
&list_uids=00501121&dopt=GenBank>U10367</a>    773    ...............g............
748
<a name = 501117></a><a
href=http://www.ncbi.nlm.nih.gov:80/entrez/query.fcgi?cmd=Retrieve&db=Nucleotide
&list_uids=00501117&dopt=GenBank>U10364</a>    773    ...............g............
748
<a name = 2924255></a><a
href=http://www.ncbi.nlm.nih.gov:80/entrez/query.fcgi?cmd=Retrieve&db=Nucleotide
&list_uids=02924255&dopt=GenBank>Z96068</a>    869    .....................g......
844
<a name = 4098253></a><a
href=http://www.ncbi.nlm.nih.gov:80/entrez/query.fcgi?cmd=Retrieve&db=Nucleotide
&list_uids=04098253&dopt=GenBank>U76507</a>    773    ................t..........
749
<a name = 5596617></a><a
href=http://www.ncbi.nlm.nih.gov:80/entrez/query.fcgi?cmd=Retrieve&db=Nucleotide
```

```
&list_uids=05596617&dopt=GenBank>AF157466</a>  791      ..................
772
<a name = 5596613></a><a
href=http://www.ncbi.nlm.nih.gov:80/entrez/query.fcgi?cmd=Retrieve&db=Nucleotide
&list_uids=05596613&dopt=GenBank>AF157464</a>  793      ..................
774
<a name = 5596611></a><a
href=http://www.ncbi.nlm.nih.gov:80/entrez/query.fcgi?cmd=Retrieve&db=Nucleotide
&list_uids=05596611&dopt=GenBank>AF157463</a>  793      ..................
774
<a name = 13096063></a><a
href=http://www.ncbi.nlm.nih.gov:80/entrez/query.fcgi?cmd=Retrieve&db=Nucleotide
&list_uids=13096063&dopt=GenBank>AY016019</a>  93      ..................
74
<a name = 4590012></a><a
href=http://www.ncbi.nlm.nih.gov:80/entrez/query.fcgi?cmd=Retrieve&db=Nucleotide
&list_uids=04590012&dopt=GenBank>AF027330</a>  869      ..................
850
<a name = 4590011></a><a
href=http://www.ncbi.nlm.nih.gov:80/entrez/query.fcgi?cmd=Retrieve&db=Nucleotide
&list_uids=04590011&dopt=GenBank>AF027329</a>  869      ..................
850
<a name = 4590010></a><a
href=http://www.ncbi.nlm.nih.gov:80/entrez/query.fcgi?cmd=Retrieve&db=Nucleotide
&list_uids=04590010&dopt=GenBank>AF027328</a>  869      ..................
850
<a name = 4590009></a><a
href=http://www.ncbi.nlm.nih.gov:80/entrez/query.fcgi?cmd=Retrieve&db=Nucleotide
&list_uids=04590009&dopt=GenBank>AF027327</a>  869      ..................
850
<a name = 4590008></a><a
href=http://www.ncbi.nlm.nih.gov:80/entrez/query.fcgi?cmd=Retrieve&db=Nucleotide
&list_uids=04590008&dopt=GenBank>AF027326</a>  869      ..................
850
<a name = 4590007></a><a
href=http://www.ncbi.nlm.nih.gov:80/entrez/query.fcgi?cmd=Retrieve&db=Nucleotide
&list_uids=04590007&dopt=GenBank>AF027325</a>  869      ..................
850
<a name = 4590006></a><a
href=http://www.ncbi.nlm.nih.gov:80/entrez/query.fcgi?cmd=Retrieve&db=Nucleotide
&list_uids=04590006&dopt=GenBank>AF027324</a>  869      ..................
850
<a name = 4590005></a><a
href=http://www.ncbi.nlm.nih.gov:80/entrez/query.fcgi?cmd=Retrieve&db=Nucleotide
&list_uids=04590005&dopt=GenBank>AF027323</a>  869      ..................
850
<a name = 4590004></a><a
href=http://www.ncbi.nlm.nih.gov:80/entrez/query.fcgi?cmd=Retrieve&db=Nucleotide
&list_uids=04590004&dopt=GenBank>AF027322</a>  869      ..................
850
<a name = 4590003></a><a
href=http://www.ncbi.nlm.nih.gov:80/entrez/query.fcgi?cmd=Retrieve&db=Nucleotide
&list_uids=04590003&dopt=GenBank>AF027321</a>  869      ..................
850
<a name = 4590002></a><a
href=http://www.ncbi.nlm.nih.gov:80/entrez/query.fcgi?cmd=Retrieve&db=Nucleotide
```

```
&list_uids=04590002&dopt=GenBank>AF027320</a>  869  ....................
850
<a name = 4590001></a><a
href=http://www.ncbi.nlm.nih.gov:80/entrez/query.fcgi?cmd=Retrieve&db=Nucleotide
&list_uids=04590001&dopt=GenBank>AF027319</a>  869  ....................
850
<a name = 4590000></a><a
href=http://www.ncbi.nlm.nih.gov:80/entrez/query.fcgi?cmd=Retrieve&db=Nucleotide
&list_uids=04590000&dopt=GenBank>AF027318</a>  869  ....................
850
<a name = 4589999></a><a
href=http://www.ncbi.nlm.nih.gov:80/entrez/query.fcgi?cmd=Retrieve&db=Nucleotide
&list_uids=04589999&dopt=GenBank>AF027317</a>  869  ....................
850
<a name = 4589998></a><a
href=http://www.ncbi.nlm.nih.gov:80/entrez/query.fcgi?cmd=Retrieve&db=Nucleotide
&list_uids=04589998&dopt=GenBank>AF027316</a>  869  ....................
850
<a name = 4589997></a><a
href=http://www.ncbi.nlm.nih.gov:80/entrez/query.fcgi?cmd=Retrieve&db=Nucleotide
&list_uids=04589997&dopt=GenBank>AF027315</a>  869  ....................
850
<a name = 4589996></a><a
href=http://www.ncbi.nlm.nih.gov:80/entrez/query.fcgi?cmd=Retrieve&db=Nucleotide
&list_uids=04589996&dopt=GenBank>AF027314</a>  869  ....................
850
<a name = 4589995></a><a
href=http://www.ncbi.nlm.nih.gov:80/entrez/query.fcgi?cmd=Retrieve&db=Nucleotide
&list_uids=04589995&dopt=GenBank>AF027313</a>  869  ....................
850
<a name = 4589994></a><a
href=http://www.ncbi.nlm.nih.gov:80/entrez/query.fcgi?cmd=Retrieve&db=Nucleotide
&list_uids=04589994&dopt=GenBank>AF027312</a>  869  ....................
850
<a name = 4589993></a><a
href=http://www.ncbi.nlm.nih.gov:80/entrez/query.fcgi?cmd=Retrieve&db=Nucleotide
&list_uids=04589993&dopt=GenBank>AF027311</a>  869  ....................
850
<a name = 4589992></a><a
href=http://www.ncbi.nlm.nih.gov:80/entrez/query.fcgi?cmd=Retrieve&db=Nucleotide
&list_uids=04589992&dopt=GenBank>AF027310</a>  869  ....................
850
<a name = 4589991></a><a
href=http://www.ncbi.nlm.nih.gov:80/entrez/query.fcgi?cmd=Retrieve&db=Nucleotide
&list_uids=04589991&dopt=GenBank>AF027309</a>  869  ....................
850
<a name = 4589990></a><a
href=http://www.ncbi.nlm.nih.gov:80/entrez/query.fcgi?cmd=Retrieve&db=Nucleotide
&list_uids=04589990&dopt=GenBank>AF027308</a>  869  ....................
850
<a name = 4589989></a><a
href=http://www.ncbi.nlm.nih.gov:80/entrez/query.fcgi?cmd=Retrieve&db=Nucleotide
&list_uids=04589989&dopt=GenBank>AF027307</a>  869  ....................
850
<a name = 10121656></a><a
href=http://www.ncbi.nlm.nih.gov:80/entrez/query.fcgi?cmd=Retrieve&db=Nucleotide
```

```
&list_uids=10121656&dopt=GenBank>AF266188</a>   371    ....................
352
<a name = 13095017></a><a
href=http://www.ncbi.nlm.nih.gov:80/entrez/query.fcgi?cmd=Retrieve&db=Nucleotide
&list_uids=13095017&dopt=GenBank>AF324034</a>   408    ....................
389
<a name = 12006255></a><a
href=http://www.ncbi.nlm.nih.gov:80/entrez/query.fcgi?cmd=Retrieve&db=Nucleotide
&list_uids=12006255&dopt=GenBank>AF272639</a>   869    ....................
850
<a name = 12006249></a><a
href=http://www.ncbi.nlm.nih.gov:80/entrez/query.fcgi?cmd=Retrieve&db=Nucleotide
&list_uids=12006249&dopt=GenBank>AF272636</a>   869    ....................
850
<a name = 12006245></a><a
href=http://www.ncbi.nlm.nih.gov:80/entrez/query.fcgi?cmd=Retrieve&db=Nucleotide
&list_uids=12006245&dopt=GenBank>AF272634</a>   869    ....................
850
<a name = 12006243></a><a
href=http://www.ncbi.nlm.nih.gov:80/entrez/query.fcgi?cmd=Retrieve&db=Nucleotide
&list_uids=12006243&dopt=GenBank>AF272633</a>   869    ....................
850
<a name = 7262992></a><a
href=http://www.ncbi.nlm.nih.gov:80/entrez/query.fcgi?cmd=Retrieve&db=Nucleotide
&list_uids=07262992&dopt=GenBank>AF182711</a>   712    ....................
693
<a name = 7262944></a><a
href=http://www.ncbi.nlm.nih.gov:80/entrez/query.fcgi?cmd=Retrieve&db=Nucleotide
&list_uids=07262944&dopt=GenBank>AF182687</a>   774    ....................
755
<a name = 8698642></a><a
href=http://www.ncbi.nlm.nih.gov:80/entrez/query.fcgi?cmd=Retrieve&db=Nucleotide
&list_uids=08698642&dopt=GenBank>AF155422</a>   869    ....................
850
<a name = 5410547></a><a
href=http://www.ncbi.nlm.nih.gov:80/entrez/query.fcgi?cmd=Retrieve&db=Nucleotide
&list_uids=05410547&dopt=GenBank>AF155400</a>   869    ....................
850
<a name = 5410532></a><a
href=http://www.ncbi.nlm.nih.gov:80/entrez/query.fcgi?cmd=Retrieve&db=Nucleotide
&list_uids=05410532&dopt=GenBank>AF155385</a>   869    ....................
850
<a name = 5410531></a><a
href=http://www.ncbi.nlm.nih.gov:80/entrez/query.fcgi?cmd=Retrieve&db=Nucleotide
&list_uids=05410531&dopt=GenBank>AF155384</a>   869    ....................
850
<a name = 8885870></a><a
href=http://www.ncbi.nlm.nih.gov:80/entrez/query.fcgi?cmd=Retrieve&db=Nucleotide
&list_uids=08885870&dopt=GenBank>AF155592</a>   869    ....................
850
<a name = 8885868></a><a
href=http://www.ncbi.nlm.nih.gov:80/entrez/query.fcgi?cmd=Retrieve&db=Nucleotide
&list_uids=08885868&dopt=GenBank>AF155591</a>   869    ....................
850
<a name = 8885866></a><a
href=http://www.ncbi.nlm.nih.gov:80/entrez/query.fcgi?cmd=Retrieve&db=Nucleotide
```

```
&list_uids=08885866&dopt=GenBank>AF155590</a>   869   ....................
850
<a name = 8885864></a><a
href=http://www.ncbi.nlm.nih.gov:80/entrez/query.fcgi?cmd=Retrieve&db=Nucleotide
&list_uids=08885864&dopt=GenBank>AF155589</a>   869   ....................
850
<a name = 8885862></a><a
href=http://www.ncbi.nlm.nih.gov:80/entrez/query.fcgi?cmd=Retrieve&db=Nucleotide
&list_uids=08885862&dopt=GenBank>AF155588</a>   869   ....................
850
<a name = 7573899></a><a
href=http://www.ncbi.nlm.nih.gov:80/entrez/query.fcgi?cmd=Retrieve&db=Nucleotide
&list_uids=07573899&dopt=GenBank>AF123531</a>   771   ....................
752
<a name = 8308177></a><a
href=http://www.ncbi.nlm.nih.gov:80/entrez/query.fcgi?cmd=Retrieve&db=Nucleotide
&list_uids=08308177&dopt=GenBank>AF264047</a>   869   ....................
850
<a name = 7861845></a><a
href=http://www.ncbi.nlm.nih.gov:80/entrez/query.fcgi?cmd=Retrieve&db=Nucleotide
&list_uids=07861845&dopt=GenBank>AF206531</a>   771   ....................
752
<a name = 6539823></a><a
href=http://www.ncbi.nlm.nih.gov:80/entrez/query.fcgi?cmd=Retrieve&db=Nucleotide
&list_uids=06539823&dopt=GenBank>AF192706</a>   863   ....................
844
<a name = 5835988></a><a
href=http://www.ncbi.nlm.nih.gov:80/entrez/query.fcgi?cmd=Retrieve&db=Nucleotide
&list_uids=05835988&dopt=GenBank>NC_000884</a>  15032 ....................
15013
<a name = 2921010></a><a
href=http://www.ncbi.nlm.nih.gov:80/entrez/query.fcgi?cmd=Retrieve&db=Nucleotide
&list_uids=02921010&dopt=GenBank>AF004572</a>   869   ....................
850
<a name = 5052150></a><a
href=http://www.ncbi.nlm.nih.gov:80/entrez/query.fcgi?cmd=Retrieve&db=Nucleotide
&list_uids=05052150&dopt=GenBank>AF088932</a>   869   ....................
850
<a name = 2052316></a><a
href=http://www.ncbi.nlm.nih.gov:80/entrez/query.fcgi?cmd=Retrieve&db=Nucleotide
&list_uids=02052316&dopt=GenBank>U62697</a>     176   ....................
157
<a name = 1488214></a><a
href=http://www.ncbi.nlm.nih.gov:80/entrez/query.fcgi?cmd=Retrieve&db=Nucleotide
&list_uids=01488214&dopt=GenBank>U62681</a>     179   ....................
160
<a name = 2052341></a><a
href=http://www.ncbi.nlm.nih.gov:80/entrez/query.fcgi?cmd=Retrieve&db=Nucleotide
&list_uids=02052341&dopt=GenBank>U62707</a>     179   .............g........n..
154
<a name = 9967917></a><a
href=http://www.ncbi.nlm.nih.gov:80/entrez/query.fcgi?cmd=Retrieve&db=Nucleotide
&list_uids=09967917&dopt=GenBank>AJ004315</a>   773   ...............t......n.....
748
</PRE>

<PRE>
```

```
Database: nt
  Posted date:  Mar 2, 2001 12:20 AM
Number of letters in database: 2,863,827,885
Number of sequences in database:  807,597

Lambda     K        H
   1.37    0.711    1.31

Gapped
Lambda     K        H
   1.37    0.711    1.31

Matrix: blastn matrix:1 -3
Gap Penalties: Existence: 5, Extension: 2
Number of Hits to DB: 19068
Number of Sequences: 807597
Number of extensions: 19068
Number of successful extensions: 7580
Number of sequences better than 10.0: 2441
length of query: 26
length of database: 2,863,827,885
effective HSP length: 17
effective length of query: 9
effective length of database: 2,850,098,736
effective search space: 25650888624
effective search space used: 25650888624
T: 0
A: 30
X1: 6 (11.9 bits)
X2: 15 (29.7 bits)
S1: 12 (24.3 bits)
S2: 16 (32.2 bits)

</PRE>

</BODY>
</HTML>
</FORM>
</BODY>
</HTML>
```

Table 12. Other animal belonging to distantly related animal species, investigated to confirm the universal nature of primers 'mcb398' and 'mcb869'. Gel photograph showing the PCR amplicons from these animals are shown in FIG. 4.

TABLE 12

The other animals belonging to distantly related species analyzed by our primers to demonstrate its universal nature

| SN. | Name of the animal |
|---|---|
| 1. | Indian black buck no.1 |
| 2. | Indian black buck no 2 |
| 3 | sheep |
| 4 | pig |
| 5 | dog |
| 6 | chimpanzee (chimss) |
| 7 | human (humsk) |
| 8 | Hamster |
| 9 | crocodile no1 |
| 10 | crocodile no2 |

TABLE 12-continued

The other animals belonging to distantly related species analyzed by our primers to demonstrate its universal nature

| SN. | Name of the animal |
|---|---|
| 11 | turtle no1 |
| 12 | turtle no2 |
| 13 | mouse |
| 14 | varanus |
| 15 | Naga-naga snake |
| 16 | Indian elephant |
| 17 | hen |
| 18 | dugong |
| 19 | lizard |
| 20 | weaver bird no1 |
| 21 | weaver bird no2 |
| 22 | buffalo no1 |
| 23 | buffalo no 2 |

The invention claimed is:

1. A universal primer pair for amplifying a fragment of cytochrome b gene of an animal species in a polymerase chain reaction (PCR) or determining the identity of the biological material of an animal of unknown origin at species and sub-species level, said primer pair consisting essentially of SEQ ID NO: 1 and SEQ ID NO: 2 and being capable of selectively amplifying a fragment of about 472 base pairs of a mitochondrial cytochrome b gene of any of at least 221 animal species, wherein the fragment being selectively amplified has a sequence that varies among each of the at least 221 animal species.

2. A reaction mixture comprising the primer pair of claim 1 and the fragment of the mitochondrial cytochrome b gene flanked by sequences that are highly conserved amongst the at least 221 animal species.

3. The reaction mixture as claimed in claim 2, wherein the fragment of mitochondrial cytochrome b gene is polymorphic inter-specifically but monomorphic at intra species sources.

4. The reaction mixture as claimed in claim 2, wherein the fragment comprises SEQ ID NO: 211.

5. The A universal primer pair for amplifying a fragment of cytochrome b gene of an animal species in a polymerase chain reaction (PCR) or determining the identity of the biological material of an animal of unknown origin at species and sub-species level, which consists of SEQ ID NO: 1 and SEQ ID NO: 2.

6. An isolated primer consisting of SEQ ID NO: 1.

7. An isolated primer consisting of SEQ ID NO: 2.

8. A method for the identification of an animal from a biological sample comprising DNA of the animal, said method comprising the steps of:
   a) isolating and amplifying the DNA with the primer pair as claimed in claim 1 to form amplified products,
   b) sequencing the amplified products,
   c) blasting the sequence resolved in step (b) against a database and determining the most likely family of the animal source of the biological sample,
   d) blasting the sequence resolved in step (b) against a non-redundant (nr) database and determining the most likely genus, species or sub-species of the animal source of the biological sample,
   e) identifying the most significant alignment of the sequence resolved with cytochrome b gene sequence of the animal identified in steps (c) and (d) respectively and selection of these animals as 'reference animals' for further studies,
   f) isolating and amplifying and sequencing the DNA sequences from the referencel animals on both strands in triplicate using the primer pair
   g) aligning the sequences obtained and identifying the variable sites amongst the animals analyzed,
   h) comparing the nucleotide sequences pair-wise to determine the variation among the animals resolved and identifying the nucleotide sequence to which the DNA sequence of the biological sample bears maximum similarity as the source animal of the biological sample.

9. A method as claimed in claim 8 wherein the Amplification reactions should be carried out in 2011 reaction volume containing approximately 20 ηg of template DNA, 100 μm each of dNTPs, 1.25 pmole of each primer, 1.5 mM $MgCl_2$, 0.5 unit of AmpliTaq Gold (Perkin-Elmer-Cetus, USA) DNA polymerase and 1× PCR buffer (10 mM Tris-HCl, pH 8.3, and 50 mM KCl). The amplification profiles followed should be: an initial denaturation at 95° C. for 45 s, annealing at 51° C. for 1 min, and extension at 72° C. for 2 min. The extension step at $35^{th}$ cycles should be held for 10 min.

10. A method as claimed in claim 8 wherein the method enables identification of species of analyzed material (i.e. the DNA isolated from confiscated animal remain of unknown origin) using the public databases such as GenBank, NCBI etc.

11. A method as claimed in claim 8 wherein the method is used for animal identification to establish the crime with the criminal beyond a reasonably doubt.

12. A method as claimed in claim 8 wherein the method is used to establish the identity of biological materials such as skin, horns, etc confiscated from animal poachers, if it is that of an endangered species.

13. A method as claimed in claim 8 wherein the method is used for establishment of the identity of confiscated animal parts and products of endangered animal species for the purpose of production of molecular evidence of animal hunting and related crime in the court of law, so that the human violation of the wildlife resources could be controlled.

14. A method as claimed in claim 6 wherein the method is used to have an idea of the geographical location of the commitment of wildlife crime based on the cytochrome b gene haplotype of poached animal identified by the universal primer invented.

15. A method as claimed in claim 8 wherein the method is used for animal identification to detect the adulteration of animal meat in food products for the purpose of food fortification, by the food fortification agencies.

16. A method as claimed in claim 8 wherein the method is used to provide a universal technique for detection of the origin of blood or blood stains etc collected from the scene of crime related to offences such as murder, rape etc, in order to establish the origin of blood found at scene of crime when it sounds as if criminals have wontedly spread the blood of an animal at the scene of crime, to confuse the crime investigation agencies and forensic scientists with human blood.

* * * * *